US012570636B2

(12) United States Patent
Imaizumi

(10) Patent No.: US 12,570,636 B2
(45) Date of Patent: Mar. 10, 2026

(54) LUMINESCENCE DEVICE AND NITROGEN-CONTAINING COMPOUND FOR SAME

(71) Applicant: Samsung Display Co., Ltd., Yongin-si (KR)

(72) Inventor: Taku Imaizumi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 953 days.

(21) Appl. No.: 17/688,926

(22) Filed: Mar. 8, 2022

(65) Prior Publication Data

US 2022/0376186 A1 Nov. 24, 2022

(30) Foreign Application Priority Data

Apr. 16, 2021 (KR) ........................ 10-2021-0049647

(51) Int. Cl.
*C07D 403/10* (2006.01)
*C07D 403/14* (2006.01)
(Continued)

(52) U.S. Cl.
CPC ......... *C07D 403/10* (2013.01); *C07D 403/14* (2013.01); *C07D 405/10* (2013.01);
(Continued)

(58) Field of Classification Search
CPC .. C07D 403/10; C07D 405/10; C07D 409/10; H10K 85/6572; H10K 85/6574; H10K 85/6576; H10K 50/15
See application file for complete search history.

(56) References Cited

U.S. PATENT DOCUMENTS 10,062,852 B2 8/2018 Kim et al.
10,155,724 B2 12/2018 Jung et al.
(Continued)

FOREIGN PATENT DOCUMENTS

CN 109928962 6/2019
EP 3109247 12/2016
(Continued)

OTHER PUBLICATIONS

Wang et al., Journal of Photochemistry and Photobiology C: Photochemistry Reviews 17 (2013) 69-104.*

*Primary Examiner* — Vu A Nguyen
(74) *Attorney, Agent, or Firm* — Womble Bond Dickinson (US) LLP

(57) ABSTRACT

A luminescence device, includes: a first electrode; a hole transport region disposed on the first electrode; an emission layer disposed on the hole transport region; an electron transport region disposed on the emission layer; and a second electrode disposed on the electron transport region,
(Continued)

wherein the hole transport region includes a compound of Formula 1:

Formula 1

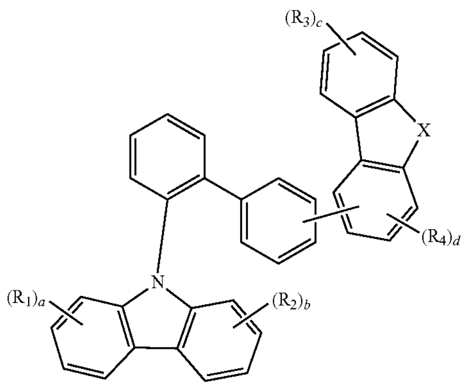

in Formula 1, the variables are described herein.

18 Claims, 6 Drawing Sheets

(51) Int. Cl.

| | |
|---|---|
| ***C07D 405/10*** | (2006.01) |
| ***C07D 405/14*** | (2006.01) |
| ***C07D 417/10*** | (2006.01) |
| ***C07D 417/14*** | (2006.01) |
| ***H10K 50/15*** | (2023.01) |
| ***H10K 50/17*** | (2023.01) |
| ***H10K 85/60*** | (2023.01) |

(52) U.S. Cl.

CPC ......... *C07D 405/14* (2013.01); *C07D 417/10* (2013.01); *C07D 417/14* (2013.01); *H10K 85/626* (2023.02); *H10K 85/6572* (2023.02); *H10K 85/6574* (2023.02); *H10K 85/6576* (2023.02); *H10K 50/15* (2023.02); *H10K 50/17* (2023.02)

(56) References Cited

U.S. PATENT DOCUMENTS

| | | | | |
|---|---|---|---|---|
| 10,243,149 | B2 | 3/2019 | Kang et al. | |
| 11,515,489 | B2 | 11/2022 | Wolohan et al. | |
| 2020/0091439 | A1 | 3/2020 | Ihn et al. | |
| 2020/0168811 | A1* | 5/2020 | Wolohan .............. | C07D 403/14 |
| 2020/0199110 | A1 | 6/2020 | Min et al. | |
| 2023/0329101 | A1* | 10/2023 | Hyun ................... | C07D 405/10<br>257/40 |

FOREIGN PATENT DOCUMENTS

| | | | | |
|---|---|---|---|---|
| KR | 10-2011-0117513 | | 10/2011 | |
| KR | 10-2017-0082126 | | 7/2017 | |
| KR | 101773936 | | 9/2017 | |
| KR | 10-2018-0001290 | | 1/2018 | |
| KR | 10-2020-0066228 | A | 6/2020 | |
| KR | 102146105 | | 8/2020 | |
| KR | 2251836 | B1 * | 5/2021 | ............. C09K 11/06 |

* cited by examiner

LUMINESCENCE DEVICE AND NITROGEN-CONTAINING COMPOUND FOR SAME

CROSS-REFERENCE TO RELATED APPLICATIONS

This application claims priority from and the benefit of Korean Patent Application No. 10-2021-0049647, filed on Apr. 16, 2021, which is hereby incorporated by reference for all purposes as if fully set forth herein.

BACKGROUND

Field

Embodiments of the invention relate generally to display devices, and more particularly, to a luminescence device and a nitrogen-containing compound for a luminescence device.

Discussion of the Background

Recently, the use of a luminescence display as an image display is being actively developed. The luminescence display is different from a liquid crystal display and is so-called a self-luminescent display in which holes and electrons injected from a first electrode and a second electrode recombine in an emission layer so that a light-emitting material in the emission layer emits light to achieve display.

There is a demand for use of a luminescence device to a display, the decrease of its driving voltage, and the increase of emission efficiency and the lifespan of the luminescence device. Accordingly, there also is demand for materials for an organic electroluminescence device that can stably achieve these characteristics.

The above information disclosed in this Background section is only for understanding of the background of the inventive concepts, and, therefore, it may contain information that does not constitute prior art.

SUMMARY

Luminescence devices constructed according to the principles and illustrative implementations of the invention include a novel nitrogen-containing compound for the same, More particularly, when a nitrogen-containing compound made according to the principles and embodiments of the invention is included in a hole transport region of a luminescence device, the luminescence device has high efficiency and/or other favorable characteristics.

Additional features of the inventive concepts will be set forth in the description which follows, and in part will be apparent from the description, or may be learned by practice of the inventive concepts.

According to one aspect of the invention, a luminescence device, includes: a first electrode; a hole transport region disposed on the first electrode; an emission layer disposed on the hole transport region; an electron transport region disposed on the emission layer; and a second electrode disposed on the electron transport region, wherein the hole transport region includes a nitrogen-containing compound of Formula 1:

Formula 1

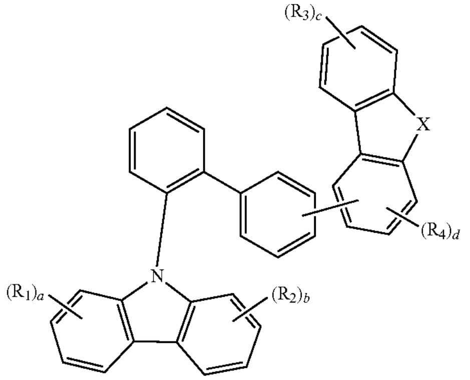

in Formula 1, the variables are described herein.

The hole transport region may include a hole injection layer disposed on the first electrode; and a hole transport layer disposed on the hole injection layer, and the nitrogen-containing compound of Formula 1 may be included in at least one of the hole injection layer or the hole transport layer.

The luminescence device may further include an electron blocking layer disposed on the hole transport layer.

The Formula 1 may be of Formula 2, as described herein.

The Formula 1 may be of Formula 3, as described herein.

The Formula 2 may be of Formula 4, as described herein.

The Formula 2 may be of Formula 5, as described herein.

The Formula 2 may be of Formula 6, as described herein.

The Formula 2 may be any one of Formula 7-1 to Formula 7-3, as described herein.

The variables $R_a$ and $R_b$ may each be, independently from one another, a hydrogen atom, a substituted or an unsubstituted alkyl group of 1 to 20 carbon atoms, a substituted or an unsubstituted aryl group of 6 to 30 ring-forming carbon atoms, or a substituted or an unsubstituted heteroaryl group of 2 to 30 ring-forming carbon atoms, with the proviso that $R_a$ and $R_b$ may not be simultaneously hydrogen atoms.

The nitrogen-containing compound of the Formula 1 may be at least one of the compounds in Compound Group 1, as described herein.

The nitrogen-containing compound of the Formula 1 may be at least one compound of the Compound Group 2, as described herein.

The nitrogen-containing compound of the Formula 1 may be at least one compound of Compound Group 3, as described herein.

According to another aspect of the invention, a nitrogen-containing compound is of Formula 1:

Formula 1

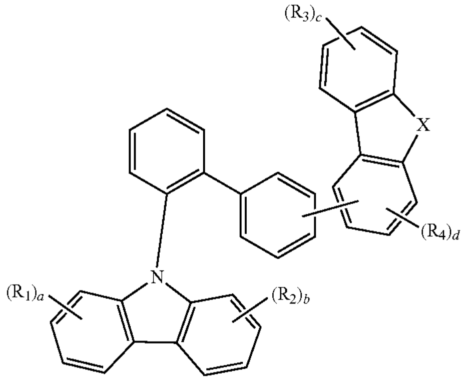

in Formula 1, the variables are described herein.

The Formula 1 may be of Formula 2, as described herein.

The Formula 2 may be any one of Formula 4 to Formula 6, as described herein.

The Formula 2 may be any one of Formula 7-1 to Formula 7-3, as described herein.

The nitrogen-containing compound of the Formula 1 may be at least one of the compounds in Compound Group 1, as described herein.

The nitrogen-containing compound of the Formula 1 may be at least one compound of the Compound Group 2, as described herein.

The nitrogen-containing compound of the Formula 1 may be at least one compound of Compound Group 3, as described herein.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

DETAILED DESCRIPTION

Figure 1:
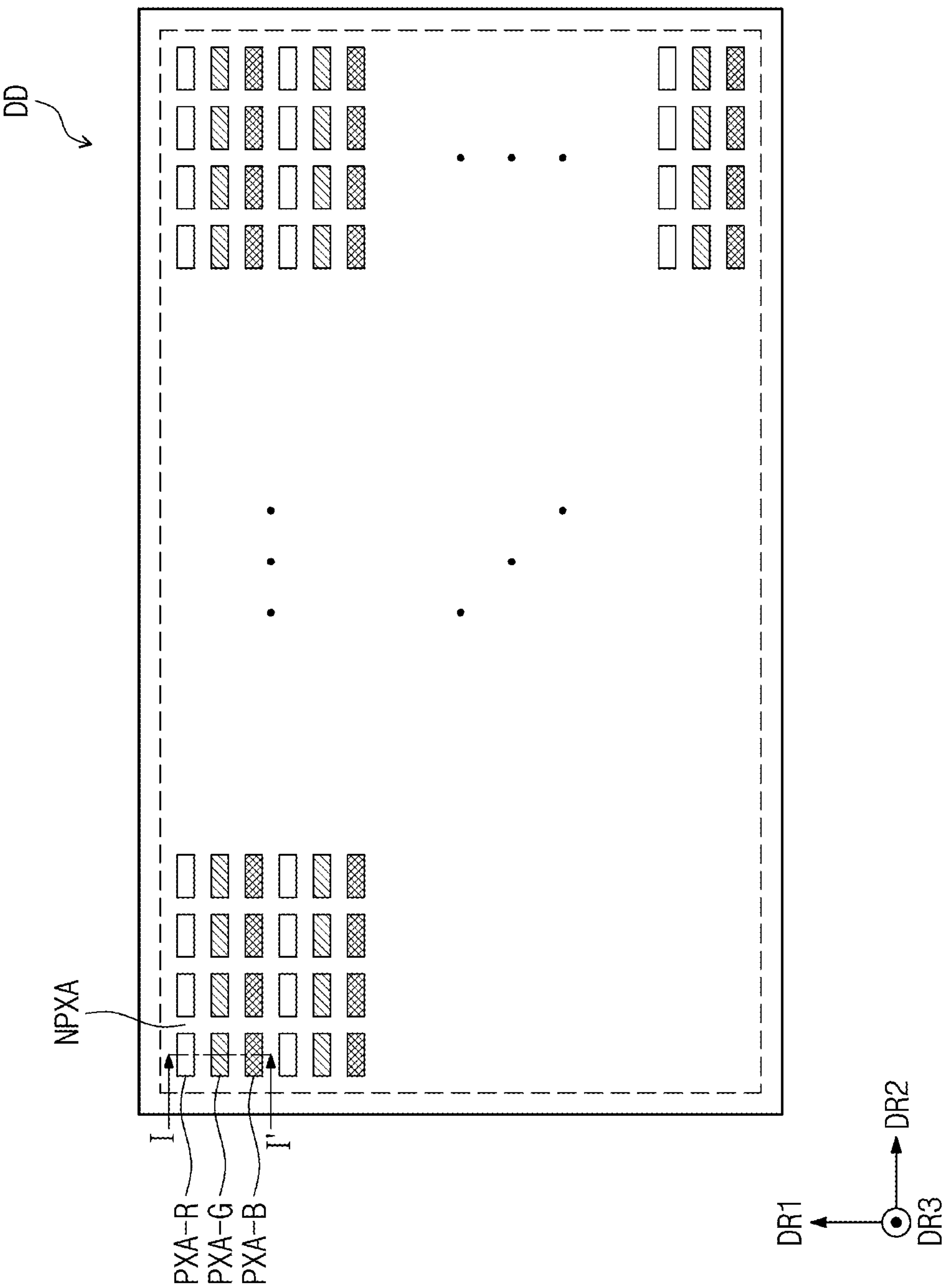
FIG. 1 is a plan view of an embodiment of a display apparatus constructed according to the principles of the invention.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, plates, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements, and repetitive explanations are omitted to avoid redundancy.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z—axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, numerals, integers, steps, operations, elements, components, parts, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Definitions

As used herein, the term "atom" may mean an element or its corresponding radical bonded to one or more other atoms.

The terms "hydrogen" and "deuterium" refer to their respective atoms and corresponding radicals with the deuterium radical abbreviated "-D", and the abbreviations "—F, —Cl, —Br, and —I" are radicals of, respectively, fluorine, chlorine, bromine, and iodine.

As used herein, the term "equivalent" means mole equivalent and may be abbreviated "equiv".

As used herein, the term "fused" may refer to a ring having one or more sides in common with another ring, and includes a condensed ring.

As used herein, the term "room temperature" may mean about 20—about 24° C.

As used herein, the term "substituted or unsubstituted" corresponds to substituted or unsubstituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. In addition, each of the exemplified substituents may be substituted or unsubstituted. For example, a biphenyl group may be interpreted as an aryl group, or a phenyl group substituted with a phenyl group.

As used herein, the term "forming a ring via the combination with an adjacent group" may mean forming a substituted or unsubstituted hydrocarbon ring, or a substituted or unsubstituted heterocycle via the combination with an adjacent group. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocycles or polycycles. In addition, the ring formed via the combination with an adjacent group may be combined with another ring to form a spiro structure.

As used herein, the term "adjacent group" may mean a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other. In addition, in 4,5-dimethylphenanthrene, two methyl groups may be interpreted as "adjacent groups" to each other.

As used herein, the halogen atom may be a fluorine atom, a chlorine atom, a bromine atom, or an iodine atom.

As used herein, the alkyl group may be a linear, branched or cyclic type. The carbon number of the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

As used herein, the hydrocarbon ring group means an optional functional group or substituent derived from an aliphatic hydrocarbon ring. The hydrocarbon ring group may be a saturated hydrocarbon ring group of 5 to 20 ring-forming carbon atoms.

As used herein, the aryl group means an optional functional group or substituent derived from an aromatic hydrocarbon ring. The aryl group may be a monocyclic aryl group or a polycyclic aryl group. The carbon number for forming the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinguephenyl, sexiphenyl, triphenylenyl, pyrenyl, benzofluoranthenyl, chrysenyl, etc., without limitation.

As used herein, the fluorenyl group may be substituted, and two substituents may be combined from each other to form a spiro structure. Examples of a substituted fluorenyl group are as follows. However, an embodiment is not limited thereto.

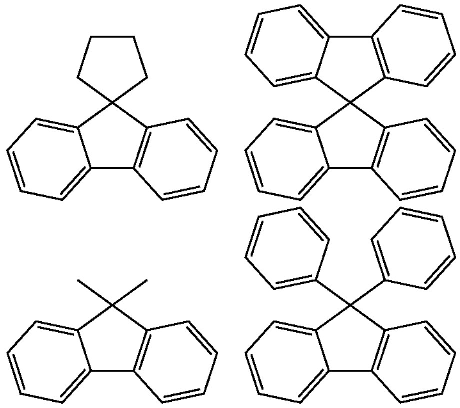

As used herein, the heterocyclic group may mean an optional functional group or substituent derived from a ring including one or more of B, O, N, P, Si and S as one or more heteroatoms. The heterocyclic group includes an aliphatic heterocyclic group and an aromatic heterocyclic group. The aromatic heterocyclic group may be a heteroaryl group. The aliphatic heterocyclic group and the aromatic heterocyclic group may be a monocycle or a polycycle.

As used herein, the heterocyclic group may include one or more of B, O, N, P, Si and S as heteroatoms. In case where the heterocyclic group includes two or more heteroatoms, the two or more heteroatoms may be the same or different. The heterocyclic group may be a monocyclic heterocyclic group or a polycyclic heterocyclic group and has the concept including a heteroaryl group. The carbon number for forming rings of the heterocyclic group may be 2 to 30, 2 to 20, or 2 to 10.

As used herein, the aliphatic heterocyclic group may include one or more of B, O, N, P, Si and S as heteroatoms. The carbon number for forming rings of the aliphatic heterocyclic group may be 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., without limitation.

As used herein, the heteroaryl group may include one or more of B, O, N, P, Si and S as heteroatoms. If the heteroaryl group includes two or more heteroatoms, two or more heteroatoms may be the same or different. The heteroaryl group may be a monocyclic heterocyclic group or a polycyclic heterocyclic group. The carbon number for forming rings of the heteroaryl group may be 2 to 30, 2 to 20, or 2 to 10. Examples of the heteroaryl group may include thiophene, furan, pyrrole, imidazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofurane, phenanthroline, thiazole, isooxazole, oxazole, oxadiazole, thiadiazole, phenothiazine, dibenzosilole, dibenzofuran, etc., without limitation.

As used herein, the explanation on the aryl group may be applied to an arylene group except that the arylene group is a divalent group. The explanation on the heteroaryl group may be applied to a heteroarylene group except that the heteroarylene group is a divalent group.

As used herein, a silyl group includes an alkyl silyl group and an aryl silyl group. Examples of the silyl group include a trimethylsilyl group, a triethylsilyl group, a t-butyldimethylsilyl group, a yinyldimethylsilyl group, a propyldimethylsilyl group, a triphenylsilyl group, a diphenylsilyl group, a phenylsilyl group, etc., without limitation.

As used herein, a thio group may include an alkyl thio group and an aryl thio group. The thio group may mean the above-defined alkyl group or aryl group combined with a sulfur atom. Examples of the thio group include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, etc., without limitation.

As used herein, the alkenyl group may be a linear chain or a branched chain. The carbon number is not specifically limited but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

As used herein, the carbon number of the amine group is not specifically limited, but may be 1 to 30. The amine group may include an alkyl amine group, an aryl amine group, or a heteroaryl amine group. Examples of the amine group include a methylamine group, a dimethylamine group, a phenylamine group, a diphenylamine group, a naphthylamine group, a 9-methyl-anthracenylamine group, a triphenylamine group, etc., without limitation.

As used herein, the alkyl group in an alkylthio group, an alkylsulfoxy group, an alkylaryl group, alkylamino group, an alkylboron group, an alkyl silyl group, and an alkyl amine group may be the same as the examples of the above-described alkyl group.

As used herein, the aryl group in an aryloxy group, an arylthio group, an arylsulfoxy group, an aryl amino group, an arylboron group, and an aryl silyl group may be the same as the examples of the above-described aryl group.

As used herein, a direct linkage may mean a single bond.

As used herein, "—*" means a position to be connected.

Hereinafter, embodiments of the invention are explained referring to the drawings.

Figure 2:
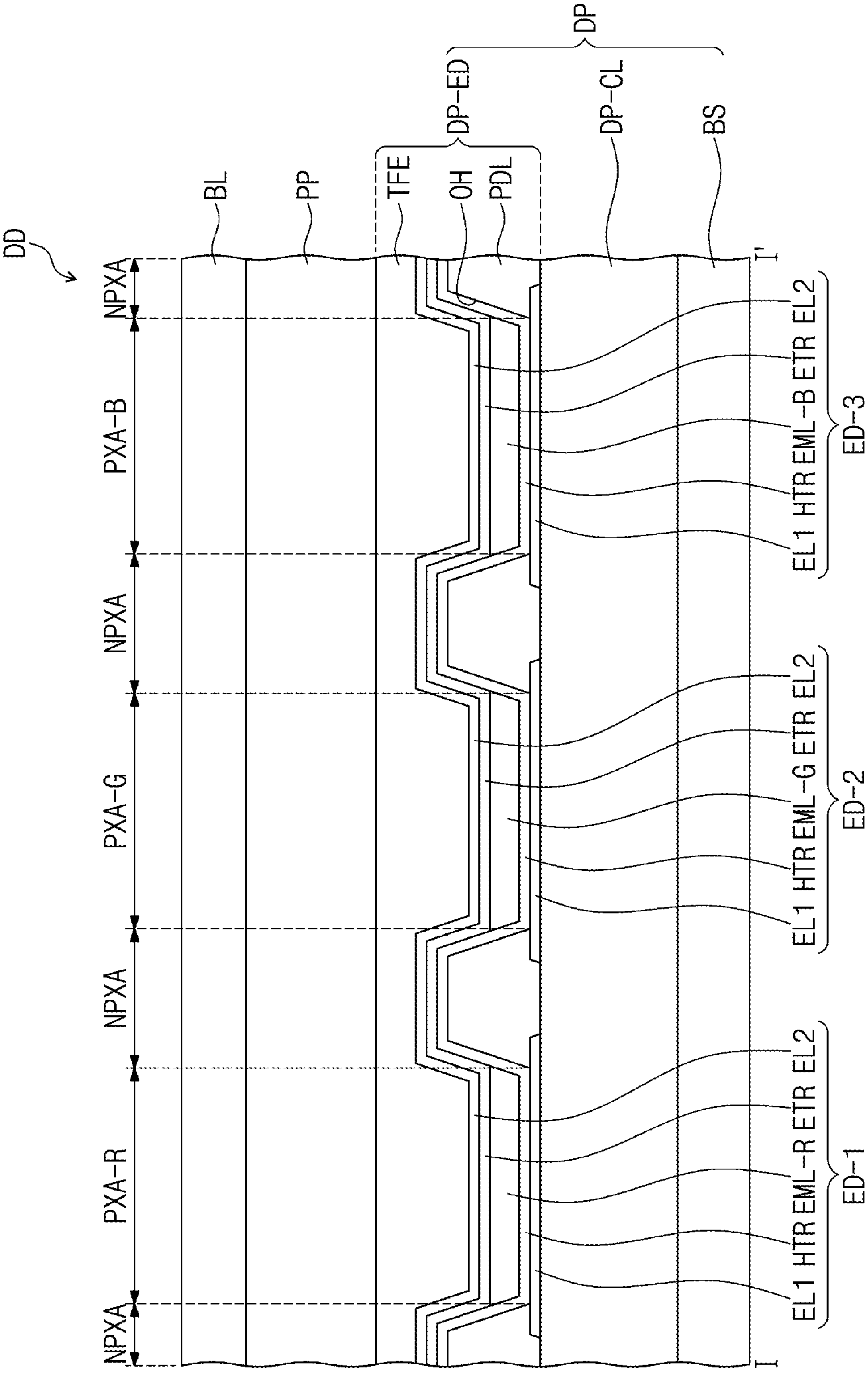
FIG. 2 is a cross-sectional view taken along line I-I' of FIG. 1.

FIG. 1 is a plan view of an embodiment of a display apparatus constructed according to the principles of the invention. FIG. 2 is a cross-sectional view taken along line I-I' of FIG. 1. Particularly, FIG. 1 is a plan view showing an embodiment of a display apparatus DD, and FIG. 2 is a cross-sectional view of a display apparatus DD of an embodiment.

The display apparatus DD may include a display panel DP and an optical layer PP disposed on the display panel DP.

The display panel DP includes luminescence devices ED-1, ED-2 and ED-3. The display apparatus DD may include multiple luminescence devices ED-1, ED-2 and ED-3. The optical layer PP may be disposed on the display panel DP and control reflected light by external light at the display panel DP. The optical layer PP may include, for example, a polarization layer or a color filter layer. Unlike the embodiment illustrated in FIG. 2, the optical layer PP may be omitted in the display apparatus DD.

On the optical layer PP, a base substrate BL may be disposed. The base substrate BL may be a member providing a base surface where the optical layer PP is disposed. The base substrate BL may be a glass substrate, a metal substrate, a plastic substrate, etc. However, embodiments of the invention are not limited thereto, and the base substrate BL may be an inorganic layer, an organic layer or a composite material layer. In addition, unlike the drawings, the base substrate BL may be omitted in an embodiment.

The display apparatus DD may further include a plugging layer. The plugging layer may be disposed between a display device layer DP-ED and a base substrate BL. The plugging layer may be an organic layer. The plugging layer may include at least one of an acrylic resin, a silicon-based resin and an epoxy-based resin.

The display panel DP may include a base layer BS, a circuit layer DP-CL provided on the base layer BS and a display device layer DP-ED. The display device layer DP-ED may include a pixel definition layer PDL, the luminescence devices ED-1, ED-2 and ED-3 disposed in the pixel definition layer PDL, and an encapsulation layer TFE disposed on the luminescence devices ED-1, ED-2 and ED-3.

Thebase layer BS may be a member providing a base surface where the display device layer DP-ED is disposed. The base layer BS may be a glass substrate, a metal substrate, a plastic substrate, etc. However, the embodiments are not limited thereto, and the base layer BS may be an inorganic layer, an organic layer or a composite material layer.

In an embodiment, the circuit layer DP-CL is disposed on the base layer BS, and the circuit layer DP-CL may include multiple transistors. Each of the transistors may include a control electrode, an input electrode, and an output electrode. For example, the circuit layer DP-CL may include switching transistors and driving transistors for driving the luminescence devices ED-1, ED-2 and ED-3 of the display device layer DP-ED.

Each of the luminescence devices ED-1, ED-2 and ED-3 may have the structures of luminescence devices ED according to FIG. 3 to FIG. 6, which will be explained below. Each of the luminescence devices ED-1, ED-2 and ED-3 may include a first electrode EL1, a hole transport region HTR, emission layers EML-R, EML-G and EML-B, an electron transport region ETR and a second electrode EL2.

In FIG. 2, shown is an embodiment where the emission layers EML-R, EML-G and EML-B of luminescence devices ED-1, ED-2 and ED-3, which are in opening portions OH defined in a pixel definition layer PDL, are disposed, and a hole transport region HTR, an electron transport region ETR and a second electrode EL2 are provided as common layers in all luminescence devices ED-1, ED-2 and ED-3. However, the embodiments are not limited thereto. Unlike FIG. 2, in an embodiment, the hole transport region HTR and the electron transport region ETR may be patterned and provided in the opening portions OH defined in the pixel definition layer PDL. For example, in an embodiment, the hole transport region HTR, the emission layers EML-R, EML-G and EML-B, and the electron transport region ETR of the luminescence devices ED-1, ED-2 and ED-3 may be patterned by an ink jet printing method.

An encapsulation layer TFE may cover the luminescence devices ED-1, ED-2 and ED-3. The encapsulation layer TFE may encapsulate the display device layer DP-ED. The encapsulation layer TFE may be a thin film encapsulation layer. The encapsulation layer TFE may be one layer or a stacked layer of multiple layers. The encapsulation layer TFE includes at least one insulating layer. The encapsulation layer TFE may include at least one inorganic layer (hereinafter, encapsulation inorganic layer). In addition, the encapsulation layer TFE may include at least one organic layer (hereinafter, encapsulation organic layer) and at least one encapsulation inorganic layer.

The encapsulation inorganic layer protects the display device layer DP-ED from at least one of moisture and oxygen, and the encapsulation organic layer protects the display device layer DP-ED from foreign materials such as dust particles. The encapsulation inorganic layer may include a silicon nitride, a silicon oxy nitride, a silicon oxide, a titanium oxide, or an aluminum oxide, without specific limitation. The encapsulation organic layer may include an acrylic compound, an epoxy-based compound, etc. The encapsulation organic layer may include a photopolymerizable organic material, without specific limitation.

The encapsulation layer TFE may be disposed on the second electrode EL2 and may be disposed while filling the opening portion OH.

Referring to FIG. 1 and FIG. 2, the display apparatus DD may include a non-luminous area NPXA and luminous areas PXA-R, PXA-G and PXA-B. The luminous areas PXA-R, PXA-G and PXA-B may be areas emitting light produced from the luminescence devices ED-1, ED-2 and ED-3, respectively. The luminous areas PXA-R, PXA-G and PXA-B may be separated from each other on a plane.

The luminous areas PXA-R, PXA-G and PXA-B may be areas separated by the pixel definition layer PDL. The non-luminous areas NPXA may be areas between neighboring luminous areas PXA-R, PXA-G and PXA-B and may be areas overlapping the pixel definition layer PDL. As described herein, each of the luminous areas PXA-R, PXA-G and PXA-B may overlap each pixel. The pixel definition layer PDL may divide the luminescence devices ED-1, ED-2 and ED-3. The emission layers EML-R, EML-G and EML-B of the luminescence devices ED-1, ED-2 and ED-3 may be disposed and divided in the opening portions OH defined in the pixel definition layer PDL.

The luminous areas PXA-R, PXA-G and PXA-B may be divided into multiple groups according to the color of light produced from the luminescence devices ED-1, ED-2 and ED-3. In the display apparatus DD, shown in FIG. 1 and FIG. 2, three luminous areas PXA-R, PXA-G and PXA-B emitting red light, green light and blue light are illustrated as an embodiment. For example, the display apparatus DD may include a red luminous area PXA-R, a green luminous area PXA-G and a blue luminous area PXA-B, which are separated from each other.

In the display apparatus DD, multiple luminescence devices ED-1, ED-2 and ED-3 may emit light having different wavelength regions. For example, in an embodiment, the display apparatus DD may include a first luminescence device ED-1 emitting red light, a second luminescence device ED-2 emitting green light, and a third luminescence device ED-3 emitting blue light. That is, each of the red luminous area PXA-R, the green luminous area PXA-G, and the blue luminous area PXA-B of the display apparatus DD may overlap the first luminescence device ED-1, the second luminescence device ED-2, and the third luminescence device ED-3.

However, the embodiments are not limited thereto, and the first to third luminescence devices ED-1, ED-2 and ED-3 may emit light in the same-wavelength region, or at least one thereof may emit light in a different wavelength region. For example, all the first to third luminescence devices ED-1, ED-2 and ED-3 may emit blue light.

The luminous areas PXA-R, PXA-G and PXA-B in the display apparatus DD may be arranged in a generally elongated (stripe) shape. Referring to FIG. 1, multiple red luminous areas PXA-R, multiple green luminous areas PXA-G and multiple blue luminous areas PXA-B may be arranged along a second direction axis DR2. In addition, the red luminous area PXA-R, the green luminous area PXA-G and the blue luminous area PXA-B may be alternatively arranged along a first direction axis DR1.

In FIG. 1 and FIG. 2, the areas of the luminous areas PXA-R, PXA-G and PXA-B are similarly depicted, but the embodiments are not limited thereto. The areas of the luminous areas PXA-R, PXA-G and PXA-B may be different from each other according to the wavelength region of light emitted. The areas of the luminous areas PXA-R, PXA-G and PXA-B may mean planar areas defined by the first direction axis DR1 and the second direction axis DR2.

The configuration of the luminous areas PXA-R, PXA-G and PXA-B is not limited to the features shown in FIG. 1, and the arrangement order of the red luminous areas PXA-R, the green luminous areas PXA-G and the blue luminous areas PXA-B may be provided in various combinations according to the properties of display quality required for the display apparatus DD. For example, the configuration of the luminous areas PXA-R, PXA-G and PXA-B may be a configuration sold under the trade designation PenTile matrix by Samsung Display Co., Ltd. of Gyeonggi-do, Republic of Korea, or a diamond configuration.

In addition, the areas of the luminous areas PXA-R, PXA-G and PXA-B may be different from each other. For example, in an embodiment, the area of the green luminous area PXA-G may be smaller than the area of the blue luminous area PXA-B, but the embodiments are not limited thereto.

FIGS. 3-6

Figure 3:
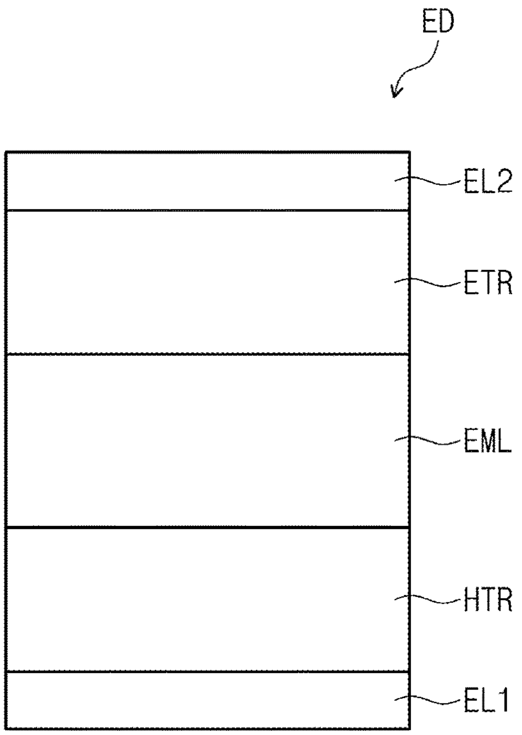
FIG. 3 is a schematic cross-sectional view of an embodiment of a luminescence device constructed according to the principles of the invention.
Figure 4:
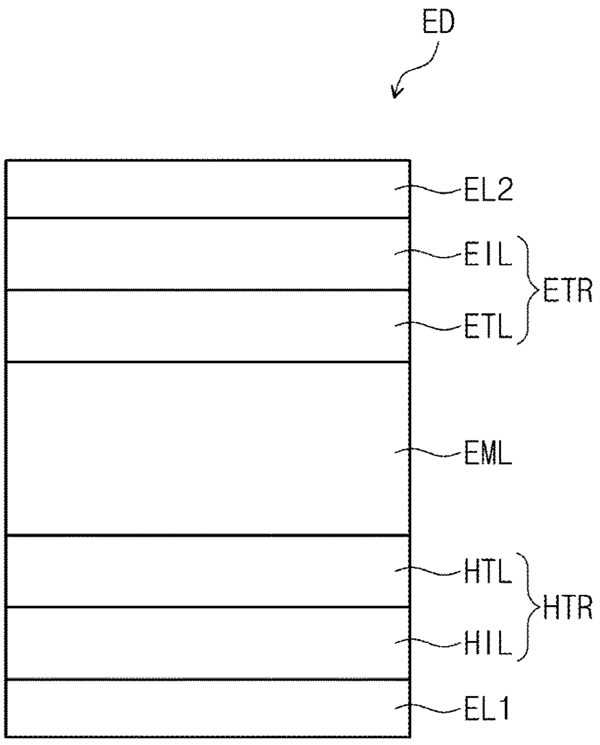
FIG. 4 is a schematic cross-sectional view of another embodiment of a luminescence device constructed according to the principles of the invention.
Figure 5:
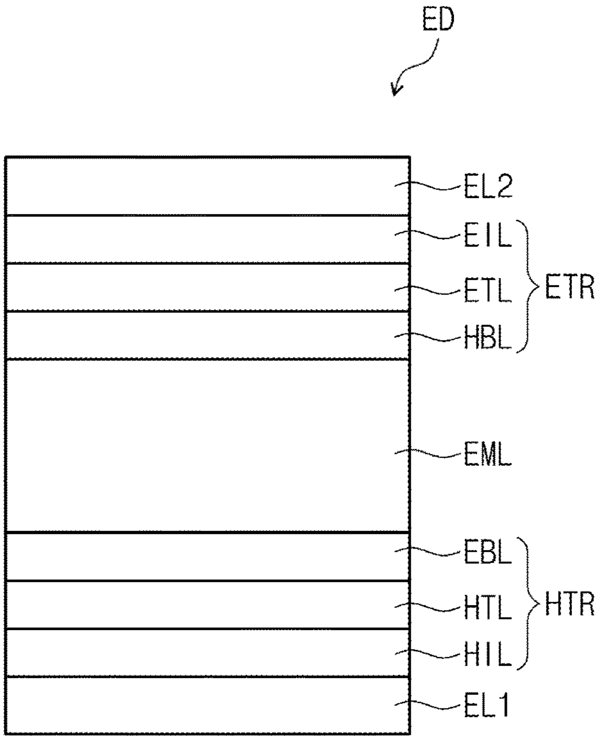
FIG. 5 is a schematic cross-sectional view of a further embodiment of a luminescence device constructed according to the principles of the invention.
Figure 6:
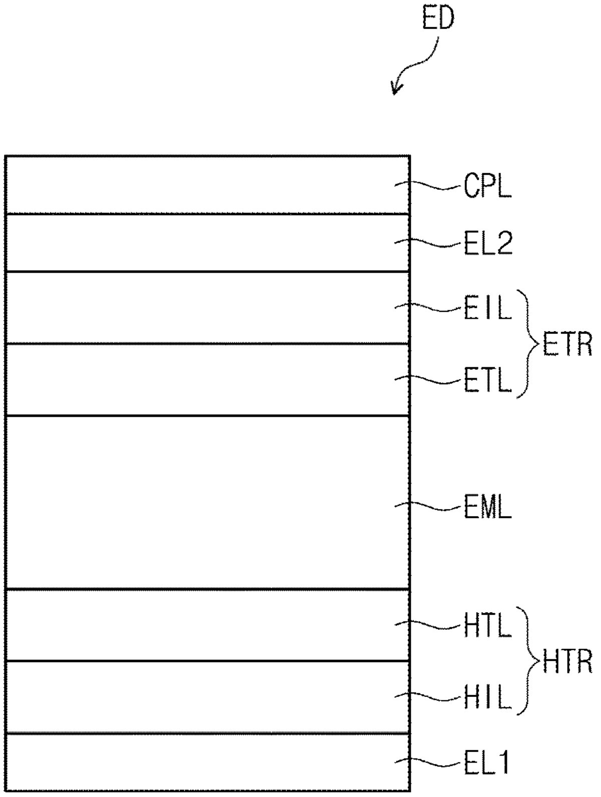
FIG. 6 is a schematic cross-sectional view of yet another embodiment of a luminescence device constructed according to the principles of the invention.

FIG. 3 is a schematic cross-sectional view of an embodiment of a luminescence device constructed according to the principles of the invention. FIG. 4 is a schematic cross-sectional view of another embodiment of a luminescence device constructed according to the principles of the invention. FIG. 5 is a schematic cross-sectional view of a further embodiment of a luminescence device constructed according to the principles of the invention. FIG. 6 is a schematic cross-sectional view of yet another embodiment of a luminescence device constructed according to the principles of the invention.

Hereinafter, FIG. 3 to FIG. 6 are cross-sectional views schematically showing various embodiments of luminescence devices. The embodiments of the luminescence device ED may include a first electrode EL1, a hole transport region HTR, an emission layer EML, and a second electrode EL2 stacked in order.

When compared with FIG. 3, FIG. 4 shows the cross-sectional view of a luminescence device ED, wherein a hole transport region HTR includes a hole injection layer HIL and a hole transport layer HTL, and an electron transport region ETR includes an electron injection layer EIL and an electron transport layer ETL. When compared with FIG. 3, FIG. 5 shows the cross-sectional view of a luminescence device ED of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. When compared with FIG. 4, FIG. 6 shows the cross-sectional view of a luminescence device ED, including a capping layer CPL disposed on the second electrode EL2.

The first electrode EL1 has conductivity. The first electrode EL1 may be formed using a metal alloy or a conductive compound. The first electrode EL1 may be an anode or a cathode. However, embodiments are not limited thereto. In addition, the first electrode EL1 may be a pixel electrode. The first electrode EL1 may be a transmissive electrode, a transflective electrode, or a reflective electrode. If the first electrode EL1 is the transmissive electrode, the first electrode EL1 may include a transparent metal oxide such as an indium tin oxide (ITO), an indium zinc oxide (IZO), a zinc oxide (ZnO), and an indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, compounds thereof, or mixtures thereof (for example, a mixture of Ag and Mg). Also, the first electrode EL1 may have a structure of multiple layers including a reflective layer or a transflective layer formed using the above materials, and a transmissive conductive layer formed using the ITO, IZO, ZnO, or ITZO. For example, the first electrode EL1 may include a three-layer structure of an ITO/Ag/ITO. However, embodiments are not limited thereto. The thickness of the first electrode EL1 may be from about 700 Å to about 10,000 Å. For example, the thickness of the first electrode EL1 may be from about 1,000 Å to about 3,000 Å.

The hole transport region HTR is provided on the first electrode EL1. The hole transport region HTR may include at least one of a hole injection layer HIL, a hole transport layer HTL, a hole buffer layer, and an electron blocking layer EBL. The thickness of the hole transport region HTR may be, for example, from about 50 Å to about 15,000 Å.

The hole transport region HTR may have a single layer formed using a single material, a single layer formed using multiple different materials, or a multilayer structure including multiple layers formed using multiple different materials.

For example, the hole transport region HTR may have the structure of a single layer of a hole injection layer HIL or a hole transport layer HTL, and may have a structure of a single layer formed using a hole injection material and a hole transport material. Otherwise, the hole transport region HTR may have a structure of a single layer formed using multiple different materials, or a structure stacked from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, without limitation.

The hole transport region HTR of the luminescence device ED includes an amine compound made according to an embodiment of the invention. Embodiments of the nitrogen-containing compound are represented by Formula 1 below.

Formula 1

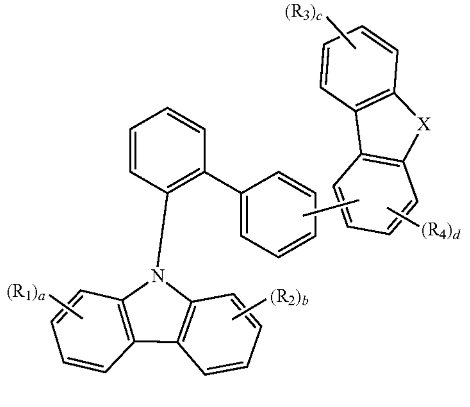

In Formula 1, X is O, S, or $NR_5$.

In Formula 1, $R_1$ to $R_5$ are each independently a substituted or unsubstituted oxy group, a substituted or unsubstituted silyl group, a substituted or unsubstituted thiol group, a substituted or unsubstituted alkyl group of 1 to 20 carbon atoms, a substituted or unsubstituted alkenyl group of 2 to 20 carbon atoms, a substituted or unsubstituted alkynyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula 1, "a" is an integer of 1 to 4, and, if "a" is 2 or more, multiple $R_1$ groups are the same or different.

In Formula 1, "b" and "c" are each independently an integer of 0 to 4, and, if "b" is 2 or more, multiple $R_2$ groups are the same or different, and if "c" is 2 or more, multiple $R_3$ groups are the same or different.

In Formula 1, "d" is an integer of 0 to 3, and, if "d" is 2 or more, multiple $R_4$ groups are the same or different.

In Formula 1, if "b" to "d" are 0, it means a case where the benzene ring of a hetero group does not have a substituent. In other words, if "b" is 0, $R_2$ groups are all hydrogen atoms, if "c" is 0, $R_3$ groups are all hydrogen atoms, and if "d" is 0, $R_4$ groups are all hydrogen atoms. In addition, in Formula 1, "a" is 1 or more, andthe nitrogen-containing compound absolutely has one or more $R_1$ substituents. Formula 1 may be represented by Formula 2 below.

Formula 2

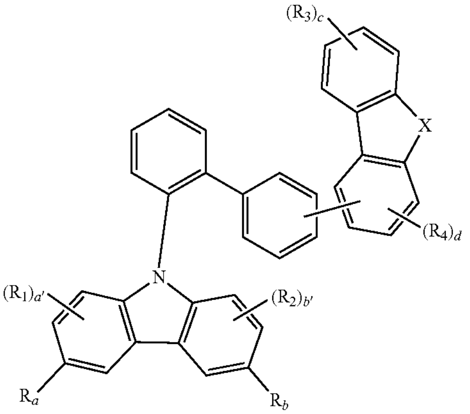

In Formula 2, "a'" and "b'" are each independently an integer of 0 to 3, and, if "a'" is 2 or more, multiple $R_1$ groups are the same or different, and if "b'" is 2 or more, multiple $R_2$ groups are the same or different.

In Formula 2, $R_a$ and $R_b$ may be each independently a hydrogen atom, a substituted or unsubstituted oxy group, a substituted or unsubstituted silyl group, a substituted or unsubstituted thiol group, a substituted or unsubstituted alkyl group of 1 to 20 carbon atoms, a substituted or unsubstituted alkenyl group of 2 to 20 carbon atoms, a substituted or unsubstituted alkynyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula 2, X, $R_1$ to $R_4$, "c", and "d" are the same as defined in Formula 1.

In Formula 2, $R_a$ and $R_b$ are not hydrogen atoms simultaneously. In other words, the nitrogen-containing compound represented by Formula 2 may absolutely have one or more substituents at position 3 or position 6 of a carbazole group.

In an embodiment, $R_a$ and $R_b$ may be each independently a hydrogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, where $R_a$ and $R_b$ are not hydrogen atoms simultaneously.

In an embodiment, Formula 1 may be represented by Formula 3 below.

Formula 3

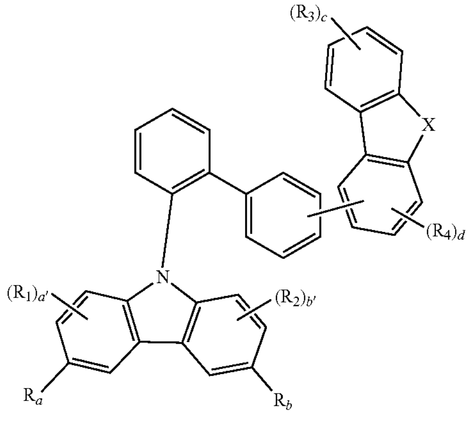

In Formula 3, "a'" and "b'" are each independently an integer of 0 to 3, and, if "a'" is 2 or more, multiple $R_1$ groups are the same or different, and if "b'" is 2 or more, multiple $R_2$ groups are the same or different.

In Formula 3, $R_a$ and $R_b$ may be each independently a hydrogen atom, a substituted or unsubstituted oxy group, a substituted or unsubstituted silyl group, a substituted or unsubstituted thiol group, a substituted or unsubstituted alkyl group of 1 to 20 carbon atoms, a substituted or unsubstituted alkenyl group of 2 to 20 carbon atoms, a substituted or unsubstituted alkynyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula 3, X, $R_1$ to $R_4$, "c", and "d" are the same as defined in Formula 1.

The nitrogen-containing compound represented by Formula 3 may absolutely have one or more substituents at position 3 or position 6 of a carbazole group. In an embodiment, Formula 2 may be represented by Formula 4 below.

Formula 4

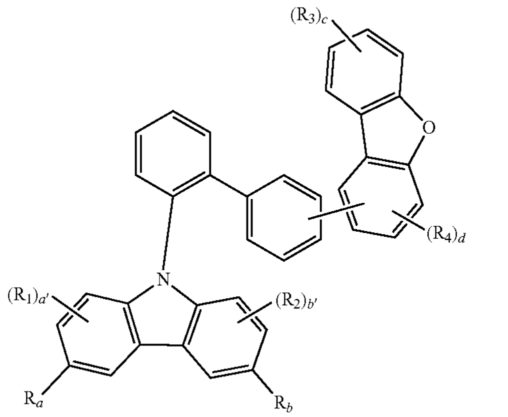

In Formula 4, $R_1$ to $R_4$, $R_a$, $R_b$, "c", "d", "a'" and "b'" are the same as defined in Formula 2. In an embodiment, Formula 2 may be represented by Formula 5 below.

Formula 5

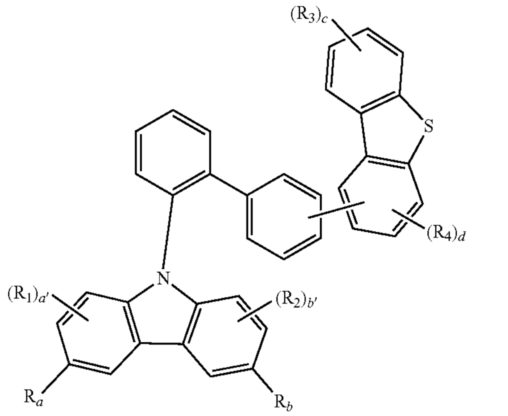

In Formula 5, $R_1$ to $R_4$, $R_a$, $R_b$, "c", "d", "a'" and "b'" are the same as defined in Formula 2. In an embodiment, Formula 2 may be represented by Formula 6 below.

Formula 6

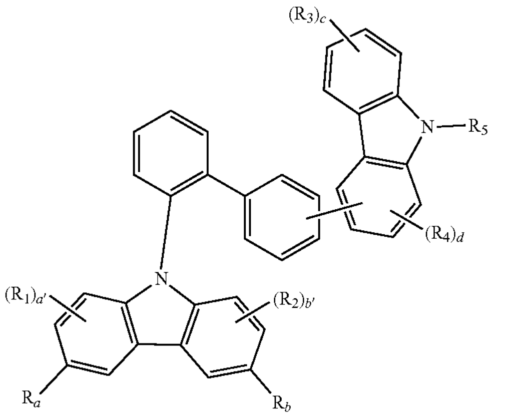

In Formula 6, $R_5$ may be a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula 6, $R_1$ to $R_4$, $R_a$, $R_b$, "c", "d", "a'" and "b'" are the same as defined in Formula 2. In an embodiment, Formula 2 may be represented by any one of Formula 7-1 to Formula 7-3 below.

Formula 7-1

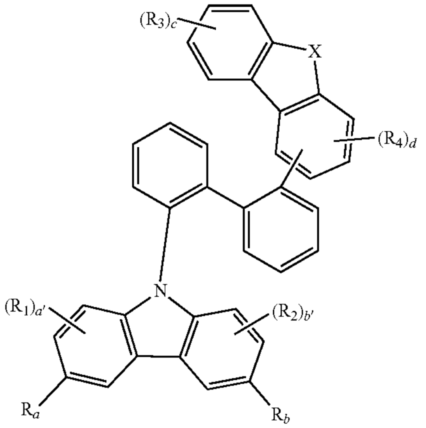

Formula 7-2

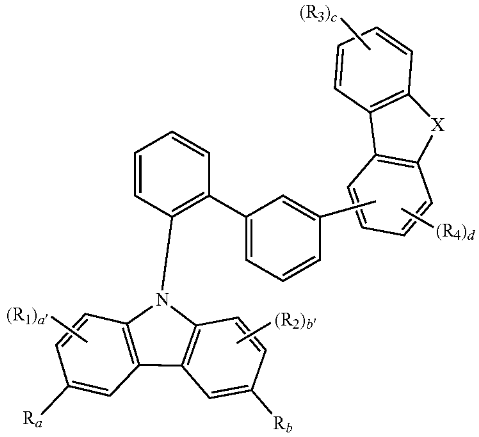

Formula 7-3

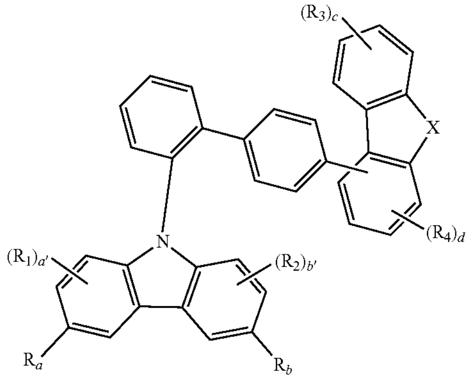

In Formula 7-1 to Formula 7-3, X, $R_1$ to $R_4$, $R_a$, $R_b$, "c", "d", "a'" and "b'" are the same as defined in Formula 2. The nitrogen-containing compound according to an embodiment includes a compound in which optional hydrogen is substituted with deuterium.

The nitrogen-containing compound represented by Formula 1 according to an embodiment of the invention may be any one selected of the compounds represented in Compound Groups 1 to 3 below. However, embodiments are not limited thereto.

Compound Group 1

A1

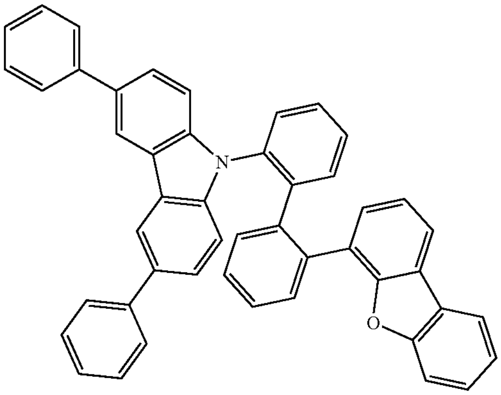

A2

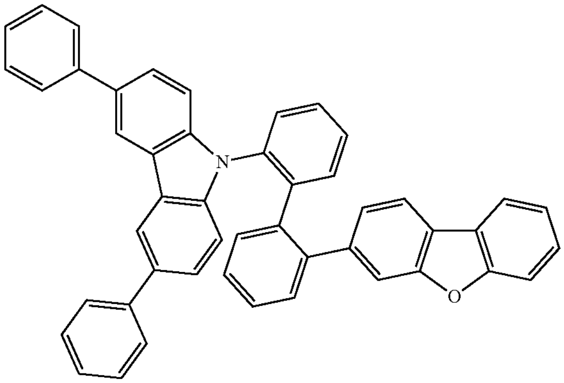

A3

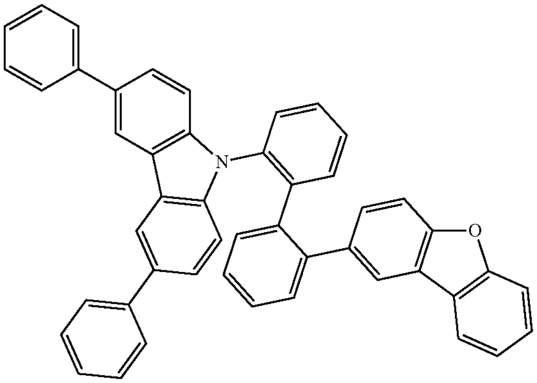

-continued

A4

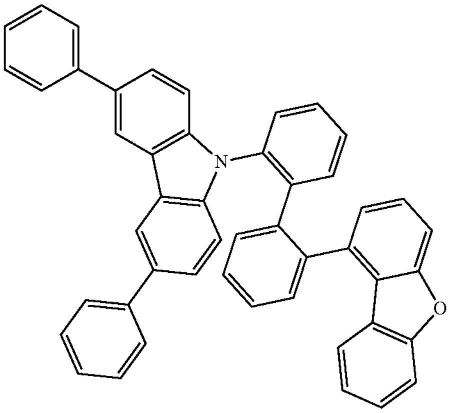

A5

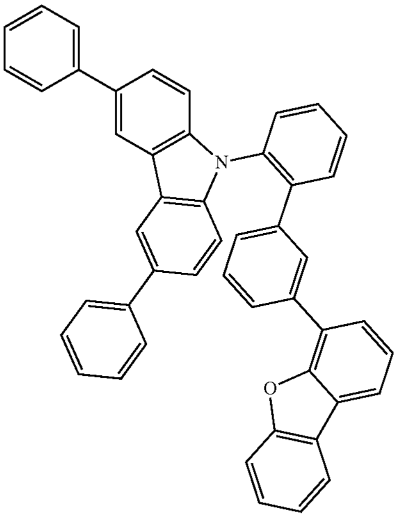

A6

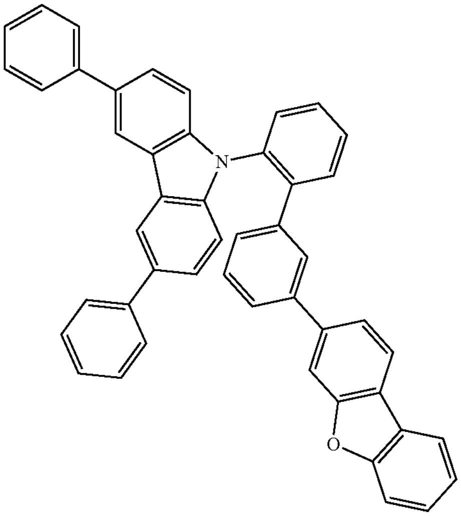

-continued
A7
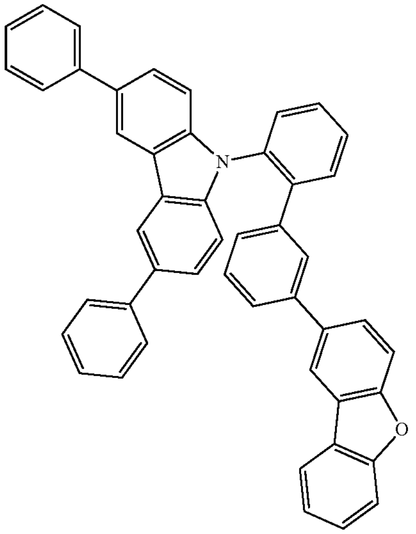
A8
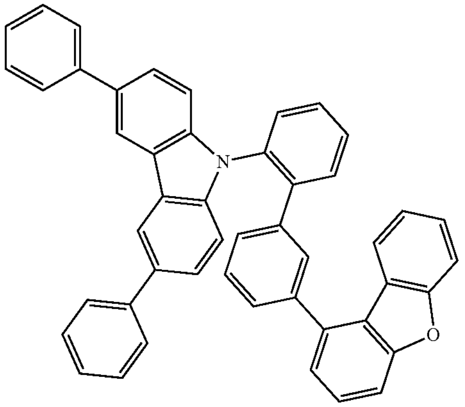
A9
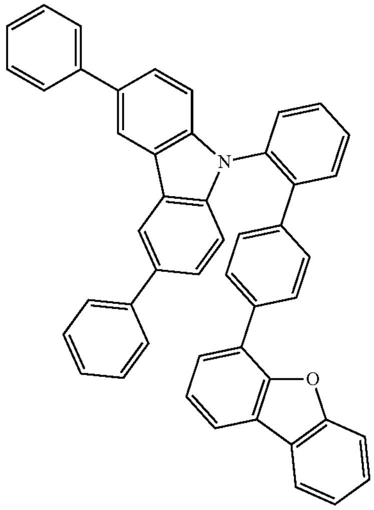
-continued
A10
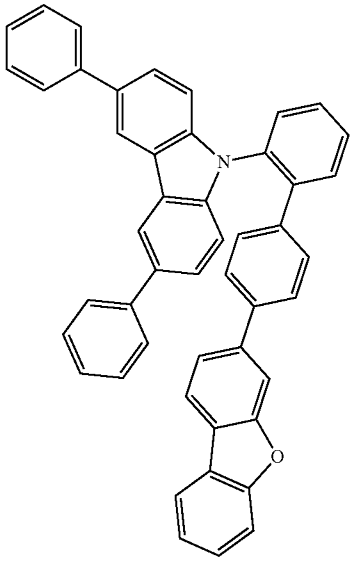
A11
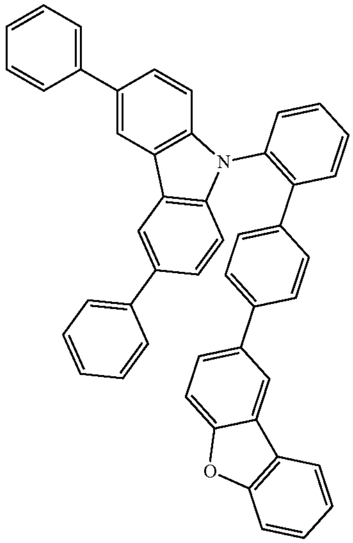
A12
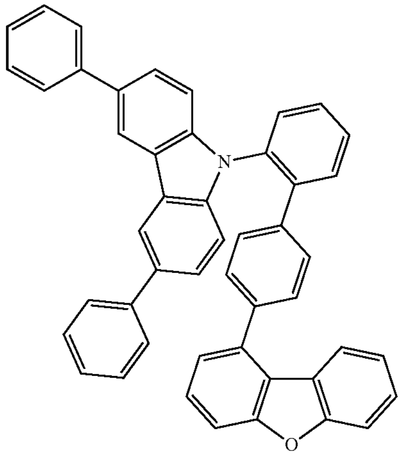

-continued
A13
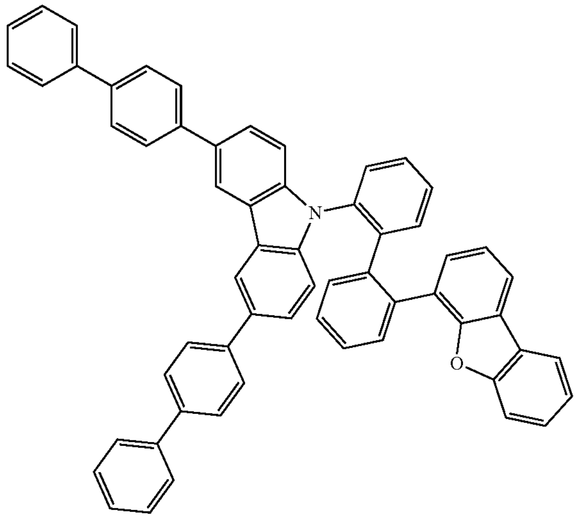
A14
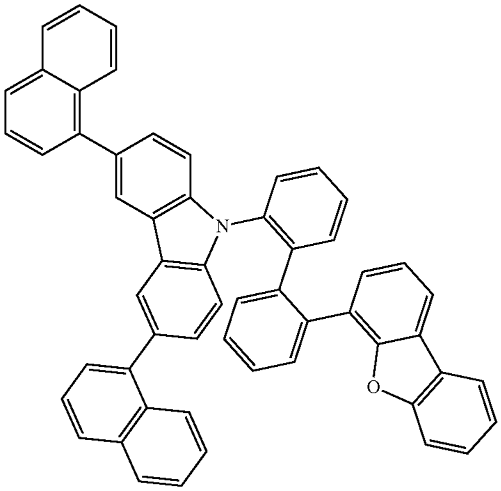
A15
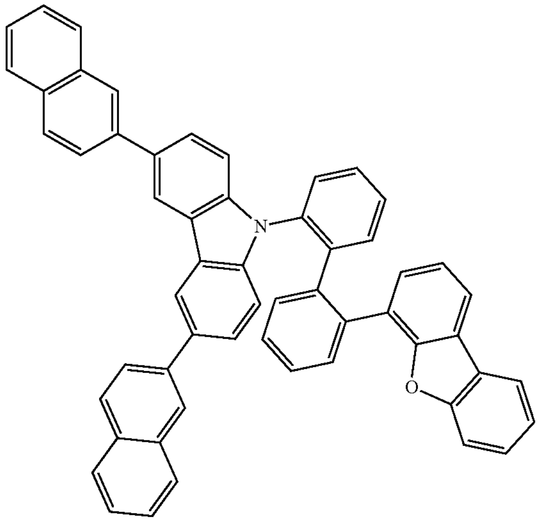
-continued
A16
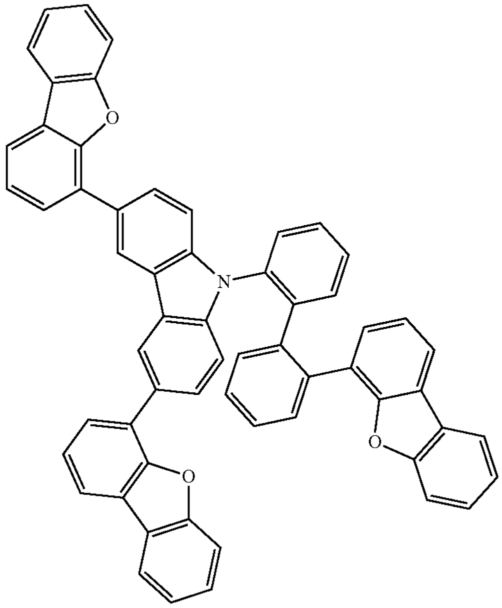
A17
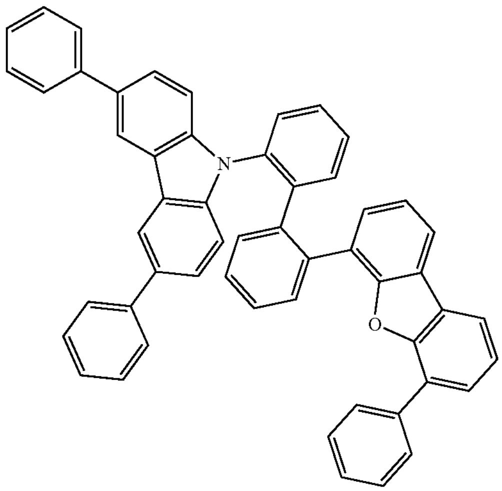
A18
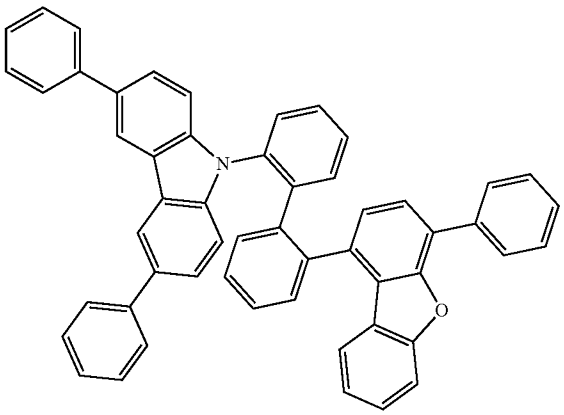

-continued
A19
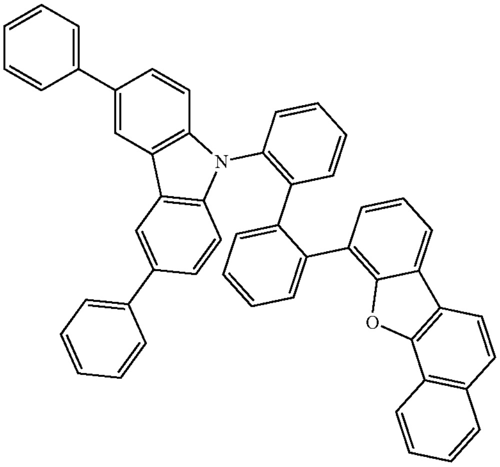
A20
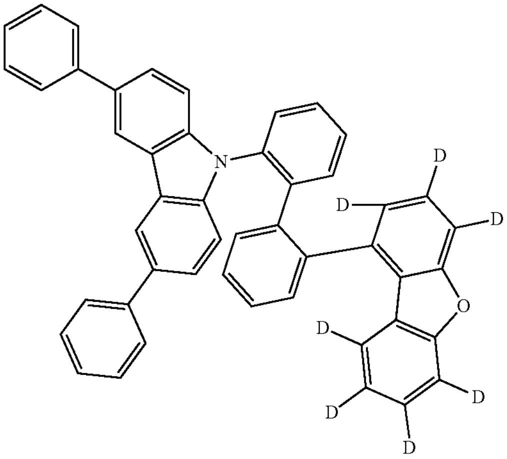
A21
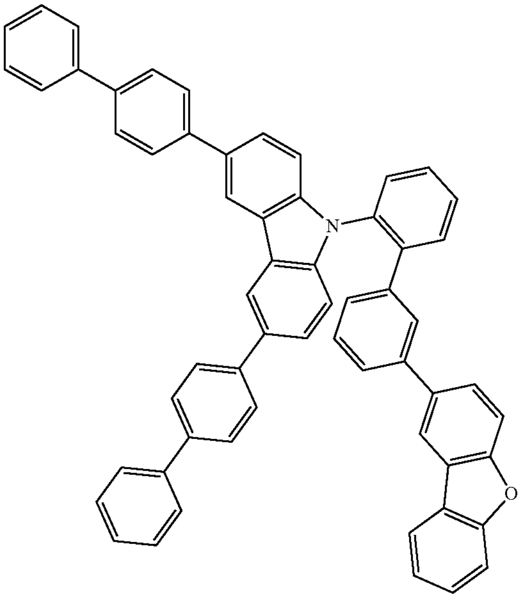
-continued
A22
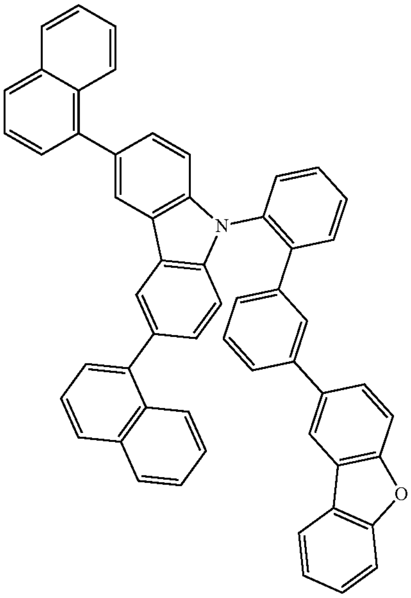
A23
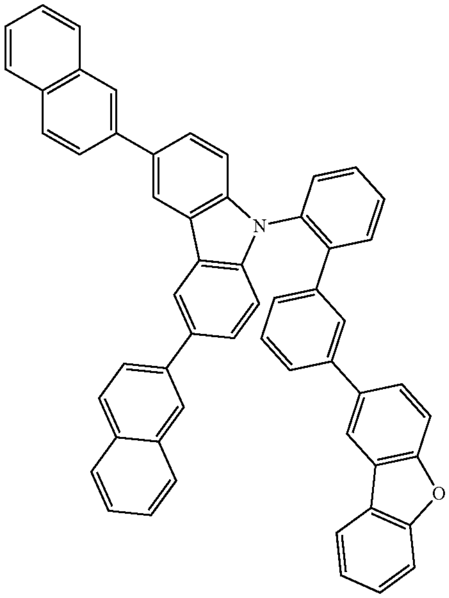

-continued
A24
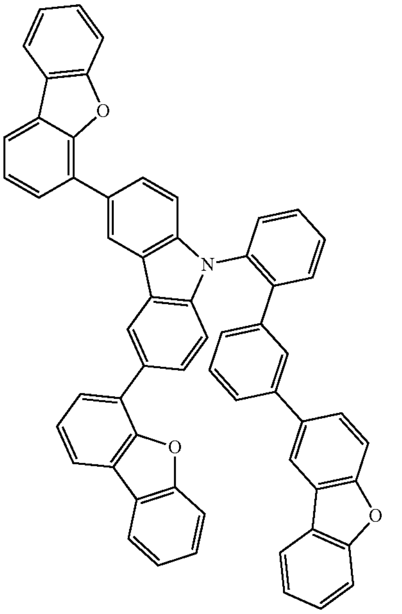
A25
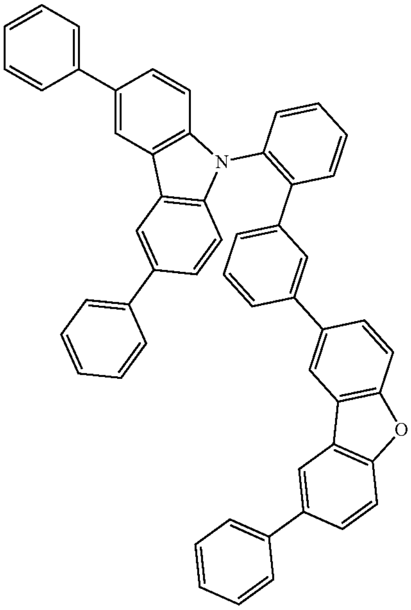
-continued
A26
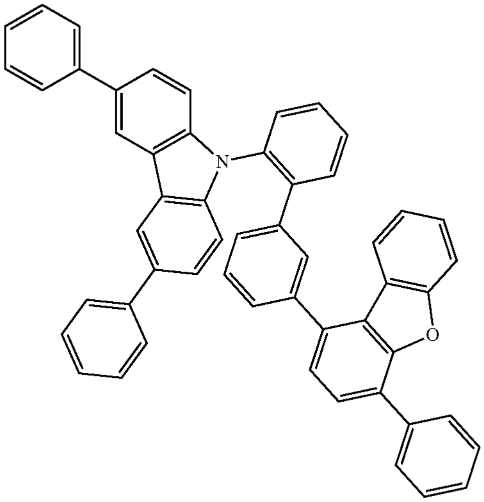
A27
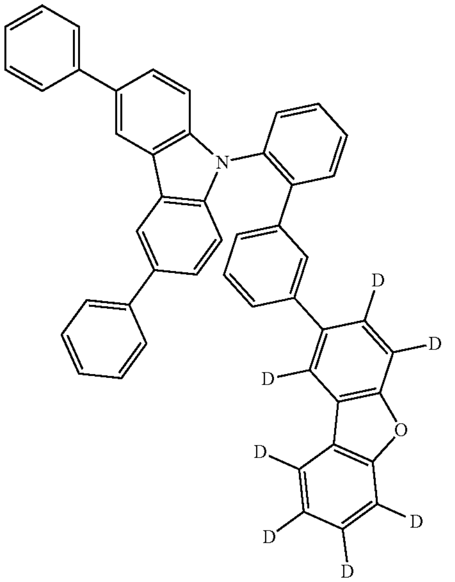
A28
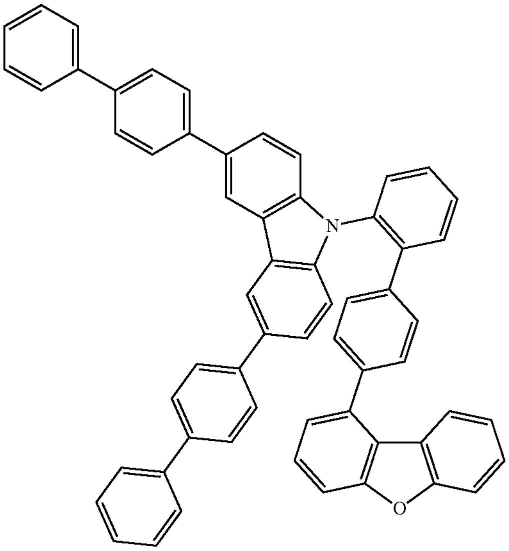

-continued
A29
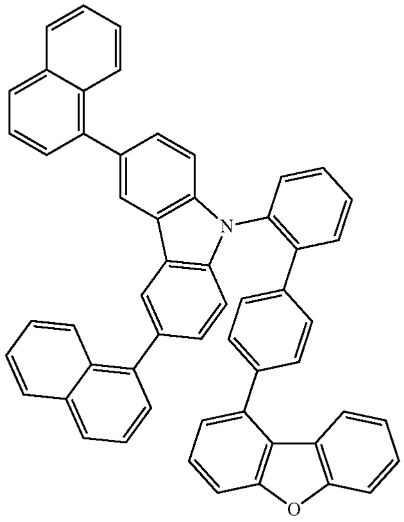
A30
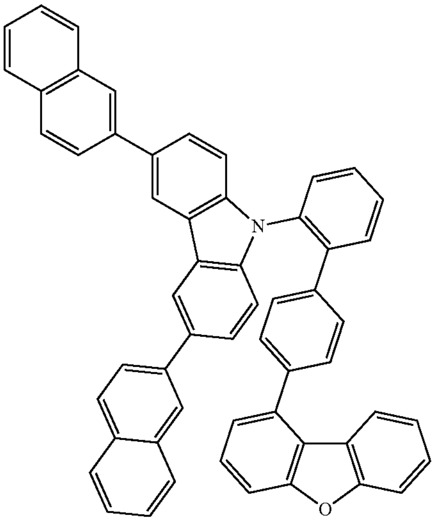
A31
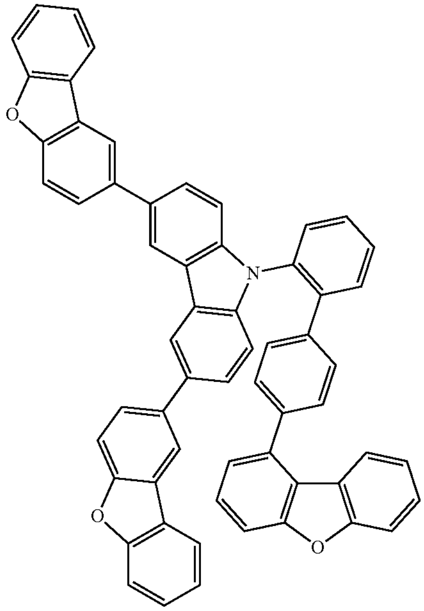
-continued
A32
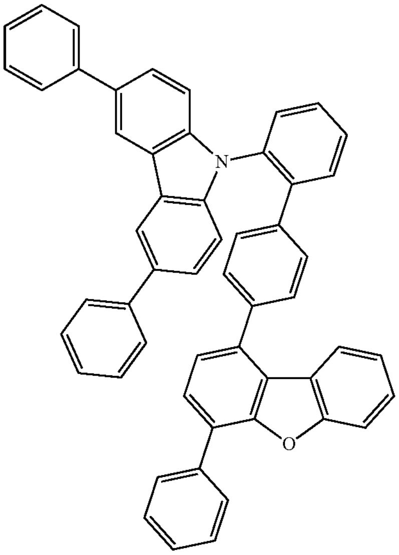
A33
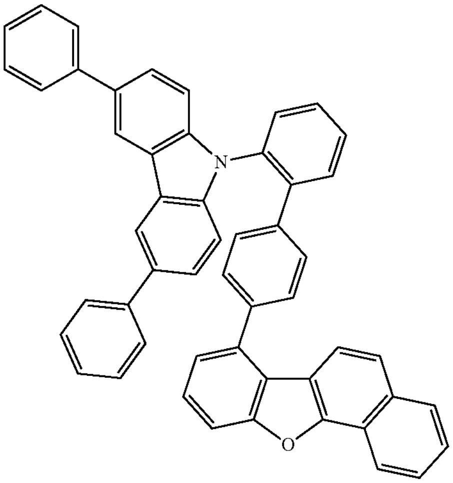
A34
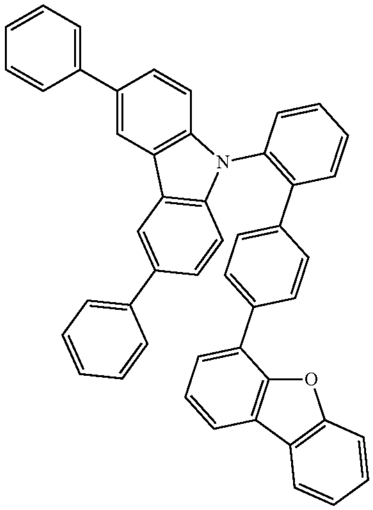

-continued
A35
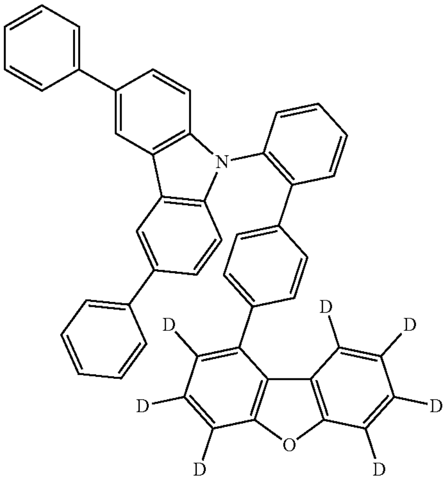
B1
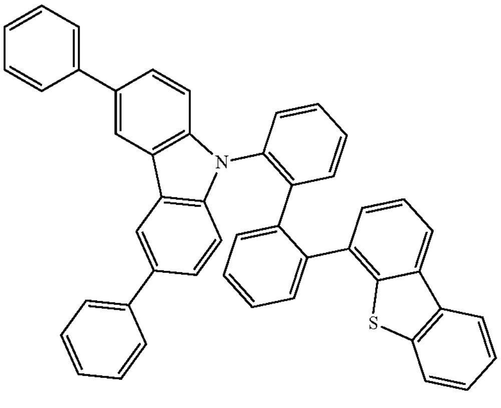
B2
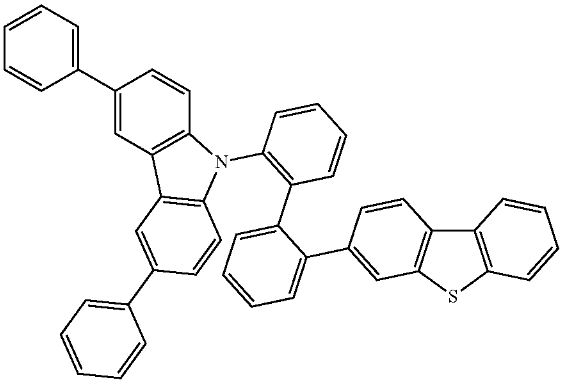
-continued
B3
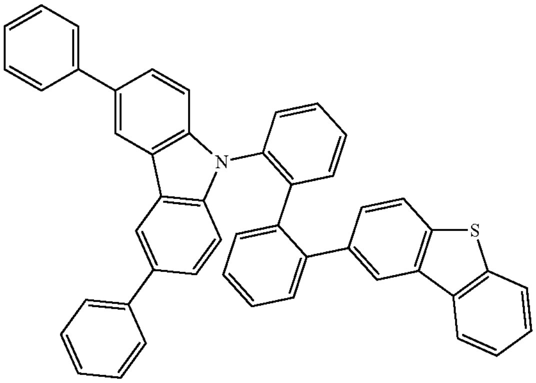
B4
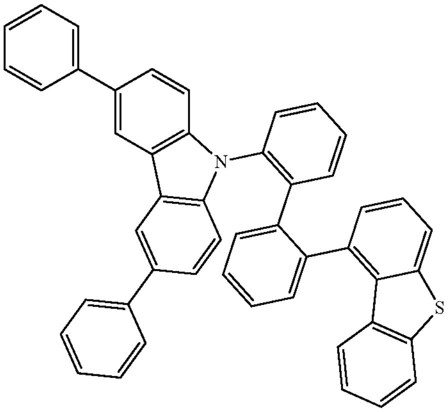
B5
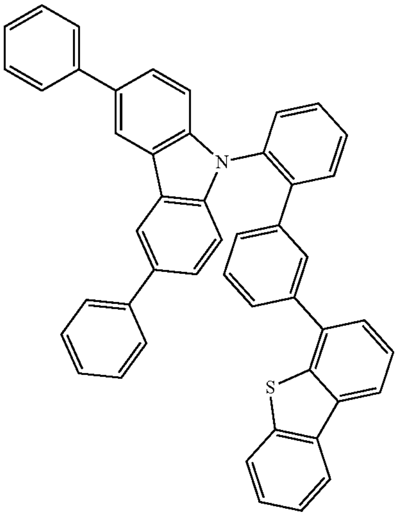

-continued
B6
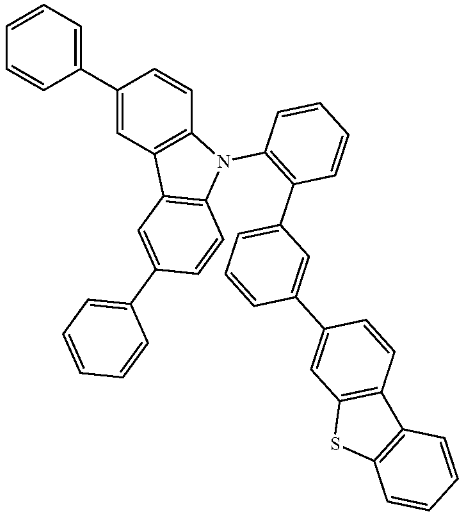
B7
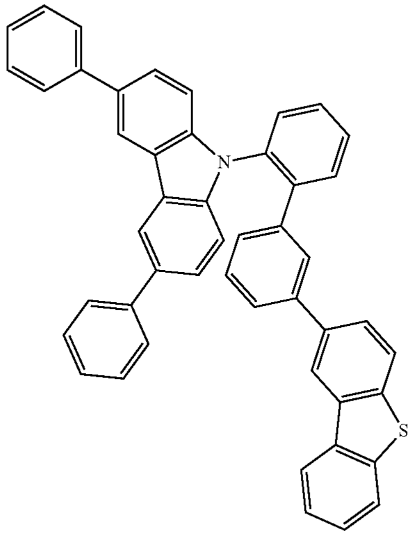
B8
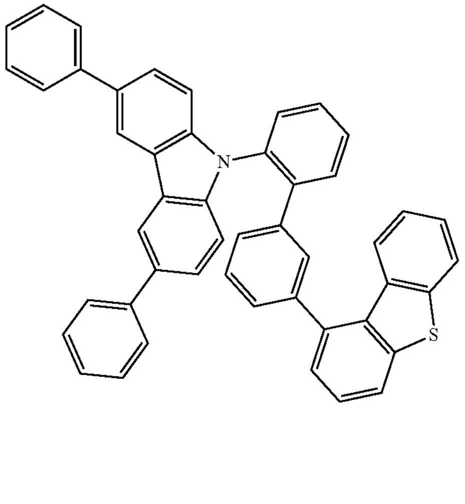
-continued
B9
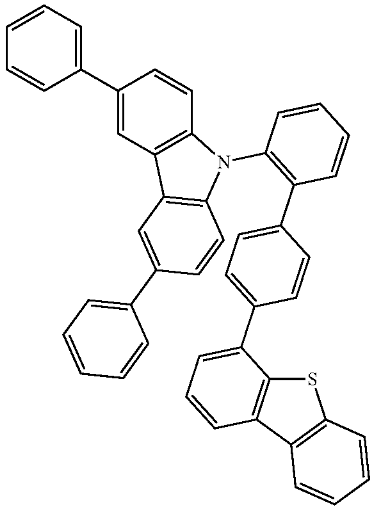
B10
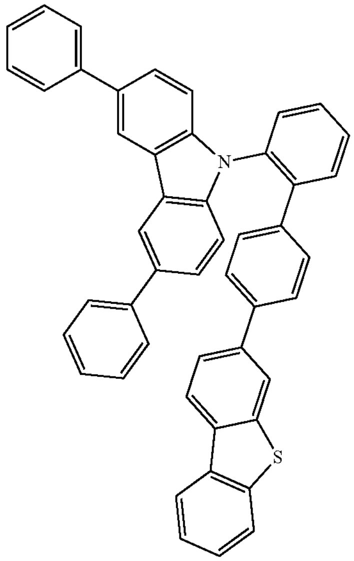
B11
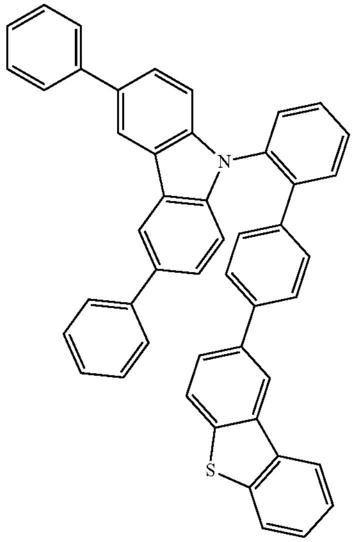

-continued
B12
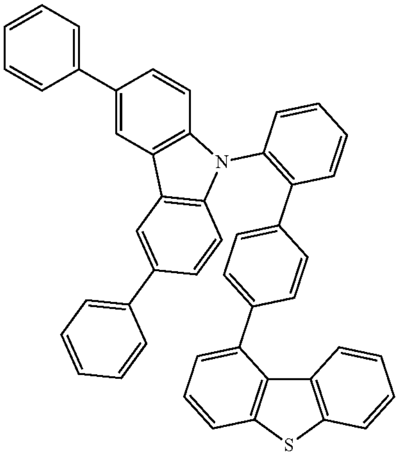
B13
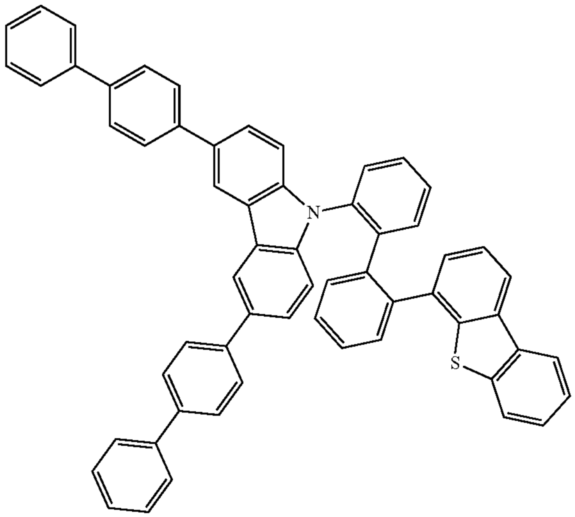
B14
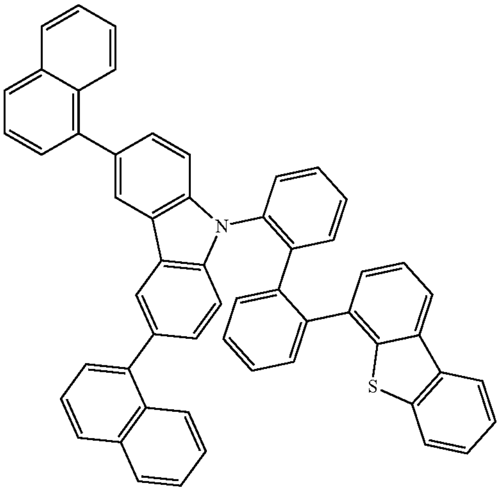
-continued
B15
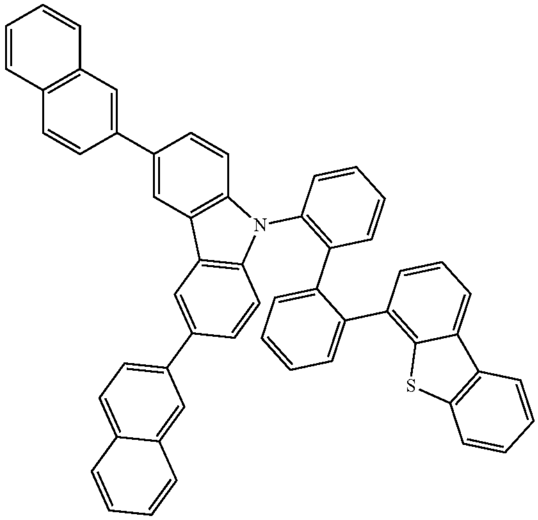
B16
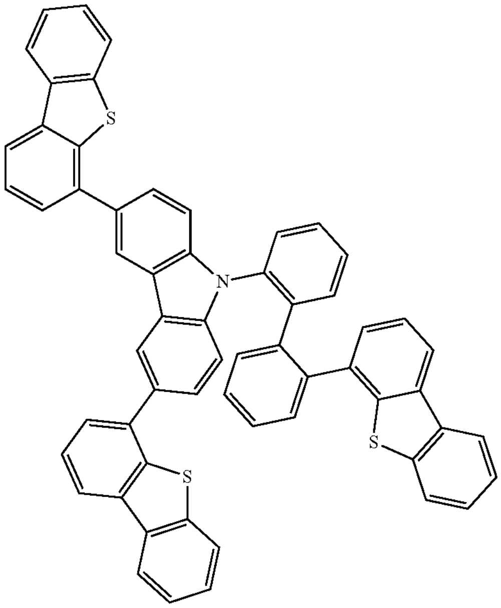
B17
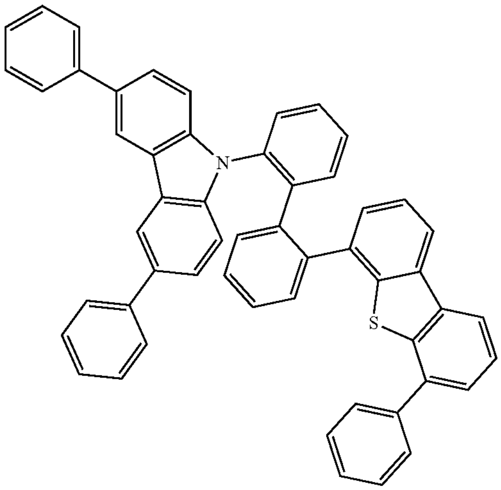

-continued
B18
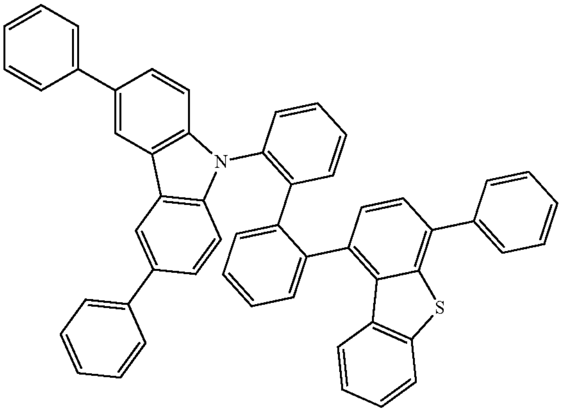
B19
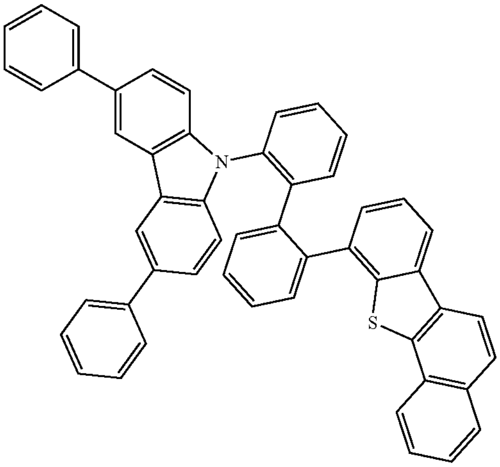
B20
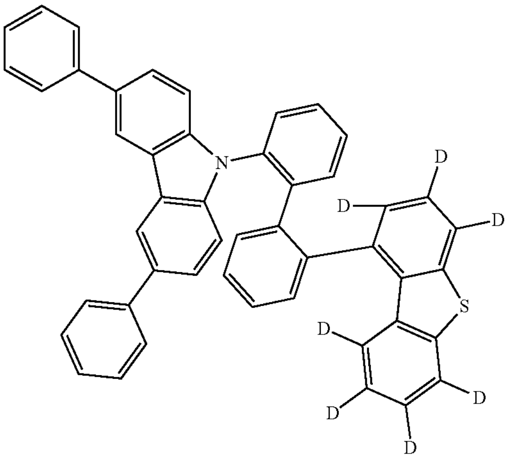
-continued
B21
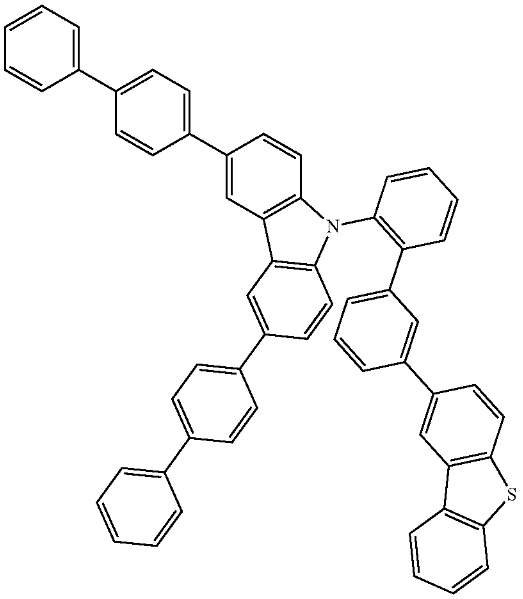
B22
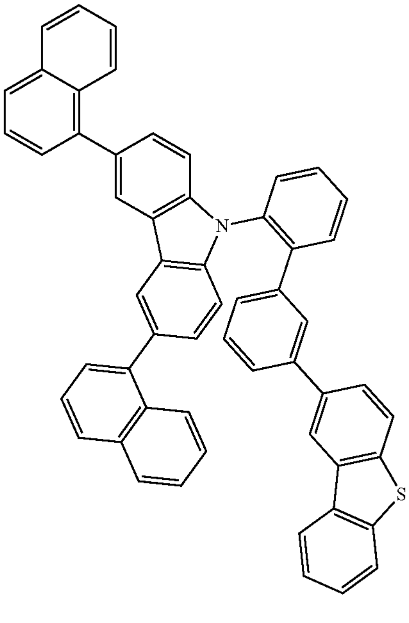

-continued
B23
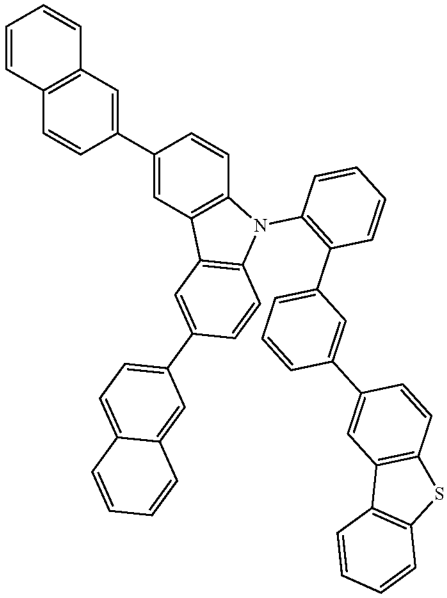
B24
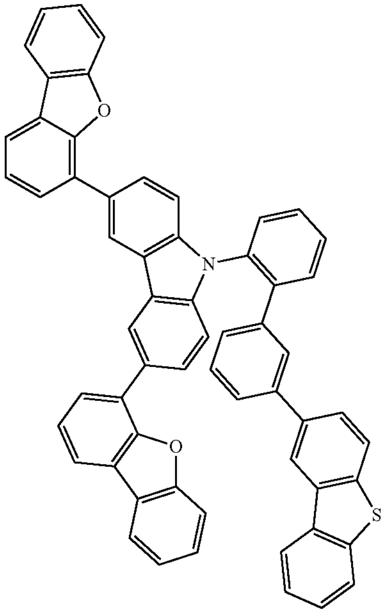
-continued
B25
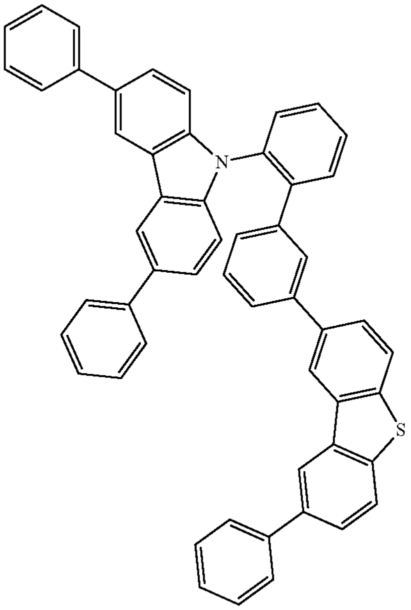
B26
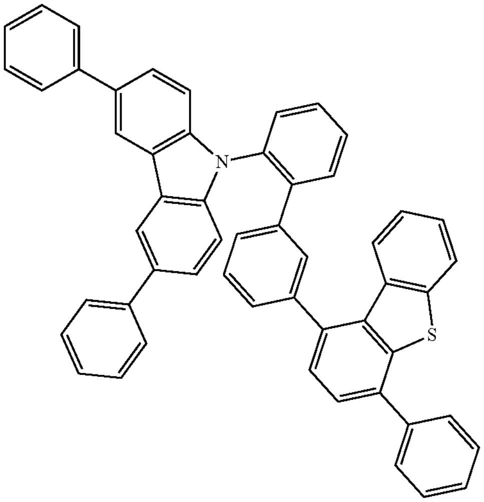

-continued
B27
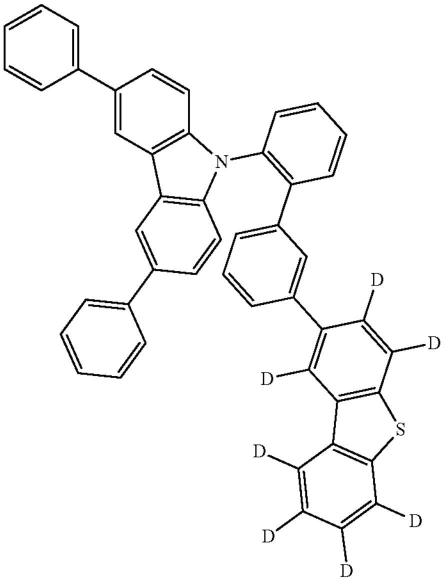
B28
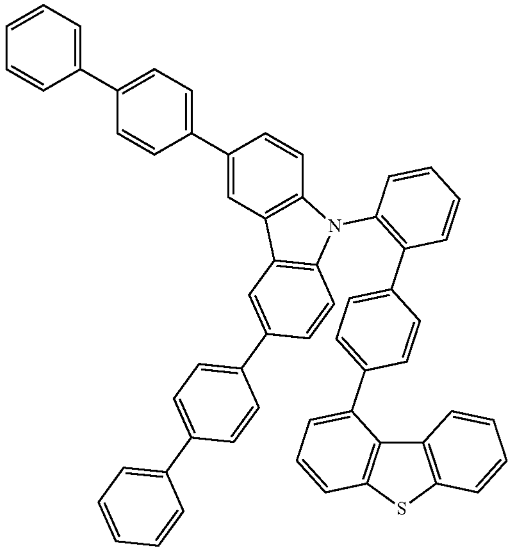
B29
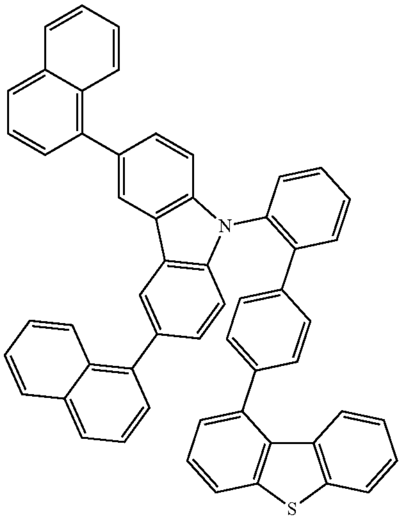
-continued
B30
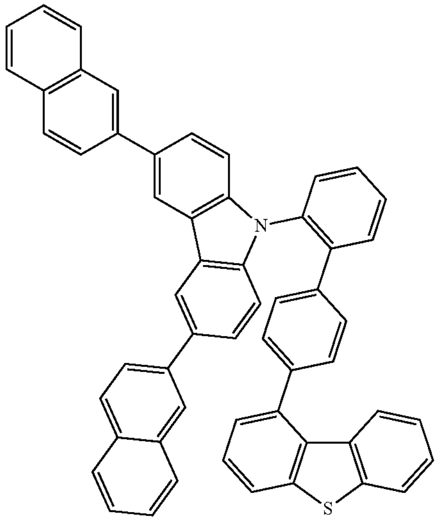
B31
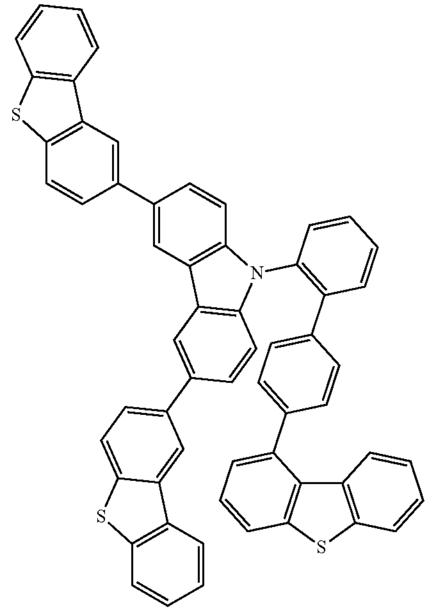

-continued
B32
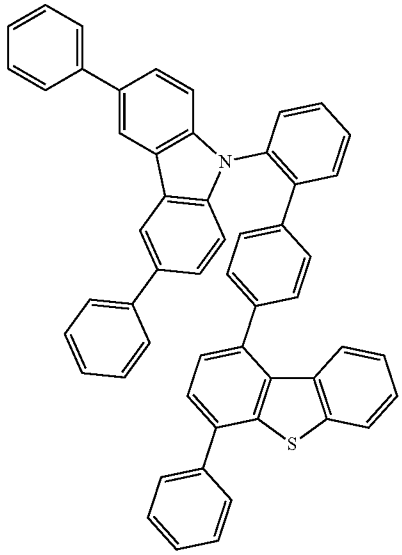
B33
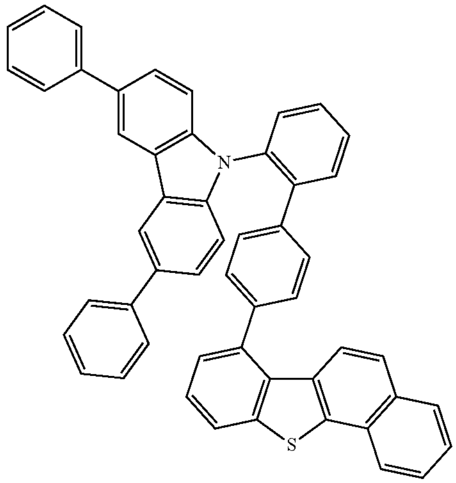
B34
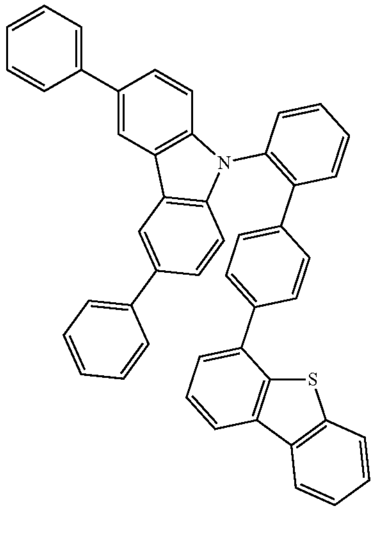
-continued
B35
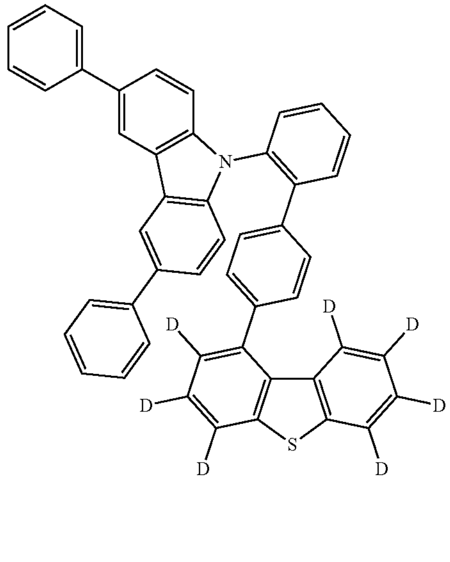
C1
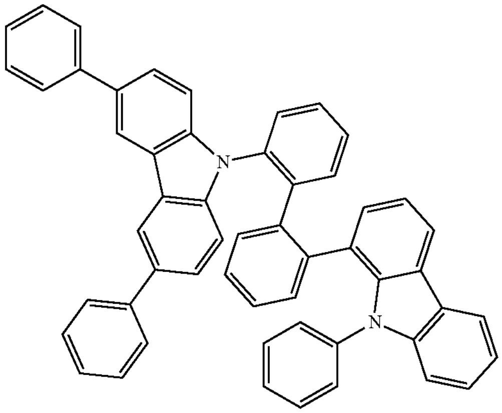
C2
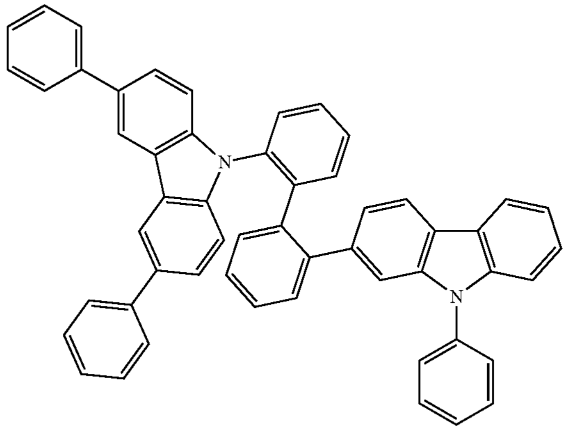

-continued
C3
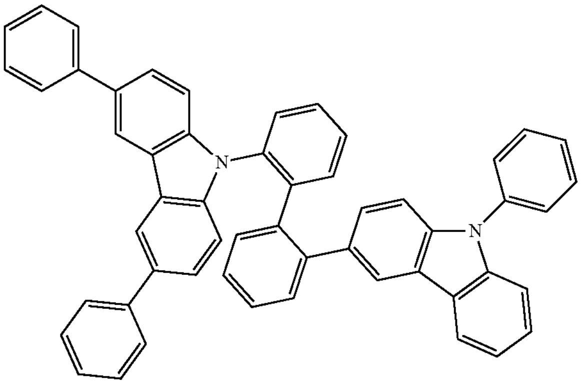
C4
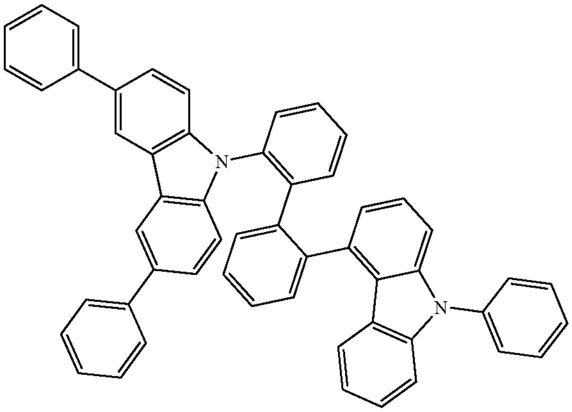
C5
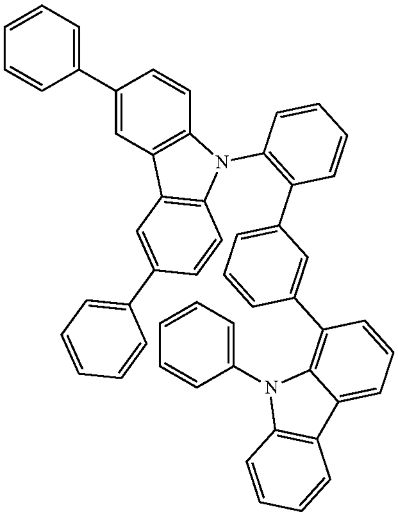
-continued
C6
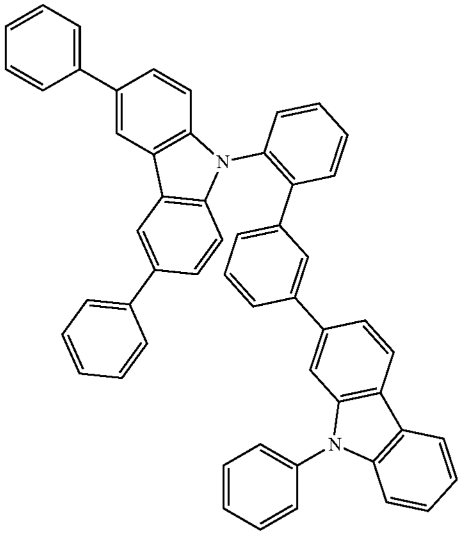
C7
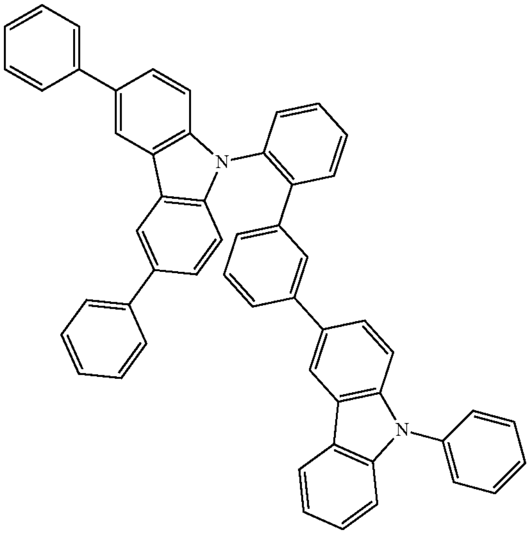
C8
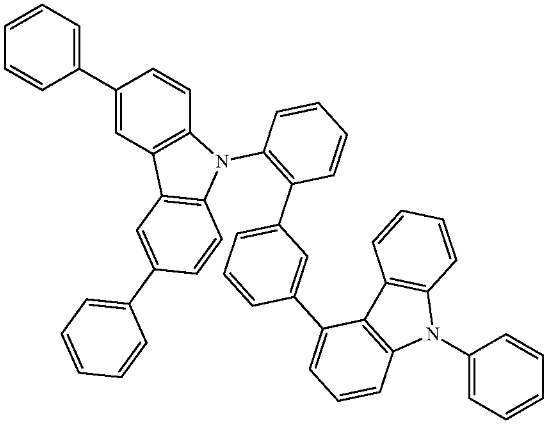

-continued
C9
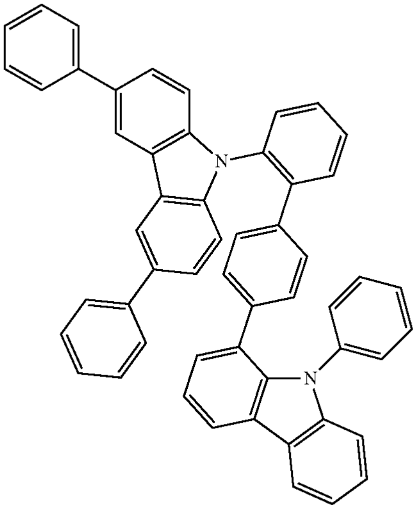
C10
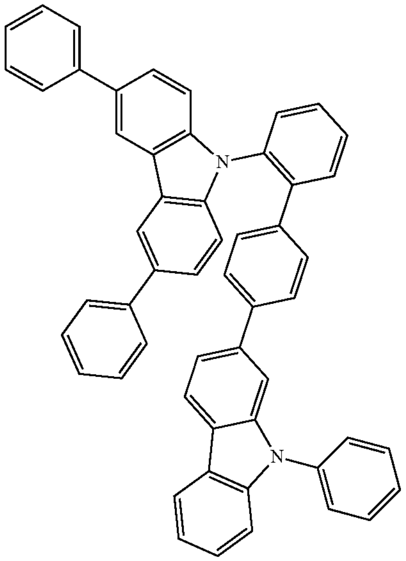
C11
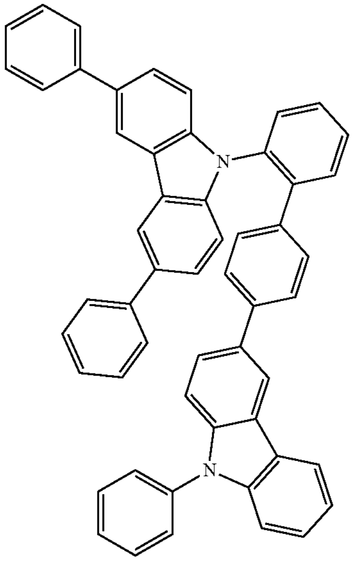
-continued
C12
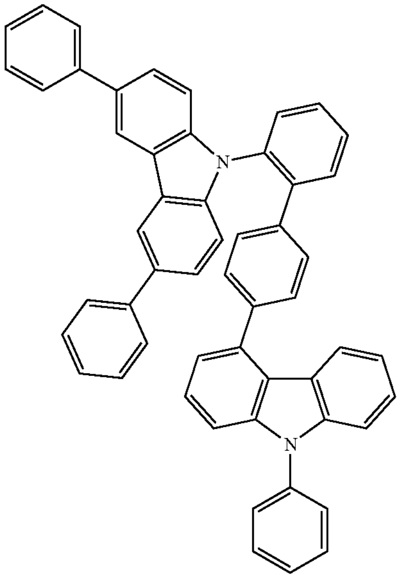
C13
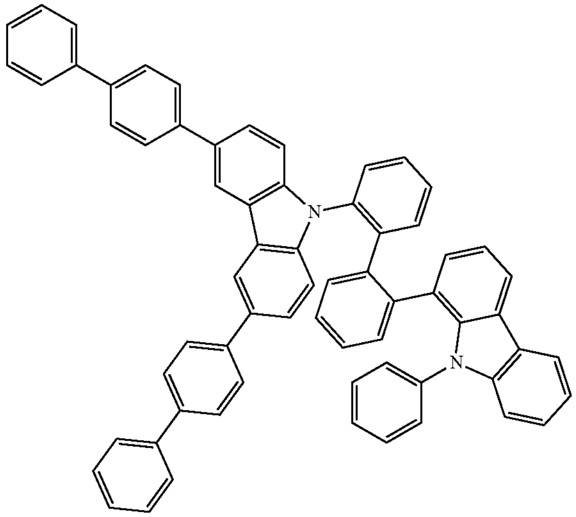
C14
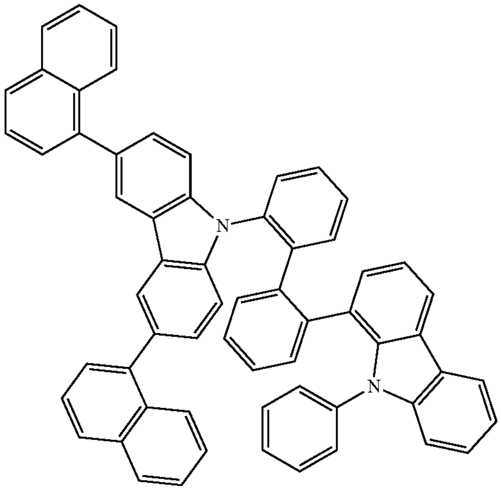

-continued
C15
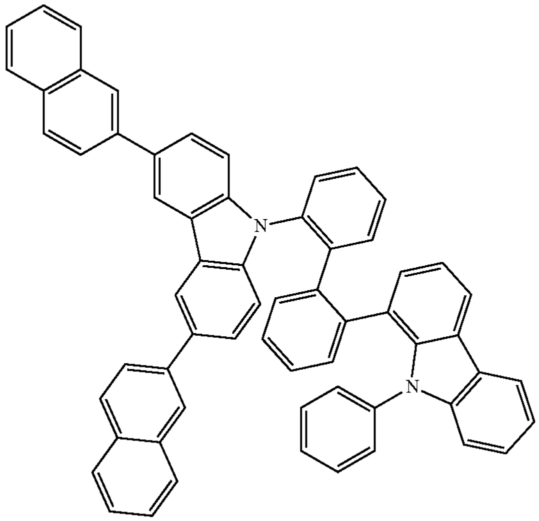
C16
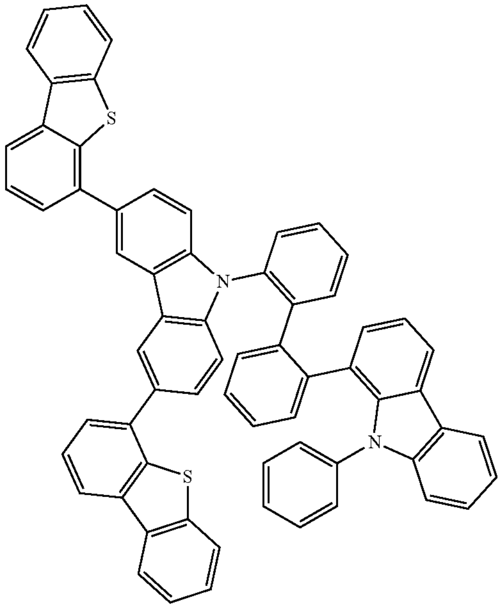
C17
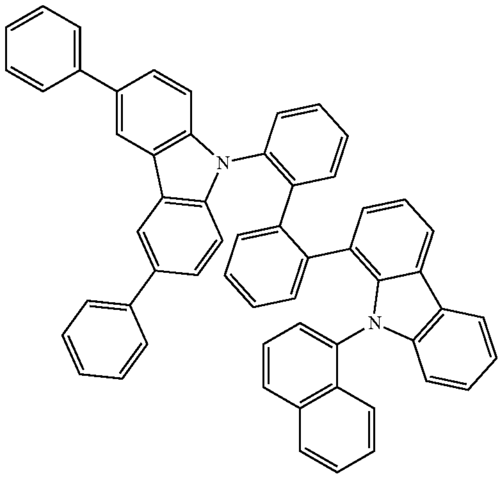
-continued
C18
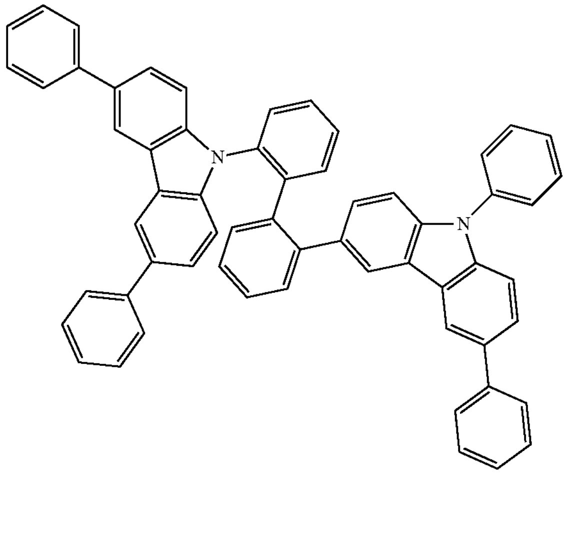
C19
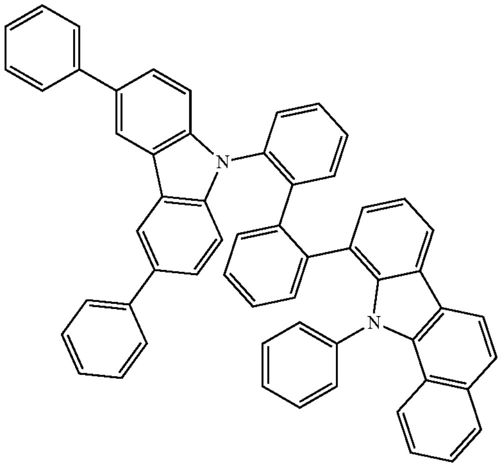
C20
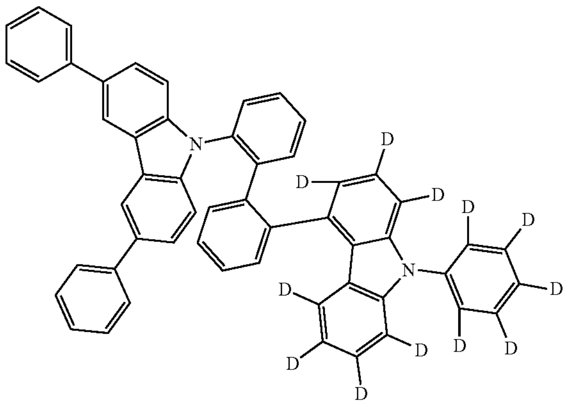

-continued
C21
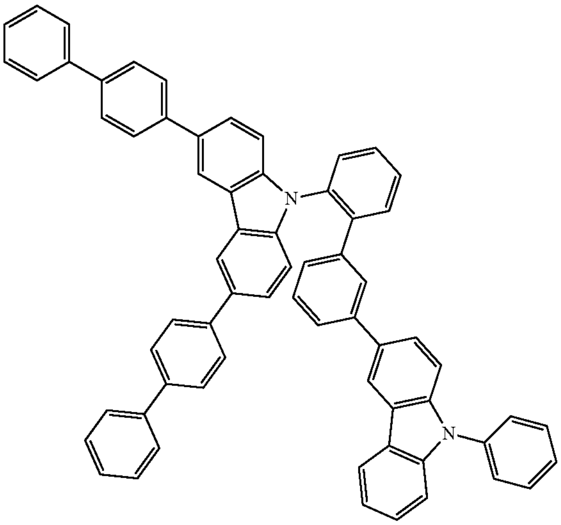
C22
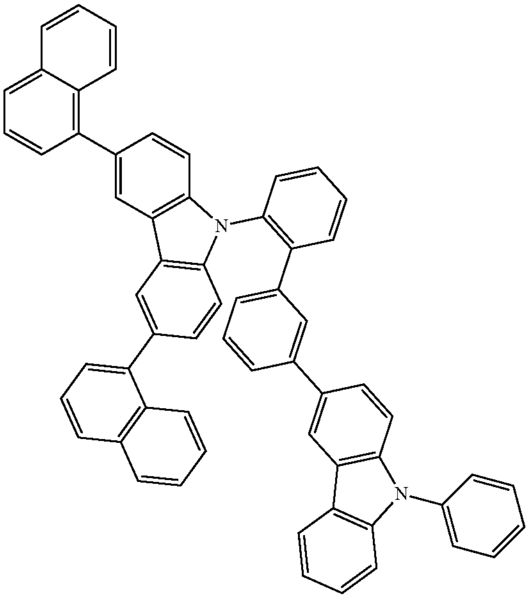
-continued
C23
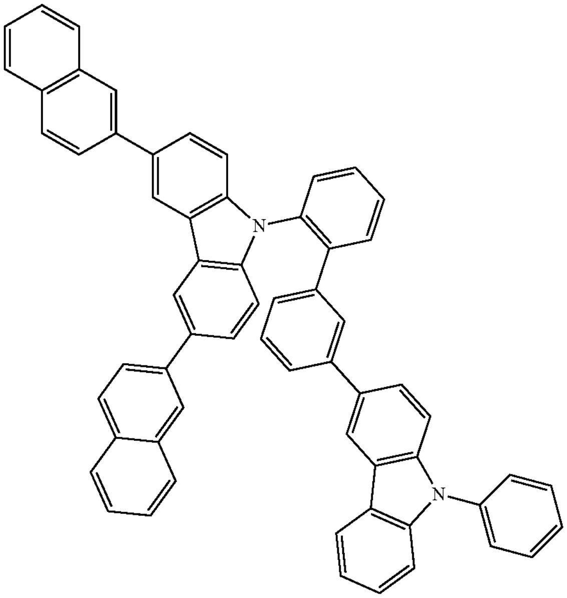
C24
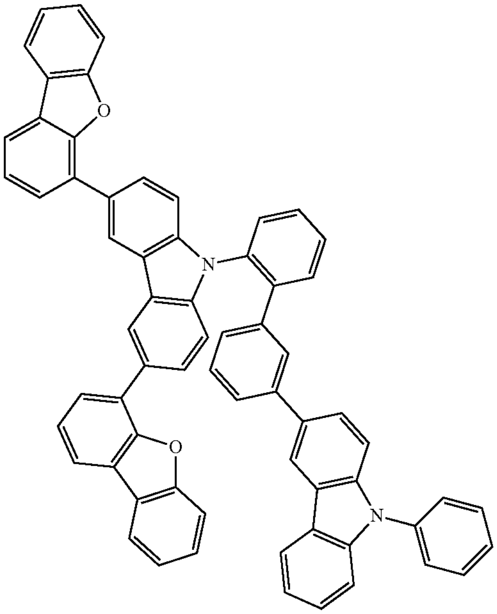

-continued
C25
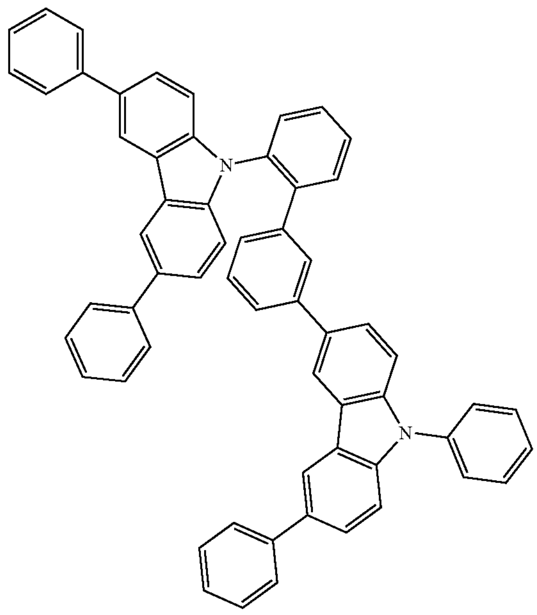
C26
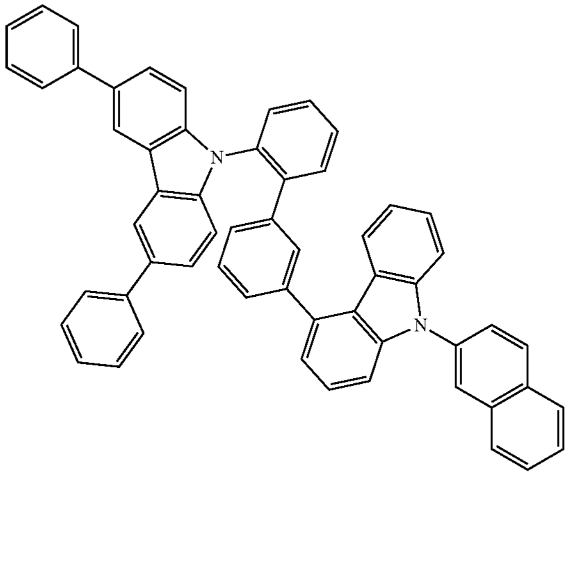
-continued
C27
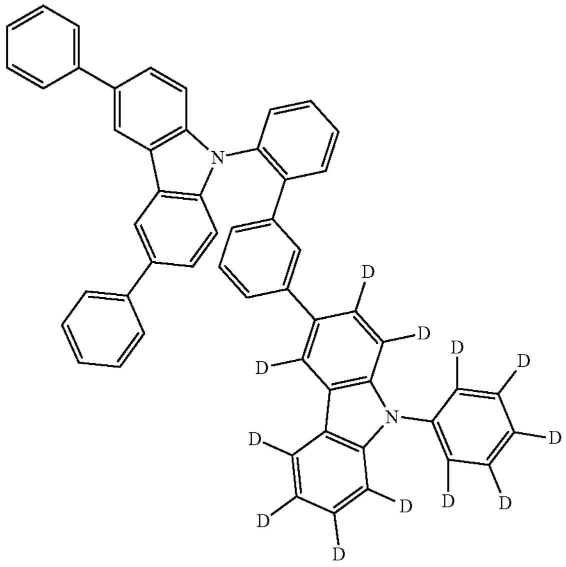
C28
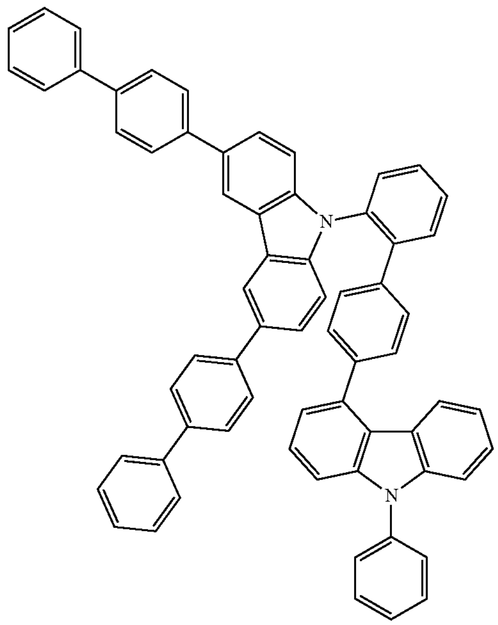

-continued
C29
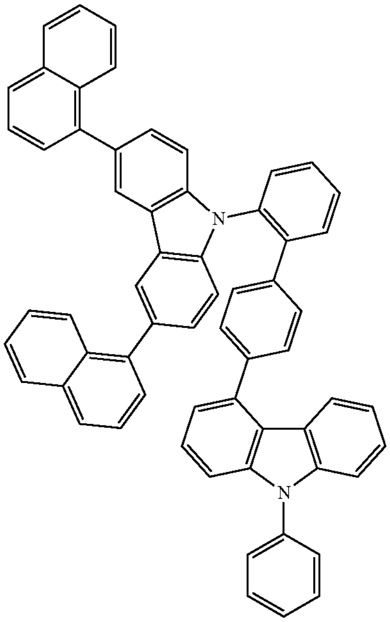
C30
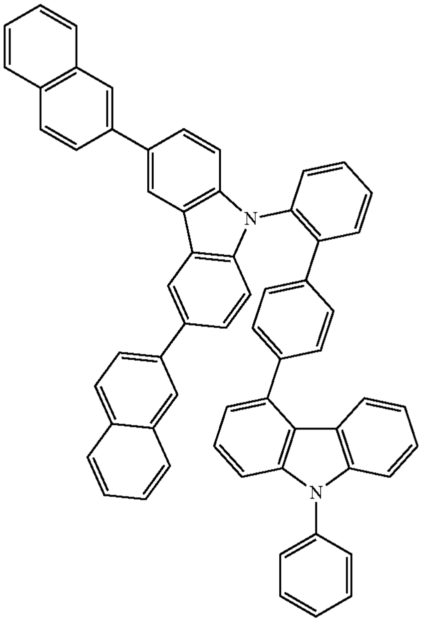
-continued
C31
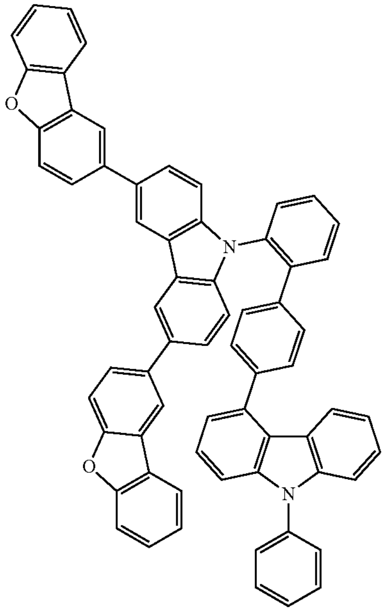
C32
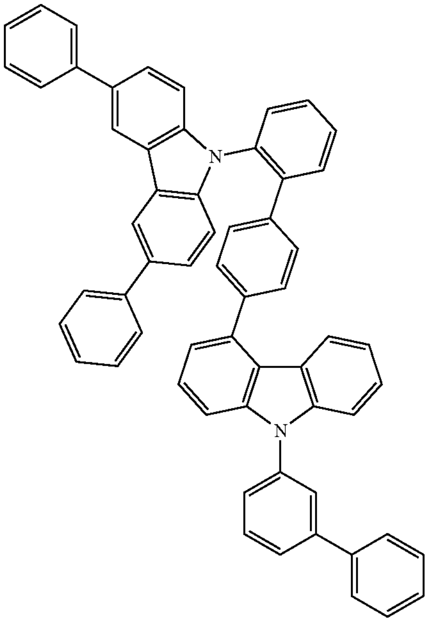

-continued
C33
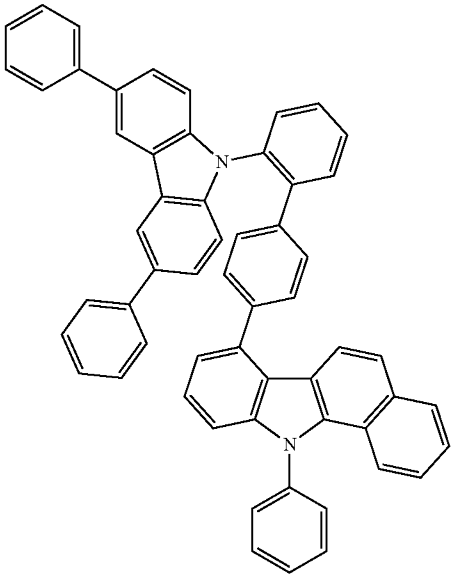
C34
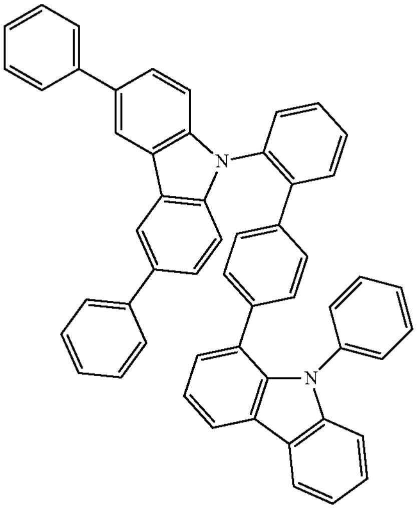
-continued
C35
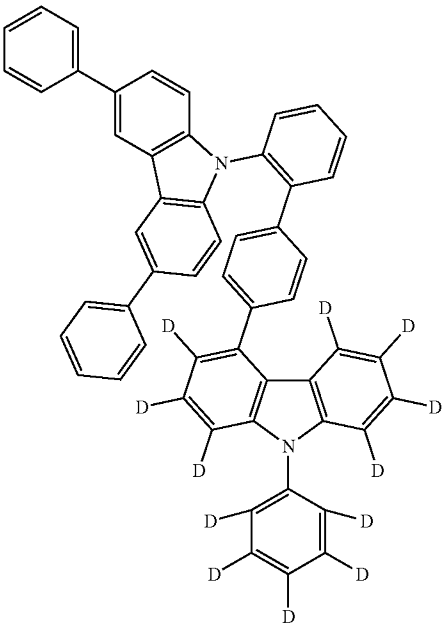
Compound Group 2
D1
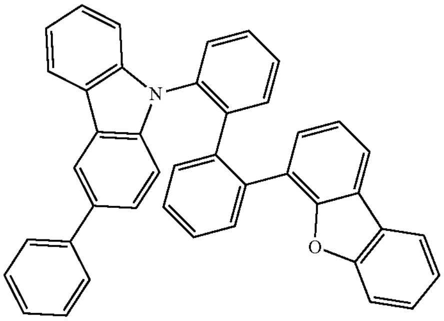
D2
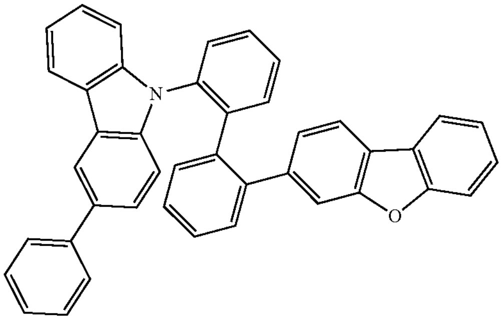

-continued
D3
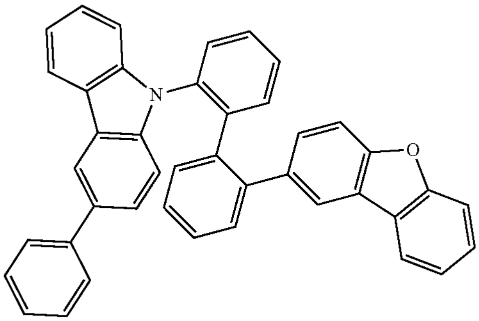
D4
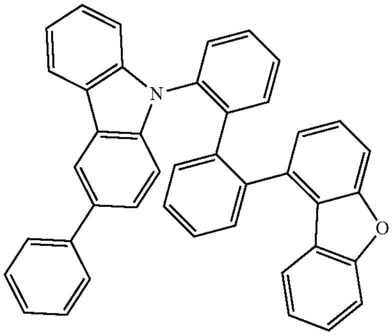
D5
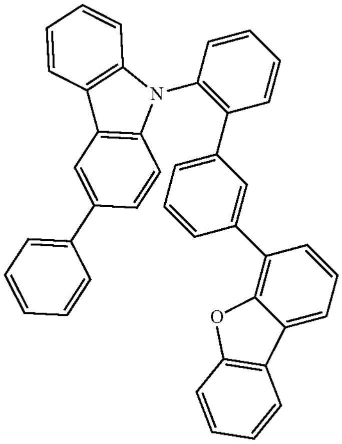
D6
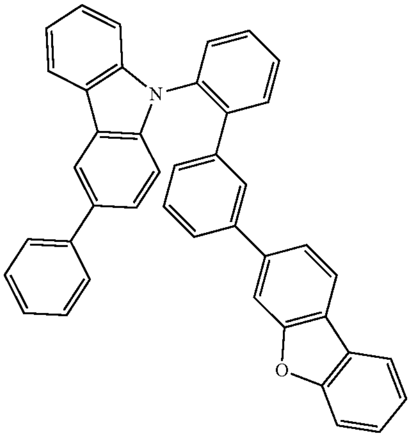
-continued
D7
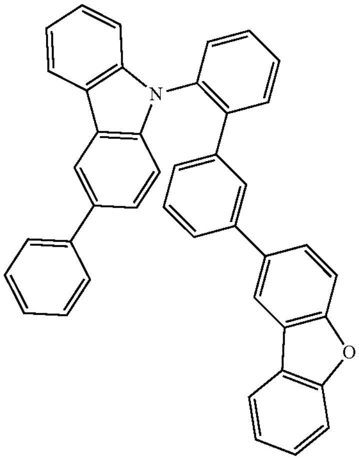
D8
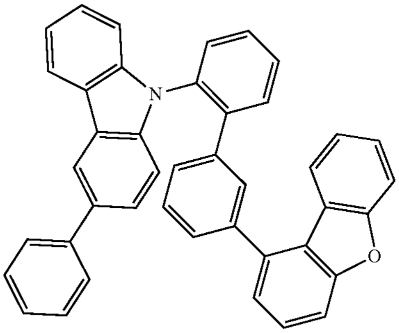
D9
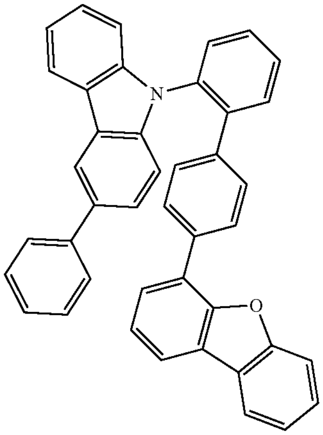

-continued
D10
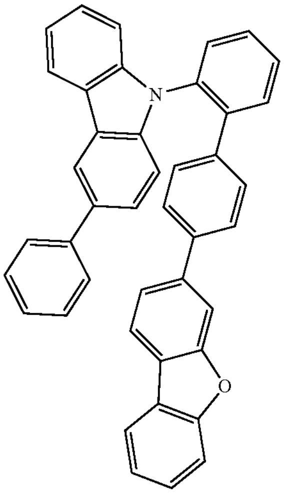
D11
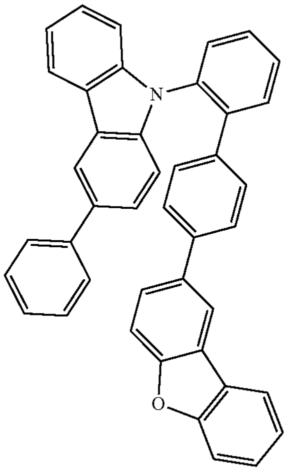
D12
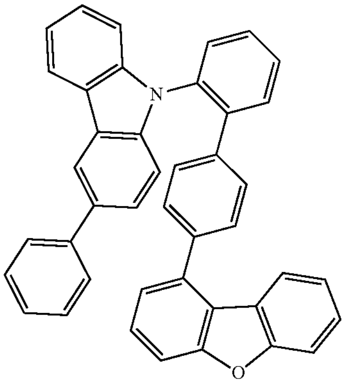
-continued
D13
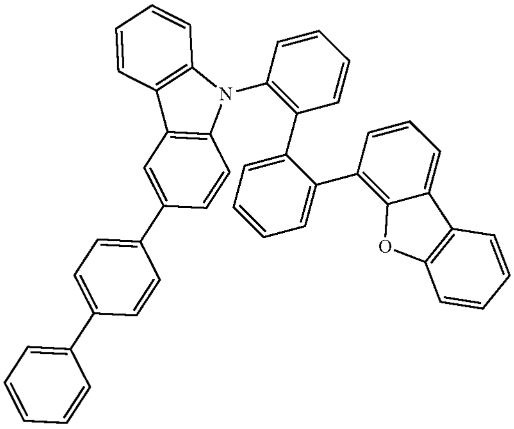
D14
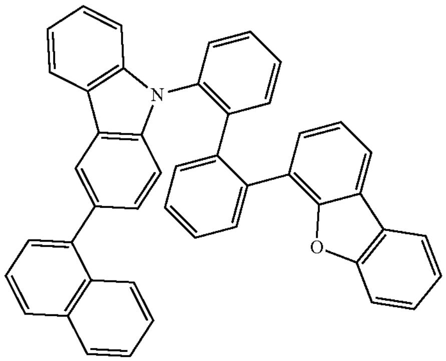
D15
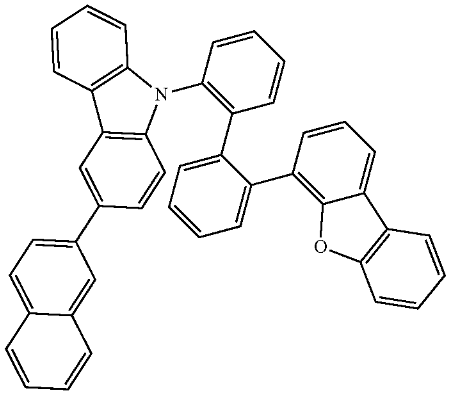
D16
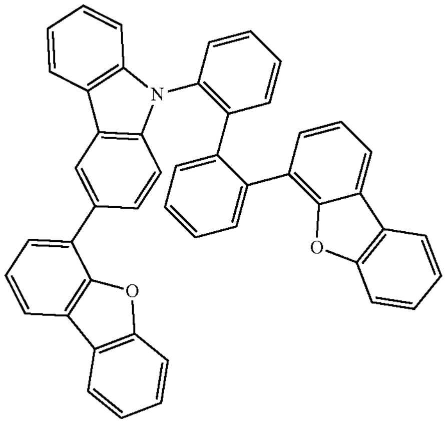

-continued
D17
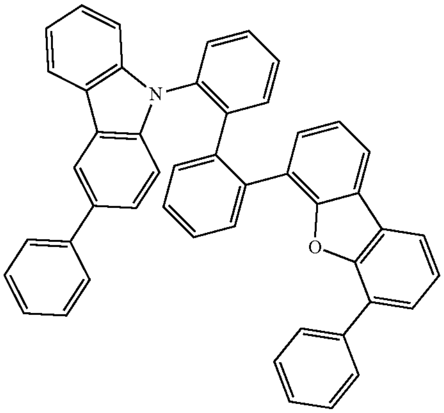
D18
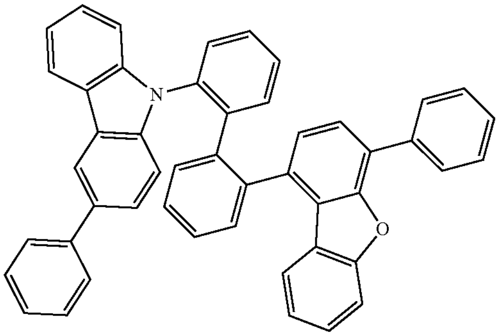
D19
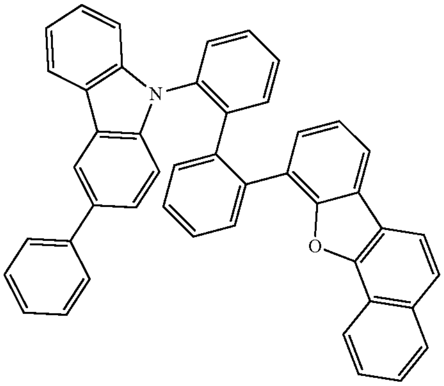
D20
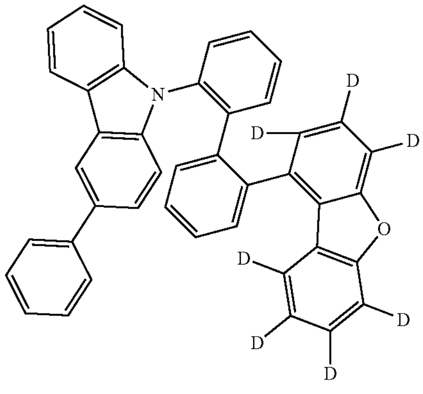
-continued
D21
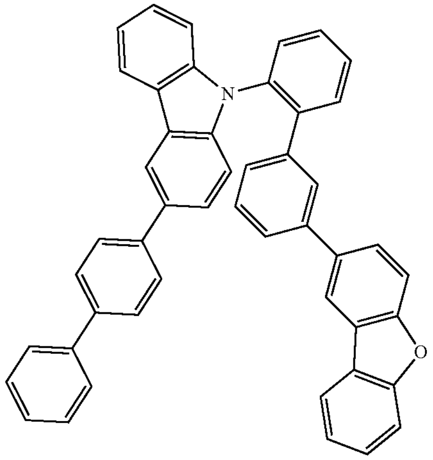
D22
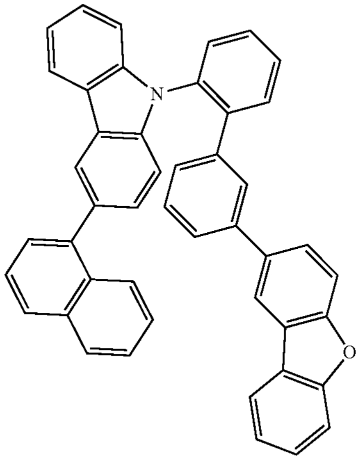
D23
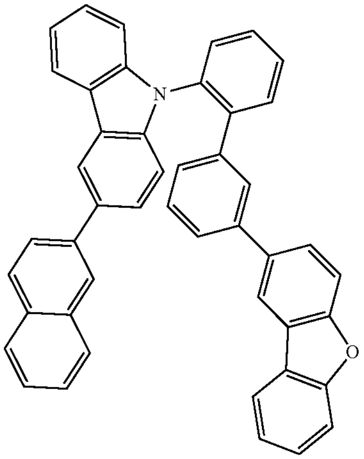

-continued
D24
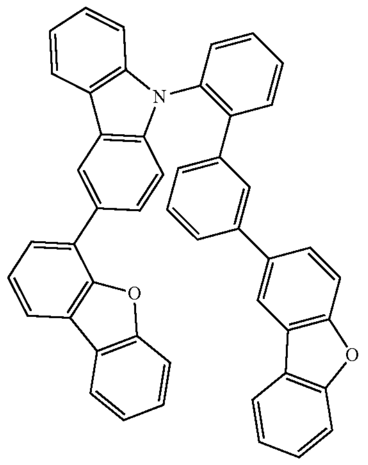
D25
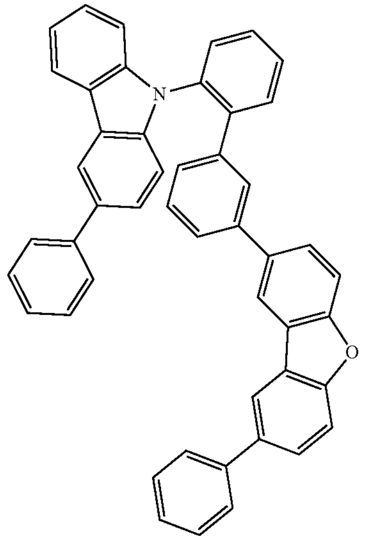
D26
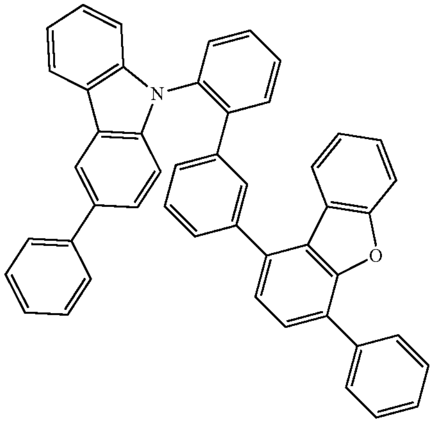
-continued
D27
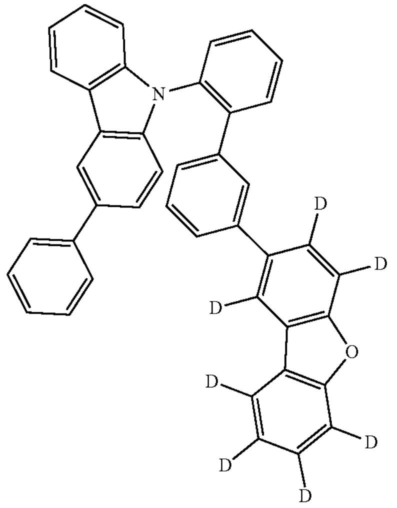
D28
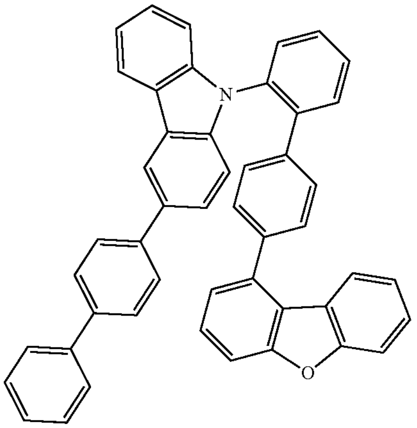
D29
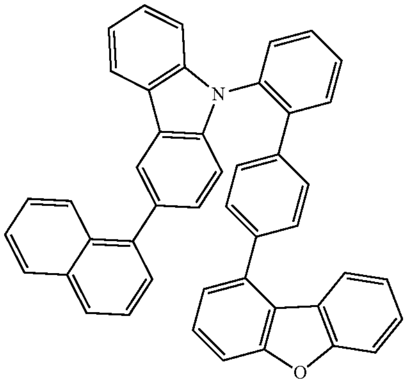

-continued
D30
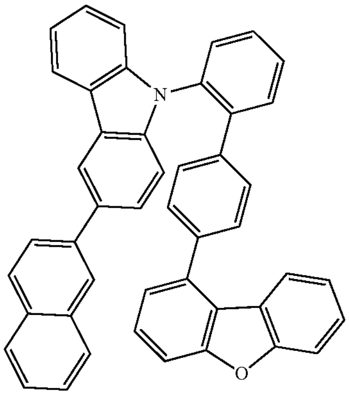
D31
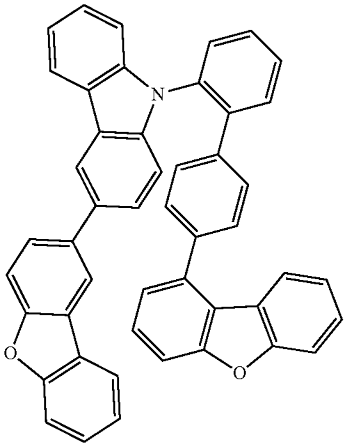
D32
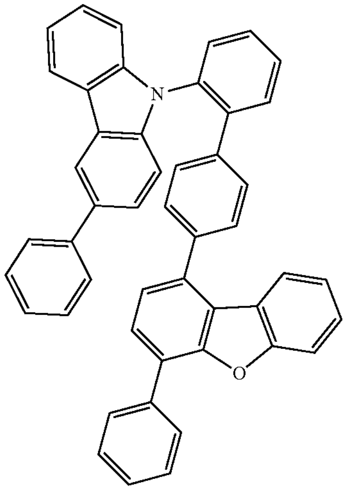
-continued
D33
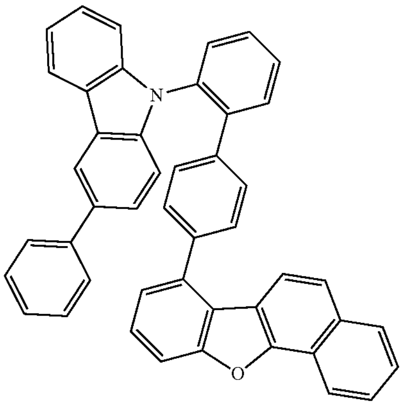
D34
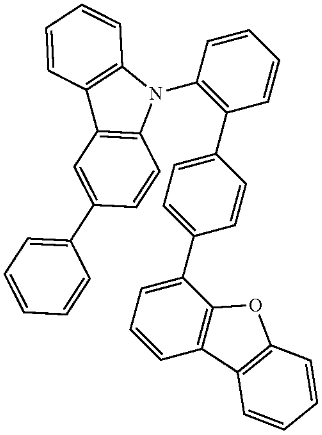
D35
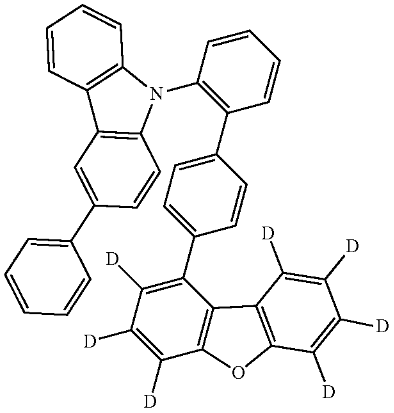
E1
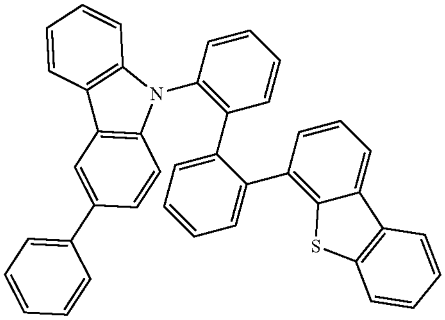

-continued
E2
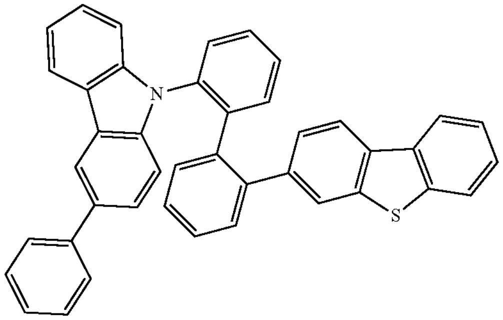
E3
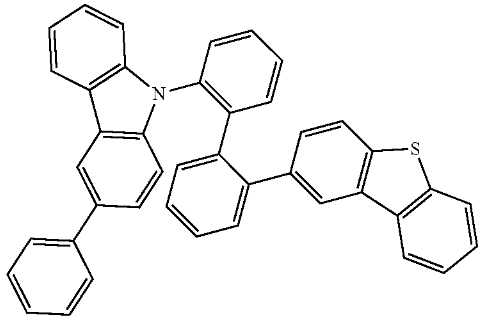
E4
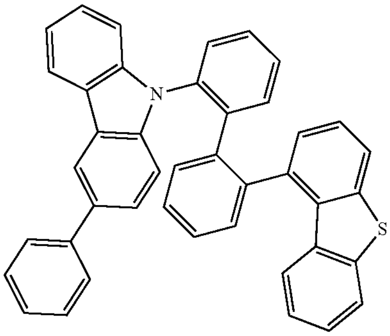
E5
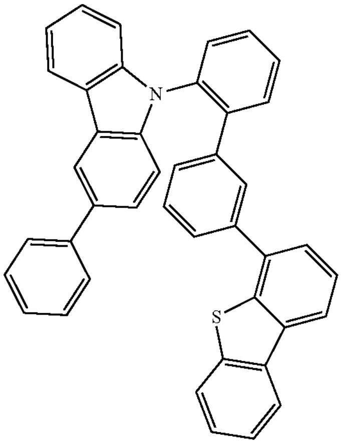
-continued
E6
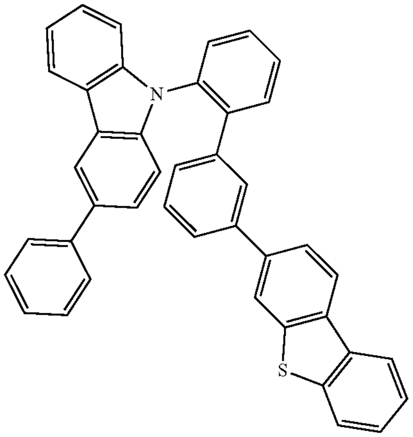
E7
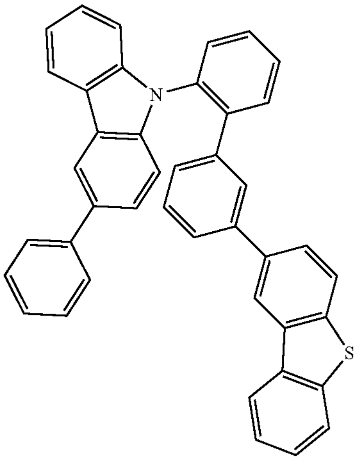
E8
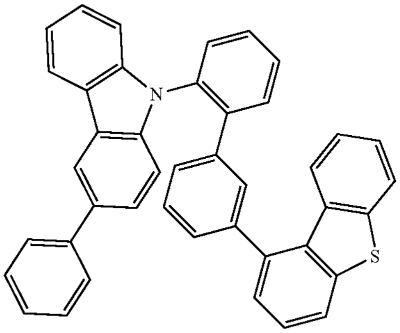

-continued
E9
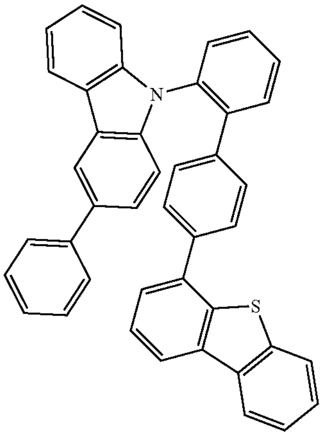
E10
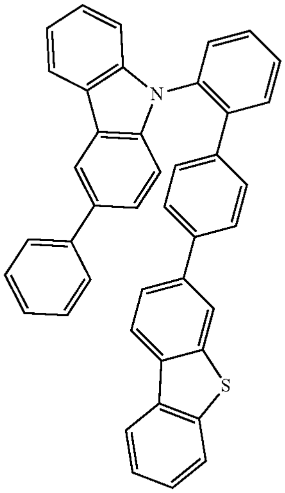
E11
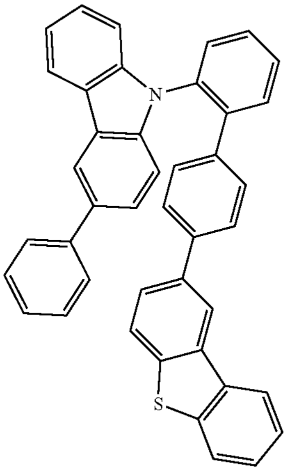
-continued
E12
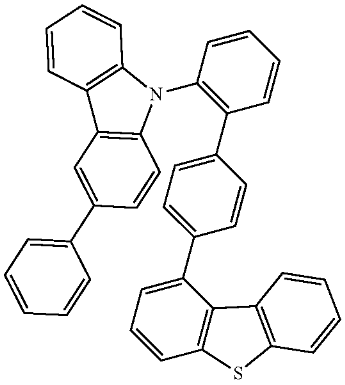
E13
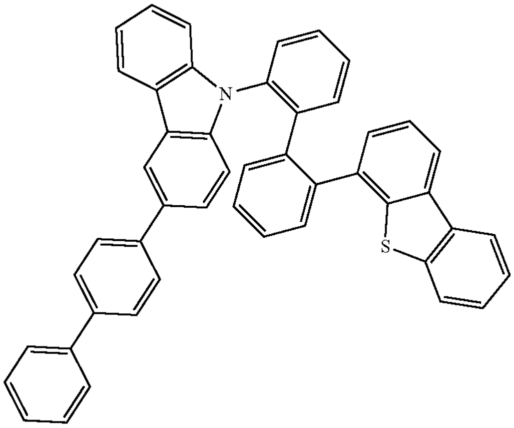
E14
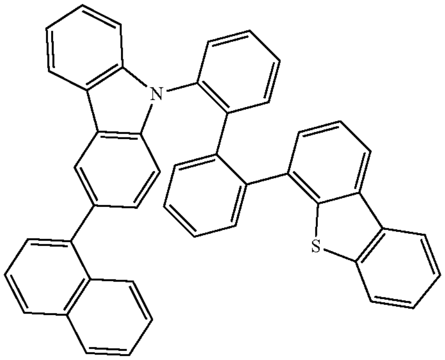
E15
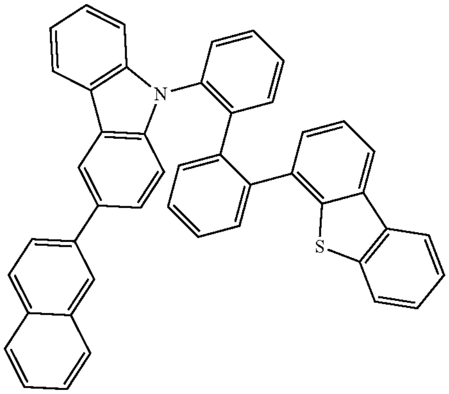

-continued
E16
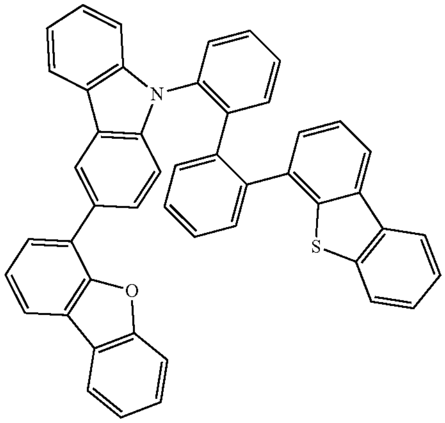
E17
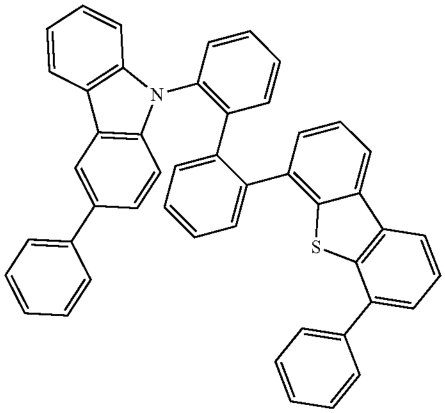
E18
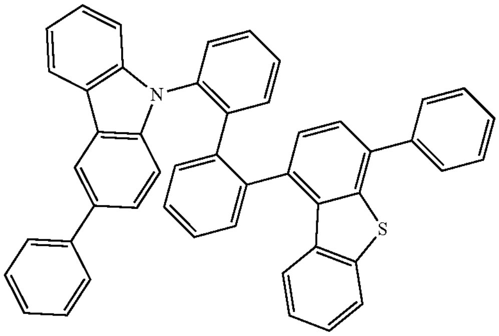
E19
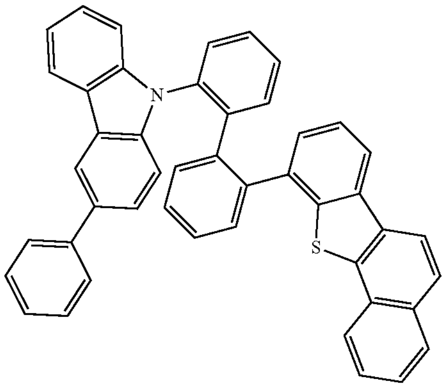
-continued
E20
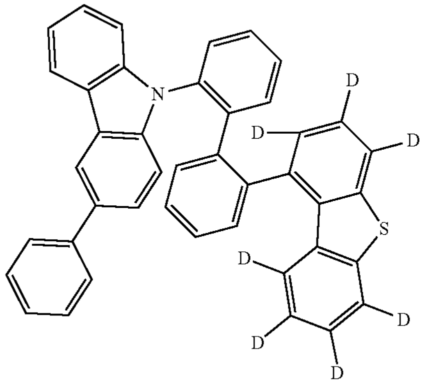
E21
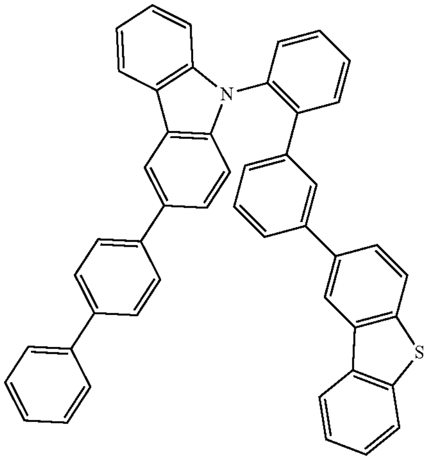
E22
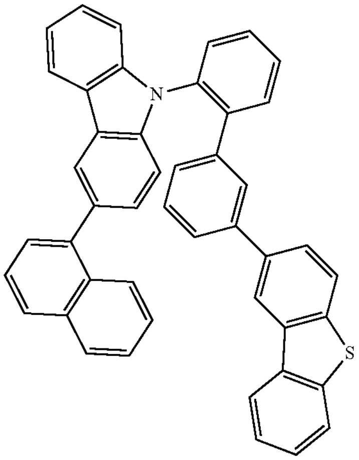

-continued
E23
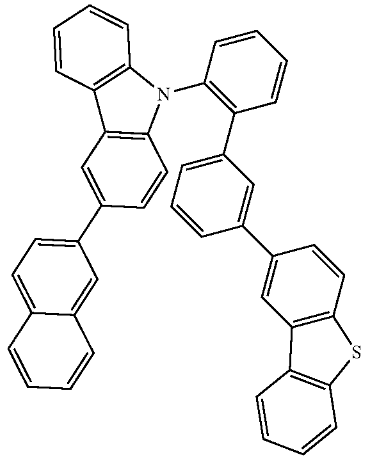
E24
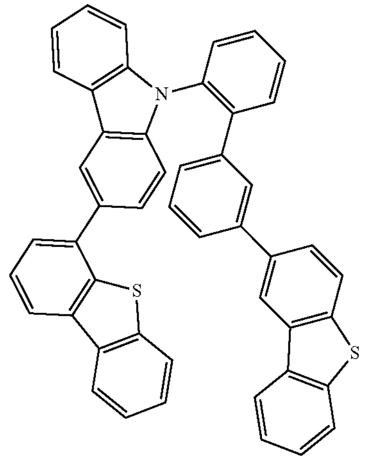
E25
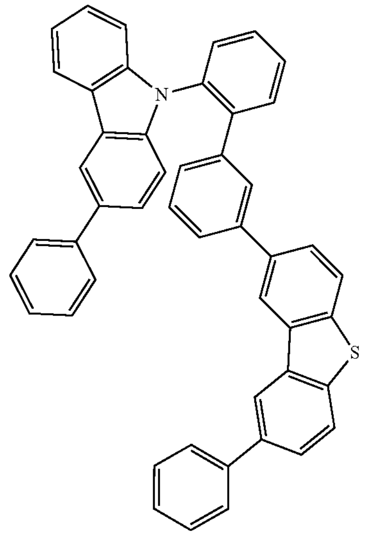
-continued
E26
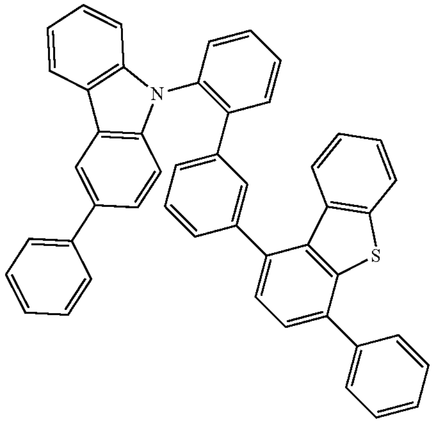
E27
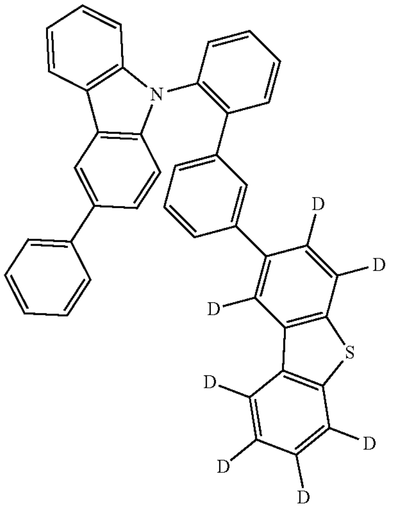
E28
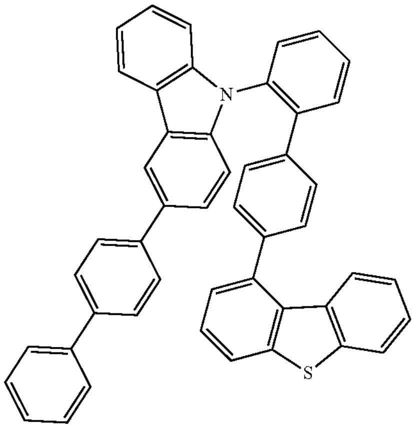

E29
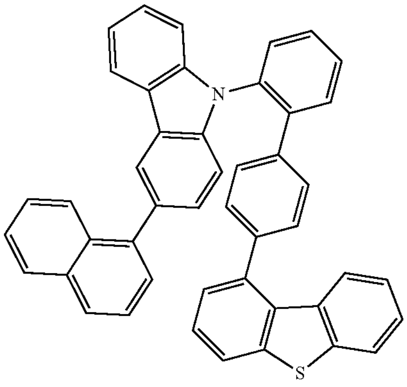
E30
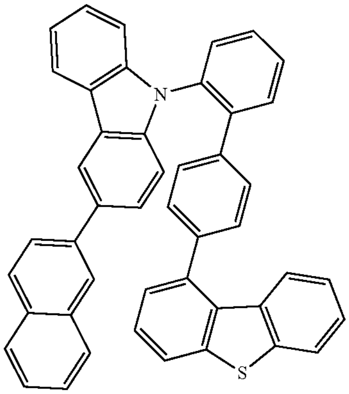
E31
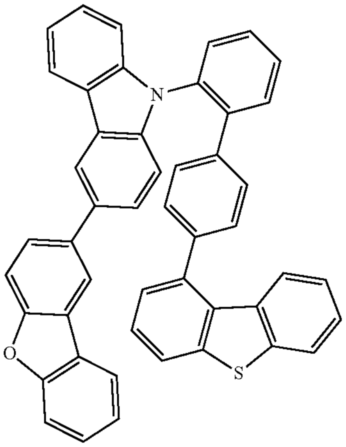
E32
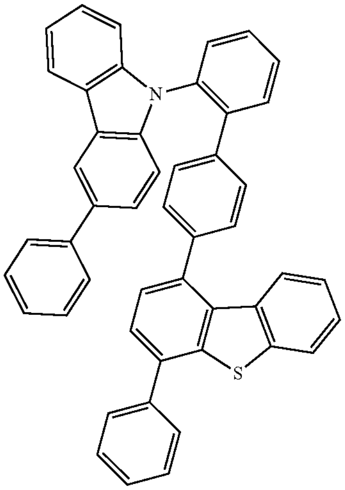
E33
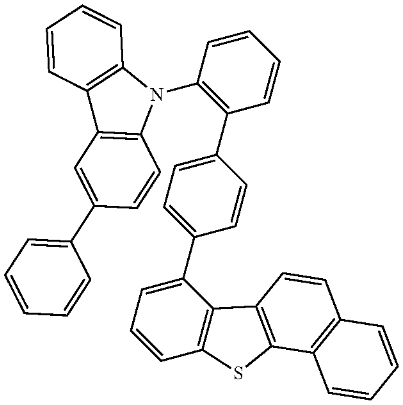
E34
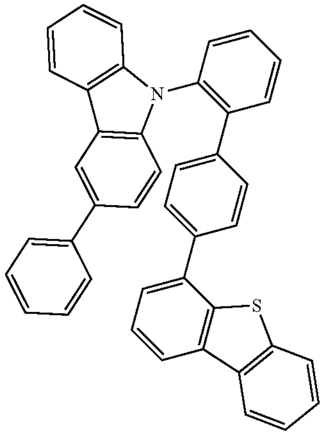

-continued
E35
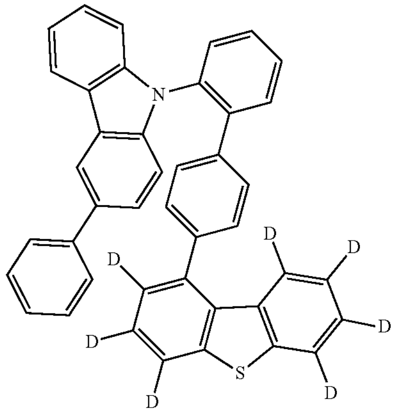
F1
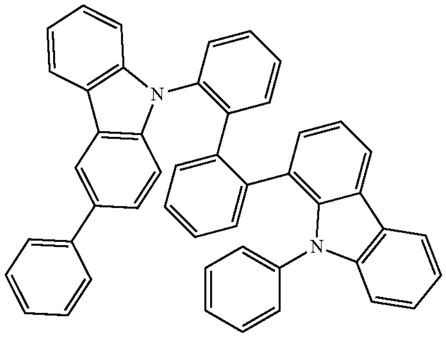
F2
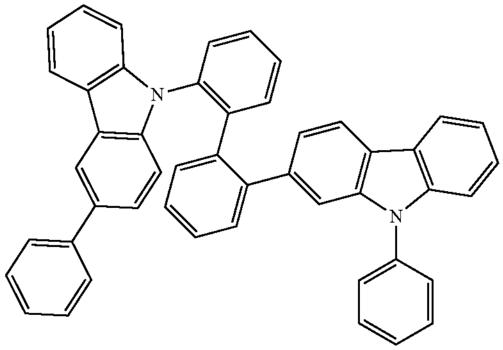
F3
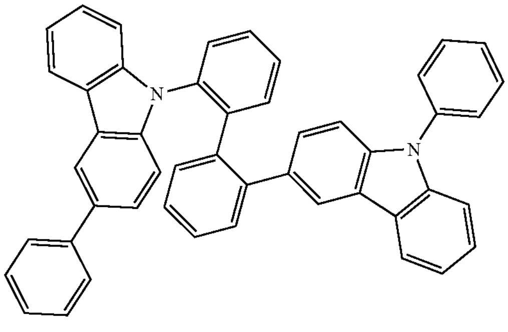
-continued
F4
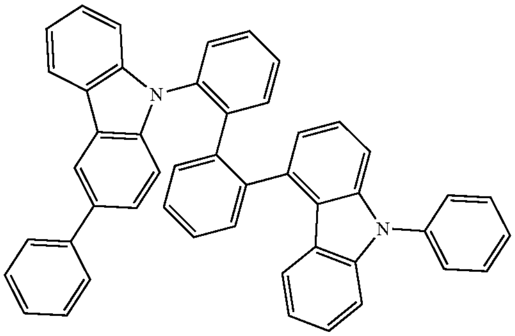
F5
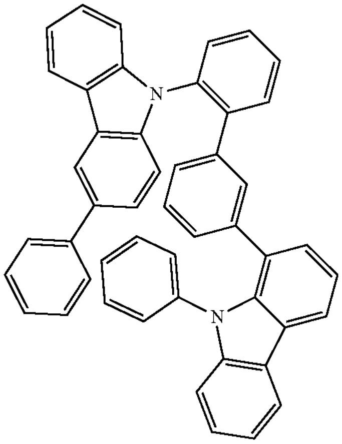
F6
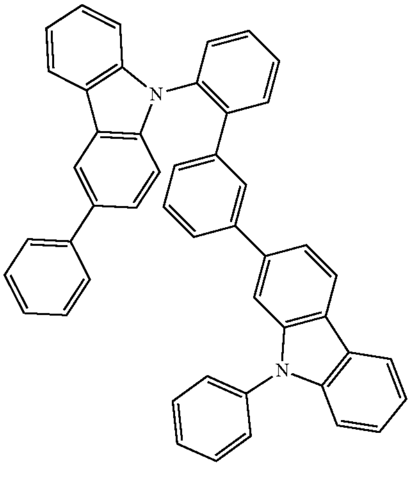

-continued
F7
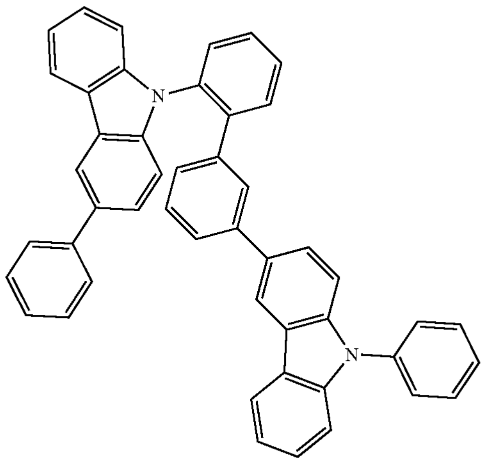
F8
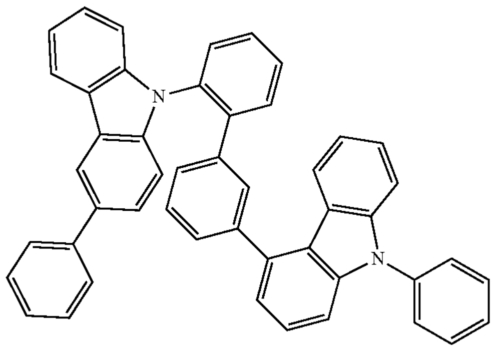
F9
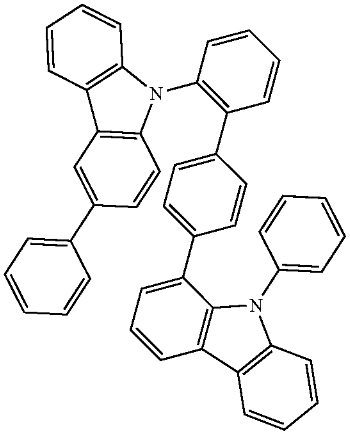
-continued
F10
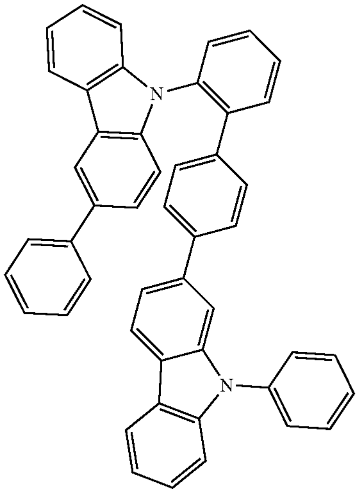
F11
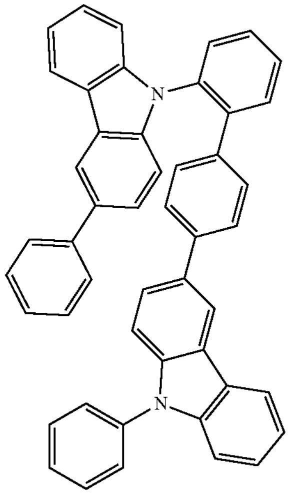
F12
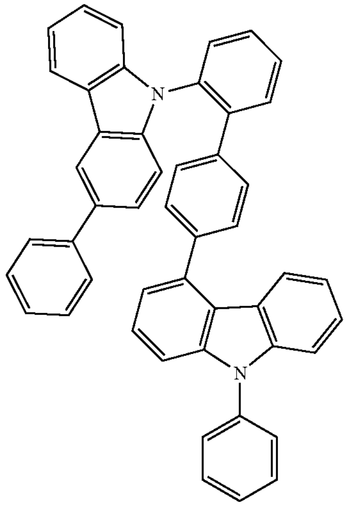

-continued
F13
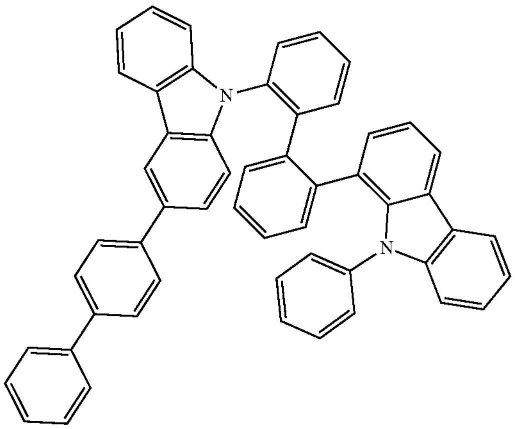
F14
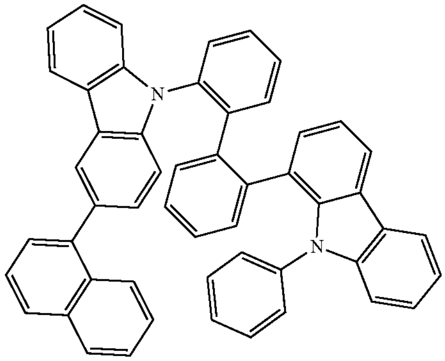
F15
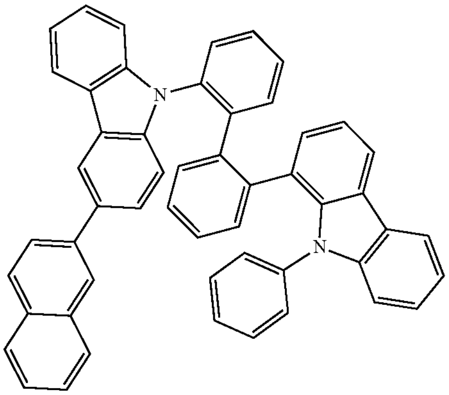
F16
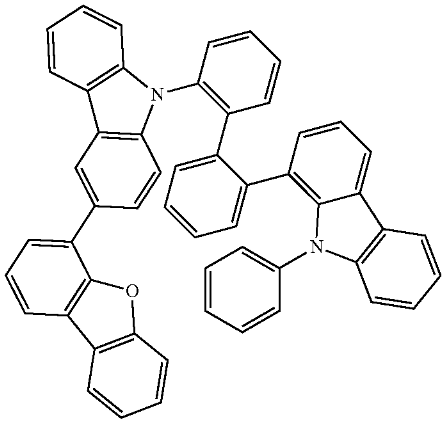
-continued
F17
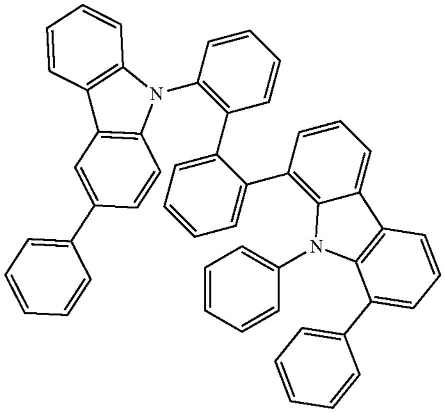
F18
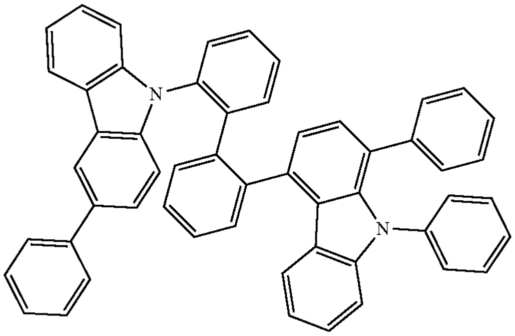
F19
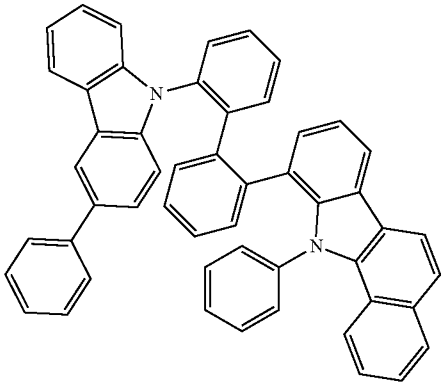
F20
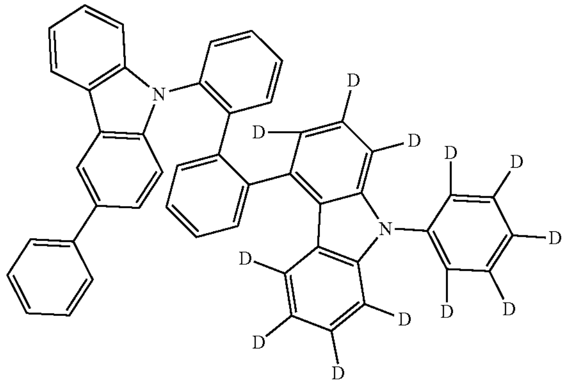

-continued
F21
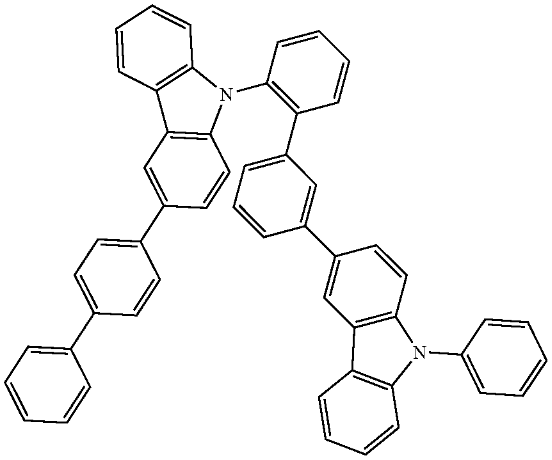
F22
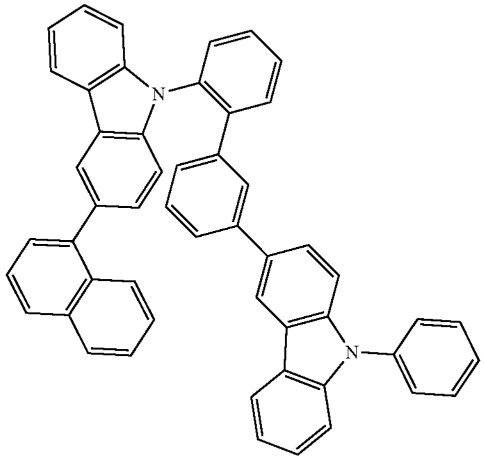
F23
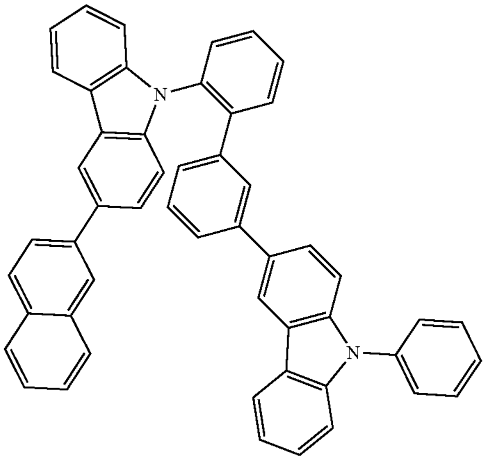
-continued
F24
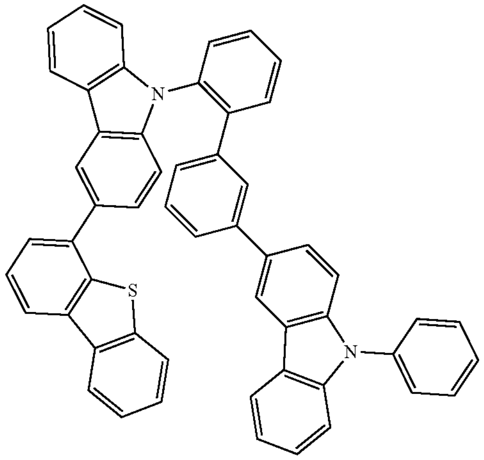
F25
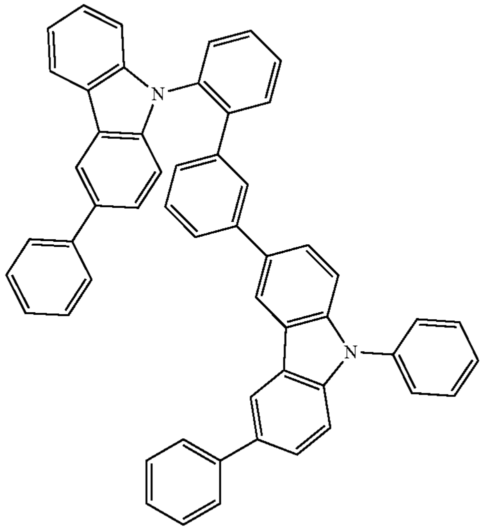
F26
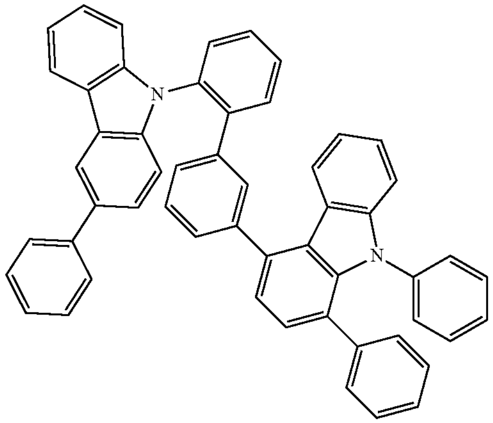

-continued
F27
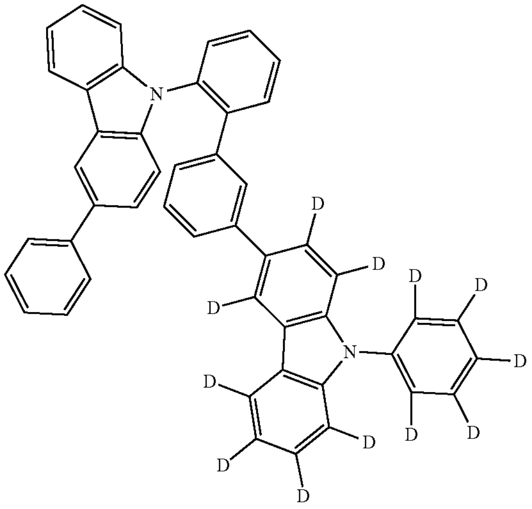
F28
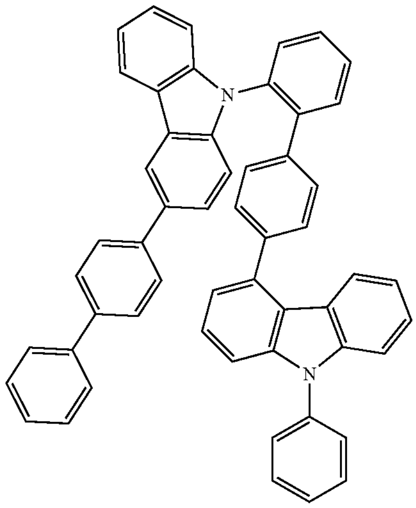
F29
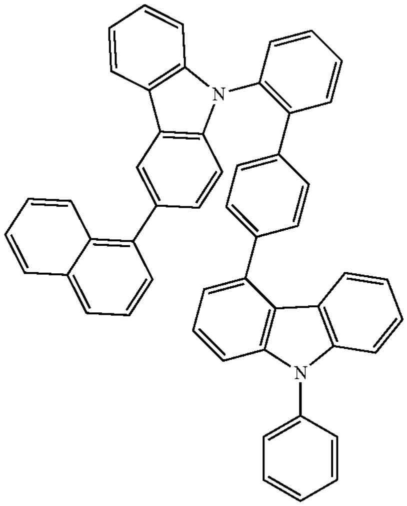
-continued
F30
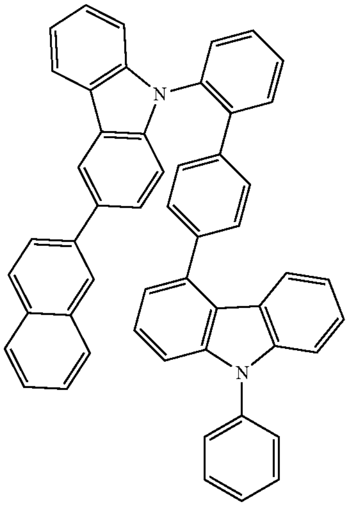
F31
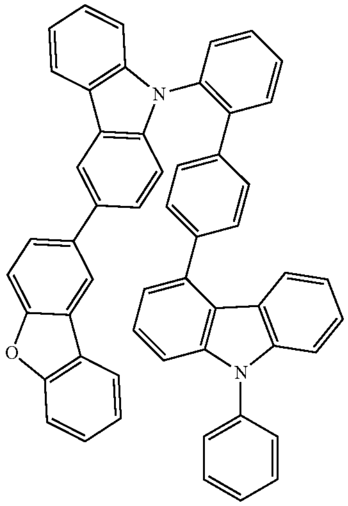
F32
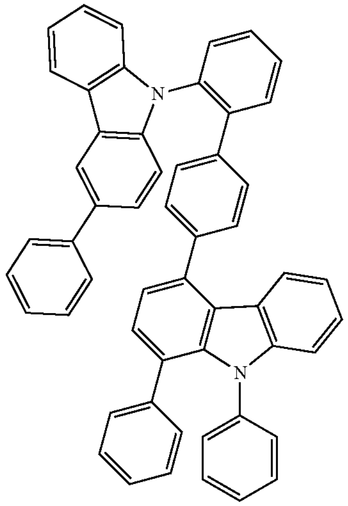

-continued
F33
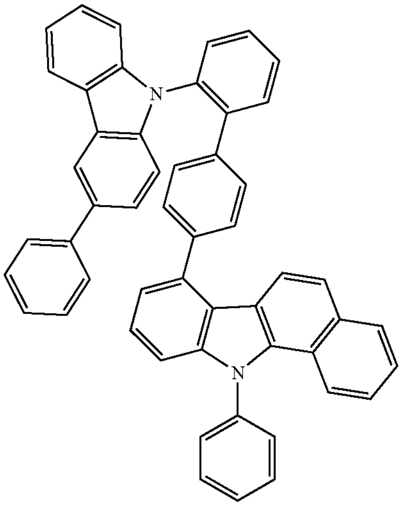
F34
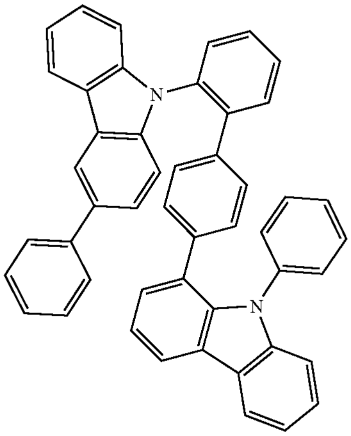
F35
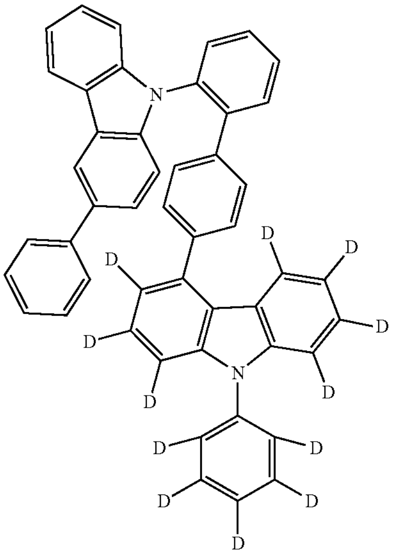
-continued
J1
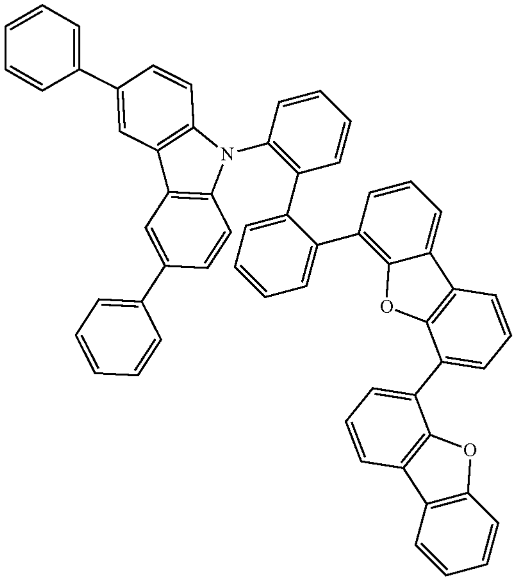
J2
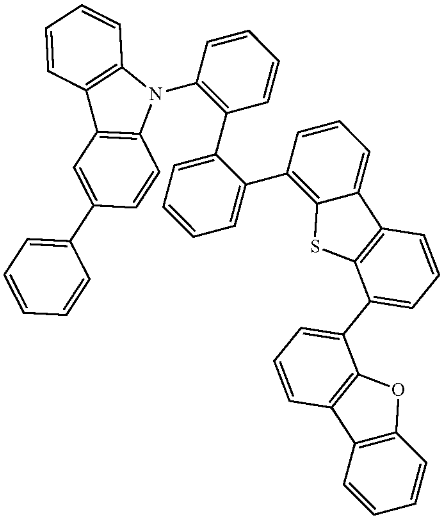
J3
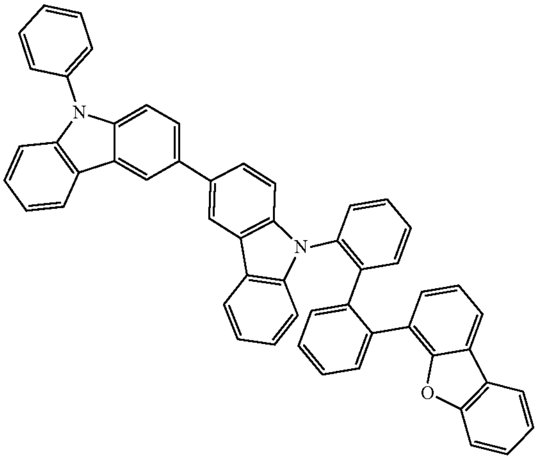

-continued
J4
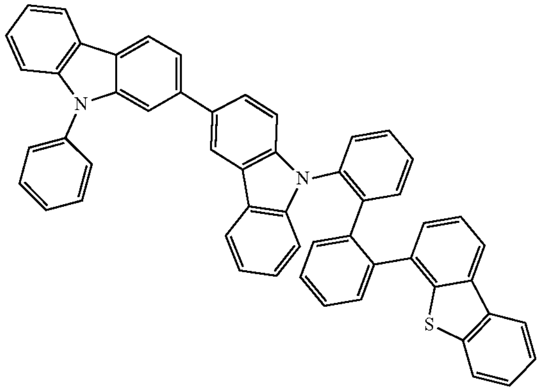
K1
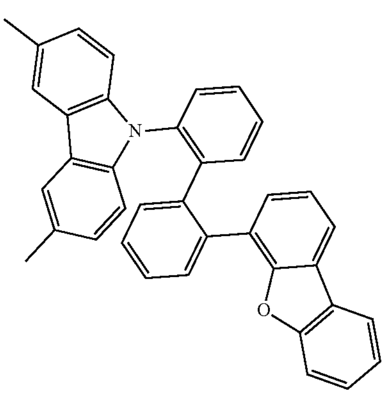
K2
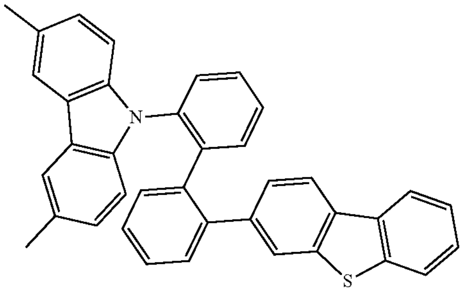
K3
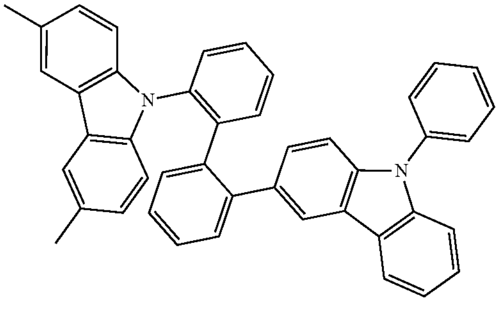
-continued
K4
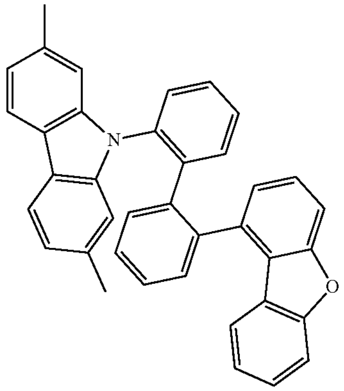
K5
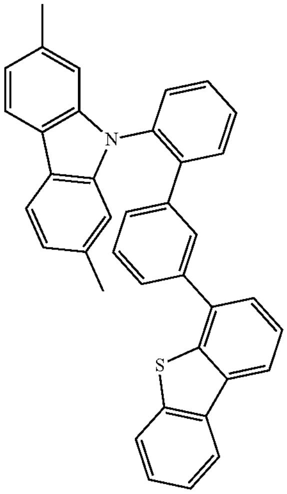
K6
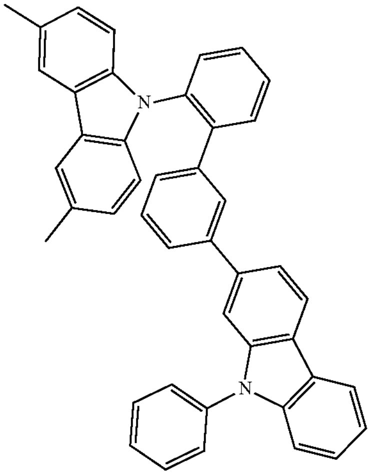

-continued
K7
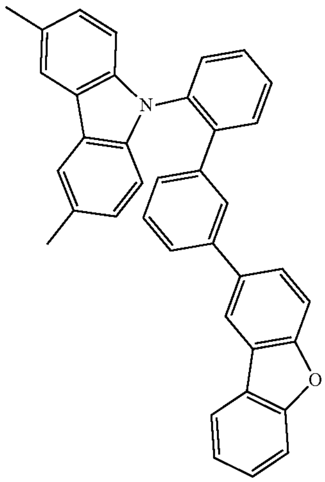
K8
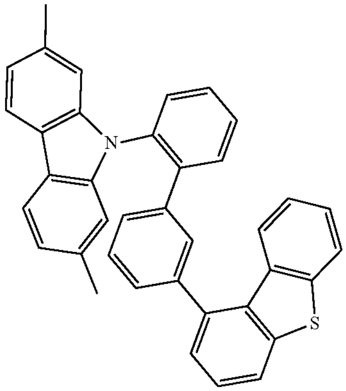
K9
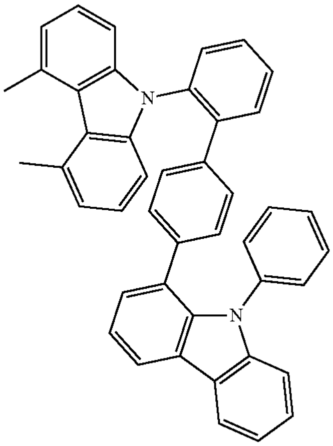
-continued
K10
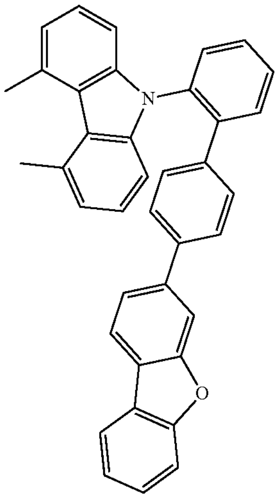
K11
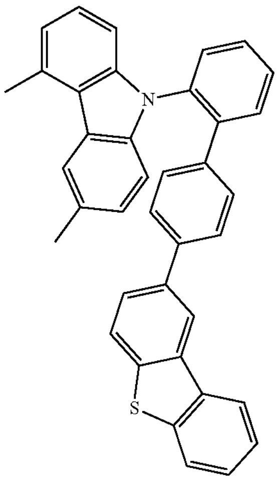
K12
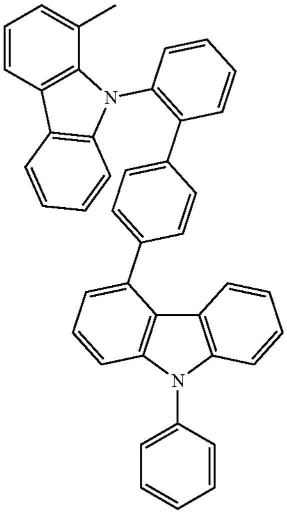

-continued
K13
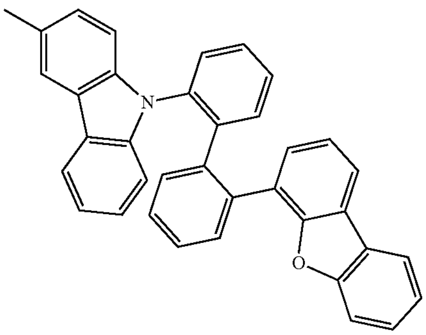
K14
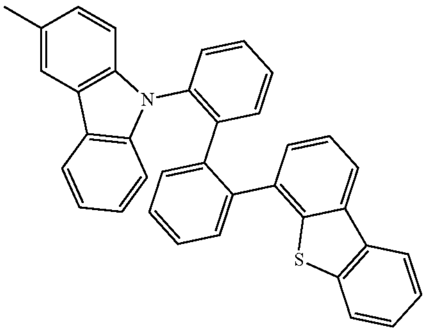
K15
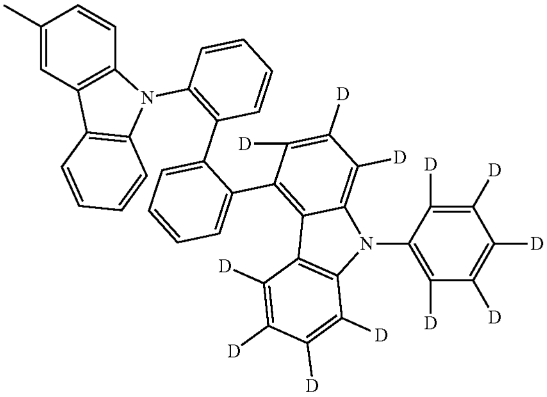
L1
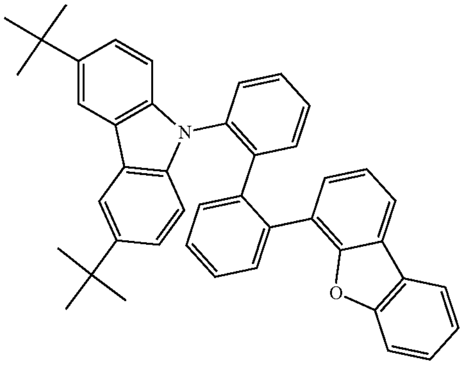
-continued
L2
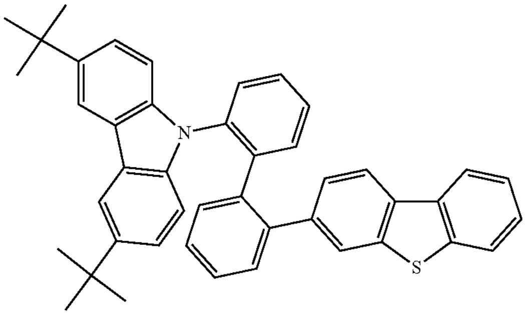
L3
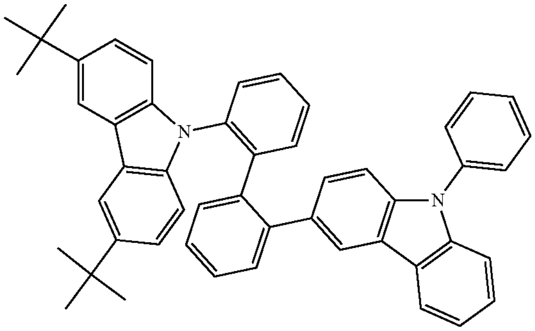
L4
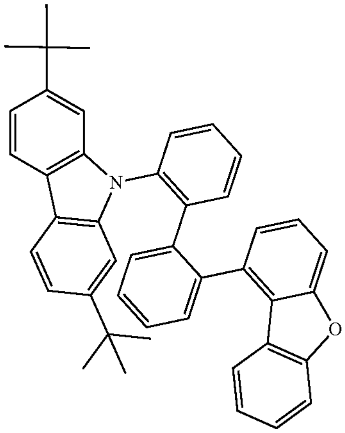

-continued
L5
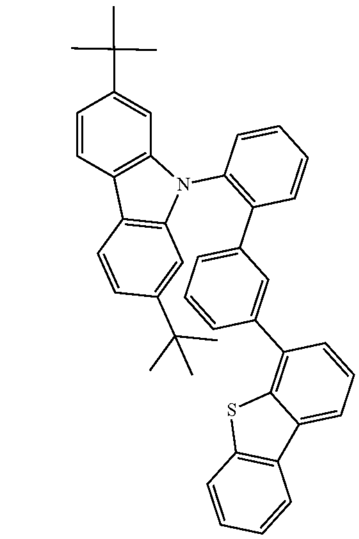
L6
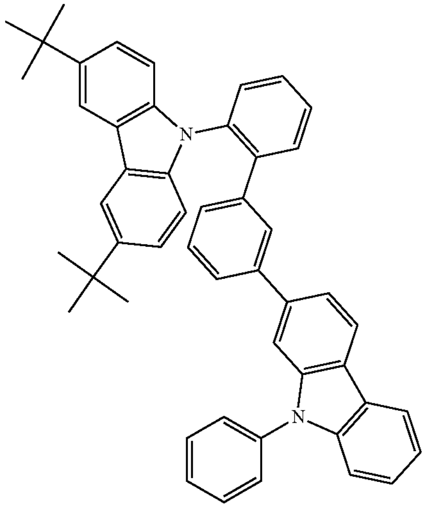
L7
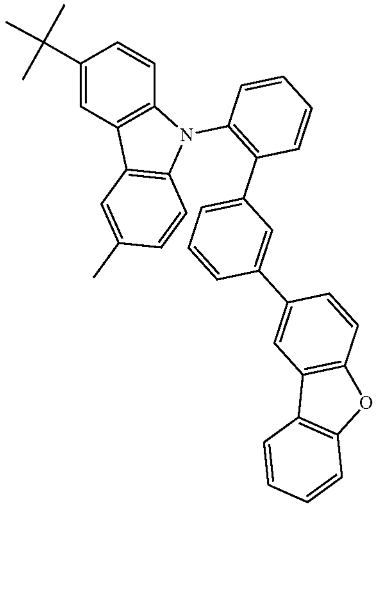
-continued
L8
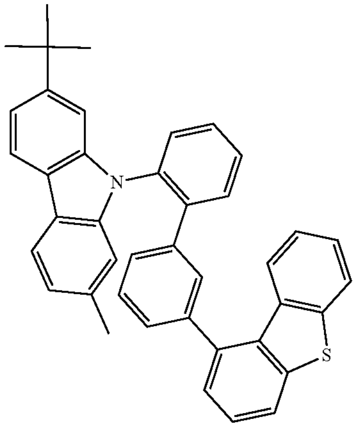
L9
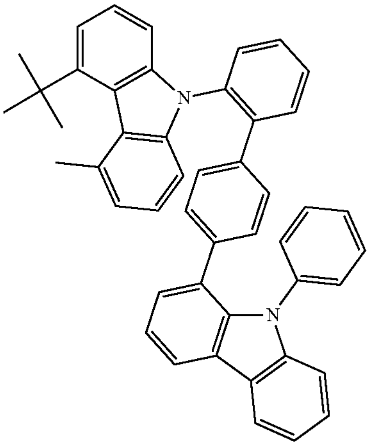
L10
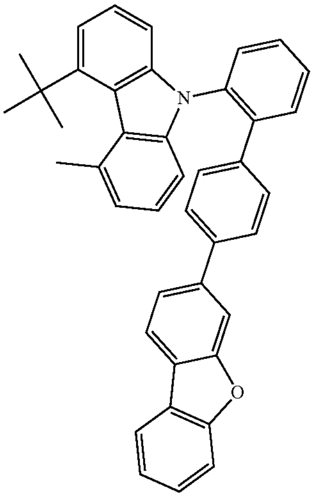

-continued
L11
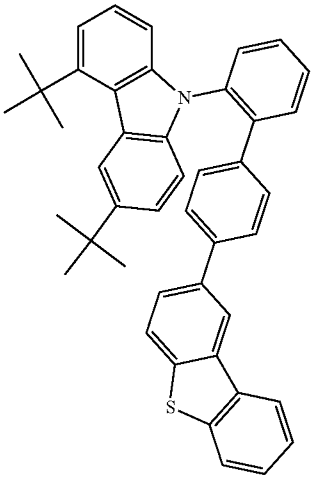
L12
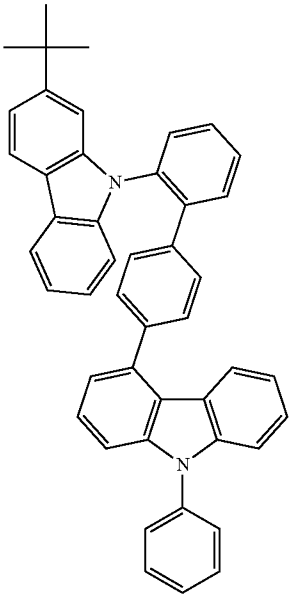
L13
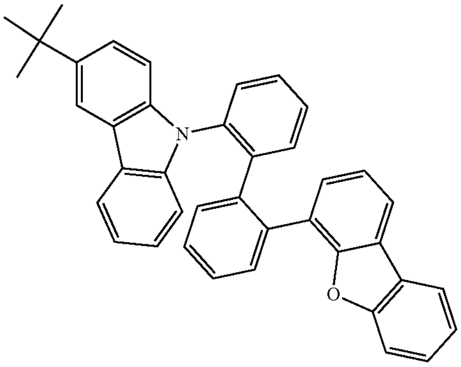
-continued
L14
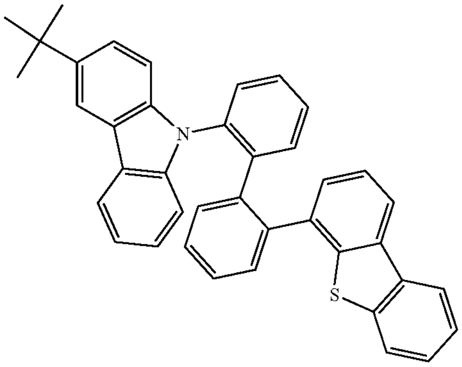
L15
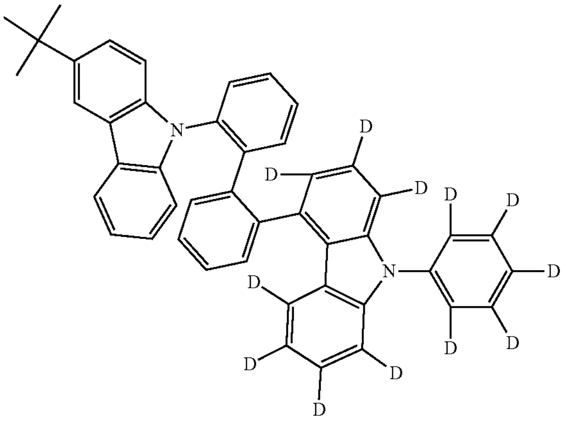
M1
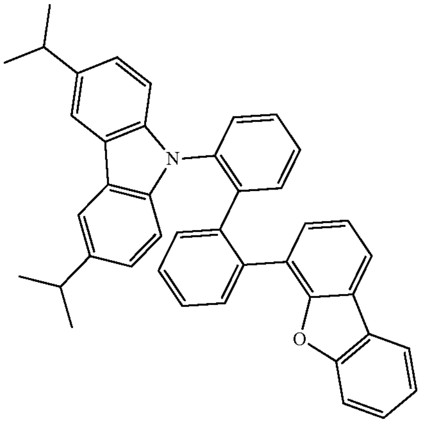
M2
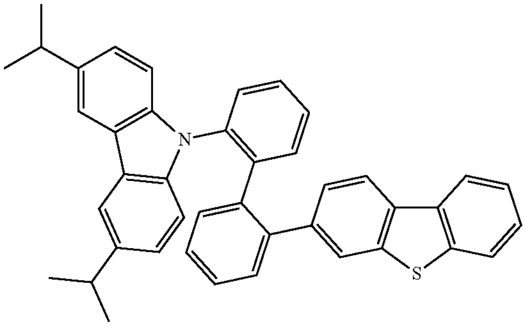

-continued
M3
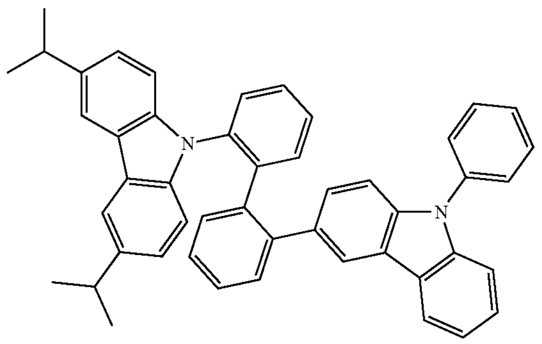
M4
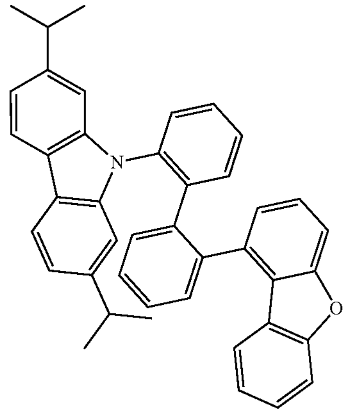
M5
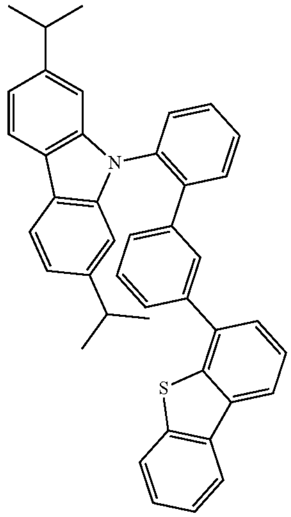
-continued
M6
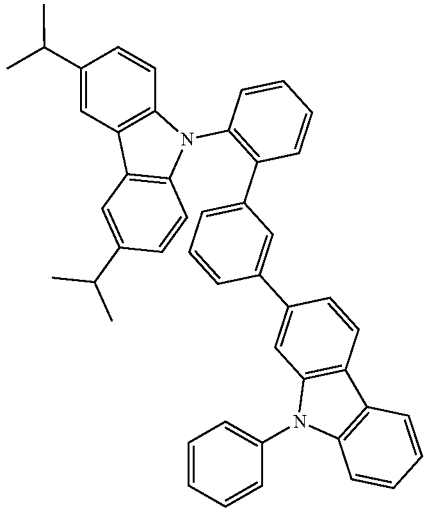
M7
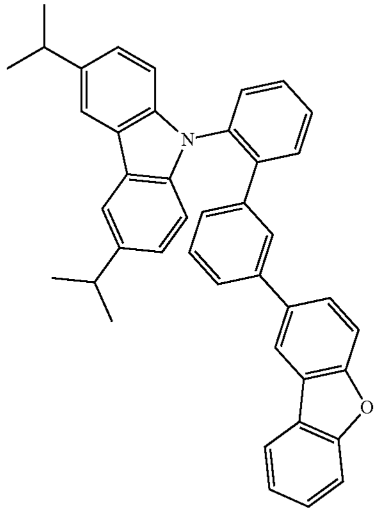
M8
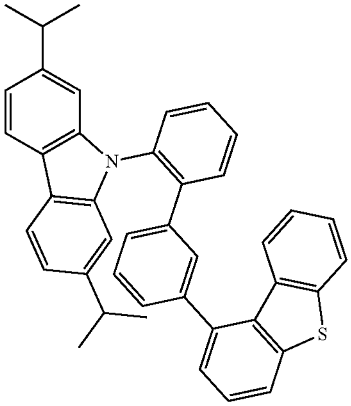

M9
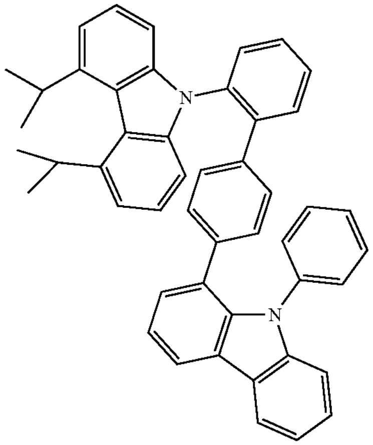
M10
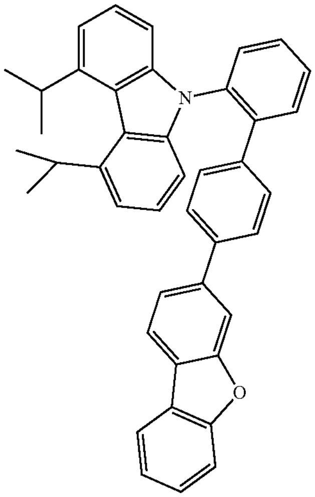
M11
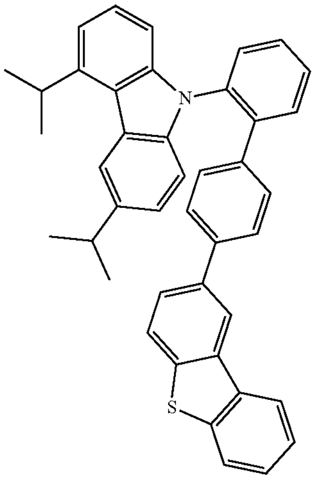
M12
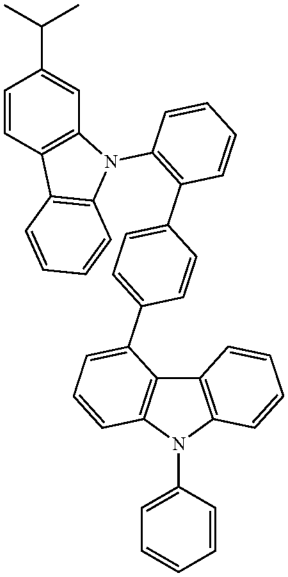
M13
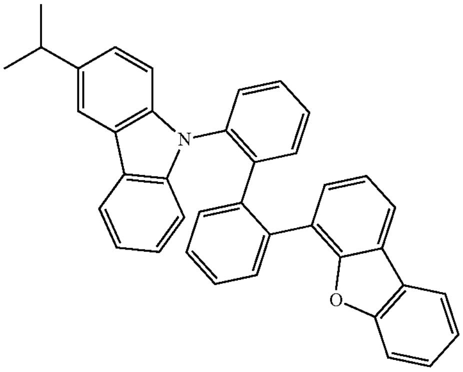
M14
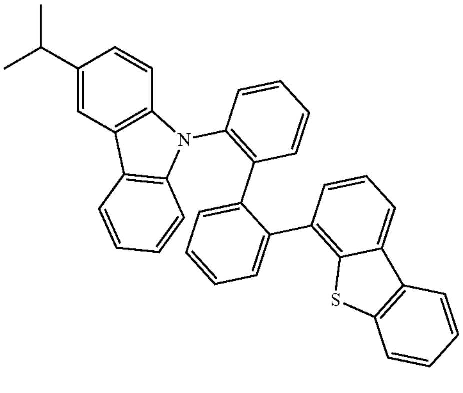

-continued
M15
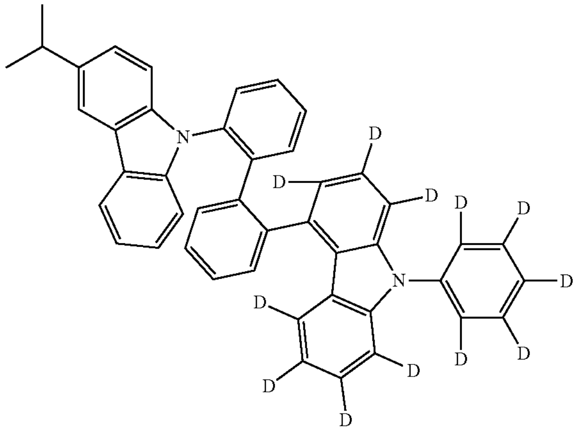
N1
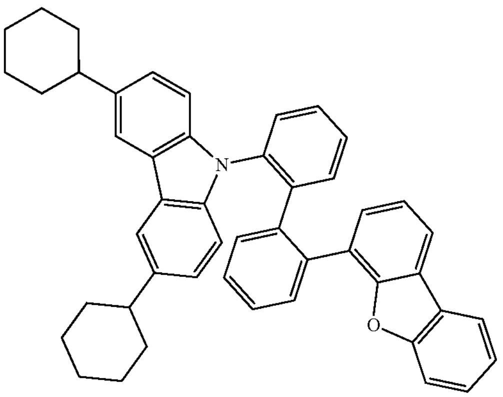
N2
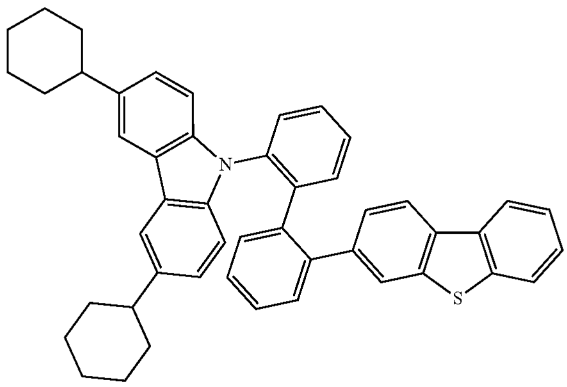
-continued
N3
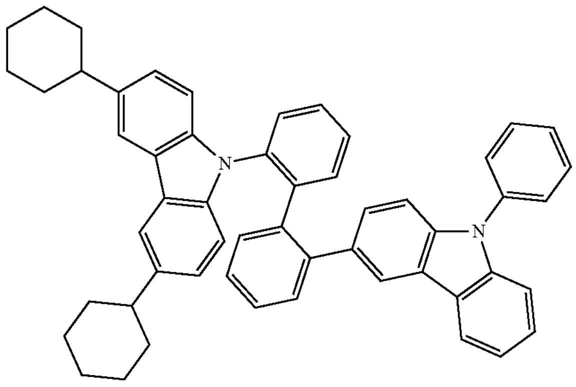
N4
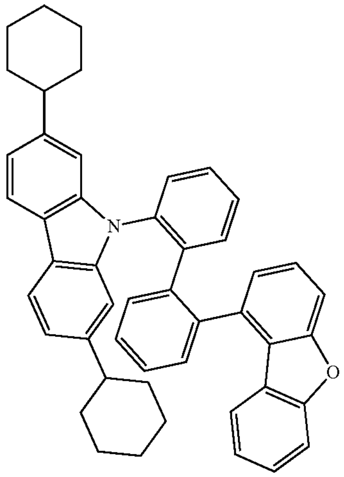
N5
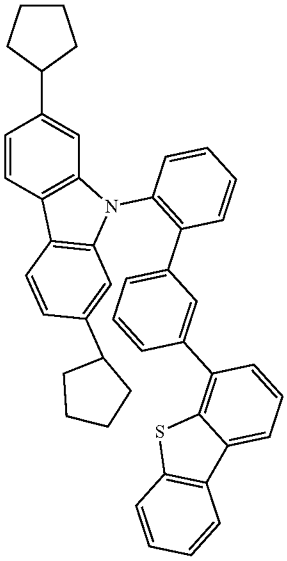

-continued
N6
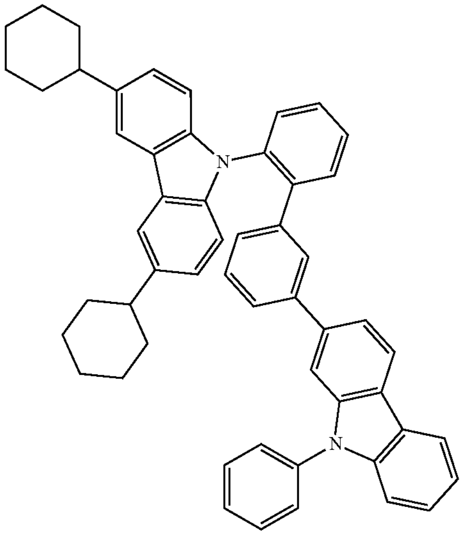
N7
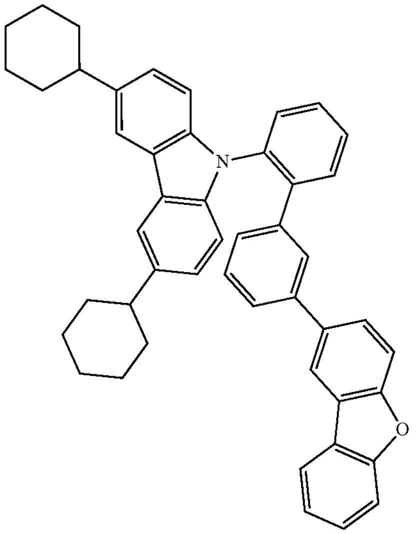
N8
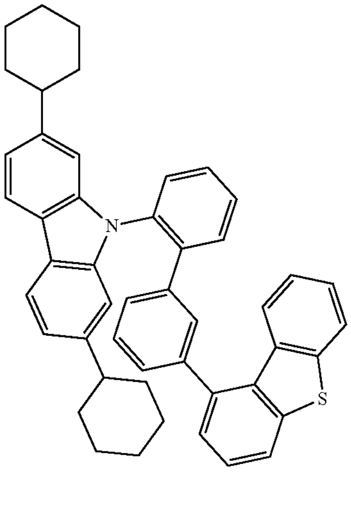
-continued
N9
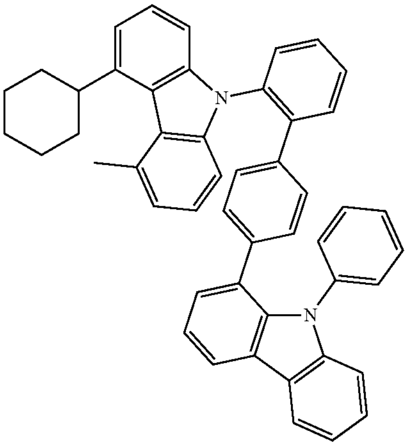
N10
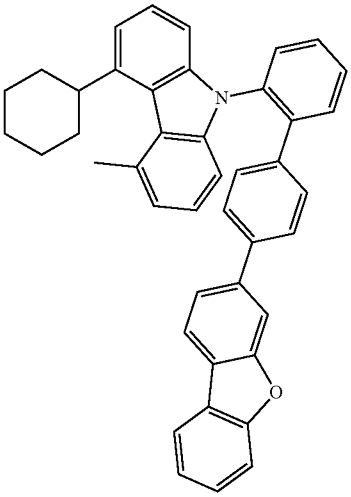
N11
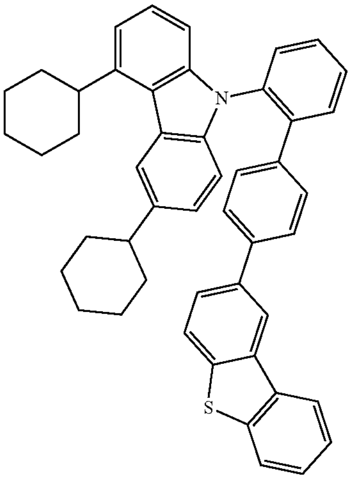

-continued
N12
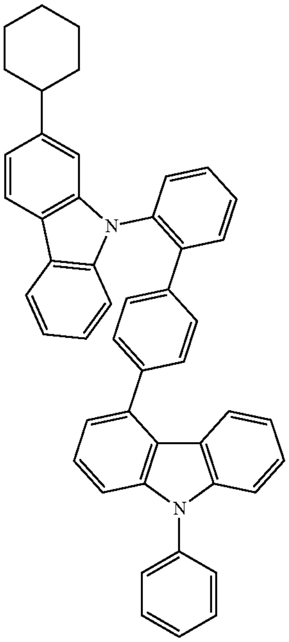
N13
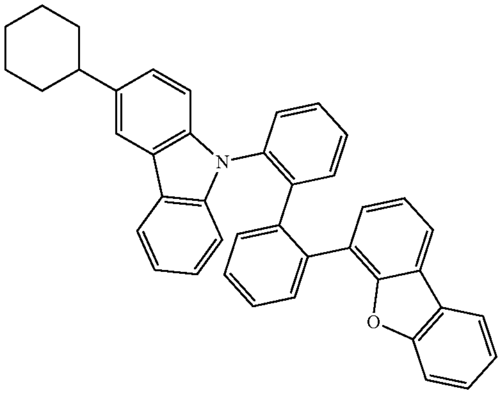
N14
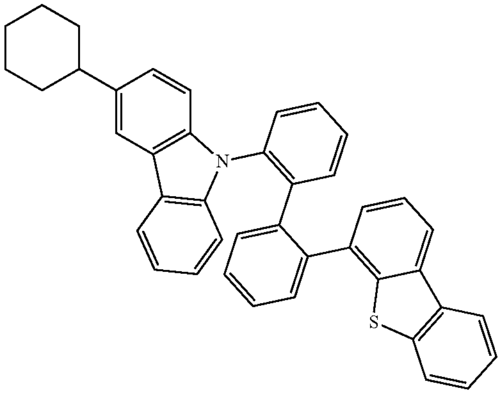
-continued
N15
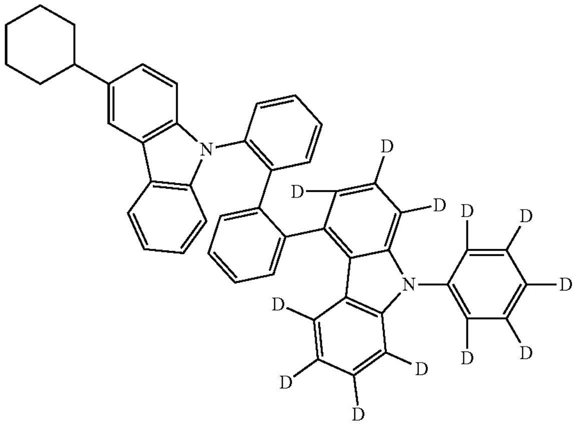
O1
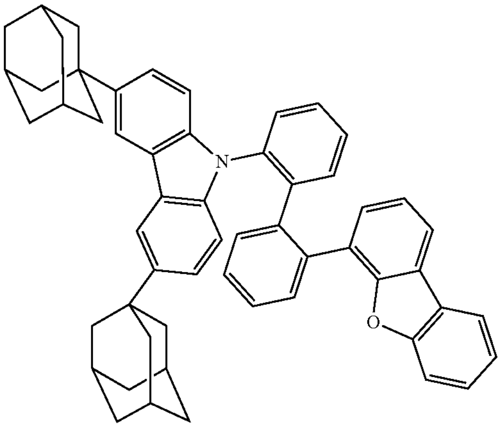
O2
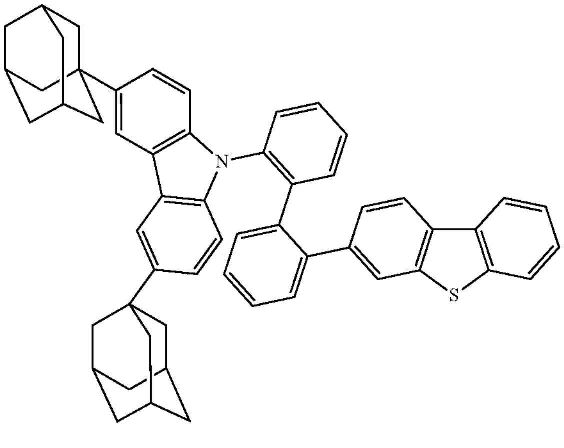

O3
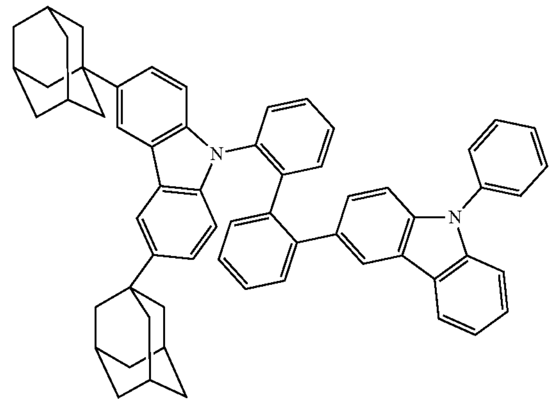
O4
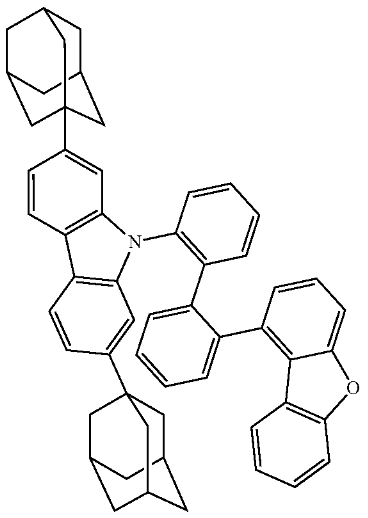
O5
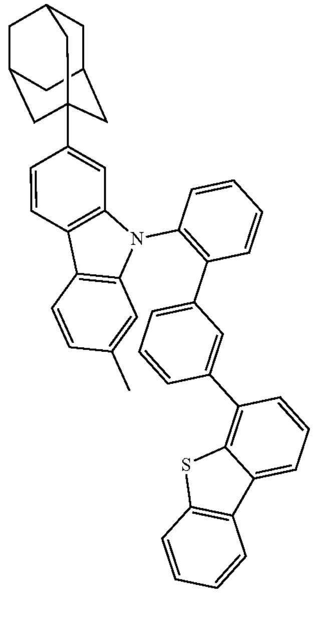
O6
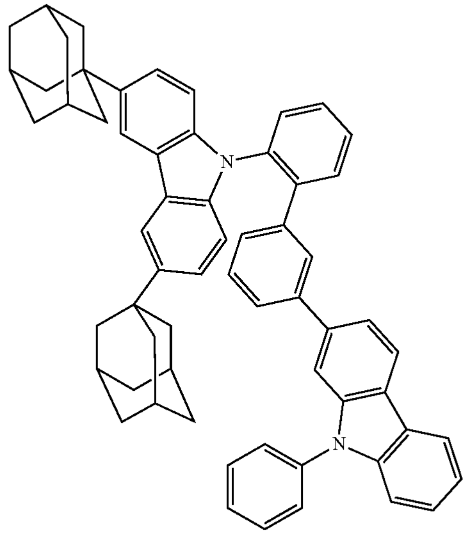
O7
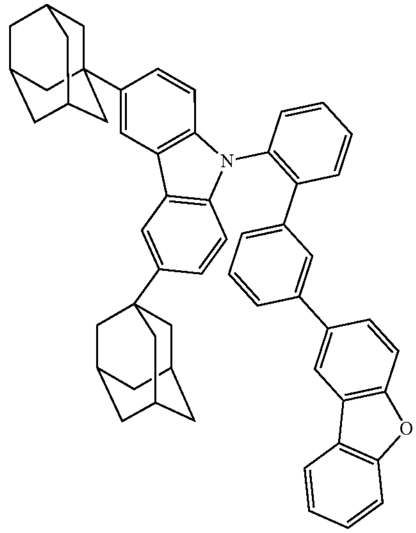
O8
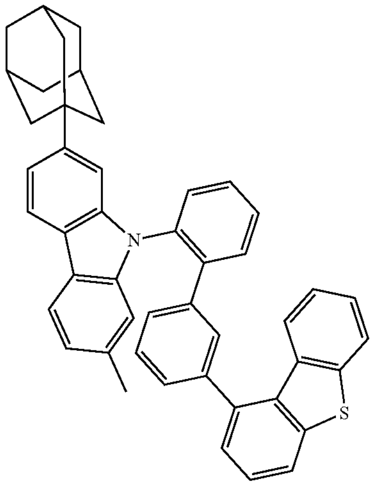

-continued
O9
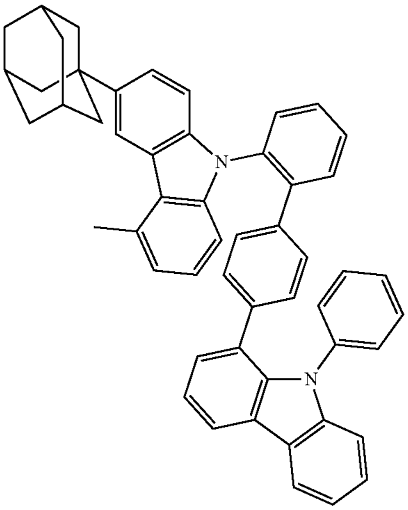
O10
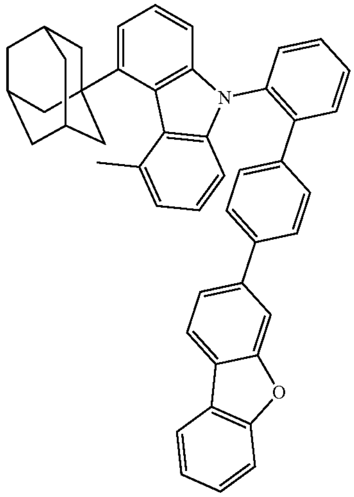
O11
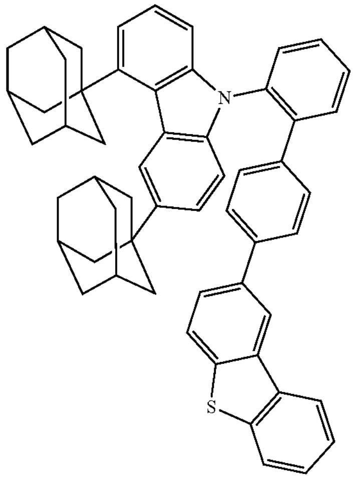
-continued
O12
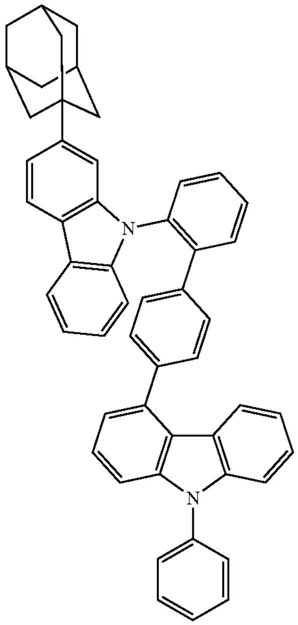
O13
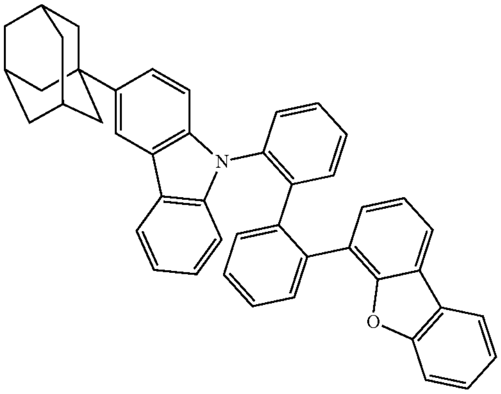
O14
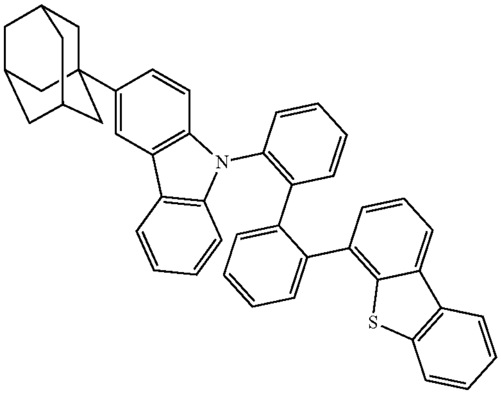

-continued
O15
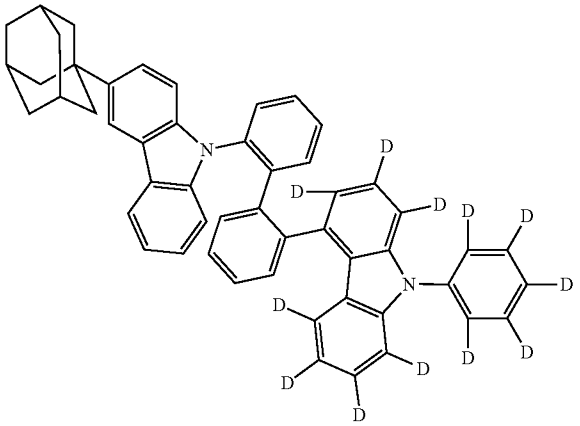
P1
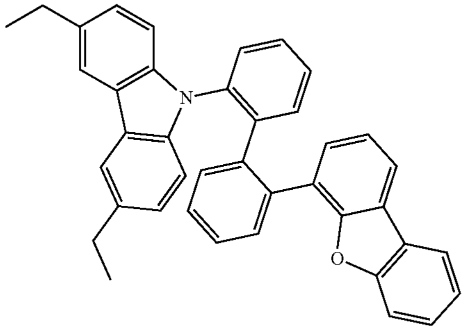
P2
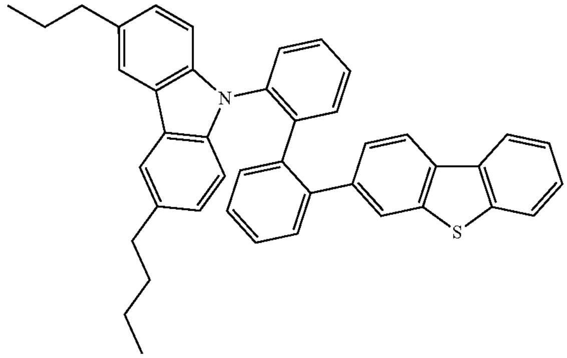
P3
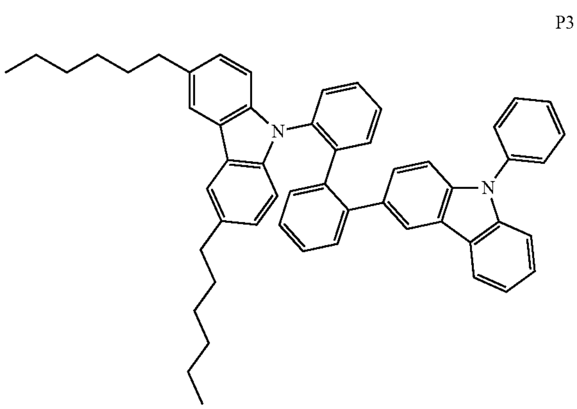
-continued
P4
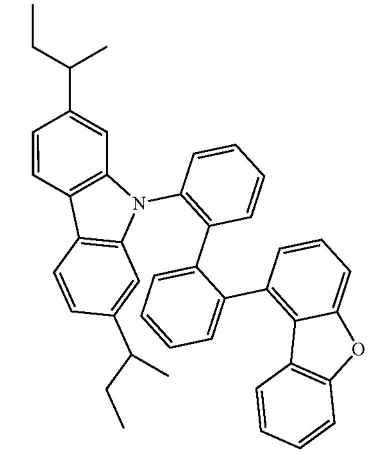
P5
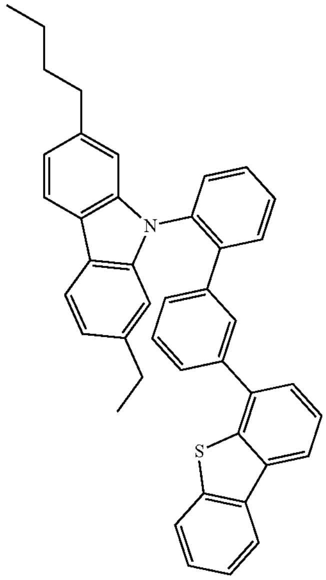
Compound Group 3
G1
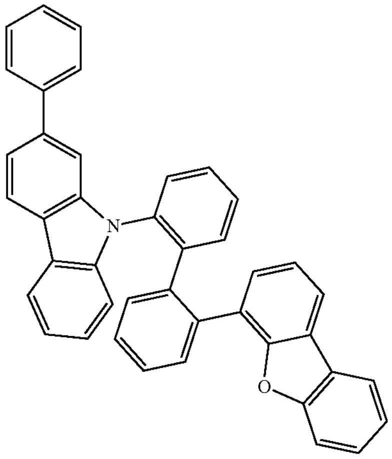

-continued
G2
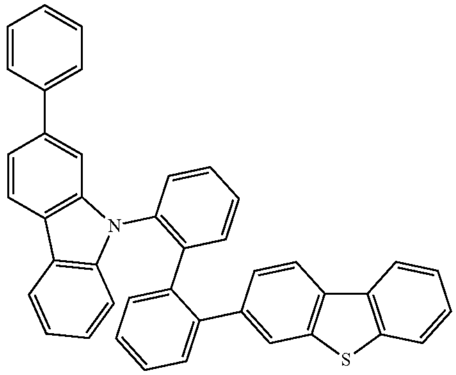
G3
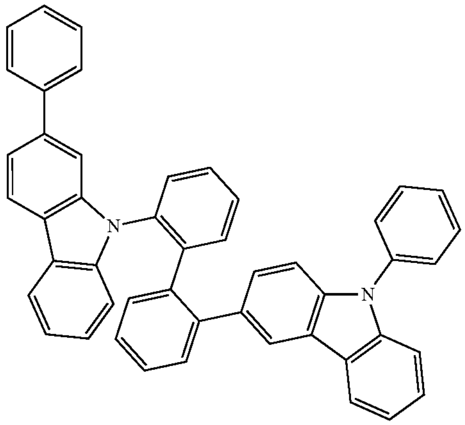
G4
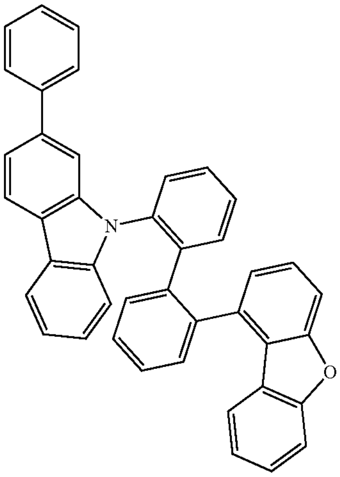
-continued
G5
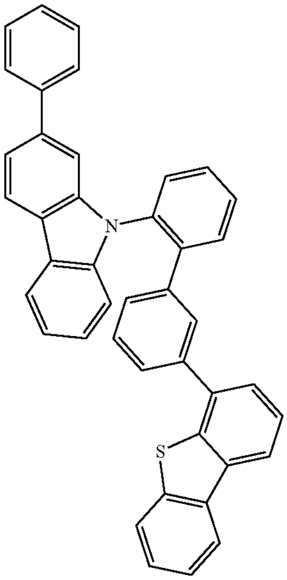
G6
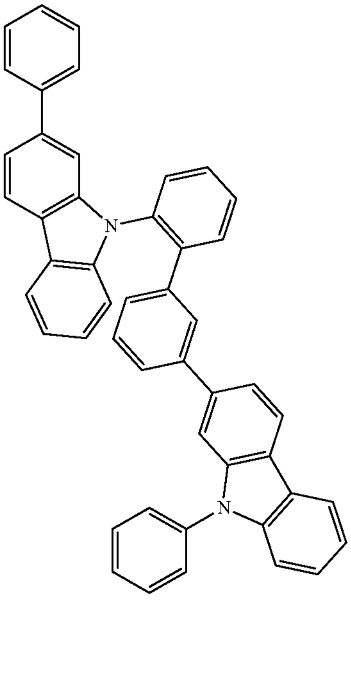

-continued
G7
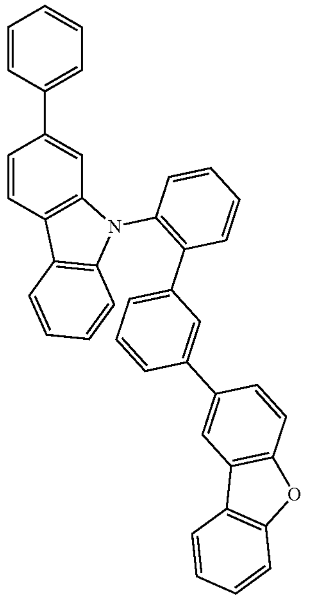
G8
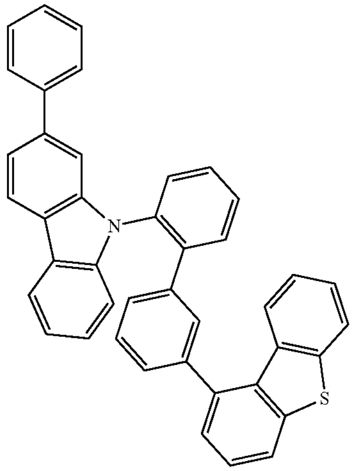
G9
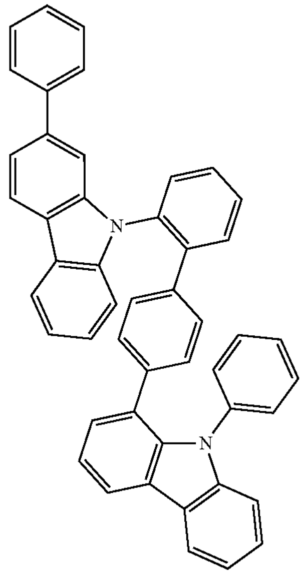
-continued
G10
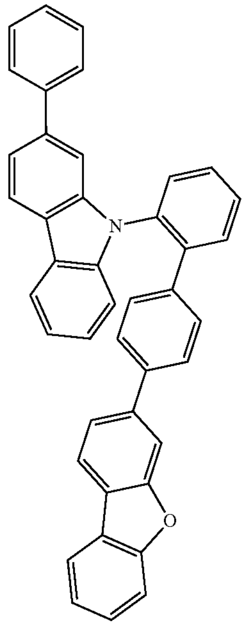
G11
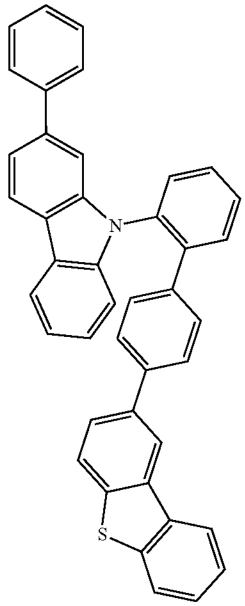

-continued
G12
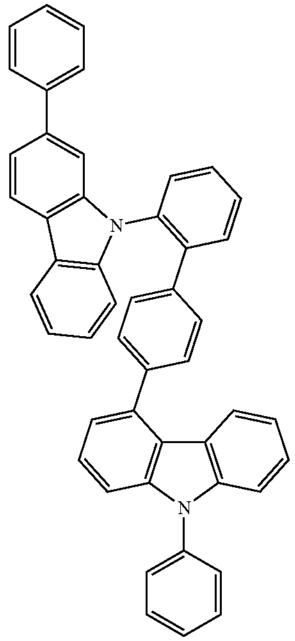
G13
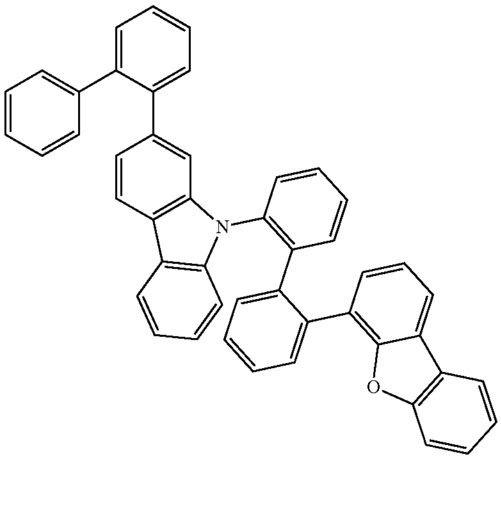
-continued
G14
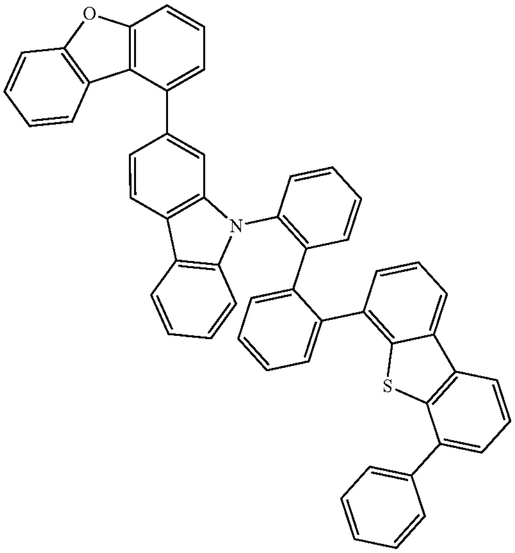
G15
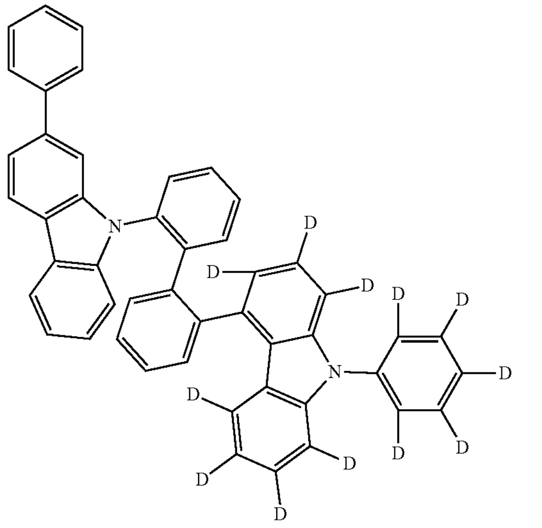
H1
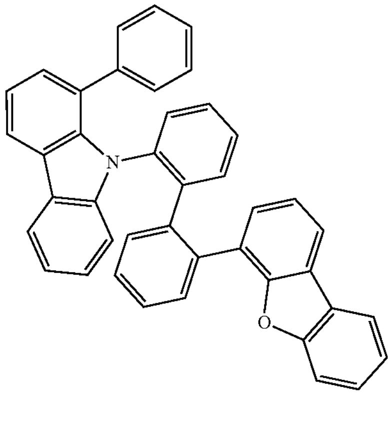

-continued
H2
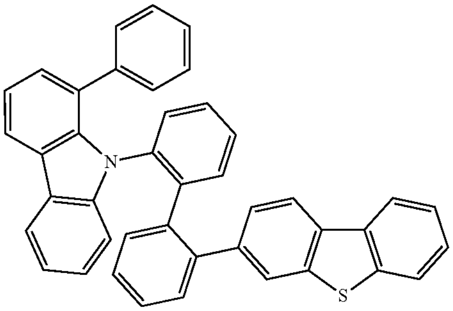
H3
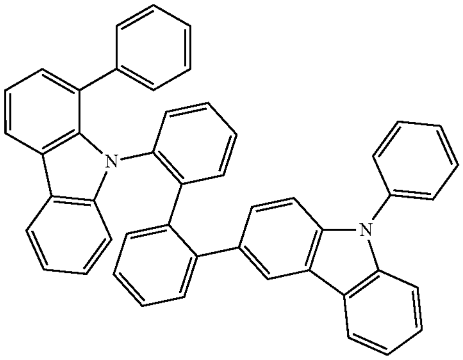
H4
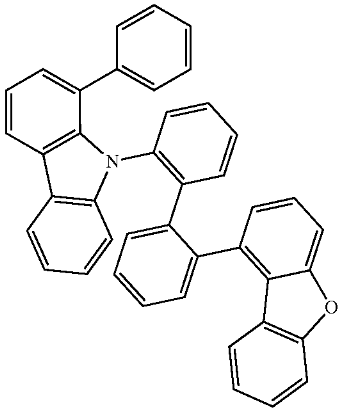
H5
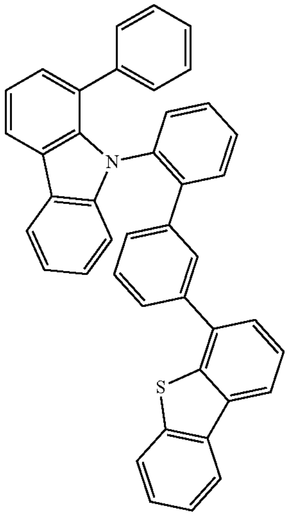
-continued
H6
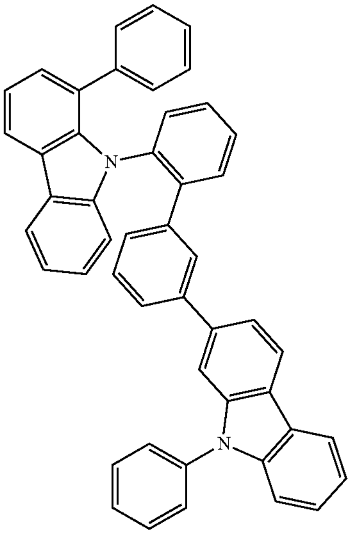
H7
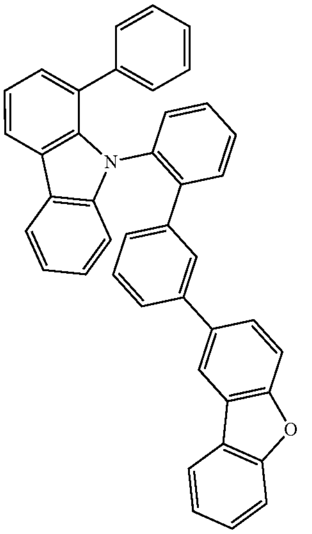
H8
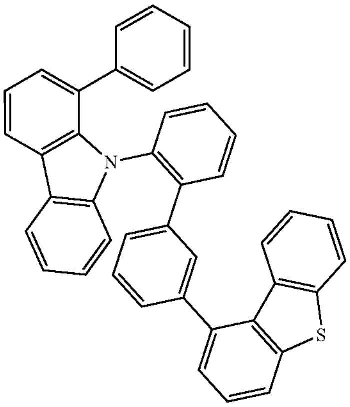

-continued
H9
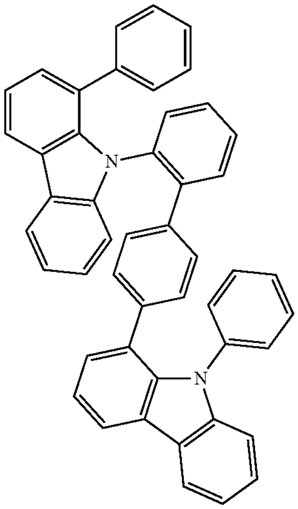
H10
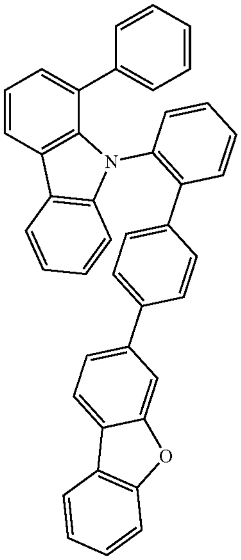
H11
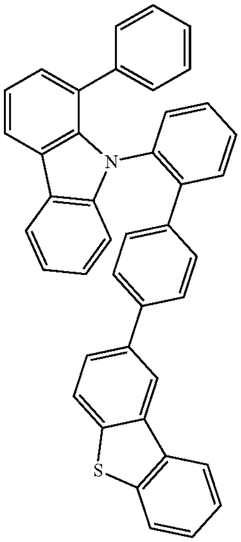
-continued
H12
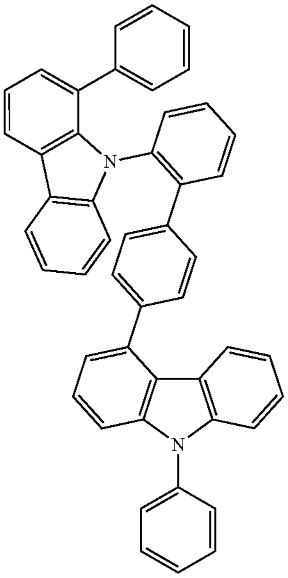
H13
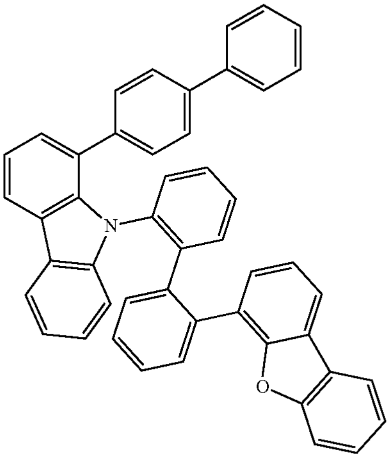
H14
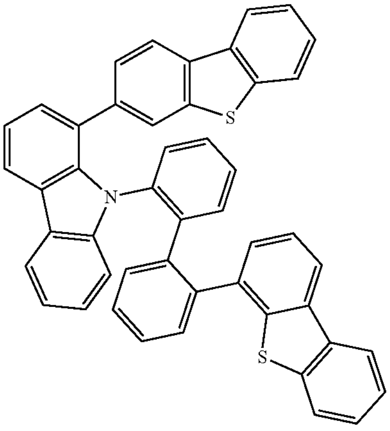

-continued
H15
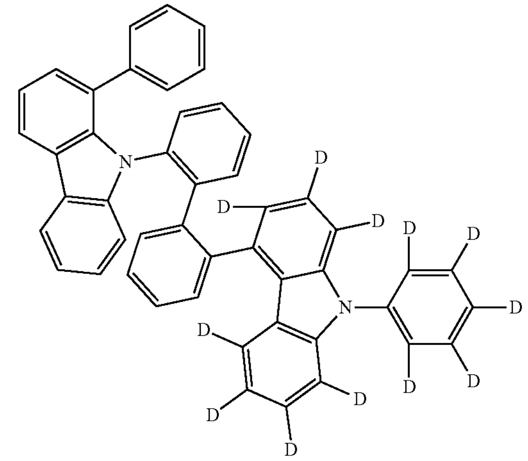
I1
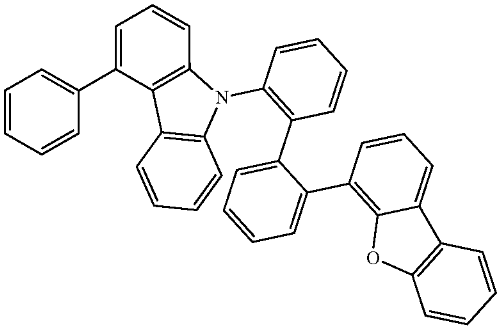
I2
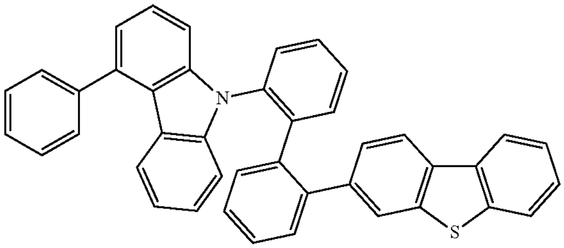
I3
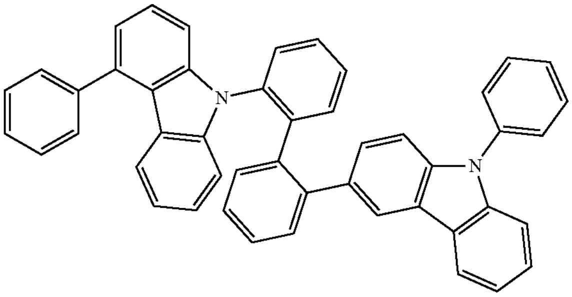
-continued
I4
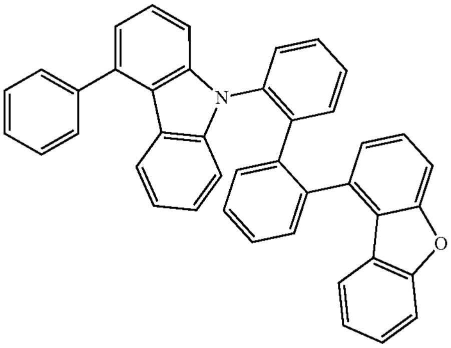
I5
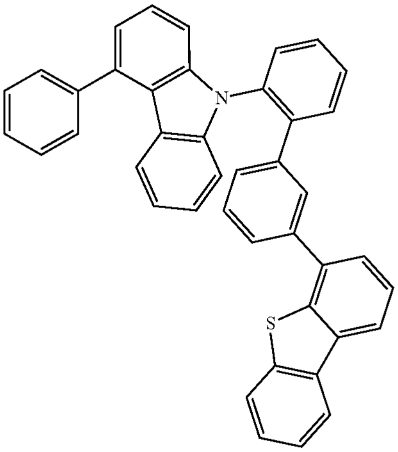
I6
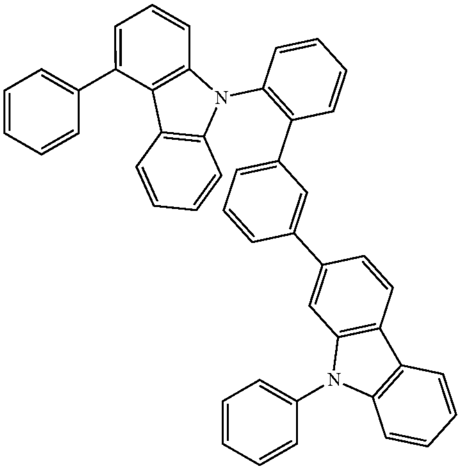

-continued
I7
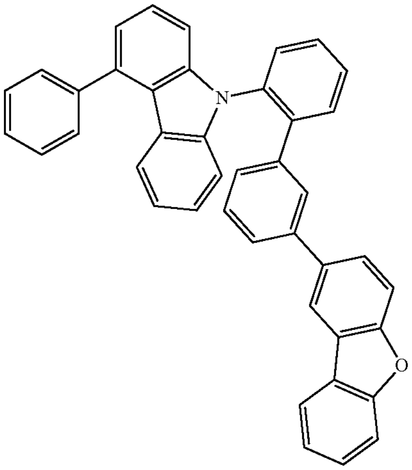
I8
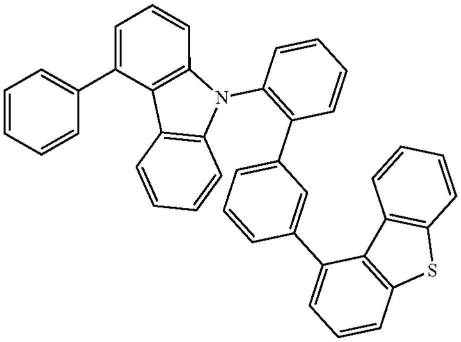
I9
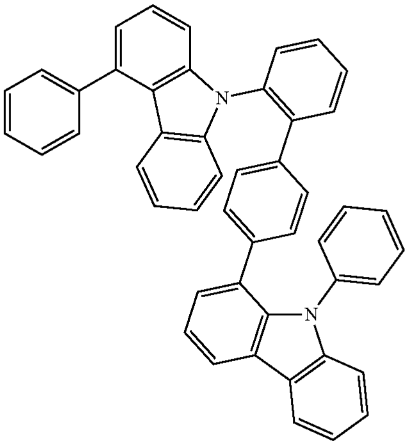
-continued
I10
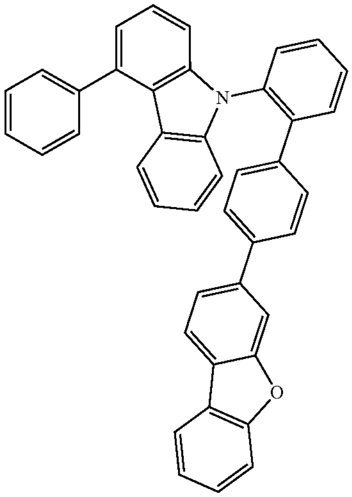
I11
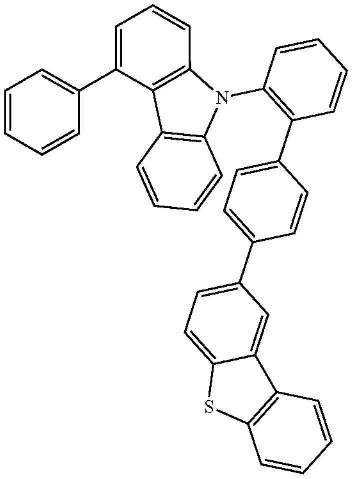
I12
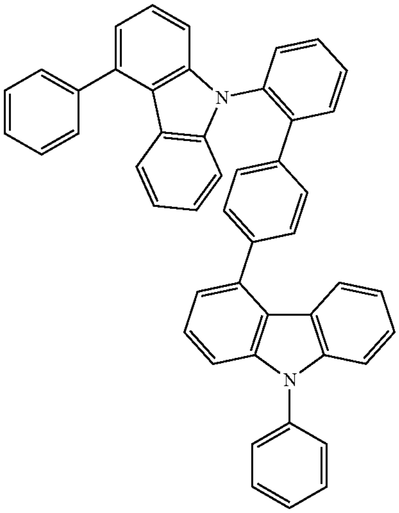

-continued

I13

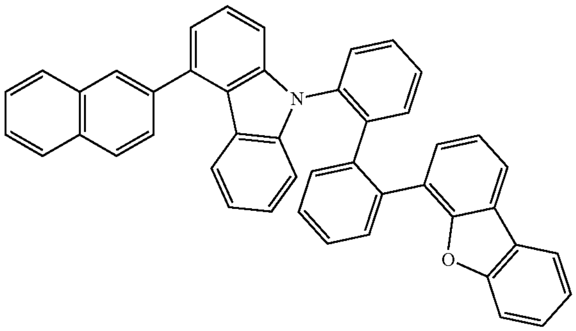

I14

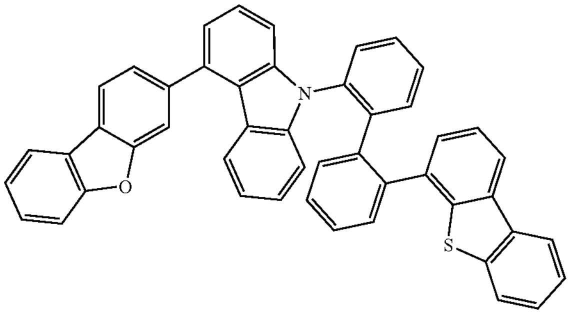

I15

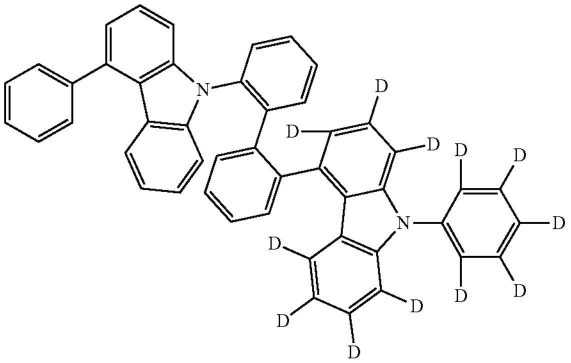

Referring to FIG. 3 to FIG. 6 again, embodiments of the luminescence device ED will be explained.

As described above, a hole transport region HTR includes an embodiment of the aforementioned nitrogen-containing compound. For example, the hole transport region HTR includes the nitrogen-containing compound represented by Formula 1.

If the hole transport region HTR has a multilayer structure having multiple layers, any one layer of the multiple layers may include the nitrogen-containing compound represented by Formula 1. For example, a hole transport region HTR may include a hole injection layer HIL disposed on a first electrode EL1 and a hole transport layer HTL disposed on the hole injection layer HIL, and the hole transport layer HTL may include the nitrogen-containing compound represented by Formula 1. However, the embodiments are not limited thereto, and for example, the hole injection layer HIL may include the nitrogen-containing compound represented by Formula 1.

The hole transport region HTR may include one or two or more types of the nitrogen-containing compound represented by Formula 1. For example, the hole transport region HTR may include at least one selected from the compounds represented in Compound Groups 1 to 3. The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may further include a compound represented by Formula H-1 below.

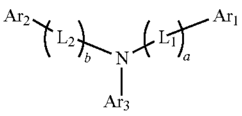

Formula H-1

In Formula H-1 above, $L_1$ and $L_2$ may be each independently a direct linkage, a substituted or unsubstituted arylene group of 6 to 30 ring-forming carbon atoms, or a substituted or unsubstituted heteroarylene group of 2 to 30 ring-forming carbon atoms. When "a" and "b" may be each independently an integer of 0 to 10. If "a" or "b" is an integer of 2 or more, multiple $L_1$ and $L_2$ may be each independently a substituted or unsubstituted arylene group of 6 to 30 ring-forming carbon atoms, or a substituted or unsubstituted heteroarylene group of 2 to 30 ring-forming carbon atoms.

In Formula H-1, $Ar_1$ and $Ar_2$ may be each independently a substituted or unsubstituted aryl group of 6 to 30 ring-forming carbon atoms, or a substituted or unsubstituted heteroaryl group of 2 to 30 ring-forming carbon atoms. In addition, in Formula H-1, $Ar_3$ may be a substituted or unsubstituted aryl group of 6 to 30 ring-forming carbon atoms.

The compound represented by Formula H-1 may be a monoamine compound. Otherwise, the compound represented by Formula H-1 may be a diamine compound in which at least one of $Ar_1$ to $Ar_3$ includes an amine group as a substituent. In addition, the compound represented by Formula H-1 may be a carbazole-based compound in which at least one of $Ar_1$ to $Ar_3$ includes a substituted or unsubstituted carbazole group, or a fluorene-based compound in which at least one of $Ar_1$ to $Ar_3$ includes a substituted or unsubstituted fluorene group.

The compound represented by Formula H-1 may be represented by any one of the compounds in Compound Group H below. However; the compounds shown in Compound Group H are only illustrations, and the compound represented by Formula H-1 is not limited to the compounds represented in Compound Group H below.

Compound Group H

H-1-1

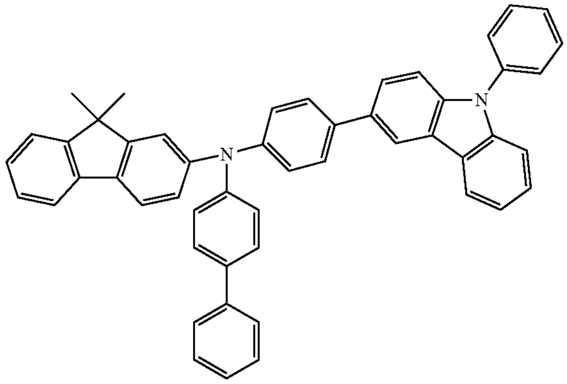

-continued
H-1-2
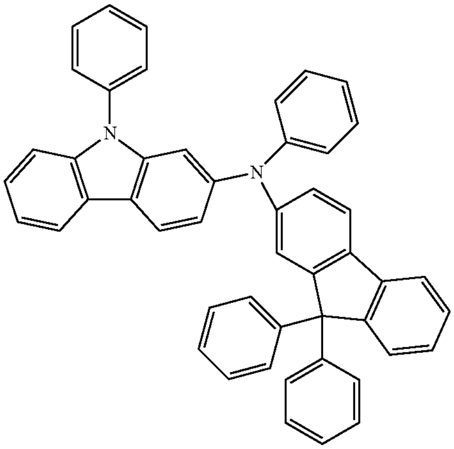
H-1-3
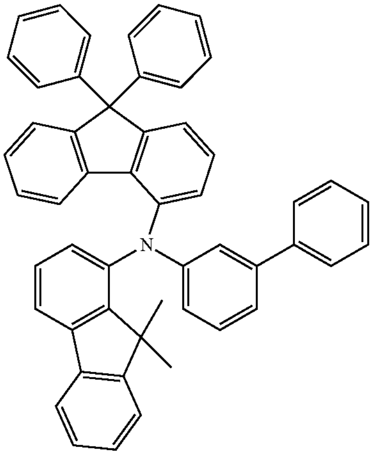
H-1-4
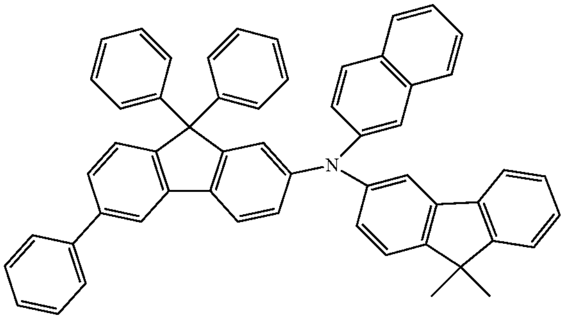
H-1-5
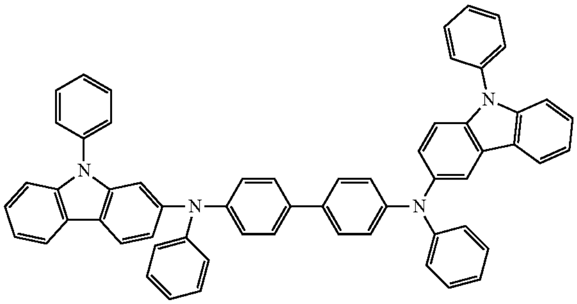
-continued
H-1-6
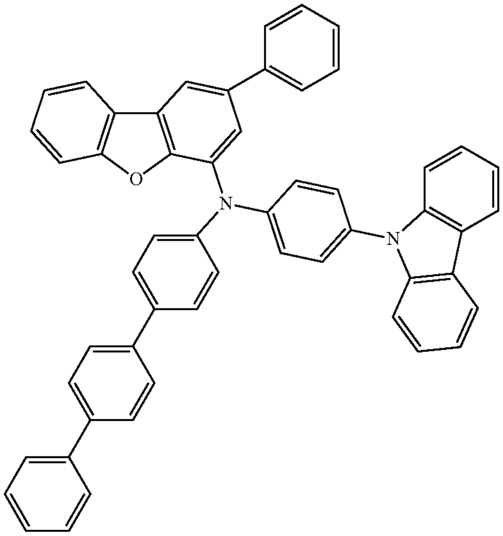
H-1-7
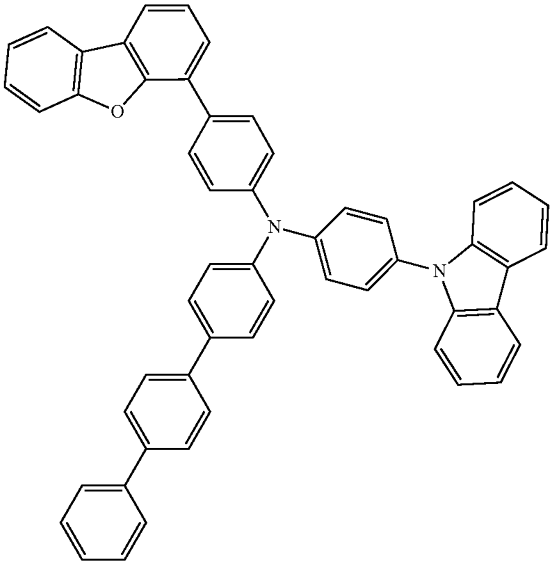
H-1-8
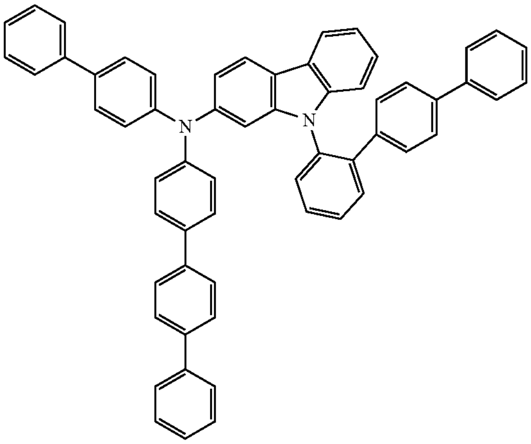

-continued
H-1-9
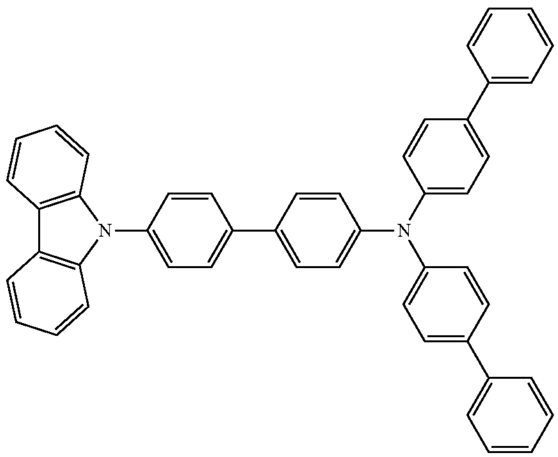
H-1-10
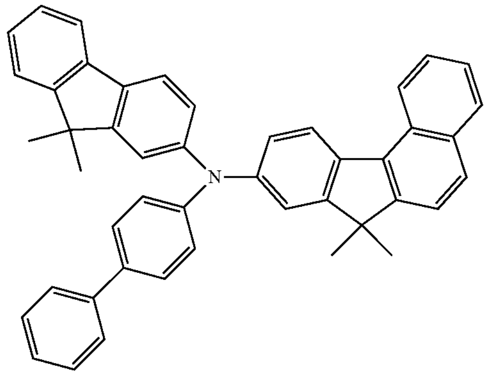
H-1-11
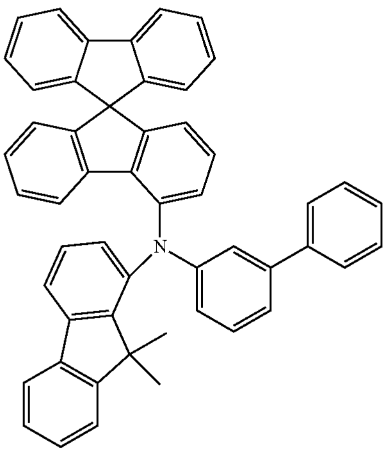
-continued
H-1-12
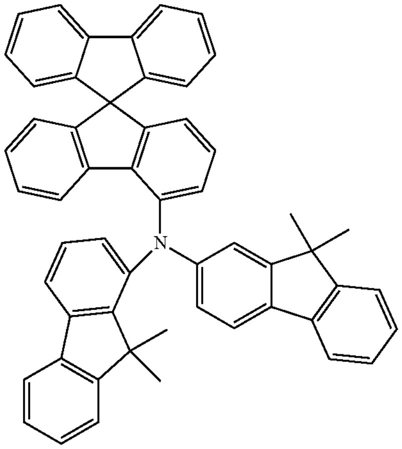
H-1-13
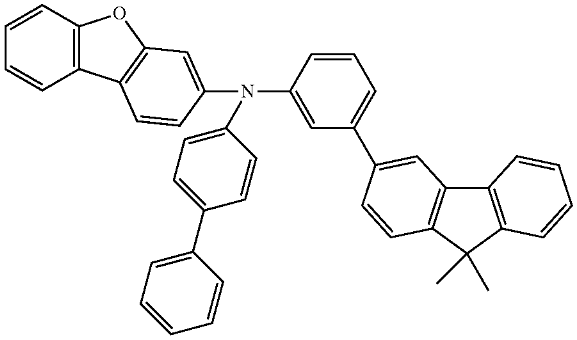
H-1-14
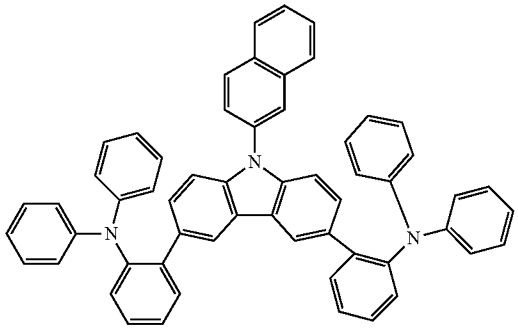
H-1-15
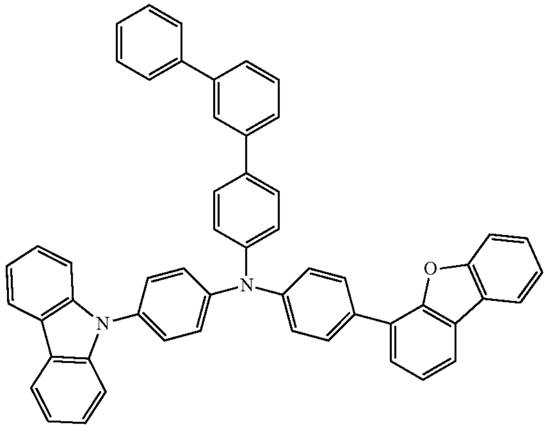

-continued

H-1-16

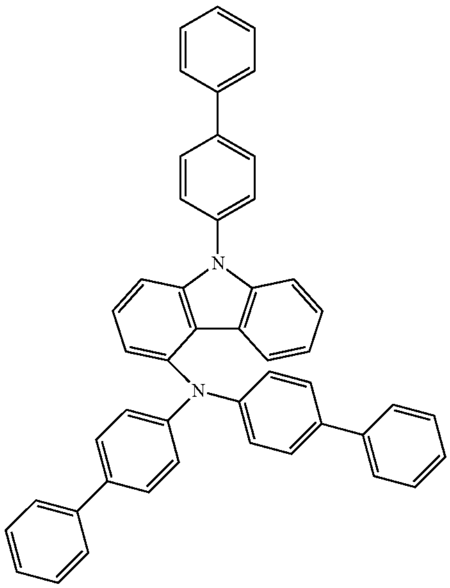

H-1-17

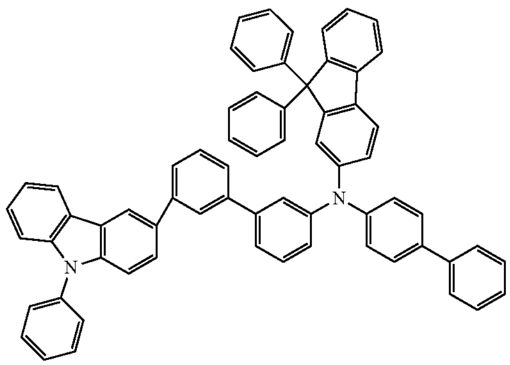

H-1-18

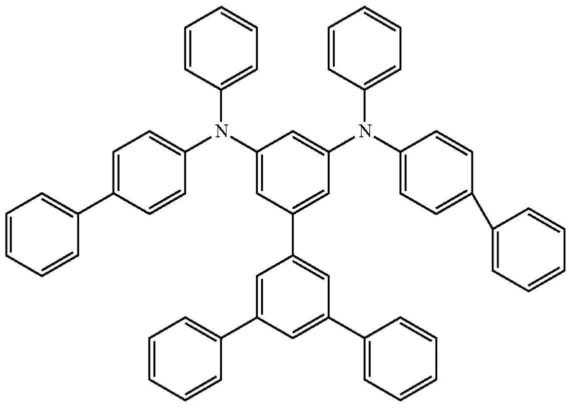

-continued

H-1-19

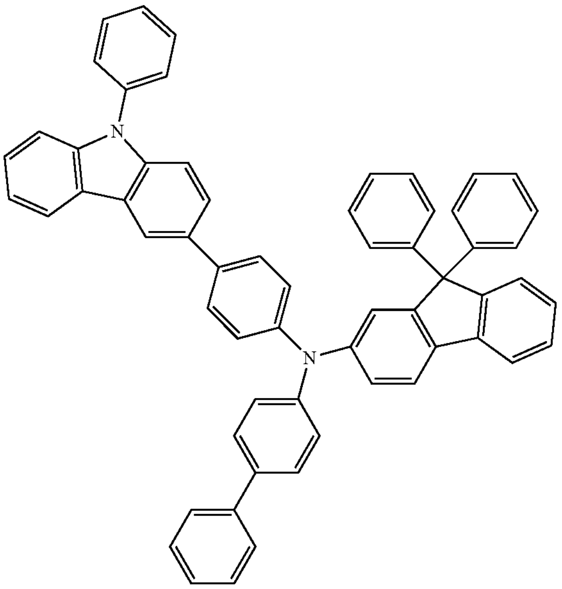

The hole transport region HTR may include a phthalocyanine compound such as copper phthalocyanine, $N^1,N^{1'}$-([1,1'-biphenyl]-4,4'-diyl)bis($N^1$-phenyl-$N^4,N^4$-di-m-tolyl-benzene-1,4-diamine) (DNTPD), 4,4',4"-[tris(3-methylphenyl)phenylamino]triphenylamine (m-MTDATA), 4,4',4"-tris(N,N-diphenylamino)triphenylamine (TDATA), 4,4',4"-tris[N(1-naphthyl)-N-phenylamino]-triphenylamine (1-TNATA), 4,4',4"-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-including polyetherketone (TPAPEK), 4-isopropyl-4'-methyldiphenyliodonium [tetrakis(pentafluorophenyl) borate], and dipyrazino[2,3-f:2',3'-h]quinoxaline-2,3,6,7,10,11-hexacarbonitrile (HAT-CN).

The hole transport region HTR may include, for example, carbazole derivatives such as N-phenyl carbazole and polyvinyl carbazole, fluorene-based derivatives, N,N'-bis(3-methylphenyl)-N,N'-diphenyl-[1,1'-biphenyl]-4,4'-diamine (TPD), triphenylamine-based derivatives such as 4,4',4"-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzeneamine (TAPC), 4,4'-bis[N,N'-(3-tolyl)amino]-3,3'-dimethylbiphenyl (HMTPD), 1,3 di(carbazol-9-yl)benzene (mCP), etc.

The hole transport region HTR may include 9-(4-tert-butylphenyl)-3,6-bis(triphenylsilyl)-9H-carbazole (CzSi), 9-phenyl-9H-3,9'-bicarbazole (CCP), 1,3-bis(1,8-dimethyl-9H-carbazol-9-yl)benzene (mDCP), etc. The hole transport region HTR may include the compounds of the hole transport region in at least one of the hole injection layer HIL, hole transport layer HTL, and electron blocking layer EBL.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å. The thickness of the hole transport layer HTL may be from about 30 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may further include a charge generating material to increase conductivity in addition to the above-described materials. The charge generating material may be dispersed uniformly or non-uniformly in the hole transport region HTR. The charge generating material may be, for example, a p-dopant. The p-dopant may include any one of quinone derivatives, metal oxides, and cyano group-containing compounds, without limitation. For example, non-limiting examples of the p-dopant may include quinone derivatives such as tetracyanoquinodimethane (TCNQ) and 2,3,5,6-tetrafluoro-7,7',8,8-tetracyanoquinodimethane (F4-TCNQ), metal oxides such as a tungsten oxide and a molybdenum oxide, etc., without limitation.

As described above, the hole transport region HTR may further include at least one of a hole buffer layer or an electron blocking layer EBL in addition to the hole injection layer HIL and the hole transport layer HTL. The hole buffer layer may compensate resonance for a distance according to the wavelength of light emitted from an emission layer EML and, although not wanting to be bound by theory, may increase light emitting efficiency. As materials included in the hole buffer layer, materials which may be included in the hole transport region HTR may be used. The electron blocking layer EBL is a layer playing the role of blocking the injection of electrons from an electron transport region ETR to a hole transport region HTR.

The emission layer EML is provided on the hole transport region HTR. The emission layer EML may have a thickness of, for example, about 100 Å to about 1,000 Å or about 100 Å to about 300 Å. The emission layer EML may have a single layer formed using a single material, a single layer formed using multiple different materials, or a multilayer structure having multiple layers formed using multiple different materials.

In an embodiment the luminescence device ED, the emission layer EML may include anthracene derivatives, pyrene derivatives, fluoranthene derivatives, chrysene derivatives, dihydrobenzanthracene derivatives, or triphenylene derivatives. Particularly, the emission layer EML may further include anthracene derivatives or pyrene derivatives.

In the luminescence devices ED, shown in FIG. 3 to FIG. 6, the emission layer EML may include a host and a dopant, and the emission layer EML may include a compound represented by Formula E-1 below. The compound represented by Formula E-1 below may be used as a fluorescence host material.

Formula E-1

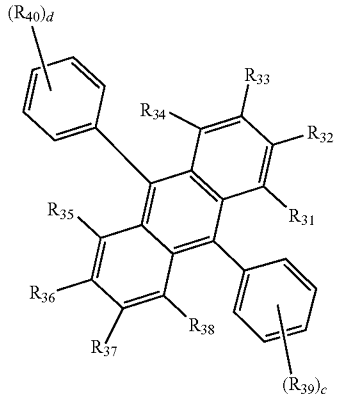

In Formula E-1, $R_{31}$ to $R_{40}$ may be each independently a hydrogen atom, a deuterium atom, a halogen atom, a substituted or unsubstituted silyl group, a substituted or unsubstituted thio group, a substituted or unsubstituted oxy group, a substituted or unsubstituted alkyl group of 1 to 10 carbon atoms, a substituted or unsubstituted alkenyl group of 1 to 10 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring. The variables $R_{31}$ to $R_{40}$ may be combined with an adjacent group to form a saturated hydrocarbon ring, an unsaturated hydrocarbon ring, a saturated heterocycle, or an unsaturated heterocycle.

In Formula E-1, "c" and "d" may be each independently an integer of 0 to 5.

Formula E-1 may be represented by any one of Compound E1 to Compound E19 below.

E1

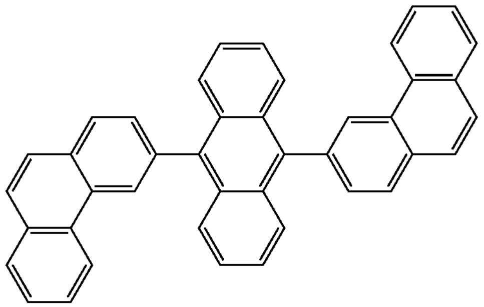

E2

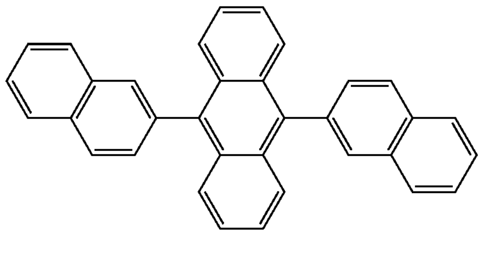

-continued
E3
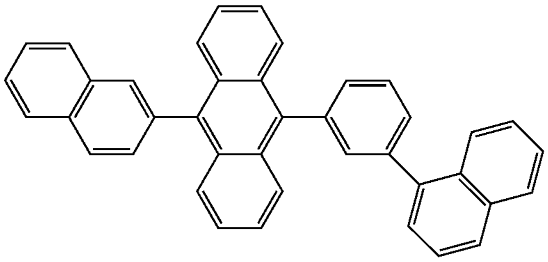
E4
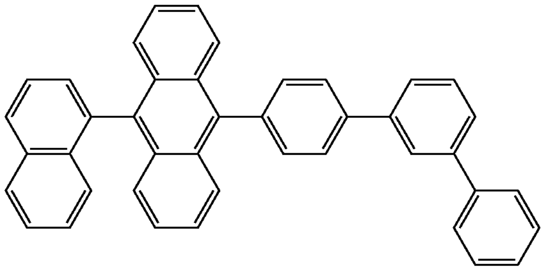
E5
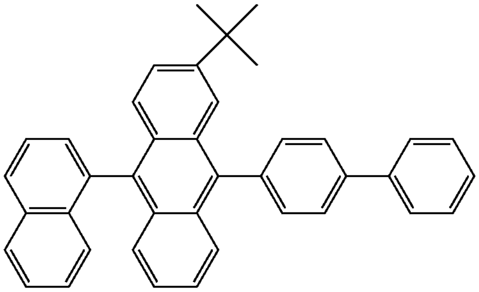
E6
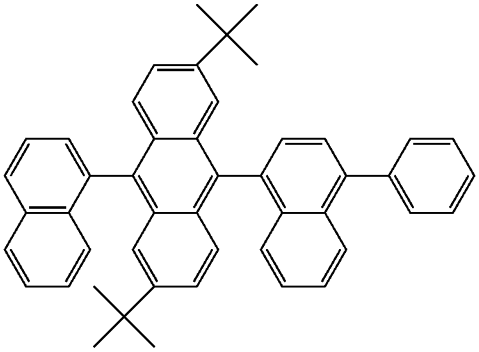
E7
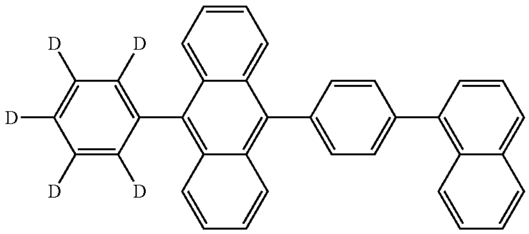
-continued
E8
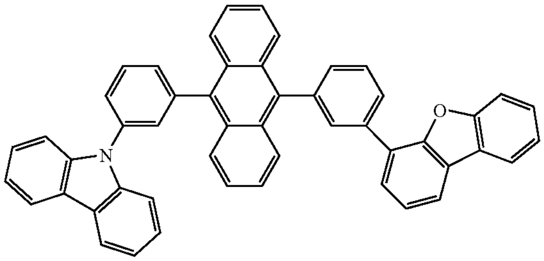
E9
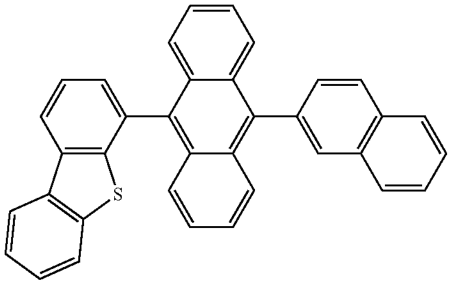
E10
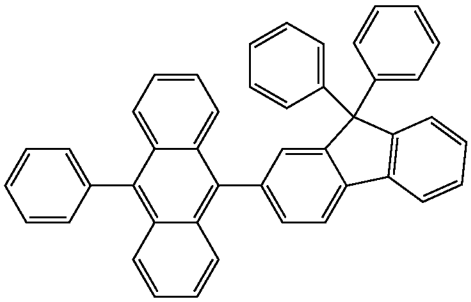
E11
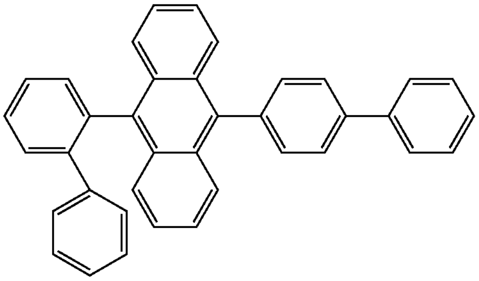
E12
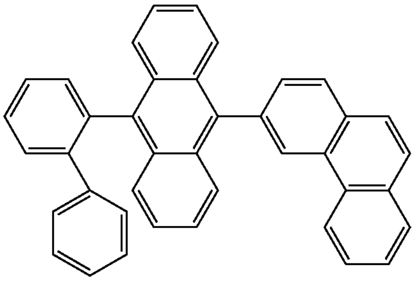

-continued
E13
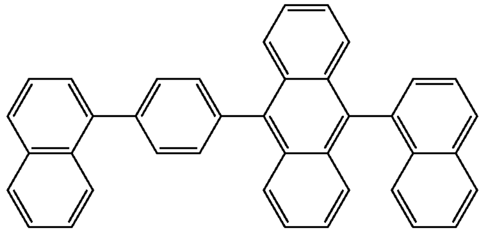
E14
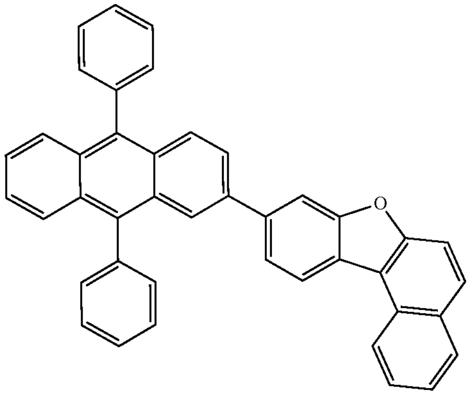
E15
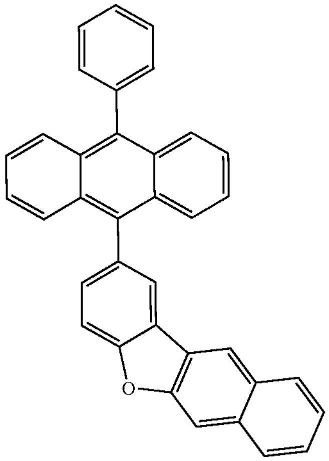
E16
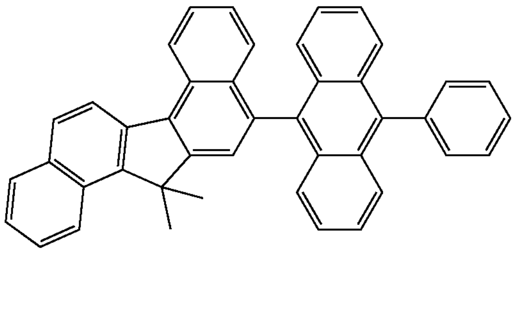
-continued
E17
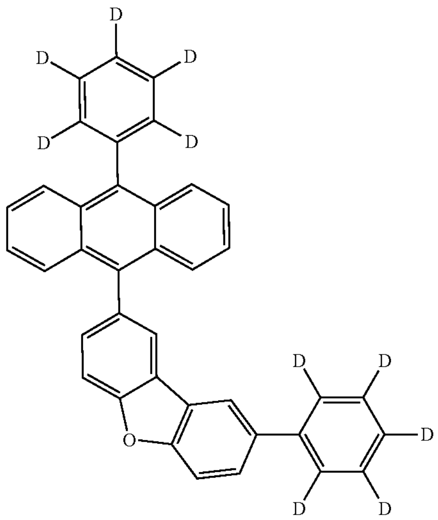
E18
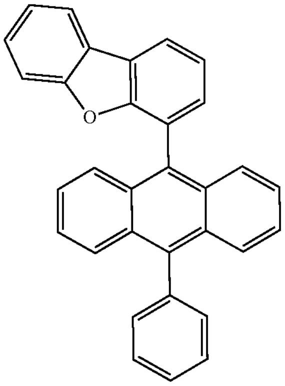
E19
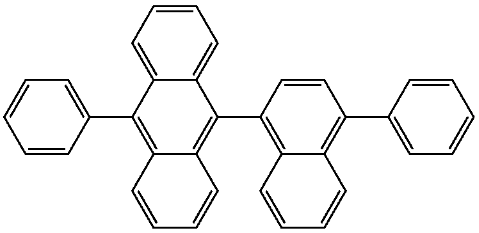
The emission layer EML may include a compound represented by Formula E-2a or Formula E-2b below. The compound represented by Formula E-2a or Formula E-2b below may be used as a phosphorescence host material.

Formula E-2a

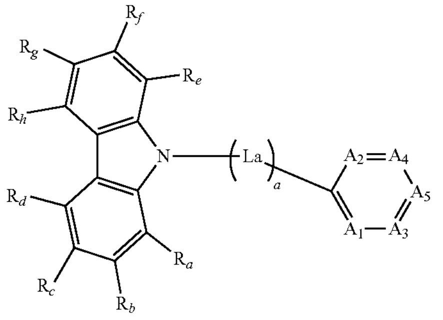

In Formula E-2b, "a" may be an integer of 0 to 10, La may be a direct linkage, a substituted or unsubstituted arylene group of 6 to 30 ring-forming carbon atoms, or a substituted or unsubstituted heteroarylene group of 2 to 30 ring-forming carbon atoms. If "a" is an integer of 2 or more, multiple La's may be each independently a substituted or unsubstituted arylene group of 6 to 30 ring-forming carbon atoms, or a substituted or unsubstituted heteroarylene group of 2 to 30 ring-forming carbon atoms.

In addition, in Formula E-2a, $A_1$ to $A_5$ may be each independently N or CRi. The variables $R_a$ to $R_1$ may be each independently a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. The variables $R_a$ to $R_i$ may be combined with an adjacent group to form a hydrocarbon ring or a heterocycle including N, O, S, etc. as a ring-forming atom. In Formula E-2a, two or three selected from $A_1$ to $A_5$ may be N, and the remainder may be $CR_i$.

Formula E-2b $$(Cbz1)-(L_b)_b-(Cbz2)$$

In Formula E-2b, Cbz1 and Cbz2 may be each independently an unsubstituted carbazole group, or a carbazole group substituted with an aryl group of 6 to 30 ring-forming carbon atoms. The variable $L_b$ may be a direct linkage, a substituted or unsubstituted arylene group of 6 to 30 ring-forming carbon atoms, or a substituted or unsubstituted heteroarylene group of 2 to 30 ring-forming carbon atoms. The variable "b" is an integer of 0 to 10, and if "b" is an integer of 2 or more, multiple $L_b$'s may be each independently a substituted or unsubstituted arylene group of 6 to 30 ring-forming carbon atoms, or a substituted or unsubstituted heteroarylene group of 2 to 30 ring-forming carbon atoms.

The compound represented by Formula E-2a or Formula E-2b may be represented by any one of the compounds in Compound Group E-2 below. However, the compounds shown in Compound Group E-2 below are only illustrations, and the compound represented by Formula E-2a or Formula E-2b is not limited to the compounds represented in Compound Group E-2 below.

Compound Group E-2

E-2-1

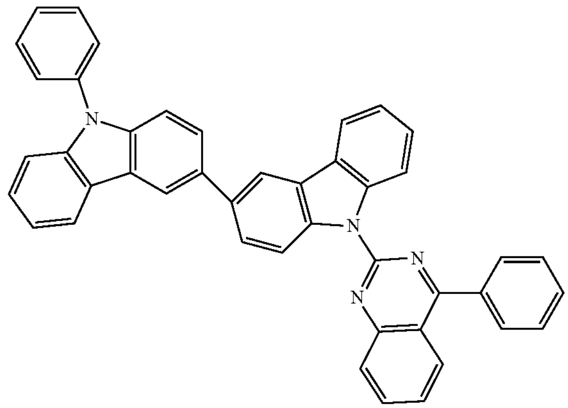

E-2-2

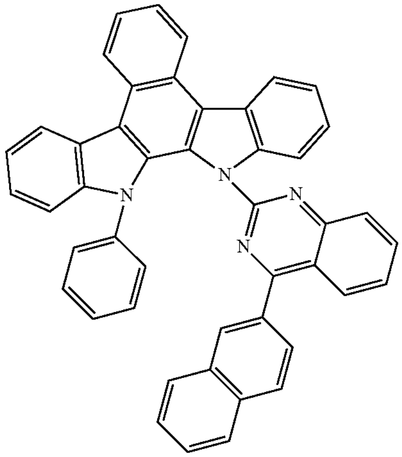

E-2-3

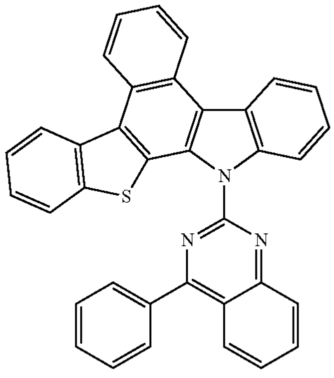

-continued
E-2-4
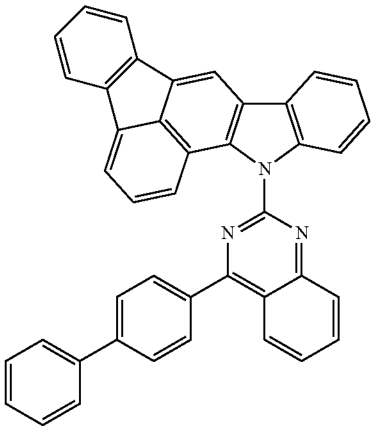
E-2-5
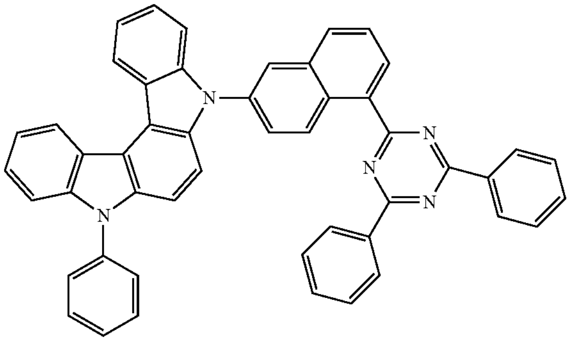
E-2-6
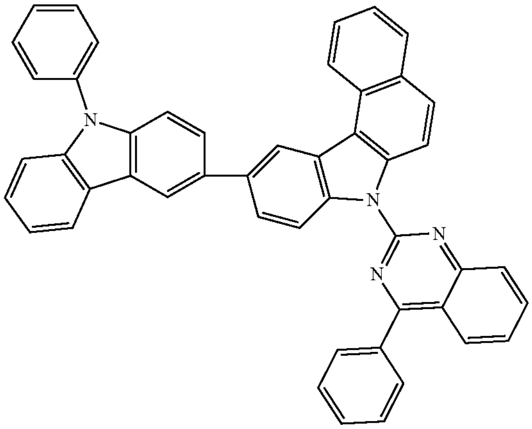
-continued
E-2-7
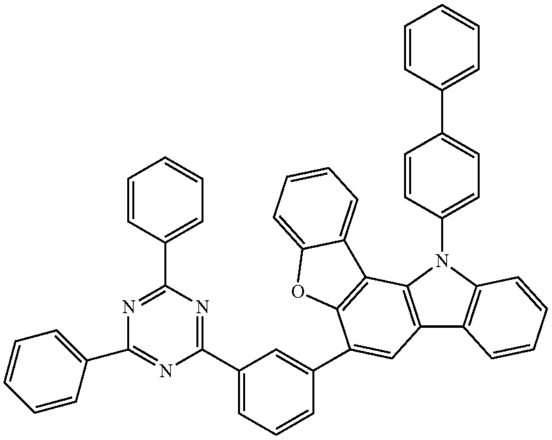
E-2-8
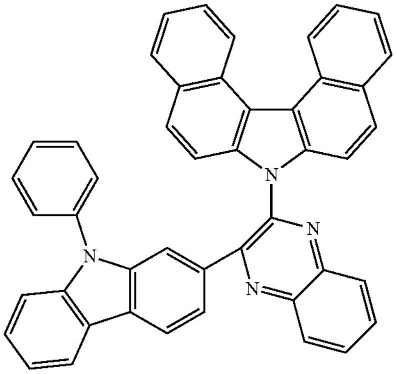
E-2-9
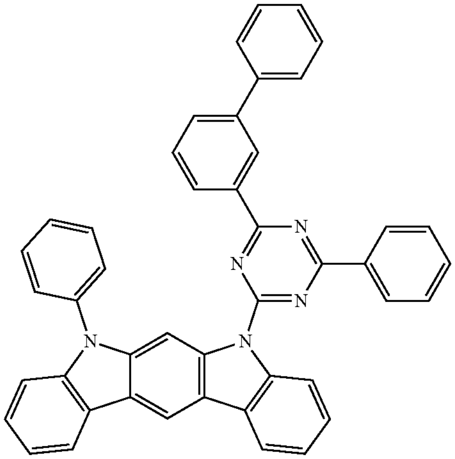

-continued
E-2-10
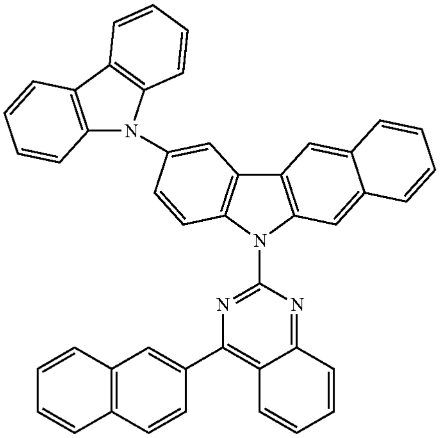
E-2-11
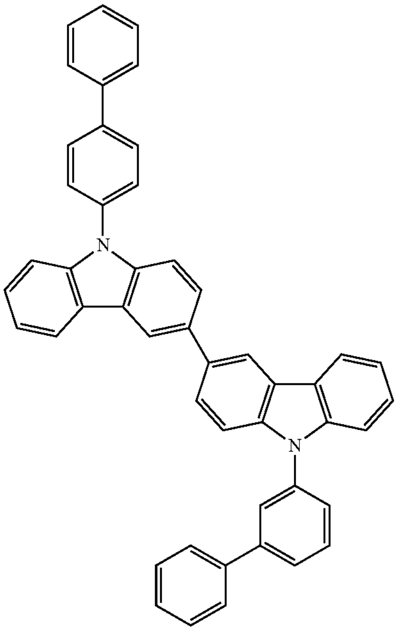
E-2-12
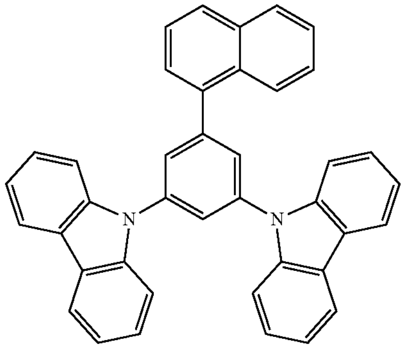
-continued
E-2-13
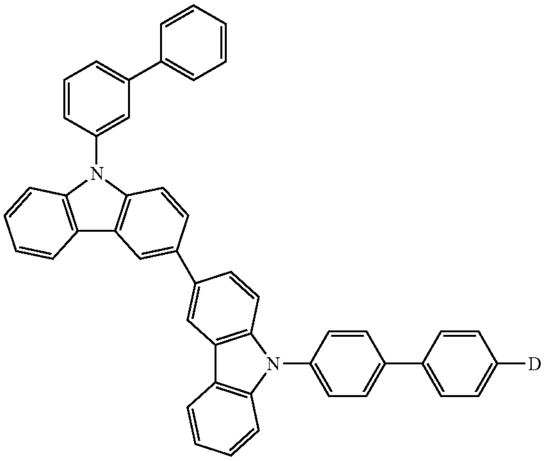
E-2-14
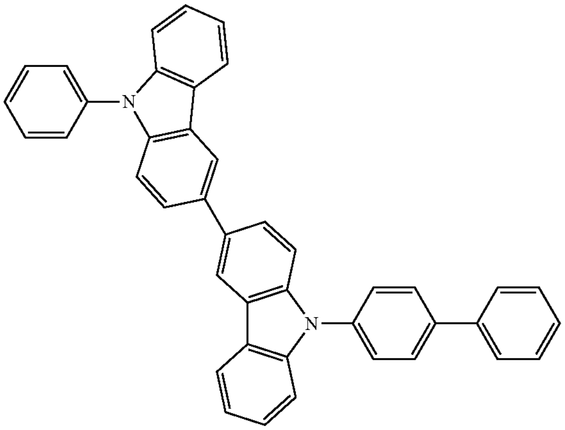
E-2-15
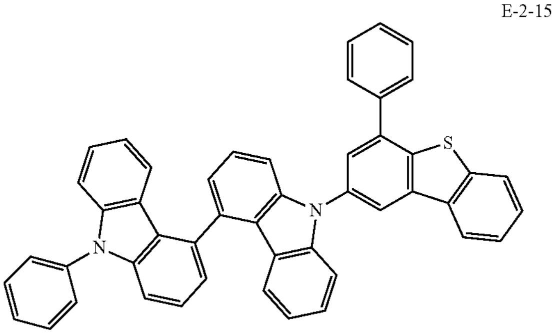

-continued
E-2-16
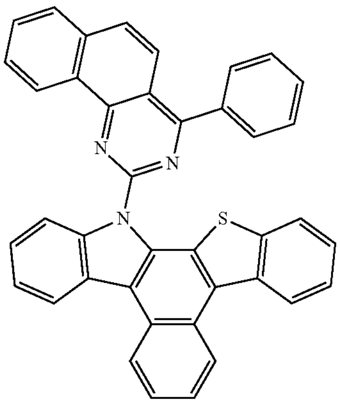
E-2-17
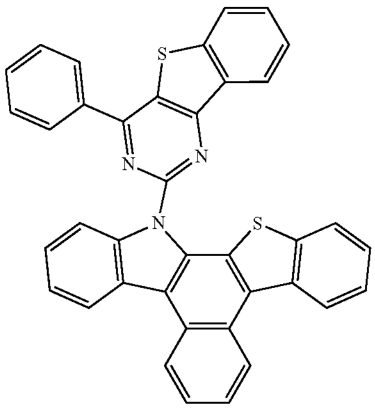
E-2-18
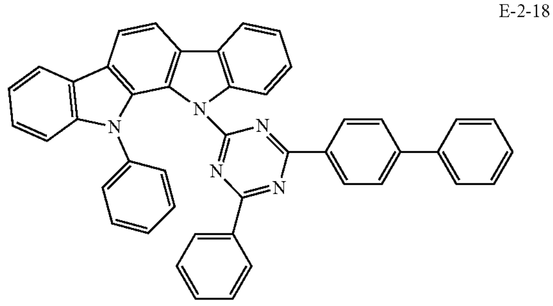
E-2-19
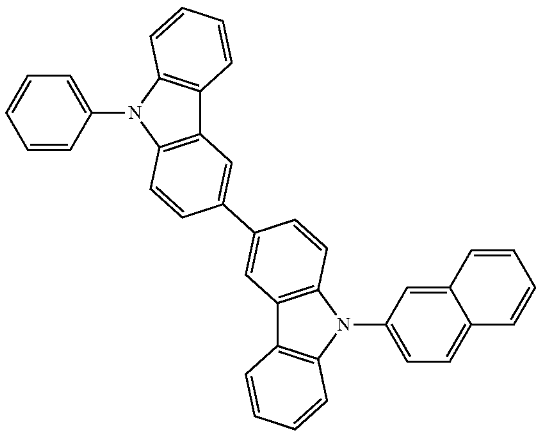
-continued
E-2-20
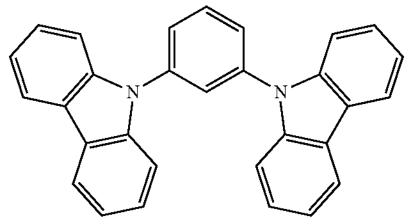
E-2-21
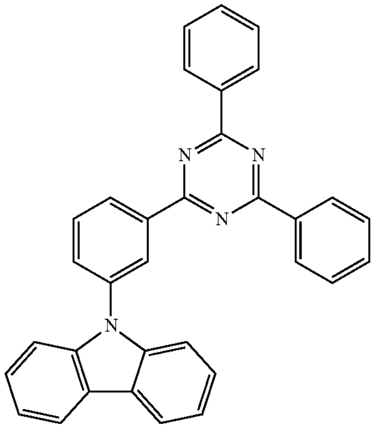
E-2-22
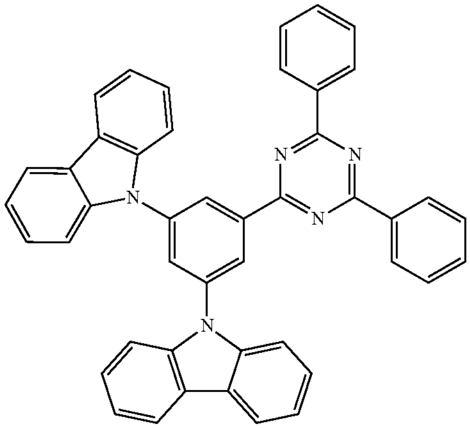
E-2-23
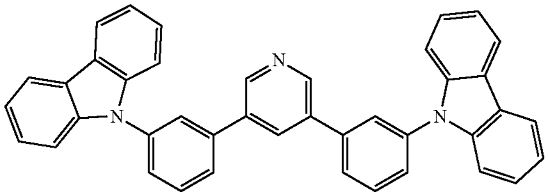

-continued

E-2-24

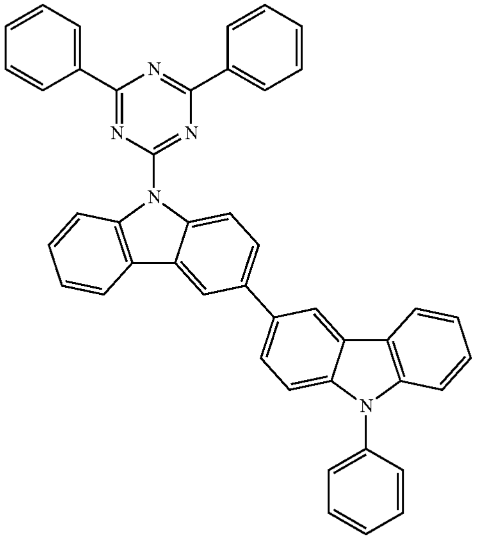

The emission layer EML may further include a common material well-known in the art as a host material. For example, the emission layer EML may include as a host material, at least one of bis(4-(9H-carbazol-9-yl) phenyl) diphenylsilane (BCPDS), (4-(1-(4-(diphenylamino) phenyl) cyclohexyl) phenyl) diphenyl-phosphine oxide (POPCPA), bis[2-(diphenylphosphino)phenyl]ether oxide (DPEPO), 4,4'-bis(carbazol-9-yl)-1,1'-biphenyl (CBP), 1,3-bis(carbazol-9-yl)benzene (mCP), 2,8-bis(diphenylphosphoryl) dibenzo[b,d]furan (PPF), 4,4',4''-tris(carbazol-9-yl)-triphenylamine (TCTA), or 1,3,5-tris(1-phenyl-1H-benzo[d] imidazole-2-yl)benzene (TPBi). However, embodiments are not limited thereto. For example, tris(8-hydroxyquinolino) aluminum ($Alq_3$), 9,10-di(naphthalene-2-yl)anthracene (ADN), 2-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), etc. may be used as the host material.

The emission layer EML may include a compound represented by Formula M-a or Formula M-b below. The compound represented by Formula M-a or Formula M-b may be used as a phosphorescence dopant material.

Formula M-a

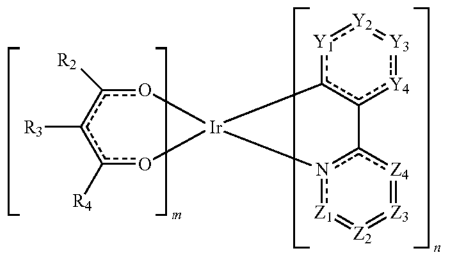

In Formula M-a, $Y_1$ to $Y_4$, and $Z_1$ to $Z_4$ may be each independently $CR_1$ or N, and $R_1$ to $R_4$ may be each independently a hydrogen atom, a deuterium atom, a substituted or unsubstituted amine group, a substituted or unsubstituted thio group, a substituted or unsubstituted oxy group; a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula M-a, "m" is 0 or 1, and "n" is 2 or 3. In Formula M-a, if "m" is 0, "n" is 3, and if "m" is 1, "n" is 2.

The compound represented by Formula M-a may be used as a phosphorescence dopant. The compound represented by Formula M-a may be represented by any one of Compounds M-a1 to M-a25 below. However, Compounds M-a1 to M-a25 below are illustrations, and the compound represented by Formula M-a is not limited to the compounds represented by Compounds M-a1 to M-a25 below.

M-a1

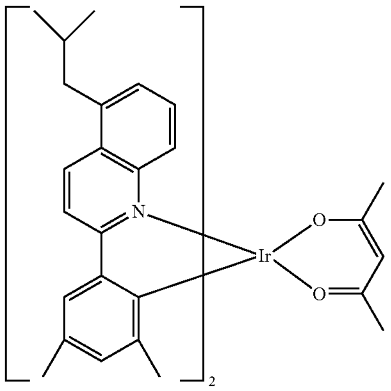

M-a2

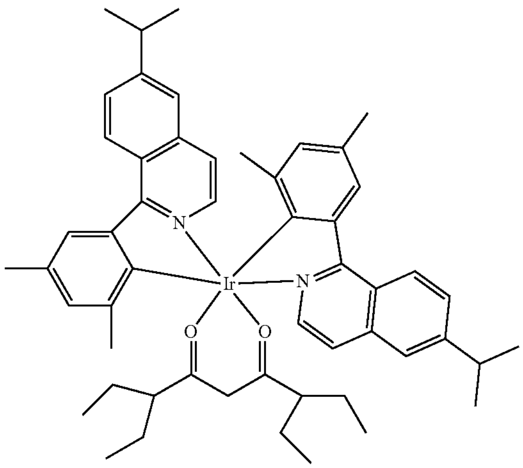

-continued
M-a3
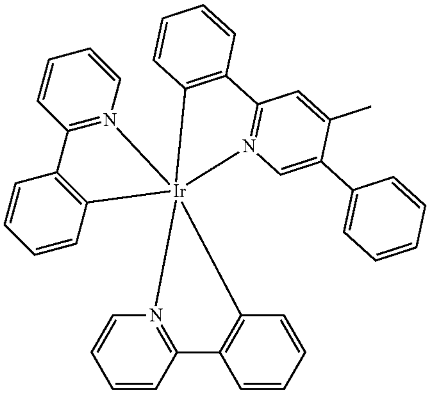
M-a4
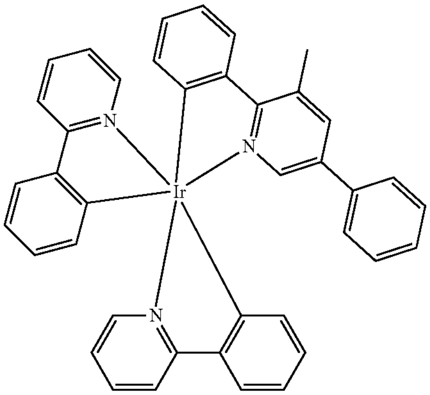
M-a5
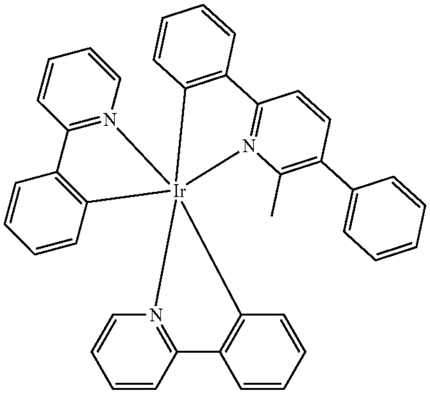
M-a6
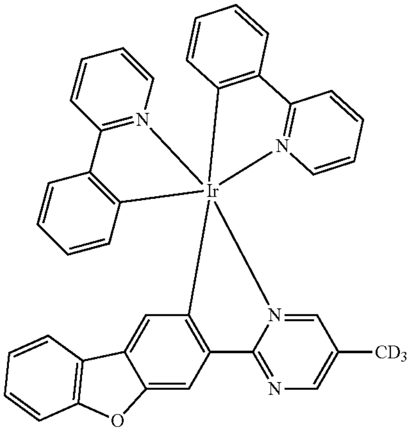
-continued
M-a7
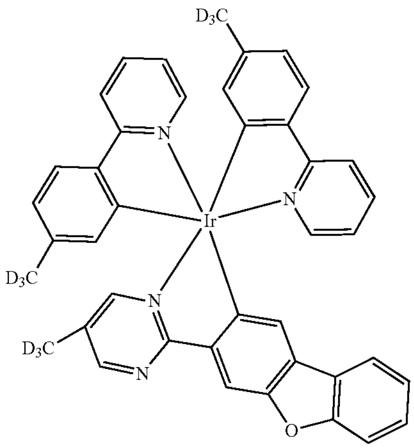
M-a8
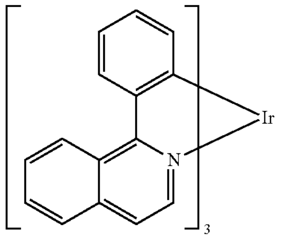
M-a9
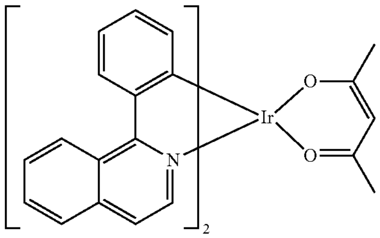
M-a10
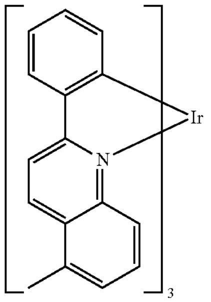
M-a11
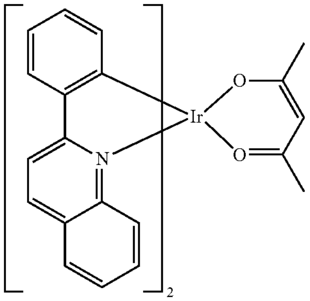

-continued
M-a12
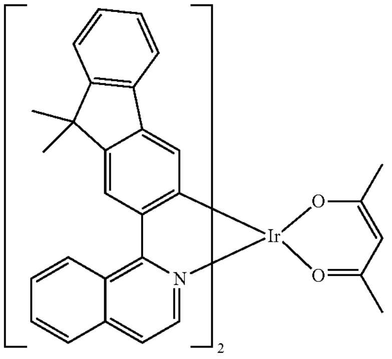
M-a13
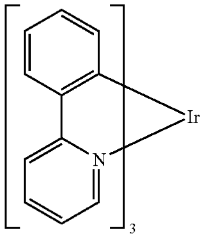
M-a14
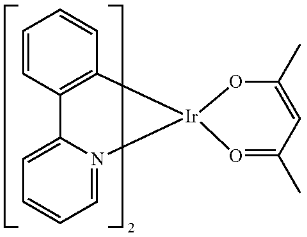
M-a15
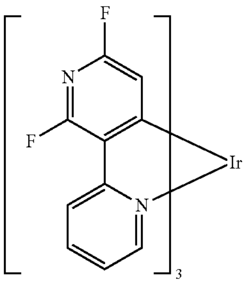
M-a16
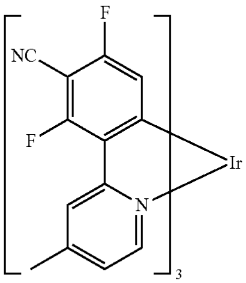
-continued
M-a17
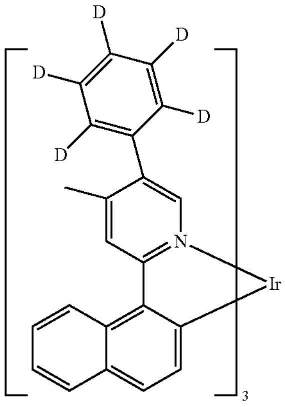
M-a18
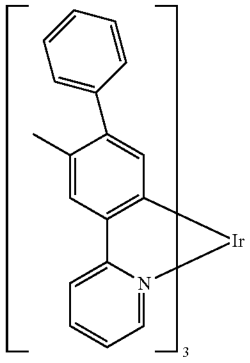
M-a19
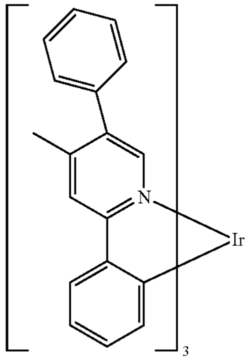
M-a20
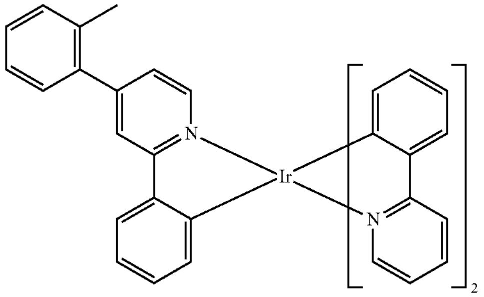

-continued

M-a21

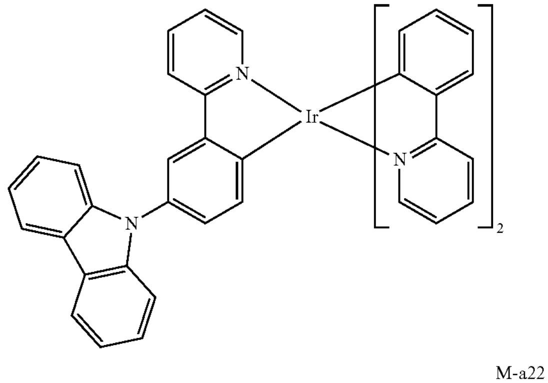

M-a22

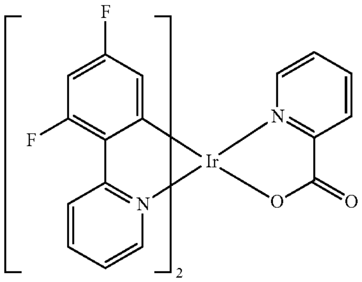

M-a23

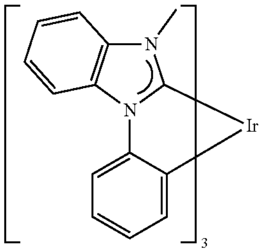

M-a24

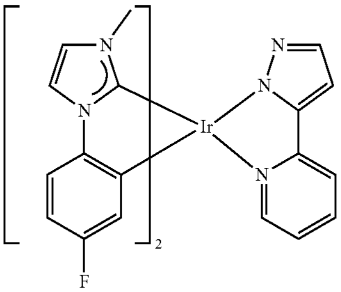

M-a25

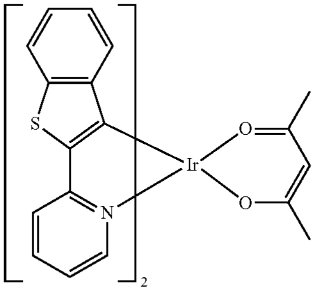

Compound M-a1 and Compound M-a2 may be used as red dopant materials, and Compound M-a3 and Compound M-a4 may be used as green dopant materials.

Formula M-b

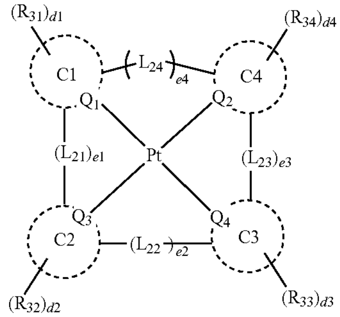

In Formula M-b, $Q_1$ to $Q_4$ are each independently C or N; $C_1$ to $C_4$ are each independently a substituted or unsubstituted hydrocarbon ring of 5 to 30 ring-forming carbon atoms, or a substituted or unsubstituted heterocycle of 2 to 30 ring-forming carbon atoms. The variables $L_{21}$ to $L_{24}$ are each independently a direct linkage,

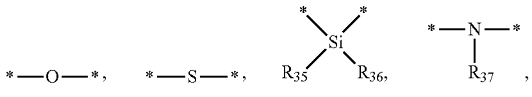

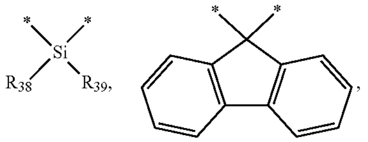

a substituted or unsubstituted divalent alkyl group of 1 to 20 carbon atoms, a substituted or unsubstituted arylene group of 6 to 30 ring-forming carbon atoms, or a substituted or unsubstituted heteroarylene group of 2 to 30 ring-forming carbon atoms, and $e_1$ to $e_4$ are each independently 0 or 1. The variables $R_{31}$ to $R_{39}$ are each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, and d1 to d4 are each independently an integer of 0 to 4.

The compound represented by Formula M-b may be used as a blue phosphorescence dopant or a green phosphorescence dopant. The compound represented by Formula M-b may be represented by any one of the compounds below. However, the compounds below are illustrations, and the compound represented by Formula M-b is not limited to the compounds represented below.

-continued
M-b-1
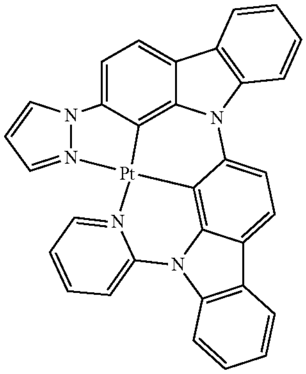
M-b-2
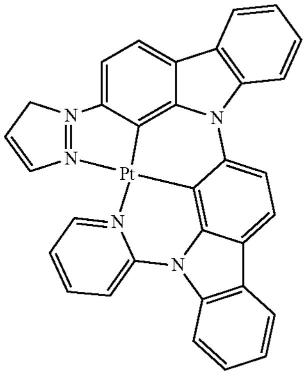
M-b-3
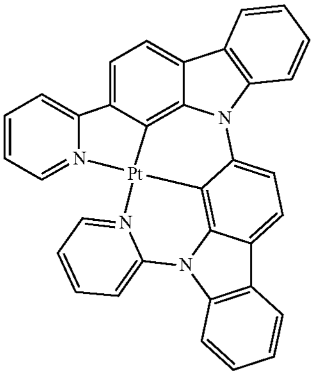
M-b-4
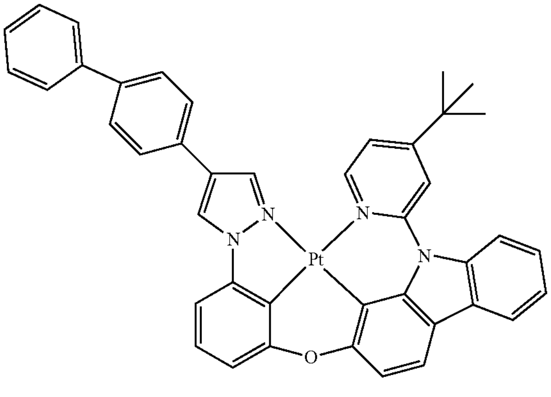
M-b-5
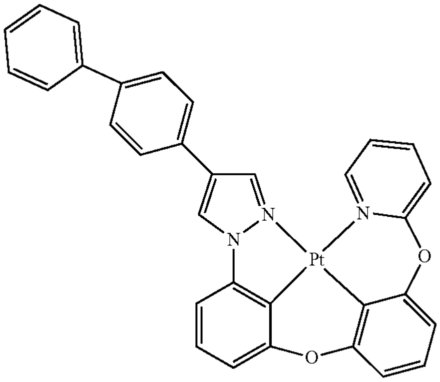
M-b-6
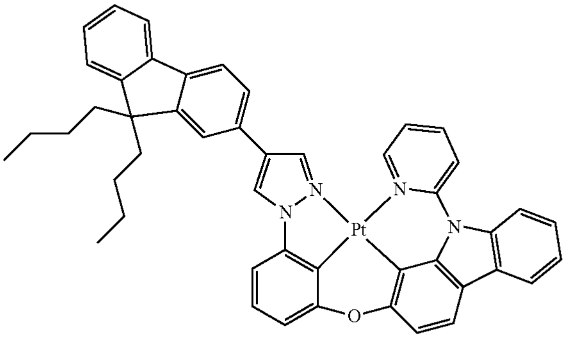
M-b-7
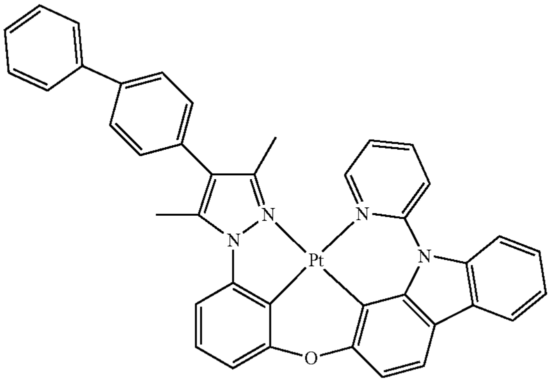
M-b-8
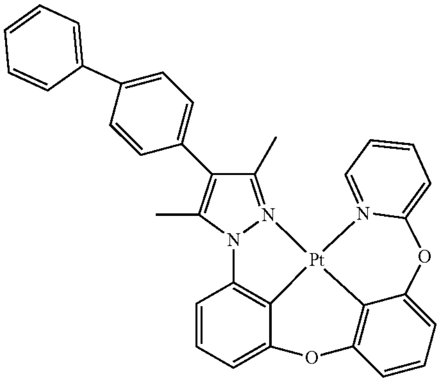

-continued

M-b-9

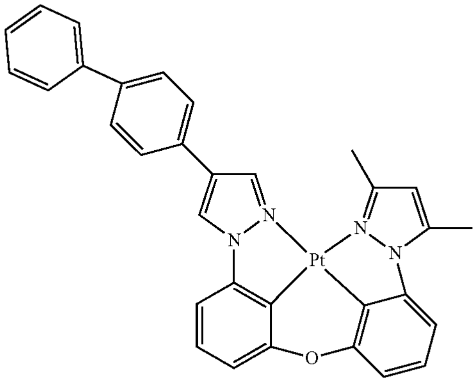

M-b-10

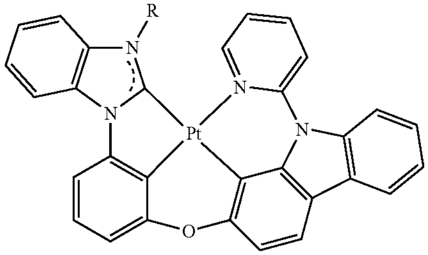

M-b-11

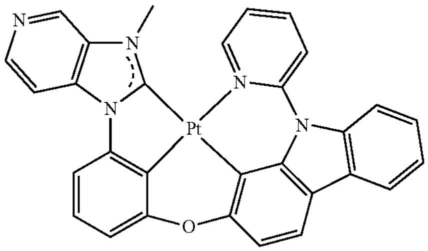

M-b-12

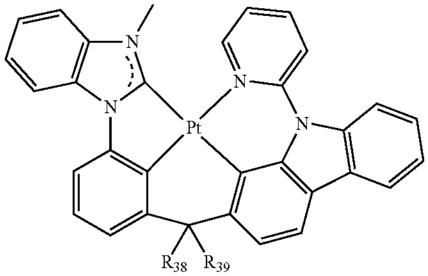

In the compounds above, R, $R_{38}$, and $R_{39}$ may be each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

The emission layer EML may include any one of Formula F-a to Formula F-c below. The compounds represented by Formula F-a to Formula F-c below may be used as fluorescence dopant materials.

Formula F-a

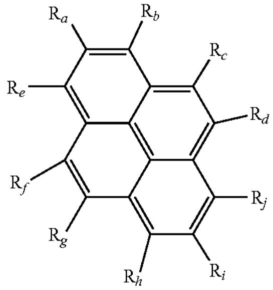

In Formula F-a, two selected from $R_a$ to $R_j$ may be each independently substituted with *—$NAr_1Ar_2$. The remainder not substituted with *—$NAr_1Ar_2$ of $R_a$ to $R_j$ may be each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. In *—$NAr_1Ar_2$, Ar and $Ar_2$ may be each independently a substituted or unsubstituted aryl group of 6 to 30 ring-forming carbon atoms, or a substituted or unsubstituted heteroaryl group of 2 to 30 ring-forming carbon atoms. For example, at least one of $Ar_1$ and $Ar_2$ may be a heteroaryl group including O or S as a ring-forming atom.

Formula F-b

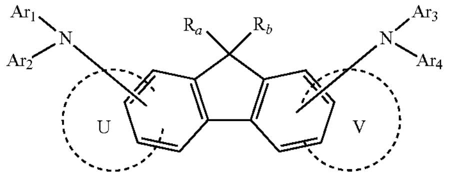

In Formula F-b, $R_a$ and $R_b$ may be each independently a hydrogen atom, a deuterium atom, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to ring-forming carbon atoms, or may be combined with an adjacent group to form a ring. The groups $Ar_1$ to $Ar_4$ may be each independently a substituted or unsubstituted aryl group of 6 to 30 ring-forming carbon atoms, or a substituted or unsubstituted heteroaryl group of 2 to 30 ring-forming carbon atoms. In Formula F-b, U and V may be each independently a substituted or unsubstituted hydrocarbon ring of 5 to 30 ring-forming carbon atoms, or a substituted or unsubstituted heterocycle of 2 to 30 ring-forming carbon atoms.

In Formula F-b, the number of rings represented by U and V may be each independently 0 or 1. For example, in Formula F-b, if the number of U or V is 1, one ring forms a fused ring at the designated part by U or V, and if the number of U or V is 0, a ring is not present at the designated part by U or V. Particularly, if the number of U is 0, and the number of V is 1, or if the number of U is 1, and the number of V is 0, a fused ring having the fluorene core of Formula F-b may be a ring compound with four rings. In addition, if the number of both U and V is 0, the fused ring of Formula F-b may be a ring compound with three rings. In addition, if the number of both U and V is 1, a fused ring having the fluorene core of Formula F-b may be a ring compound with five rings.

Formula F-c

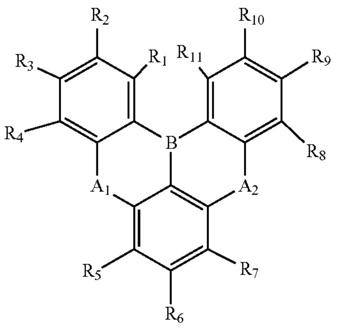

In Formula F-c, $A_1$ and $A_2$ may be each independently O, S, Se, or $NR_m$, and $R_m$ may be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. The variables $R_1$ to $R_{11}$ are each independently a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring.

In Formula F-c, $A_1$ and $A_2$ may be each independently combined with the substituents of an adjacent ring to form a fused ring. For example, if $A_1$ and $A_2$ may be each independently $NR_m$, $A_1$ may be combined with $R_4$ or $R_5$ to form a ring. In addition, $A_2$ may be combined with $R_7$ or $R_8$ to form a ring.

In an embodiment, the emission layer EML may include as a known dopant material, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino) styryl)naphthalen-2-yl)vinyl)phenyl)-N-phenylbenzenamine (N-BDAVBi), perylene and the derivatives thereof (for example, 2,5,8,11-tetra-t-butylperylene (TBP)), pyrene and the derivatives thereof (for example, 1,1-dipyrene, 1,4-dipyrenylbenzene, and 1,4-bis(N,N-diphenylamino)pyrene), etc.

The emission layer EML may include a known phosphorescence dopant material. For example, the phosphorescence dopant may use a metal complex including iridium (Ir), platinum (Pt), osmium (Os), gold (Au), titanium (Ti), zirconium (Zr), hafnium (Hf), europium (Eu), terbium (Tb) or thulium (Tm). Particularly, iridium(III) bis(4,6-difluorophenylpyridinato-N,C2')picolinate (FIrpic), bis(2,4-difluorophenylpyridinato)-tetrakis(1-pyrazolyl)borate iridium(III) (Fir6), or platinum octaethyl porphyrin (PtOEP) may be used as the phosphorescence dopant. However, embodiments are not limited thereto.

The emission layer EML may include a quantum dot material. The core of the quantum dot may be selected from a compound of Groups II-VI, a compound of Groups III-VI, a compound of Groups I-III-VI, a compound of Groups III-V, a compound of Groups III-II-V, a compound of Groups IV-VI, an element of Group IV, a compound of Group IV, and combinations thereof.

The compound of Groups II-VI may be selected from the group consisting of: a binary compound selected from the group consisting of CdSe, CdTe, CdS, ZnS, ZnSe, ZnTe, ZnO, HgS, HgSe, HgTe, MgSe, MgS, and mixtures thereof; a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and mixtures thereof; and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and mixtures thereof.

The compound of Groups III-VI may include a binary compound such as $In_2S_3$, and $In_2Se_3$, a ternary compound such as $InGaS_3$, and $InGaSe_3$, or optional combinations thereof. The compound of Groups I-III VI may be selected from a ternary compound selected from the group consisting of AgInS, $AgInS_2$, CuInS, $CuInS_2$, $AgGaS_2$, $CuGaS_2$, $CuGaO_2$, $AgGaO_2$, $AgAlO_2$ and mixtures thereof, or a quaternary compound such as $AgInGaS_2$, and $CuInGaS_2$.

The compound of Groups III-V may be selected from the group consisting of a binary compound selected from the group consisting of GaN, GaP, GaAs, GaSb, AlN, AlP, AlAs, AlSb, InN, InP, InAs, InSb, and mixtures thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and mixtures thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and mixtures thereof. The compound of Groups III-V may further include a metal of Group II. For example, InZnP, etc. may be selected as a compound of Groups III-II-V.

The compound of Groups IV-VI may be selected from the group consisting of a binary compound selected from the group consisting of SnS, SnSe, SnTe, PbS, PbSe, PbTe, and mixtures thereof, a ternary compound selected from the group consisting of SnSeS, SnSeTe, SnSTe, PbSeS, PbSeTe, PbSTe, SnPbS, SnPbSe, SnPbTe, and mixtures thereof, and a quaternary compound selected from the group consisting of SnPbSSe, SnPbSeTe, SnPbSTe, and mixtures thereof. The element of Group IV may be selected from the group consisting of Si, Ge, and a mixture thereof. The compound of Group IV may be a binary compound selected from the group consisting of SiC, SiGe, and a mixture thereof.

In this case, the binary compound, the ternary compound, or the quaternary compound may be present at a substantially uniform concentration in a particle or may be present at a partially different concentration distribution state in the same particle. In addition, a core/shell structure in which one quantum dot wraps another quantum dot may be possible. The interface of the core and the shell may have a concentration gradient in which the concentration of an element present in the shell is decreased toward the center.

In some embodiments, the quantum dot may have the above-described core-shell structure including a core including a nanocrystal and a shell wrapping the core. The shell of the quantum dot may playthe role of a protection layer for preventing the chemical deformation of the core to maintain semiconductor properties and/or a charging layer for imparting the quantum dot with electrophoretic properties. The shell may have a single layer or a multilayer. The interface of the core and shell may have concentration gradient of decreasing the concentration of elements present in the shell toward the center. Examples of the shell of the quantum dot may include a metal or a non-metal oxide, a semiconductor compound, or combinations thereof.

For example, the metal or non-metal oxide may include a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$ and NiO, or a ternary compound such as $MgAl_2O_4$, $CoFe_2O_4$, $NiFe_2O_4$ and $CoMn_2O_4$, but embodiments are not limited thereto.

Also, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb; etc., but embodiments are not limited thereto.

The quantum dot may have a full width of half maximum (FWHM) of emission wavelength spectrum of about 45 nanometer (nm) or less, preferably, about 40 nm or less, more preferably, about 30 nm or less. Within this range, color purity or color reproducibility may be improved. In addition, light emitted via such quantum dot is emitted in all directions, and light view angle properties may be improved.

In addition, the shape of the quantum dot may be generally used shapes in the art, without specific limitation. More particularly, the shape of a generally spherical, a generally pyramidal, a generally multi-armed, or a generally cubic nanoparticle, or a generally nanotube-shaped, a generally nanowire-shaped, a generally nanofiber-shaped, or a generally nanoplate-shaped particle, etc. may be used. The quantum dot may control the color of light emitted according to the particle size, and accordingly, the quantum dot may have various emission colors such as blue, red, and green.

In the luminescence devices ED shown in FIG. 3 to FIG. 6, the electron transport region ETR is provided on the emission layer EML. The electron transport region ETR may include at least one of a hole blocking layer HBL, an electron transport layer ETL or an electron injection layer EIL. However, embodiments are not limited thereto. The electron transport region ETR may have a single layer formed using a single material, a single layer formed using multiple different materials, or a multilayer structure having multiple layers formed using multiple different materials.

For example, the electron transport region ETR may have a single layer structure of an electron injection layer EIL or an electron transport layer ETL, or a single layer structure formed using an electron injection material and an electron transport material. Further, the electron transport region ETR may have a single layer structure formed using multiple different materials, or a structure stacked from the emission layer EML of electron transport layer ETL/electron injection layer EIL, or hole blocking layer HBL/electron transport layer ETL/electron injection layer EIL, without limitation. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method. The electron transport region ETR may include a compound represented by Formula ET-1 below. Formula ET-1

Formula ET-1

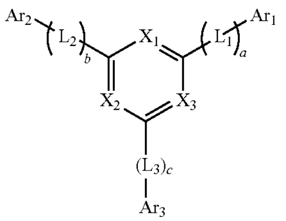

In Formula ET-1, at least one of $X_1$ to $X_3$ is N, and the remainder are $CR_a$. The variable $R_a$ may be a hydrogen atom, a deuterium atom, a substituted or unsubstituted alkyl of 1 to 20 carbon atoms, a substituted or unsubstituted aryl group of 6 to 30 ring-forming carbon atoms, or a substituted or unsubstituted heteroaryl group of 2 to 30 ring-forming carbon atoms. The variables $Ar_1$ to $Ar_3$ may be each independently a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula ET-1, "a" to "c" may be each independently an integer of 0 to 10. In Formula ET-1, $L_1$ to $L_3$ may be each independently a direct linkage, a substituted or unsubstituted arylene group of 6 to 30 ring-forming carbon atoms, or a substituted or unsubstituted heteroarylene group of 2 to 30 ring-forming carbon atoms. If "a" to "c" are integers of 2 or more, $L_1$ to $L_3$ may be each independently a substituted or unsubstituted arylene group of 6 to 30 ring-forming carbon atoms, or a substituted or unsubstituted heteroarylene group of 2 to 30 ring-forming carbon atoms.

The electron transport region ETR may include an anthracene-based compound. However, embodiments are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate ($Bebg_2$), 9,10-di(naphthalene-2-yl)anthracene (ADN), 1,3-bis[3,5-di(pyridin-3-yl)phenyl]benzene (BmPyPhB), and mixtures thereof, without limitation.

The electron transport region ETR may include at least one of Compounds ET1 to ET36 below.

ET1
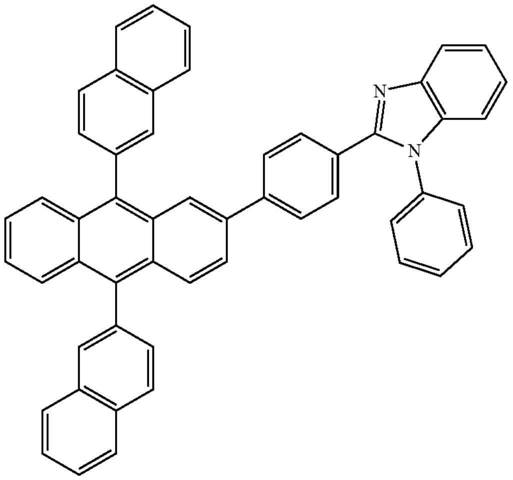
ET2
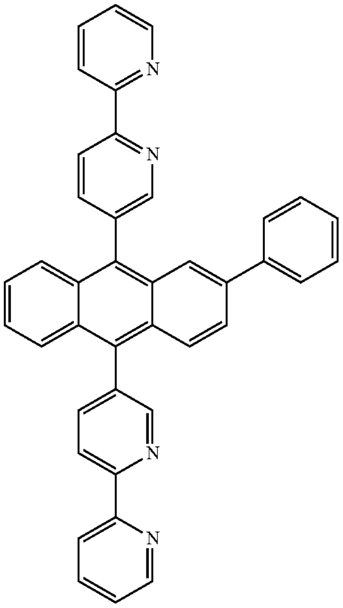
ET3
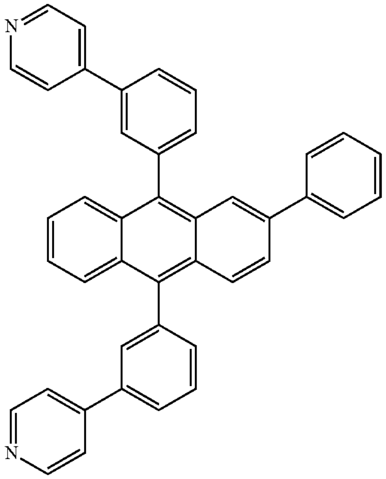
-continued
ET4
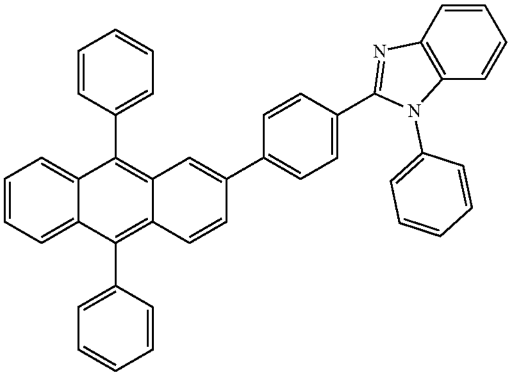
ET5
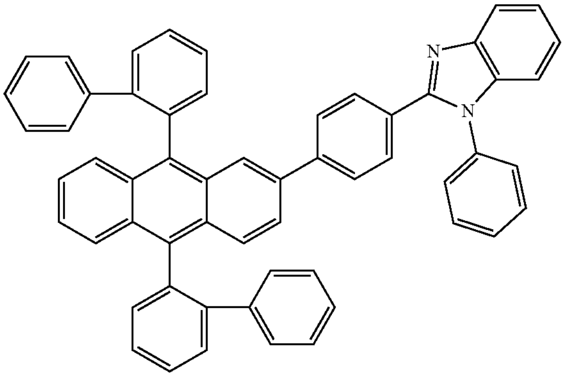
ET6
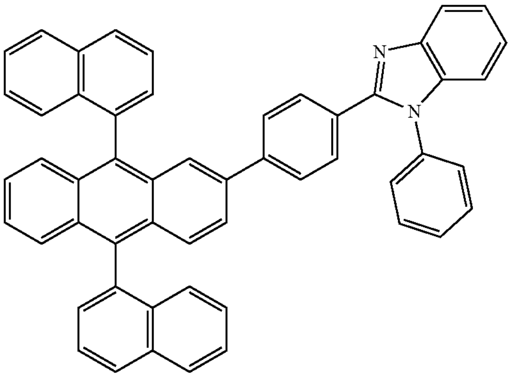

-continued
ET7
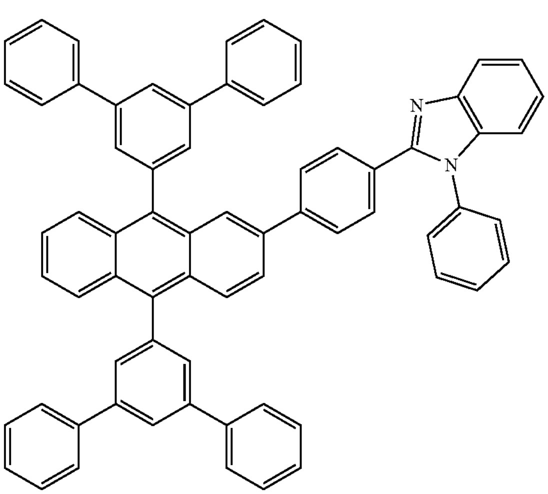
ET8
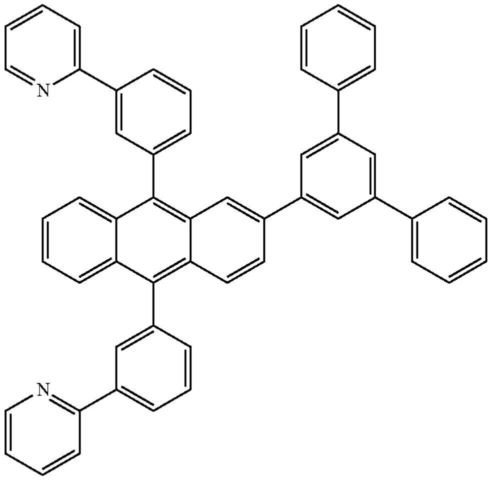
ET9
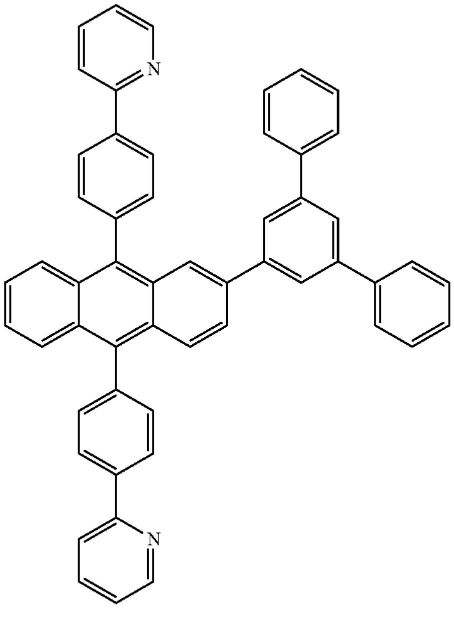
-continued
ET10
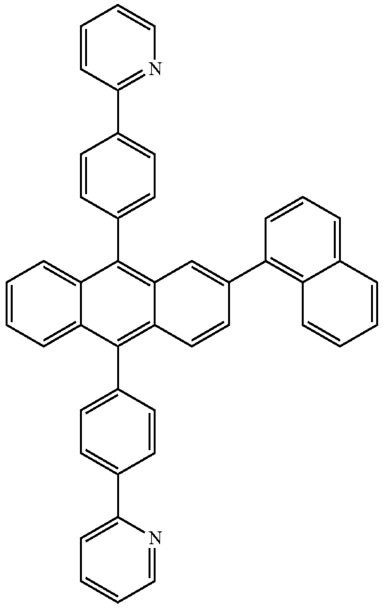
ET11
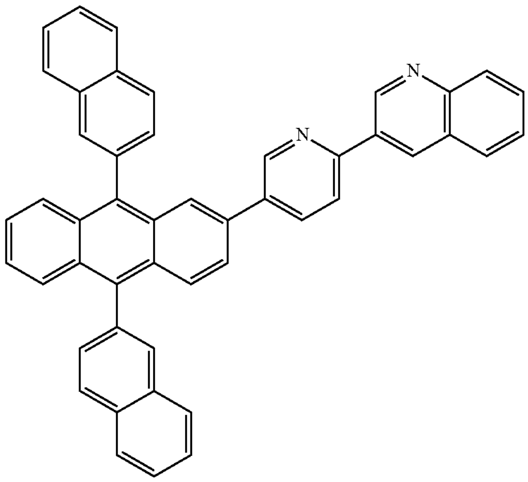
ET12
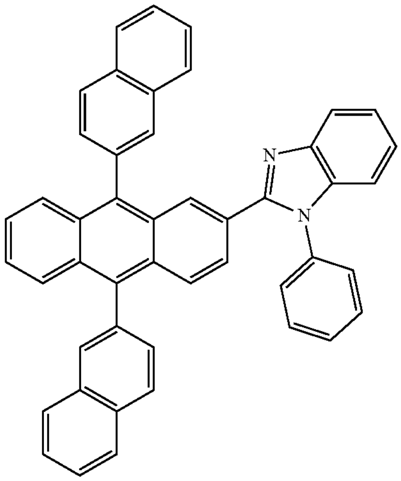

-continued
ET13
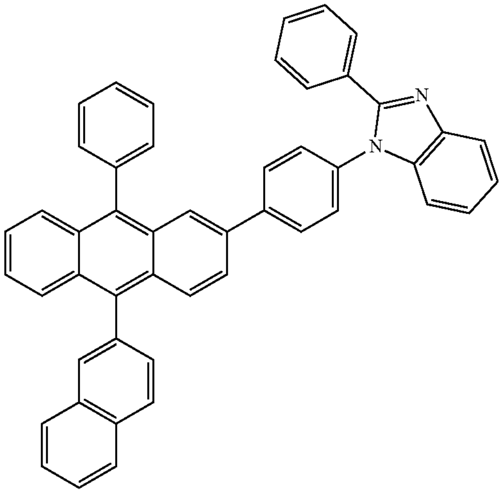
ET14
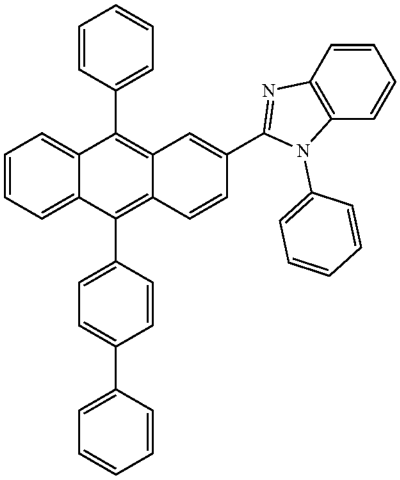
ET15
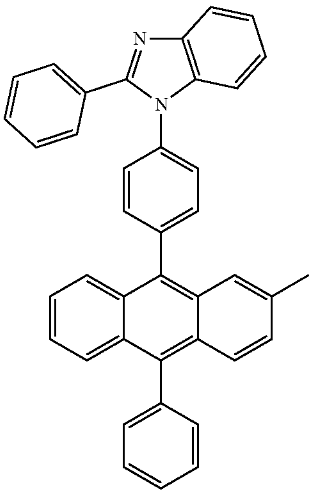
-continued
ET16
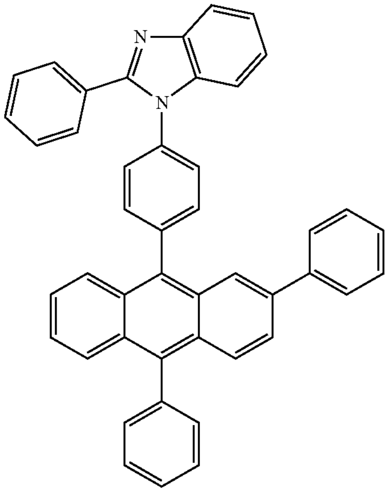
ET17
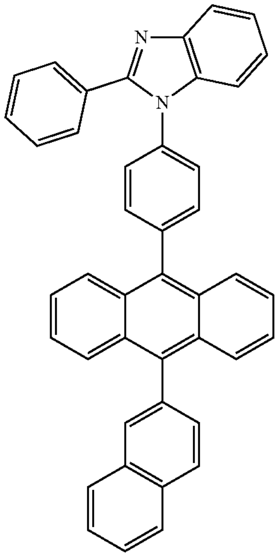
ET18
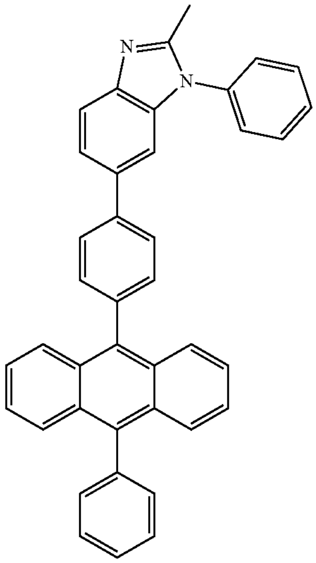

-continued
ET19
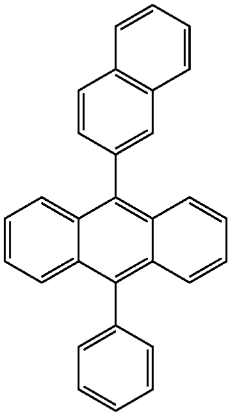
ET20
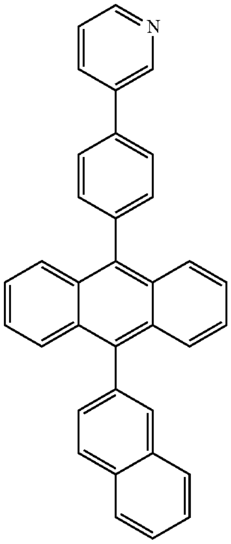
ET21
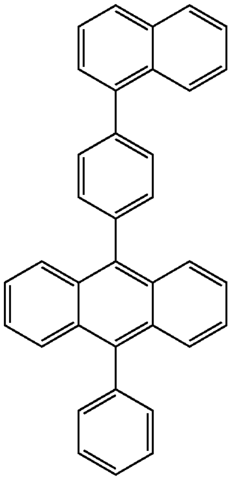
-continued
ET22
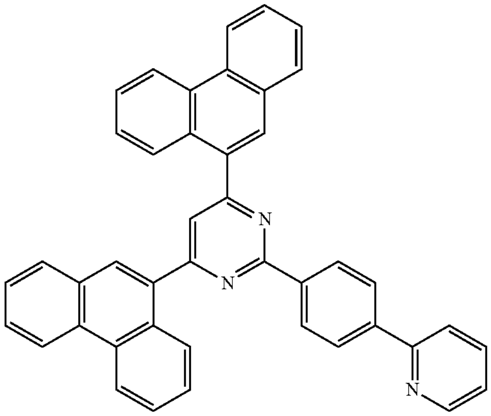
ET23
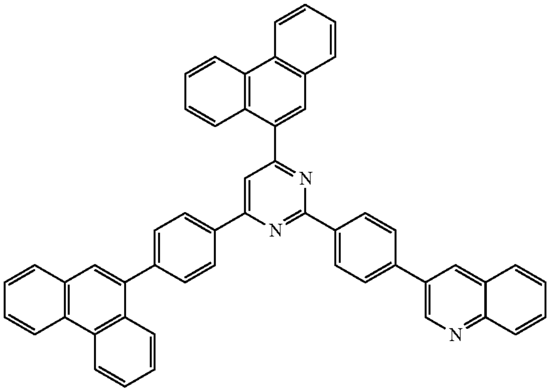
ET24
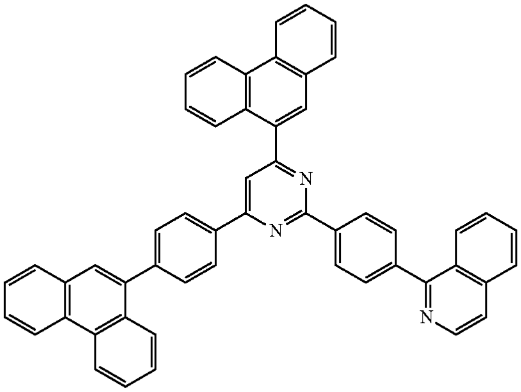

ET25
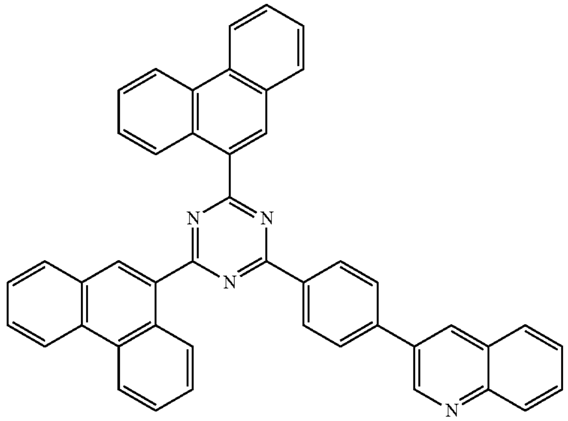
ET26
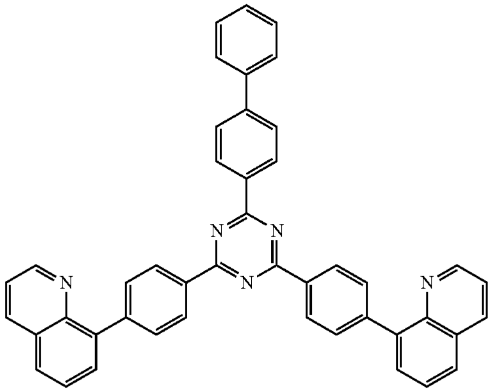
ET27
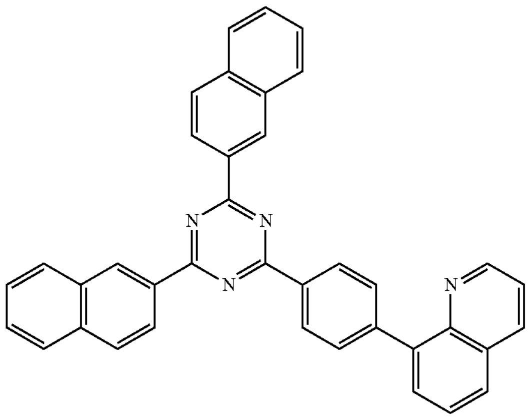
ET28
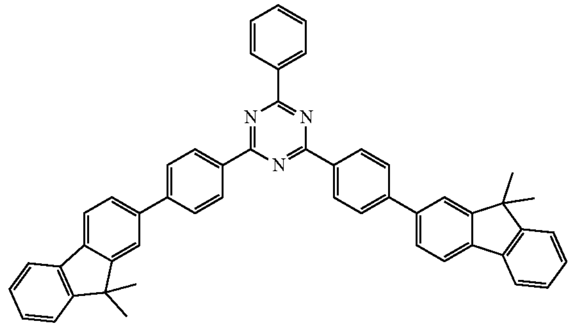
ET29
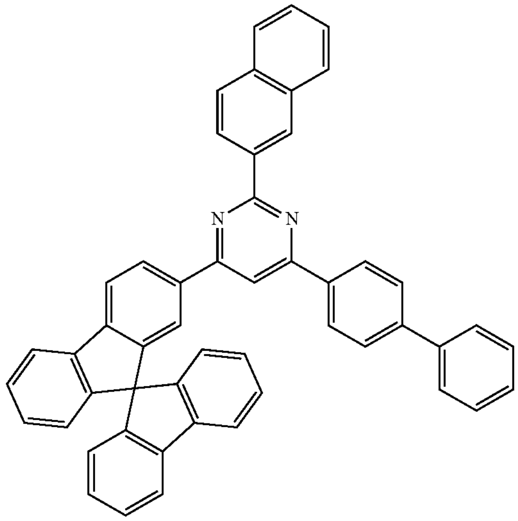
ET30
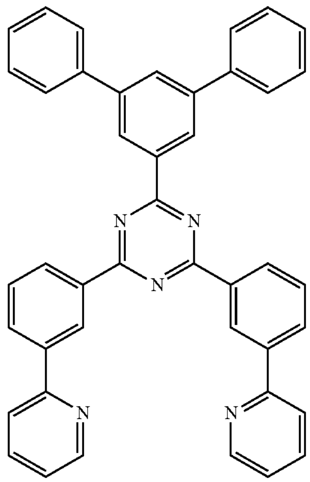
ET31
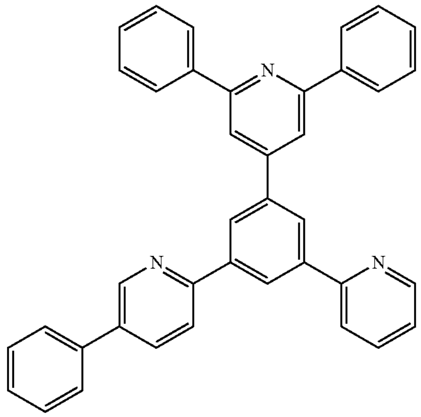

-continued

ET32

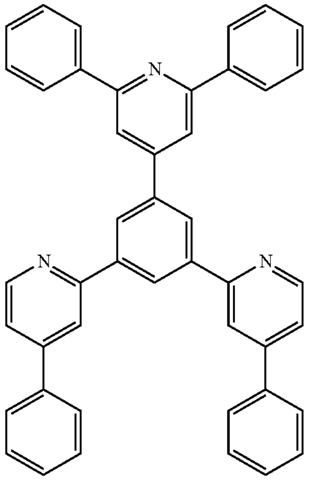

ET33

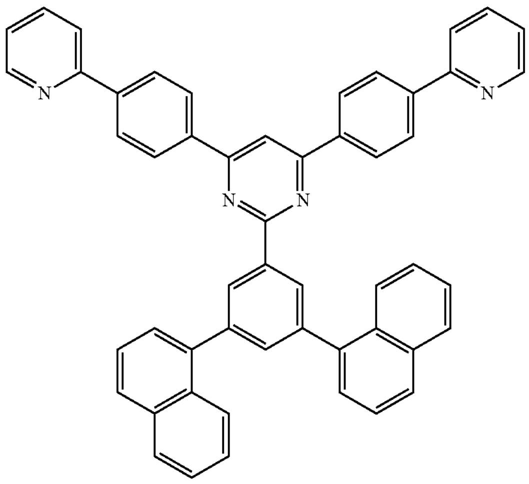

ET34

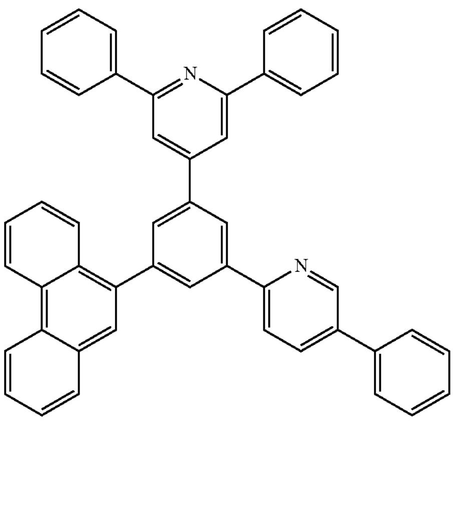

-continued

ET35

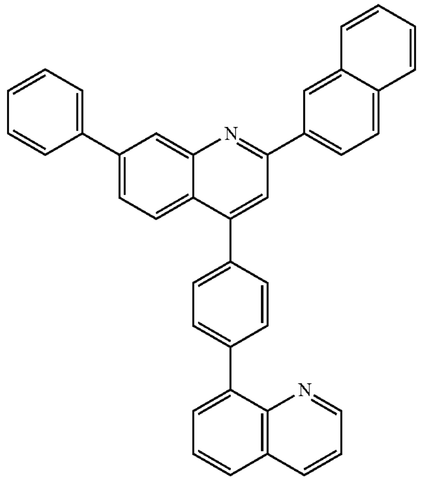

ET36

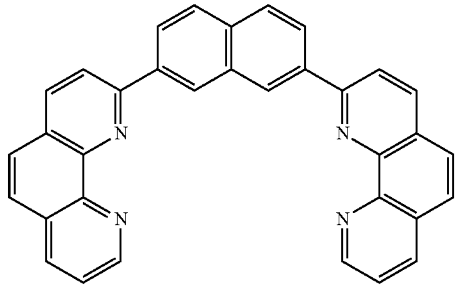

In addition, the electron transport region ETR may include a metal halide such as LiF, NaCl, CsF, RbCl, RbI, CuI and KI, a metal in lanthanoides such as Yb, or a co-depositing material of the metal halide and the metal in lanthanoides. For example, the electron transport region ETR may include KI:Yb, RbI:Yb, etc., as the co-depositing material. The electron transport region ETR may use a metal oxide such as $Li_2O$ and BaO, or 8-hydroxy-lithium quinolate (Liq). However, embodiments are not limited thereto. The electron transport region ETR also may be formed using a mixture material of an electron transport material and an insulating organo metal salt. The organo metal salt may be a material having an energy band gap of about 4 electron volt (eV) or more. Particularly, the organo metal salt may include, for example, metal acetates, metal benzoates, metal acetoacetates, metal acetylacetonates, or metal stearates.

The electron transport region ETR may include at least one of 2,9-dimethyl-4,7-diphenyl-1,10-phenanthroline (BCP) or 4,7-diphenyl-1,10-phenanthroline (Bphen) in addition to the above-described materials. However, embodiments are not limited thereto. The electron transport region ETR may include the compounds of the electron transport region in at least one of an electron injection layer EIL, an electron transport layer ETL, and a hole blocking layer HBL.

If the electron transport region ETR includes the electron transport layer ETL, the thickness of the electron transport layer ETL may be from about 100 Å to about 1,000 Å, for example, from about 150 Å to about 500 Å. If the thickness of the electron transport layer ETL satisfies the above-described range, satisfactory electron transport properties may be obtained without substantial increase of a driving voltage. If the electron transport region ETR includes the electron injection layer EIL, the thickness of the electron injection layer EIL may be from about 1 Å to about 100 Å, and from about 3 Å to about 90 Å. If the thickness of the electron injection layer EIL satisfies the above described range, satisfactory electron injection properties may be obtained without inducing substantial increase of a driving voltage.

The second electrode EL2 is provided on the electron transport region ETR. The second electrode EL2 may be a common electrode. The second electrode EL2 may be a cathode or an anode, but embodiments are not limited thereto. For example, if the first electrode EL1 is an anode, the second cathode EL2 may be a cathode, and if the first electrode EL1 is a cathode, the second electrode EL2 may be an anode.

The second electrode EL2 may be a transmissive electrode, a transflective electrode or a reflective electrode. If the second electrode EL2 is the transmissive electrode, the second electrode EL2 may include a transparent metal oxide, for example, an ITO, an IZO, a ZnO, an ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, compounds including thereof, or mixtures thereof (for example, AgMg, AgYb, or MgYb). Otherwise, the second electrode EL2 may have a multilayered structure including a reflective layer or a transflective layer formed using the above-described materials and a transparent conductive layer formed using an ITO, an IZO, a ZnO, an ITZO, etc. For example, the second electrode EL2 may include the aforementioned metal materials, combinations of two or more metal materials selected from the aforementioned metal materials, or oxides of the aforementioned metal materials.

The second electrode EL2 may be connected with an auxiliary electrode. If the second electrode EL2 is connected with the auxiliary electrode, the resistance of the second electrode EL2 may decrease. On the second electrode EL2 in the luminescence device ED, a capping layer CPL may be further disposed. The capping layer CPL may include a multilayef or a single layer.

In an embodiment, the capping layer CPL may be an organic layer or an inorganic layer. For example, if the capping layer CPL includes an inorganic material, the inorganic material may include an alkali metal compound such as LiF, an alkaline earth metal compound such as $MgF_2$, SiON, $SiN_x$, SiOy, etc.

For example, if the capping layer CPL includes an organic material, the organic material may include 2,2'-Dimethyl-N,N'-di-[(1-naphthyl)-N,N'-diphenyl]-1,1'-biphenyl-4,4'-diamine (α-NPD), NPB, TPD, m-MTDATA, $Alq_3$, Copper(II) phthalocyanine (CuPc), N4,N4,N4',N4'-tetra(biphenyl-4-yl) biphenyl-4,4'-diamine (TPD15), 4,4',4"-tris(carbazol sol-9-yl) triphenylamine (TCTA), etc., or includes an epoxy resin, or acrylate such as methacrylate. In addition, a capping layer CPL may include at least one of Compounds P1 to P5 below, but embodiments are not limited thereto.

P1

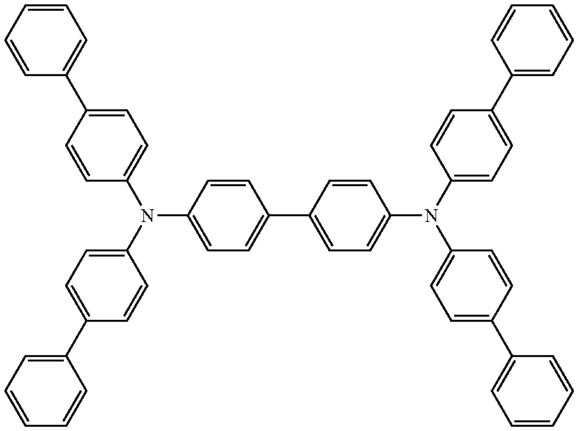

P2

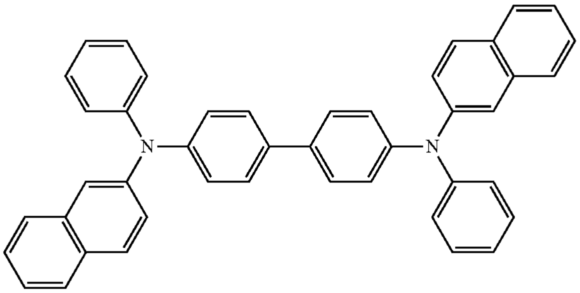

P3

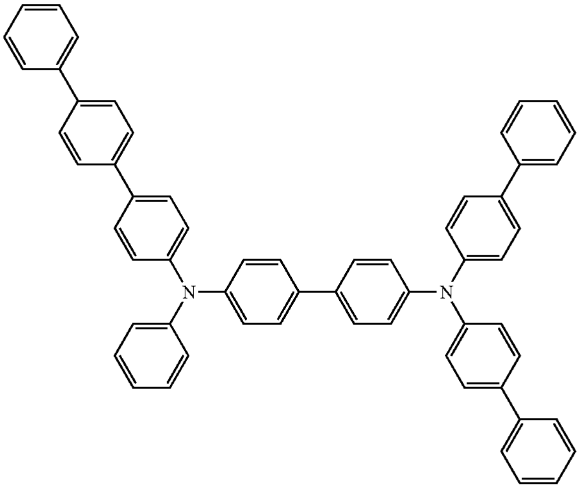

P4

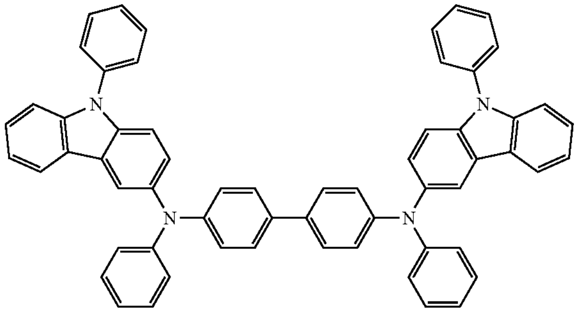

-continued

P5

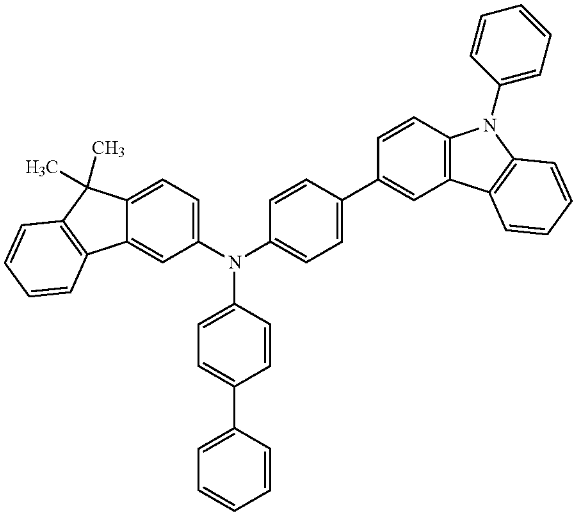

The refractive index of the capping layer CPL may be about 1.6 or more. Particularly, the refractive index of the capping layer CPL with respect to light in a wavelength range of about 550 nm to about 660 nm may be about 1.6 or more.

Figure 7:
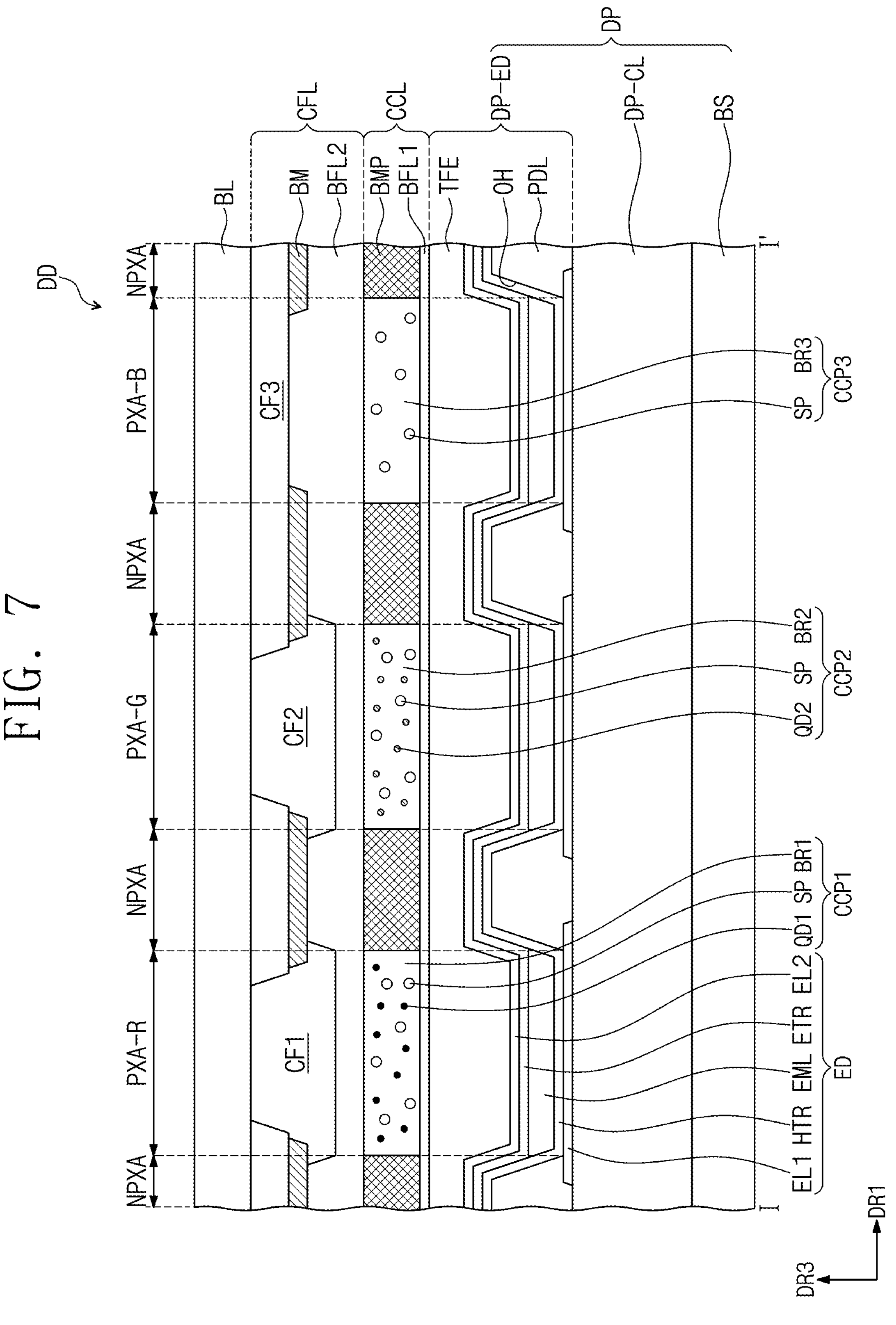
FIG. 7 is a cross-sectional view of another embodiment of a display apparatus including a luminescence device constructed according to the principles of the invention.
Figure 8:
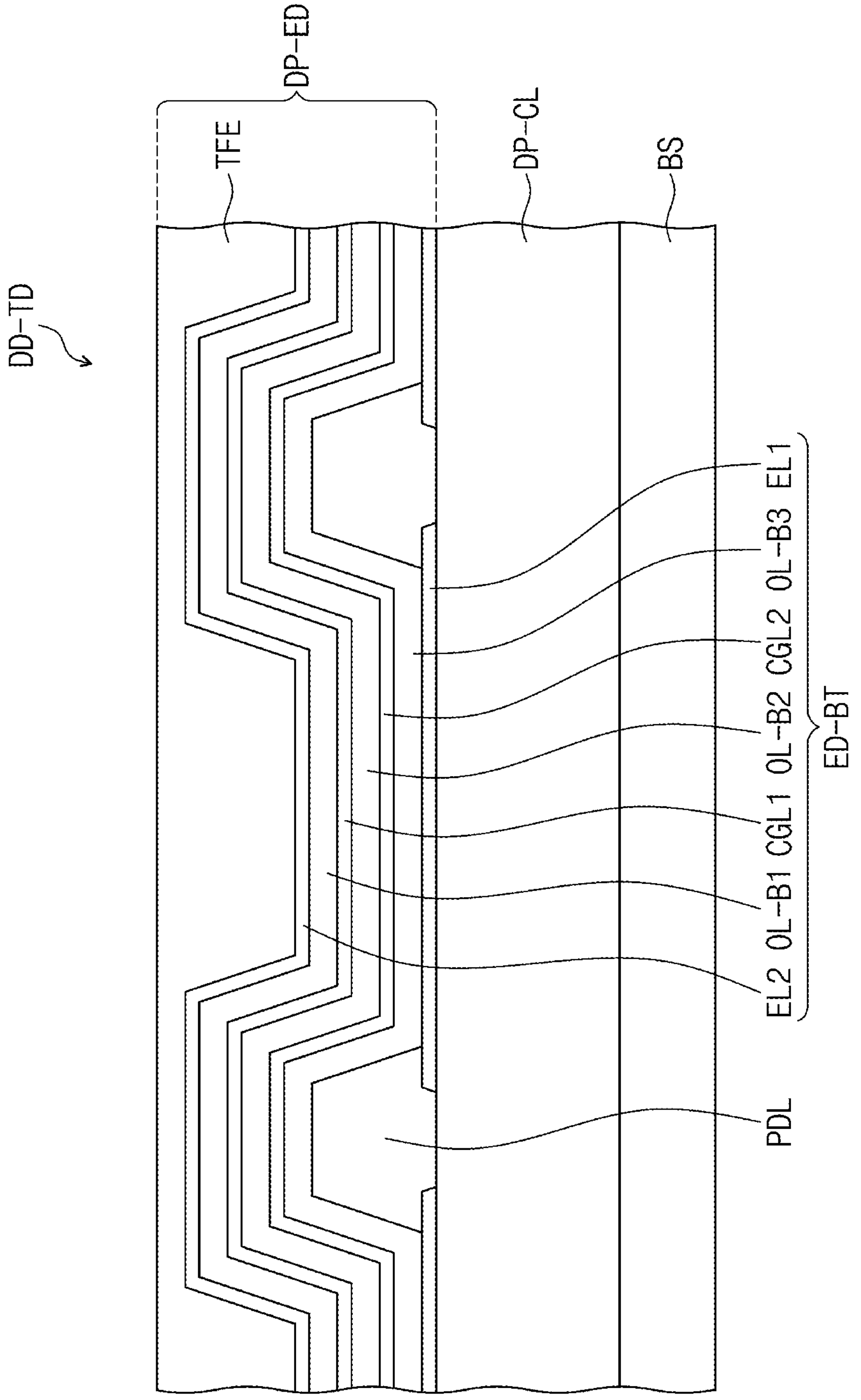
FIG. 8 is a cross-sectional view of a further embodiment of a display apparatus including a luminescence device constructed according to the principles of the invention.

FIG. 7 is a cross-sectional view of another embodiment of a display apparatus including a luminescence device constructed according to the principles of the invention. FIG. 8 is a cross-sectional view of a further embodiment of a display apparatus including a luminescence device constructed according to the principles of the invention.

In the explanation of the embodiments of the display apparatuses shown in FIG. 7 and FIG. 8, repetitive descriptions of features overlapping with the embodiments of FIG. 1 to FIG. 6 will not be explained again, but the different features mainly will be explained to avoid redundancy. Referring to FIG. 7, the display apparatus DD may include a display panel DP including a display device layer DP-ED, a light controlling layer CCL disposed on the display panel DP and a color filter layer CFL.

In an embodiment shown in FIG. 7, the display panel DP includes a base layer BS, a circuit layer DP-CL provided on the base layer BS and a display device layer DP-ED, and the display device layer DP-ED may include a luminescence device ED.

The luminescence device ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed onthe electron transport region ETR. The same structures of the luminescence devices of FIG. 3 to FIG. 6 may be applied to the structure of the luminescence device ED shown in FIG. 7.

Referring to FIG. 7, the emission layer EML may be disposed in an opening part OH defined in a pixel definition layer PDL. For example, the emission layer EML divided by the pixel definition layer PDL and overlapping each of luminous areas PXA-R, PXA-G and PXA-B may emit light in the same wavelength region. In the display apparatus DD, the emission layer EML may emit blue light. Unlike what is shown in FIG. 7, in another embodiment, the emission layer EML may be provided as a common layer for all luminous areas PXA-R, PXA-G and PXA-B.

The light controlling layer CCL may be disposed on the display panel DP. The light controlling layer CCL may include a light converter. The light converter may be a quantum dot or a phosphor. The light converter may transform the wavelength of light and then emit.

That is, the light controlling layer CCL may be a layer including a quantum dot or a layer including a phosphor. The light controlling layer CCL may include multiple light controlling parts CCP1, CCP2 and CCP3. The light controlling parts CCP1, CCP2 and CCP3 may be separated from one another.

Referring to FIG. 7, a partition pattern BMP may be disposed between the separated light controlling parts CCP1, CCP2 and CCP3, but embodiments are not limited thereto. In FIG. 7, the partition pattern BMP is shown as not overlapping with the light controlling parts CCP1, CCP2 and CCP3, but at least a portion of the edge of the light controlling parts CCP1, CCP2 and CCP3 may overlap with the partition pattern BMP.

The light controlling layer CCL may include a first light controlling part CCP1 including a first quantum dot QD1 converting first color light provided from the luminescence device ED into second color light, a second light controlling part CCP2 including a second quantum dot QD2 converting first color light into third color light, and a third light controlling part CCP3 transmitting first color light.

In an embodiment, the first light controlling part CCP1 may provide red light which is the second color light, and the second light controlling part CCP2 may provide green light which is the third color light. The third color controlling part CCP3 may transmit and provide blue light which is the first color light provided from the luminescence device ED. For example, the first quantum dot QD1 may be a red quantum dot, and the second quantum dot QD2 may be a green quantum dot. The same explanation as described above may be applied to the quantum dots QD1 and QD2.

In addition, the light controlling layer CCL may further include a scatterer SP. The first light controlling part CCP1 may include the first quantum dot QD1 and the scatterer SP, the second light controlling part CCP2 may include the second quantum dot QD2 and the scatterer SP, and the third light controlling part CCP3 may not include a quantum dot but include the scatterer SP.

The scatterer SP may be an inorganic particle. For example, the scatterer SP may include at least one of a $TiO_2$, a ZnO, an $Al_2O_3$, a $SiO_2$, and a hollow silica. The scatterer SP may include at least one of the $TiO_2$, ZnO, $Al_2O_3$, $SiO_2$, and hollow silica, or may be a mixture of two or more materials selected of the $TiO_2$, ZnO, $Al_2O_3$, $SiO_2$, and hollow silica.

Each of the first light controlling part CCP1, the second light controlling part CCP2, and the third light controlling part CCP3 may include base resins BR1, BR2 and BR3 dispersing the quantum dots QD1 and QD2 and the scatterer SP. In an embodiment, the first light controlling part CCP1 may include the first quantum dot QD1 and the scatterer SP dispersed in the first base resin BR1, the second light controlling part CCP2 may include the second quantum dot QD2, and the scatterer SP dispersed in the second base resin BR2, and the third light controlling part CCP3 may include the scatterer particle SP dispersed in the third base resin BR3. The base resins BR1, BR2 and BR3 are mediums in which the quantum dots QD1 and QD2 and the scatterer SP are dispersed, and may be composed of various resin compositions which may be generally referred to as a binder. For example, the base resins BR1, BR2 and BR3 may be acrylic resins, urethane-based resins, silicone-based resins, epoxy-based resins, etc. The base resins BR1, BR2 and BR3 may be transparent resins. In an embodiment, the first base resin BR1, the second base resin BR2 and the third base resin BR3 may be the same or different from each other.

The light controlling layer CCL may include a barrier layer BFL1. The barrier layer BFL1 may play the role of blocking the penetration of moisture and/or oxygen (hereinafter, will be referred to as “humidity/oxygen”). The barrier layer BFL1 may be disposed on the light controlling parts CCP1, CCP2 and CCP3 to block the exposure of the light controlling parts CCP1, CCP2 and CCP3 to humidity/oxygen. The barrier layer BFL1 may cover the light controlling parts CCP1, CCP2 and CCP3. In addition, the barrier layer BFL2 may be provided between the light controlling parts CCP1, CCP2 and CCP3 and a color filter layer CFL.

The barrier layers BFL1 and BFL2 may include at least one inorganic layer. That is, the barrier layers BFL1 and BFL2 may be formed by including an inorganic material. For example, the barrier layers BFL1 and BFL2 may be formed by including a silicon nitride, an aluminum nitride, a zirconium nitride, a titanium nitride, a hafnium nitride, a tantalum nitride, a silicon oxide, an aluminum oxide, a titanium oxide, a tin oxide, a cerium oxide and a silicon oxynitride or a metal thin film securing light transmittance. The barrier layers BFL1 and BFL2 may further include an organic layer. The barrier layers BFL1 and BFL2 may be composed of a single layer of multiple layers.

In the display apparatus DD, the color filter layer CFL may be disposed on the light controlling layer CCL. For example, the color filter layer CFL may be disposed directly on the light controlling layer CCL. In this case, the barrier layer BFL2 may be omitted.

The color filter layer CFL may include a light blocking part BM and filters CF-B, CF-G and CF-R. The color filter layer CFL may include a first filter CF1 transmitting second color light, a second filter CF2 transmitting third color light, and a third filter CF3 transmitting first color light. For example, the first filter CF1 may be a red filter, the second filter CF2 may be a green filter, and the third filter CF3 may be a blue filter. Each of the filters CF1, CF2 and CF3 may include a polymer photosensitive resin and a pigment or a dye. The first filter CF1 may include a red pigment or a dye, the second filter CF2 may include a green pigment or a dye, and the third filter CF3 may include a blue pigment or a dye. But the embodiments are not limited thereto, and the third filter CF3 may not include the pigment or dye. The third filter CF3 may include a polymer photosensitive resin and not include a pigment or a dye. The third filter CF3 may be transparent. The third filter CF3 may be formed using a transparent photosensitive resin.

In addition, in an embodiment, the first filter CF1 and the second filter CF2 may be yellow filters. The first filter CF1 and the second filter CF2 may be provided in one unitary body.

The light blocking part BM may be a black matrix. The light blocking part BM may be formed by including an organic light blocking material or an inorganic light blocking material including a black pigment or a black dye. The light blocking part BM may prevent or reduce light leakage phenomenon and define the boundaries between adjacent filters CF1, CF2 and CF3. In addition, in an embodiment, the light blocking part BM may be formed as a blue filter.

Each of the first to third filters CF1, CF2 and CF3 may overlap each of a red luminous area PXA-R, green luminous area PXA-G, and blue luminous area PXA-B. On the color filter layer CFL, a base substrate BL may be disposed. The base substrate BL may be a member providing a base surface on which the color filter layer CFL, the light controlling layer CCL, etc. are disposed. The base substrate BL may be a glass substrate, a metal substrate, a plastic substrate, etc. However, embodiments are not limited thereto, and the base substrate BL may be an inorganic layer, an organic layer, or a composite material layer. In addition, in an embodiment unlike the drawing, the base substrate BL may be omitted.

Particularly, in FIG. 8, the cross-sectional view of a portion overlapping the display panel DP in FIG. 7 is shown. In a display apparatus DD-TD, the luminescence device ED-BT may include multiple light emitting structures OL-B1, OL-B2 and OL-B3. The luminescence device ED-BT may include oppositely disposed first electrode EL1 and second electrode EL2, and the multiple light emitting structures OL-B1, OL-B2 and OL-B3 stacked in order in the thickness direction and provided between the first electrode EL1 and the second electrode EL2. Each of the light emitting structures OL-B1, OL-B2 and OL-B3 may include an emission layer EML (FIG. 7), and a hole transport region HTR and an electron transport region ETR disposed with the emission layer EML (FIG. 7) therebetween.

That is, the luminescence device ED-BT included in the display apparatus DD-TD may be a luminescence device of a tandem structure including multiple emission layers. In the embodiment shown in FIG. 8, light emitted from the light emitting structures OL-B1, OL-B2 and OL-B3 may be all blue light. However, embodiments are not limited thereto, and the wavelength regions of light emitted from the light emitting structures OL-B1, OL-B2 and OL-B3 may be different from each other. For example, the luminescence device ED-BT including the multiple light emitting structures OL-B1, OL-B2 and OL-B3 emitting light in different wavelength regions may emit white light.

Between adjacent light emitting structures OL-B1, OL-B2 and OL-B3, a charge generating layer CGL1 and CGL2 may be disposed. The charge generating layer CGL1 and CGL2 may include a p-type charge generating layer and/or an n-type charge generating layer.

Hereinafter, the principles of the invention will be particularly explained referring to illustrative embodiments and comparative embodiments. The embodiments are only illustrations to assist the understanding of the concepts of the invention, and the scope of the invention is not limited thereto. In the synthesis examples below, the yield percent is based on the number of moles of compound.

SYNTHETIC EXAMPLES

Embodiments of the nitrogen-containing compound may be synthesized, for example, as follows. However, the synthetic methods are not limited to the examples below.

1. Synthesis of Compound A3

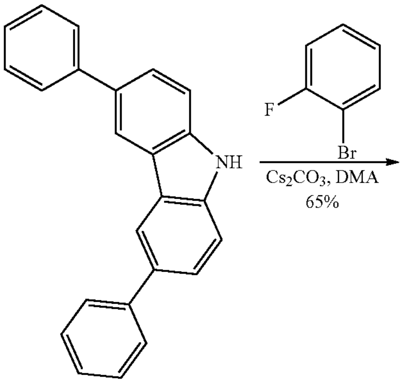

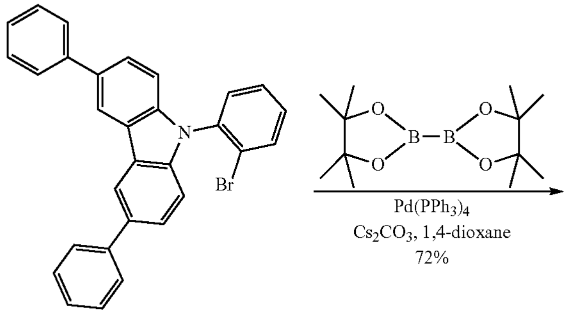

IM-1

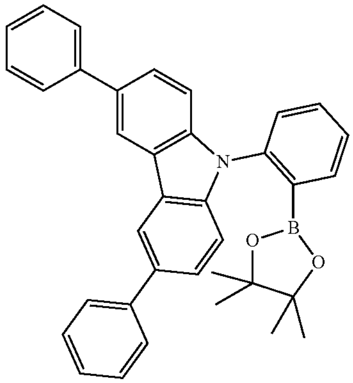

IM-2

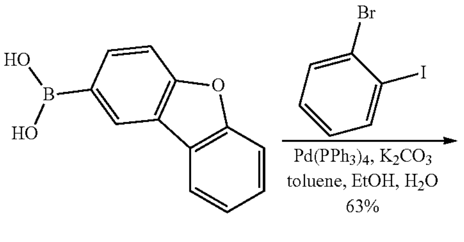

-continued

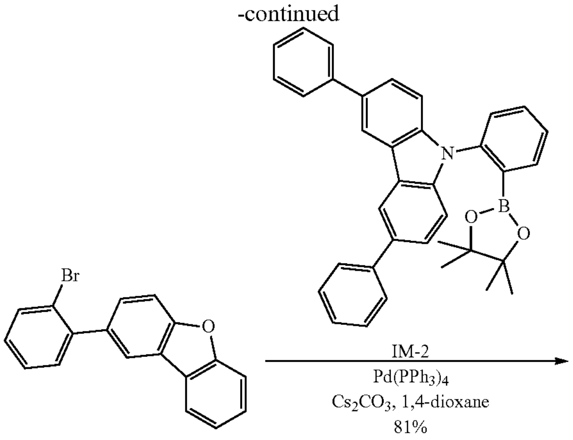

IM-3

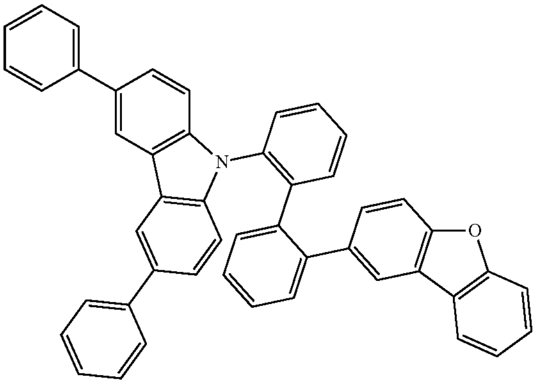

A3

(1) Synthesis of Compound IM-1

Under an argon (Ar) atmosphere, to a 200 milliliter (mL), three-neck flask, 20.00 gram (g) or 62.62 millimole (mmol) of 3,6-diphenyl-9H-carbazole, 40.80 g (2.0 equiv, 125.2 mmol) of cesium carbonate ($Cs_2CO_3$), 60 mL of N,N-dimethylacetamide (DMA) and 21.92 g (2.0 equiv, 125.2 mmol) of 1-bromo-2-fluorobenzene were added in order, and heated to about 120° C. and stirred. After cooling in the air to room temperature, water and toluene were added to the reaction solution, and an organic layer was separately taken. The organic layer was washed with a saline solution and dried with magnesium sulfate ($MgSO_4$). The $MgSO_4$ was filtered, and an organic layer was concentrated. The crude product thus obtained was separated by silica gel column chromatography (using a mixture solvent of hexane and toluene as a developing layer) to obtain Compound IM-1 (19.35 g, yield 65%). Through measuring by fast atom bombardment/mass spectroscopy (FAB-MS), mass number of m/z=473 was observed as a molecular ion peak, and Compound IM-1 was identified.

Synthesis of Compound IM-2

Under an Ar atmosphere, to a 300 mL, three-neck flask, 19.35 g (40.79 mmol) of IM-1, 9.43 g (0.20 equiv, 8.16 mmol) of tetrakis(triphenylphosphine)palladium(0) (Pd$(PPh_3)_4$), 53.16 g (4.0 equiv, 163.2 mmol) of $Cs_2CO_3$, 100 mL of 1,4-dioxane, and 41.43 g (4.0 equiv, 163.2 mmol) of bis(pinacolato)diboron were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-2 (15.30 g, yield 72%).

Through measuring FAB-MS, mass number of m/z=521 was observed as a molecular ion peak, and Compound IM-2 was identified.

(2) Synthesis of Compound IM-3

Under an Ar atmosphere, to a 1000 mL, three-neck flask, 20.00 g (94.34 mmol) of dibenzofuran-2-boronic acid, 40.03 g (1.5 equiv, 141.5 mmol) of 1-bromo-2-iodobenzene, 5.45 g (0.05 equiv, 4.72 mmol) of $Pd(PPh_3)_4$, 39.11 g (3.0 equiv, 283.0 mmol) of potassium carbonate ($K_2CO_3$), 300 mL of toluene, 150 mL of ethanol (EtOH), and 75 mL of water ($H_2O$) were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-3 (19.18 g, yield 63%). Through measuring FAB-MS, mass number of m/z=322 was observed as a molecular ion peak, and Compound IM-3 was identified.

(3) Synthesis of Compound A3

Under an Ar atmosphere, to a 100 mL, three-neck flask, 5.00 g (15.5 mmol) of IM-3, 3.58 g (0.20 equiv, 3.09 mmol) of $Pd(PPh_3)_4$, 15.1 g (3.0 equiv, 46.4 mmol) of $Cs_2CO_3$, 40 mL of 1,4-dioxane, and 8.07 g (1.0 equiv, 15.5 mmol) of IM-2 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound A3 (6.01 g, yield 61%).

Through measuring FAB-MS, mass number of m/z=637 was observed as a molecular ion peak, and Compound A3 was identified.

2. Synthesis of Compound B3

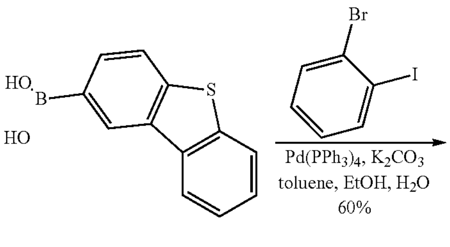

-continued

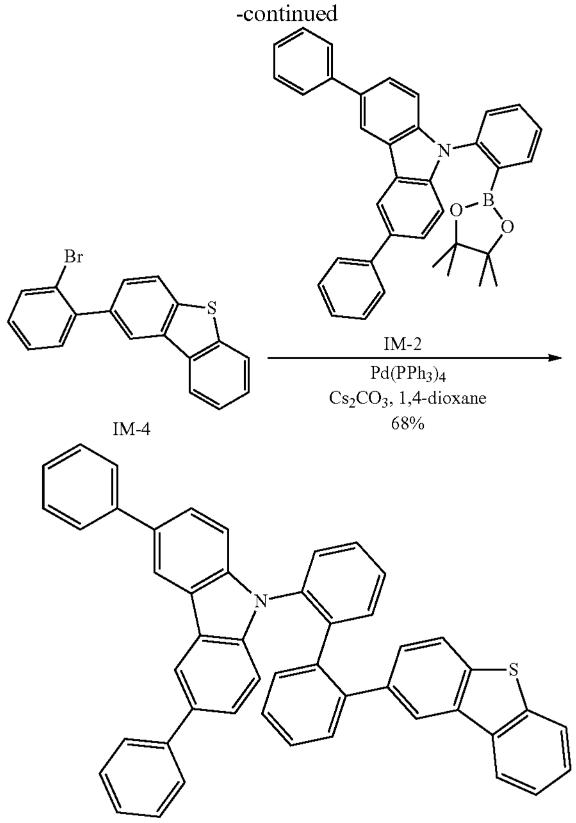

IM-4

IM-2

B3

(1) Synthesis of Compound IM-4

Under an Ar atmosphere, to a 1000 mL, three-neck flask, 20.00 g (87.69 mmol) of dibenzothiophene-2-boronic acid, 37.21 g (1.5 equiv, 131.5 mmol) of 1-bromo-2-iodobenzene, 5.06 g (0.05 equiv, 4.38 mmol) of $Pd(PPh_3)_4$, 36.36 g (3.0 equiv, 263.1 mmol) of $K_2CO_3$, 300 mL of toluene, 150 mL of EtOH, and 75 mL of $H_2O$ were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-4 (17.80 g, yield 60%). Through measuring FAB-MS, mass number of m/z=338 was observed as a molecular ion peak, and Compound IM-4 was identified.

(2) Synthesis of Compound B3

Under an Ar atmosphere, to a 100 mL, three-neck flask, 4.30 g (12.7 mmol) of IM-4, 2.93 g (0.20 equiv, 2.54 mmol) of $Pd(PPh_3)_4$, 12.4 g (3.0 equiv, 38.0 mmol) of $Cs_2CO_3$, 35 mL of 1,4-dioxane, and 6.61 g (1.0 equiv, 12.7 mmol) of IM-2 were added in order and then, heated, refluxed, and stirred. After cooling in the air, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound B3 (5.66 g, yield 68%).

Through measuring FAB-MS, mass number of m/z=653 was observed as a molecular ion peak, and Compound B3 was identified.

3. Synthesis of Compound C3

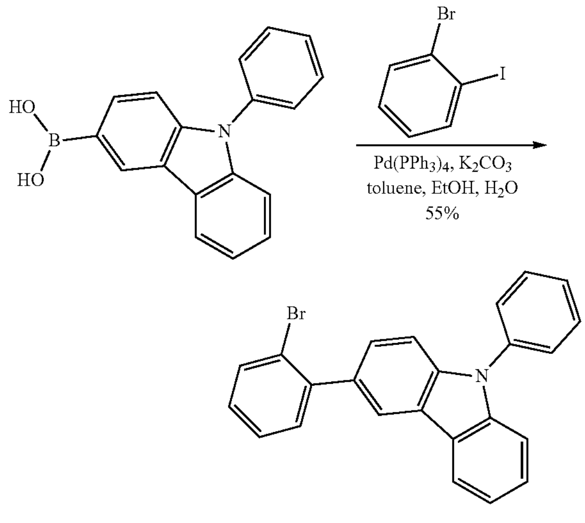

IM-5

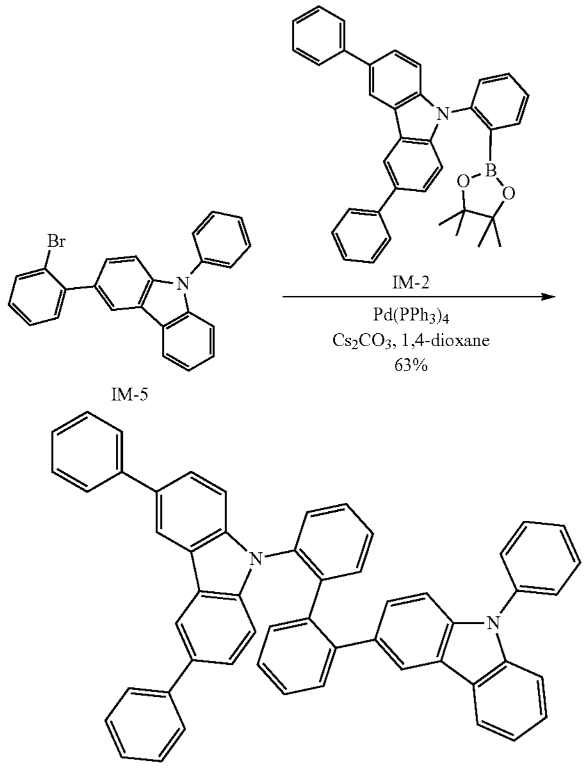

IM-2

IM-5

C3

(1) Synthesis of Compound IM-5

Under an Ar atmosphere, to a 1000 mL, three-neck flask, 20.00 g (69.65 mmol) of (9-phenyl-9H-carbazol-3-yl)boronic acid, 29.56 g (1.5 equiv, 104.5 mmol) of 1-bromo-2-iodobenzene, 4.02 g (0.05 equiv, 3.48 mmol) of $Pd(PPh_3)_4$, 28.88 g (3.0 equiv, 209.0 mmol) of $K_2CO_3$, 240 mL of toluene, 120 mL of EtOH, and 60 mL of $H_2O$ were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-5 (15.23 g, yield 55%). Through measuring FAB-MS, mass number of m/z=397 was observed as a molecular ion peak, and Compound IM-5 was identified.

(2) Synthesis of Compound C3

Under an Ar atmosphere, to a 100 mL, three-neck flask, 5.00 g (12.6 mmol) of IM-5, 2.90 g (0.20 equiv, 2.51 mmol) of $Pd(PPh_3)_4$, 12.3 g (3.0 equiv, 37.7 mmol) of $Cs_2CO_3$, 35 mL of 1,4-dioxane, and 6.55 g (1.0 equiv, 12.6 mmol) of IM-2 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound C3 (5.65 g, yield 63%). Through measuring FAB-MS, mass number of m/z=712 was observed as a molecular ion peak, and Compound C3 was identified.

4. Synthesis of Compound A1

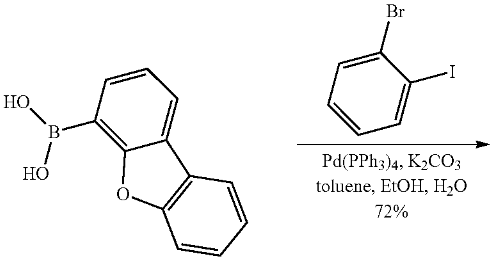

-continued

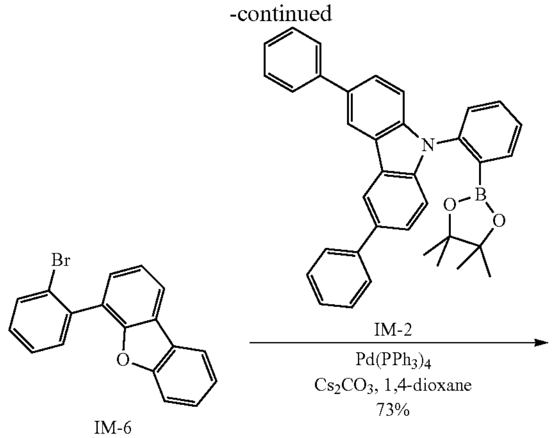

IM-6

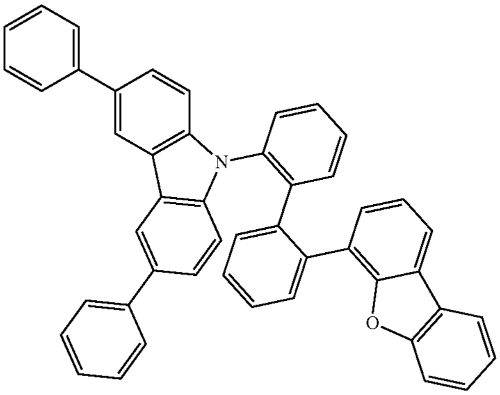

A1

(1) Synthesis of Compound IM-6

Under an Ar atmosphere, to a 1000 mL, three-neck flask, 18.00 g (84.90 mmol) of dibenzofuran-4-boronic acid, 36.03 g (1.5 equiv, 127.4 mmol) of 1-bromo-2-iodobenzene, 4.91 g (0.05 equiv, 4.25 mmol) of $Pd(PPh_3)_4$, 35.20 g (3.0 equiv, 255.0 mmol) of $K_2CO_3$, 280 mL of toluene, 140 mL of EtOH, and 70 mL of $H_2O$ were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-6 (19.76 g, yield 72%).

Through measuring FAB-MS, mass number of m/z=322 was observed as a molecular ion peak, and Compound IM-6 was identified.

(2) Synthesis of Compound A1

Under an Ar atmosphere, to a 100 mL, three-neck flask, 5.00 g (15.5 mmol) of IM-6, 3.58 g (0.20 equiv, 3.09 mmol) of $Pd(PPh_3)_4$, 15.1 g (3.0 equiv, 46.4 mmol) of $Cs_2CO_3$, 40 mL of 1,4-dioxane, and 8.07 g (1.0 equiv, 15.5 mmol) of IM-2 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound A1 (7.15 g, yield 73%).

Through measuring FAB-MS, mass number of m/z=637 was observed as a molecular ion peak, and Compound A1 was identified.

5. Synthesis of Compound A2

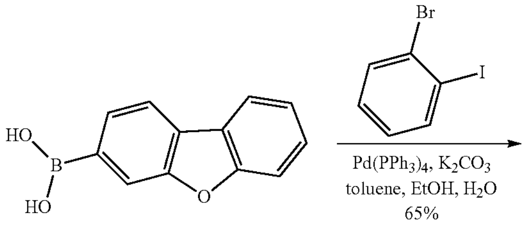

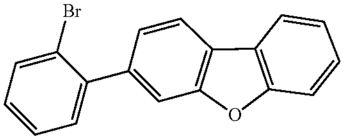

IM-7

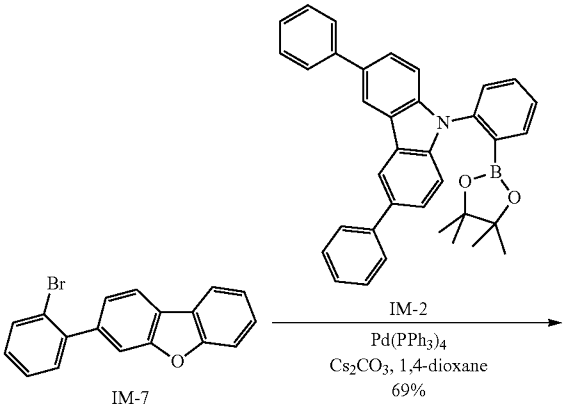

IM-7

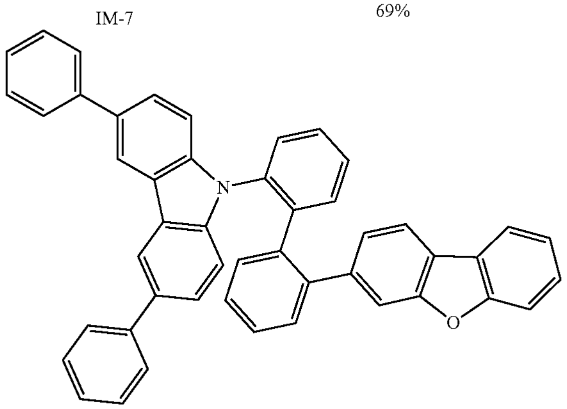

A2

(1) Synthesis of Compound IM-7

Under an Ar atmosphere, to a 1000 mL, three-neck flask, 20.00 g (94.34 mmol) of dibenzofuran-3-boronic acid, 40.03 g (1.5 equiv, 141.5 mmol) of 1-bromo-2-iodobenzene, 5.45 g (0.05 equiv, 4.72 mmol) of $Pd(PPh_3)_4$, 39.11 g (3.0 equiv, 283.0 mmol) of $K_2CO_3$, 300 mL of toluene, 150 mL of EtOH, and 75 mL of $H_2O$ were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-7 (17.80 g, yield 65%).

Through measuring FAB-MS, mass number of m/z=322 was observed as a molecular ion peak, and Compound IM-7 was identified.

(2) Synthesis of Compound A2

Under an Ar atmosphere, to a 100 mL, three-neck flask, 5.00 g (15.5 mmol) of IM-7, 3.58 g (0.20 equiv, 3.09 mmol) of $Pd(PPh_3)_4$, 15.1 g (3.0 equiv, 46.4 mmol) of $Cs_2CO_3$, 40 mL of 1,4-dioxane, and 8.07 g (1.0 equiv, 15.5 mmol) of IM-2 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound A2 (6.81 g, yield 69%).

Through measuring FAB-MS, mass number of m/z=637 was observed as a molecular ion peak, and Compound A2 was identified.

6. Synthesis of Compound A4

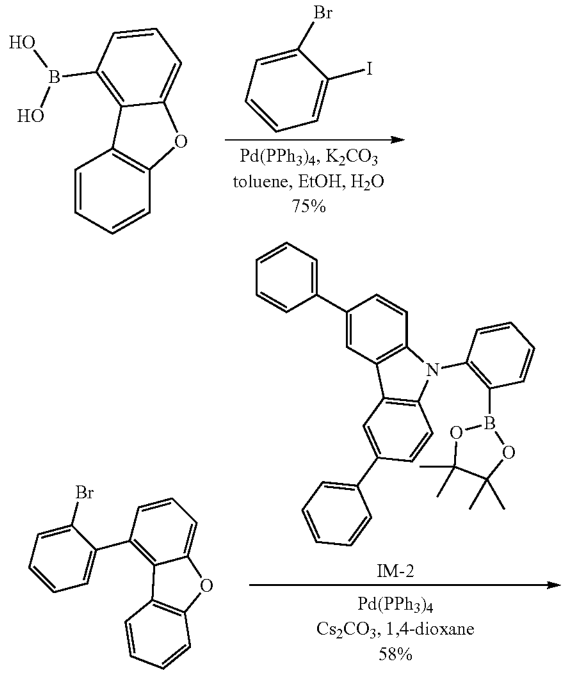

IM-8

-continued

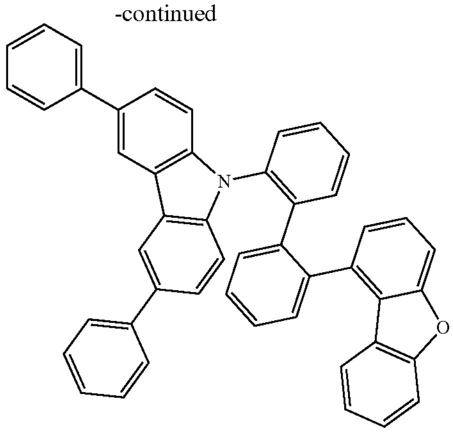

A4

(1) Synthesis of Compound IM-8

Under an Ar atmosphere, to a 1000 mL, three-neck flask, 15.00 g (70.75 mmol) of dibenzofuran-1-boronic acid, 30.02 g (1.5 equiv, 106.1 mmol) of 1-bromo-2-iodobenzene, 4.09 g (0.05 equiv, 3.54 mmol) of $Pd(PPh_3)_4$, 29.33 g (3.0 equiv, 212.3 nmol) of $K_2CO_3$, 240 mL of toluene, 120 mL of EtOH, and 60 mL of $H_2O$ were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-8 (17.17 g, yield 75%).

Through measuring FAB-MS, mass number of m/z=322 was observed as a molecular ion peak, and Compound IM-8 was identified.

(2) Synthesis of Compound A4

Under an Ar atmosphere, to a 100 mL, three-neck flask, 5.00 g (15.5 mmol) of IM-8, 3.58 g (0.20 equiv, 3.09 mmol) of $Pd(PPh_3)_4$, 15.1 g (3.0 equiv, 46.4 mmol) of $Cs_2CO_3$, 40 mL of 1,4-dioxane, and 8.07 g (1.0 equiv, 15.5 mmol) of IM-2 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound A4 (5.72 g, yield 58%).

Through measuring FAB-MS, mass number of m/z=637 was observed as a molecular ion peak, and Compound A4 was identified.

7. Synthesis of Compound A5

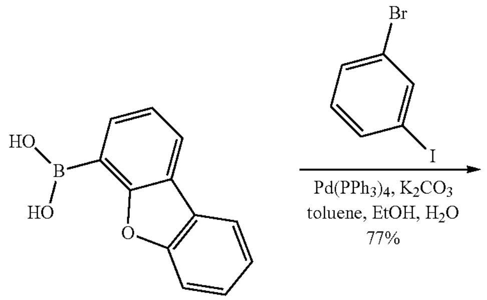

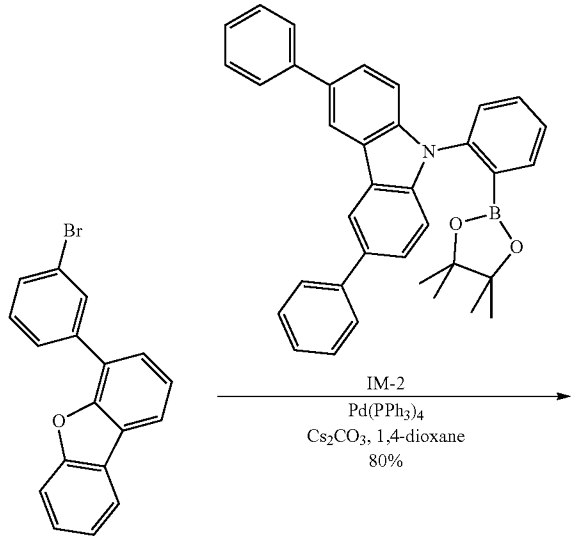

IM-9

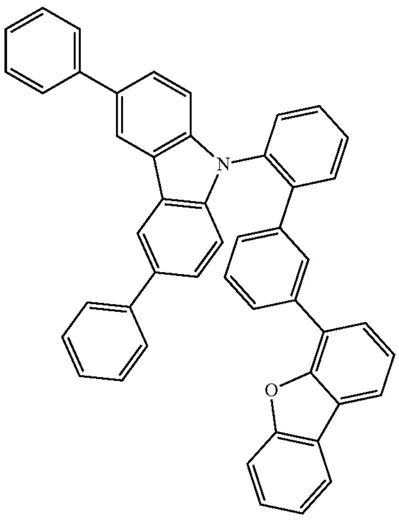

A5

(1) Synthesis of Compound IM-9

Under an Ar atmosphere, to a 1000 mL, three-neck flask, 20.00 g (94.34 mmol) of dibenzofuran-4-boronic acid, 40.03 g (1.5 equiv, 141.5 mmol) of 1-bromo-3-iodobenzene, 5.45 g (0.05 equiv, 4.72 mmol) of $Pd(PPh_3)_4$, 39.11 g (3.0 equiv, 283.0 mmol) of $K_2CO_3$, 300 mL of toluene, 150 mL of EtOH, and 75 mL of $H_2O$ were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-9 (23.50 g, yield 77%).

Through measuring FAB-MS, mass number of m/z=322 was observed as a molecular ion peak, and Compound IM-9 was identified.

(2) Synthesis of Compound A5

Under an Ar atmosphere, to a 100 mL, three-neck flask, 4.50 g (13.9 mmol) of IM-9, 3.21 g (0.20 equiv, 2.78 mmol) of $Pd(PPh_3)_4$, 13.6 g (3.0 equiv, 41.8 mmol) of $Cs_2CO_3$, 40 mL of 1,4-dioxane, and 7.26 g (1.0 equiv, 13.9 mmol) of IM-2 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound A5 (7.05 g, yield 80%).

Through measuring FAB-MS, mass number of m/z=637 was observed as a molecular ion peak, and Compound A5 was identified.

8. Synthesis of Compound A34

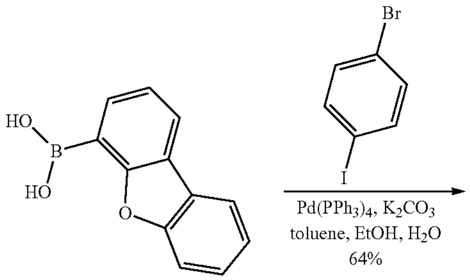

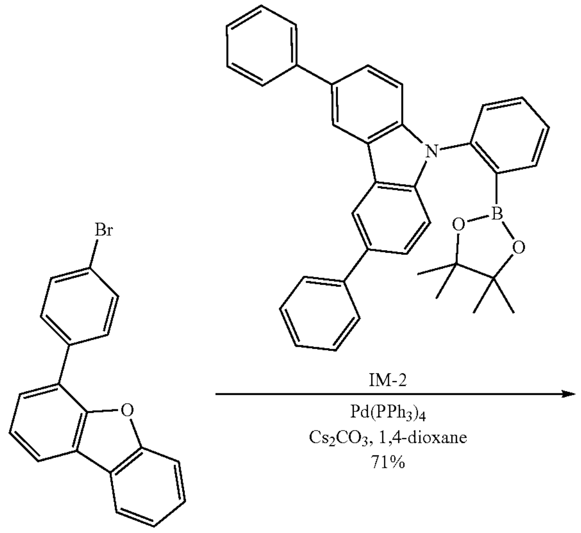

IM-10

-continued

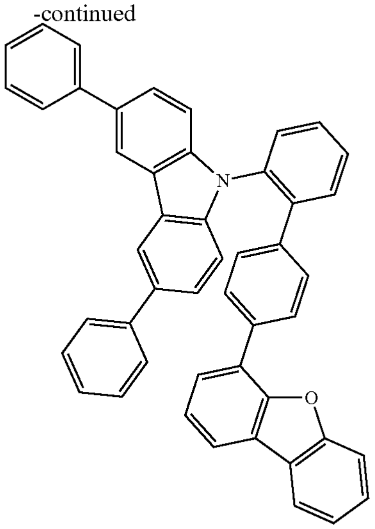

A34

(1) Synthesis of Compound IM-10

Under an Ar atmosphere, to a 1000 mL, three-neck flask, 20.00 g (94.34 mmol) of dibenzofuran-4-boronic acid, 40.03 g (1.5 equiv, 141.5 mmol) of 1-bromo-4-iodobenzene, 5.45 g (0.05 equiv, 4.72 mmol) of $Pd(PPh_3)_4$, 39.11 g (3.0 equiv, 283.0 mmol) of $K_2CO_3$, 300 mL of toluene, 150 mL of EtOH, and 75 mL of $H_2O$ were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-10 (19.50 g, yield 64%).

Through measuring FAB-MS, mass number of m/z=322 was observed as a molecular ion peak, and Compound IM-10 was identified.

(2) Synthesis of Compound A34

Under an Ar atmosphere, to a 100 mL, three-neck flask, 4.20 g (13.0 mmol) of IM-10, 3.00 g (0.20 equiv, 2.60 mmol) of $Pd(PPh_3)_4$, 12.7 g (3.0 equiv, 39.0 mmol) of $Cs_2CO_3$, 35 mL of 1,4-dioxane, and 6.78 g (1.0 equiv, 13.0 mmol) of IM-2 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound A34 (5.92 g, yield 71%).

Through measuring FAB-MS, mass number of m/z=637 was observed as a molecular ion peak, and Compound A34 was identified.

9. Synthesis of Compound A17

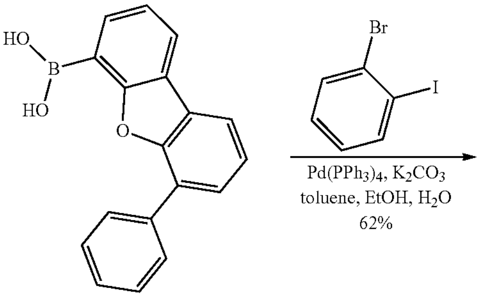

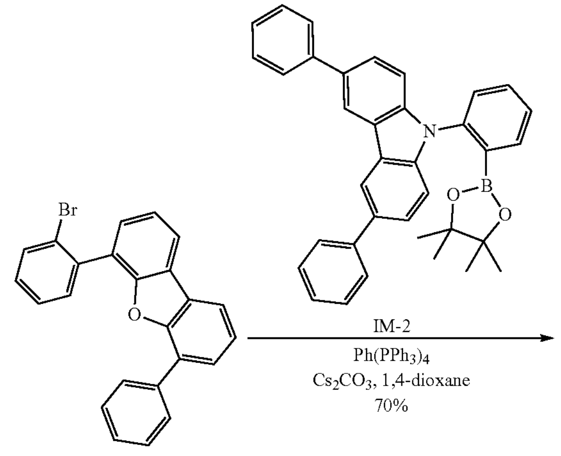

IM-11

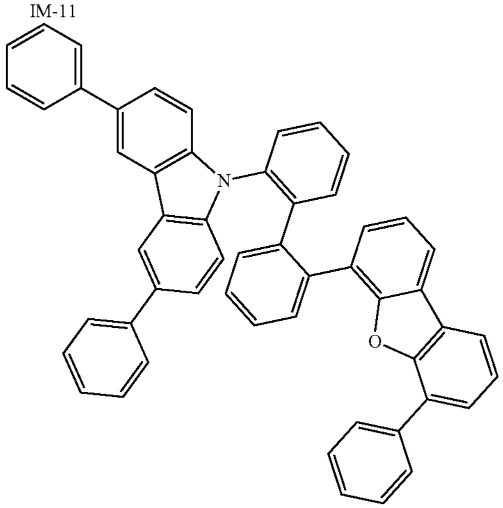

A17

(1) Synthesis of Compound IM-11

Under an Ar atmosphere, to a 1000 mL, three-neck flask, 15.00 g (52.06 mmol) of 6-phenyldibenzofuran-4-boronic acid, 22.09 g (1.5 equiv, 78.10 mmol) of 1-bromo-2-iodobenzene, 3.01 g (0.05 equiv, 2.60 mmol) of $Pd(PPh_3)_4$, 21.59 g (3.0 equiv, 156.2 mmol) of $K_2CO_3$, 180 mL of toluene, 90 mL of EtOH, and 45 mL of $H_2O$ were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-11 (12.85 g, yield 62%).

Through measuring FAB-MS, mass number of m/z=398 was observed as a molecular ion peak, and Compound IM-11 was identified.

(2) Synthesis of Compound A17

Under an Ar atmosphere, to a 100 mL, three-neck flask, 5.00 g (12.5 mmol) of IM-11, 2.89 g (0.20 equiv, 2.50 mmol) of $Pd(PPh_3)_4$, 12.24 g (3.0 equiv, 37.57 mmol) of $Cs_2CO_3$, 30 mL of 1,4-dioxane, and 6.53 g (1.0 equiv, 12.5 mmol) of IM-2 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound A17 (6.28 g, yield 70%).

Through measuring FAB-MS, mass number of m/z=713 was observed as a molecular ion peak, and Compound A17 was identified.

10. Synthesis of Compound C22

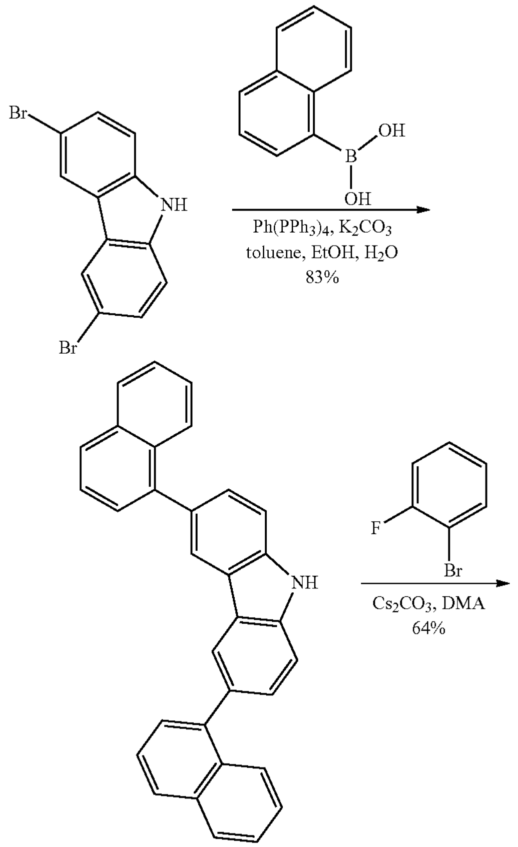

IM-12

-continued

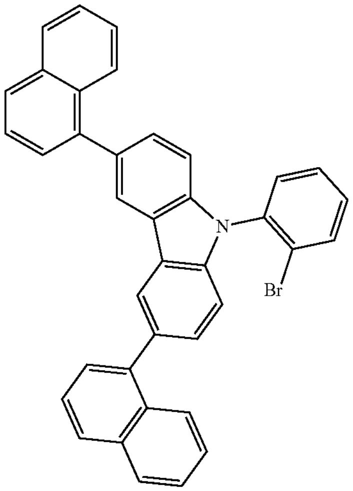

IM-13

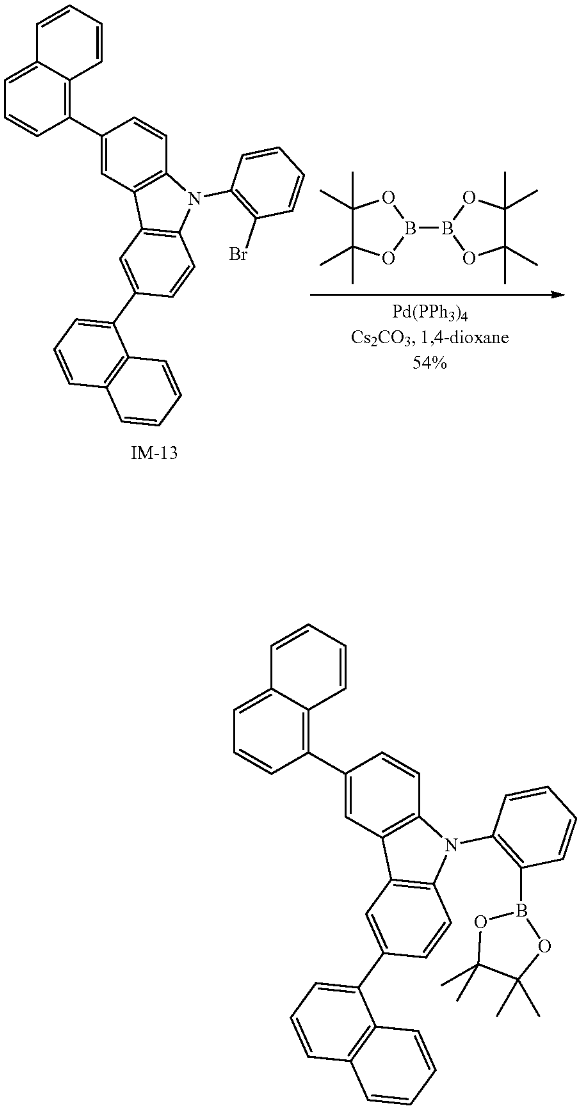

IM-13

IM-14

-continued

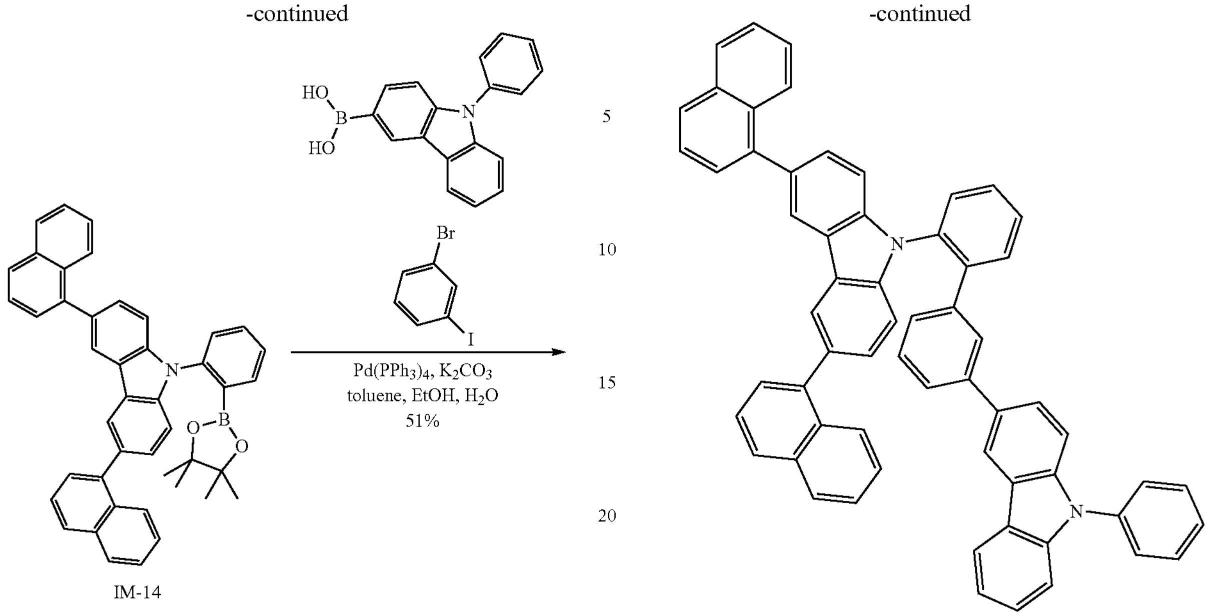

IM-14

C22

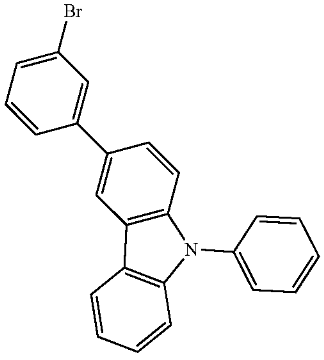

IM-15

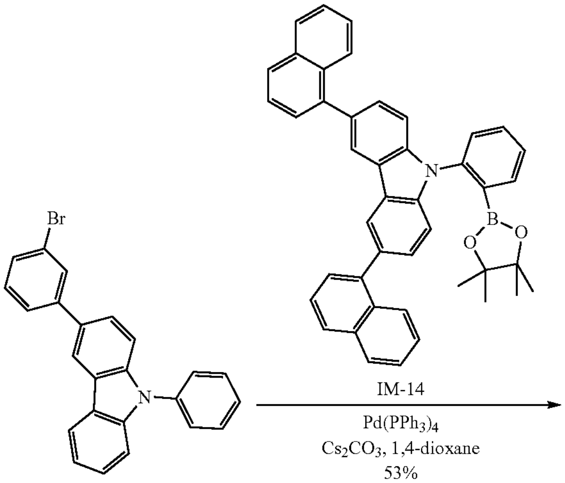

IM-14

IM-15

(1) Synthesis of Compound IM-12

Under an Ar atmosphere, to a 1000 mL, three-neck flask, 15.00 g (46.15 mmol) of 3,6-dbromocarbazole, 19.85 g (2.5 equiv, 115.4 mmol) of 1-naphthylboronic acid, 2.67 g (0.05 equiv, 2.31 mmol) of $Pd(PPh_3)_4$, 19.14 g (3.0 equiv, 138.5 mmol) of $K_2CO_3$, 160 mL of toluene, 80 mL of EtOH, and 40 mL of $H_2O$ were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-12 (16.05 g, yield 83%).

Through measuring FAB-MS, mass number of m/z=419 was observed as a molecular ion peak, and Compound IM-12 was identified.

(2) Synthesis of Compound IM-13

Under an Ar atmosphere, to a 100 mL, three-neck flask, 16.05 g (38.26 mmol) of IM-12, 24.93 g (2.0 equiv, 76.51 mmol) of $Cs_2CO_3$, 40 mL of DMA and 13.39 g (2.0 equiv, 76.51 mmol) of 1-bromo-2-fluorobenzene were added in order and then, heated to about 120° C. and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-13 (14.08 g, yield 64%).

Through measuring FAB-MS, mass number of m/z=573 was observed as a molecular ion peak, and Compound IM-13 was identified.

(3) Synthesis of Compound IM-14

Under an Ar atmosphere, to a 500 mL, three-neck flask, 14.08 g (24.51 mmol) of IM-13, 5.66 g (0.20 equiv, 4.90 mmol) of $Pd(PPh_3)_4$, 31.94 g (4.0 equiv, 98.03 mmol) of $Cs_2CO_3$, 180 mL of 1,4-dioxane, and 24.89 g (4.0 equiv, 98.03 mmol) of bis(pinacolato)diboron were added in order and then, heated, refluxed, and stirred. After cooling in the air to room temperature, water and toluene were added to the reaction solution, and an organic layer was separately taken. The organic layer was washed with a saline solution and dried with $MgSO_4$.

The $MgSO_4$ was filtered, and an organic layer was concentrated. The crude product thus obtained was separated by silica gel column chromatography (using a mixture solvent of hexane and toluene as a developing layer) to obtain Compound IM-14 (8.23 g, yield 54%).

Through measuring FAB-MS, mass number of m/z=621 was observed as a molecular ion peak, and Compound IM-14 was identified.

(4) Synthesis of Compound IM-15

Under an Ar atmosphere, to a 1000 mL, three-neck flask, 20.00 g (69.65 mmol) of (9-phenyl-9H-carbazol-3-yl)boronic acid, 29.56 g (1.5 equiv, 104.5 mmol) of 1-bromo-3-iodobenzene, 4.02 g (0.05 equiv, 3.48 mmol) of $Pd(PPh_3)_4$, 28.88 g (3.0 equiv, 209.0 mmol) of $K_2CO_3$, 240 mL of toluene, 120 mL of EtOH, and 60 mL of $H_2O$ were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-15 (14.13 g, yield 51%).

Through measuring FAB-MS, mass number of m/z=397 was observed as a molecular ion peak, and Compound IM-15 was identified.

(5) Synthesis of Compound C22

Under an Ar atmosphere, to a 100 mL, three-neck flask, 5.00 g (12.6 mmol) of IM-15, 2.90 g (0.20 equiv, 2.51 mmol) of $Pd(PPh_3)_4$, 12.3 g (3.0 equiv, 37.7 mmol) of $Cs_2CO_3$, 35 mL of 1,4-dioxane, and 7.80 g (1.0 equiv, 12.6 mmol) of IM-14 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound C22 (5.40 g, yield 53%).

Through measuring FAB-MS, mass number of m/z=812 was observed as a molecular ion peak, and Compound C22 was identified.

11. Synthesis of Compound D1

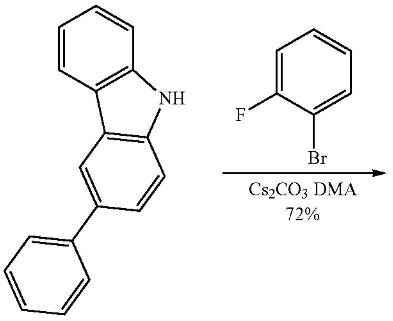

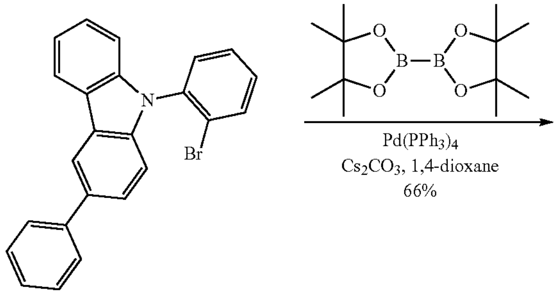

IM-16

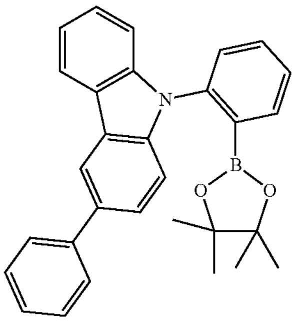

IM-17

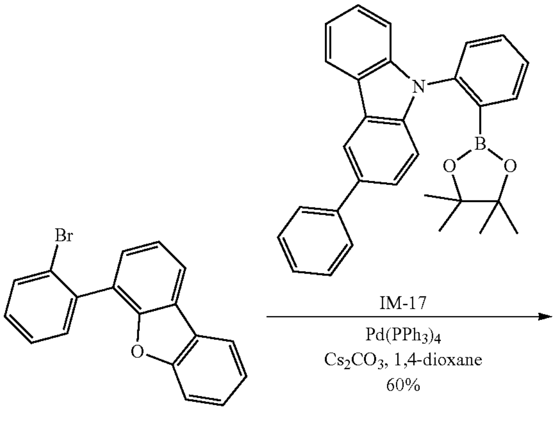

IM-6

-continued

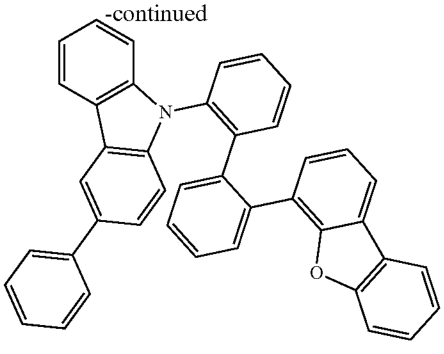

D1

(1) Synthesis of Compound IM-16

Under an Ar atmosphere, to a 200 mL, three-neck flask, 20.00 g (82.20 mmol) of 3-phenyl-9H-carbazole, 53.56 g (2.0 equiv, 164.4 mmol) of $Cs_2CO_3$, 80 mL of DMA and 28.77 g (2.0 equiv, 164.4 mmol) of 1-bromo-2-fluorobenzene were added in order and then, heated to about 120° C. and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-16 (23.55 g, yield 72%).

Through measuring FAB-MS, mass number of m/z=397 was observed as a molecular ion peak, and Compound IM-16 was identified.

(2) Synthesis of Compound IM-17

Under an Ar atmosphere, to a 500 mL, three-neck flask, 23.55 g (59.13 mmol) of IM-16, 13.64 g (0.20 equiv, 11.83 mmol) of $Pd(PPh_3)_4$, 77.06 g (4.0 equiv, 236.5 mmol) of $Cs_2CO_3$, 250 mL of 1,4-dioxane, and 60.06 g (4.0 equiv, 236.5 mmol) of bis(pinacolato)diboron were added in order and then, heated, refluxed, and stirred. After cooling in the air to room temperature, water and toluene were added to the reaction solution, and an organic layer was separately taken. The organic layer was washed with a saline solution and dried with $MgSO_4$.

The $MgSO_4$ was filtered, and an organic layer was concentrated. The crude product thus obtained was separated by silica gel column chromatography (using a mixture solvent of hexane and toluene as a developing layer) to obtain Compound IM-17 (17.39 g, yield 66%).

Through measuring FAB-MS, mass number of m/z=445 was observed as a molecular ion peak, and Compound IM-17 was identified.

(3) Synthesis of Compound D1

Under an Ar atmosphere, to a 200 mL, three-neck flask, 6.53 g (20.2 mmol) of IM-6, 4.67 g (0.20 equiv, 4.04 mmol) of $Pd(PPh_3)_4$, 19.7 g (3.0 equiv, 60.6 mmol) of $Cs_2CO_3$, 100 mL of 1,4-dioxane, and 9.00 g (1.0 equiv, 20.2 mmol) of IM-17 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound D1 (6.82 g, yield 60%).

Through measuring FAB-MS, mass number of m/z=561 was observed as a molecular ion peak, and Compound D1 was identified.

12. Synthesis of Compound D17

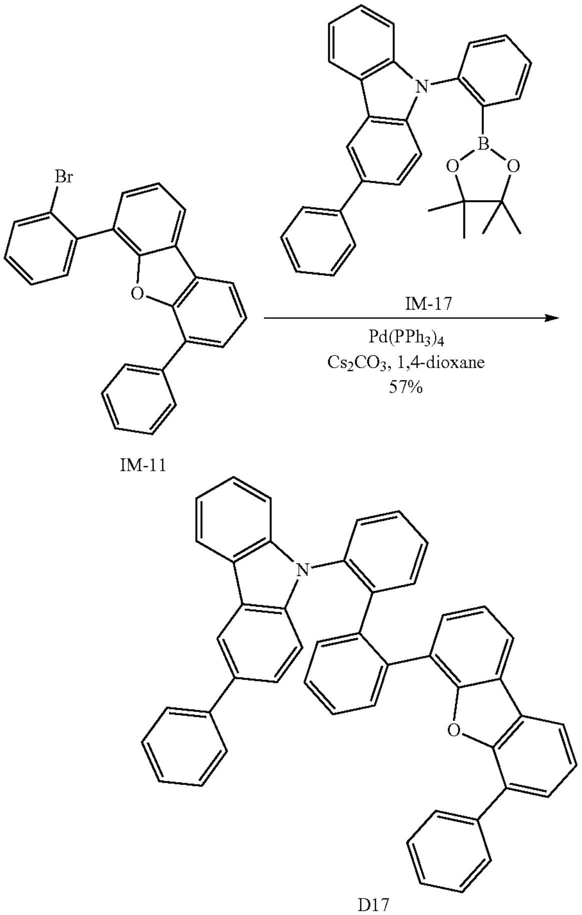

D17

Under an Ar atmosphere, to a 200 mL, three-neck flask, 7.30 g (18.3 mmol) of IM-11, 4.23 g (0.20 equiv, 3.66 mmol) of $Pd(PPh_3)_4$, 17.9 g (3.0 equiv, 54.9 mmol) of $Cs_2CO_3$, 100 mL of 1,4-dioxane, and 8.14 g (1.0 equiv, 18.3 mmol) of IM-17 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound D17 (6.65 g, yield 57%).

Through measuring FAB-MS, mass number of m/z=637 was observed as a molecular ion peak, and Compound D17 was identified.

13. Synthesis of Compound K1

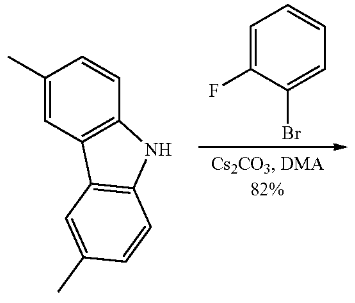

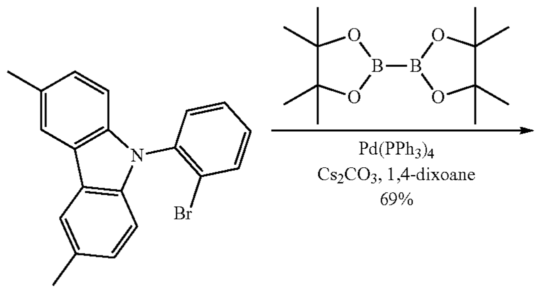

IM-18

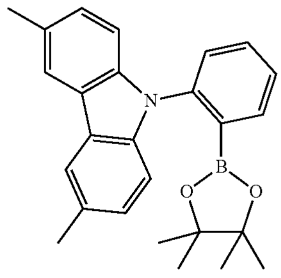

IM-19

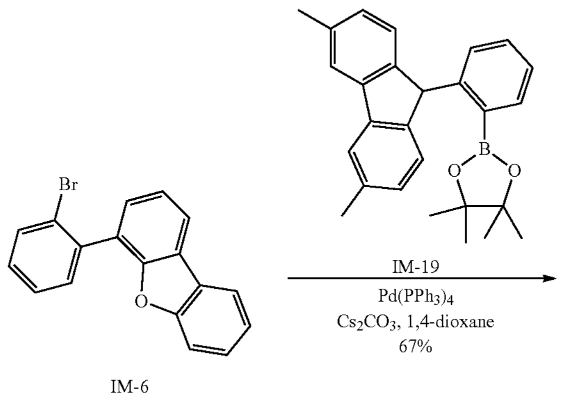

IM-6

-continued

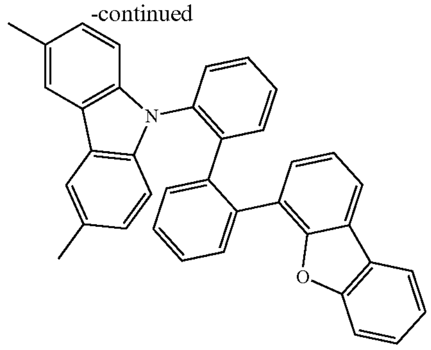

K1

(1) Synthesis of Compound IM-18

Under an Ar atmosphere, to a 200 mL, three-neck flask, 15.00 g (76.82 mmol) of 3,6-dimethyl-9H-carbazole, 50.06 g (2.0 equiv, 153.6 mmol) of $Cs_2CO_3$, 80 mL of DMA and 26.89 g (2.0 equiv, 153.6 mmol) of 1-bromo-2-fluorobenzene were added in order and then, heated to about 120° C. and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-18 (22.02 g, yield 82%).

Through measuring FAB-MS, mass number of m/z=349 was observed as a molecular ion peak, and Compound IM-18 was identified.

(2) Synthesis of Compound IM-19

Under an Ar atmosphere, to a 500 mL, three-neck flask, 22.02 g (62.87 mmol) of IM-18, 14.53 g (0.20 equiv, 12.57 mmol) of $Pd(PPh_3)_4$, 81.93 g (4.0 equiv, 251.5 mmol) of $Cs_2CO_3$, 200 mL of 1,4-dioxane, and 63.86 g (4.0 equiv, 251.5 mmol) of bis(pinacolato)diboron were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-19 (17.22 g, yield 69%).

Through measuring FAB-MS, mass number of m/z=397 was observed as a molecular ion peak, and Compound IM-19 was identified.

(3) Synthesis of Compound K1

Under an Ar atmosphere, to a 200 mL, three-neck flask, 4.88 g (15.1 mmol) of IM-6, 3.49 g (0.20 equiv, 3.02 mmol) of $Pd(PPh_3)_4$, 14.8 g (3.0 equiv, 45.3 mmol) of $Cs_2CO_3$, 100 mL of 1,4-dioxane, and 6.00 g (1.0 equiv, 15.1 mmol) of IM-19 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound K1 (5.21 g, yield 67%).

Through measuring FAB-MS, mass number of m/z=513 was observed as a molecular ion peak, and Compound K1 was identified.

14. Synthesis of Compound K13

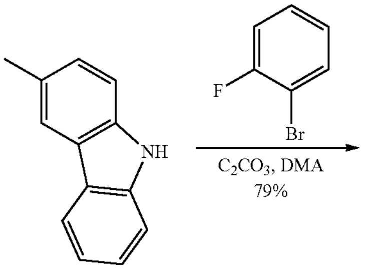

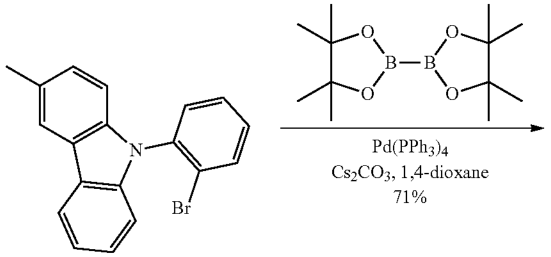

IM-20

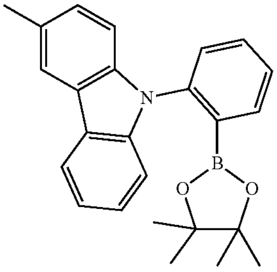

IM-21

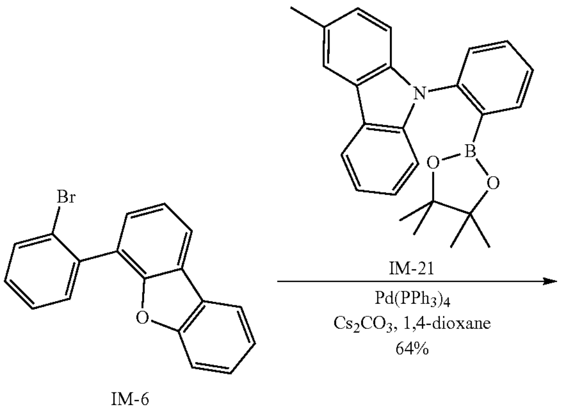

IM-6

-continued

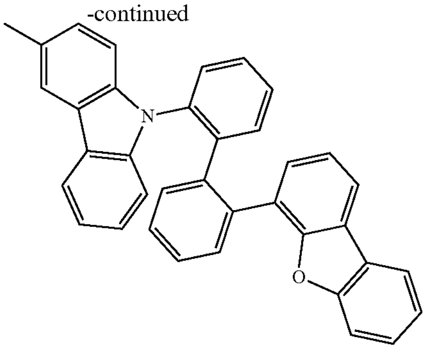

K13

(1) Synthesis of Compound IM-20

Under an Ar atmosphere, to a 200 mL, three-neck flask, 15.00 g (82.76 mmol) of 3-methyl-9H-carbazole, 53.93 g (2.0 equiv, 165.5 mmol) of $Cs_2CO_3$, 80 mL of DMA and 28.97 g (2.0 equiv, 165.5 mmol) of 1-bromo-2-fluorobenzene were added in order and then, heated to about 120° C. and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-20 (21.95 g, yield 79%).

Through measuring FAB-MS, mass number of m/z=335 was observed as a molecular ion peak, and Compound IM-20 was identified.

(2) Synthesis of Compound IM-21

Under an Ar atmosphere, to a 500 mL, three-neck flask, 21.95 g (65.28 mmol) of IM-20, 15.09 g (0.20 equiv, 13.06 mmol) of $Pd(PPh_3)_4$, 85.08 g (4.0 equiv, 261.1 mmol) of $Cs_2CO_3$, 200 mL of 1,4-dioxane, and 66.31 g (4.0 equiv, 261.1 mmol) of bis(pinacolato)diboron were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-21 (17.77 g, yield 71%).

Through measuring FAB-MS, mass number of m/z=383 was observed as a molecular ion peak, and Compound IM-21 was identified.

(3) Synthesis of Compound K13

Under an Ar atmosphere, to a 200 mL, three-neck flask, 8.43 g (26.1 mmol) of IM-6, 6.03 g (0.20 equiv, 5.22 mmol) of $Pd(PPh_3)_4$, 25.5 g (3.0 equiv, 78.3 mmol) of $Cs_2CO_3$, 100 mL of 1,4-dioxane, and 10.00 g (1.0 equiv, 26.08 mmol) of IM-21 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound K13 (8.33 g, yield 64%).

Through measuring FAB-MS, mass number of m/z=499 was observed as a molecular ion peak, and Compound K13 was identified.

15 Synthesis of Compound A20

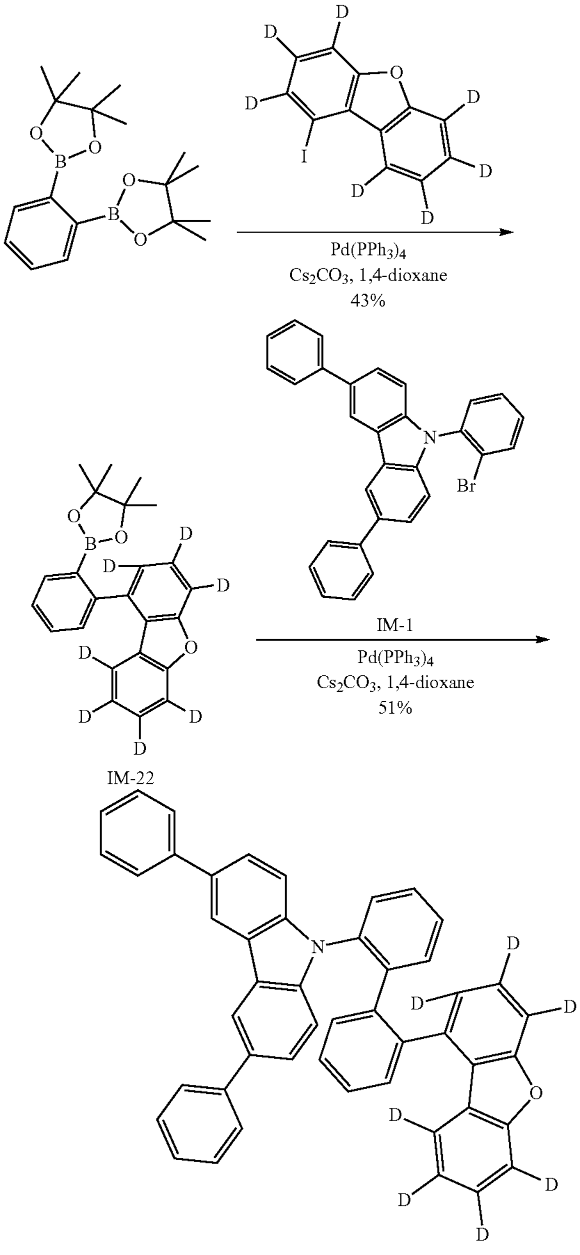

A20

(1) Synthesis of Compound IM-22

Under an Ar atmosphere, to a 500 mL, three-neck flask, 5.48 g (16.6 mmol) of 1,2-bis(4,4,5,5-tetramethyl-1,3,2-dioxaborolan-2-yl)benzene, 10.0 g (2.0 equiv, 33.2 mmol) of 1-iododibenzo[b,d]furan-2,3,4,6,7,8,9-d7, 0.96 g (0.05 equiv, 0.83 mmol) of $Pd(PPh_3)_4$, 16.23 g (3.0 equiv, 49.81 mmol) of $Cs_2CO_3$, and 150 mL of 1,4-dioxane were added in order and then, heated, refluxed and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound IM-22 (2.71 g, yield 43%).

Through measuring FAB-MS, mass number of m/z=377 was observed as a molecular ion peak, and Compound IM-22 was identified.

(2) Synthesis of Compound A20

Under an Ar atmosphere, to a 200 mL, three-neck flask, 2.71 g (7.18 mmol) of IM-22, 1.66 g (0.20 equiv, 1.44 mmol) of $Pd(PPh_3)_4$, 7.02 g (3.0 equiv, 21.6 mmol) of $Cs_2CO_3$, 70 mL of 1,4-dioxane, and 3.41 g (1.0 equiv, 7.18 mmol) of IM-1 were added in order and then, heated, refluxed, and stirred. After cooling in the air to room temperature, water and toluene were added to the reaction solution, and an organic layer was separately taken. The organic layer was washed with a saline solution and dried with $MgSO_4$. The $MgSO_4$ was filtered, and an organic layer was concentrated. The crude product thus obtained was separated by silica gel column chromatography (using a mixture solvent of hexane and toluene as a developing layer) to obtain Compound A20 (2.35 g, yield 51%).

Through measuring FAB-MS, mass number of m/z=644 was observed as a molecular ion peak, and Compound A20 was identified.

Examples of Manufacturing Devices

Luminescence devices were manufactured using Example Compounds and Comparative Compounds below as materials of a hole transport region.

Example Compounds

A3

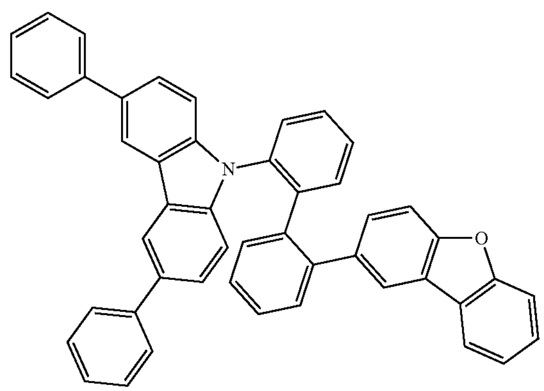

-continued
B3
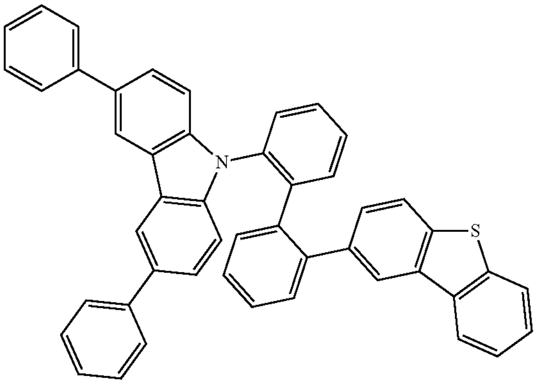
C3
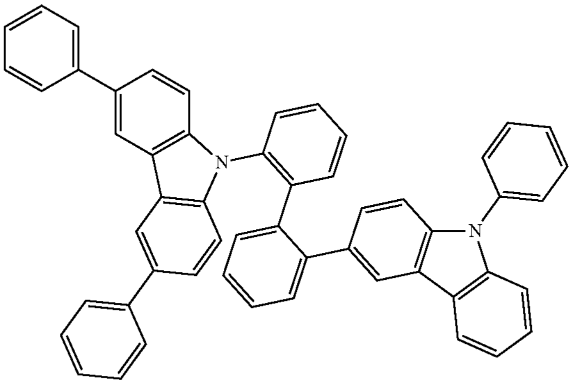
A1
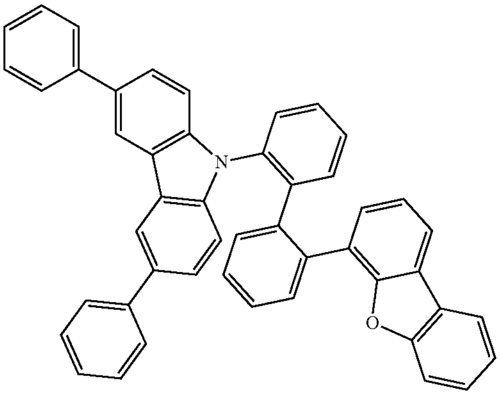
A2
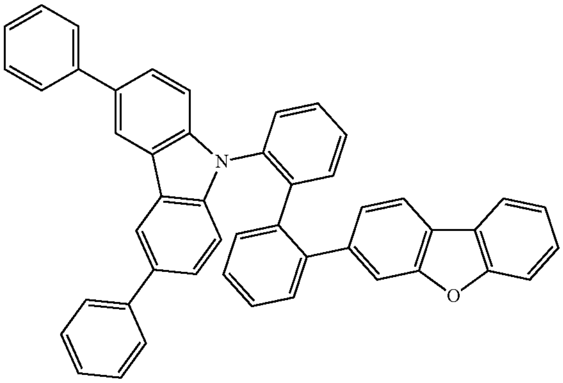
-continued
A4
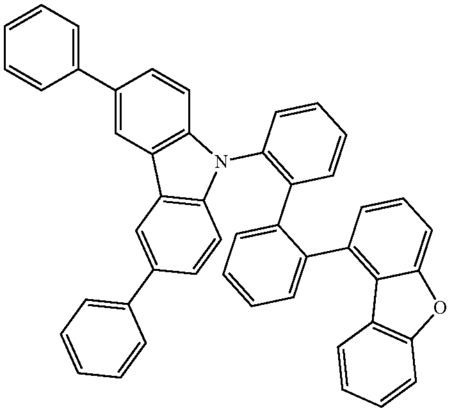
A5
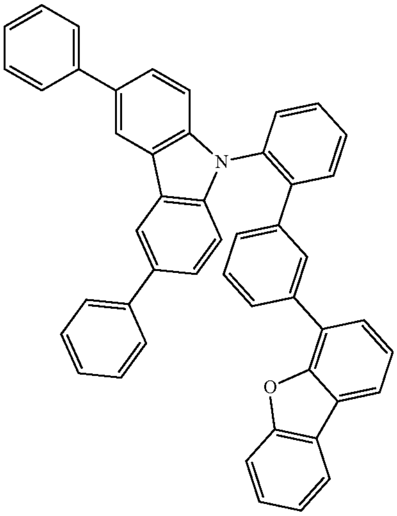
A34
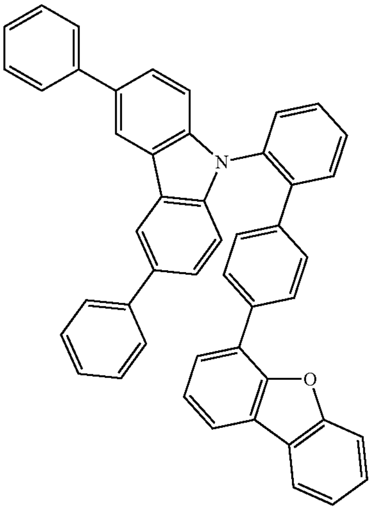

-continued
A17
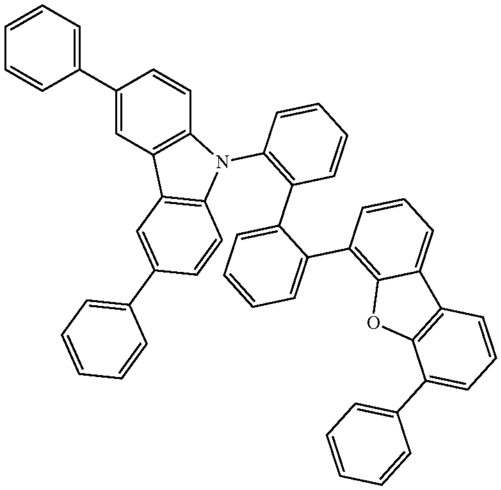
C22
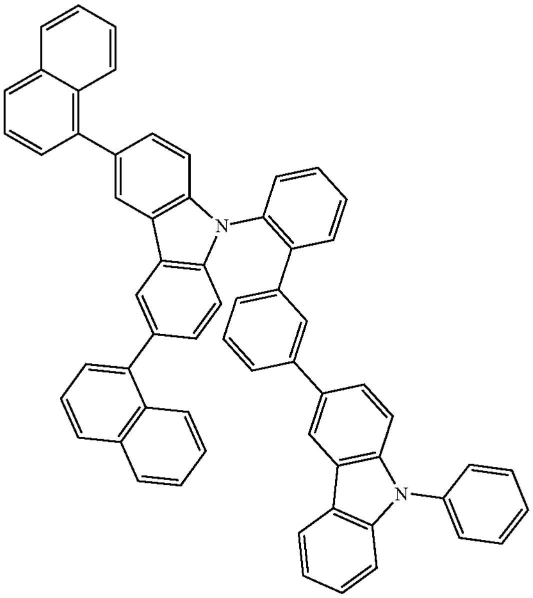
D1
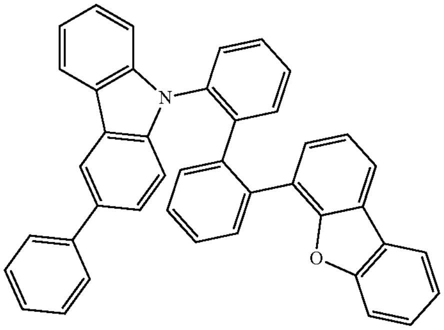
-continued
D17
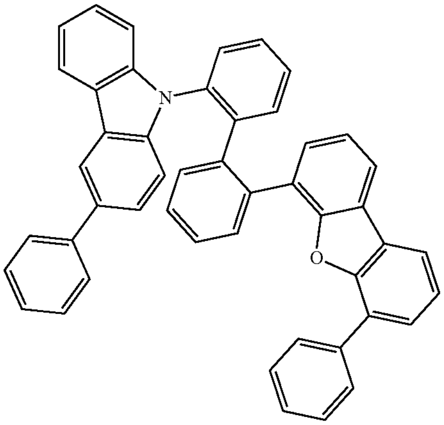
K1
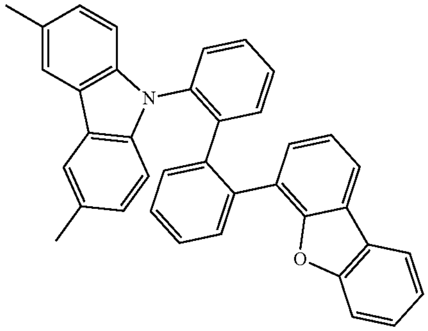
K13
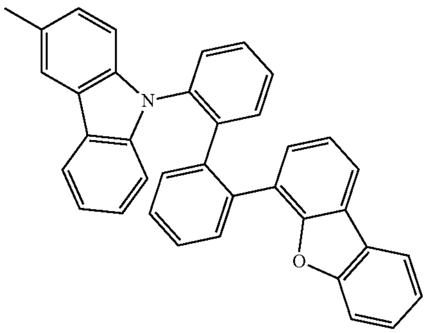
A20
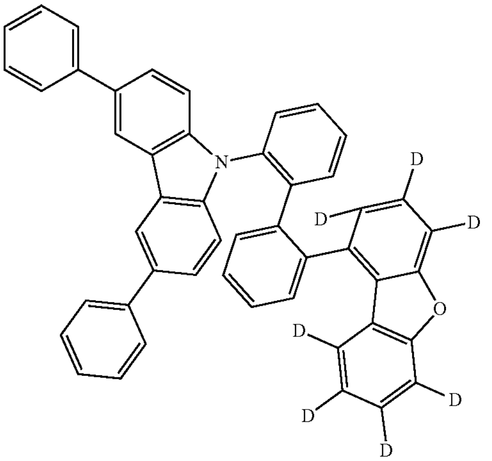

Comparative Compounds
R1
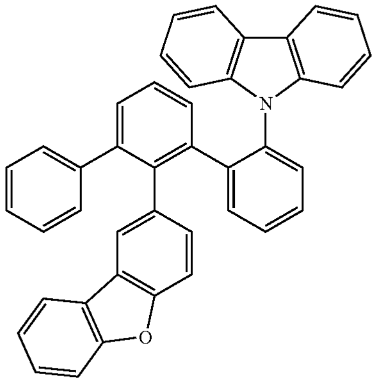
R2
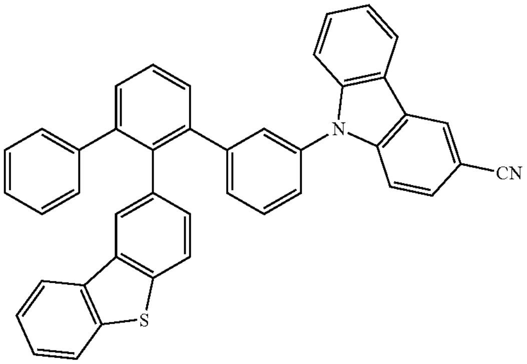
R3
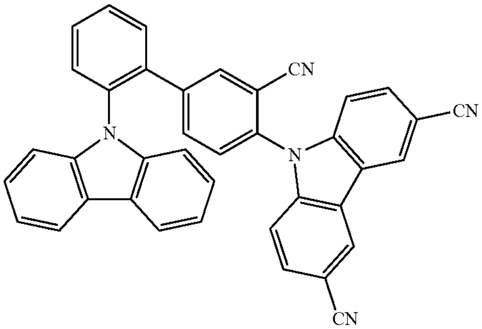
R4
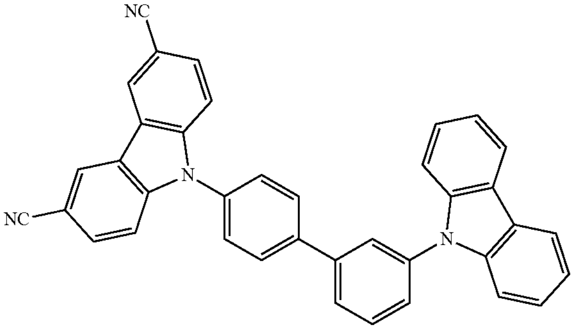
-continued
R5
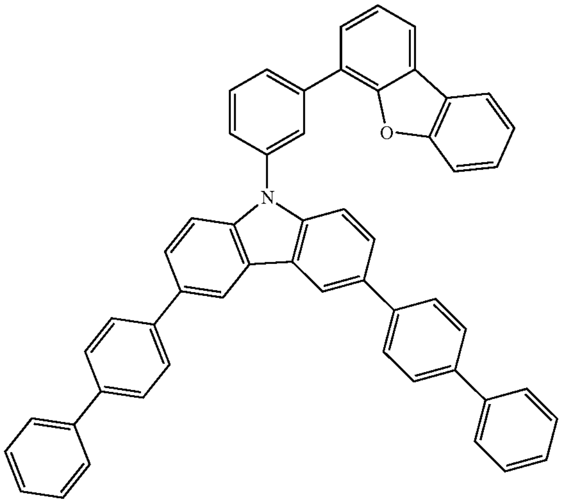
R6
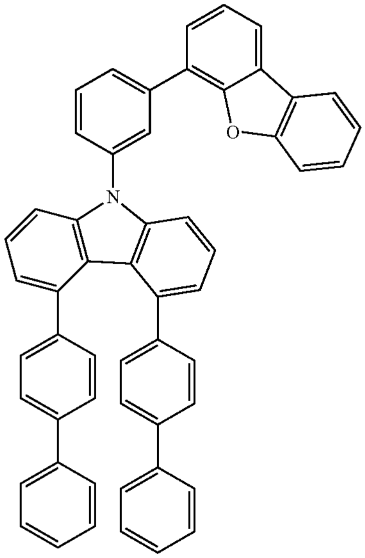
R7
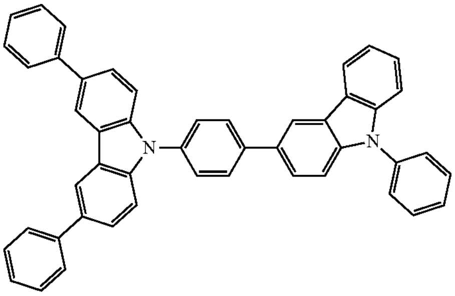

-continued
R8
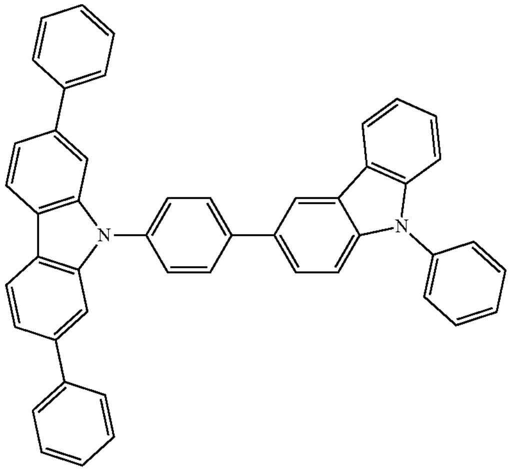
R9
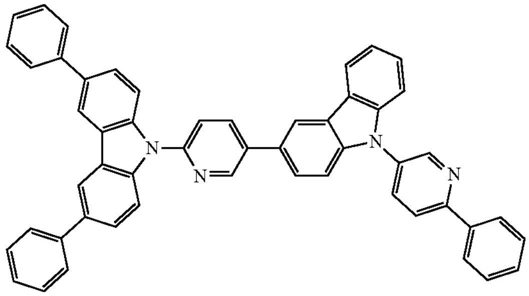
R10
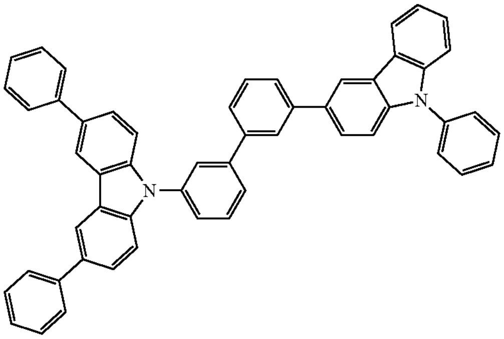
R11
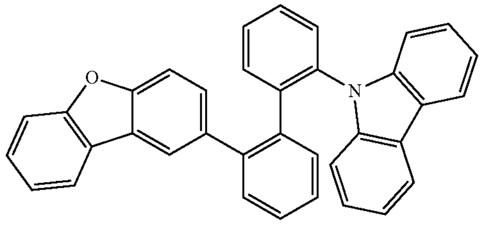
R12
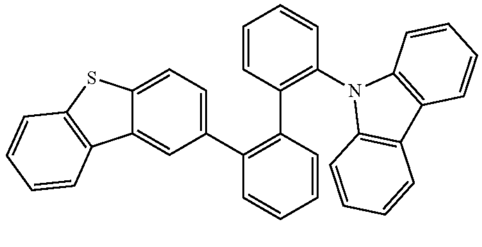
-continued
R13
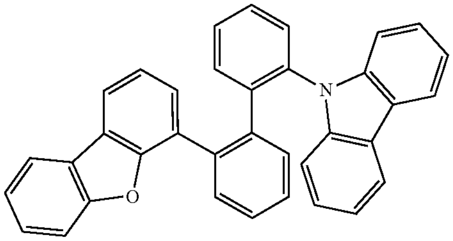
R14
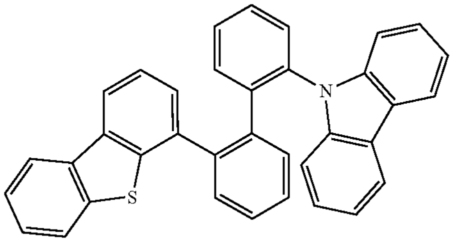
R15
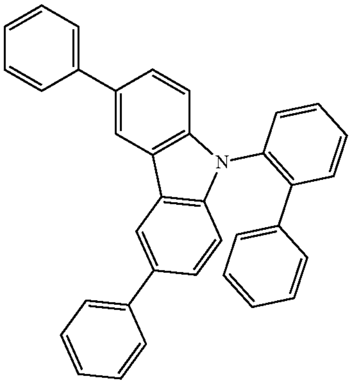
R16
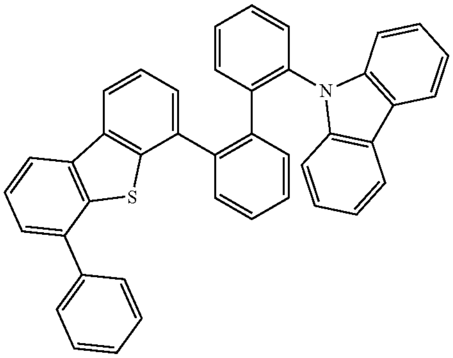
R17
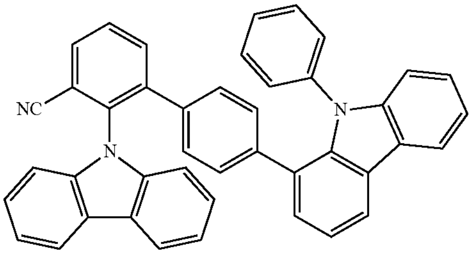

-continued

R18

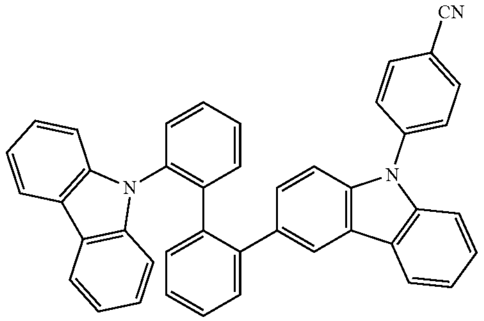

1. Experimental Example (1)

The luminescence devices of the Examples and Comparative Examples were manufactured by the method described below. On a glass substrate, ITO with a thickness of about 150 nm was patterned, washed with ultrapure water, and treated with ultraviolet (UV) ozone for about 10 minutes to form a first electrode. Then, 2-TNATA was deposited to a thickness of about 60 nm, and the Example Compound or Comparative Compound as in Table 1 was deposited to a thickness of about 30 nm to form a hole transport region. After that, an emission layer was formed using ADN doped with 3% (weight ratio) TBP to a thickness of about nm. On the emission layer, a layer was-formed using $Alq_3$ into a thickness of about 25 nm, and a layer was formed using lithium fluoride (LiF) into a thickness of about 1 nm to form an electron transport region. Then, a second electrode with a thickness of about 100 nm was formed using aluminum (Al). All layers were formed by a vacuum deposition method.

The measured values according to Examples 1 to 15 and Comparative Examples 1 to 18 are shown in Table 1 below. Maximum emission efficiency was measured at about 10 milliamp per centimeter squared ($mA/cm^2$), and half-life was measured by measuring luminance E half-hour at an initial luminance of about 100 candela per meter squared (cd/i1), in an experimental example at about 1.0 $mA/cm^2$. All are shown by percent (%) based on Comparative Example 11.

TABLE 1

| | Hole transport layer | Maximum emission efficiency | Half-life |
|---|---|---|---|
| Example 1 | Example Compound A3 | 122% | 175% |
| Example 2 | Example Compound B3 | 120% | 144% |
| Example 3 | Example Compound C3 | 133% | 132% |
| Example 4 | Example Compound A1 | 125% | 177% |
| Example 5 | Example Compound A2 | 125% | 171% |
| Example 6 | Example Compound A4 | 123% | 153% |
| Example 7 | Example Compound A5 | 117% | 133% |
| Example 8 | Example Compound A34 | 118% | 140% |
| Example 9 | Example Compound A17 | 123% | 174% |
| Example 10 | Example Compound C22 | 131% | 145% |
| Example 11 | Example Compound D1 | 112% | 118% |
| Example 12 | Example Compound D17 | 114% | 115% |
| Example 13 | Example Compound K1 | 110% | 119% |
| Example 14 | Example Compound K13 | 109% | 111% |
| Example 15 | Example Compound A20 | 126% | 161% |
| Comparative Example 1 | Comparative Compound R1 | 99% | 88% |
| Comparative Example 2 | Comparative Compound R2 | 82% | 42% |
| Comparative Example 3 | Comparative Compound R3 | 74% | 15% |
| Comparative Example 4 | Comparative Compound R4 | 78% | 32% |
| Comparative Example 5 | Comparative Compound R5 | 106% | 89% |
| Comparative Example 6 | Comparative Compound R6 | 96% | 73% |
| Comparative Example 7 | Comparative Compound R7 | 105% | 92% |
| Comparative Example 8 | Comparative Compound R8 | 104% | 91% |
| Comparative Example 9 | Comparative Compound R9 | 85% | 24% |
| Comparative Example 10 | Comparative Compound R10 | 105% | 85% |
| Comparative Example 11 | Comparative Compound R11 | 100% | 100% |
| Comparative Example 12 | Comparative Compound R12 | 98% | 97% |
| Comparative Example 13 | Comparative Compound R13 | 101% | 98% |
| Comparative Example 14 | Comparative Compound R14 | 100% | 95% |
| Comparative Example 15 | Comparative Compound R16 | 107% | 90% |
| Comparative Example 16 | Comparative Compound R17 | 98% | 102% |
| Comparative Example 17 | Comparative Compound R18 | 92% | 56% |
| Comparative Example 18 | Comparative Compound R19 | 88% | 44% |

Table 1 shows that Examples 1 to 15 all exhibited significantly and unexpectedly long life and high efficiency simultaneously when compared to Comparative Examples 1 to 18.

The nitrogen-containing compound made according to an embodiment of the invention is used in a hole transport region to contribute to the increase of the efficiency and life of a luminescence device. Although not wanting to be bound by theory, the embodiments of nitrogen-containing compound made according to the principles of the invention have a substituent at any position of position 3 and position 6 of a carbazole group, and has a heteroaryl group via a biphenyl group linker. The positions 3 and 6 of the carbazole group have relatively high reactivity with an electrophilic moiety and low tolerance to oxidation, but it is considered that by introducing a substituent at position 3 or position 6, stability was improved, and the increase of life was accomplished. In addition, with respect to a carbazole having a substituent at position 3 or position 6, it is assumed that HOMO became shallower, hole injection from an adjacent layer was improved, and as a result, hole transfer from a hole transport region to an emission layer was accelerated, thereby improving emission efficiency. It is believed that the heteroaryl group has stabilizing effects of electrons by a heteroatom and improves tolerance to electrons leaked out from an emission layer, and long-life characteristics could be obtained. In addition, since in the embodiments of the nitrogen-containing made compound according to the principles of the invention, a carbazole group is substituted at an ortho position with respect to a biphenyl linker, and a bulky 3,6-aryl-carbazole is twisted with respect to the biphenyl group, it is believed that the planarity of a molecule was largely deteriorated, the deposition temperature was reduced, and thermal decomposition during deposition was restrained.

Example 3 accomplished as long lifespan as in Examples 1 and 2, and showed further improved emission efficiency. Although not wanting to be bound by theory, as in dibenzofuran and dibenzothiophene, the carbazole group of the nitrogen-containing compound improved tolerance to electrons due to the presence of a heteroatom, and improved hole capacity due to the stacking of carbazole groups.

Comparative Example 1 showed degraded results of device life and efficiency when compared to Examples 1 to 15. A lowest unoccupied molecular orbital (LUMO) of Comparative Example 1 was calculated using a density functional theory (DFT) method at B3LYP level, using a Gaussian 09 program sold by Gaussian, Inc., Wallingford CT, 2009 Gaussian (B3LYP). Distribution is from dibenzofuran to a biphenyl group linker, and dibenzofuran having a heteroatom as the center is considered to function as an electron accepting moiety, but a dihedral angle between the dibenzofuran group and the biphenyl linker increased by aromatic ring groups at both sides of the dibenzofuran, and anion stability due to resonance was deteriorated when compared to the Examples.

Comparative Examples 2, 3, 4, 17 and 18 showed largely degraded results of device life when compared to Examples 1 to 15. Although not be wanting to be theory, it is believed that tolerance to holes was degraded when compared to the Examples due to the bonding of a cyano group which is an electron withdrawing group.

Comparative Examples 5, 7 and 10 showed degraded results of device life and efficiency when compared to Examples 1 to 15. Although having a substituent at position 3 or position 6 of a carbazole group as in the Examples, all aromatic rings in a molecule are bonded at para position or meta position, and planarity is high, and deposition temperature is high.

Comparative Examples 6 and 8 showed degraded results of device life when compared to Examples 1 to 15. Although not wanting to be bound by theory, because Comparative Examples 6 and 8 have a substituent at a position other than position 3 and position 6, highly reactive position 3 and position 6 could not be protected, and stability was degraded.

Comparative Example 9 showed largely degraded results of device life when compared to Examples 1 to 15. Although not wanting to be bound by theory, because a pyridine group which is an electron withdrawing group is bonded, tolerance to holes was degraded when compared to the Examples.

Comparative Examples 11 to 14 and 16 showed degraded results of device life and efficiency when compared to Examples 1 to 15. Although not wanting to be bound by theory, because highly reactive positions 3 and 6 of a carbazole group were not protected, stability was deteriorated.

Comparative Example 15 showed degraded results of device life when compared. to Examples 1 to 15. Although not wanting to be bound by theory, because Comparative Example 15 excluded a heteroaryl group bonded to a carbazole group via a linker, stability was deteriorated.

2. Experimental Example (2)

The luminescence devices of the Examples and Comparative Examples were manufactured by the method below. On a glass substrate, ITO with a thickness of about 150 nm was patterned, washed with ultrapure water, and treated with UV ozone for about 10 minutes to form a first electrode. Then, HAT-CN was deposited to a thickness of about 10 nm, TAPC was deposited to a thickness of about 80 nm, and the Example Compound or Comparative Compound as in Table 2 was deposited to a thickness of about 5 nm to form a hole transport region. After that, an emission layer was formed using mCBP doped with 5% (weight ratio) FIrpic to a thickness of about 20 nm. On the emission layer, a layer was formed using 3-[3-[3,5-bis(3-pyridin-3-ylphenyl)phenyl]phenyl]pyridine (TmPyPB) into a thickness of about 30 nm, and a layer was formed using LiF into a thickness of about 0.5 nm to form an electron transport region. Then, a second electrode with a thickness of about 100 nm was formed using aluminum (A1). All layers were formed by a vacuum deposition method.

The measured values according to Examples 2-1 to 2-14 and Comparative Examples 2-1 to 2-18 are shown in Table 2 below. Maximum emission efficiency was measured at about 10 mA/cm$^2$, and half-life was measured by measuring luminance half-hour at an initial luminance of about 100 cd/m$^2$, in an experimental example at about 1.0 mA/cm$^2$. All are shown by % based on Comparative Example 2-11.

TABLE 2

| | Hole transport layer | Maximum emission efficiency | Half-life |
|---|---|---|---|
| Example 2-1 | Example Compound A3 | 130% | 152% |
| Example 2-2 | Example Compound B3 | 127% | 124% |
| Example 2-3 | Example Compound C3 | 134% | 131% |
| Example 2-4 | Example Compound A1 | 128% | 161% |
| Example 2-5 | Example Compound A2 | 125% | 157% |
| Example 2-6 | Example Compound A4 | 128% | 143% |
| Example 2-7 | Example Compound A5 | 125% | 122% |
| Example 2-8 | Example Compound A34 | 120% | 133% |
| Example 2-9 | Example Compound A17 | 123% | 174% |
| Example 2-10 | Example Compound D1 | 114% | 111% |
| Example 2-11 | Example Compound D17 | 115% | 113% |
| Example 2-12 | Example Compound K1 | 113% | 117% |
| Example 2-13 | Example Compound K13 | 111% | 110% |
| Example 2-14 | Example Compound A20 | 131% | 155% |
| Comparative Example 2-1 | Comparative Compound R1 | 101% | 76% |
| Comparative Example 2-2 | Comparative Compound R2 | 82% | 22% |
| Comparative Example 2-3 | Comparative Compound R3 | 84% | 8% |
| Comparative Example 2-4 | Comparative Compound R4 | 85% | 11% |
| Comparative Example 2-5 | Comparative Compound R5 | 103% | 69% |
| Comparative Example 2-6 | Comparative Compound R6 | 69% | 31% |
| Comparative Example 2-7 | Comparative Compound R7 | 106% | 95% |
| Comparative Example 2-8 | Comparative Compound R8 | 71% | 28% |
| Comparative Example 2-9 | Comparative Compound R9 | 75% | 13% |
| Comparative Example 2-10 | Comparative Compound R10 | 106% | 75% |
| Comparative Example 2-11 | Comparative Compound R11 | 100% | 100% |
| Comparative Example 2-12 | Comparative Compound R12 | 99% | 93% |
| Comparative Example 2-13 | Comparative Compound R13 | 102% | 99% |
| Comparative Example 2-14 | Comparative Compound R14 | 98% | 91% |
| Comparative Example 2-15 | Comparative Compound R15 | 102% | 78% |
| Comparative Example 2-16 | Comparative Compound R16 | 101% | 92% |
| Comparative Example 2-17 | Comparative Compound R17 | 89% | 35% |
| Comparative Example 2-18 | Comparative Compound R18 | 86% | 28% |

Table 2 shows that Examples 2-1 to 2-14 exhibited significantly and unexpectedly long life and high efficiency simultaneously when compared to Comparative Examples 2-1 to 2-18.

The nitrogen-containing compound made according to an embodiment of the invention is used in a hole transport region even in a luminescence device which emits phosphorescence to contribute to the increase of efficiency and life in the luminescence device. The stability of a molecule may be improved for the nitrogen-containing compounds made according to the principles of the invention by the same reason described above, and hole transport capacity may be improved. Further, in a luminescence device which emits phosphorescence, it is important that a layer adjacent to an emission region confines the high triplet energy of a light emitting dopant of an emission region sufficiently. Accordingly, the nitrogen-containing compounds made according to embodiments of the invention have a high triplet energy level by a twisted skeleton, and energy loss may be suppressed, thereby accomplishing long life and high efficiency simultaneously. The luminescence device made according to the principles and embodiments of the invention have excellent efficiency.

The nitrogen-containing compound made according to the principles and embodiments of the invention may be used as a material for a hole transport region of a luminescence device, and by using the same, the efficiency of the luminescence device may be improved.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A luminescence device, comprising:

a first electrode;

a hole transport region disposed on the first electrode;

an emission layer disposed on the hole transport region;

an electron transport region disposed on the emission layer; and a second electrode disposed on the electron transport region, wherein the hole transport region comprises a nitrogen-containing compound represented by Formula 1:

Formula 1

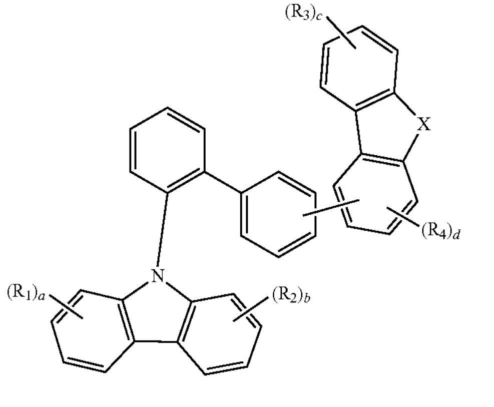

in Formula 1,

X is O, S, or $NR_5$, $R_1$ is a substituted or an unsubstituted oxy group, a substituted or an unsubstituted silyl group, a substituted or an unsubstituted thiol group, a substituted or an unsubstituted alkyl group of 1 to 20 carbon atoms, a substituted or an unsubstituted alkenyl group of 2 to 20 carbon atoms, a substituted or an unsubstituted alkynyl group of 2 to 20 carbon atoms, an unsubstituted aryl group of 6 to 30 ring-forming carbon atoms, a substituted or an unsubstituted dibenzofuran group, a substituted or an unsubstituted dibenzothiophene group, or a substituted or an unsubstituted carbazole group, $R_2$ to $R_5$ are each, independently from one another, a substituted or an unsubstituted oxy group, a substituted or an unsubstituted silyl group, a substituted or an unsubstituted thiol group, a substituted or an unsubstituted alkyl group of 1 to 20 carbon atoms, a substituted or an unsubstituted alkenyl group of 2 to 20 carbon atoms, a substituted or an unsubstituted alkynyl group of 2 to 20 carbon atoms, a substituted or an unsubstituted aryl group of 6 to 30 ring-forming carbon atoms, or a substituted or an unsubstituted heteroaryl group of 2 to 30 ring-forming carbon atoms, a is an integer of 1 to 4, b and c are each, independently from one another, an integer of 0 to 4, d is an integer of 0 to 3, and hydrogen is optionally replaced with deuterium.

2. The luminescence device of claim 1, wherein the hole transport region comprises:

a hole injection layer disposed on the first electrode; and a hole transport layer disposed on the hole injection layer, and the nitrogen-containing compound of Formula 1 is comprised in at least one of the hole injection layer or the hole transport layer.

3. The luminescence device of claim 2, further comprising an electron blocking layer disposed on the hole transport layer.

4. The luminescence device of claim 1, wherein the Formula 1 is represented by Formula 2:

Formula 2

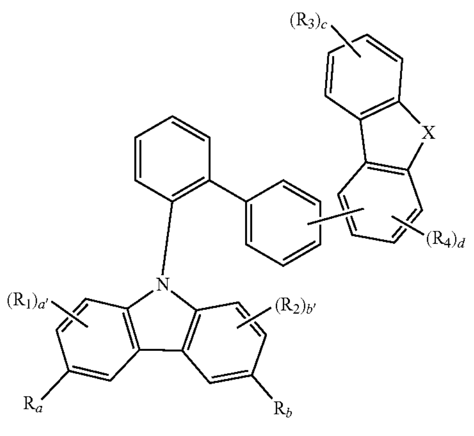

in Formula 2, a' and b' are each, independently from one another, an integer of 0 to 3, $R_a$ is a substituted or an unsubstituted oxy group, a substituted or an unsubstituted silyl group, a substituted or an unsubstituted thiol group, a substituted or an unsubstituted alkyl group of 1 to 20 carbon atoms, a substituted or an unsubstituted alkenyl group of 2 to 20 carbon atoms, a substituted or an unsubstituted alkynyl group of 2 to 20 carbon atoms, an unsubstituted aryl group of 6 to 30 ring-forming carbon atoms, a substituted or an unsubstituted dibenzofuran group, a substituted or an unsubstituted dibenzothiophene group, or a substituted or an unsubstituted carbazole group, $R_b$ is a hydrogen atom, a substituted or an unsubstituted oxy group, a substituted or an unsubstituted silyl group, a substituted or an unsubstituted thiol group, a substituted or an unsubstituted alkyl group of 1 to 20 carbon atoms, a substituted or an unsubstituted alkenyl group of 2 to carbon atoms, a substituted or an unsubstituted alkynyl group of 2 to 20 carbon atoms, a substituted or an unsubstituted aryl group of 6 to 30 ring-forming carbon atoms, or a substituted or an unsubstituted heteroaryl group of 2 to 30 ring-forming carbon atoms, and X, $R_1$ to $R_4$, c, and d have, independently from one another, the same meaning as defined in the Formula 1 in claim 1.

5. The luminescence device of claim 1, wherein the Formula 1 is represented by Formula 3:

Formula 3

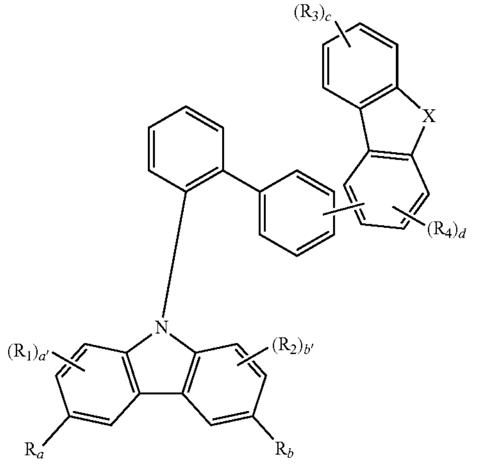

in Formula 3, a' and b' are each, independently from one another, an integer of 0 to 3, $R_a$ is a substituted or an unsubstituted oxy group, a substituted or an unsubstituted silyl group, a substituted or an unsubstituted thiol group, a substituted or an unsubstituted alkyl group of 1 to 20 carbon atoms, a substituted or an unsubstituted alkenyl group of 2 to 20 carbon atoms, a substituted or an unsubstituted alkynyl group of 2 to 20 carbon atoms, an unsubstituted aryl group of 6 to 30 ring-forming carbon atoms, a substituted or an unsubstituted dibenzofuran group, a substituted or an unsubstituted dibenzothiophene group, or a substituted or an unsubstituted carbazole group, $R_b$ is a substituted or an unsubstituted oxy group, a substituted or an unsubstituted silyl group, a substituted or an unsubstituted thiol group, a substituted or an unsubstituted alkyl group of 1 to 20 carbon atoms, a substituted or an unsubstituted alkenyl group of 2 to 20 carbon atoms, a substituted or an unsubstituted alkynyl group of 2 to 20 carbon atoms, a substituted or an unsubstituted aryl group of 6 to 30 ring-forming carbon atoms, or a substituted or an unsubstituted heteroaryl group of 2 to 30 ring-forming carbon atoms, and X, $R_1$ to $R_4$, c, and d have, independently from one another, the same meaning as defined in the Formula 1 in claim 1.

6. The luminescence device of claim 4, wherein the Formula 2 is represented by Formula 4:

Formula 4

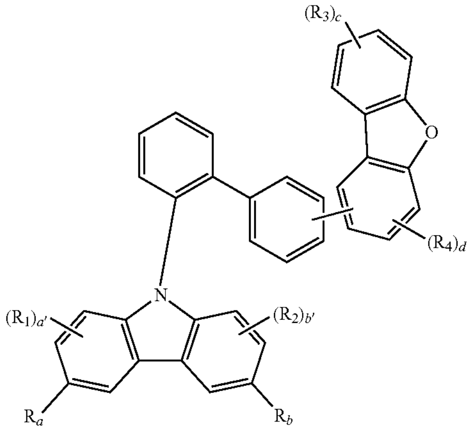

in Formula 4, $R_1$ to $R_4$, $R_a$, $R_b$, c, d, a' and b' have, independently from one another, the same meaning as defined in the Formula 2 in claim 4.

7. The luminescence device of claim 4, wherein the Formula 2 is represented by Formula 5:

Formula 5

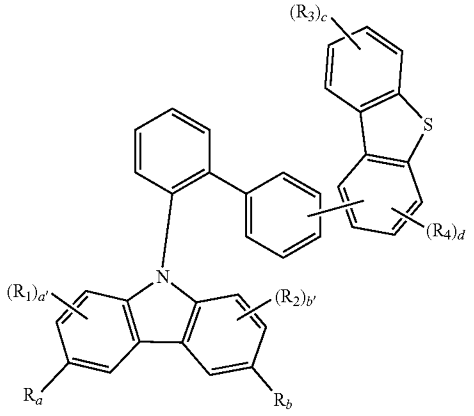

in Formula 5, $R_1$ to $R_4$, $R_a$, $R_b$, c, d, a' and b' have, independently from one another, the same meaning as defined in the Formula 2 in claim 4.

8. The luminescence device of claim 4, wherein the Formula 2 is represented by Formula 6:

Formula 6

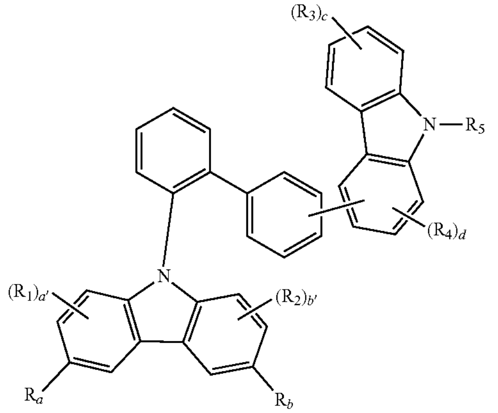

in Formula 6, $R_5$ is a substituted or an unsubstituted alkyl group of 1 to 20 carbon atoms, a substituted or an unsubstituted aryl group of 6 to 30 ring-forming carbon atoms, or a substituted or an unsubstituted heteroaryl group of 2 to 30 ring-forming carbon atoms, and $R_1$ to $R_4$, $R_a$, $R_b$, c, d, a' and b' have, independently from one another, the same meaning as defined in the Formula 2 in claim 4.

9. The luminescence device of claim 4, wherein the Formula 2 is represented by Formula 7-1 or Formula 7-2:

Formula 7-1

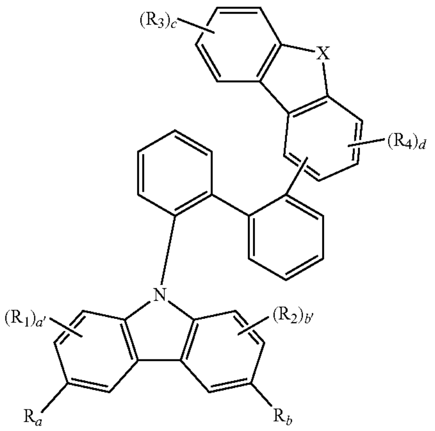

Formula 7-2

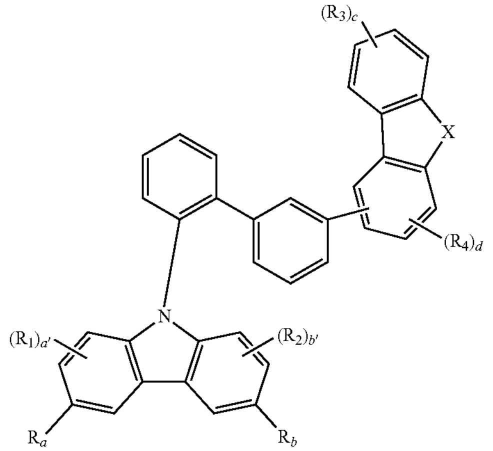

in Formula 7-1 and Formula 7-2,

X, $R_1$ to $R_4$, $R_a$, $R_b$, c, d, a' and b' have, independently from one another, the same meaning as defined in the Formula 2 in claim 4.

10. The luminescence device of claim 4, wherein $R_a$ is a substituted or an unsubstituted alkyl group of 1 to 20 carbon atoms, an unsubstituted aryl group of 6 to 30 ring-forming carbon atoms, a substituted or an unsubstituted dibenzofuran group, a substituted or an unsubstituted dibenzothiophene group, or a substituted or an unsubstituted carbazole group, and $R_b$ is a hydrogen atom, a substituted or an unsubstituted alkyl group of 1 to 20 carbon atoms, a substituted or an unsubstituted aryl group of 6 to 30 ring-forming carbon atoms, or a substituted or an unsubstituted heteroaryl group of 2 to 30 ring-forming carbon atoms.

11. The luminescence device of claim 1, wherein the nitrogen-containing compound of the Formula 1 is at least one of the compounds in Compound Group 1:

Compound Group 1

A1

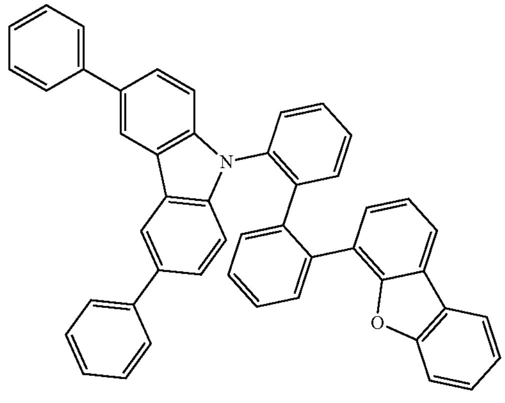

A2

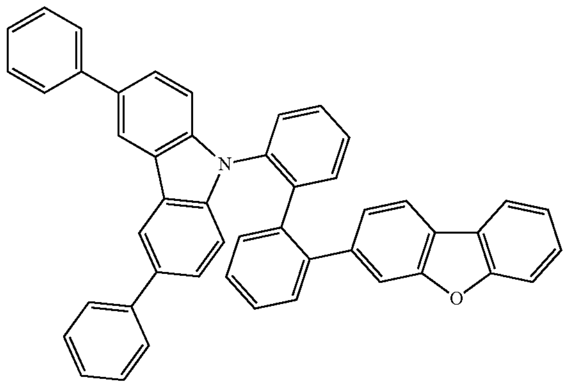

-continued
A3
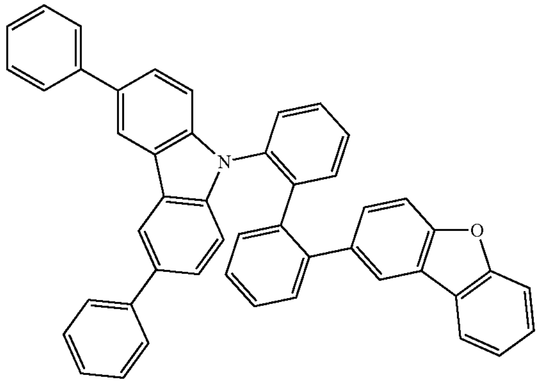
A4
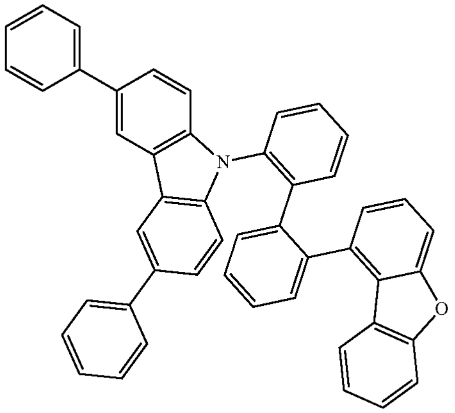
A5
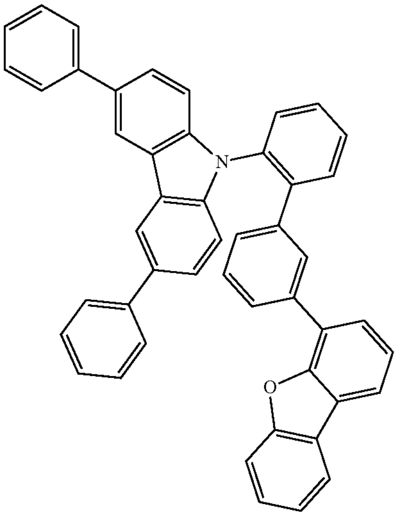
-continued
A6
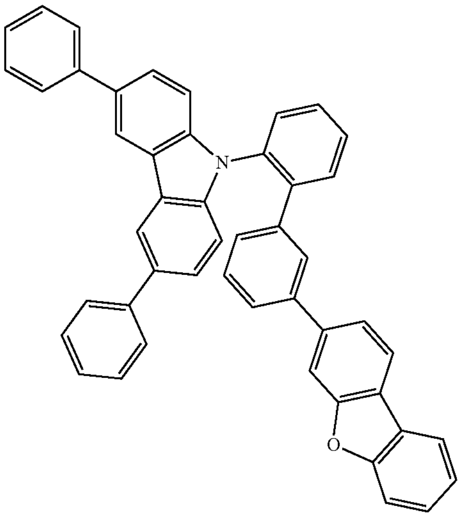
A7
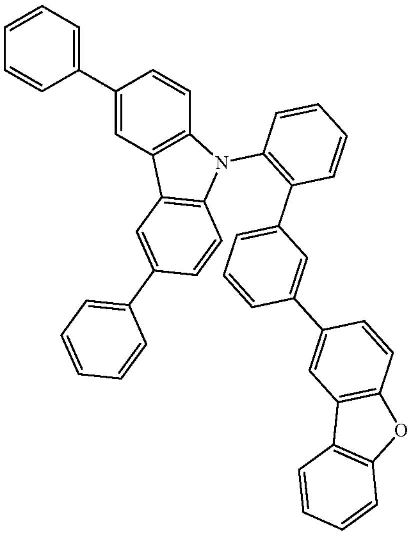
A8
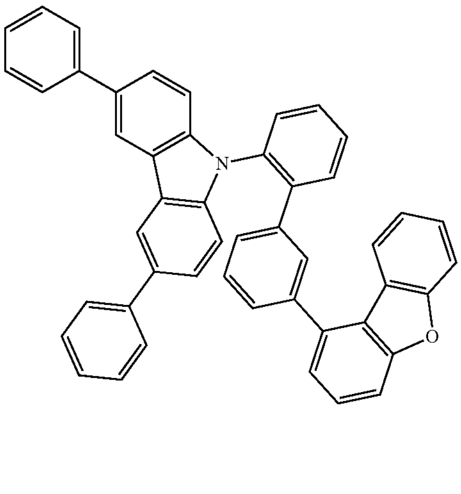

A9
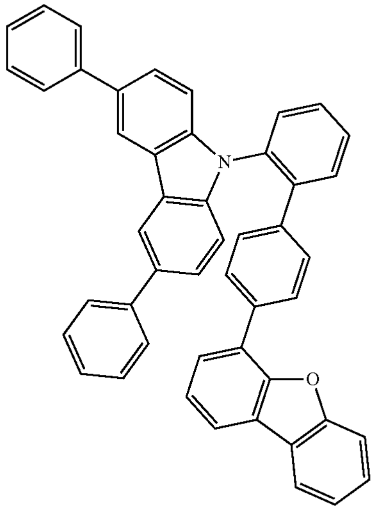
A10
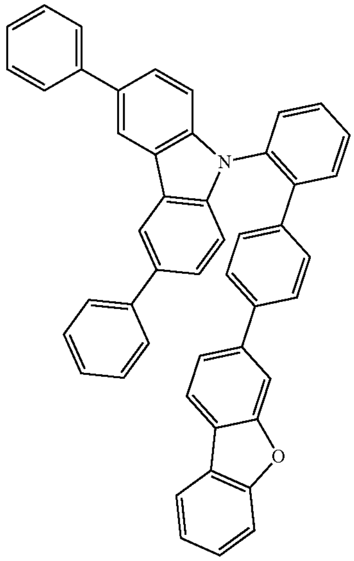
A11
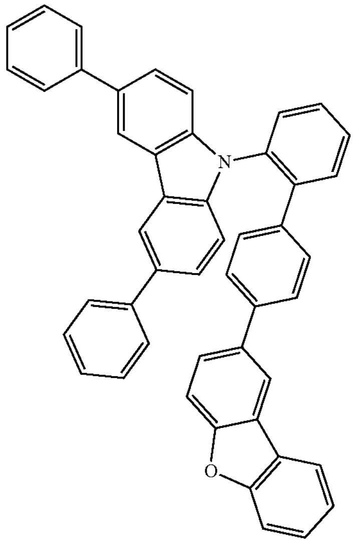
A12
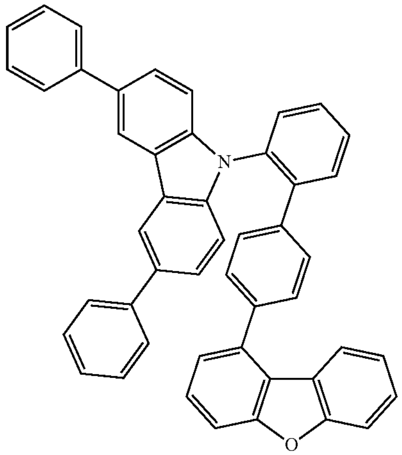
A13
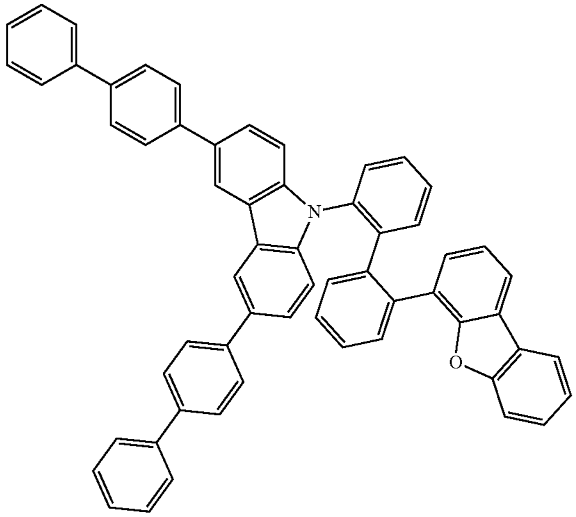
A14
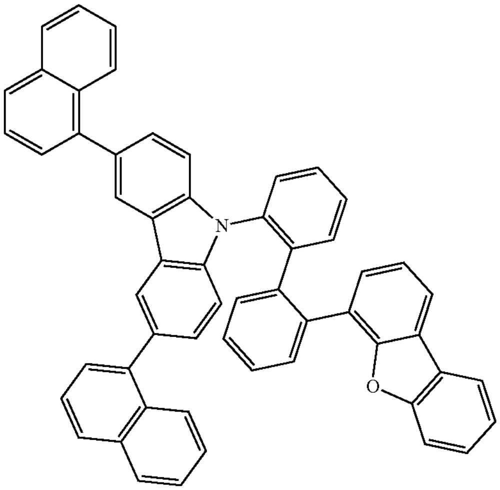

-continued
A15
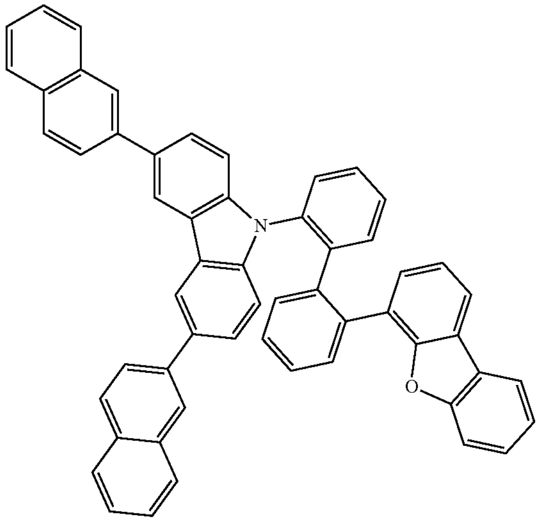
A16
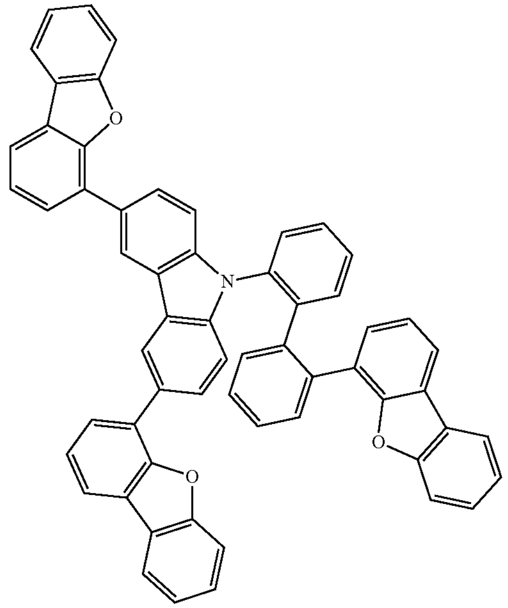
A17
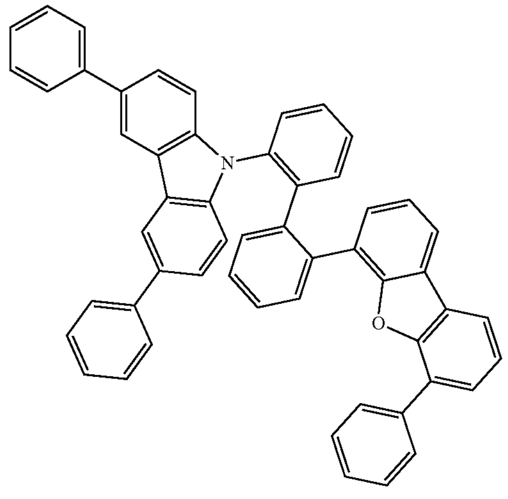
-continued
A18
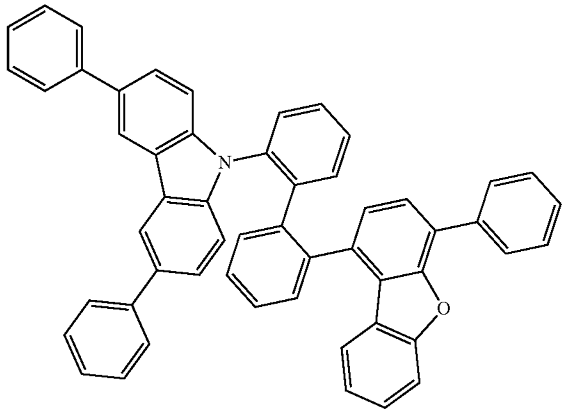
A19
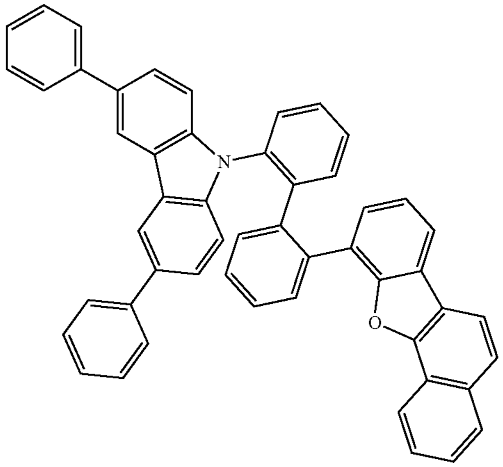
A20
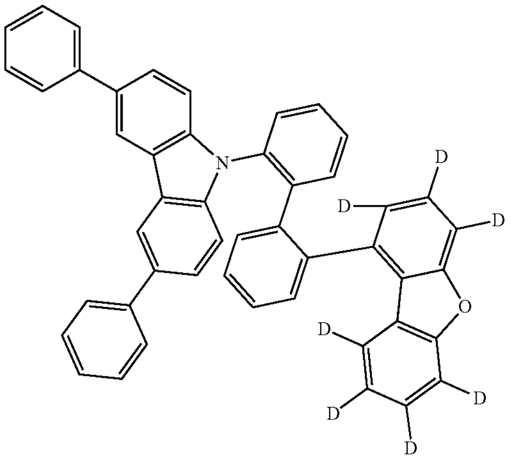

-continued
A21
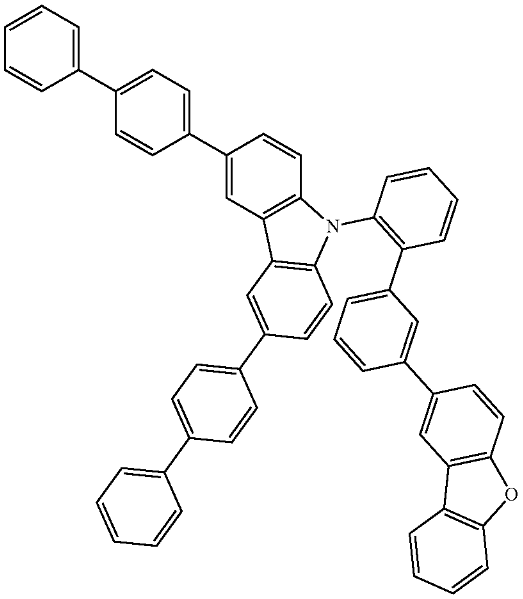
A22
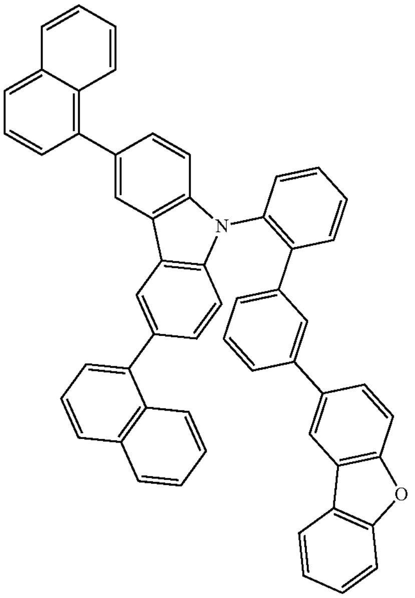
-continued
A23
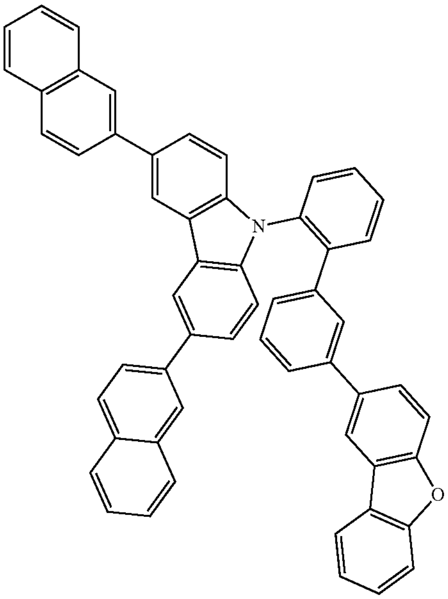
A24
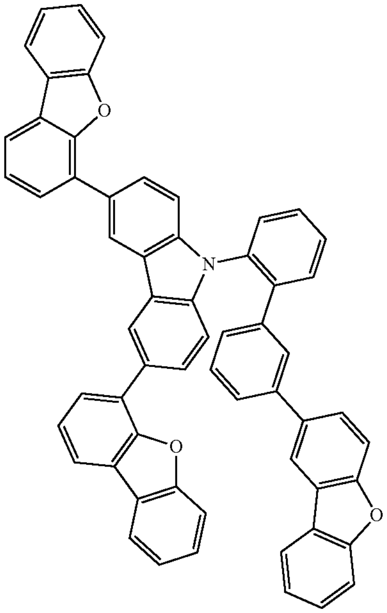

-continued
A25
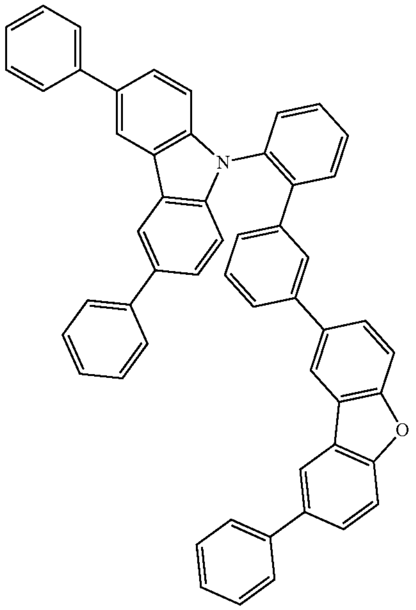
A26
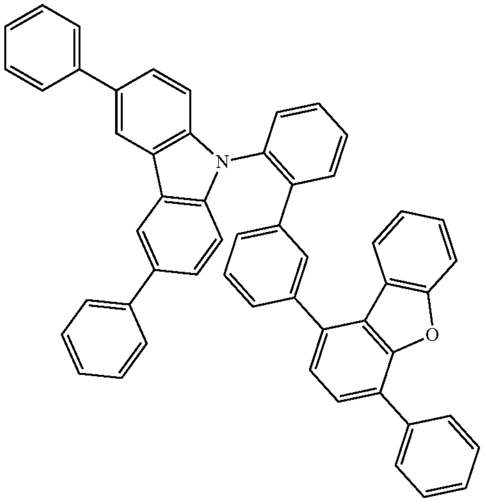
-continued
A27
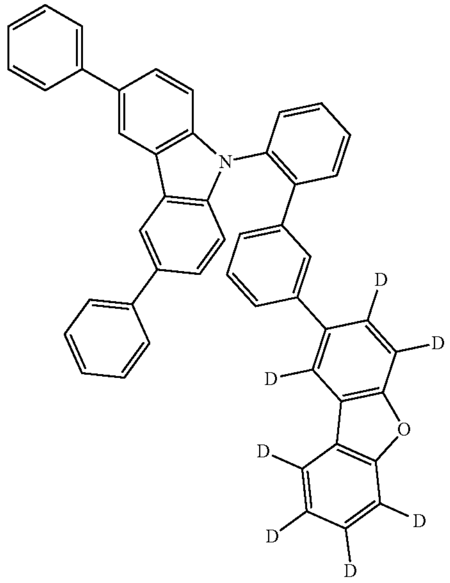
A28
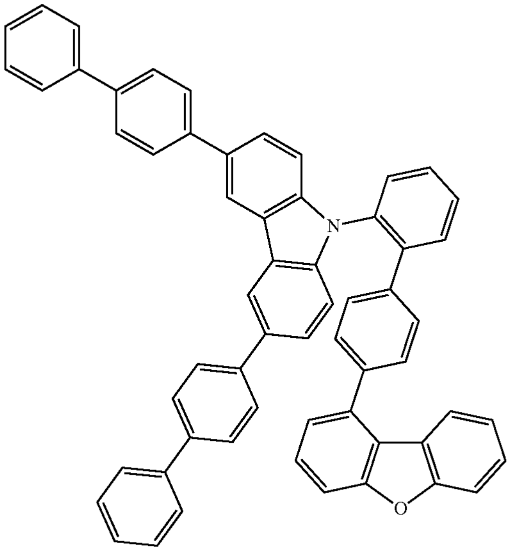
A29
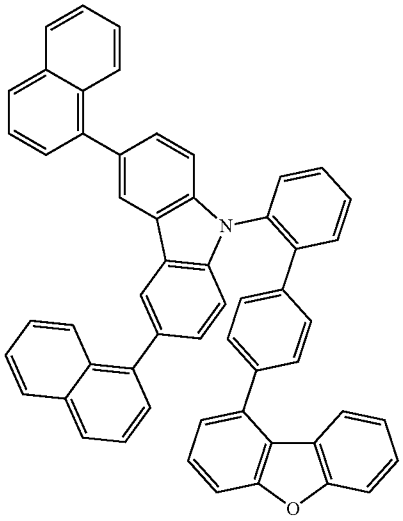

-continued
A30
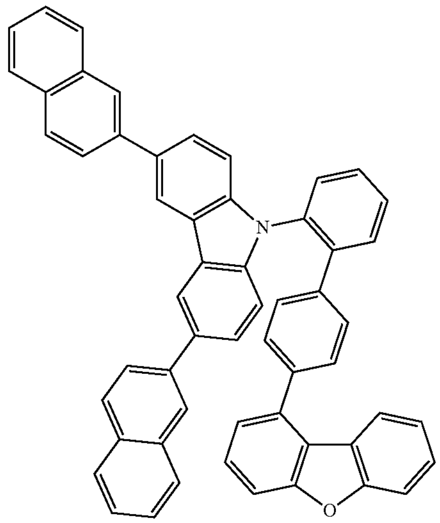
A31
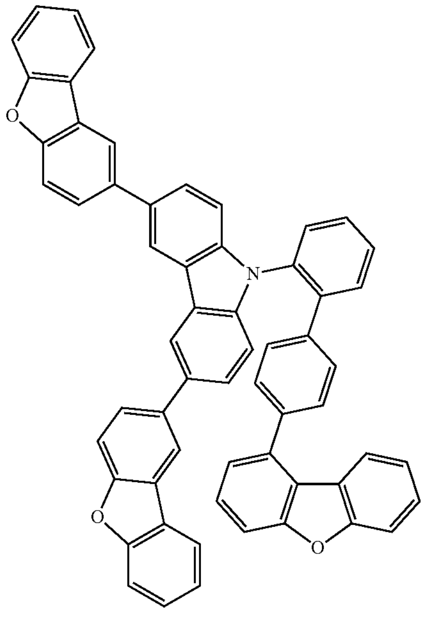
-continued
A32
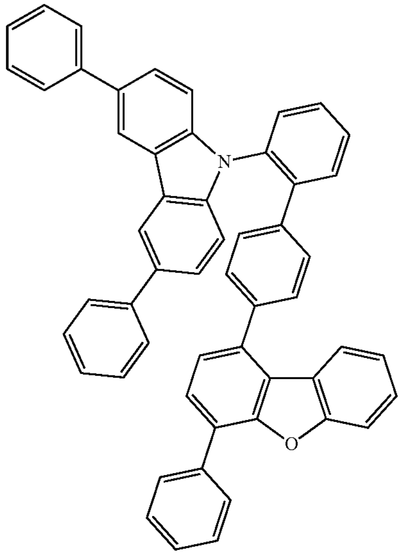
A33
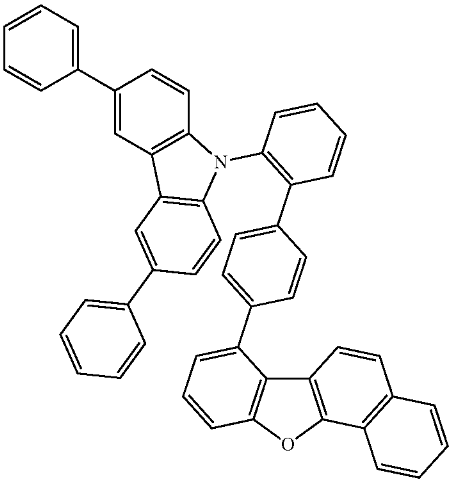
A34
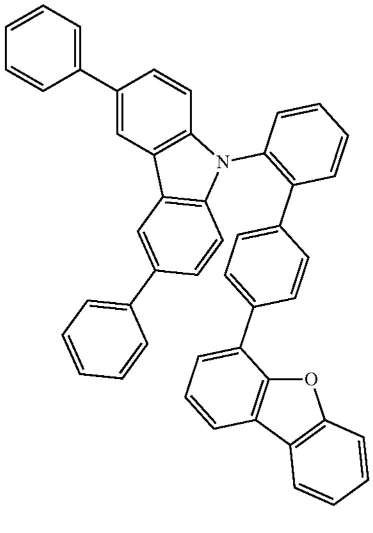

-continued
A35
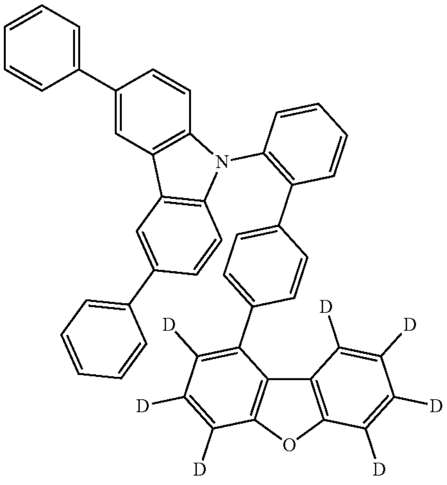
B1
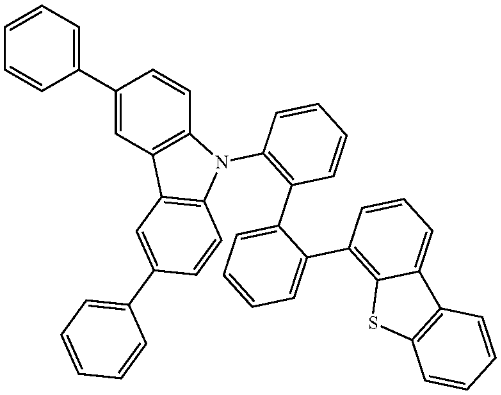
B2
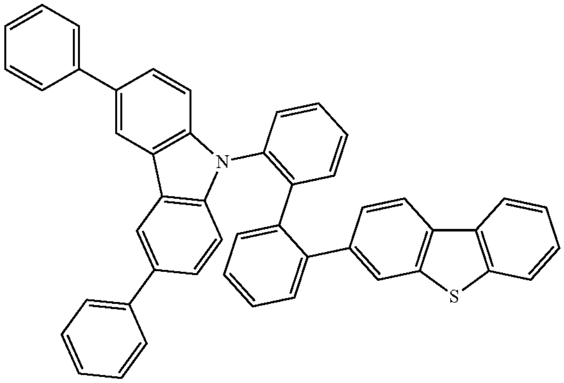
-continued
B3
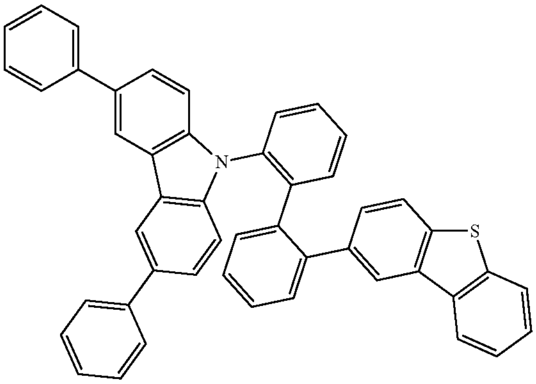
B4
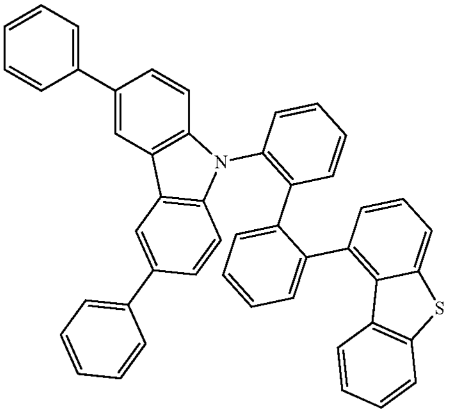
B5
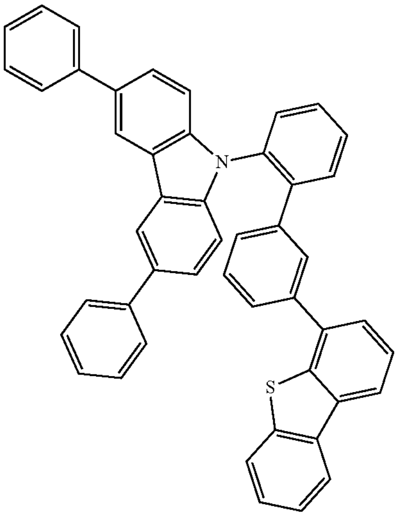

-continued
B6
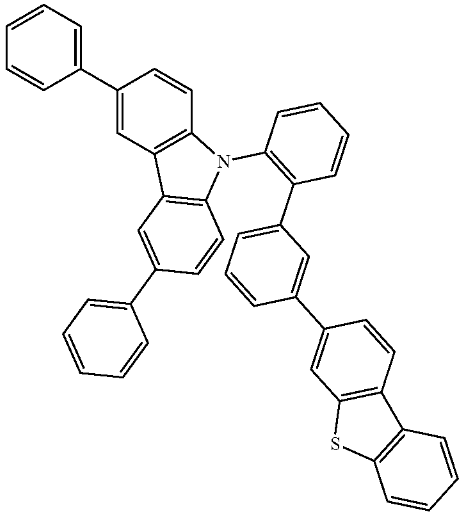
B7
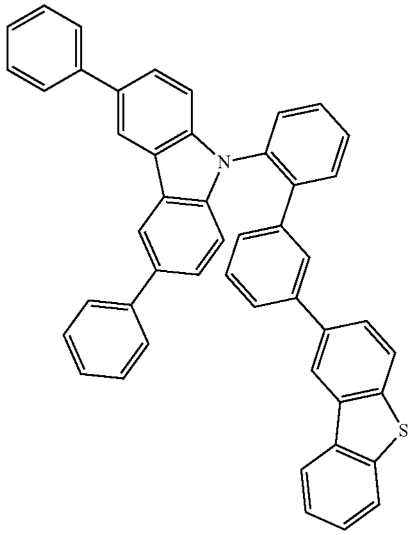
B8
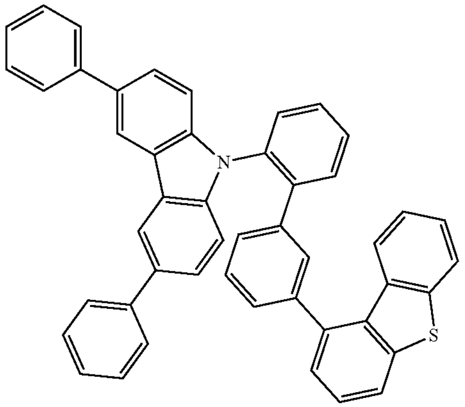
-continued
B9
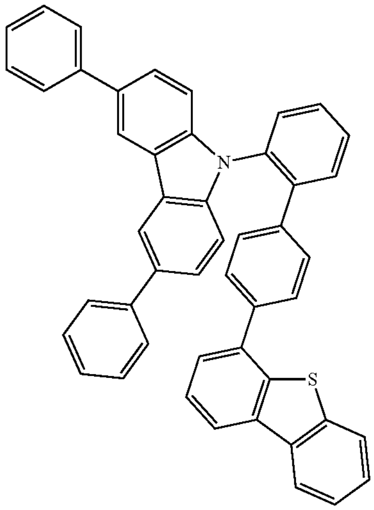
B10
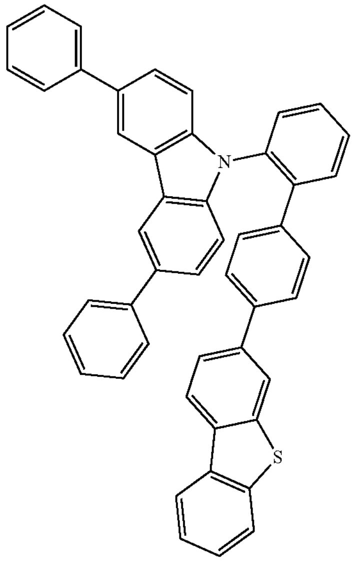
B11
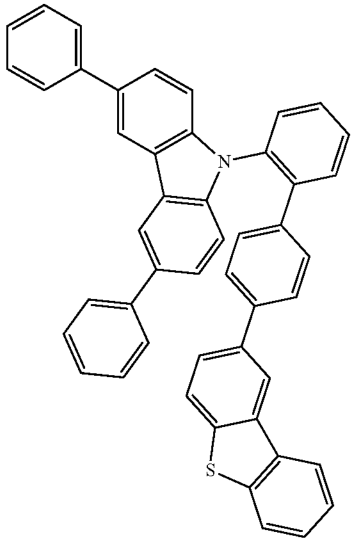

-continued
B12
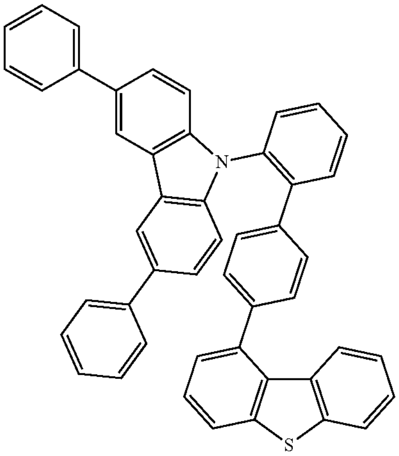
B13
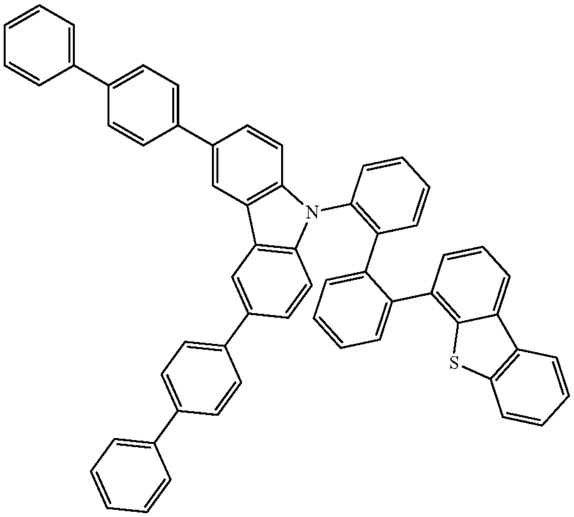
B14
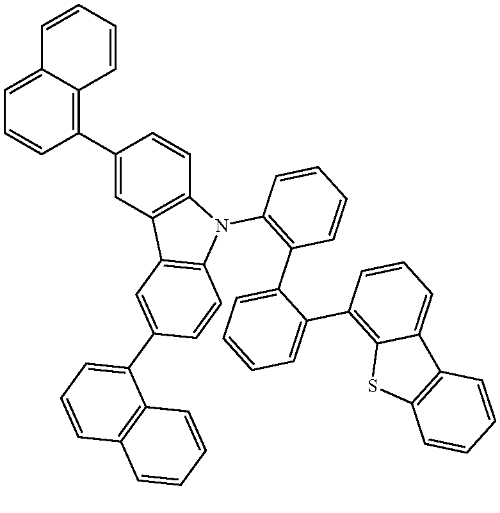
-continued
B15
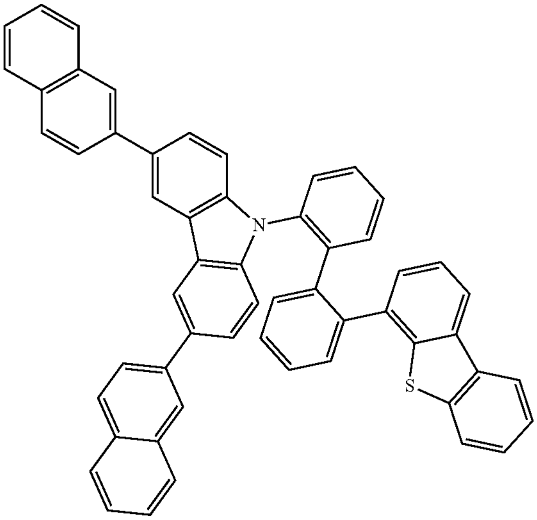
B16
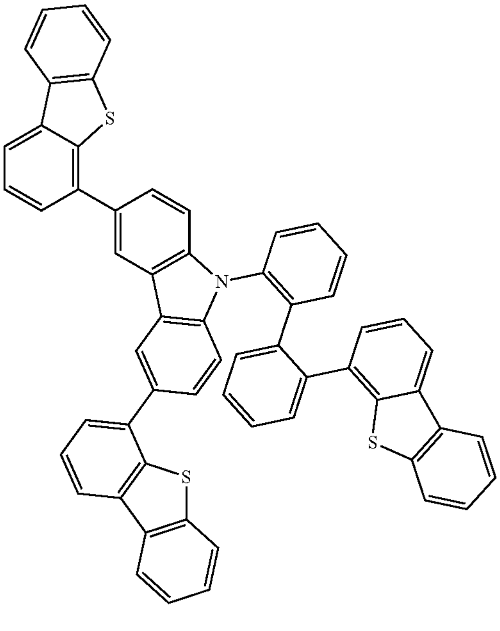
B17
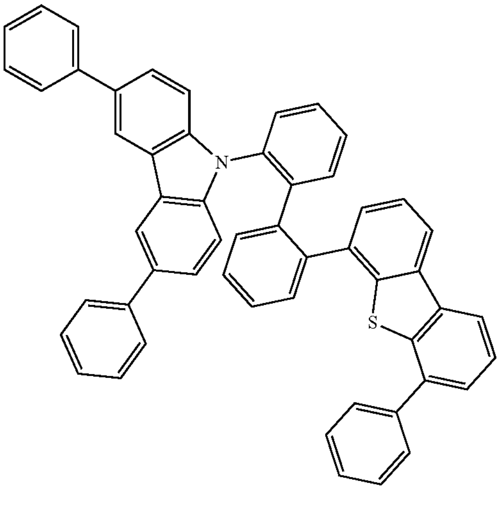

-continued
B18
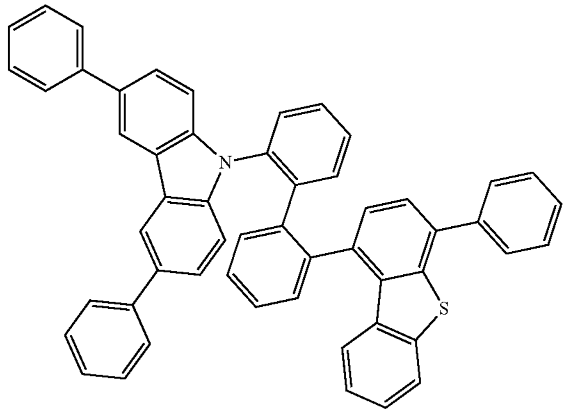
B19
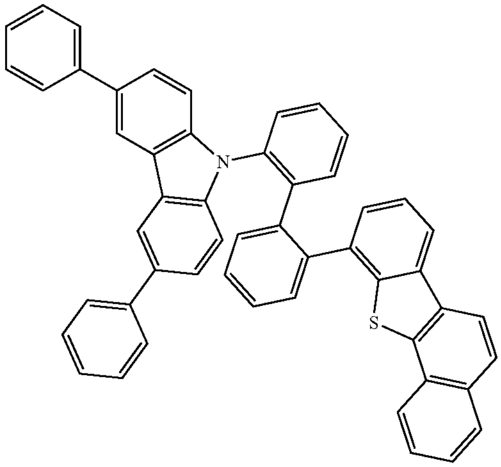
B20
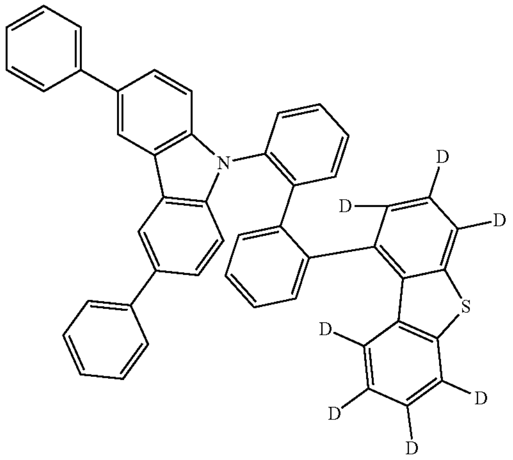
-continued
B21
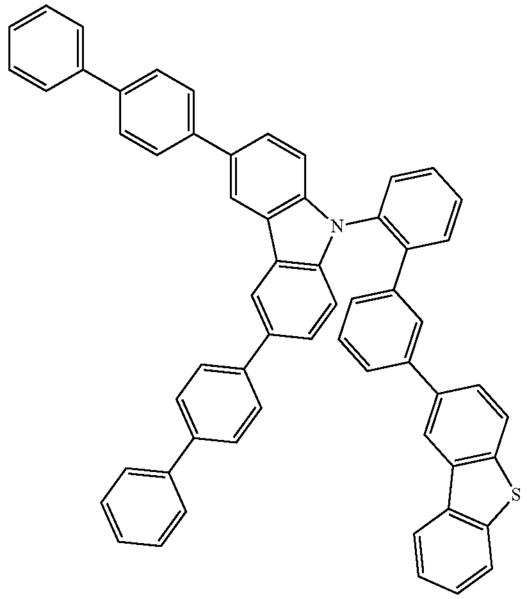
B22
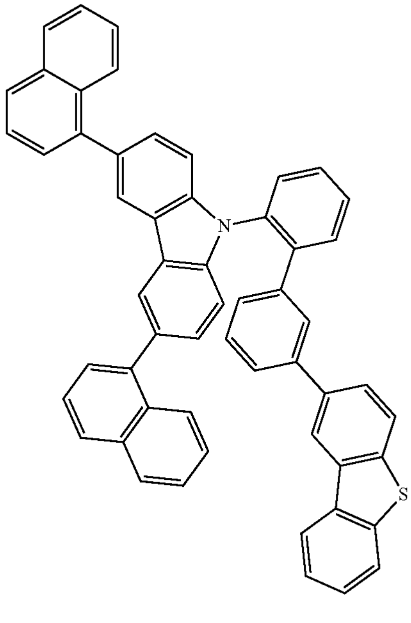

-continued
B23
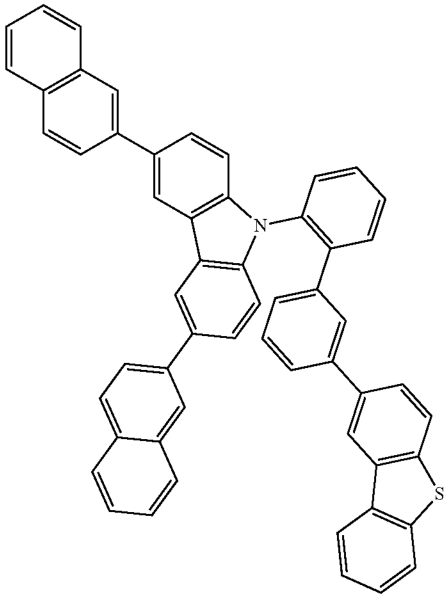
B24
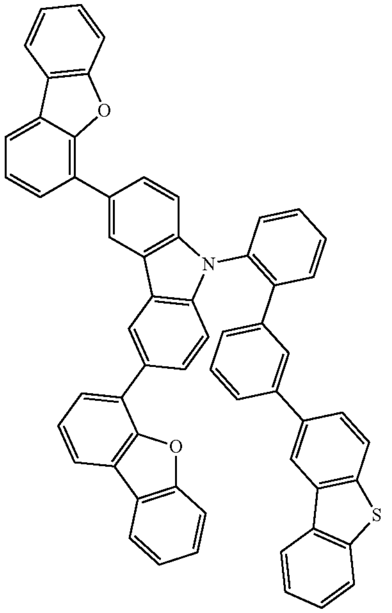
-continued
B25
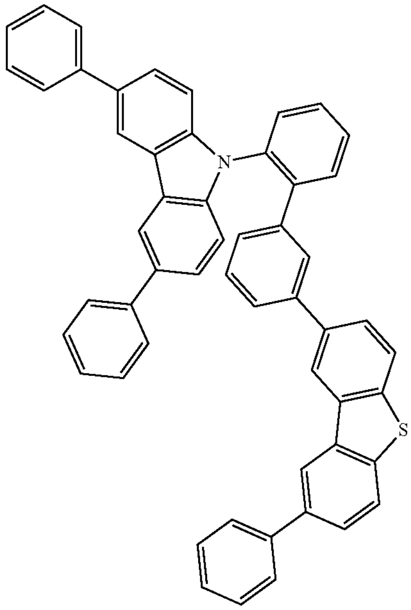
B26
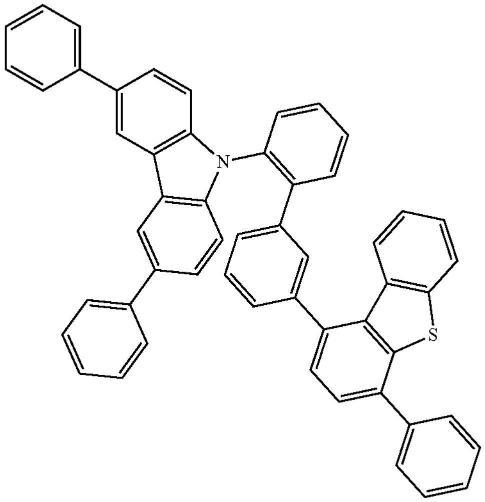

-continued
B27
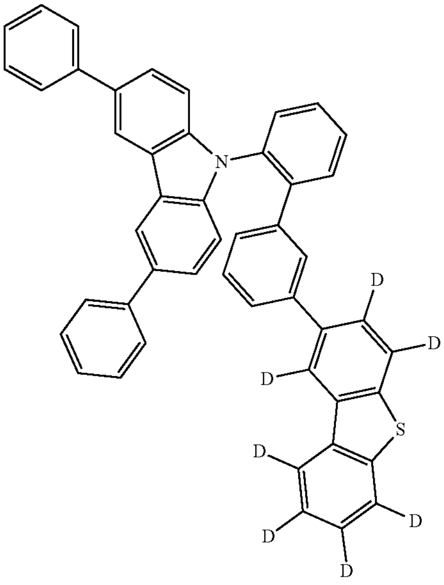
B28
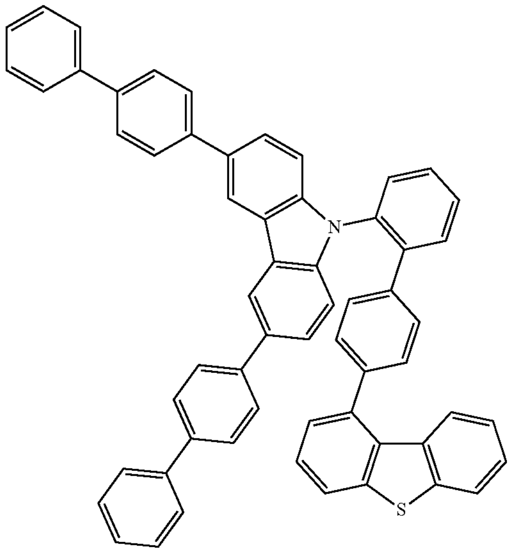
B29
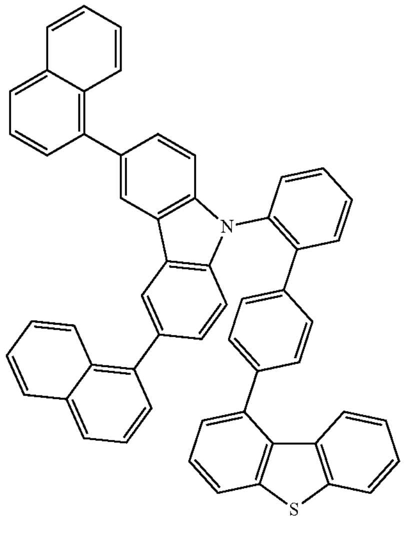
-continued
B30
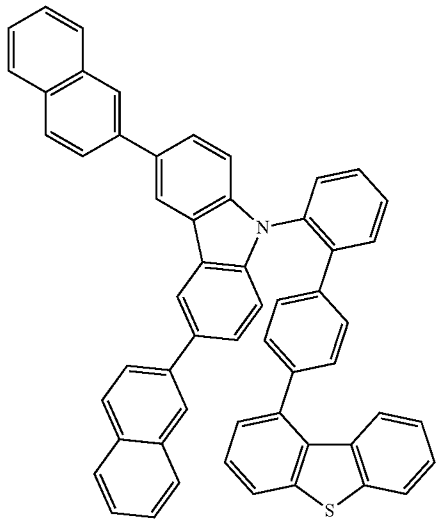
B31
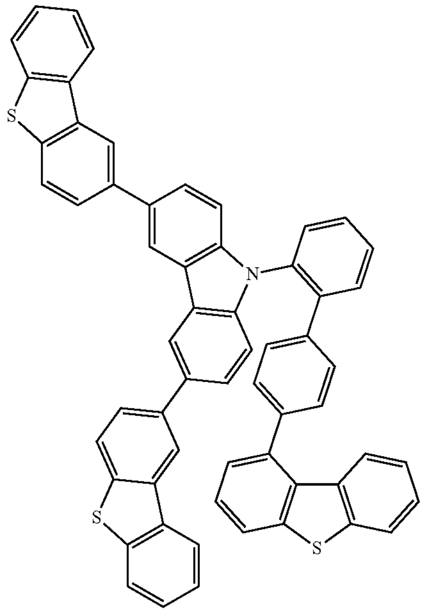

-continued
B32
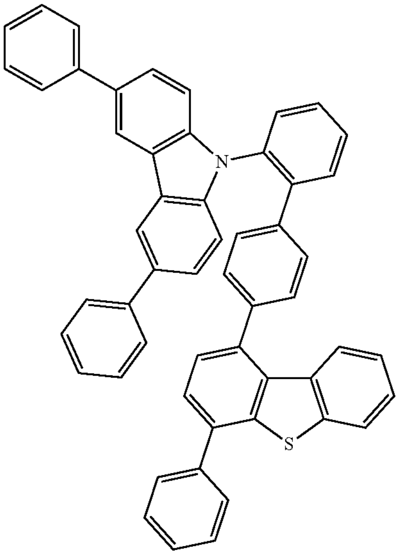
B33
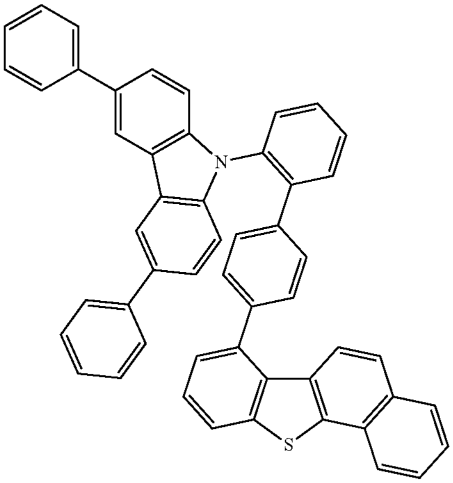
B34
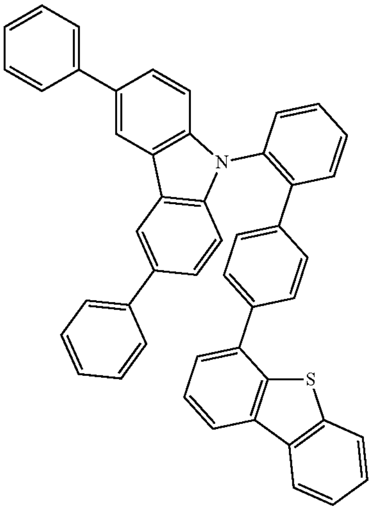
-continued
B35
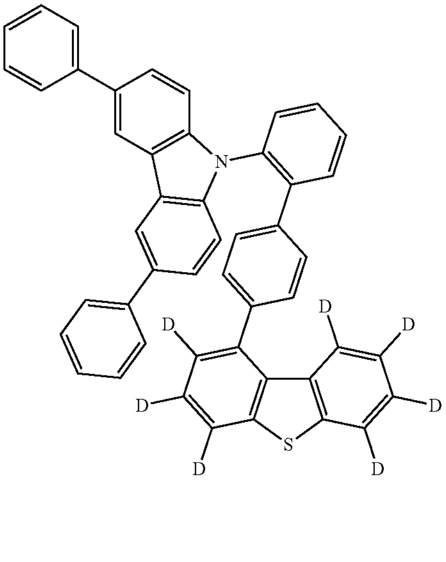
C1
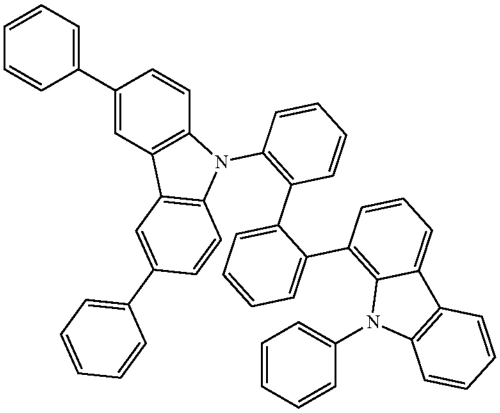
C2
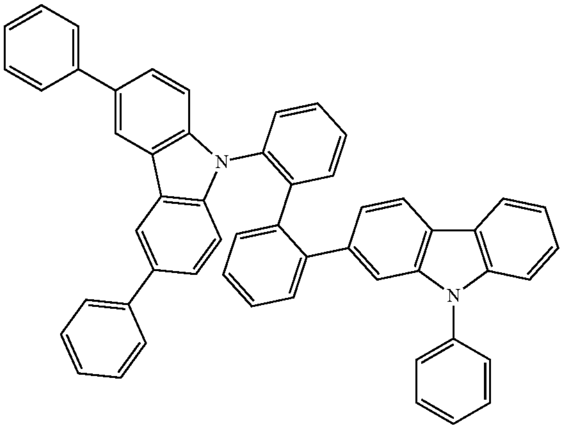

-continued
C3
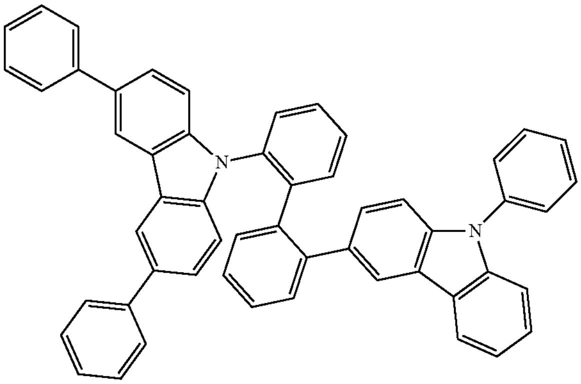
C4
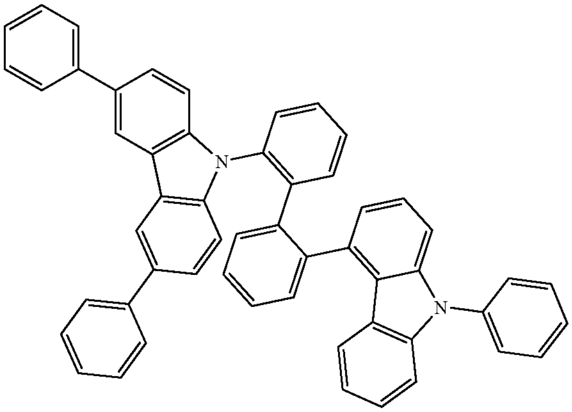
C5
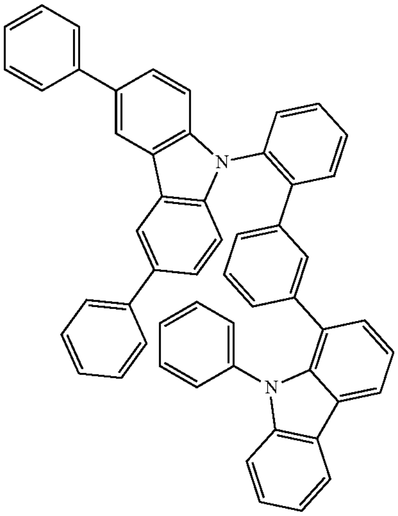
-continued
C6
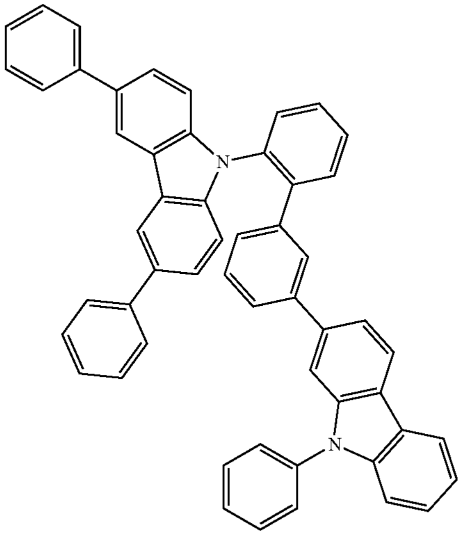
C7
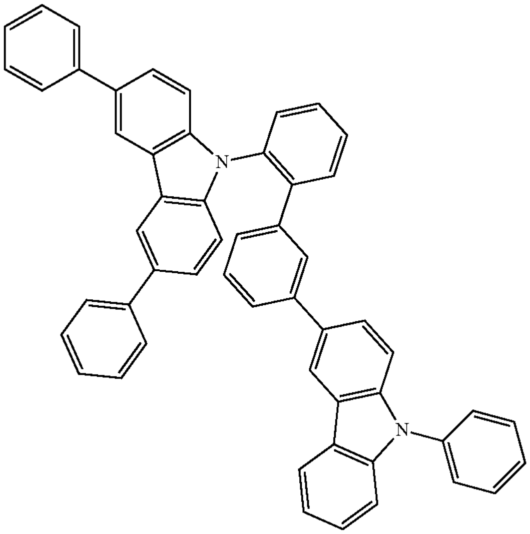
C8
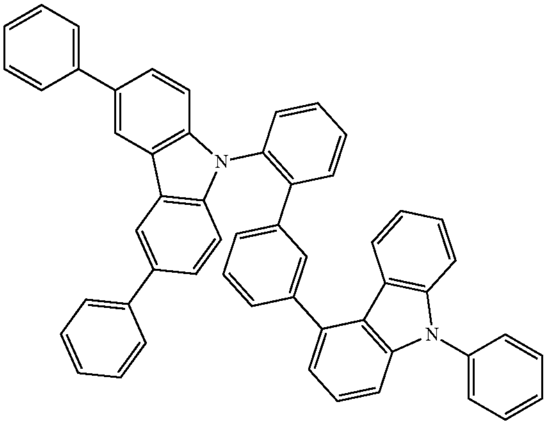

-continued
C9
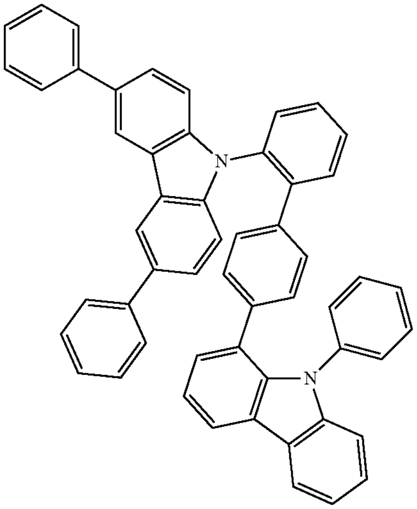
C10
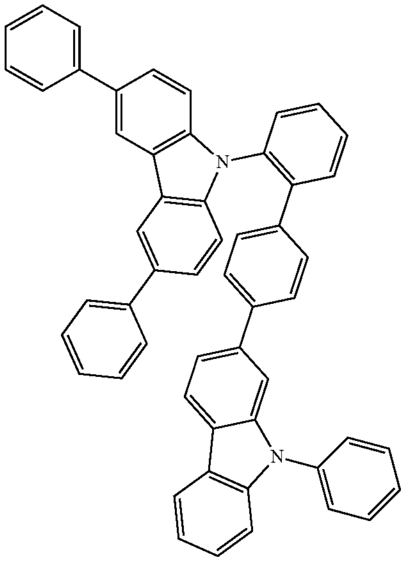
C11
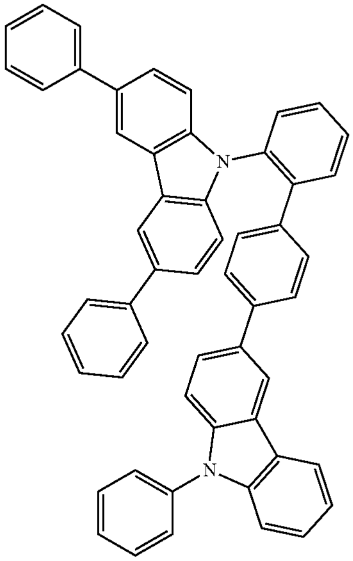
-continued
C12
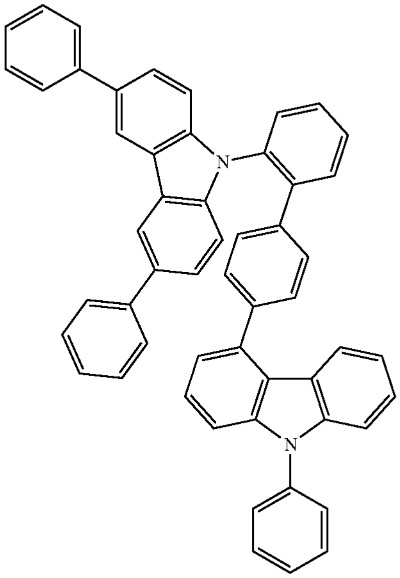
C13
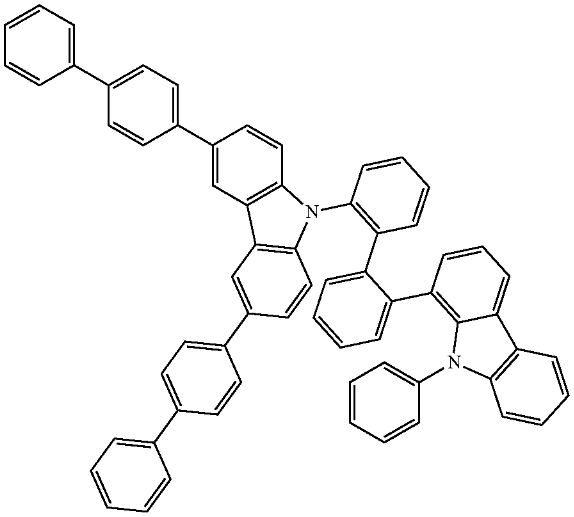
C14
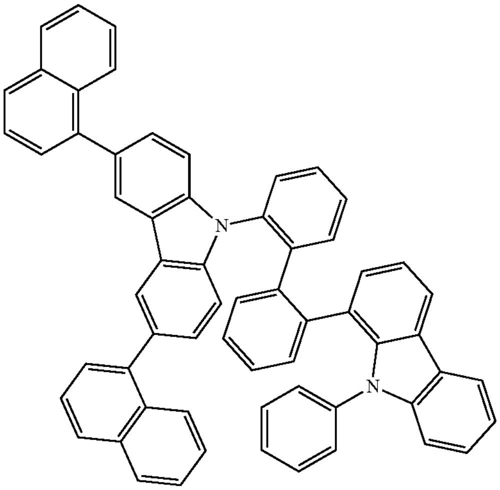

-continued
C15
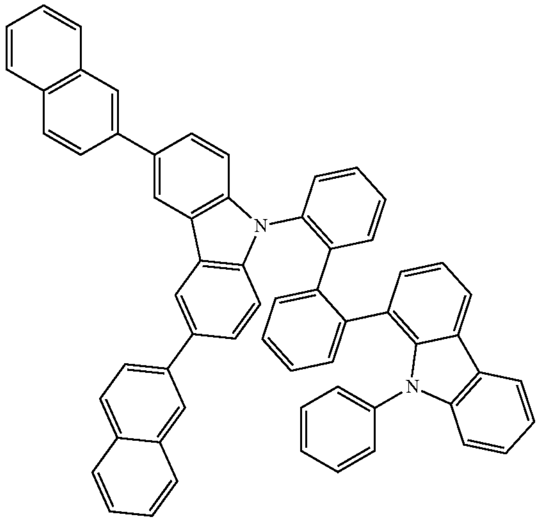
C16
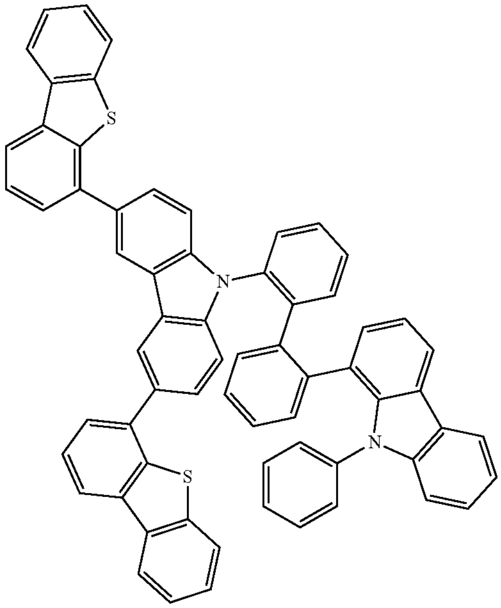
C17
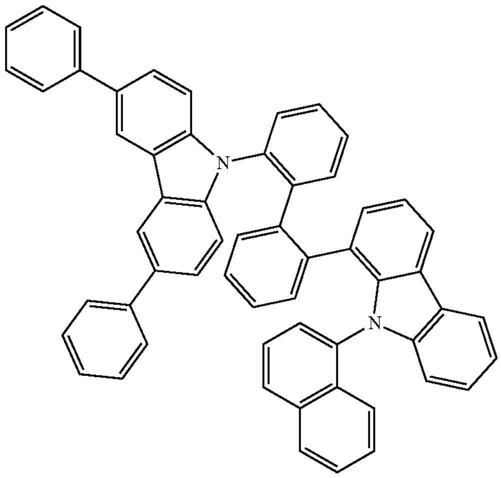
-continued
C18
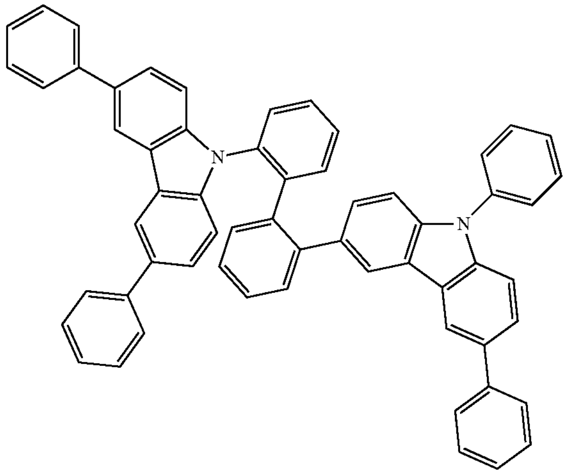
C19
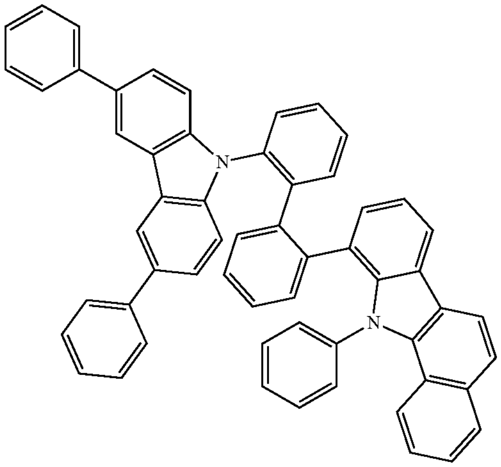
C20
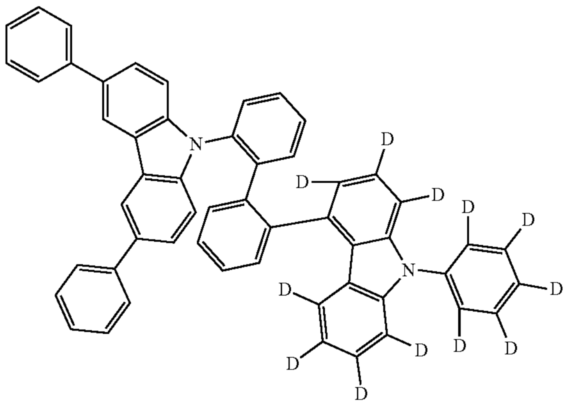

-continued
C21
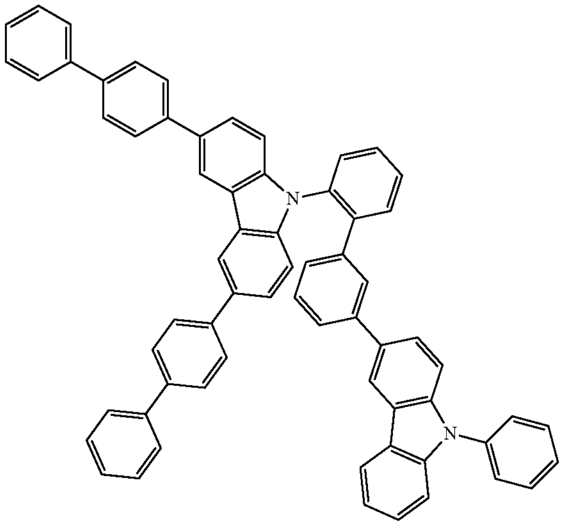
C22
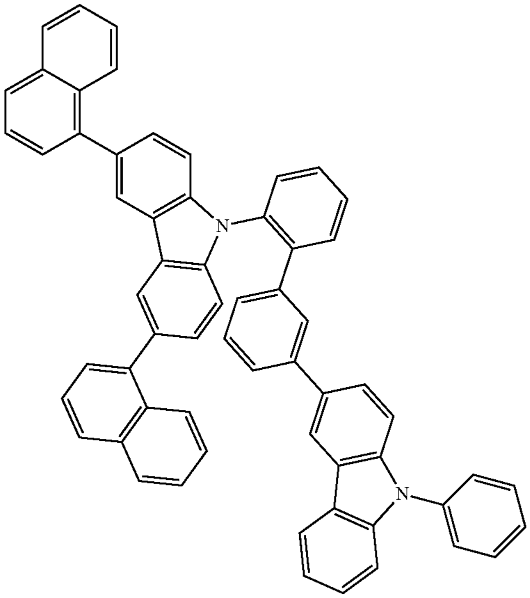
-continued
C23
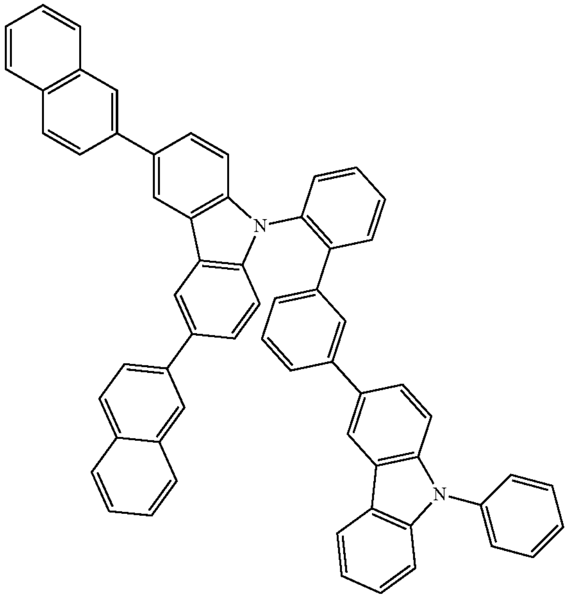
C24
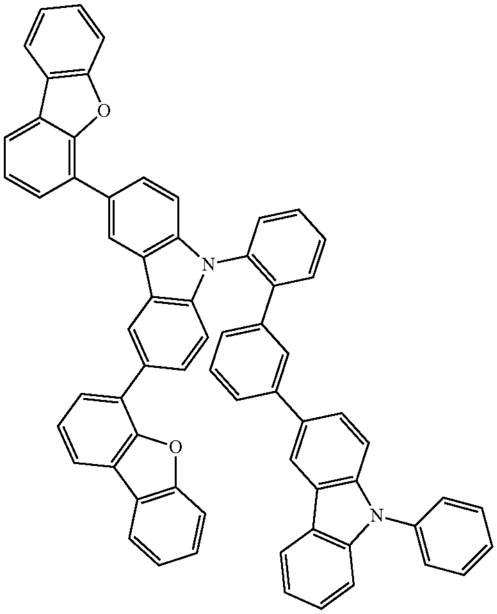

-continued
C25
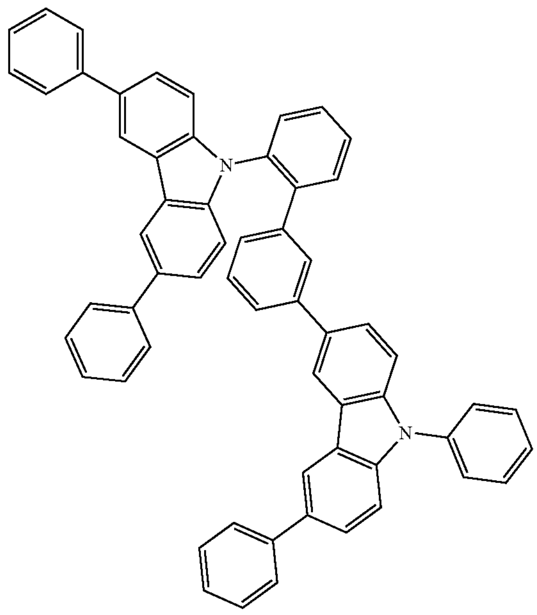
C26
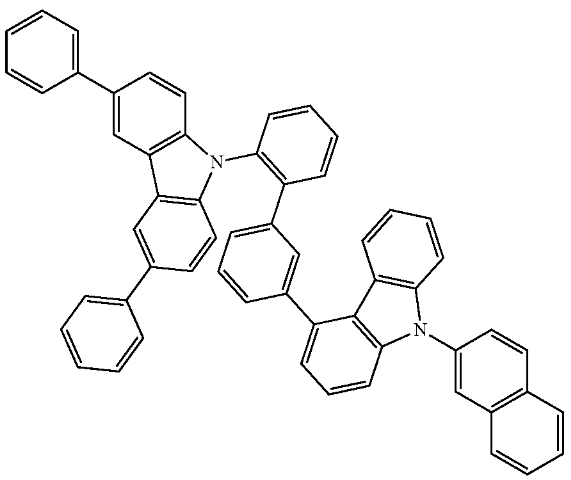
-continued
C27
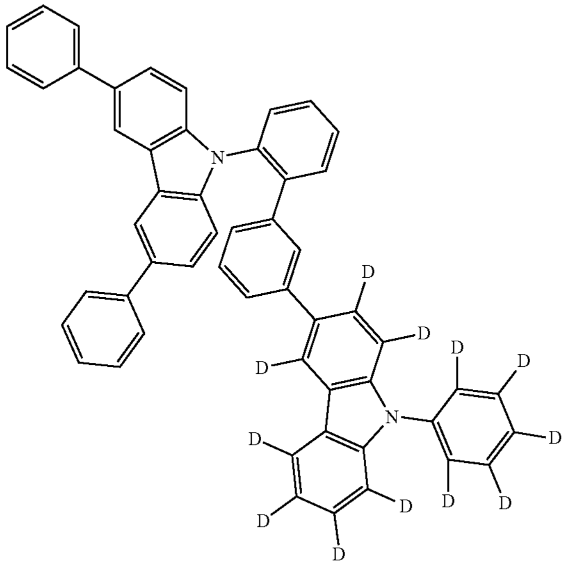
C28
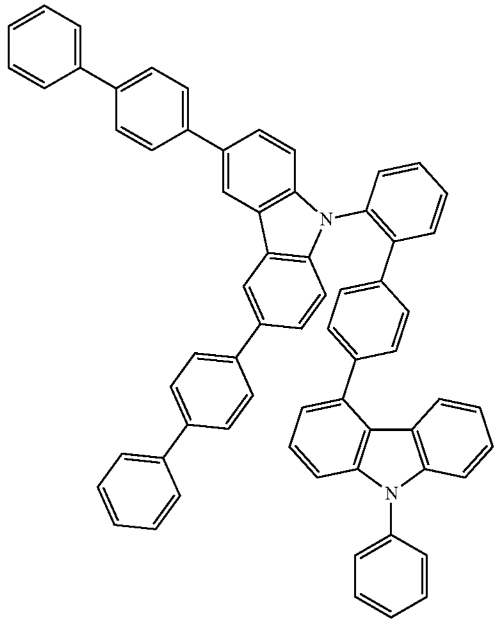

-continued
C29
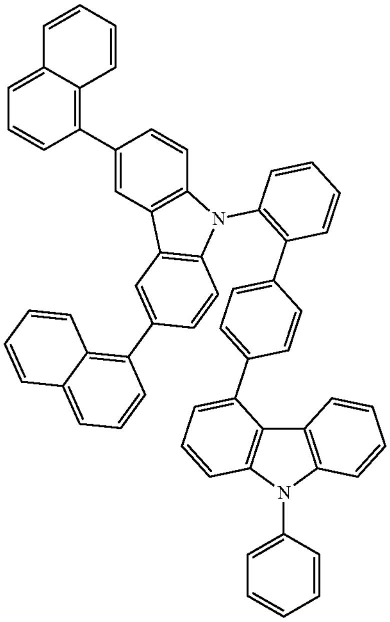
-continued
C31
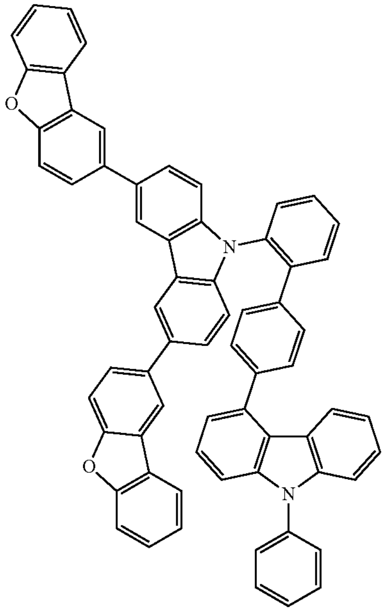
C30
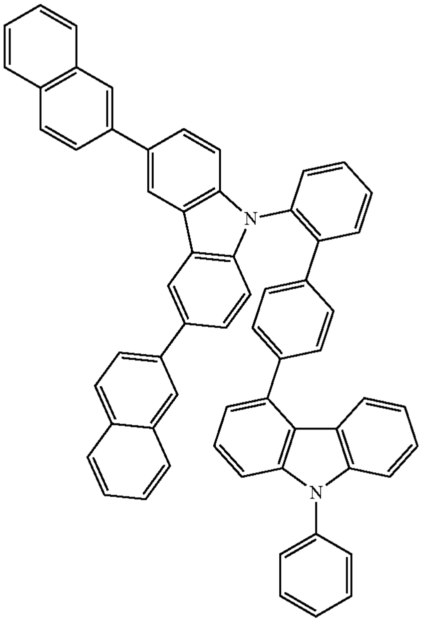
C32
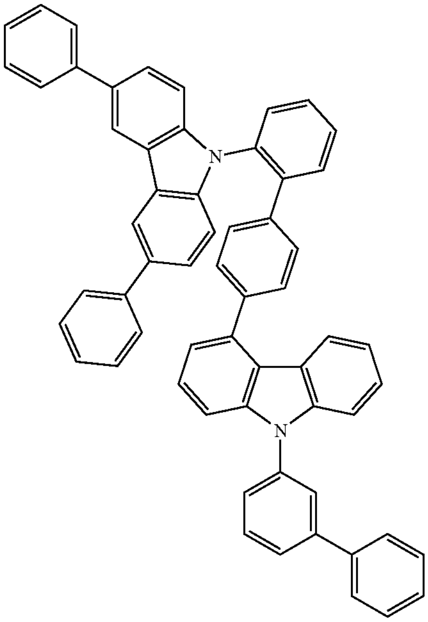

-continued
C33
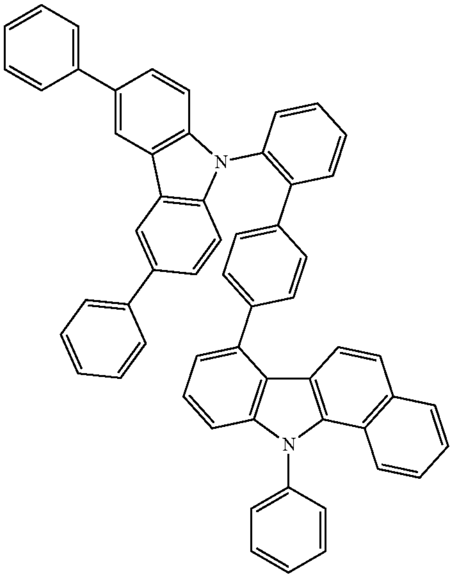
C34
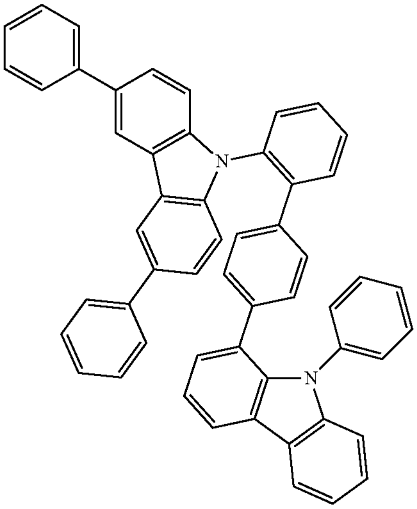
-continued
C35
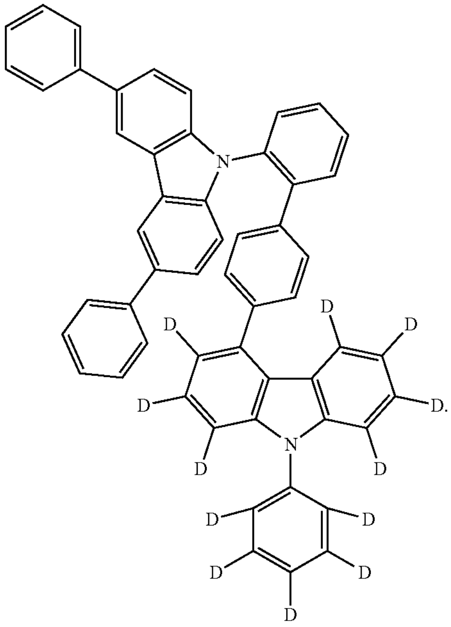
12. The luminescence device of claim 1, wherein the nitrogen-containing compound of the Formula 1 is at least one compound of the Compound Group 2:
Compound Group 2
D1
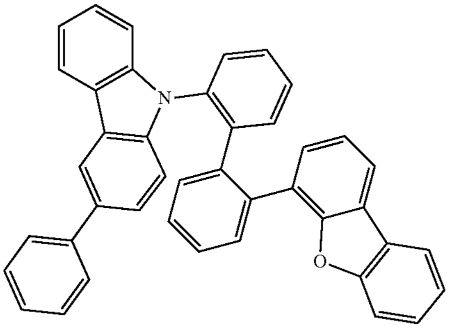
D2
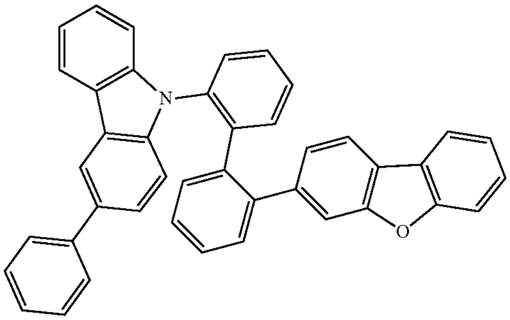

-continued
D3
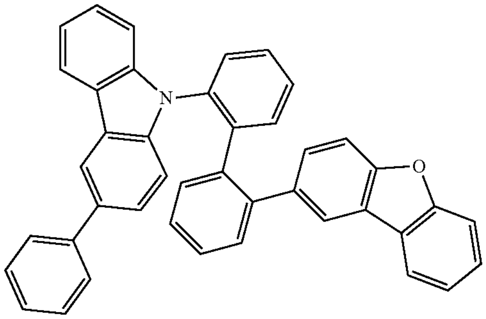
D4
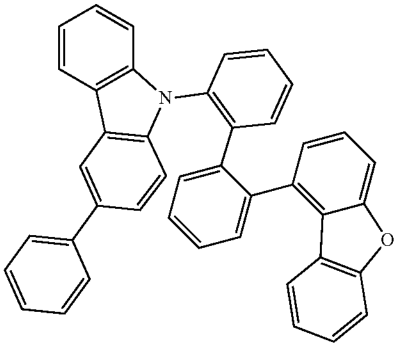
D5
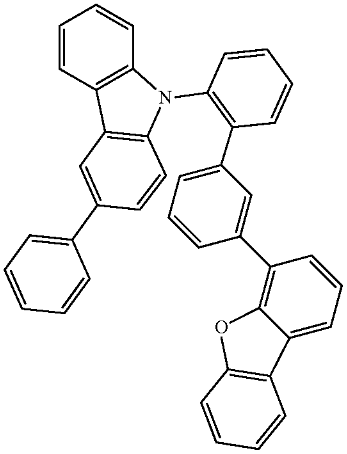
D6
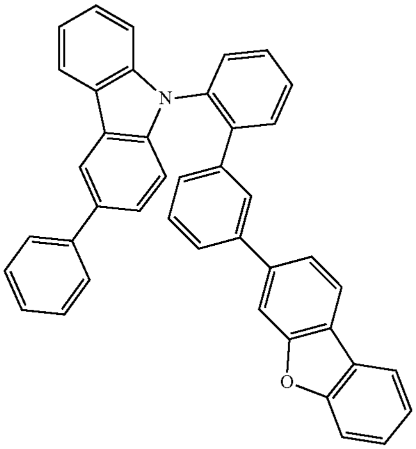
-continued
D7
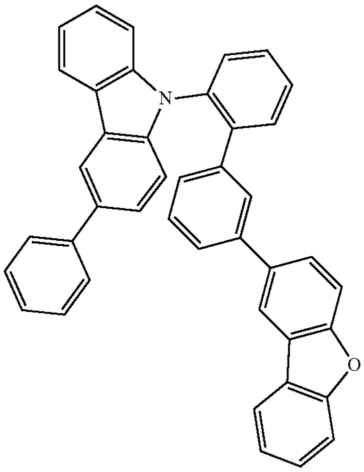
D8
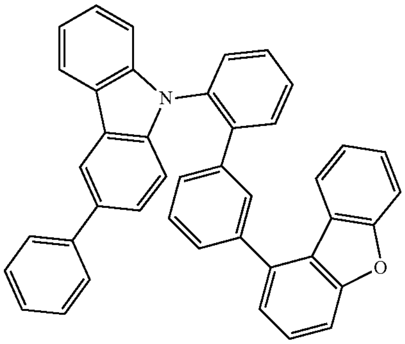
D9
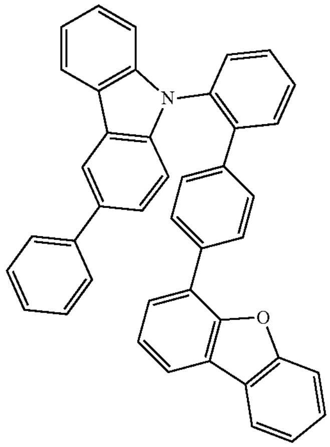

D10
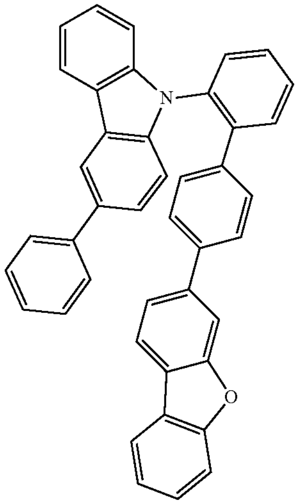
D11
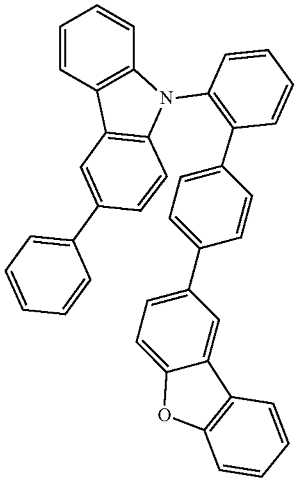
D12
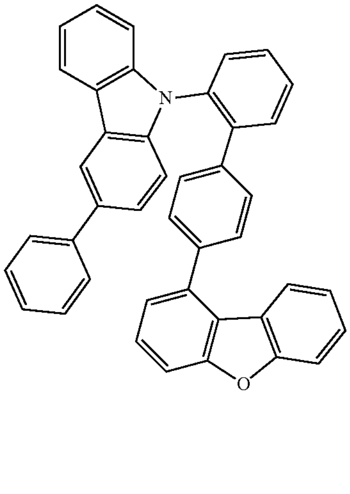
D13
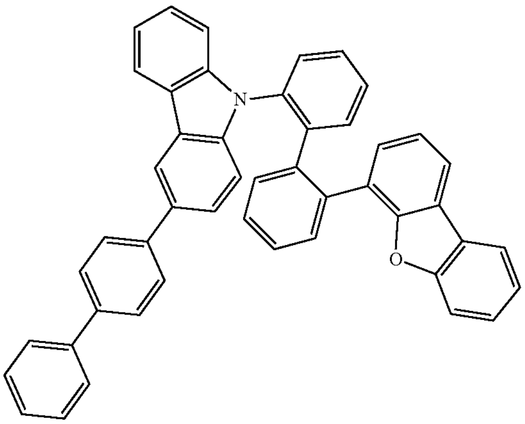
D14
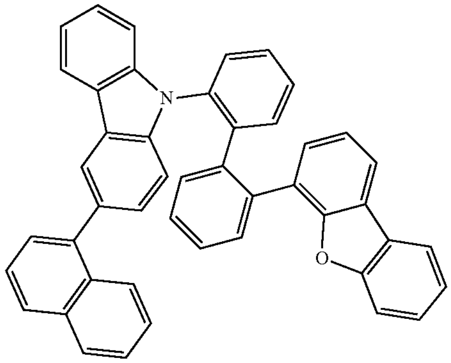
D15
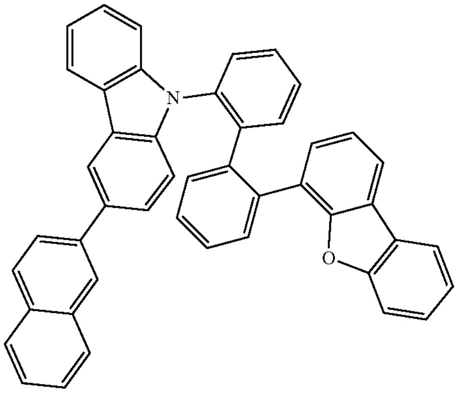
D16
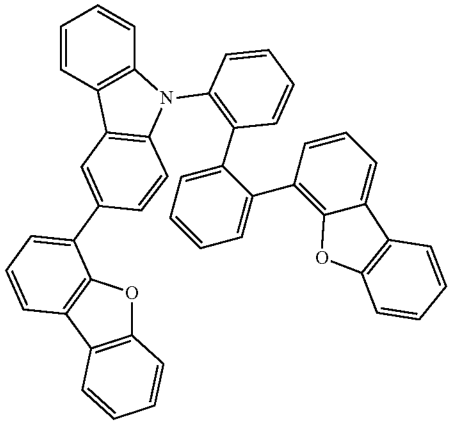

-continued
D17
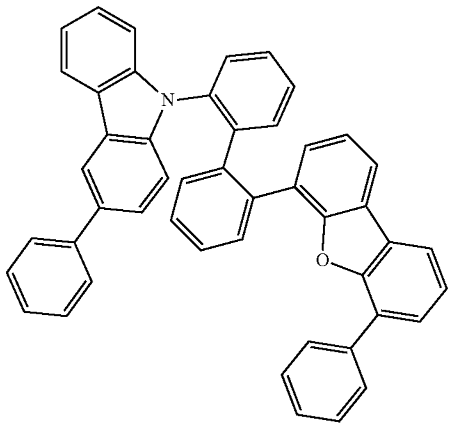
D18
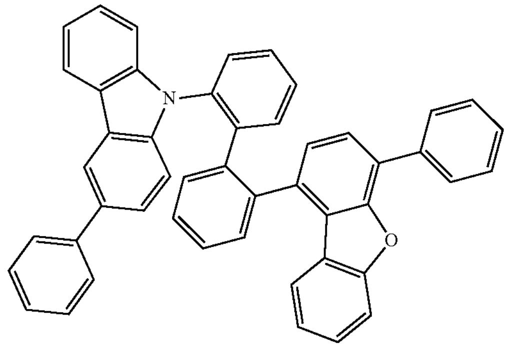
D19
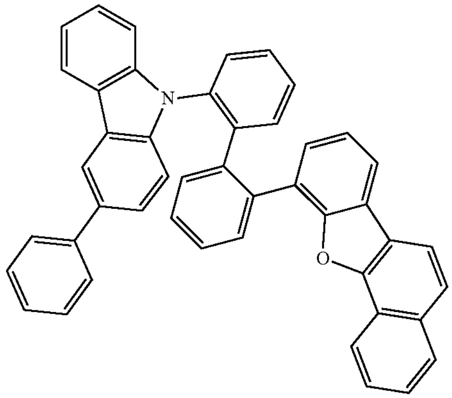
D20
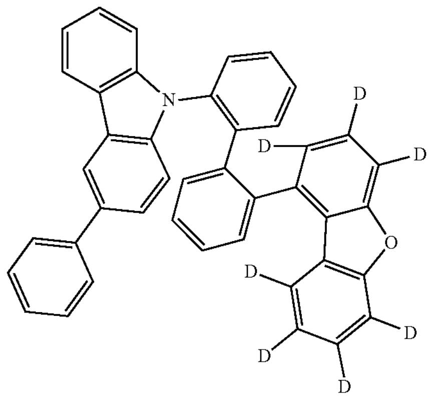
-continued
D21
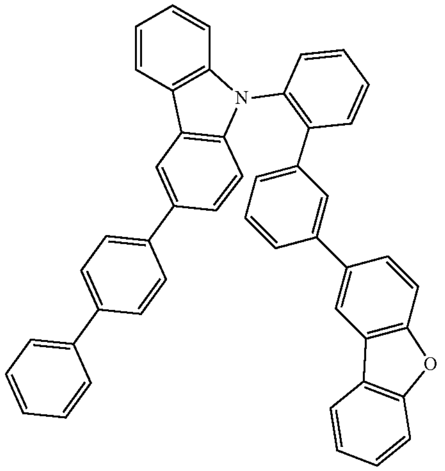
D22
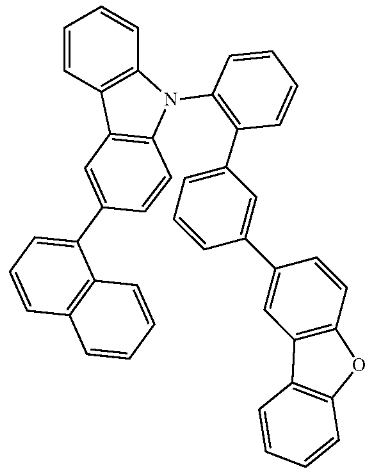
D23
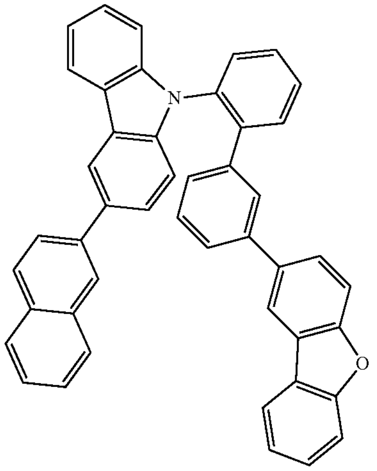

-continued
D24
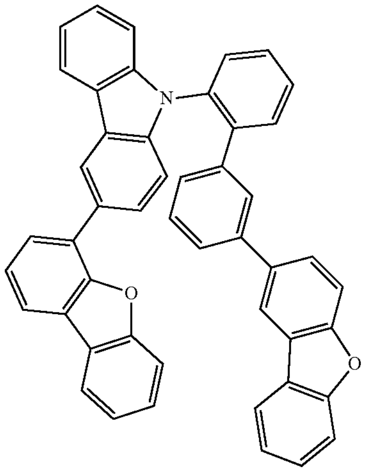
D25
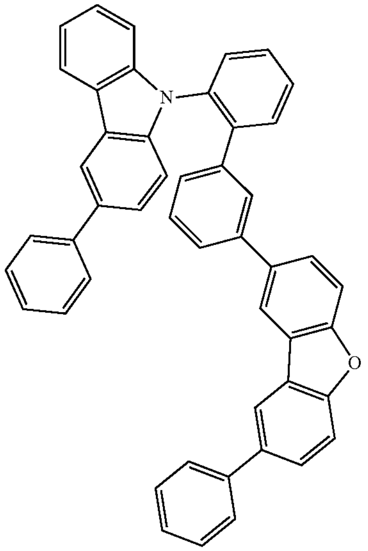
D26
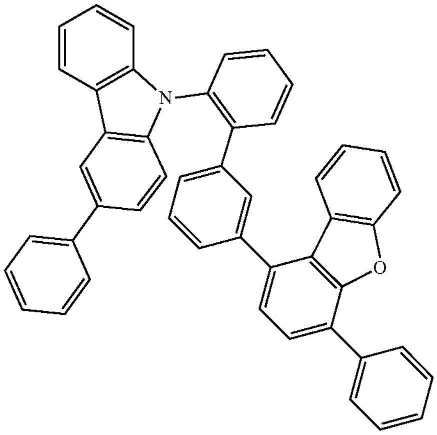
-continued
D27
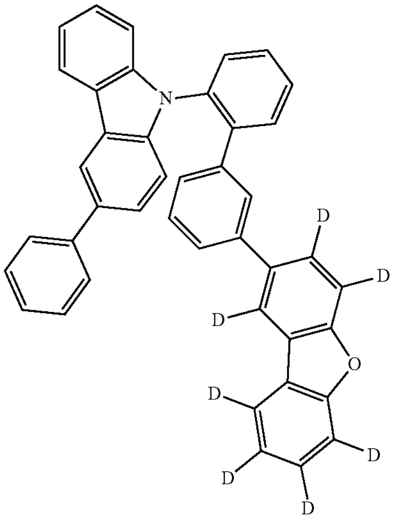
D28
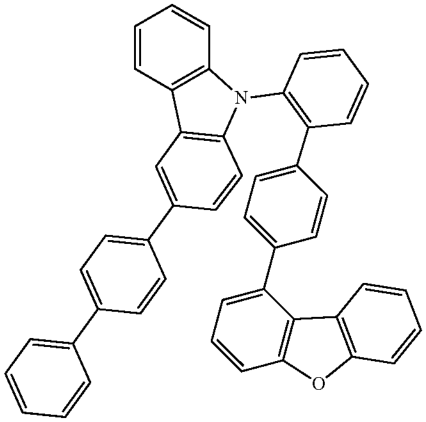
D29
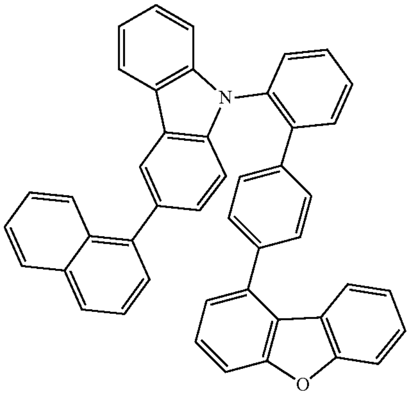

-continued
D30
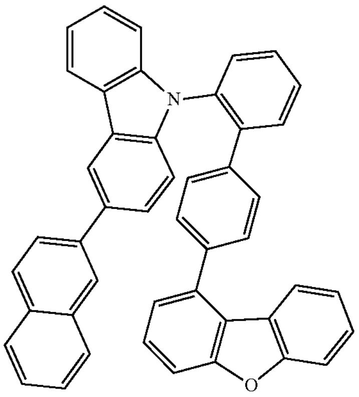
D31
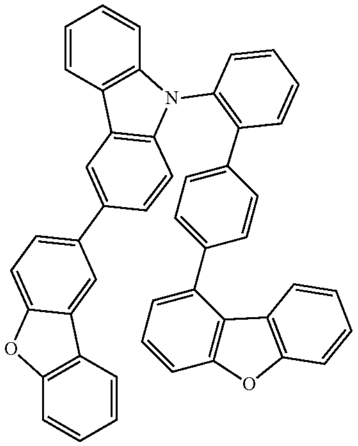
D32
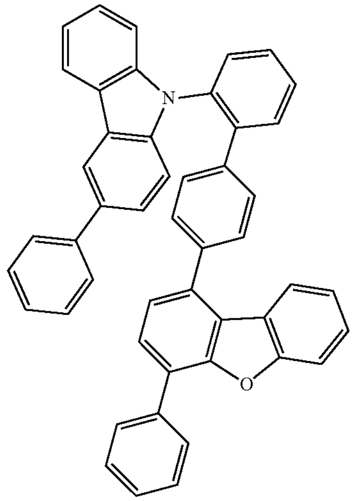
-continued
D33
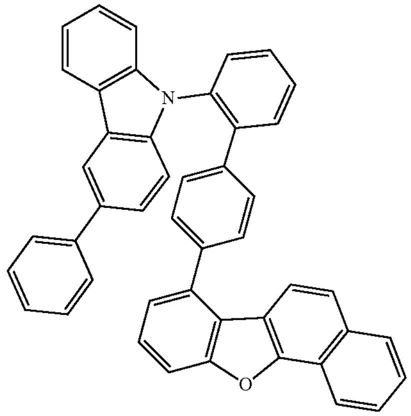
D34
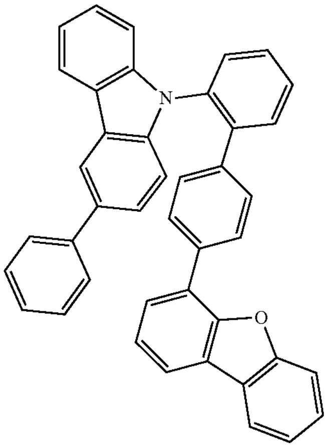
D35
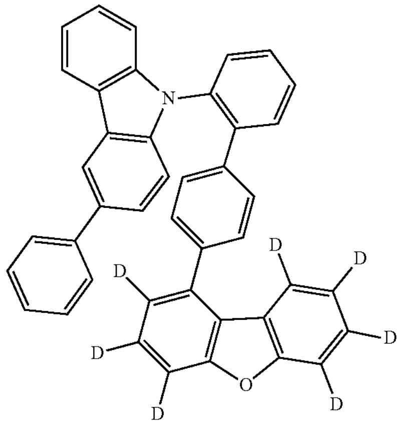
E1
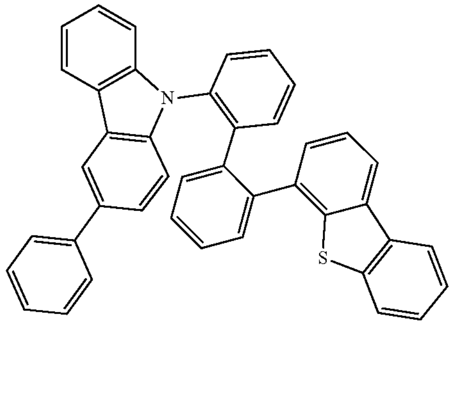

-continued
E2
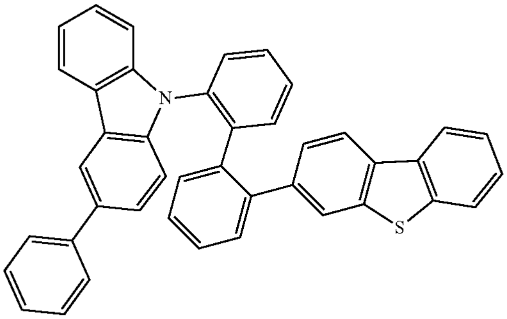
E3
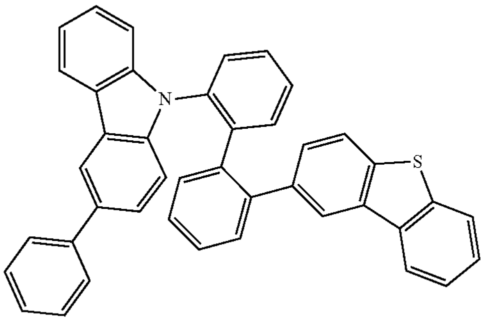
E4
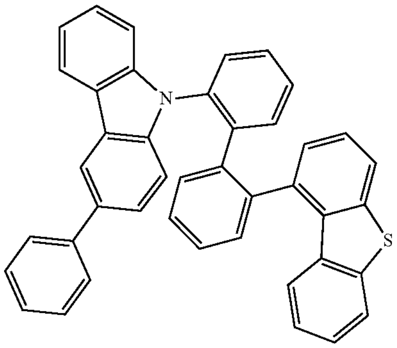
E5
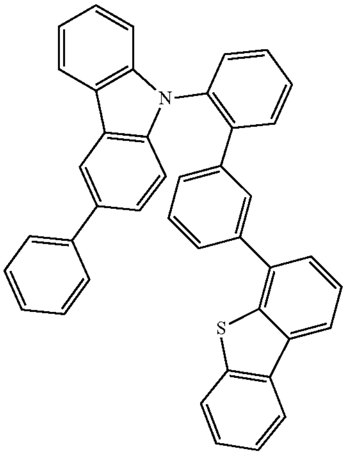
-continued
E6
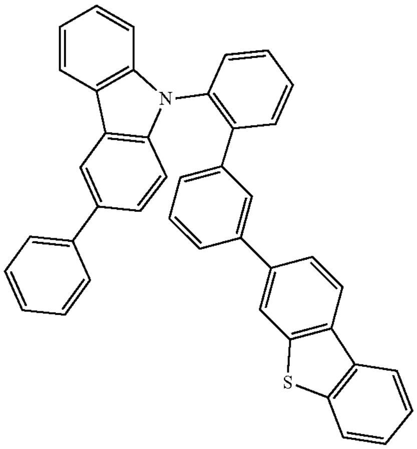
E7
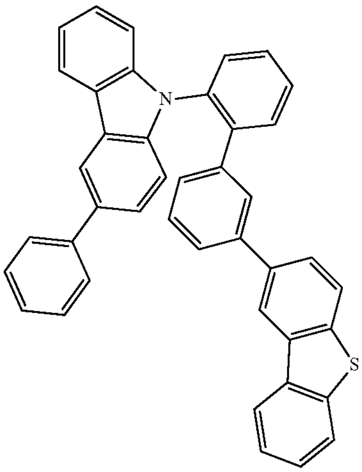
E8
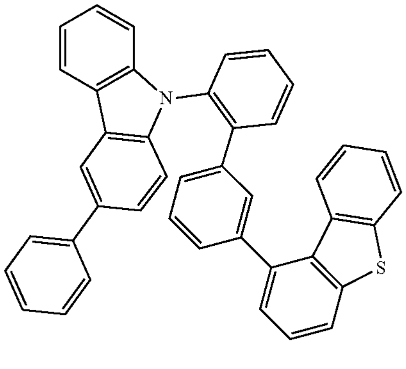

-continued
E9
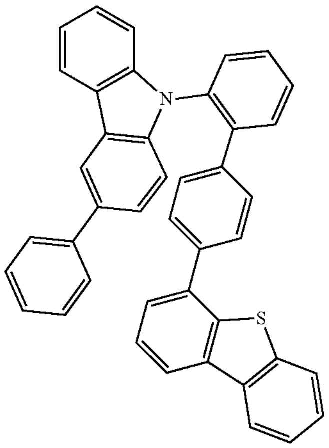
E10
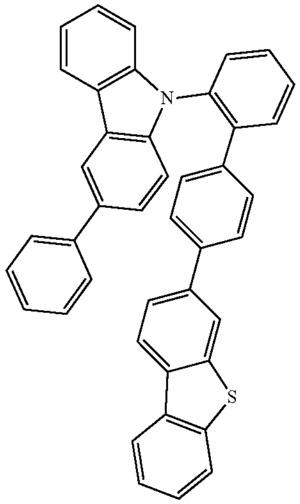
E11
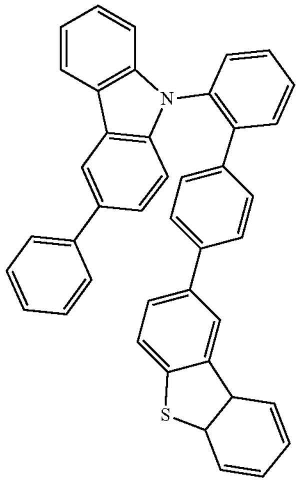
-continued
E12
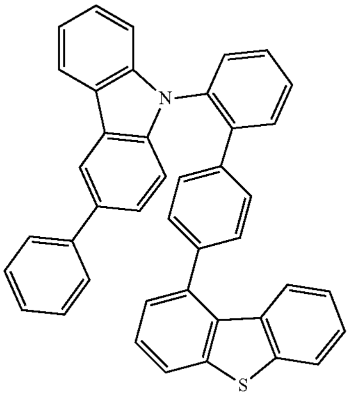
E13
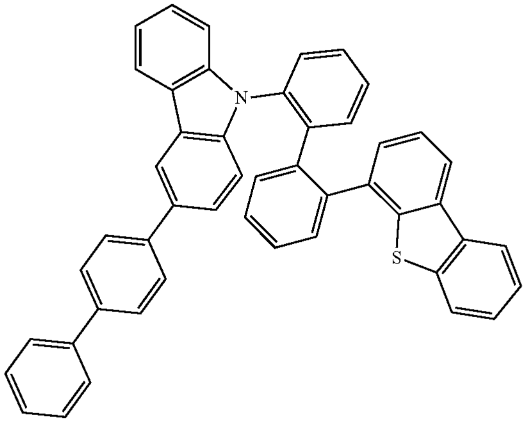
E14
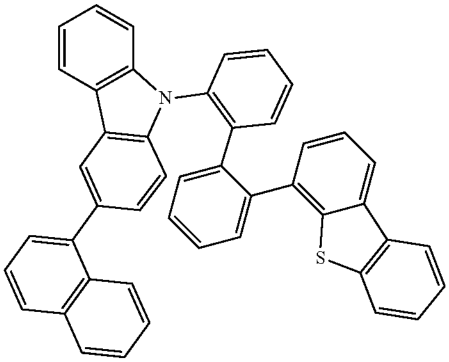
E15
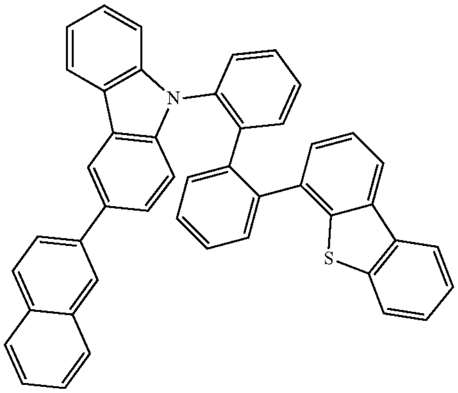

E16
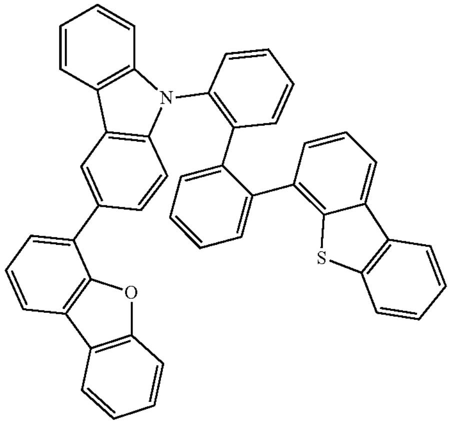
E17
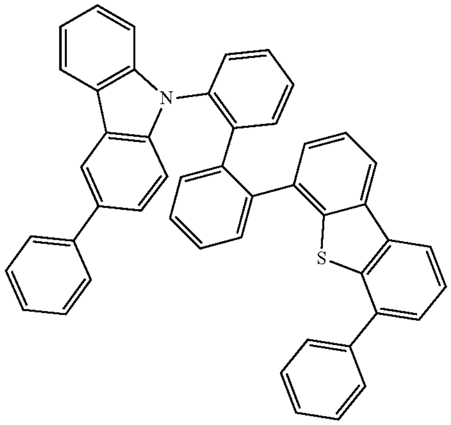
E18
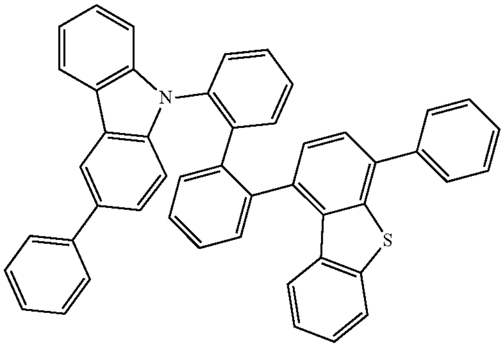
E19
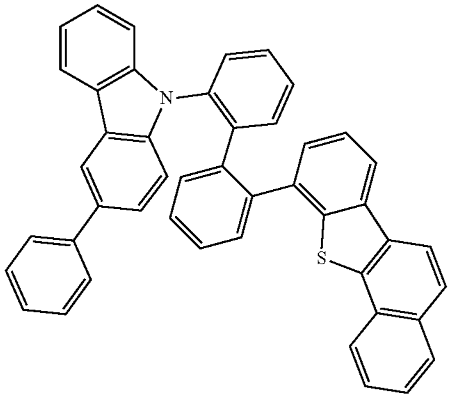
E20
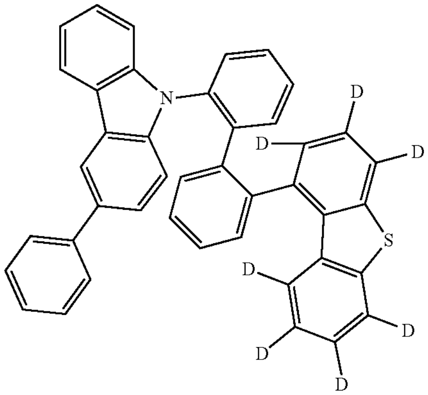
E21
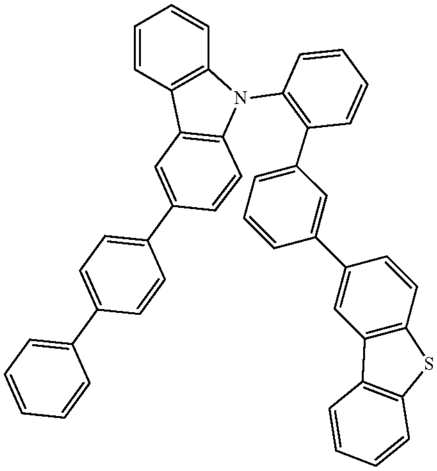
E22
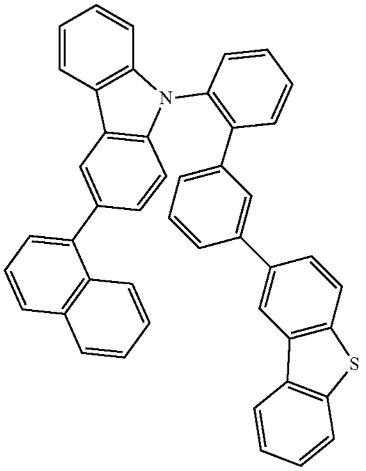

-continued
E23
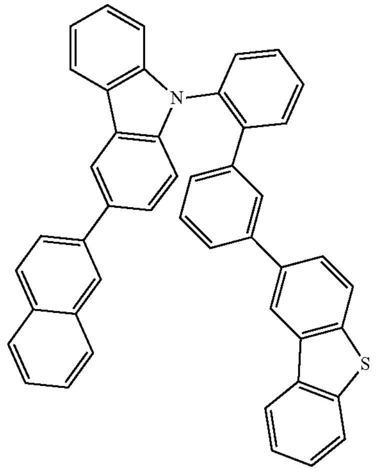
E24
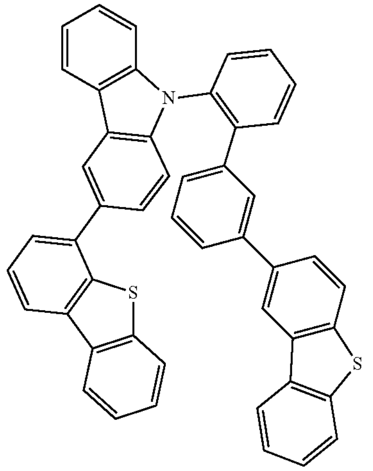
E25
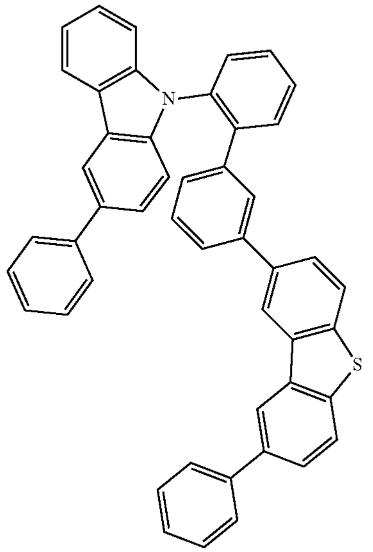
-continued
E26
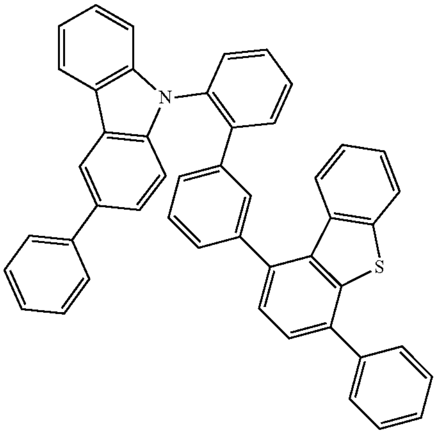
E27
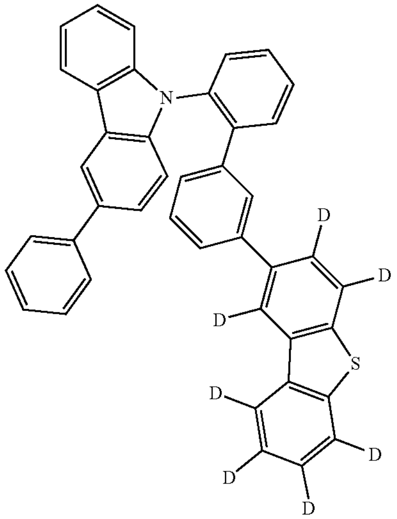
E28
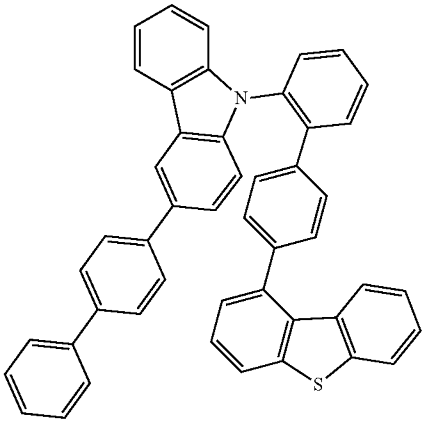

E29
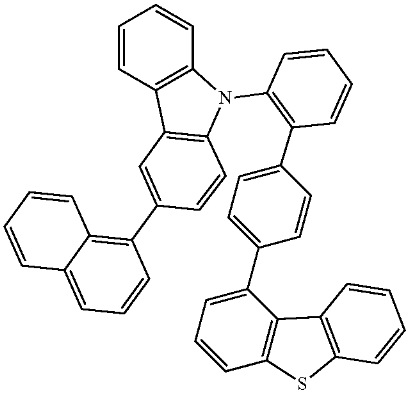
E30
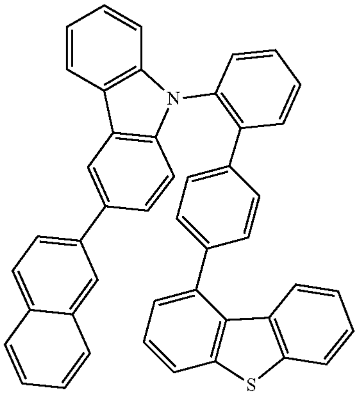
E31
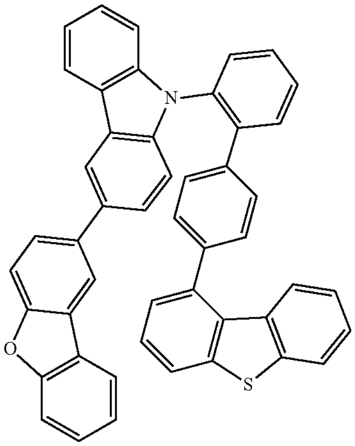
E32
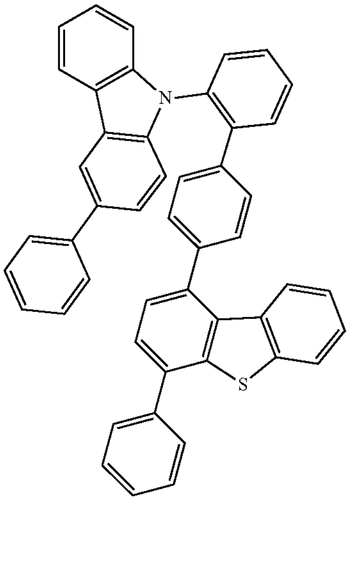
E33
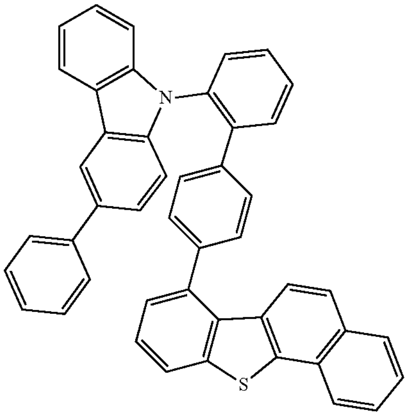
E34
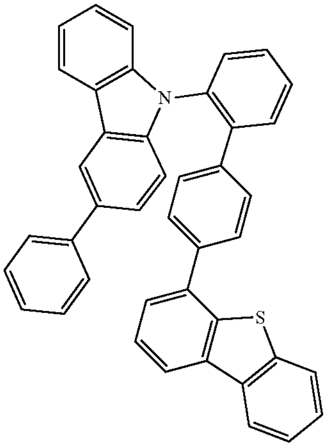

-continued
E35
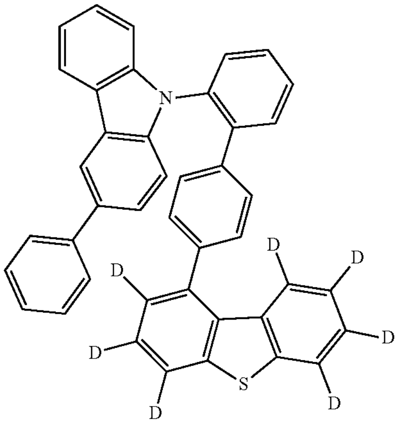
F1
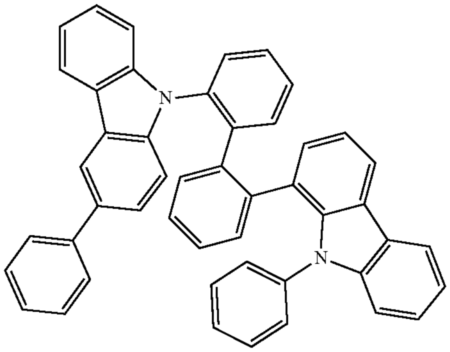
F2
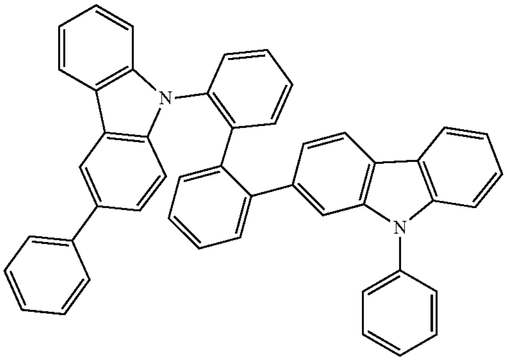
F3
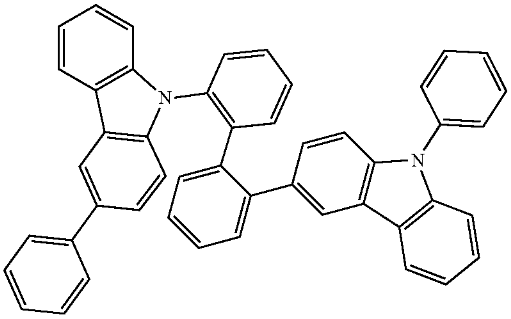
-continued
F4
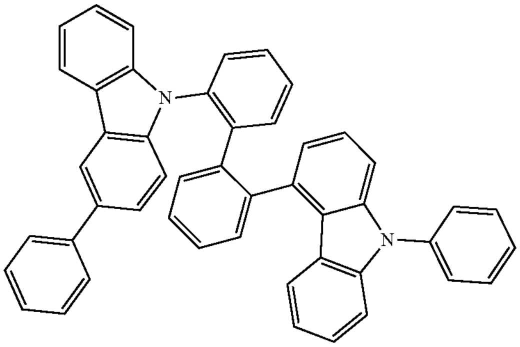
F5
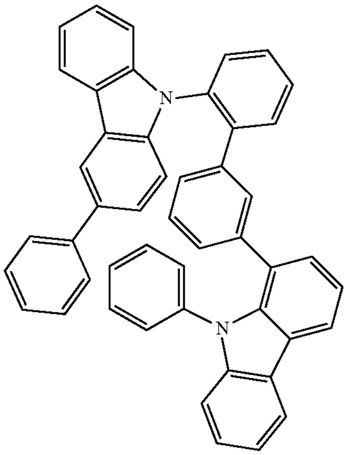
F6
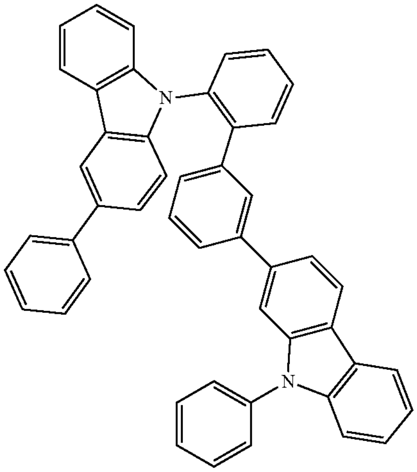

-continued
F7
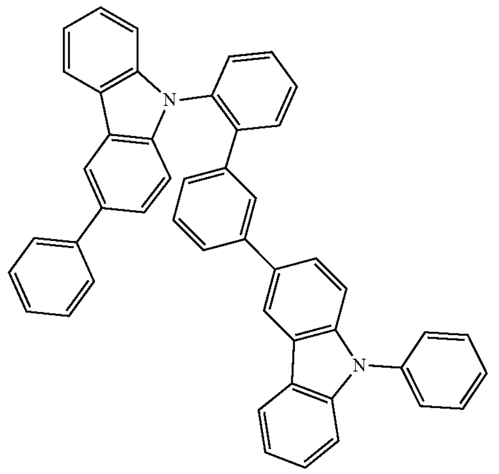
F8
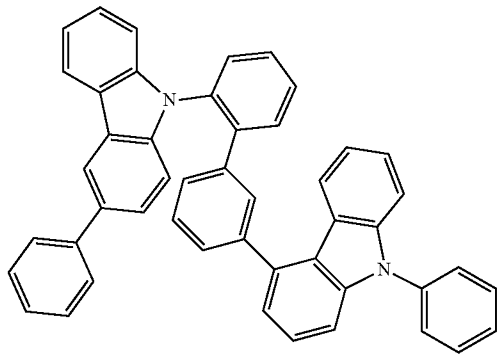
F9
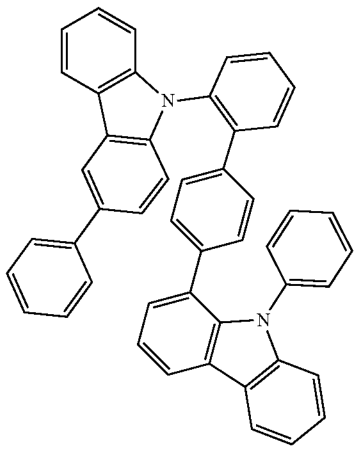
-continued
F10
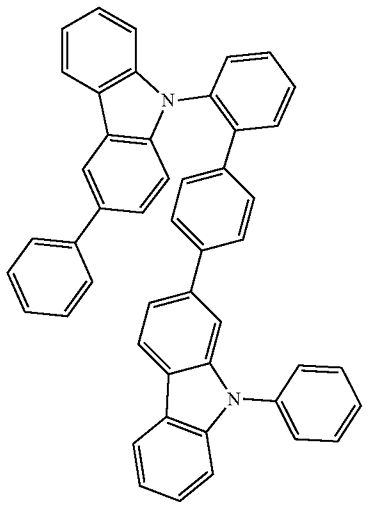
F11
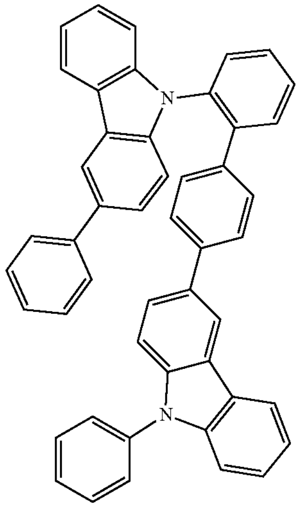
F12
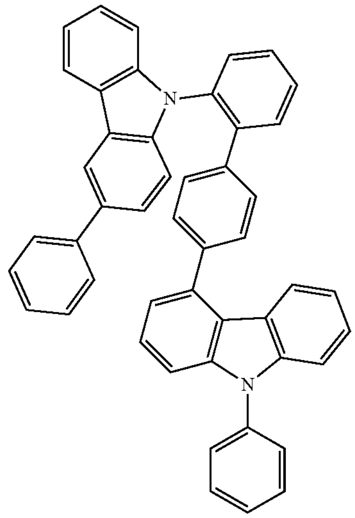

-continued
F13
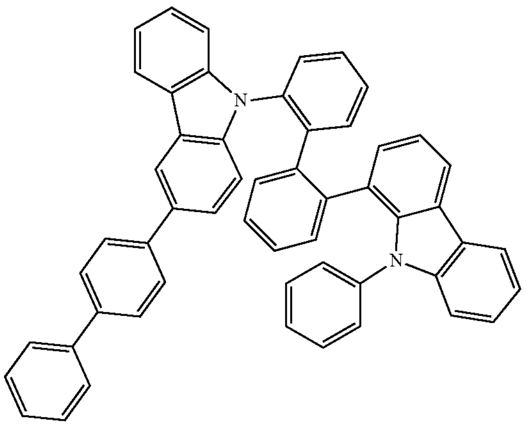
F14
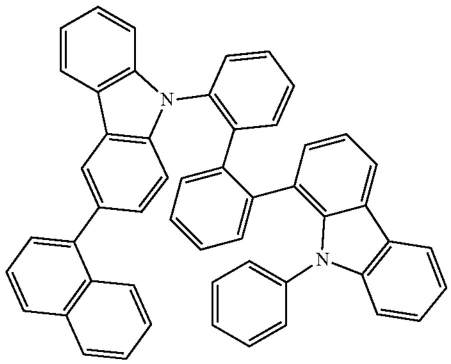
F15
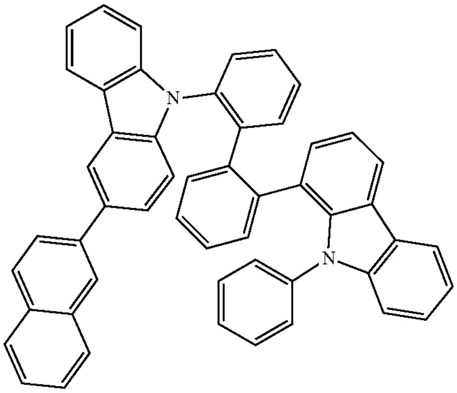
F16
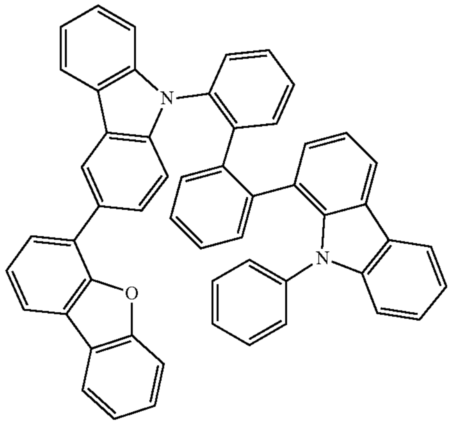
-continued
F17
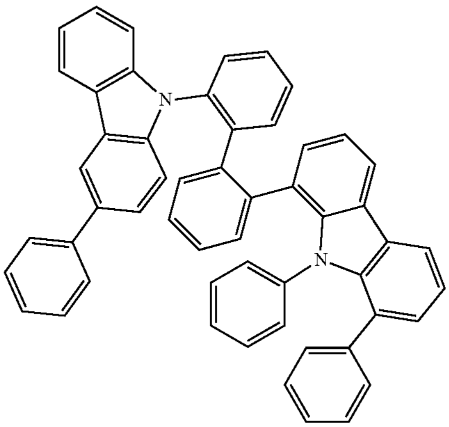
F18
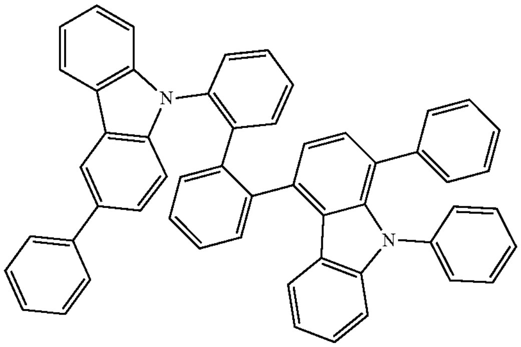
F19
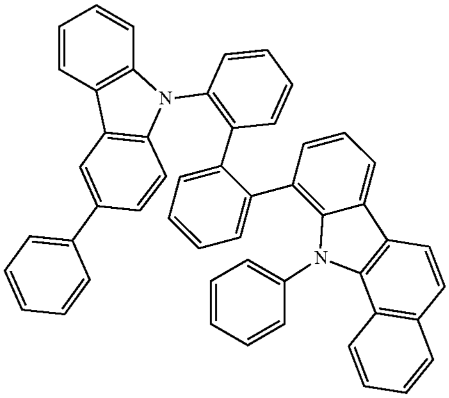
F20
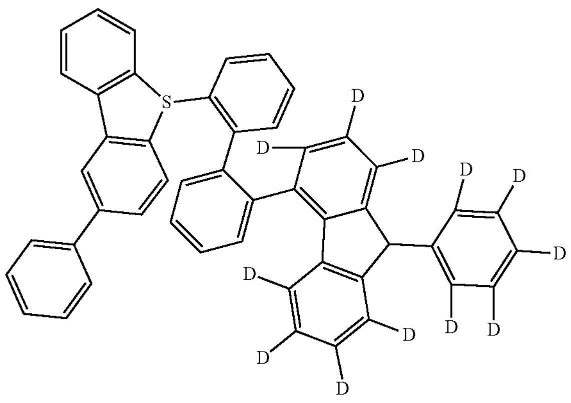

-continued
F21
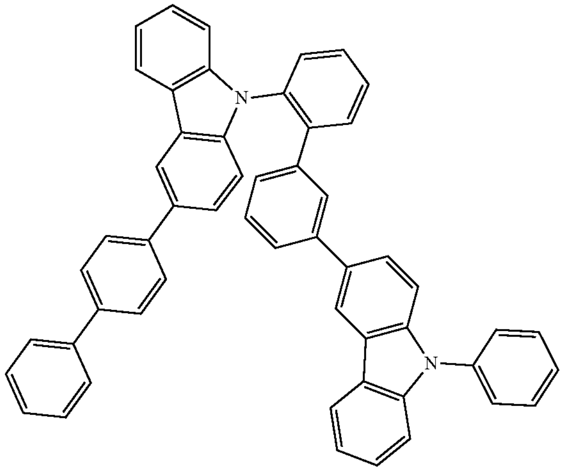
F22
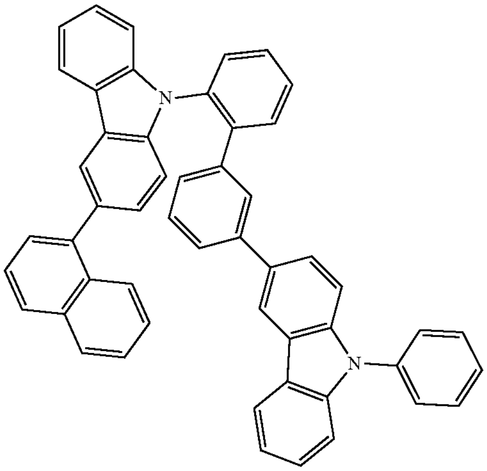
F23
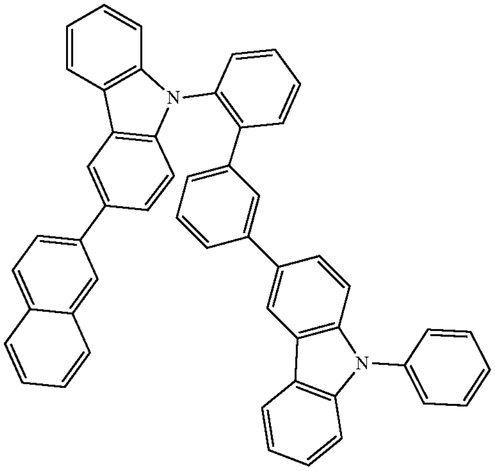
-continued
F24
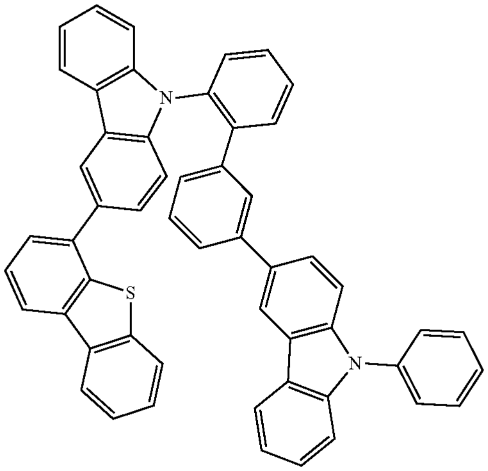
F25
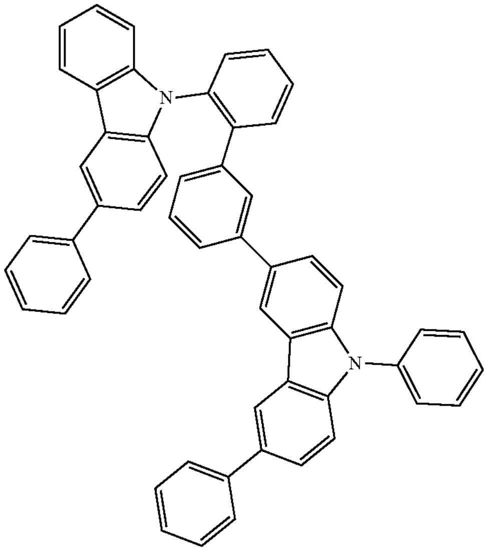
F26
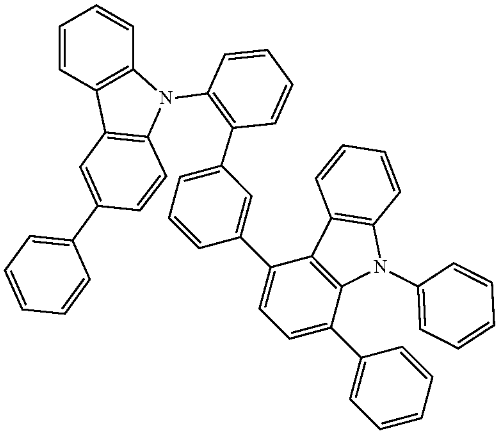

-continued
F27
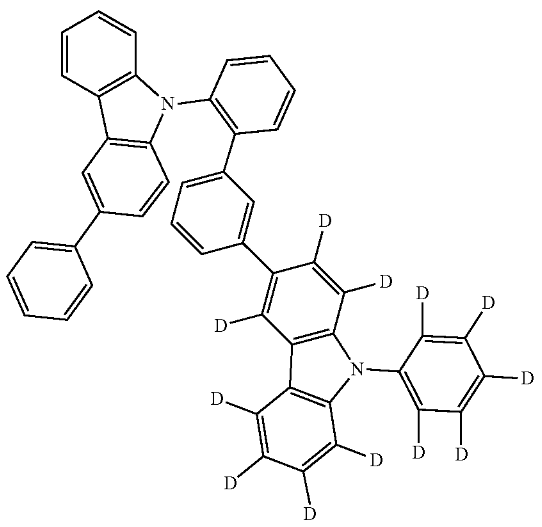
F28
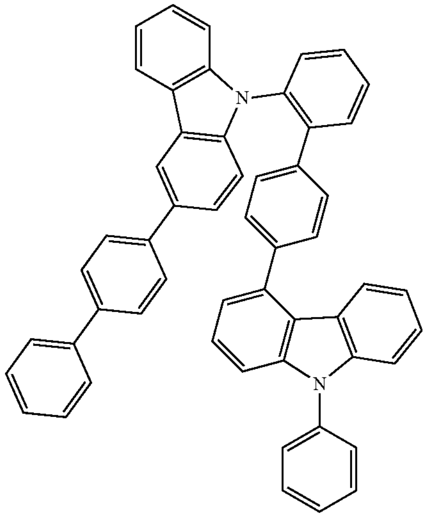
F29
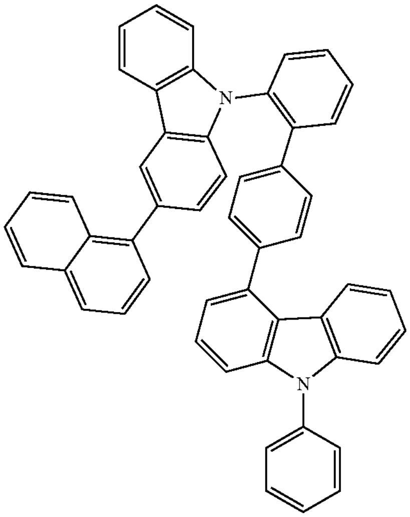
-continued
F30
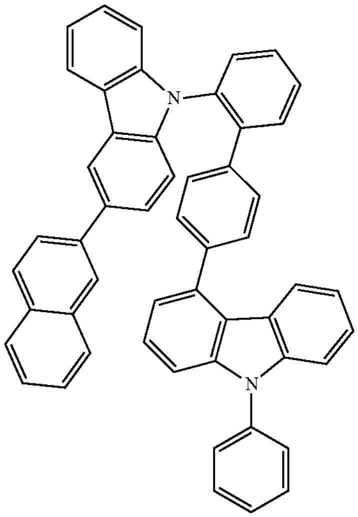
F31
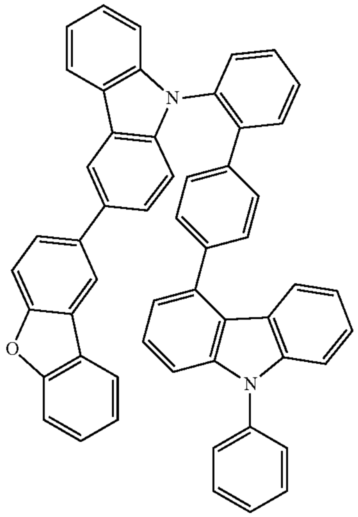
F32
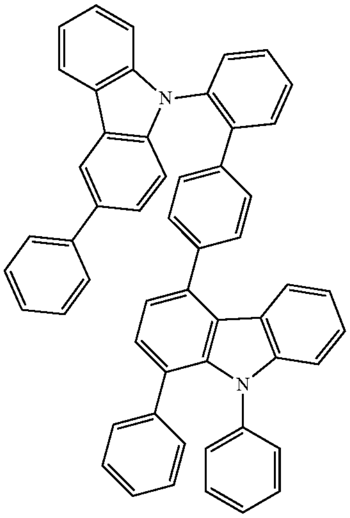

-continued
F33
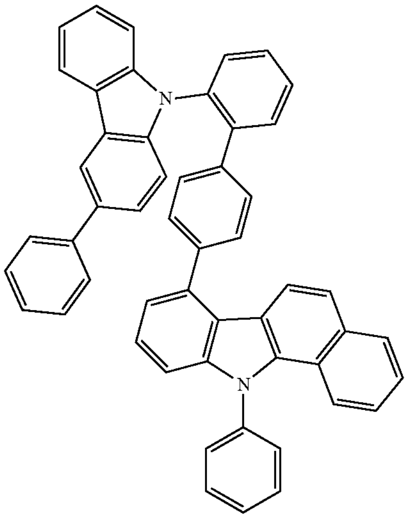
F34
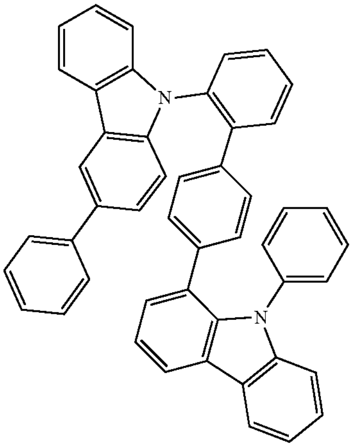
F35
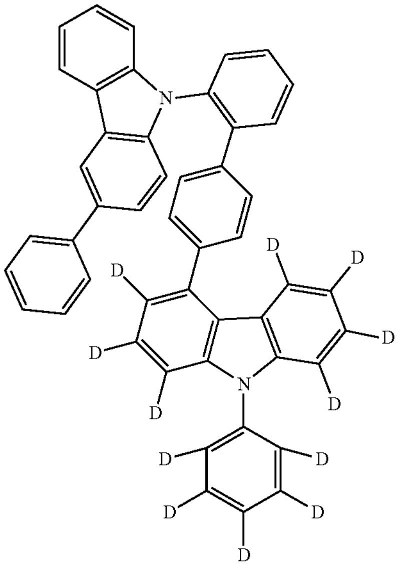
-continued
J1
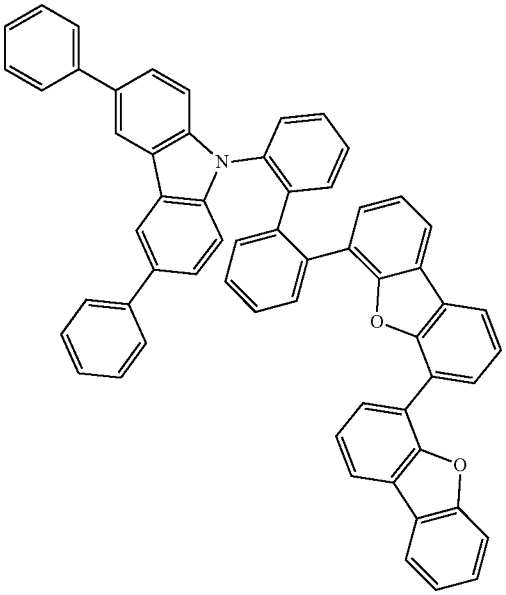
J2
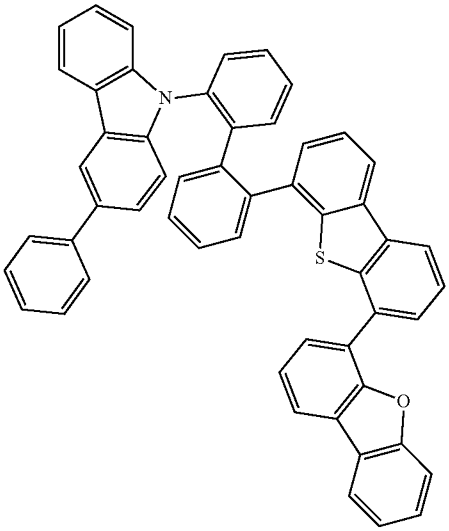
J3
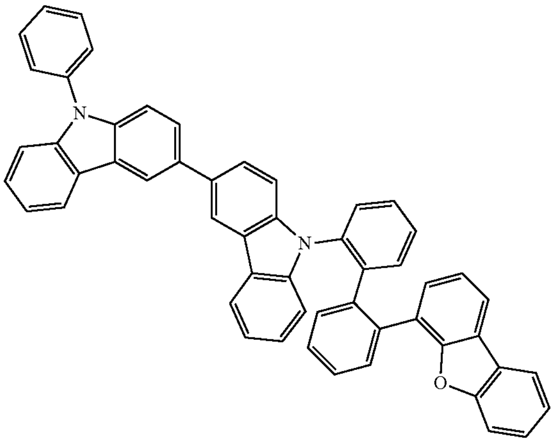

-continued
J4
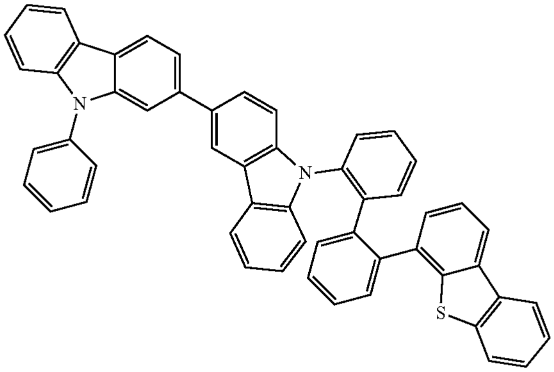
K1
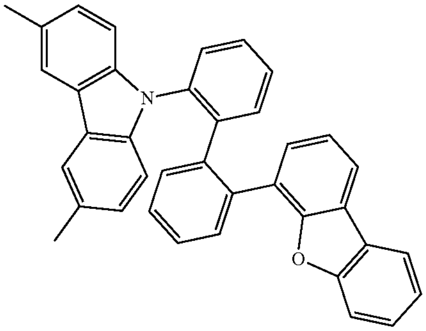
K2
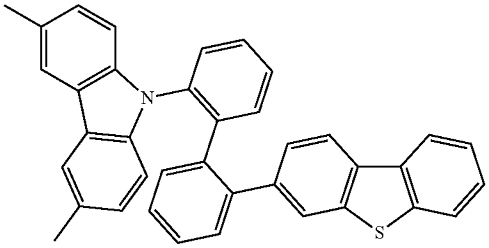
K3
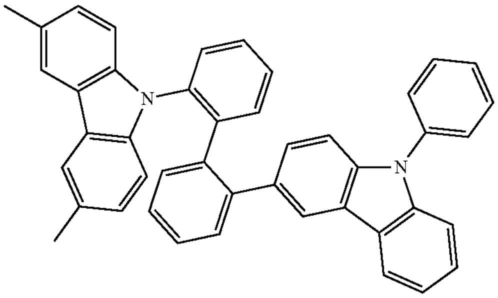
-continued
K4
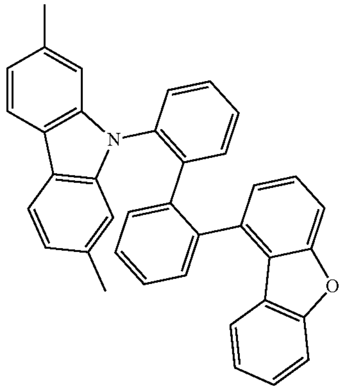
K5
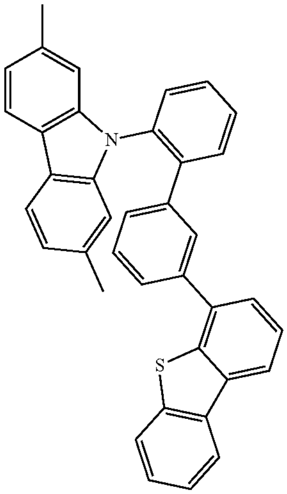
K6
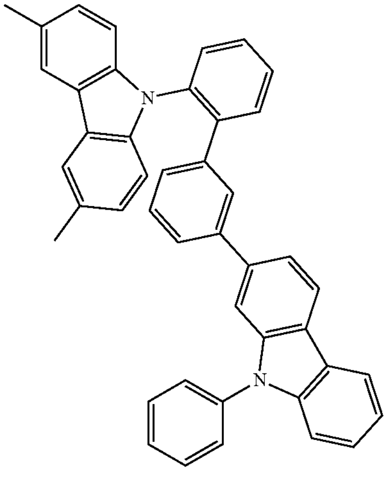

-continued
K7
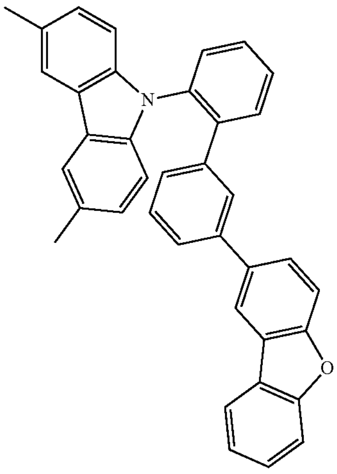
K8
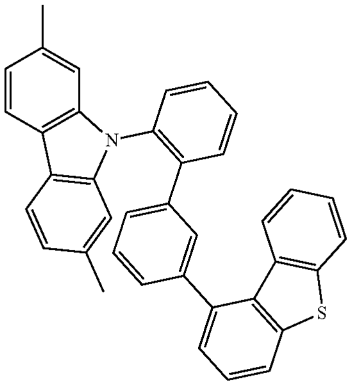
K9
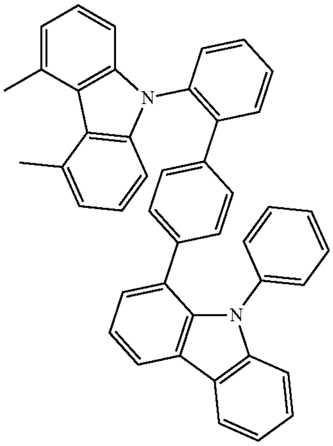
-continued
K10
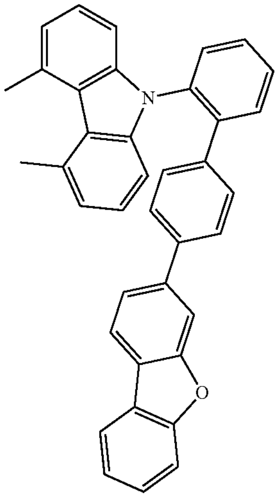
K11
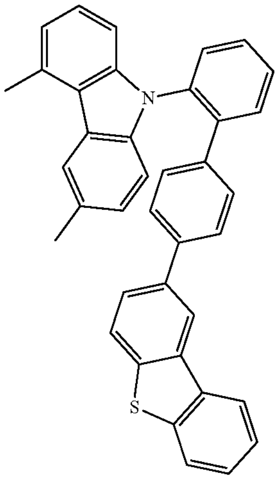
K12
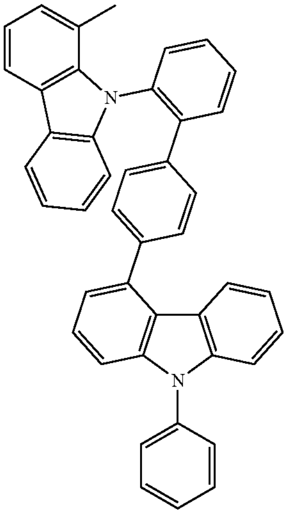

-continued
K13
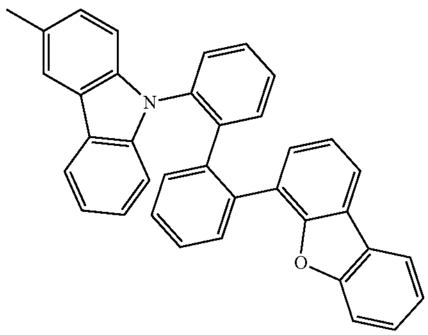
K14
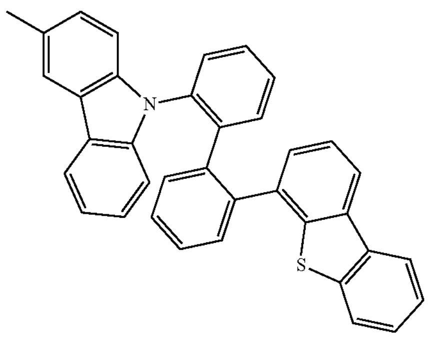
K15
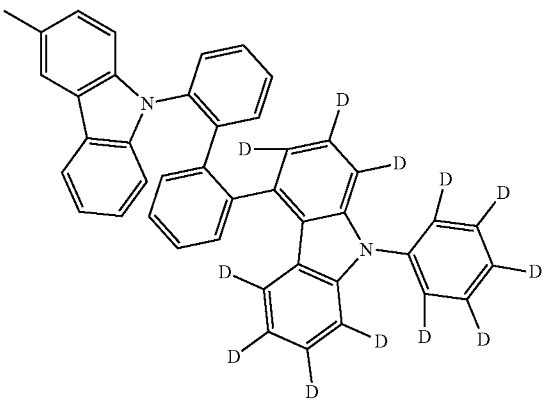
L1
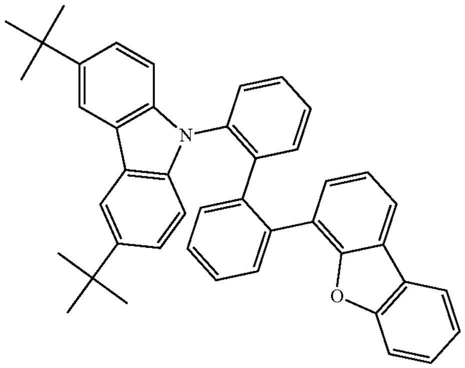
-continued
L2
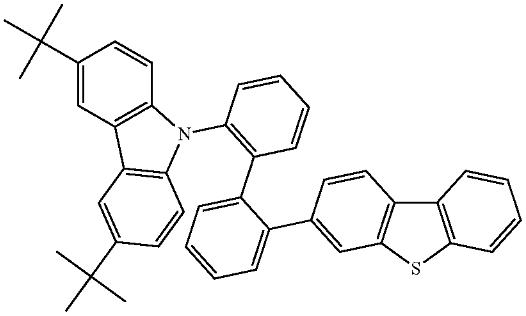
L3
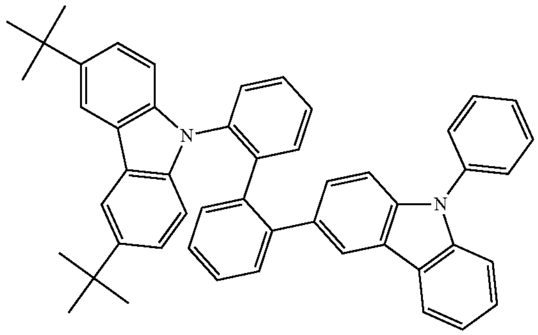
L4
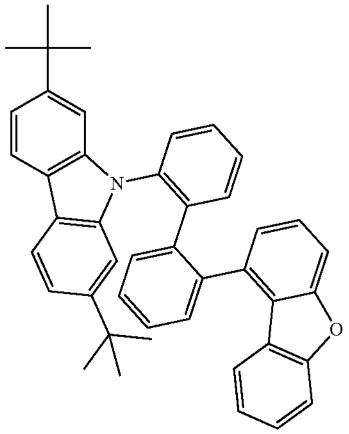
L5
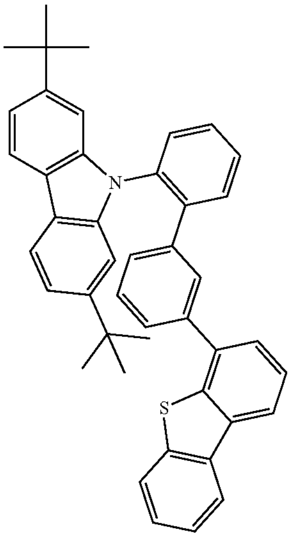

-continued
L6
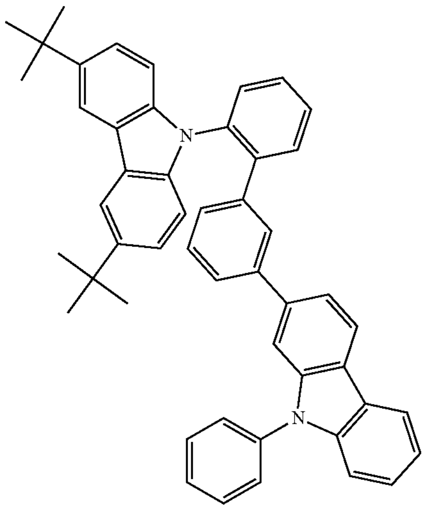
L7
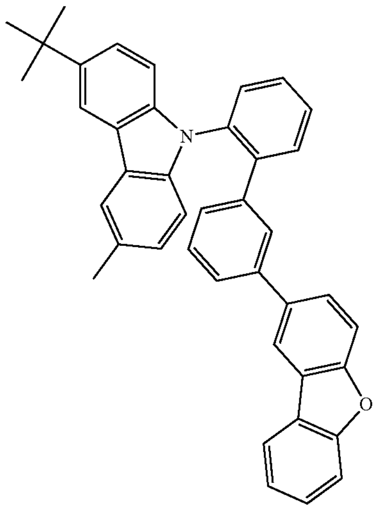
L8
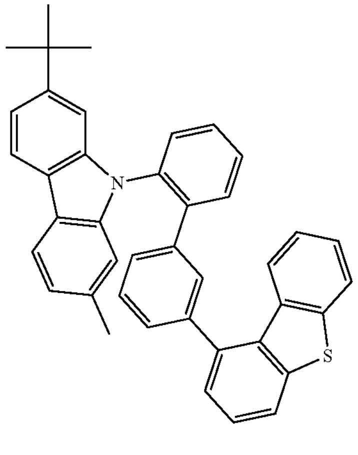
-continued
L9
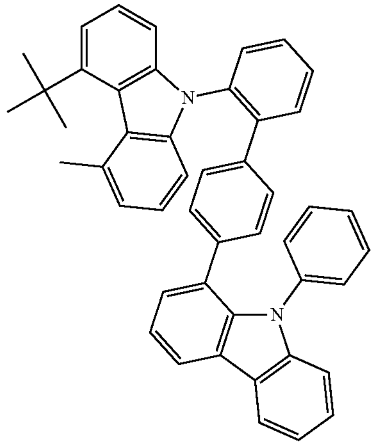
L10
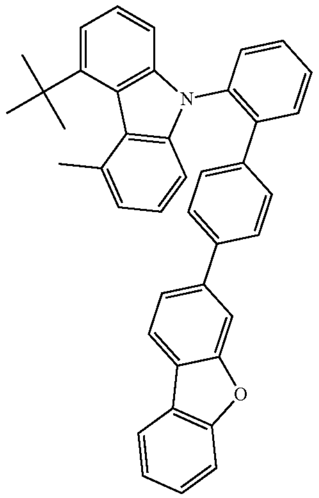
L11
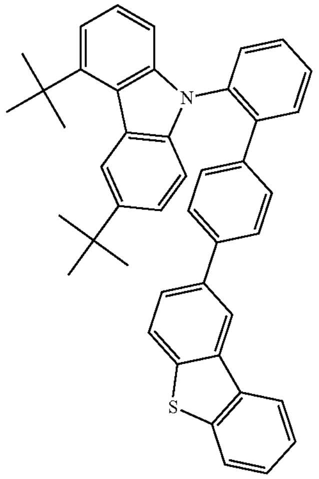

-continued
L12
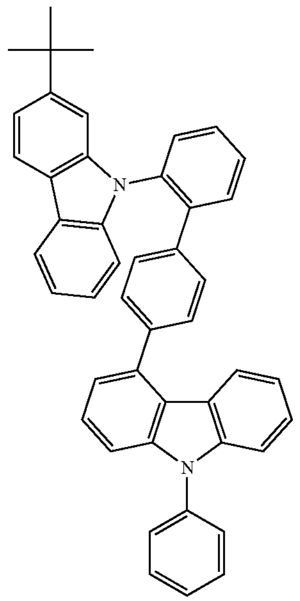
L13
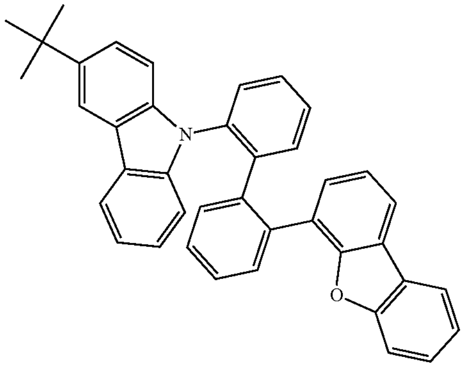
L14
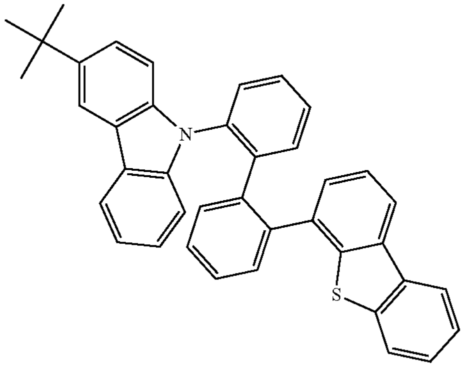
-continued
L15
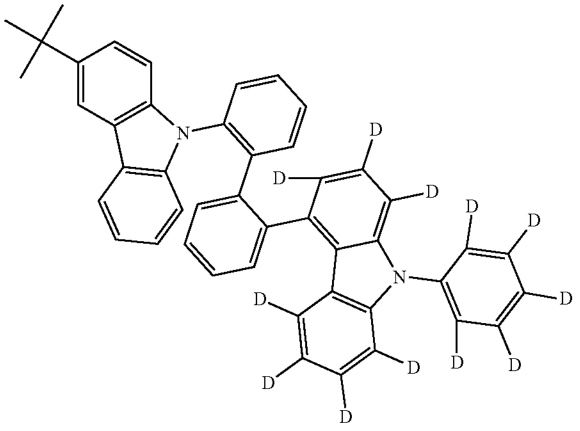
M1
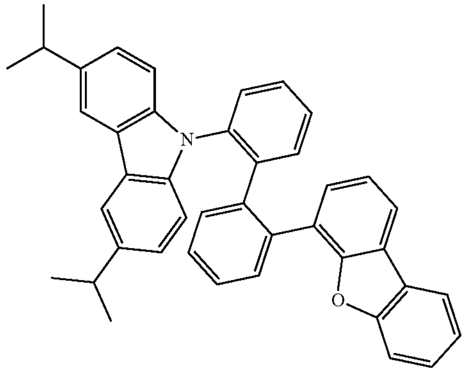
M2
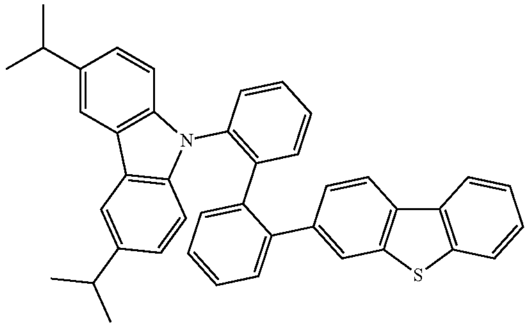
M3
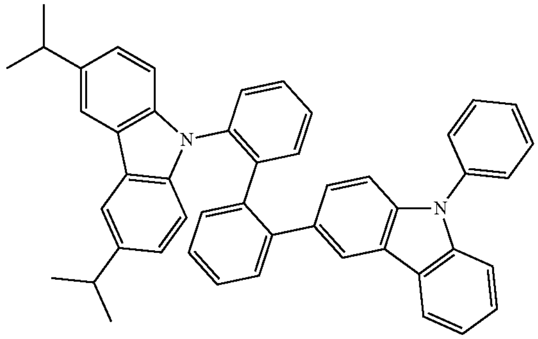

-continued
M4
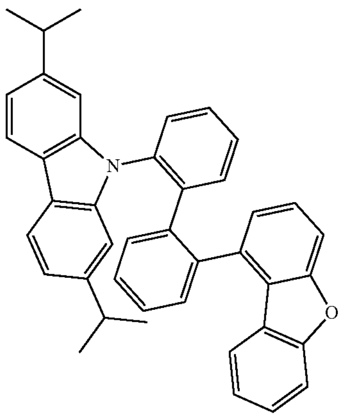
M5
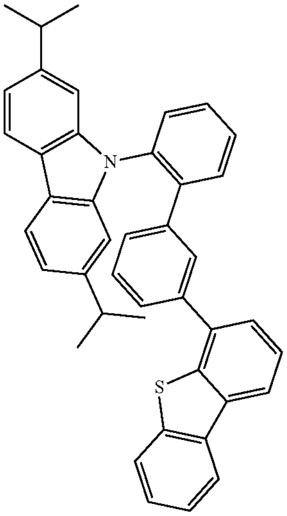
M6
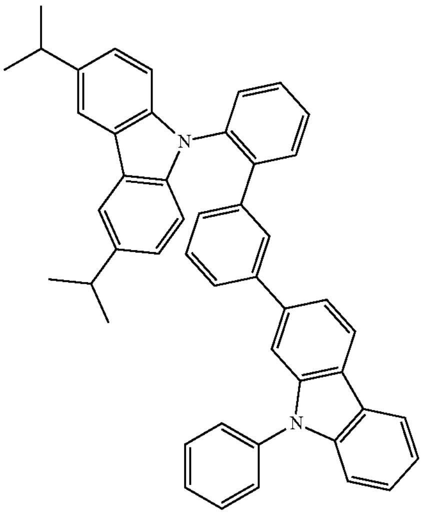
-continued
M7
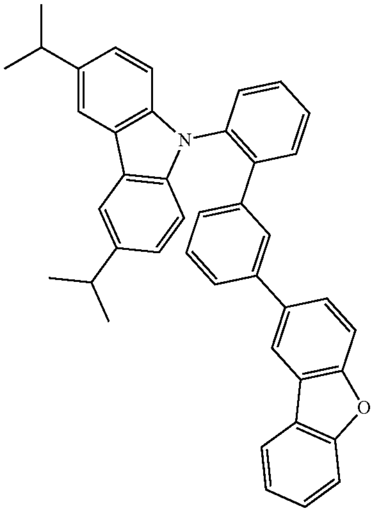
M8
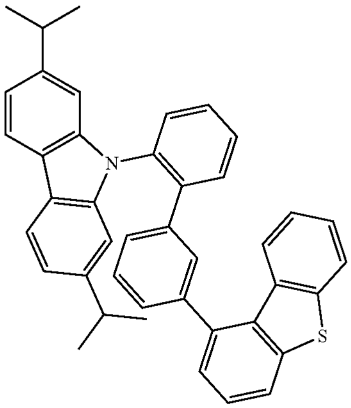
M9
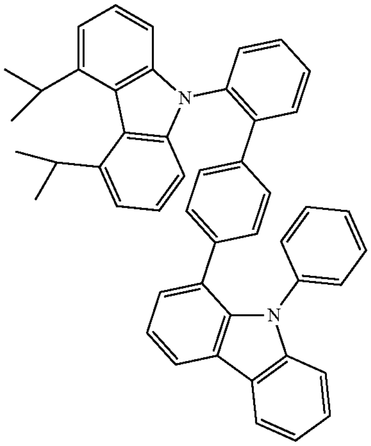

-continued
M10
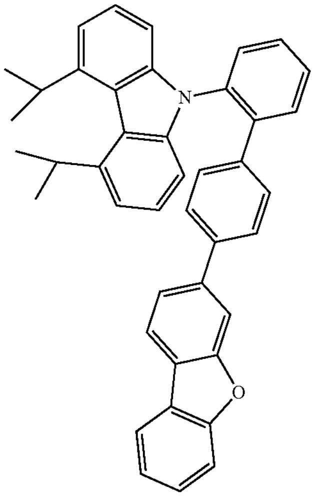
M11
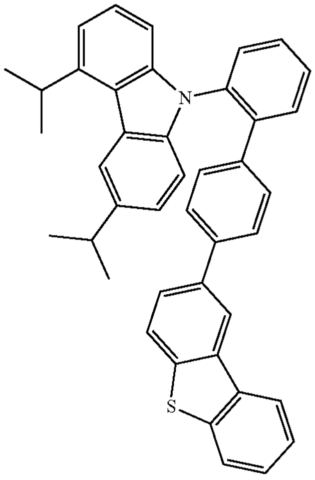
M12
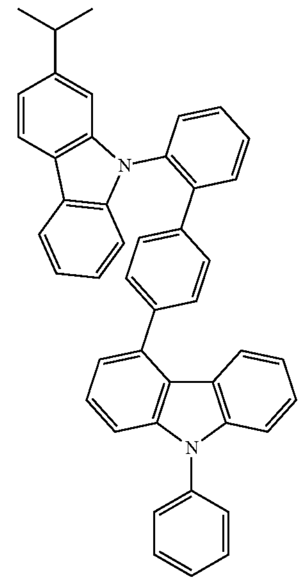
-continued
M13
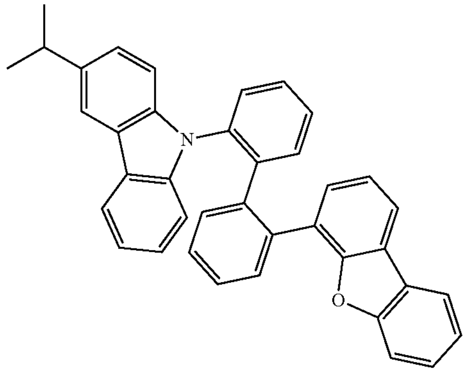
M14
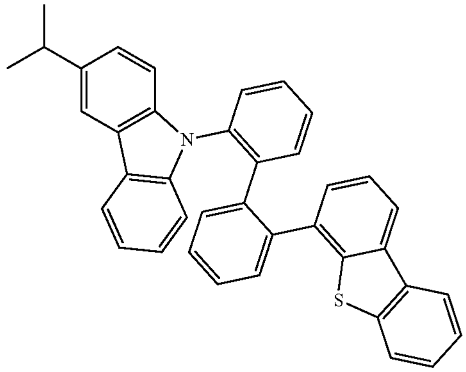
M15
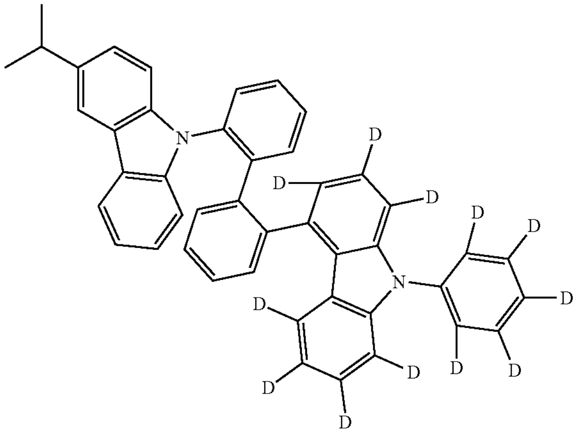
N1
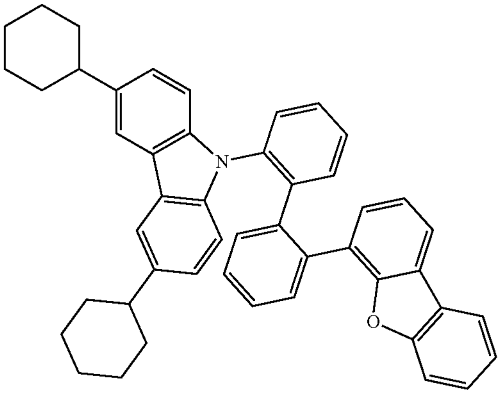

-continued
N2
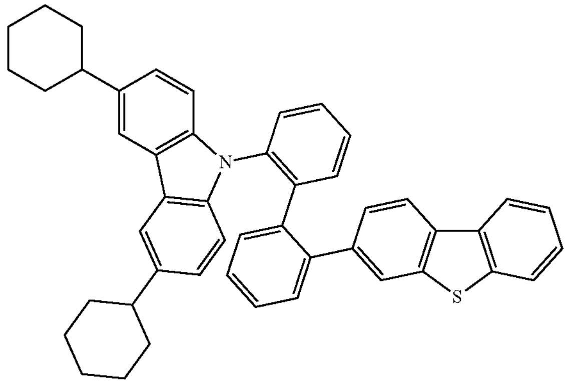
N3
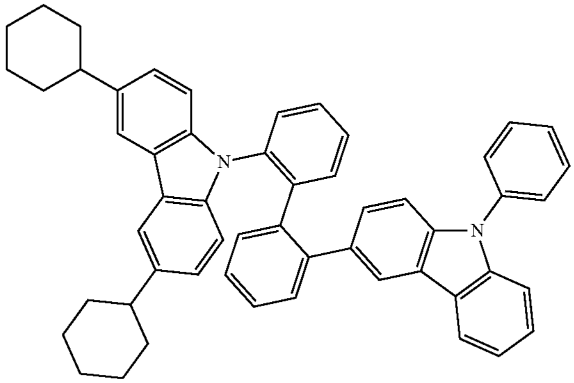
N4
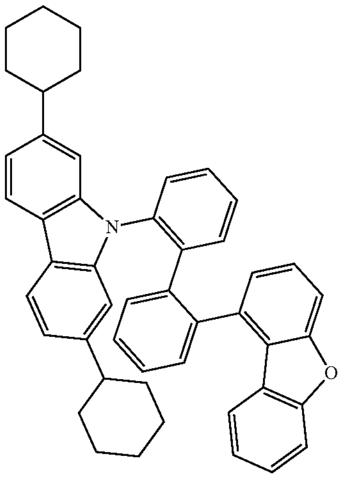
-continued
N5
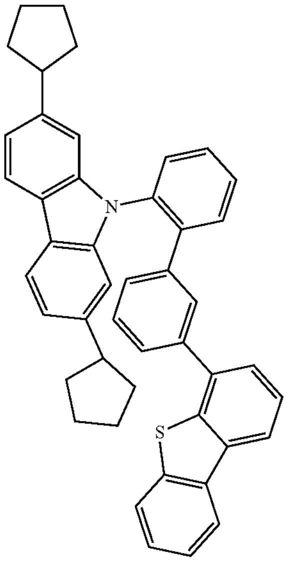
N6
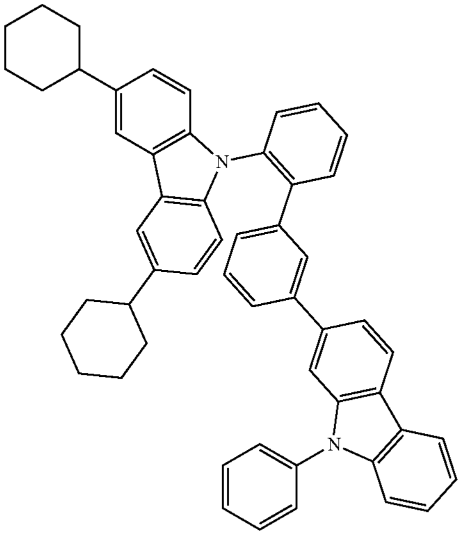
N7
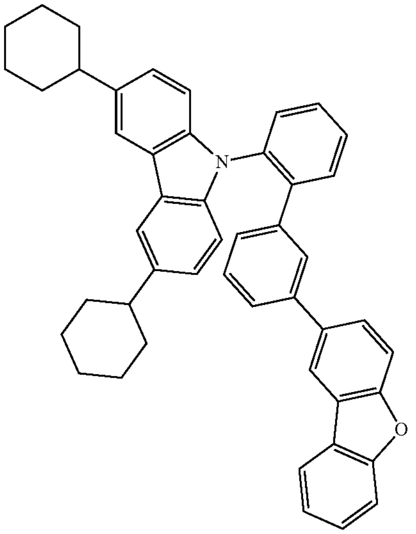

-continued
N8
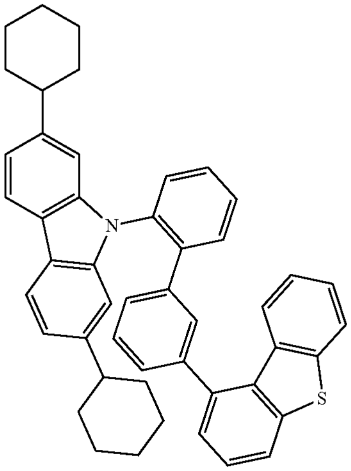
N9
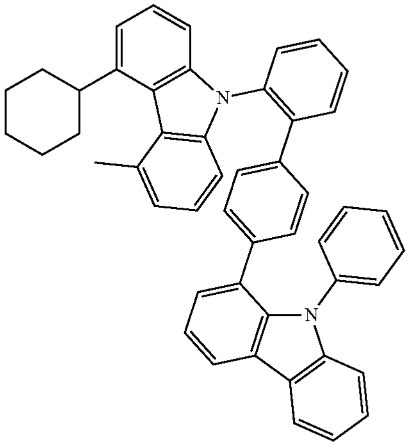
N10
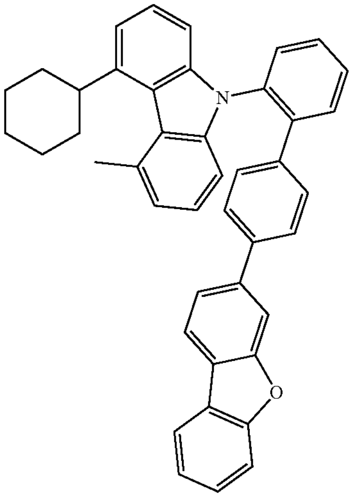
-continued
N11
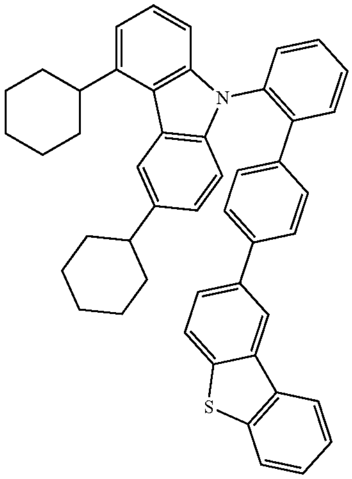
N12
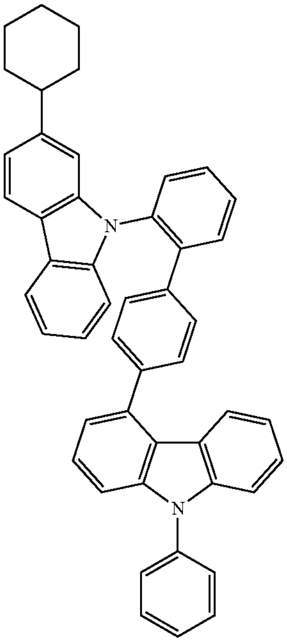
N13
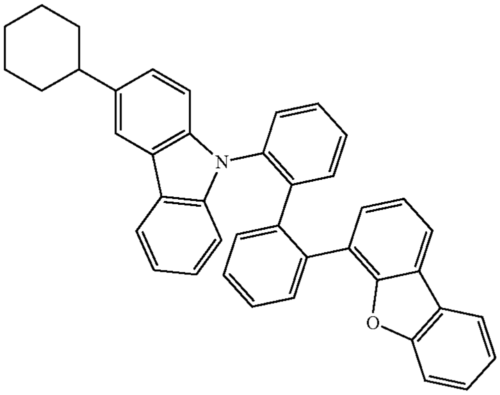

-continued
N14
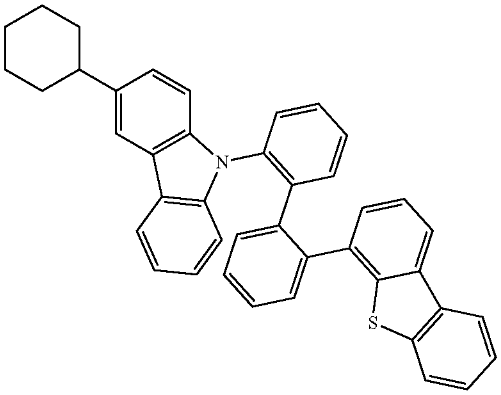
N15
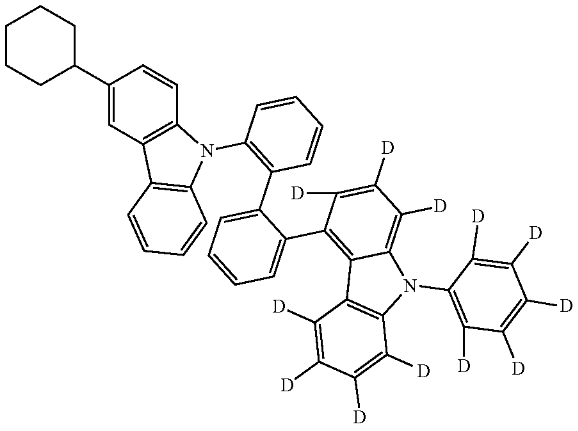
O1
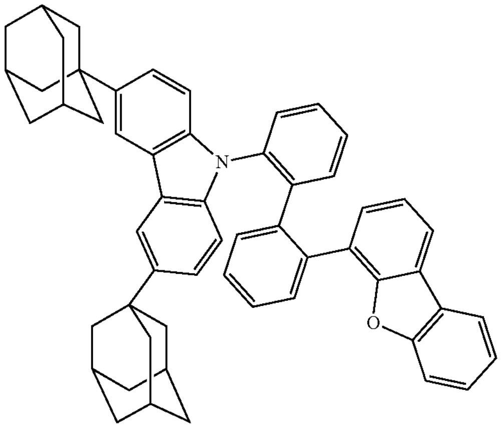
-continued
O2
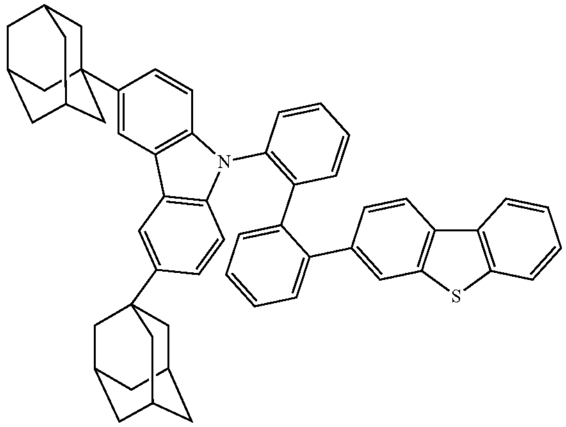
O3
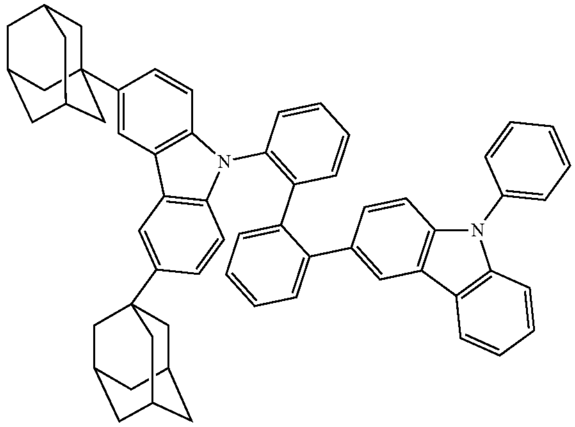
O4
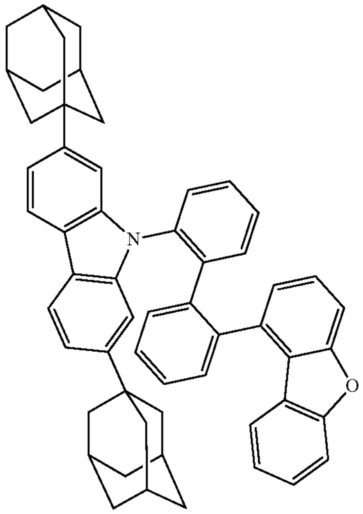

-continued
O5
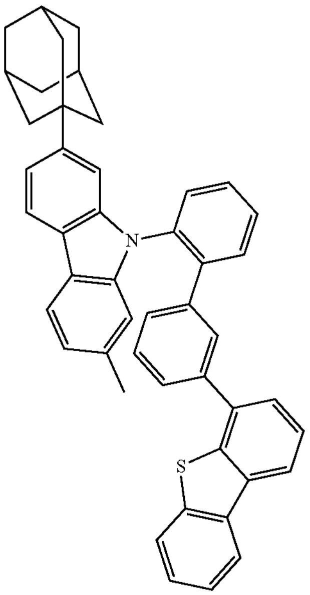
O6
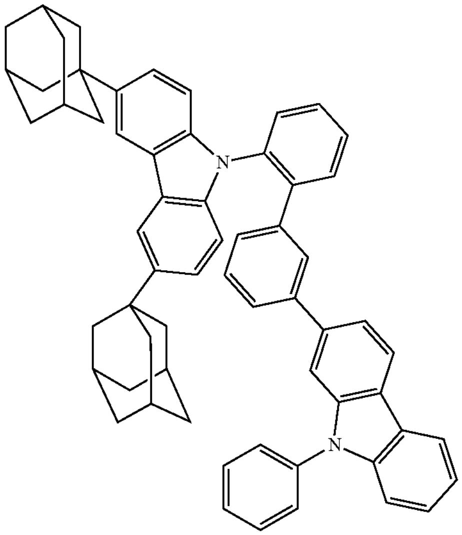
O7
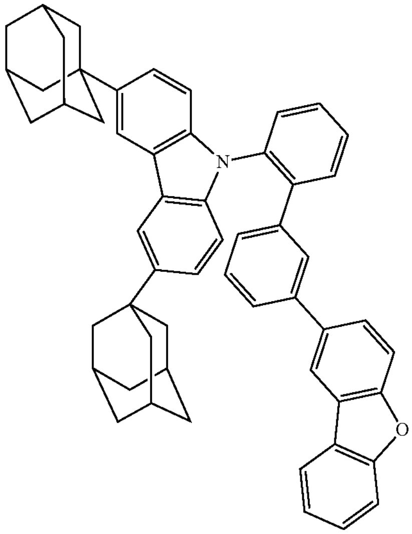
-continued
O8
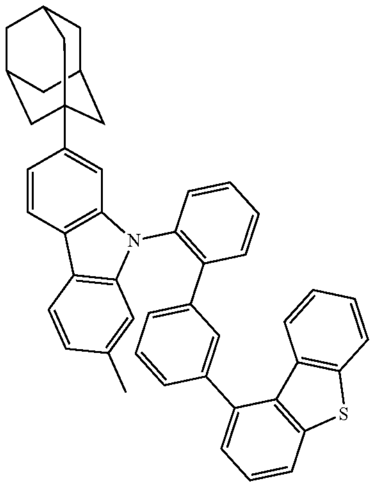
O9
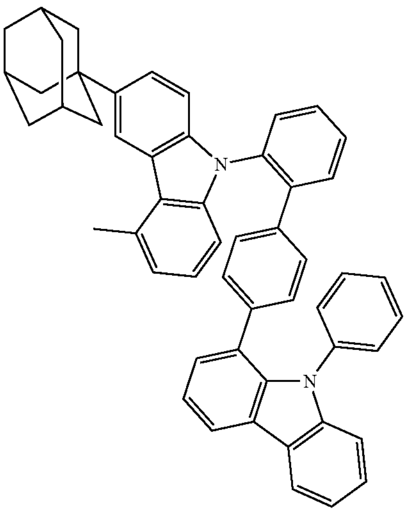
O10
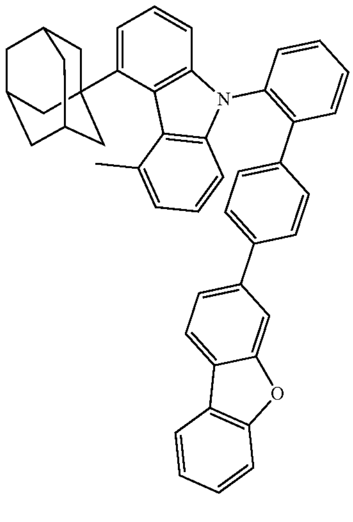

-continued
O11
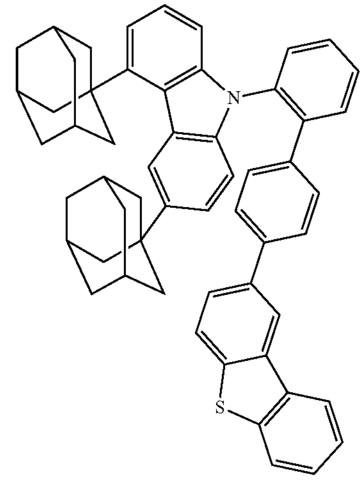
O12
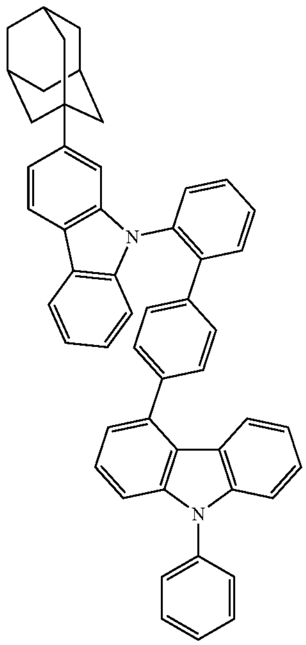
O13
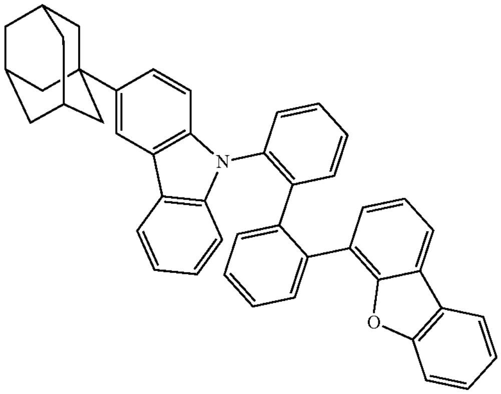
-continued
O14
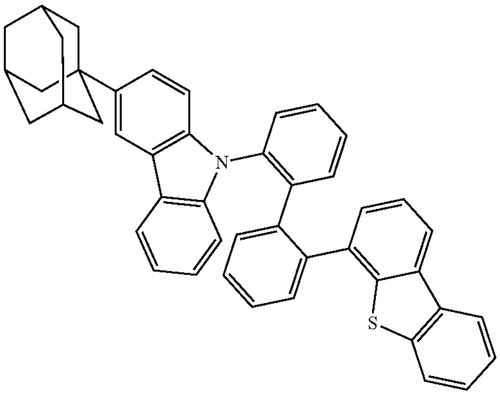
O15
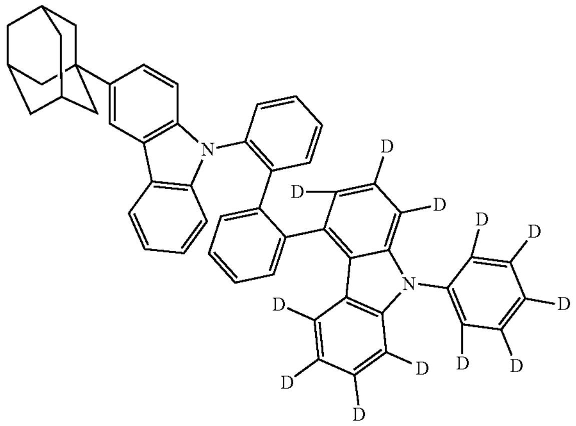
P1
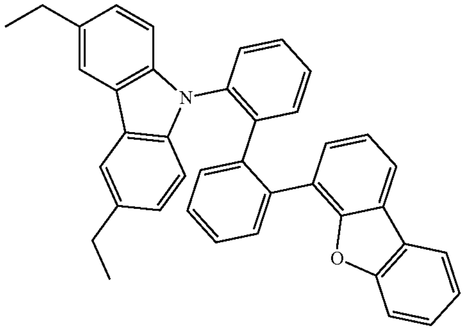
P2
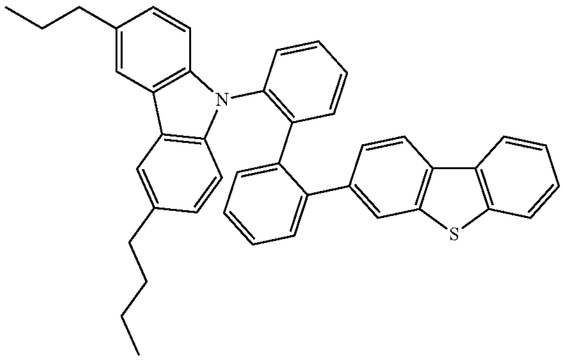

-continued
P3
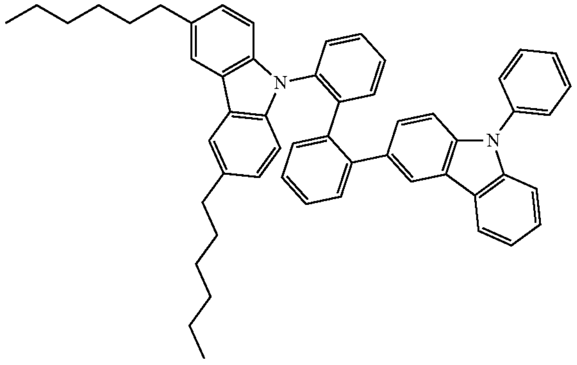
P4
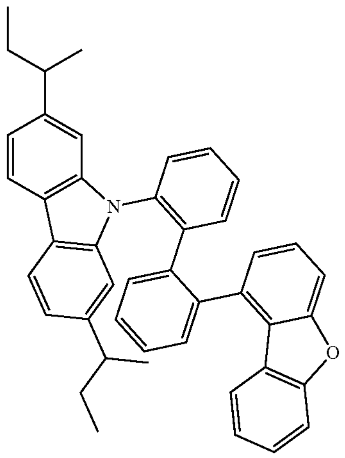
P5
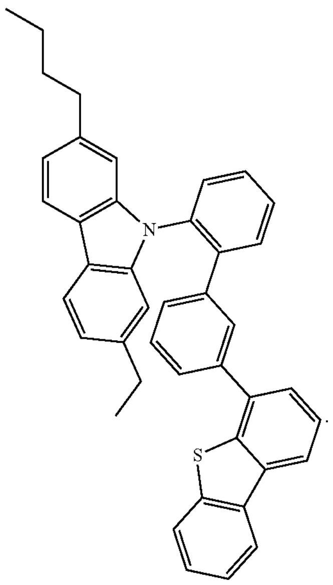
13. The luminescence device of claim 1, wherein the nitrogen-containing compound of the Formula 1 is at least one compound of Compound Group 3:
Compound Group 3
G1
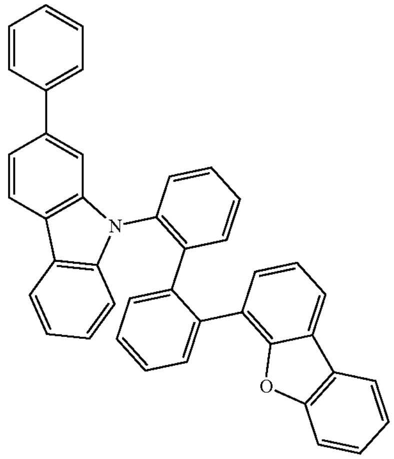
G2
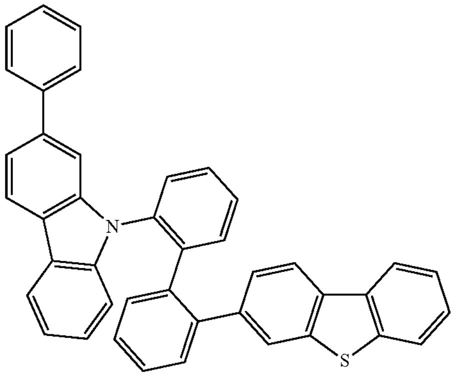
G3
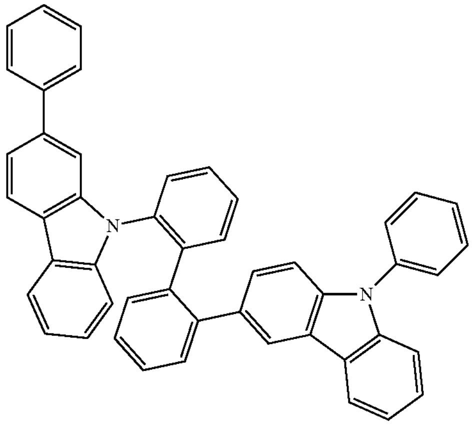

-continued
G4
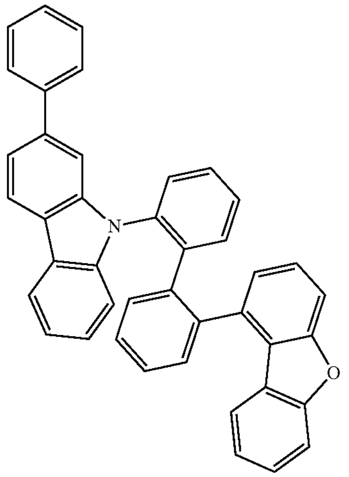
G5
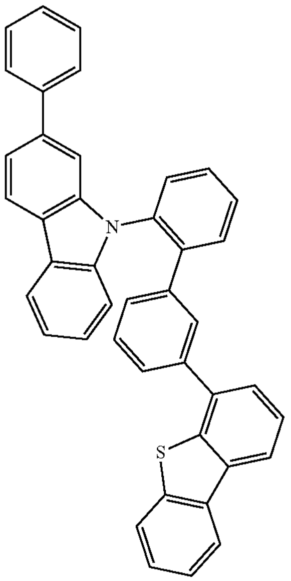
G6
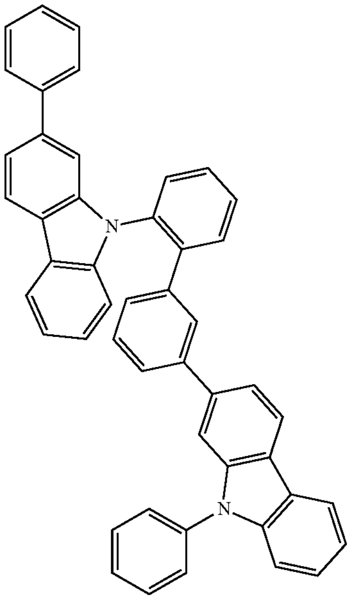
-continued
G7
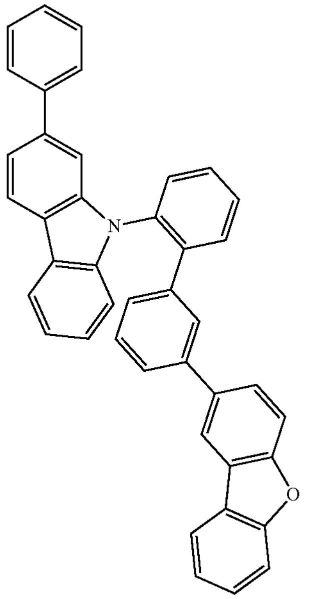
G8
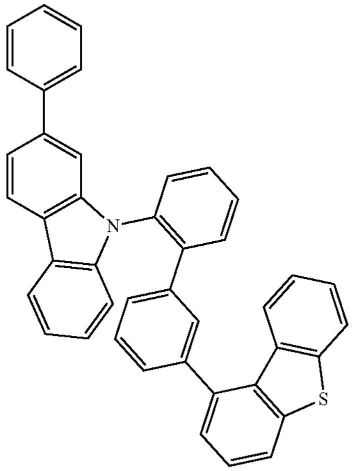
G9
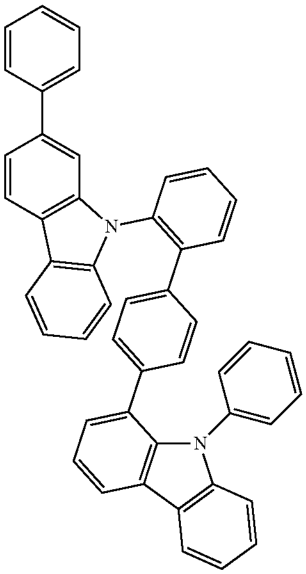

-continued
G10
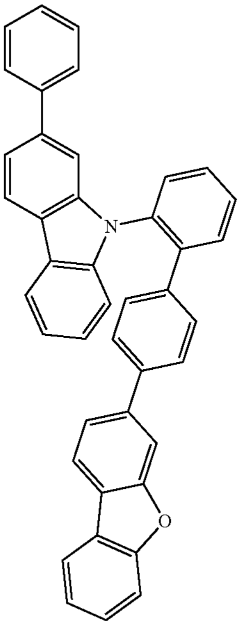
G11
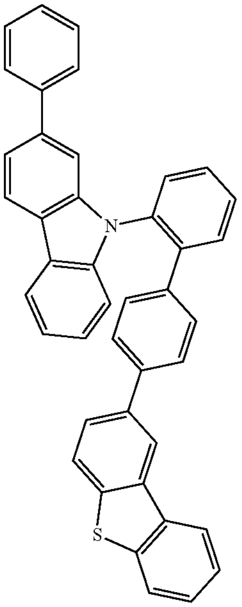
-continued
G12
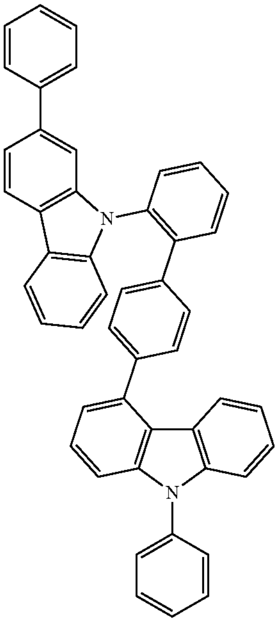
G13
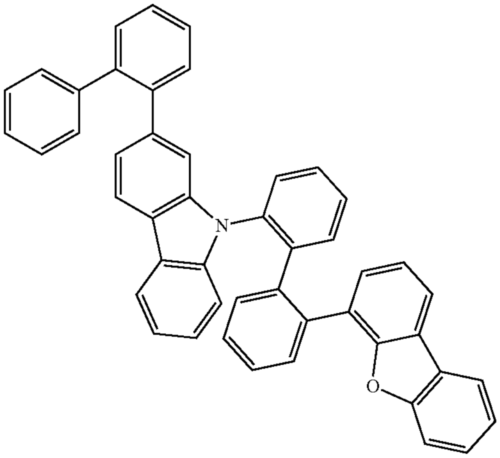
G14
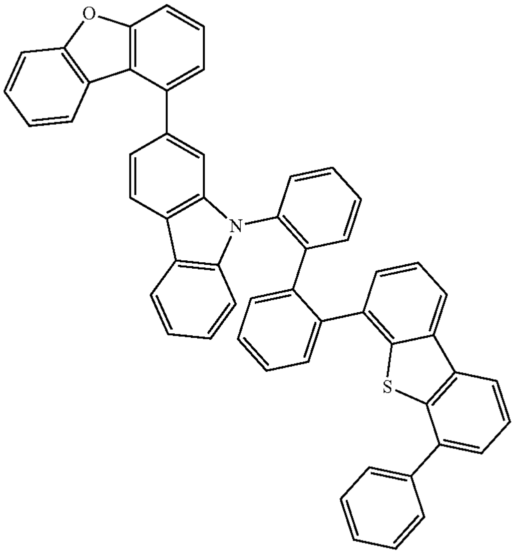

-continued
G15
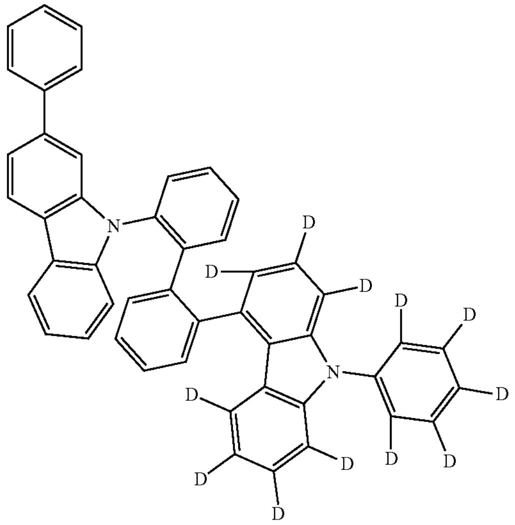
H1
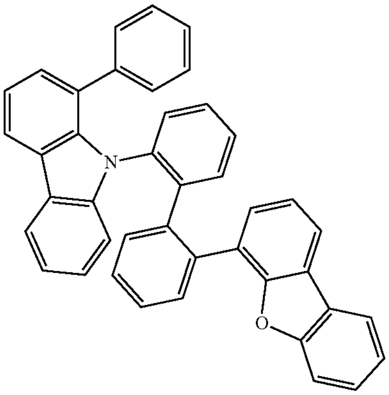
H2
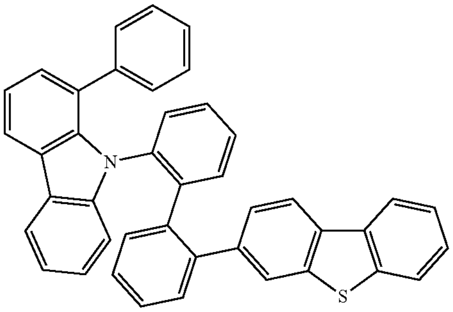
H3
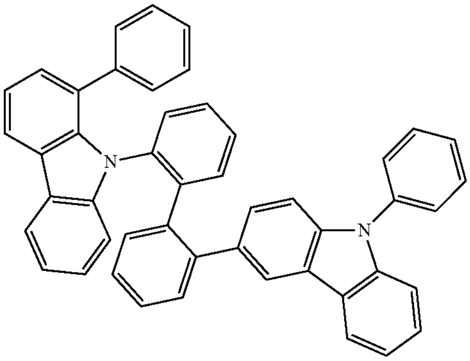
-continued
H4
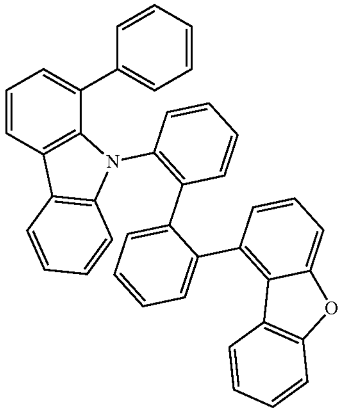
H5
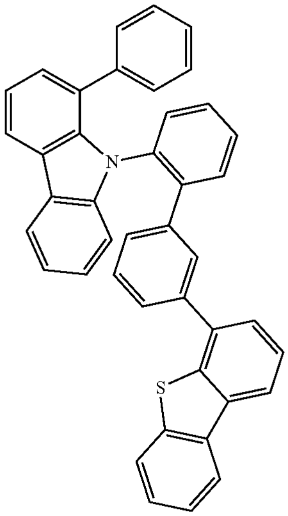
H6
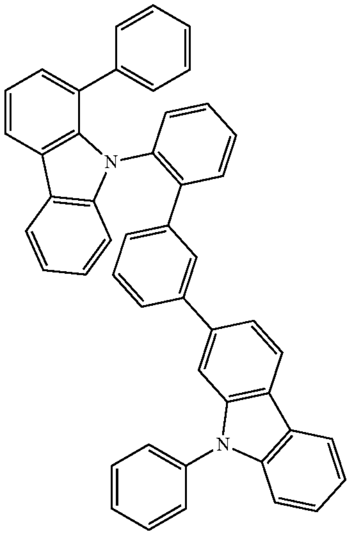

-continued
H7
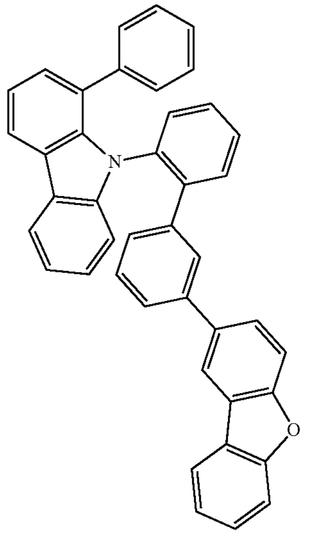
H8
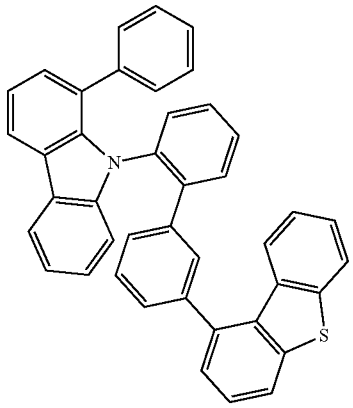
H9
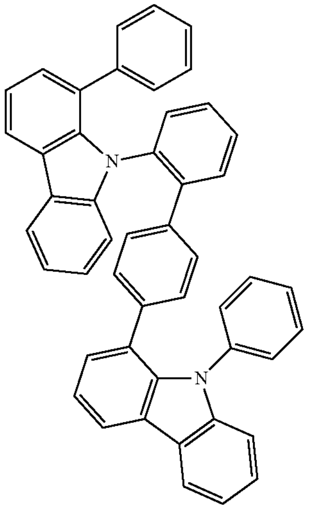
-continued
H10
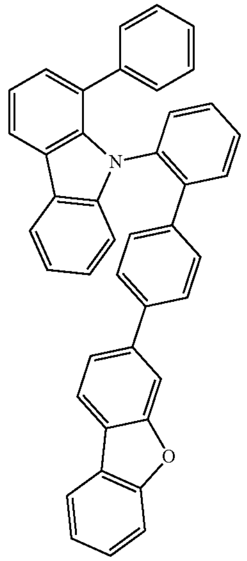
H11
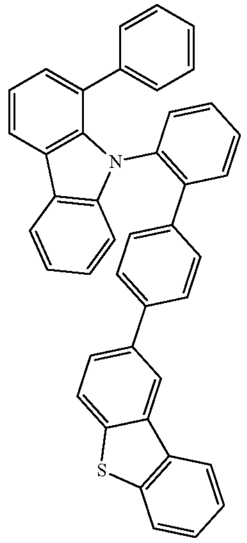

-continued
H12
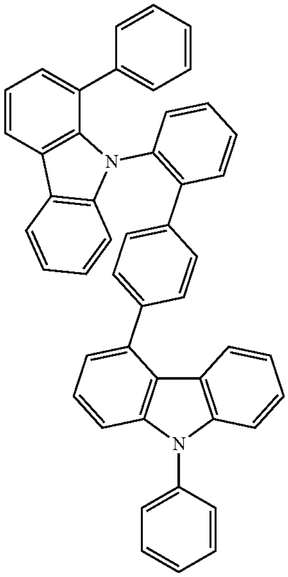
H13
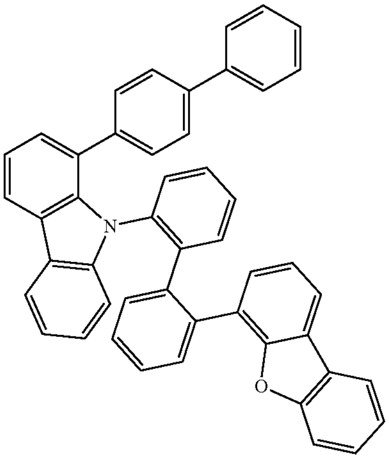
H14
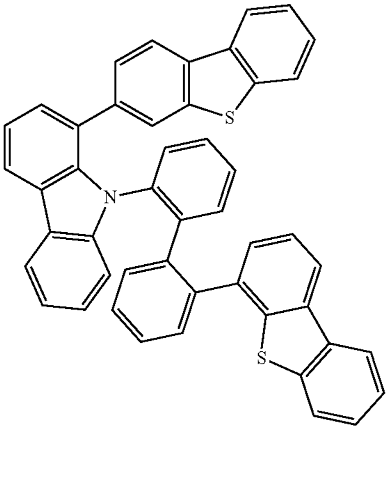
-continued
H15
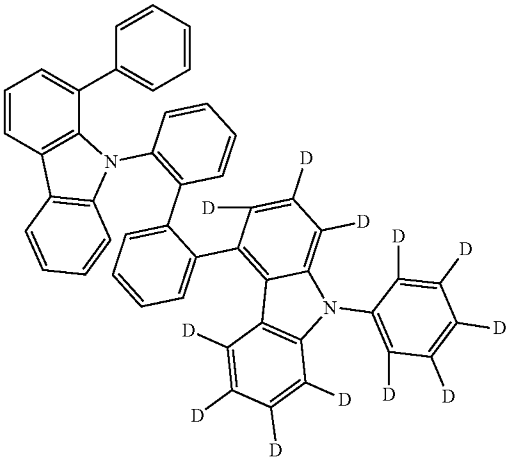
I1
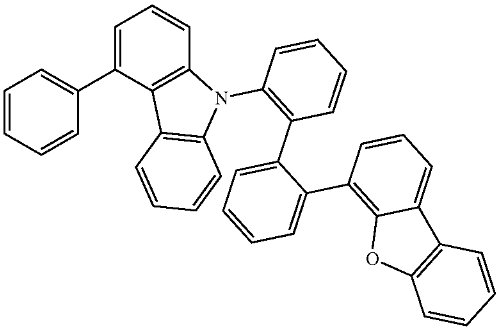
I2
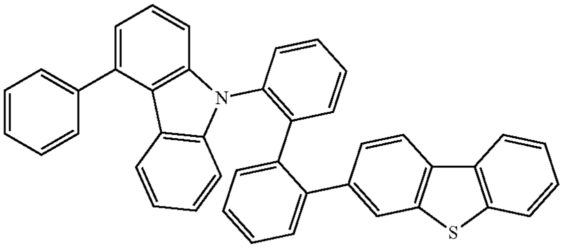
I3
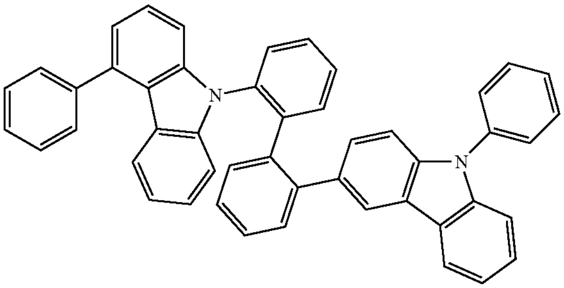

-continued
I4
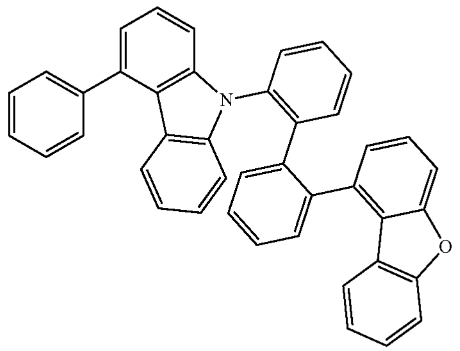
I5
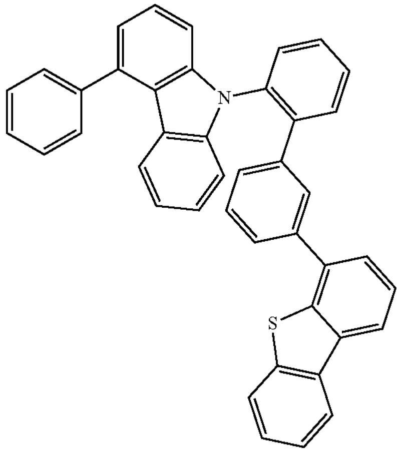
I6
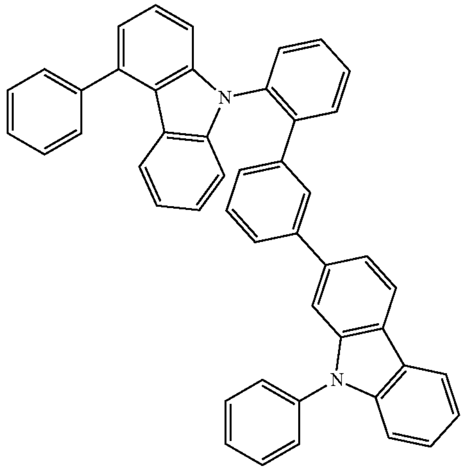
-continued
I7
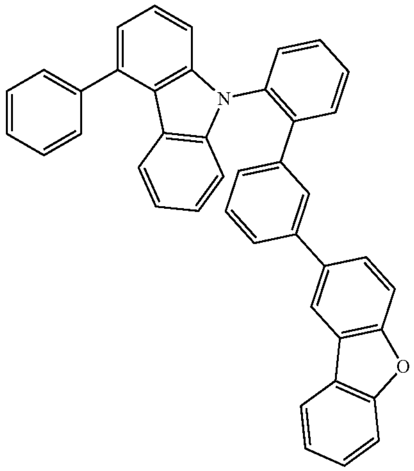
I8
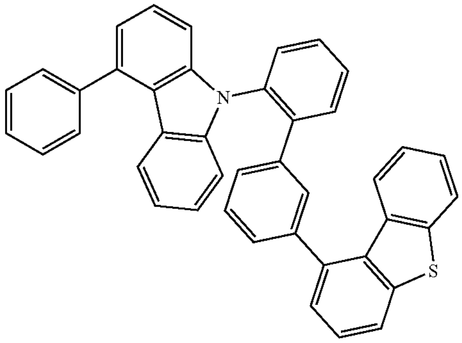
I9
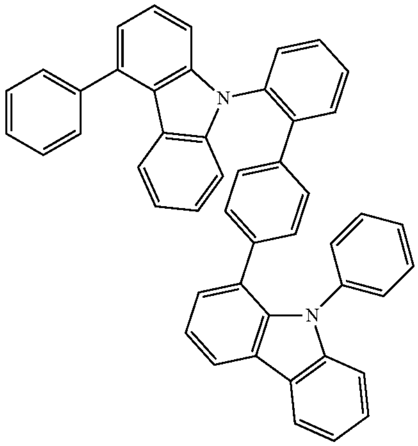

-continued
I10
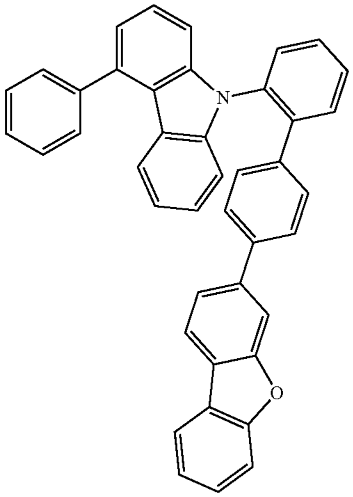
I11
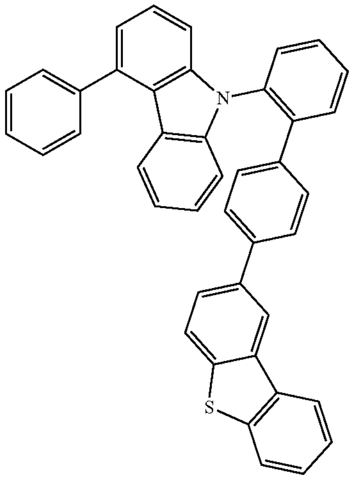
I12
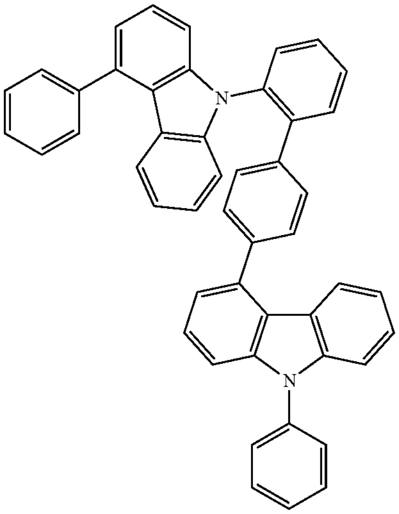
-continued
I13
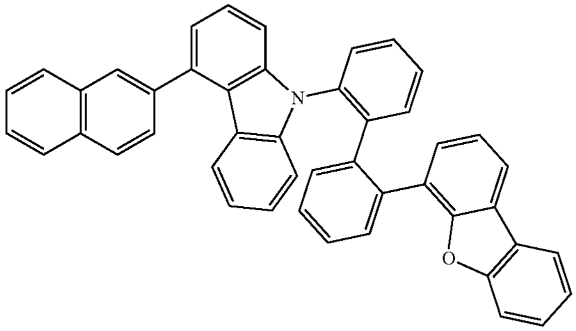
I14
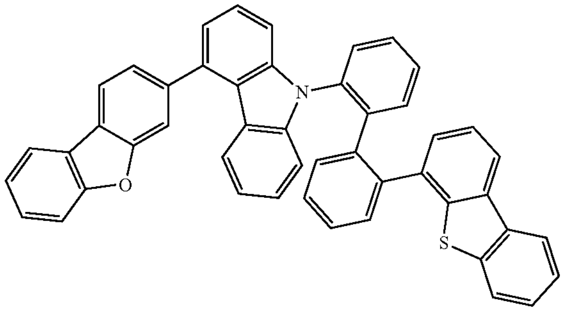
I15
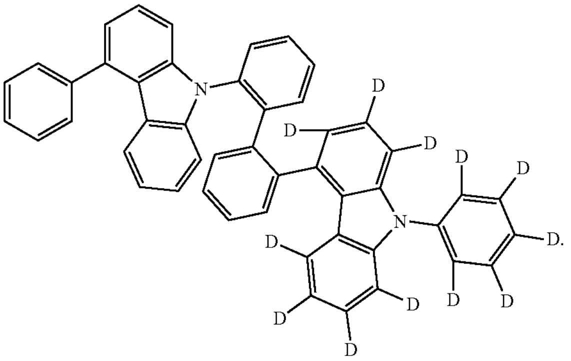
14. A nitrogen-containing compound represented by Formula 1:
Formula 1
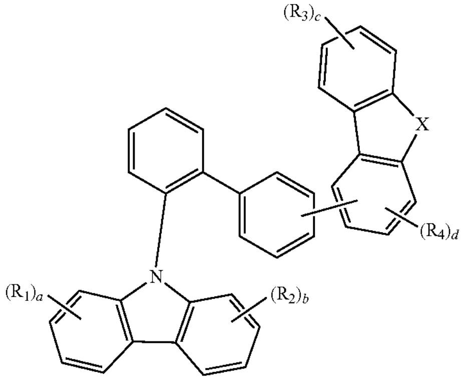

in Formula 1,

X is O, S, or $NR_5$, $R_1$ is a substituted or an unsubstituted oxy group, a substituted or an unsubstituted silyl group, a substituted or an unsubstituted thiol group, a substituted or an unsubstituted alkyl group of 1 to 20 carbon atoms, a substituted or an unsubstituted alkenyl group of 2 to 20 carbon atoms, a substituted or an unsubstituted alkynyl group of 2 to 20 carbon atoms, an unsubstituted aryl group of 6 to 30 ring-forming carbon atoms, a substituted or an unsubstituted dibenzofuran group, a substituted or an unsubstituted dibenzothiophene group, or a substituted or an unsubstituted carbazole group, $R_2$ to $R_5$ are each, independently from one another, a substituted or an unsubstituted oxy group, a substituted or an unsubstituted silyl group, a substituted or an unsubstituted thiol group, a substituted or an unsubstituted alkyl group of 1 to 20 carbon atoms, a substituted or an unsubstituted alkenyl group of 2 to 20 carbon atoms, a substituted or an unsubstituted alkynyl group of 2 to 20 carbon atoms, a substituted or an unsubstituted aryl group of 6 to 30 ring-forming carbon atoms, or a substituted or an unsubstituted heteroaryl group of 2 to 30 ring-forming carbon atoms, a is an integer of 1 to 4, b and c are each, independently from one another, an integer of 0 to 4, d is an integer of 0 to 3, and hydrogen is optionally replaced with deuterium.

15. The nitrogen-containing compound of claim 14, wherein the Formula 1 is represented by Formula 2:

Formula 2

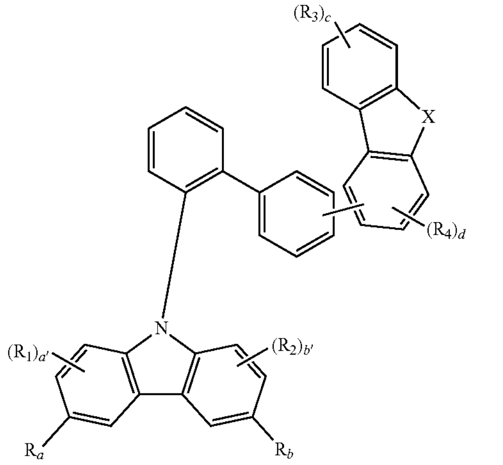

in Formula 2, a' and b' are each, independently from one another, an integer of 0 to 3, $R_a$ is a substituted or an unsubstituted oxy group, a substituted or an unsubstituted silyl group, a substituted or an unsubstituted thiol group, a substituted or an unsubstituted alkyl group of 1 to 20 carbon atoms, a substituted or an unsubstituted alkenyl group of 2 to 20 carbon atoms, a substituted or an unsubstituted alkynyl group of 2 to 20 carbon atoms, an unsubstituted aryl group of 6 to 30 ring-forming carbon atoms, a substituted or an unsubstituted dibenzofuran group, a substituted or an unsubstituted dibenzothiophene group, or a substituted or an unsubstituted carbazole group, $R_b$ is a hydrogen atom, a substituted or an unsubstituted oxy group, a substituted or an unsubstituted silyl group, a substituted or an unsubstituted thiol group, a substituted or an unsubstituted alkyl group of 1 to 20 carbon atoms, a substituted or an unsubstituted alkenyl group of 2 to carbon atoms, a substituted or an unsubstituted alkynyl group of 2 to 20 carbon atoms, a substituted or an unsubstituted aryl group of 6 to 30 ring-forming carbon atoms, or a substituted or an unsubstituted heteroaryl group of 2 to 30 ring-forming carbon atoms, and X, $R_1$ to $R_4$, c, and d have, independently from one another, the same meaning as defined in the Formula 1 in claim 14.

16. The nitrogen-containing compound of claim 15, wherein the Formula 2 is represented by any one of Formula 4 to Formula 6:

Formula 4

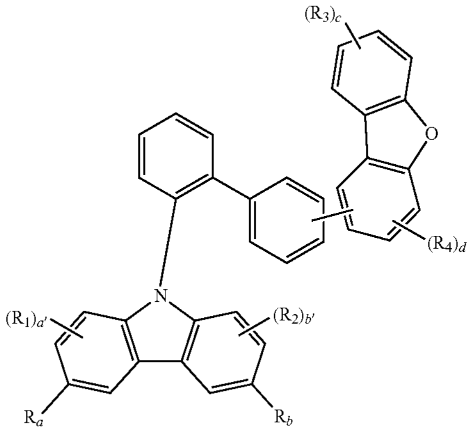

Formula 5

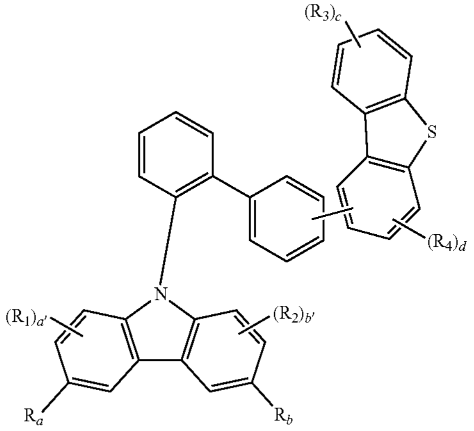

-continued

Formula 6

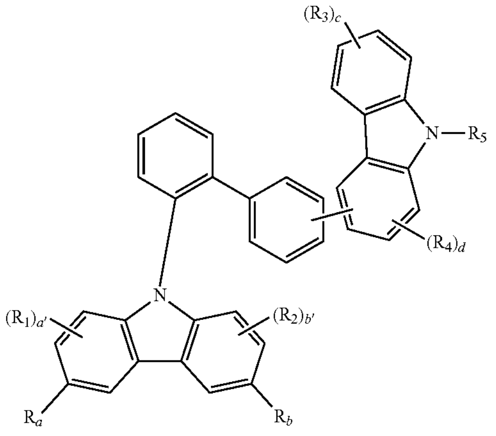

in Formula 4 to Formula 6, $R_5$ is a substituted or an unsubstituted alkyl group of 1 to 20 carbon atoms, a substituted or an unsubstituted aryl group of 6 to 30 ring-forming carbon atoms, or a substituted or an unsubstituted heteroaryl group of 2 to 30 ring-forming carbon atoms, and $R_1$ to $R_4$, $R_a$, $R_b$, c, d, a' and b' have, independently from one another, the same meaning as defined in the Formula 2 in claim 15.

17. The nitrogen-containing compound of claim 15, wherein the Formula 2 is represented by Formula 7-1 or Formula 7-2:

Formula 7-1

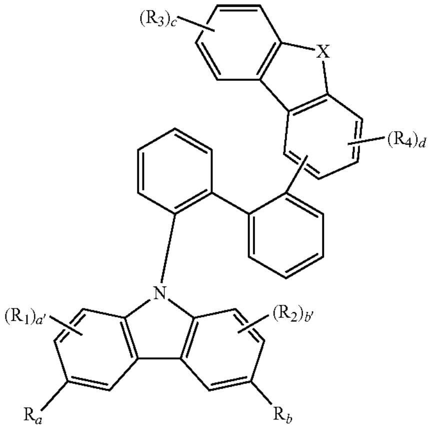

-continued

Formula 7-2

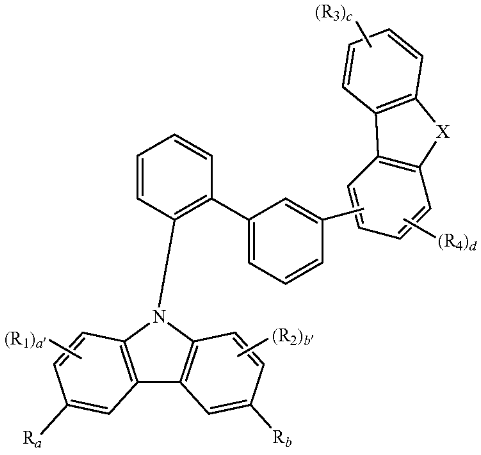

in Formula 7-1 and Formula 7-2,

X, $R_1$ to $R_4$, $R_a$, $R_b$, c, d, a' and b' have, independently from one another, the same meaning as defined in the Formula 2 in claim 15.

18. A nitrogen-containing compound is selected from the compounds in Compound Group 1, the compounds in Compound Group 2, and the compounds in Compound Group 3:

Compound Group 1

A1

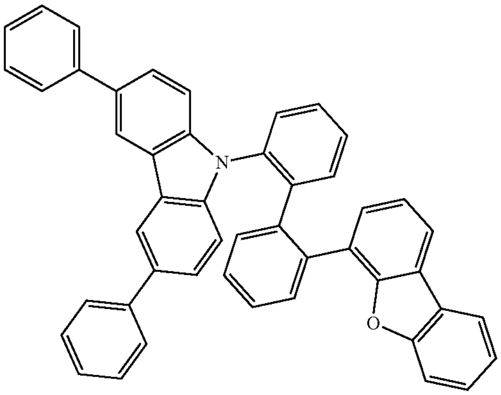

A2

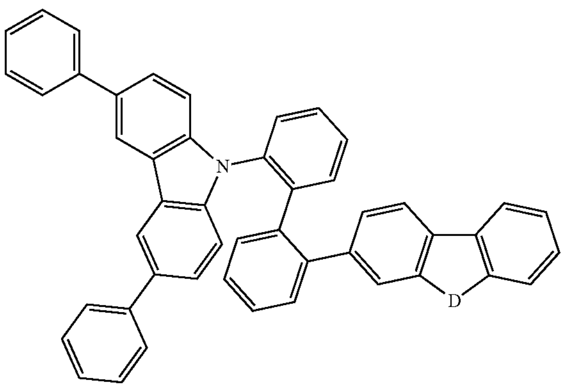

-continued
A3
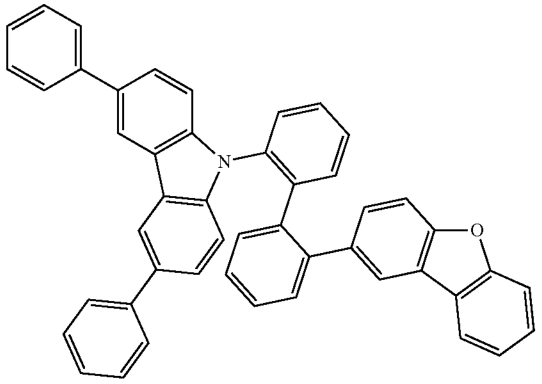
A4
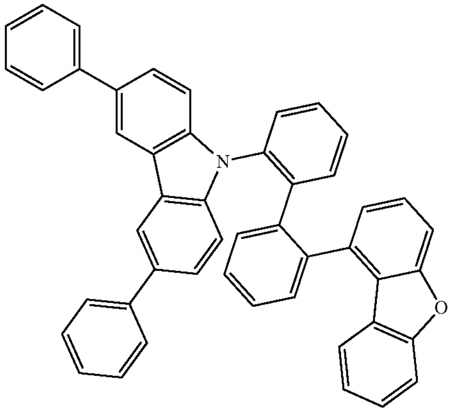
A5
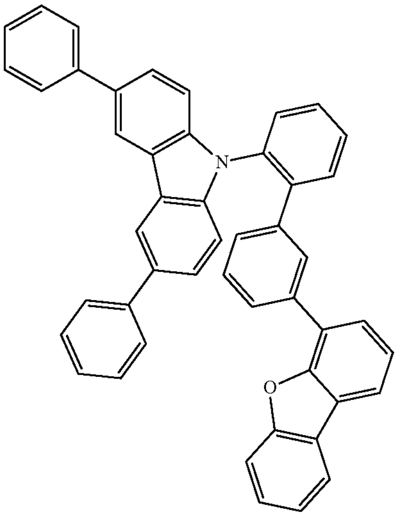
-continued
A6
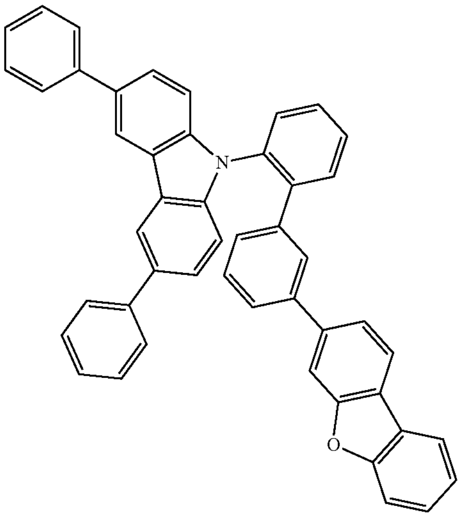
A7
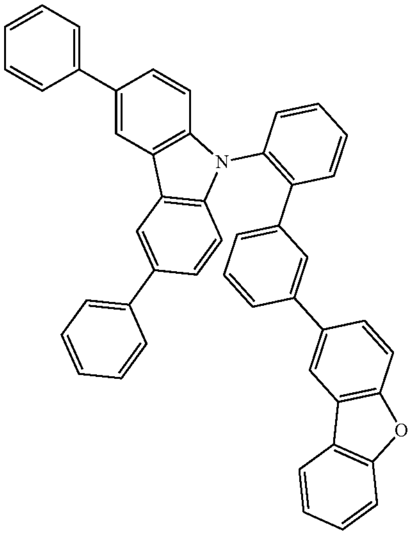
A8
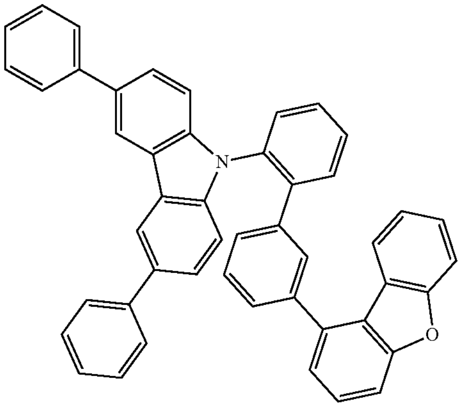

-continued
A9
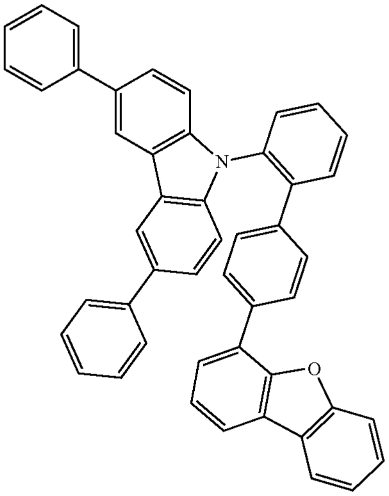
A10
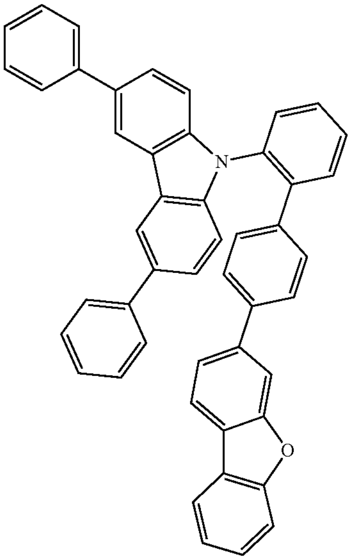
A11
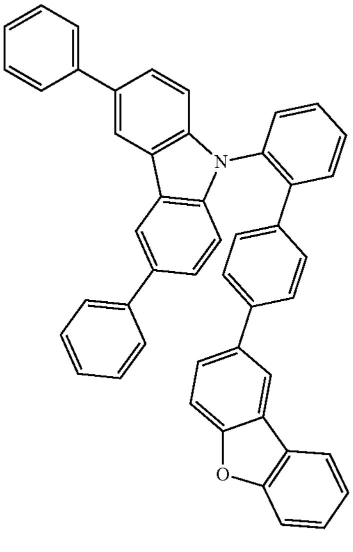
-continued
A12
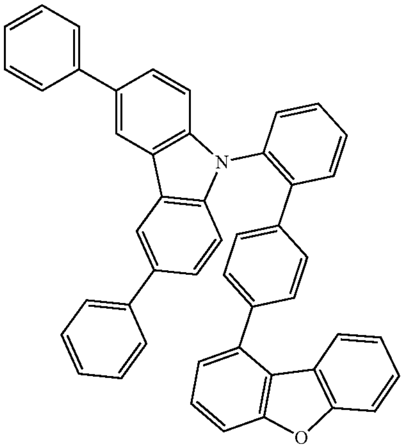
A13
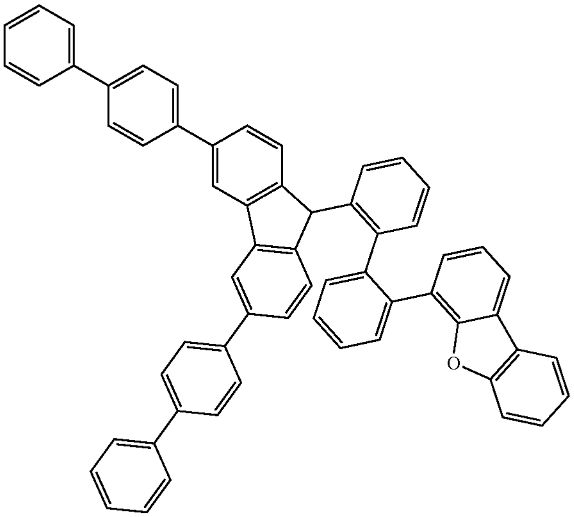
A14
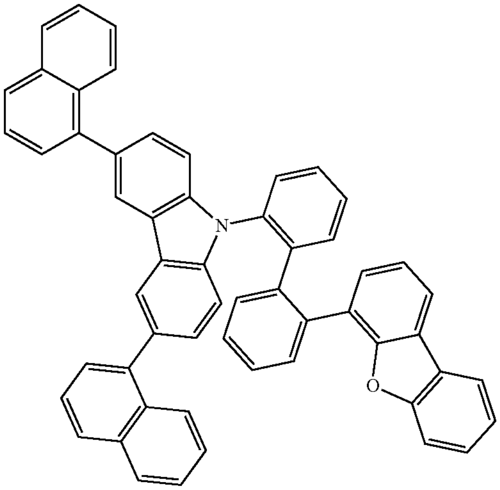

-continued
A15
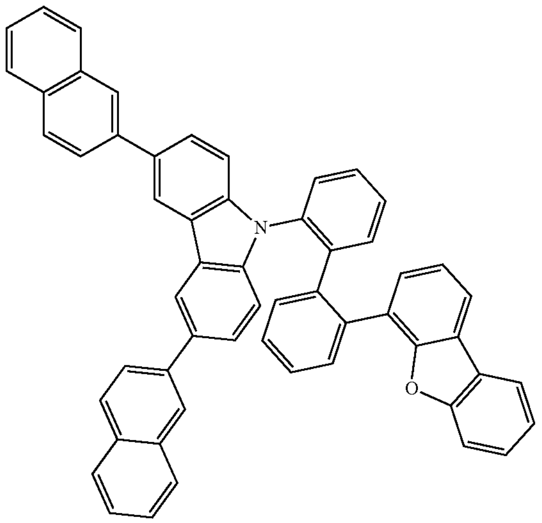
A16
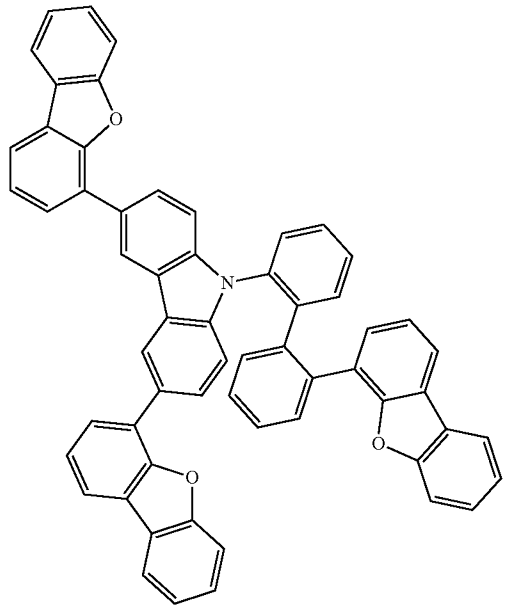
A17
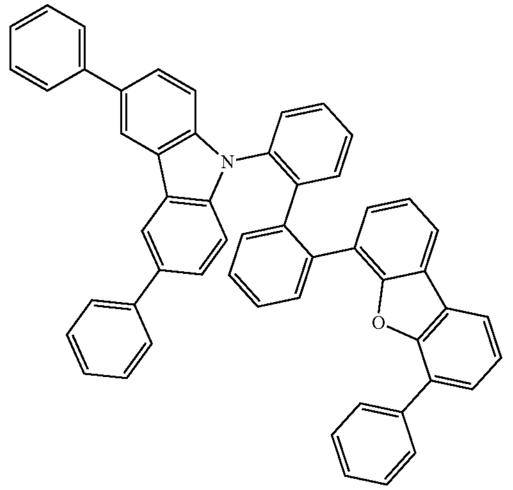
-continued
A18
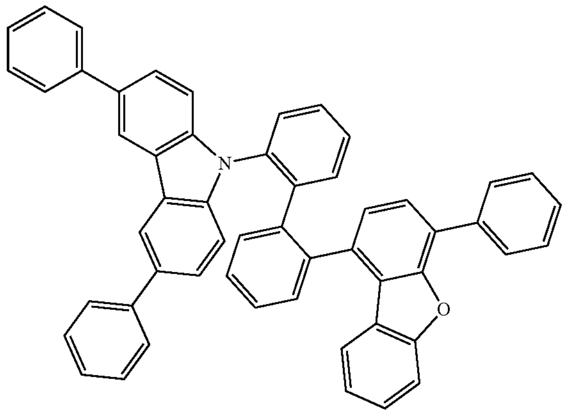
A19
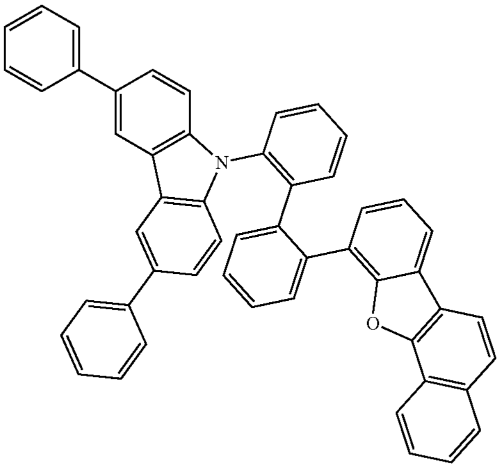
A20
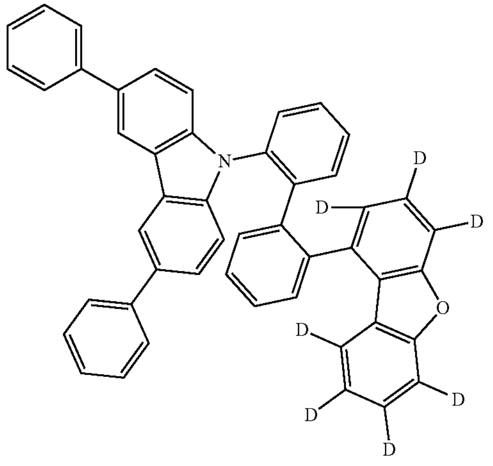

-continued
A21
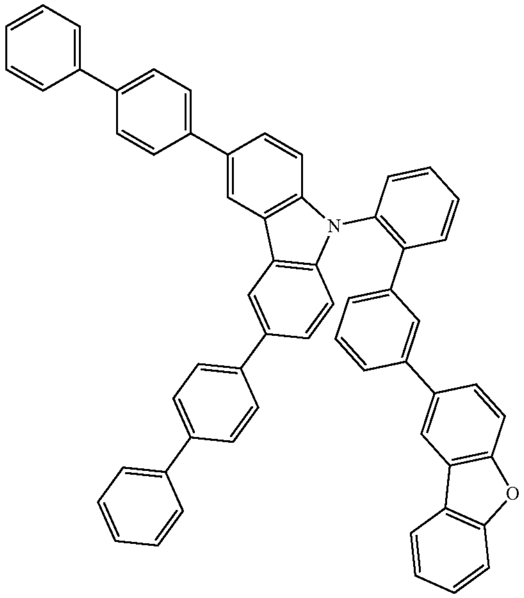
A22
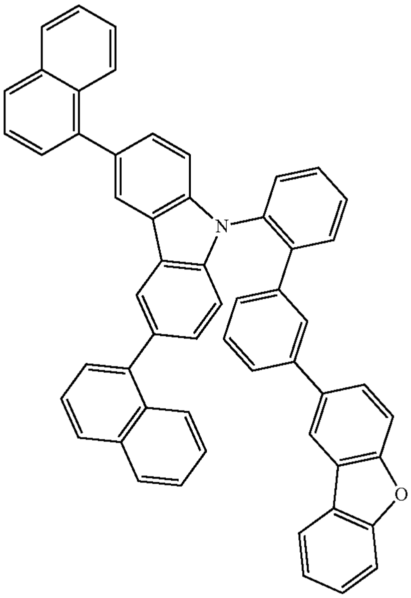
-continued
A23
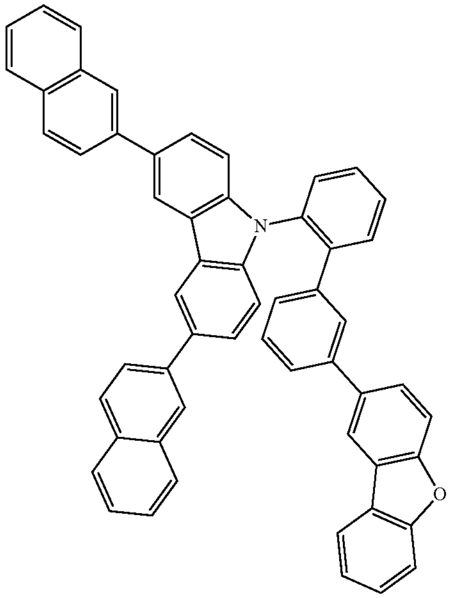
A24
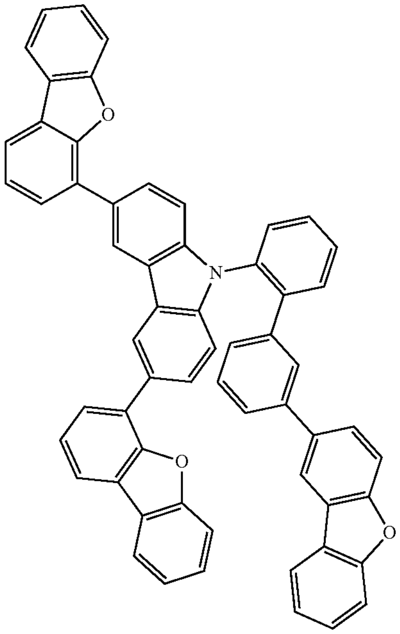

-continued
A25
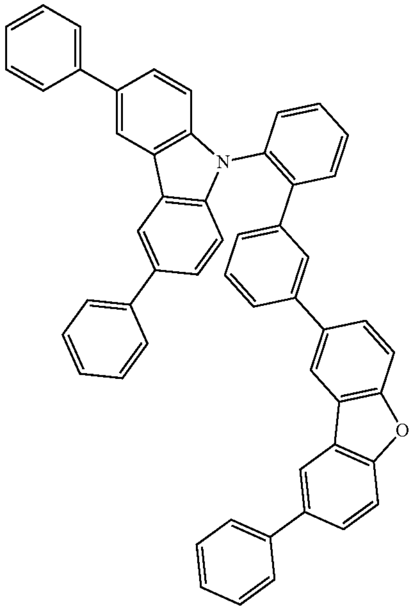
A26
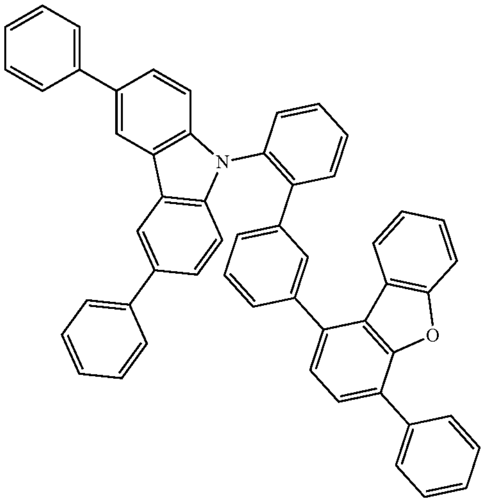
-continued
A27
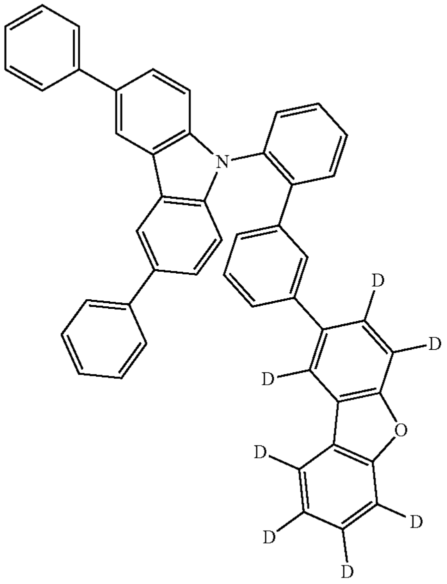
A28
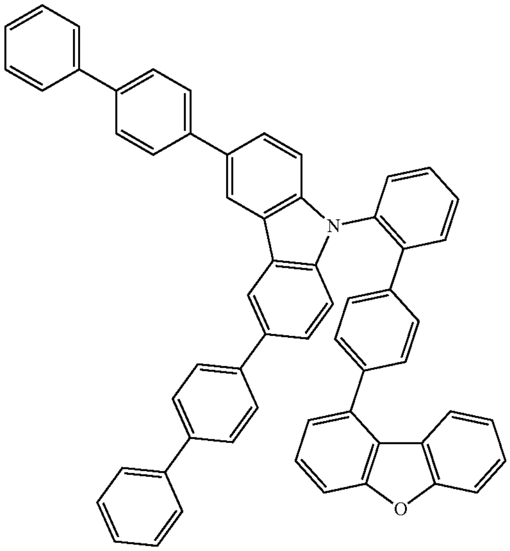

-continued
A29
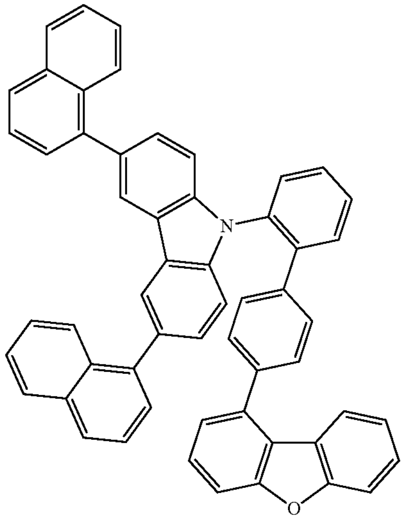
A30
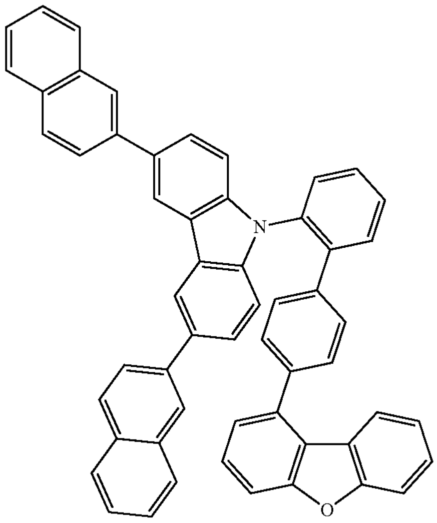
-continued
A31
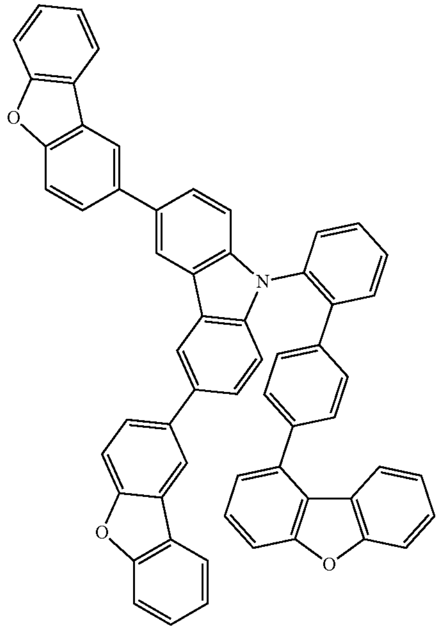
A32
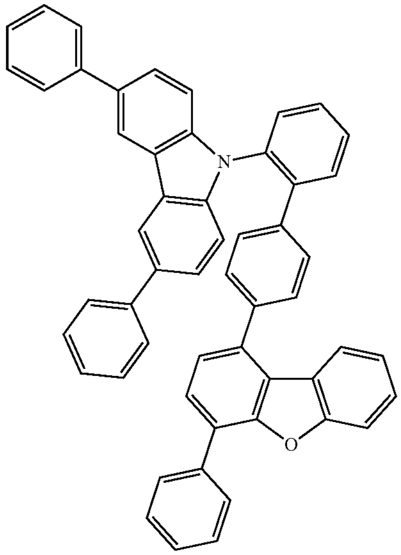
A33
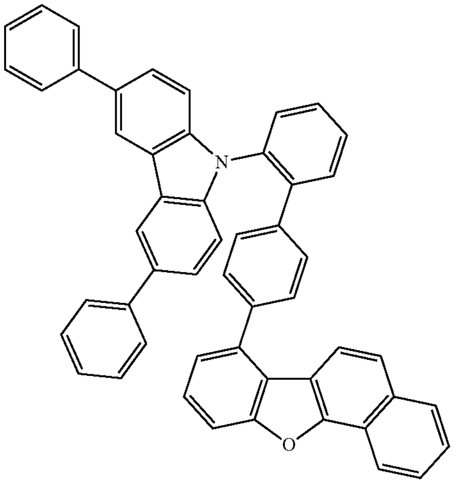

-continued
A34
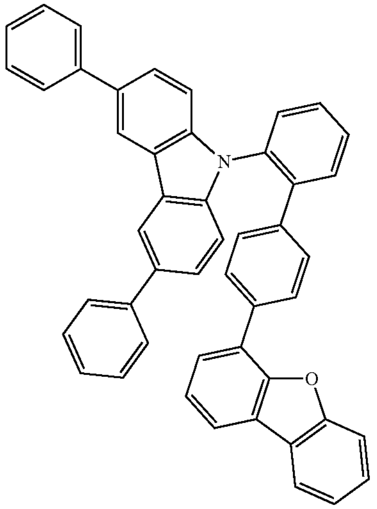
A35
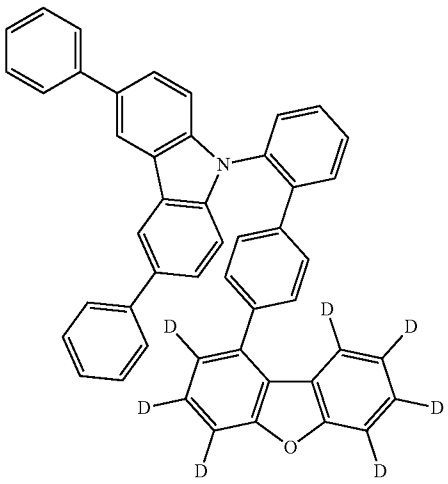
B1
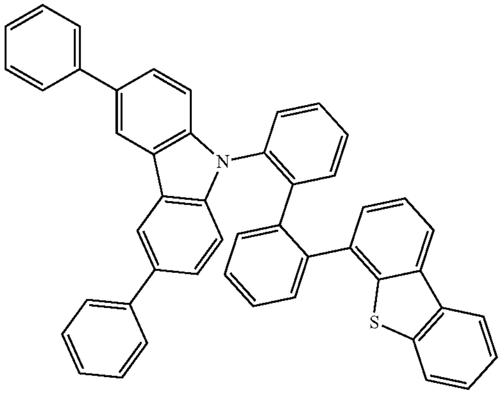
-continued
B2
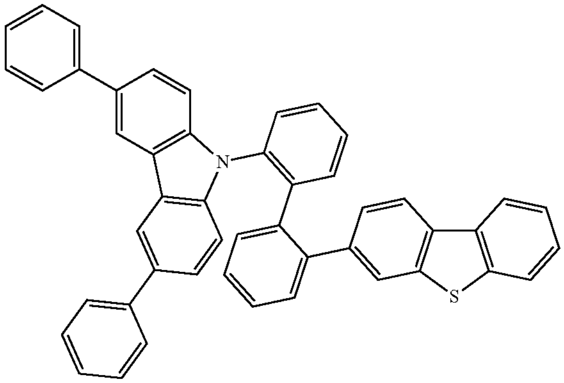
B3
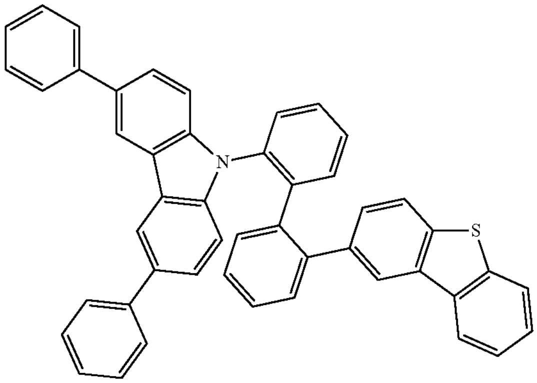
B4
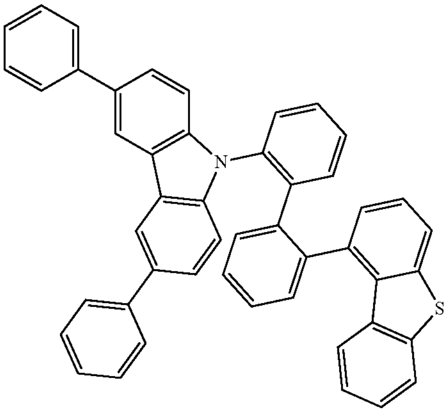

-continued
B5
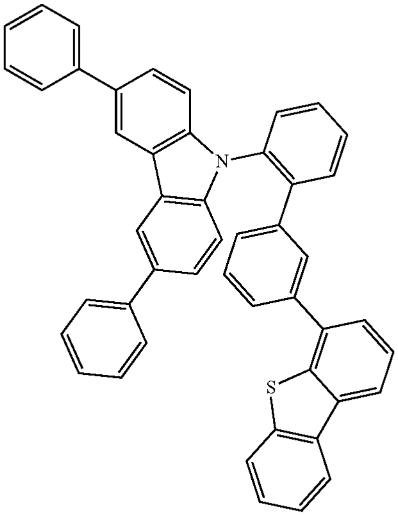
B6
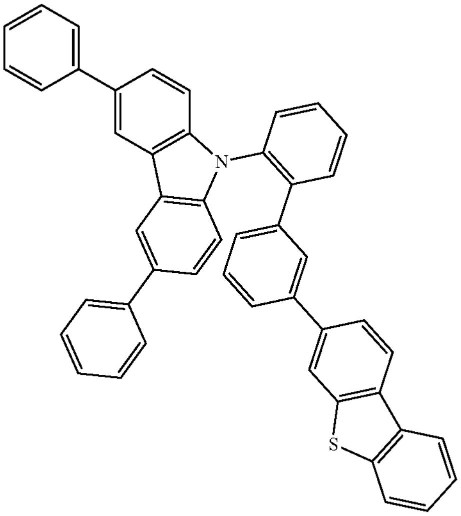
B7
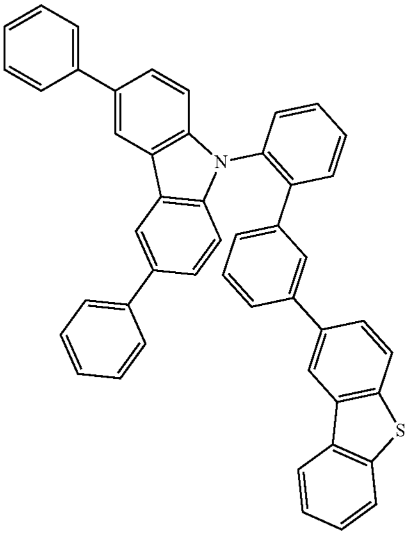
-continued
B8
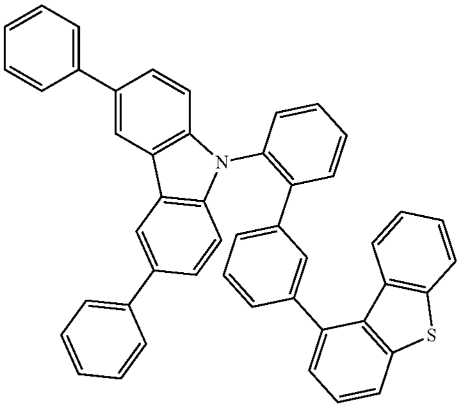
B9
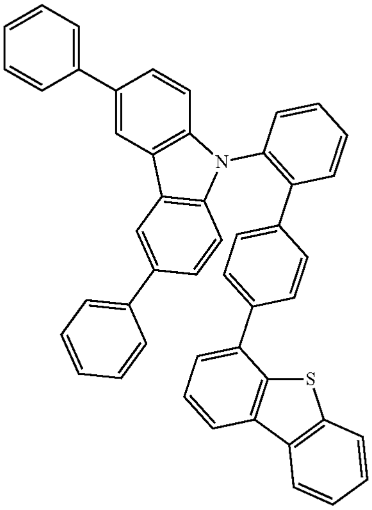
B10
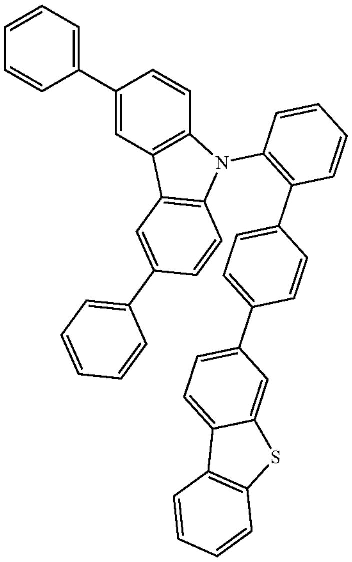

B11
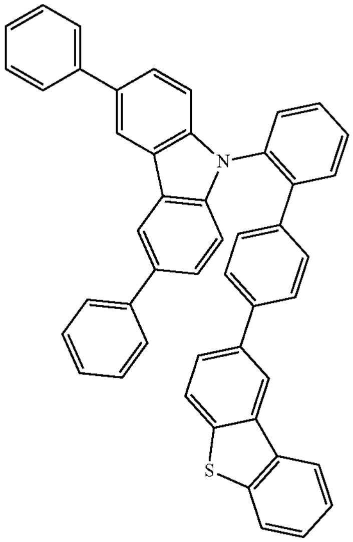
B12
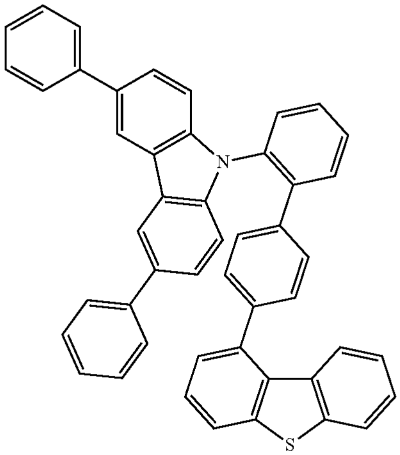
B13
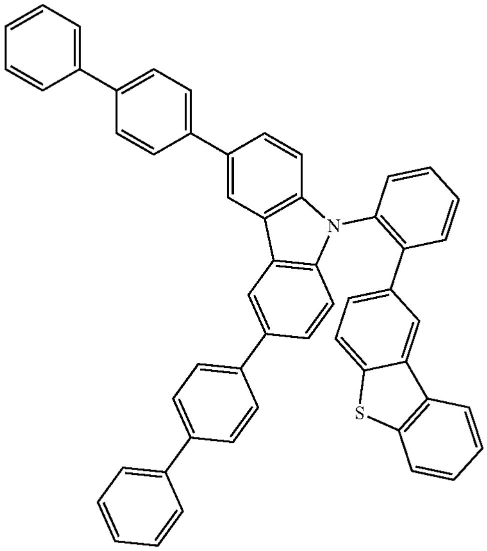
B14
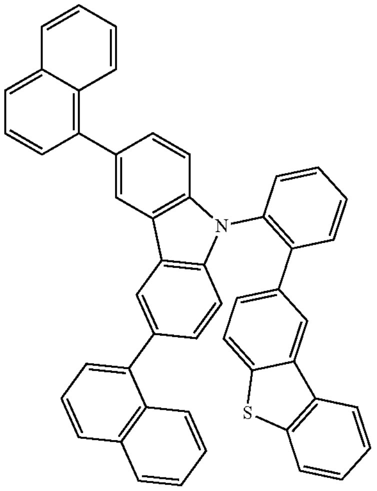
B15
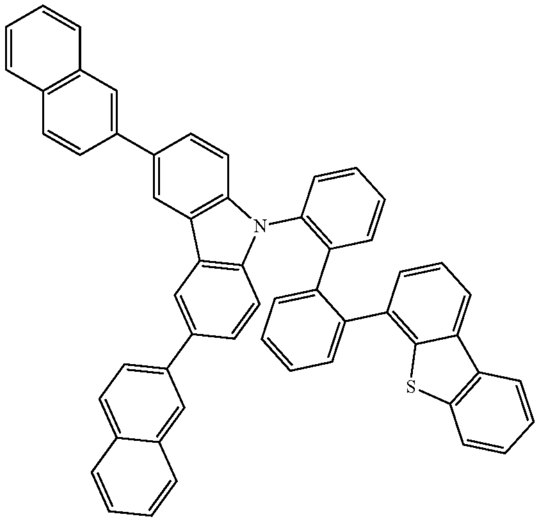
B16
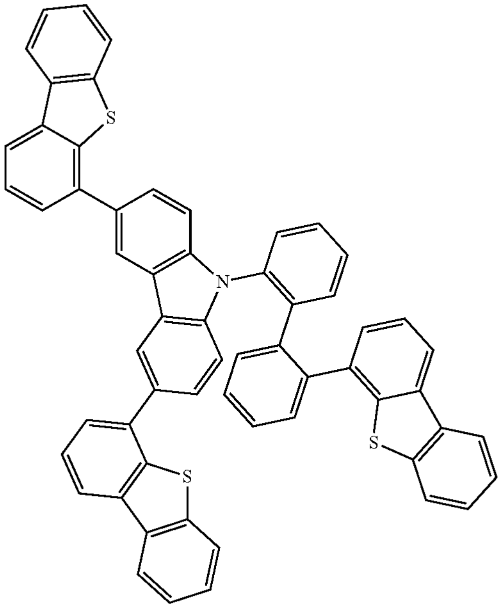

-continued
B17
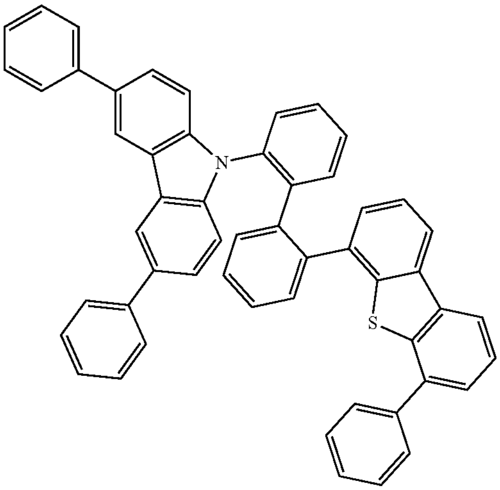
B18
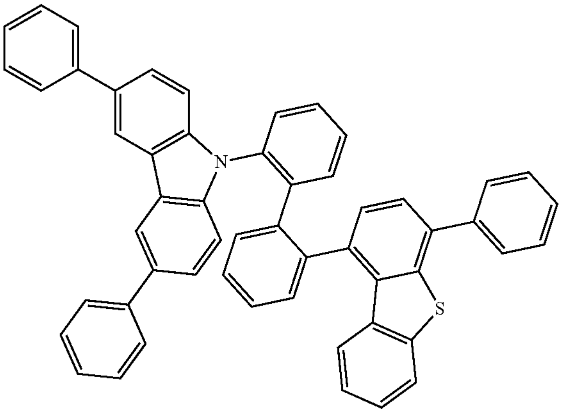
B19
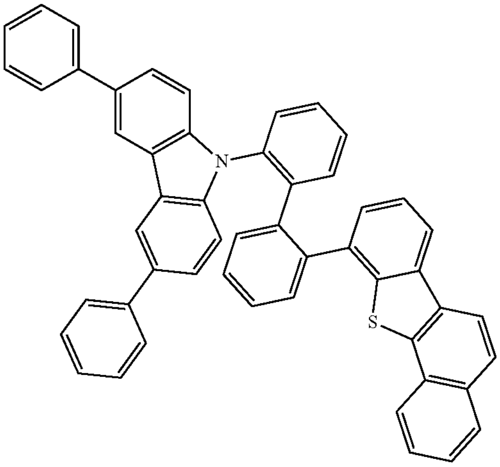
-continued
B20
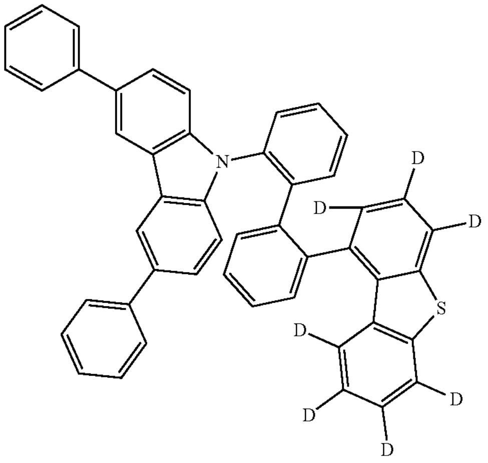
B21
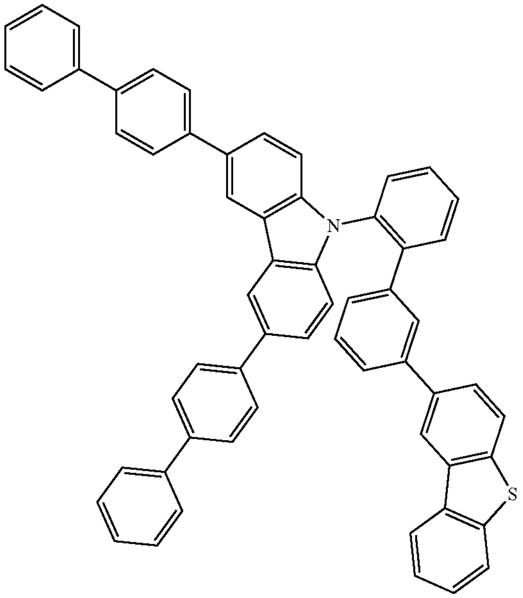

-continued
B22
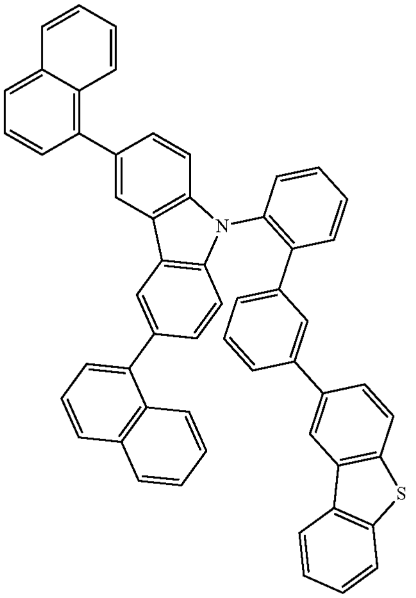
B23
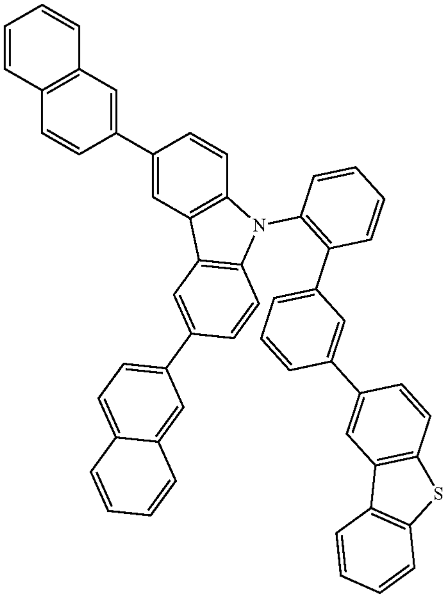
-continued
B24
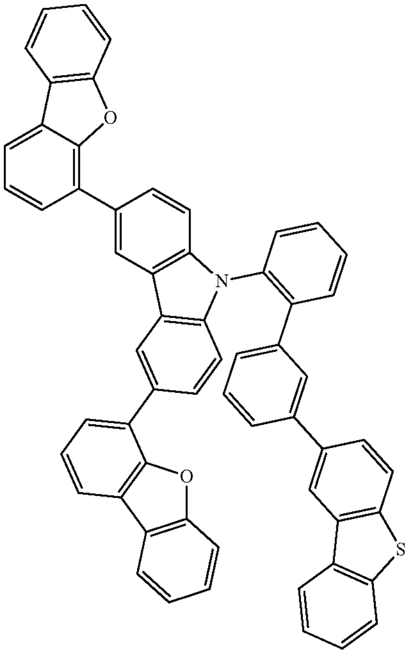
B25
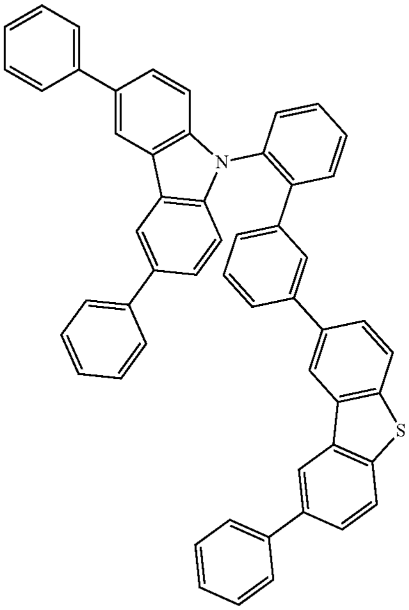

B26
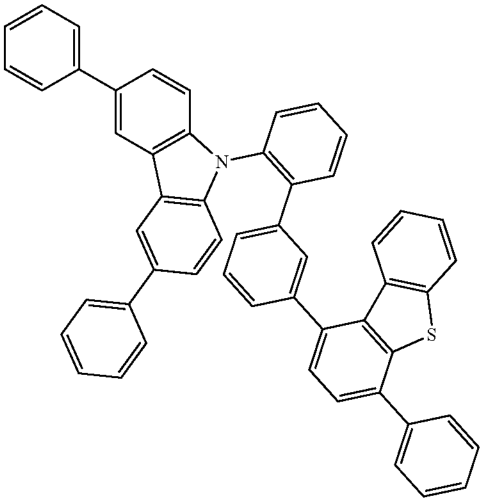
B27
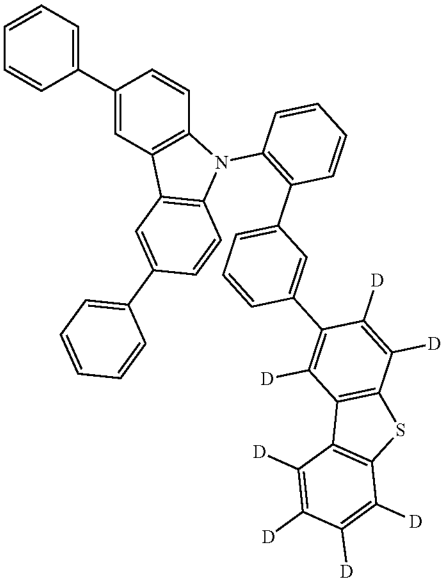
B28
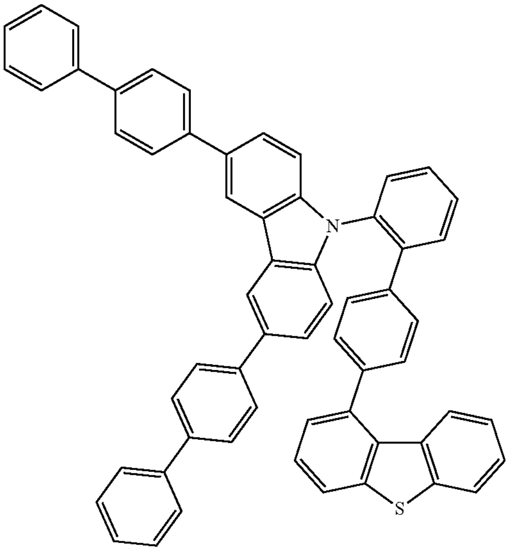
B29
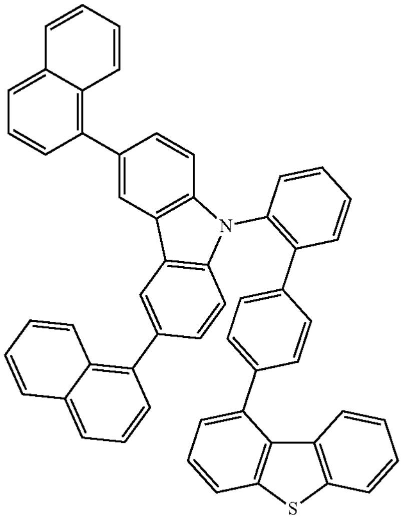
B30
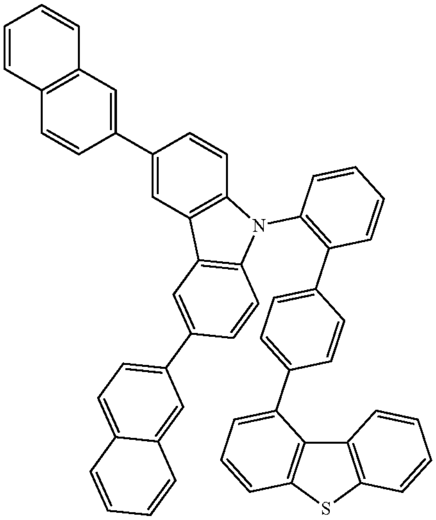

-continued
B31
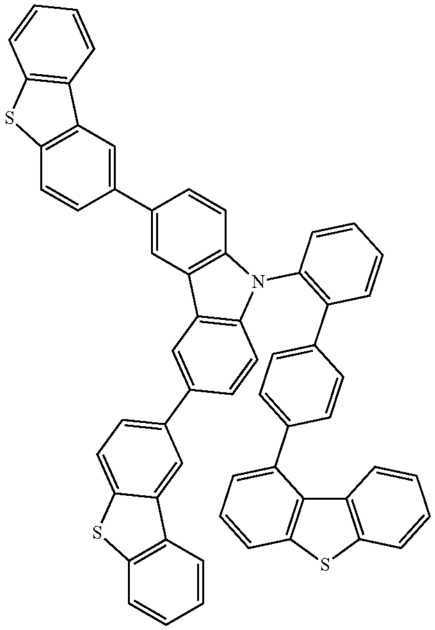
B32
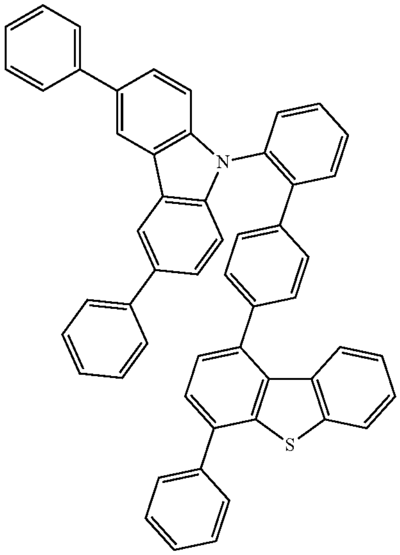
B33
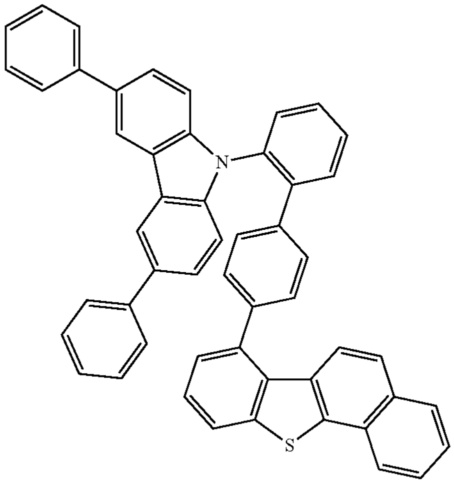
-continued
B34
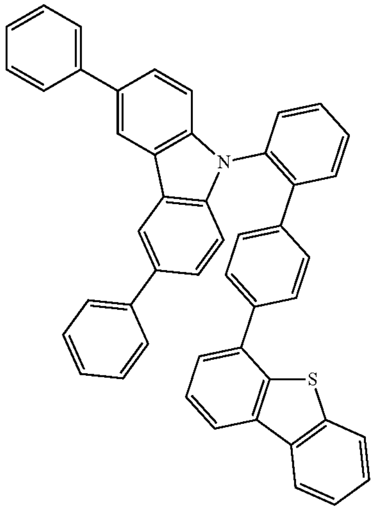
B35
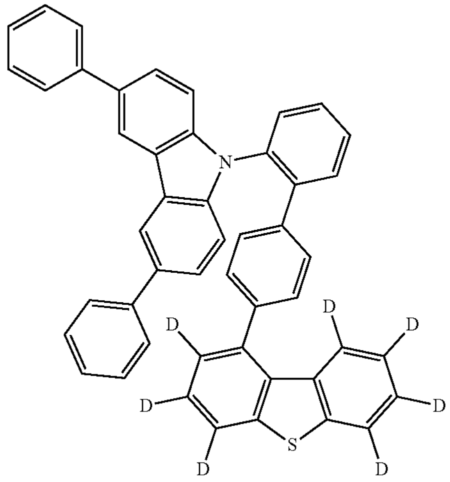
C1
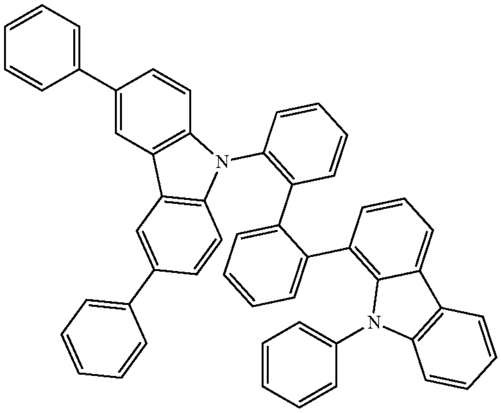

C2
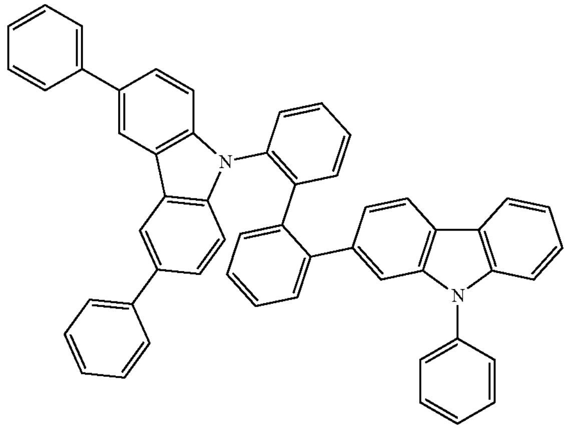
C3
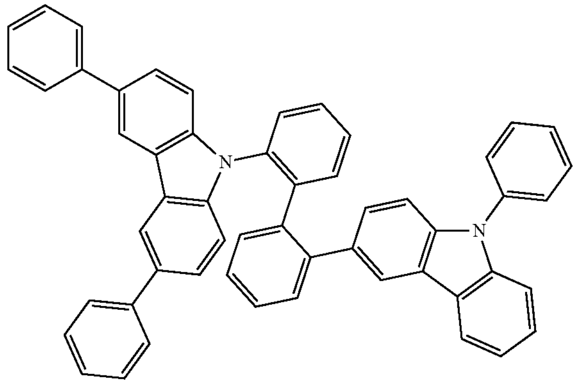
C4
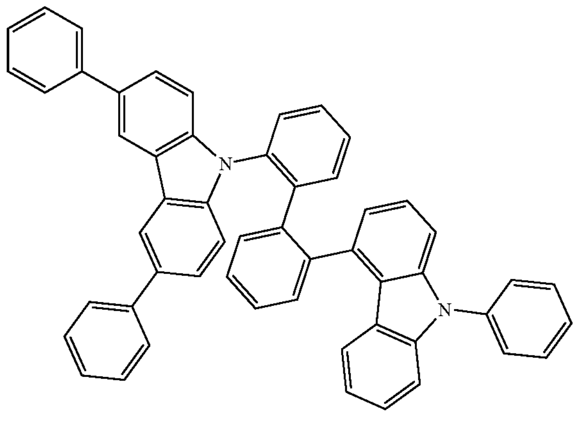
C5
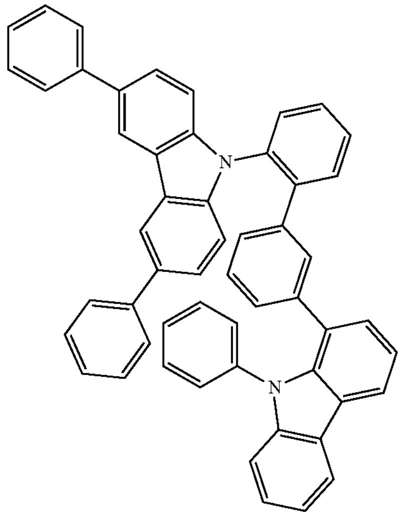
C6
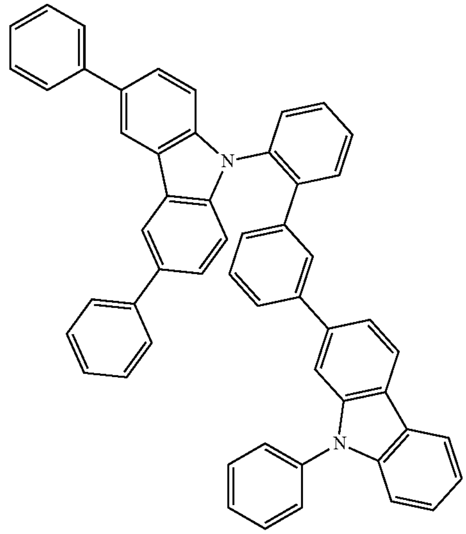
C7
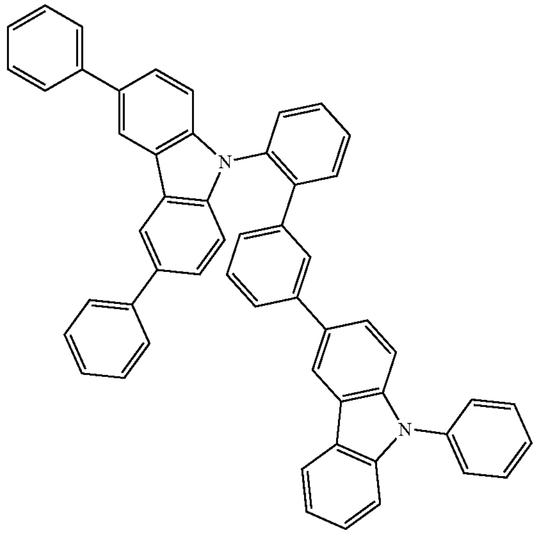

C8
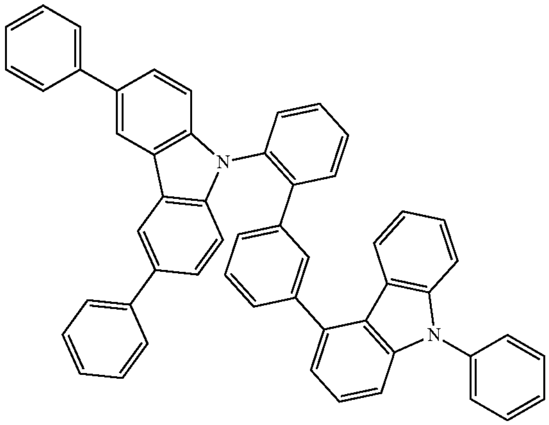
C9
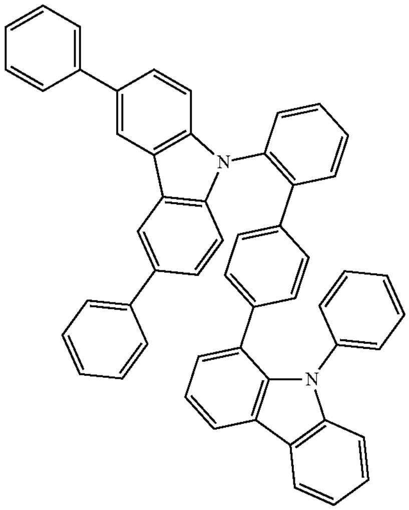
C10
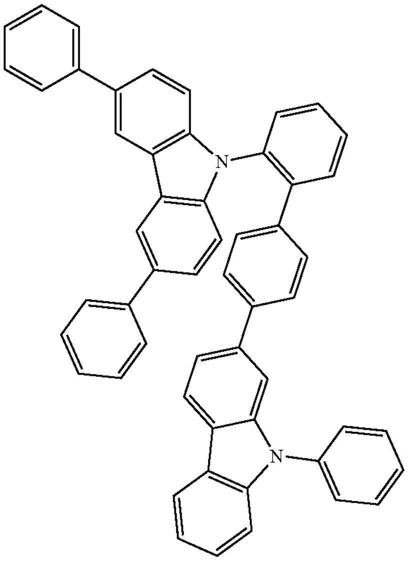
C11
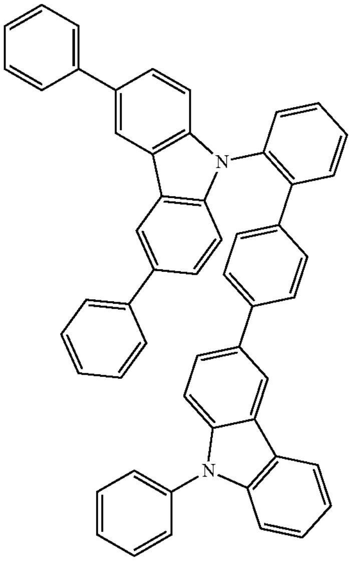
C12
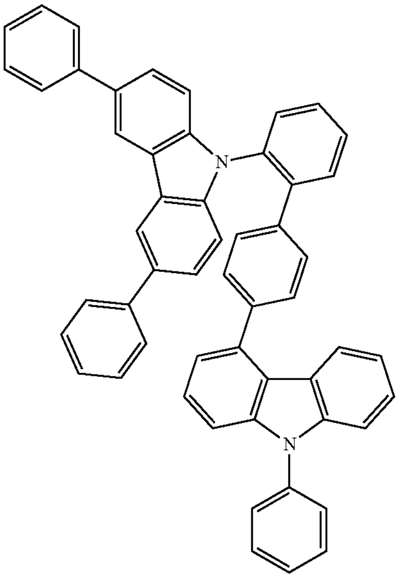

-continued
C13
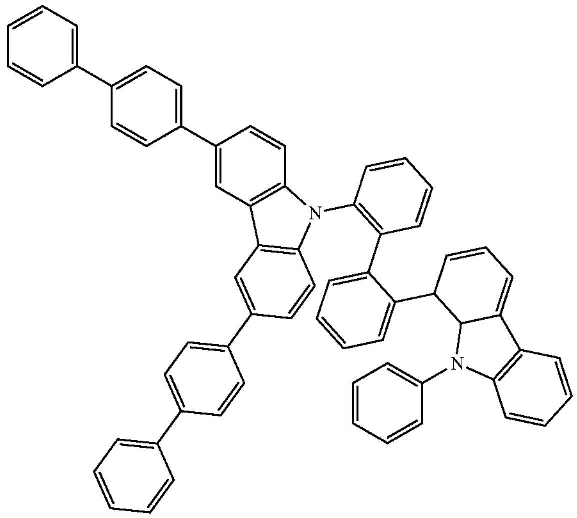
C14
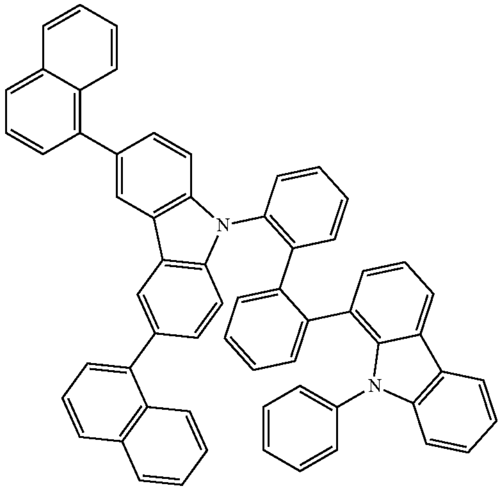
C15
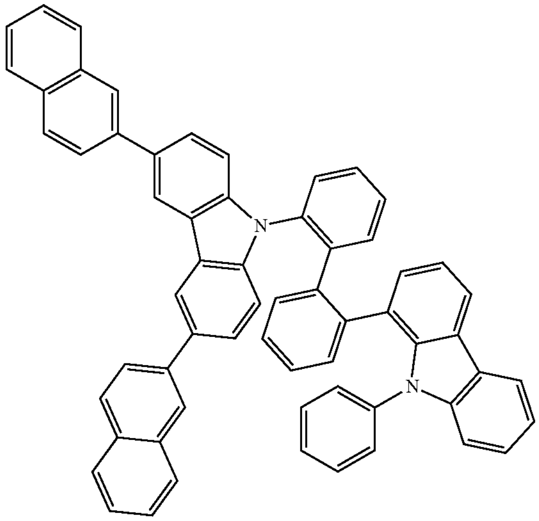
-continued
C16
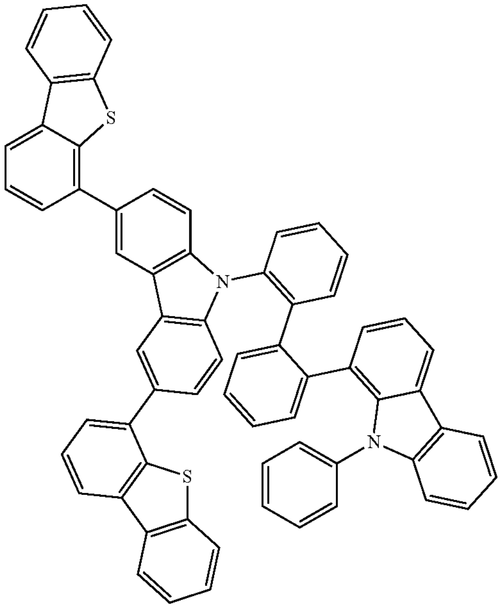
C17
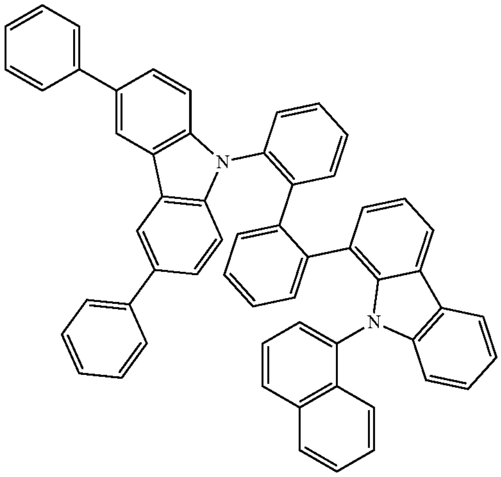
C18
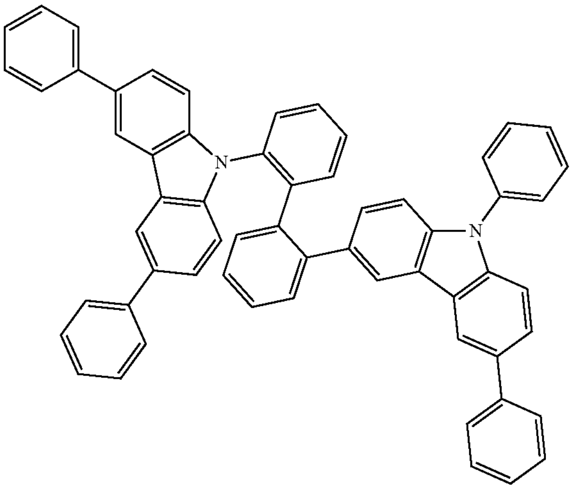

-continued
C19
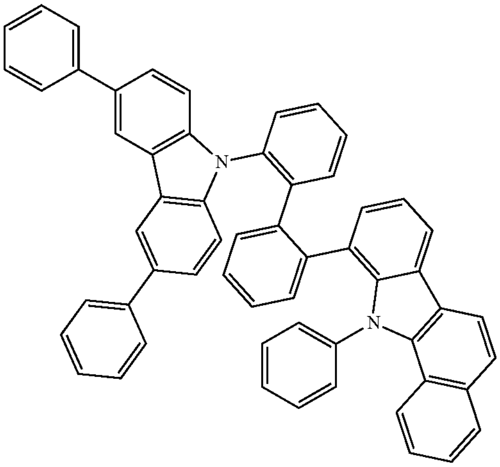
C20
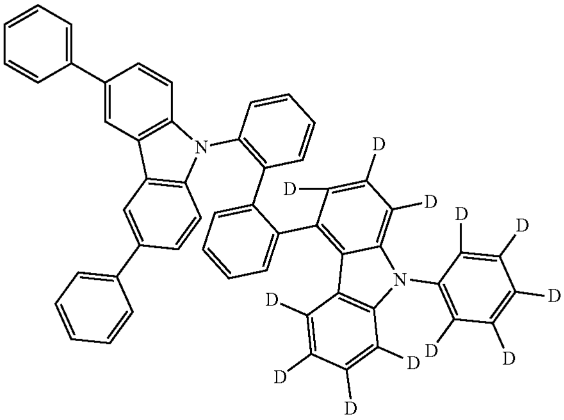
C21
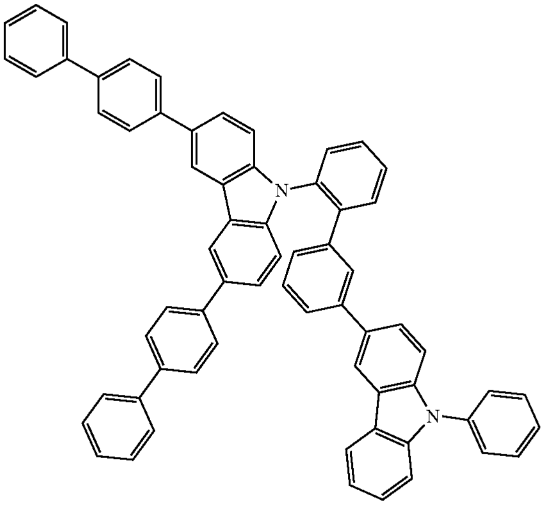
-continued
C22
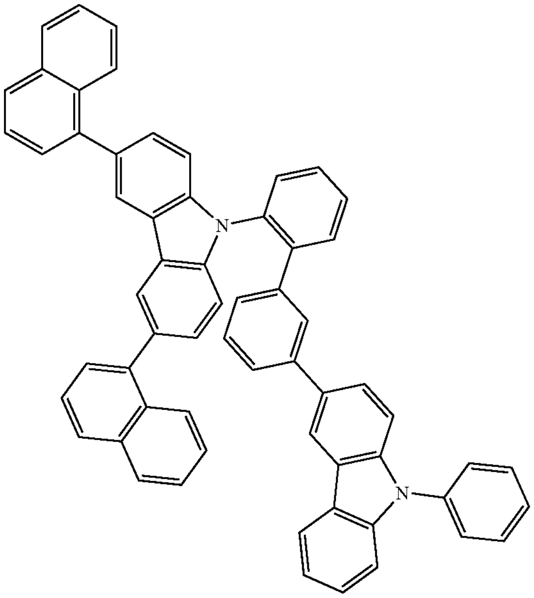
C23
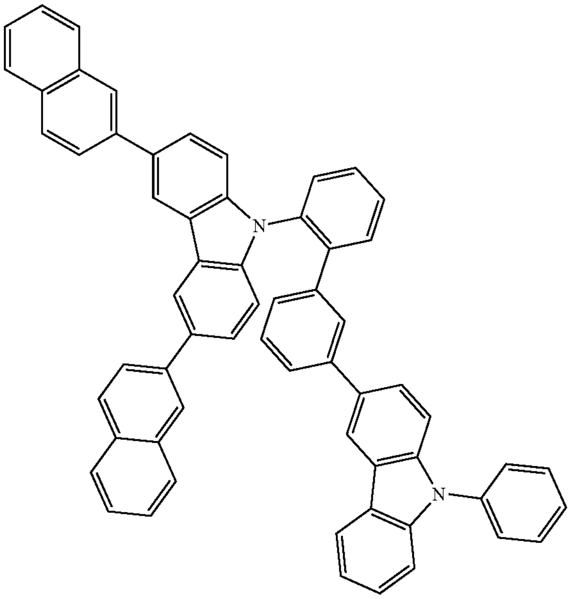

-continued
C24
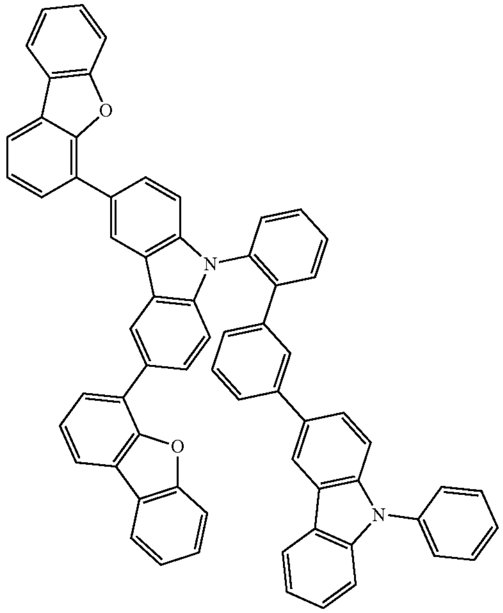
C25
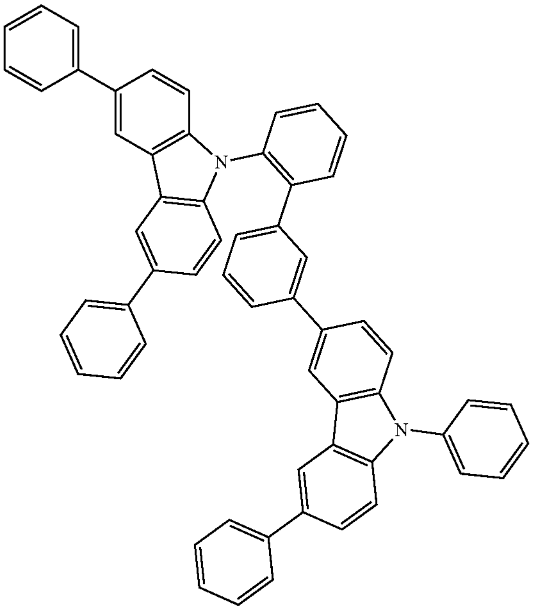
-continued
C26
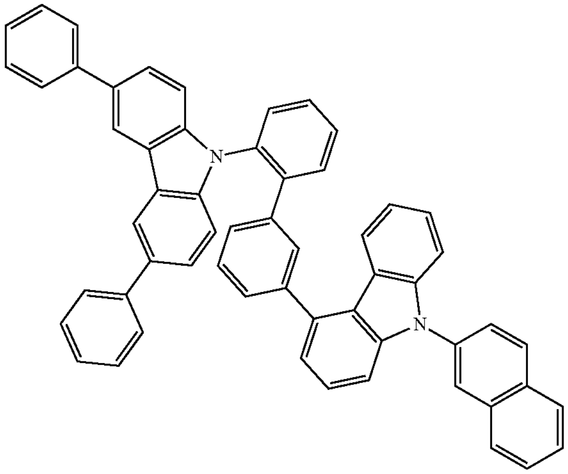
C27
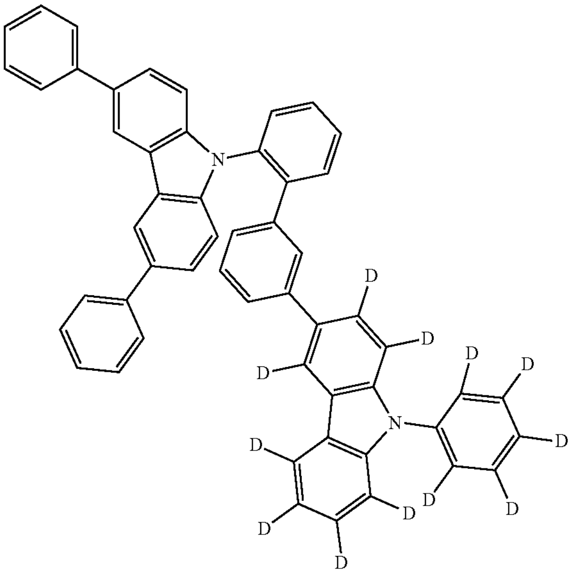

-continued
C28
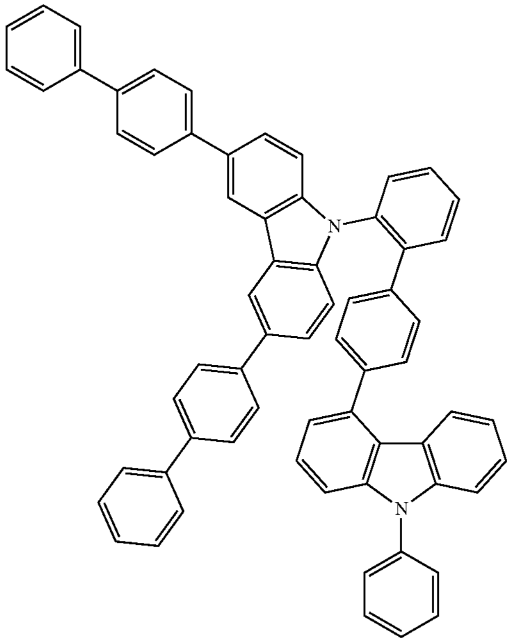
C29
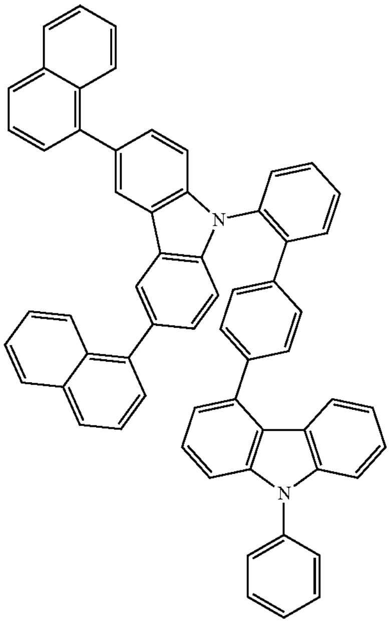
-continued
C30
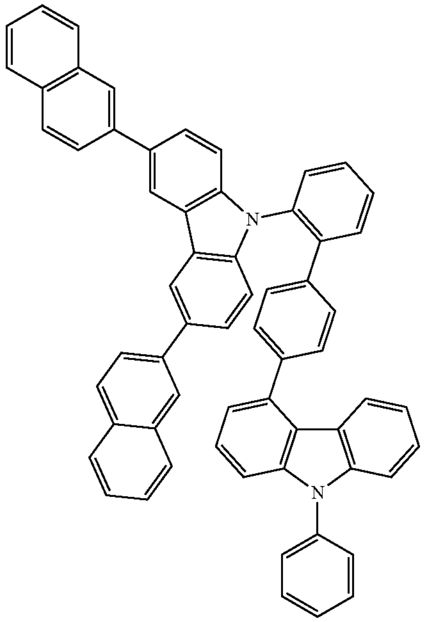
C31
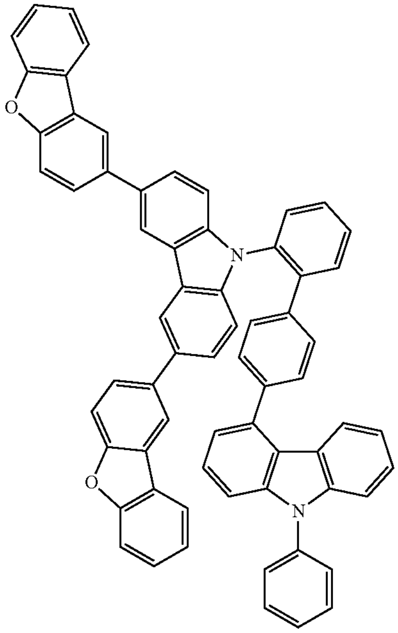

-continued
C32
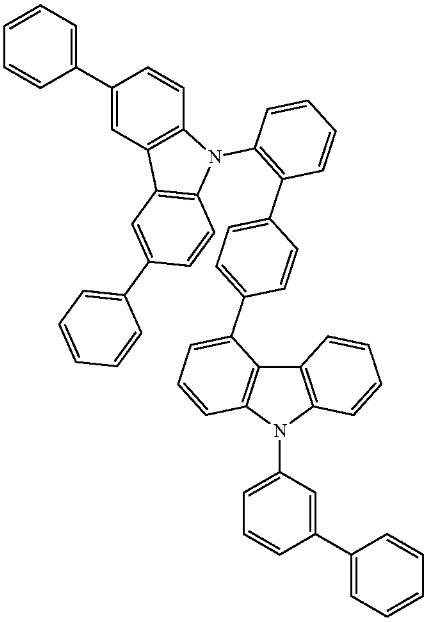
C33
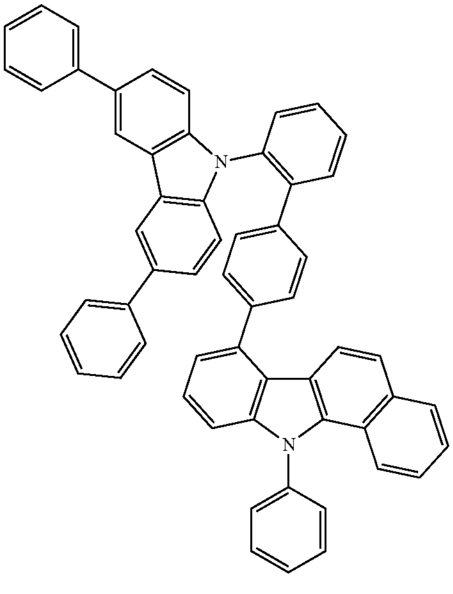
-continued
C34
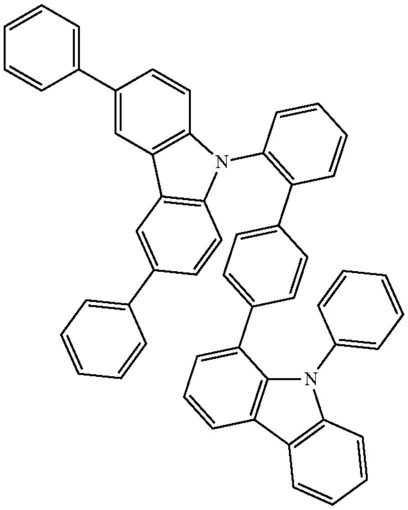
C35
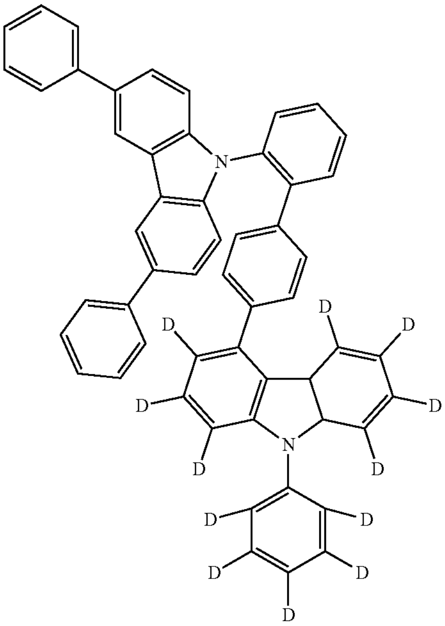
Compound Group 2
D1
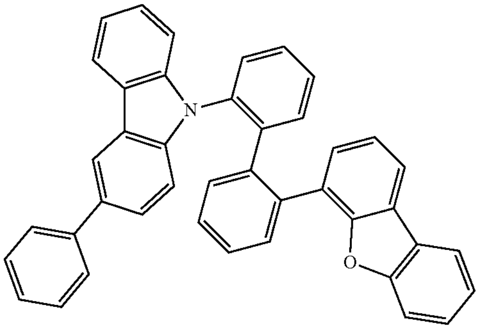

-continued
D2
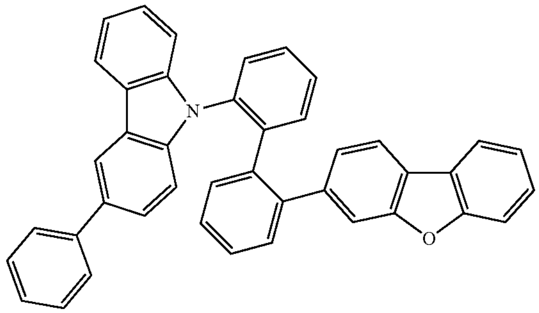
D3
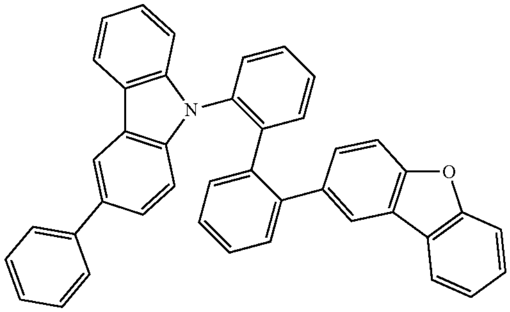
D4
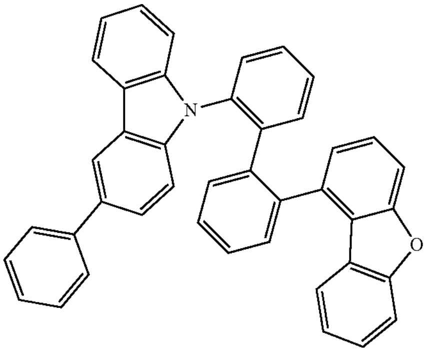
D5
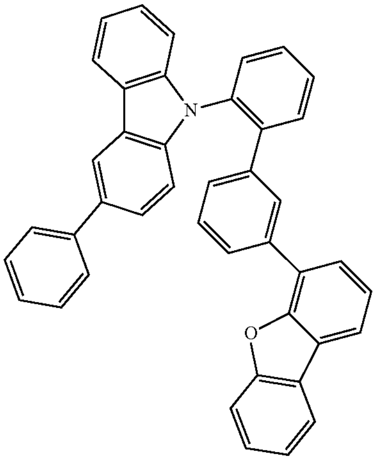
-continued
D6
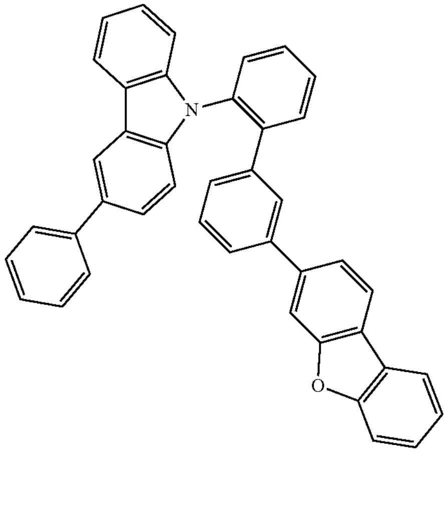
D7
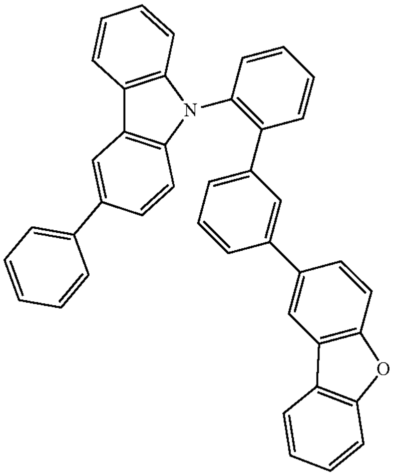
D8
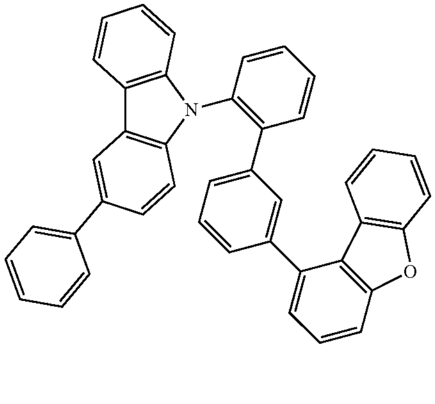

-continued
D9
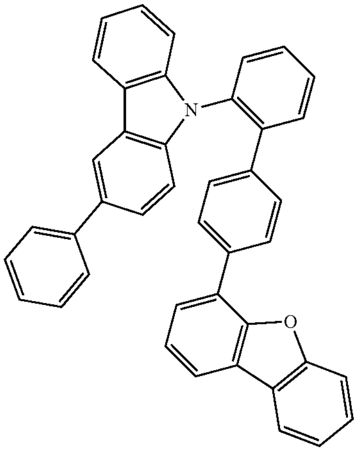
D10
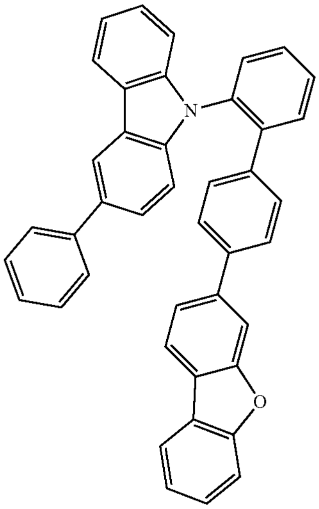
D11
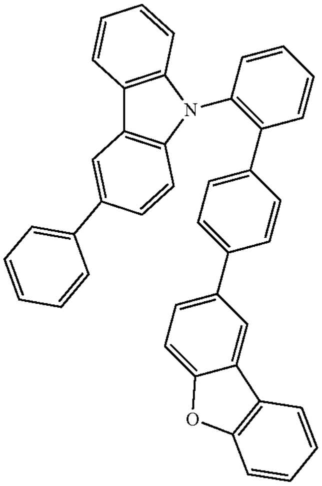
-continued
D12
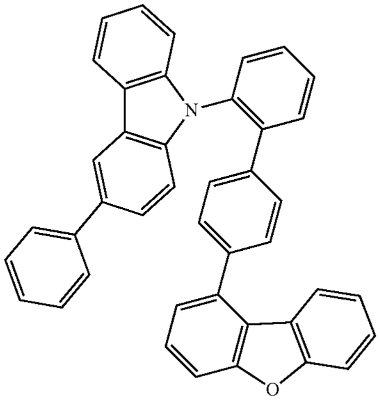
D13
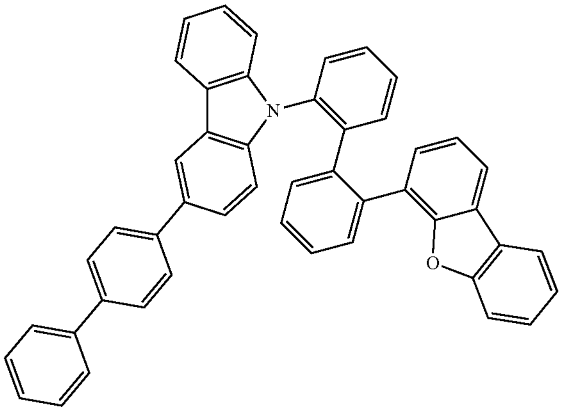
D14
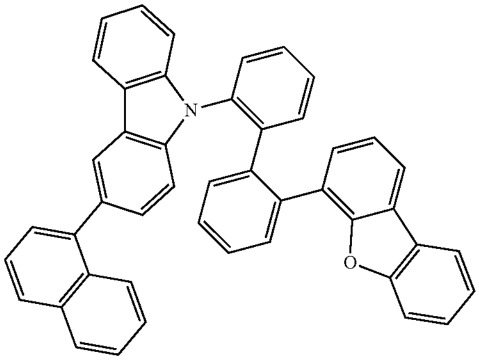
D15
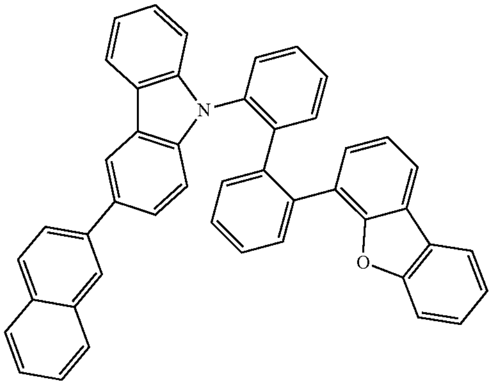

-continued
D16
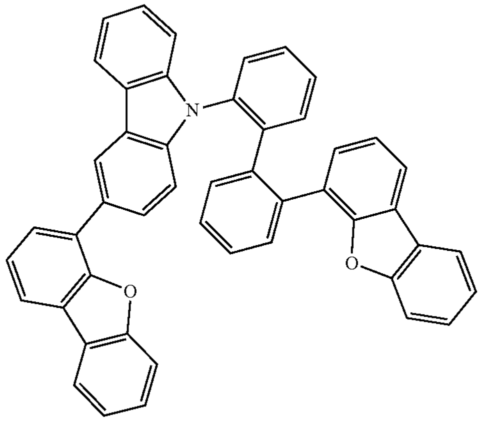
D17
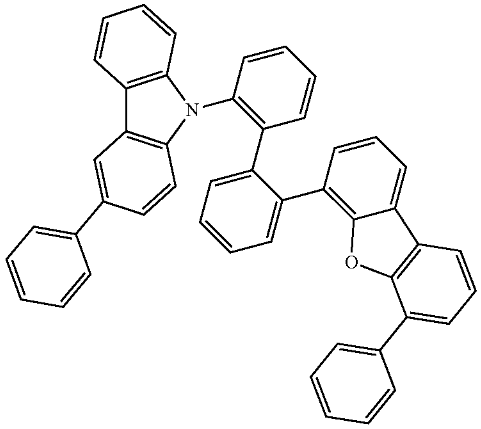
D18
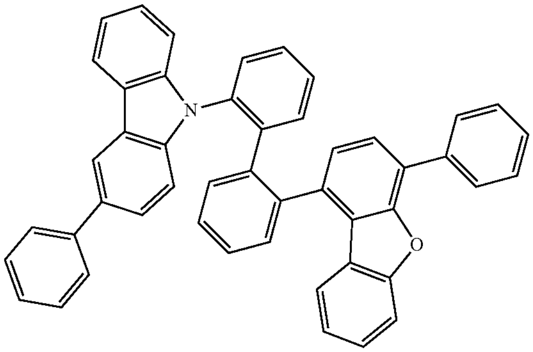
D19
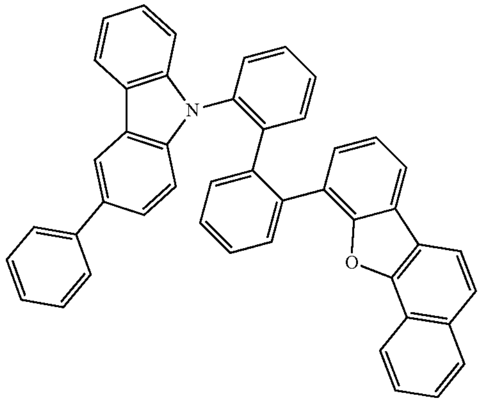
-continued
D20
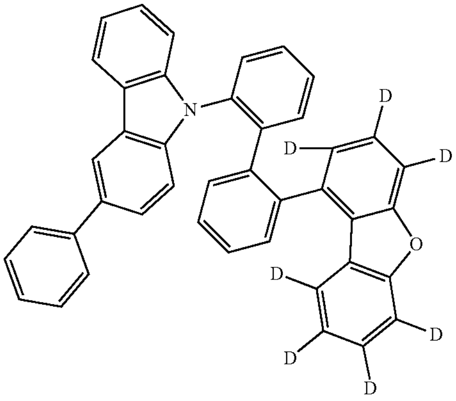
D21
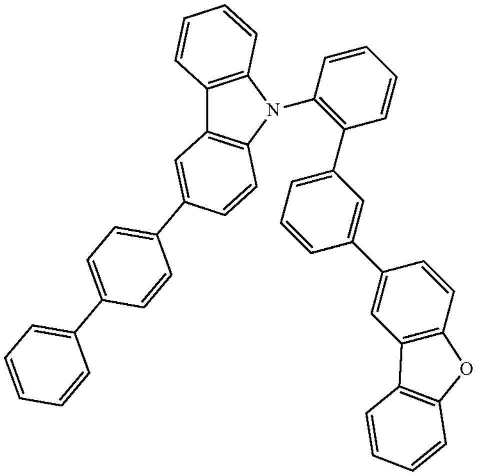
D22
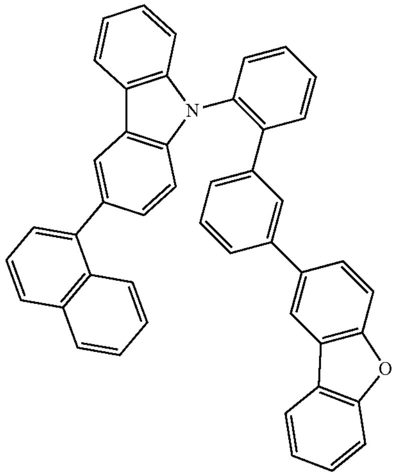

-continued
D23
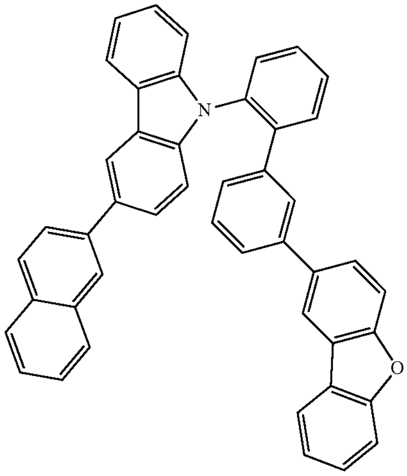
D24
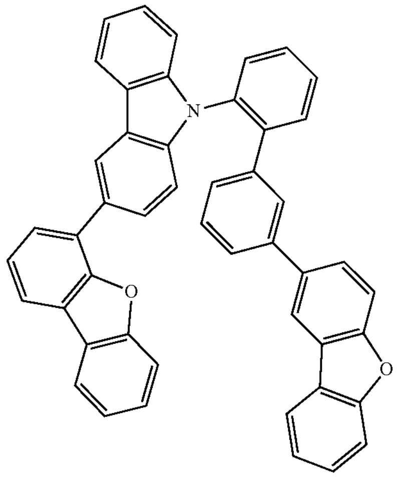
D25
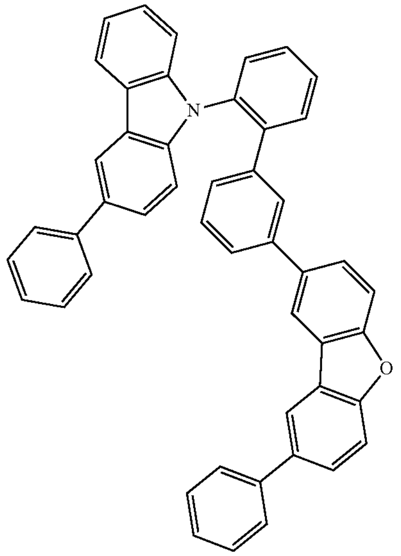
-continued
D26
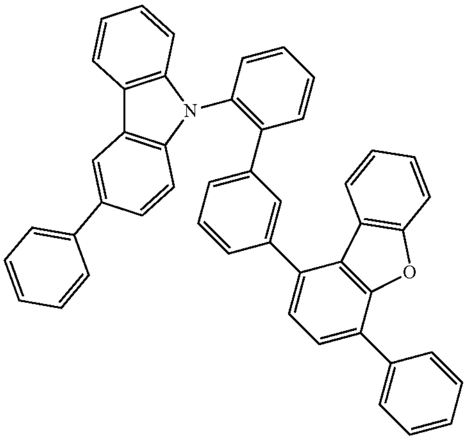
D27
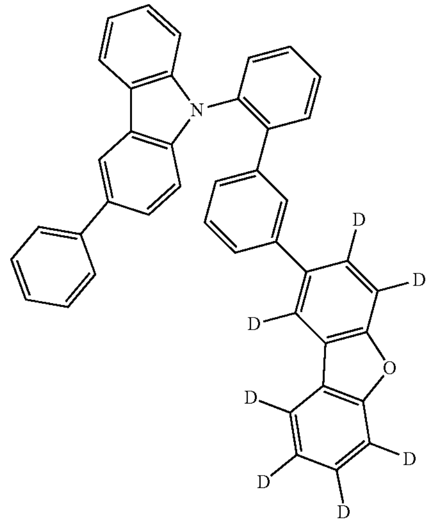
D28
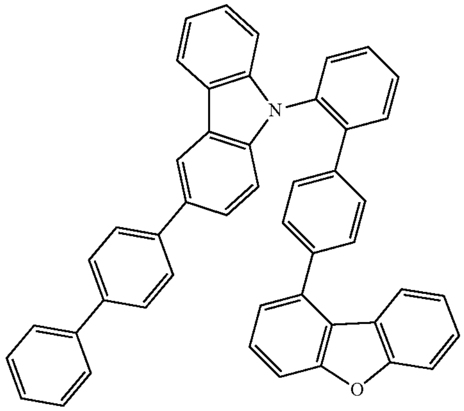

-continued
D29
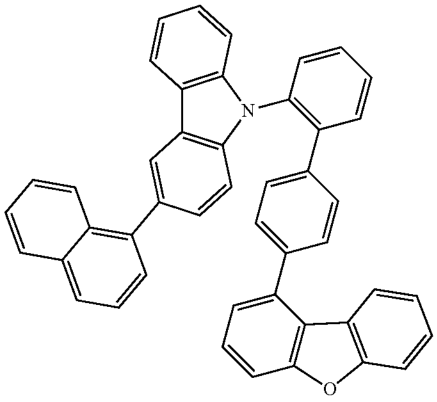
D30
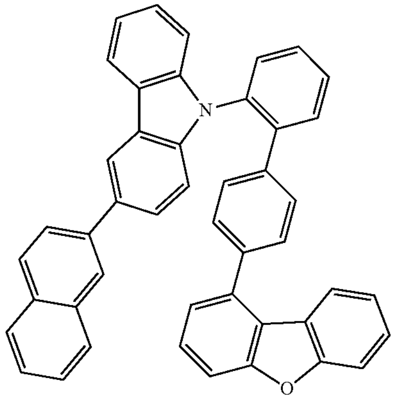
D31
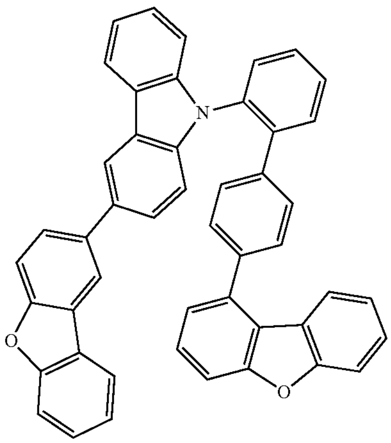
-continued
D32
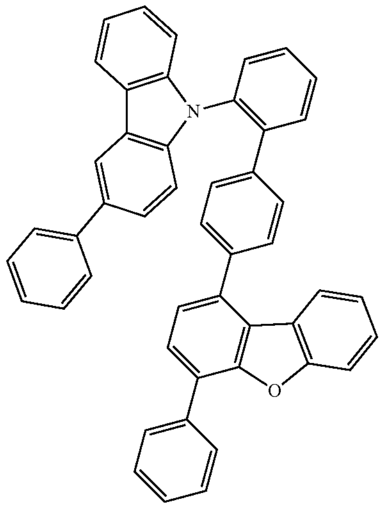
D33
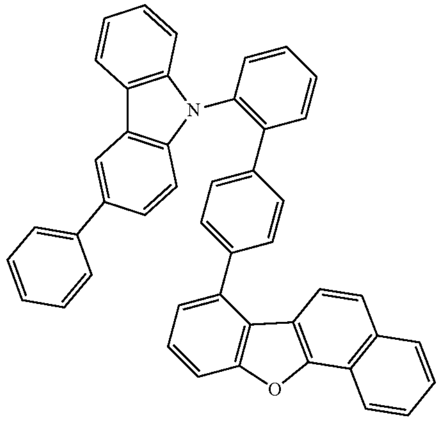
D34
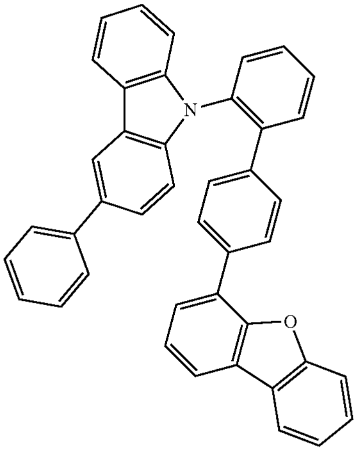

-continued
D35
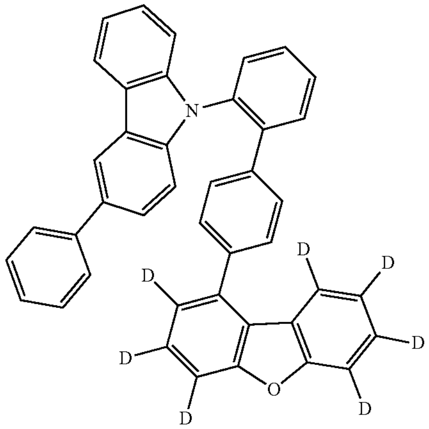
E1
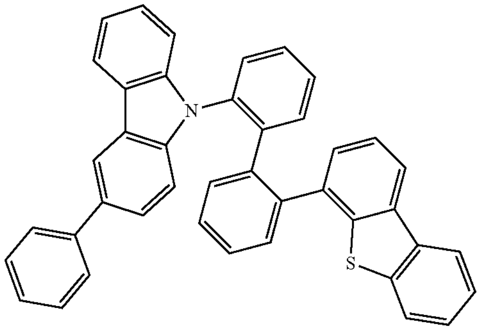
E2
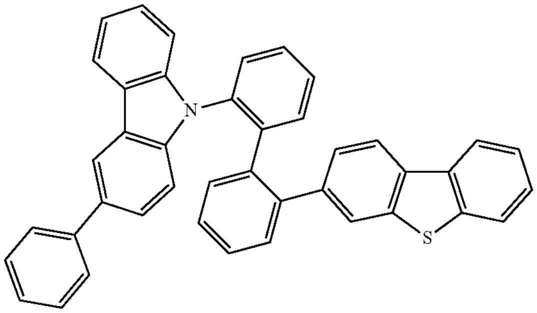
E3
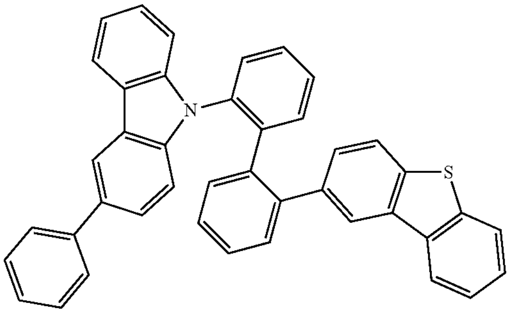
-continued
E4
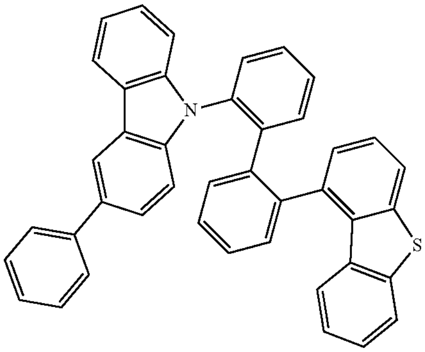
E5
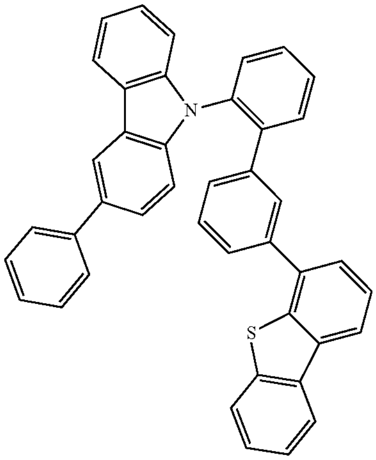
E6
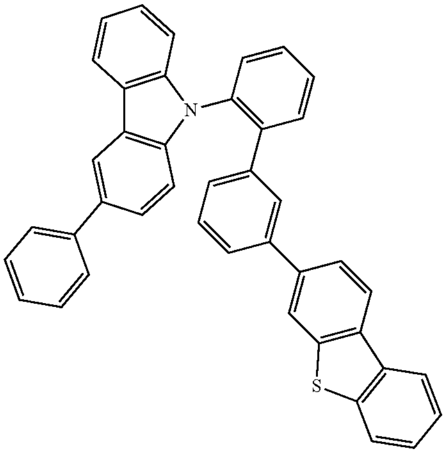

-continued
E7
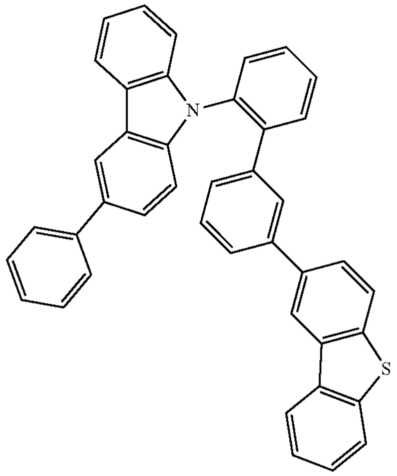
E8
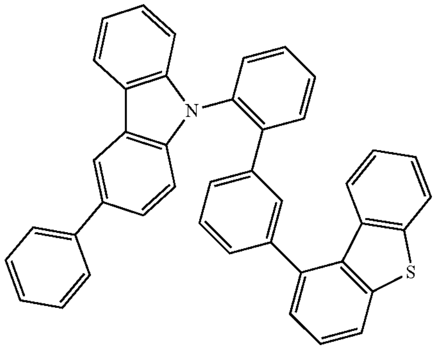
E9
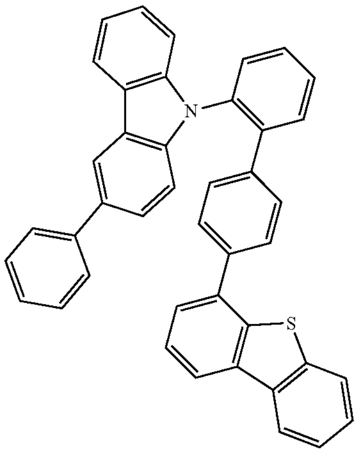
-continued
E10
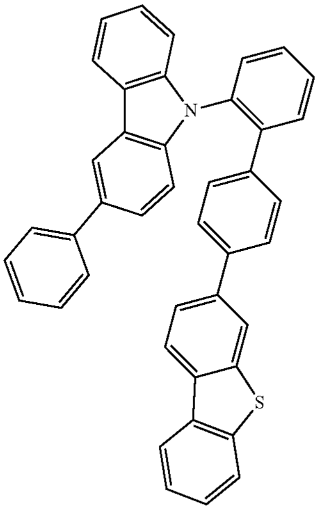
E11
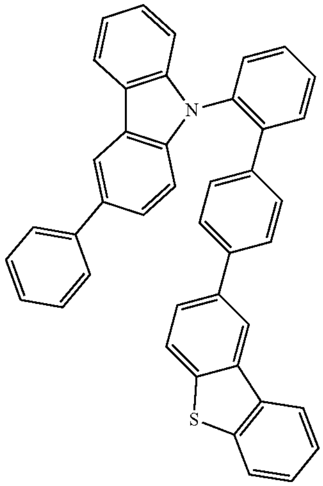
E12
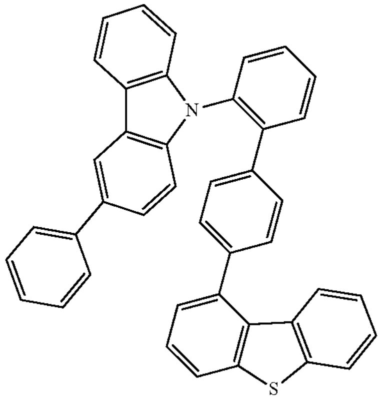

-continued
E13
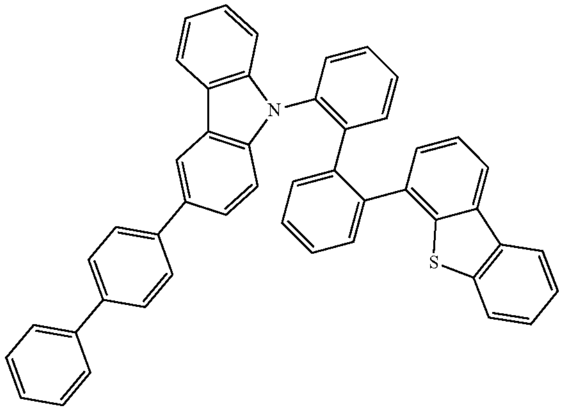
E14
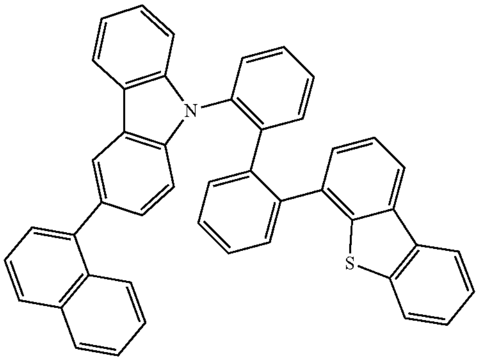
E15
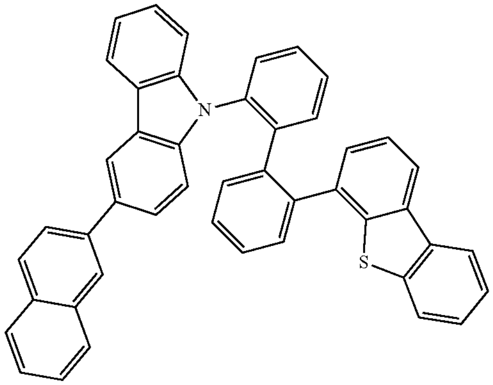
E16
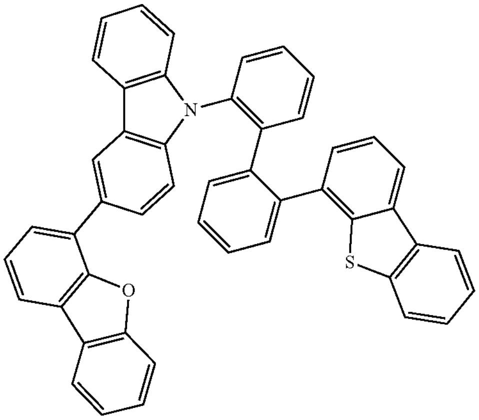
-continued
E17
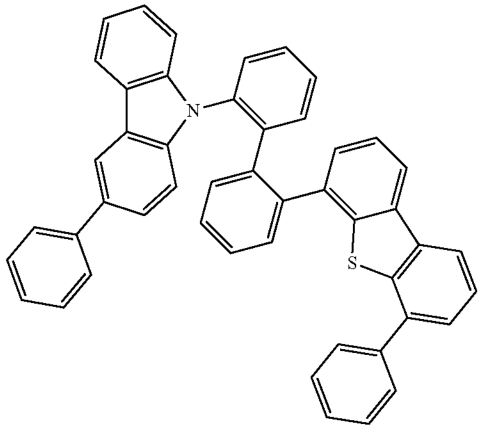
E18
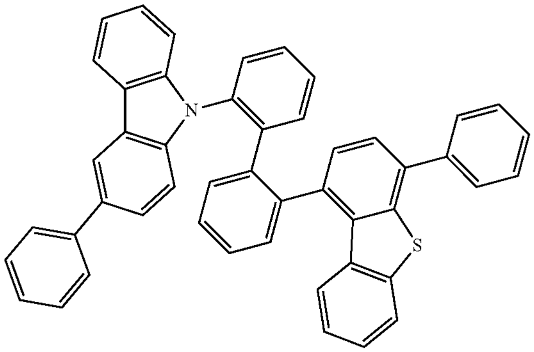
E19
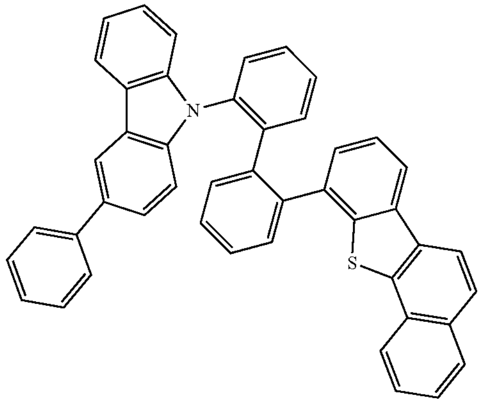
E20
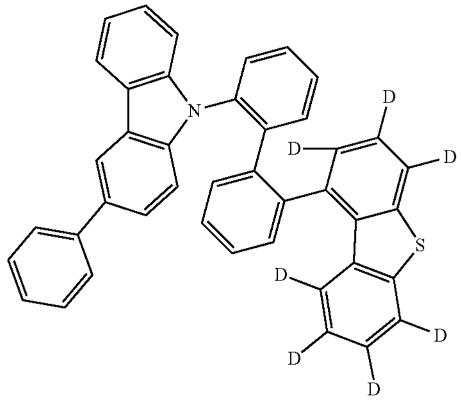

-continued
E21
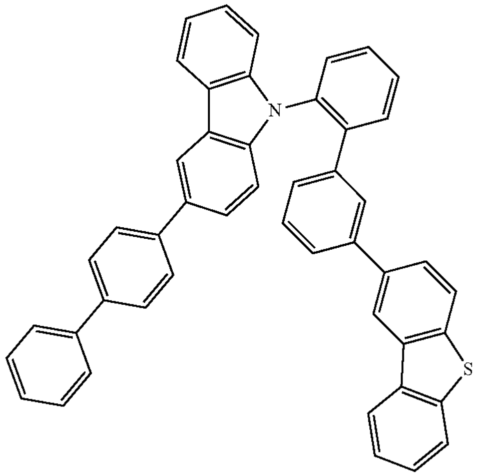
E22
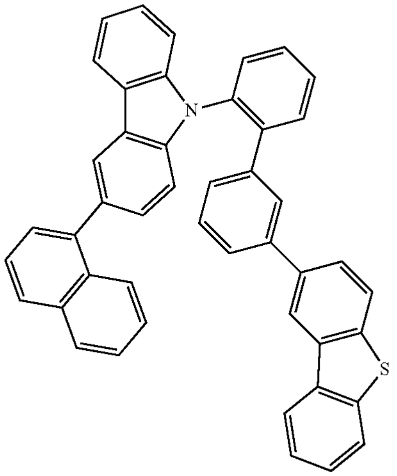
E23
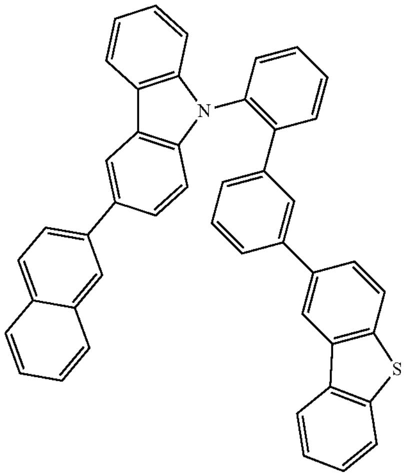
-continued
E24
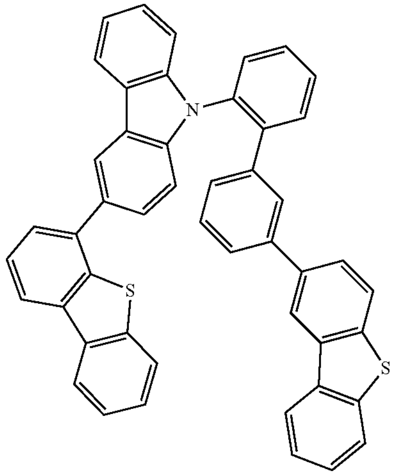
E25
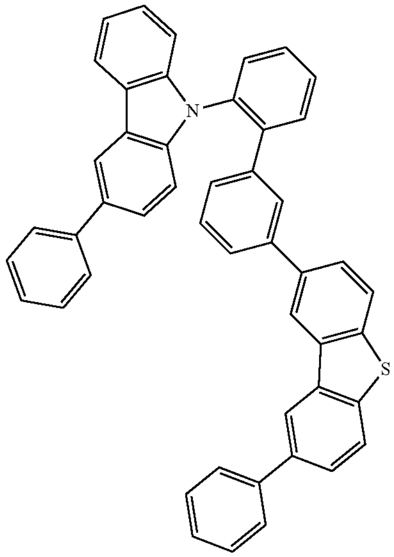
E26
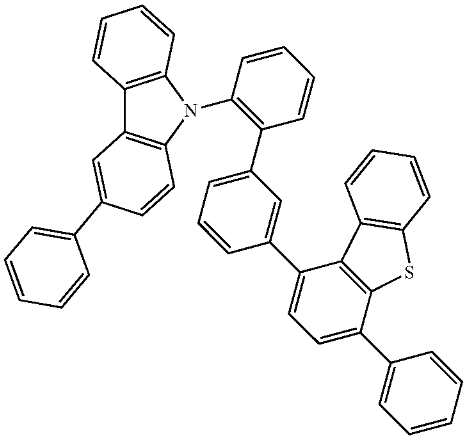

-continued
E27
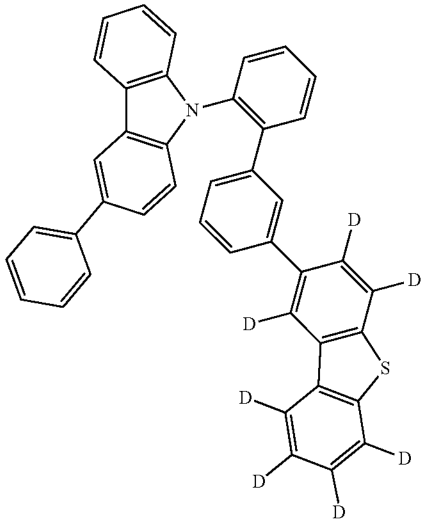
E28
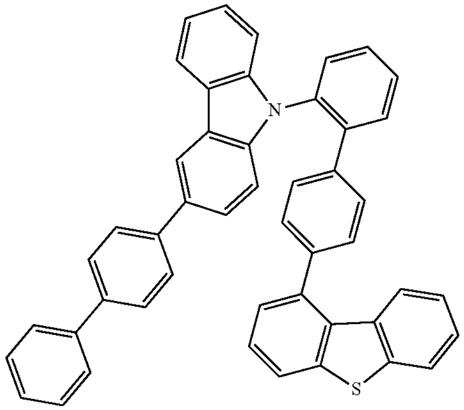
E29
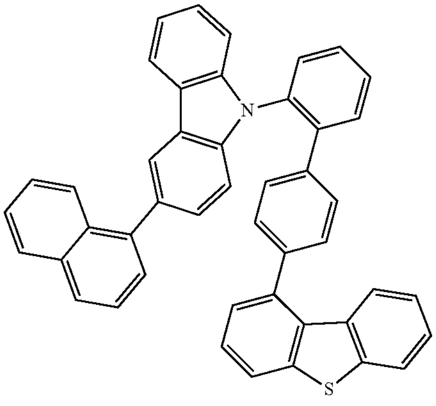
-continued
E30
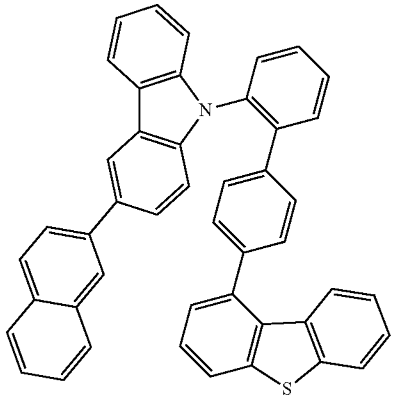
E31
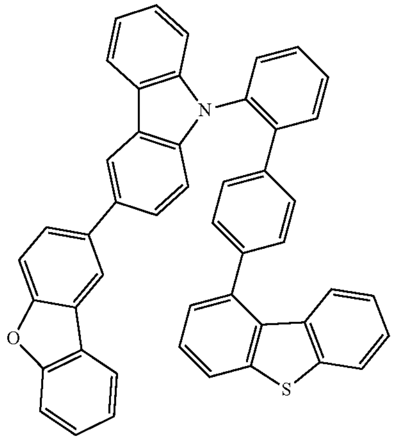
E32
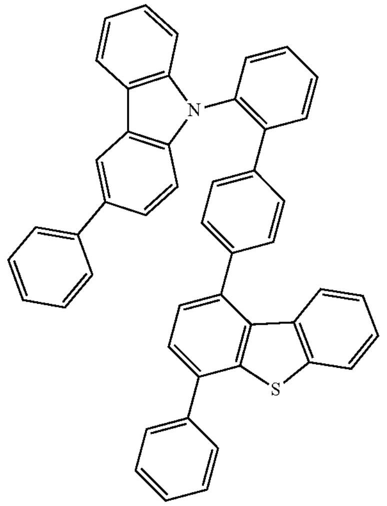

-continued
E33
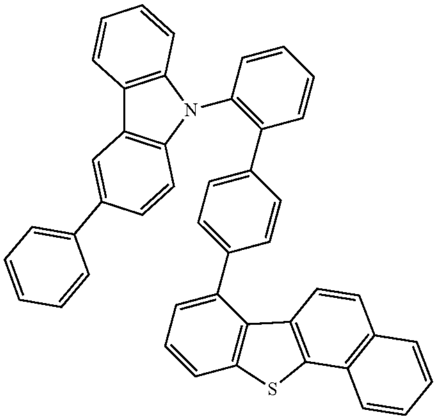
E34
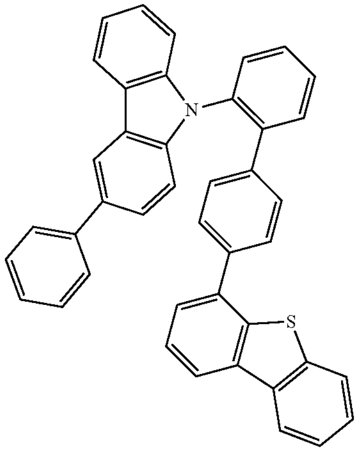
E35
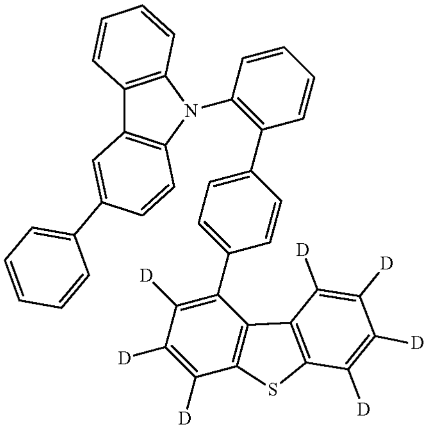
-continued
F1
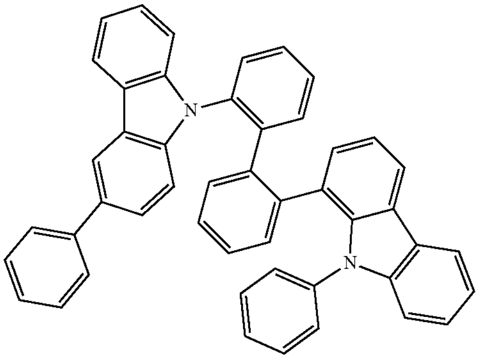
F2
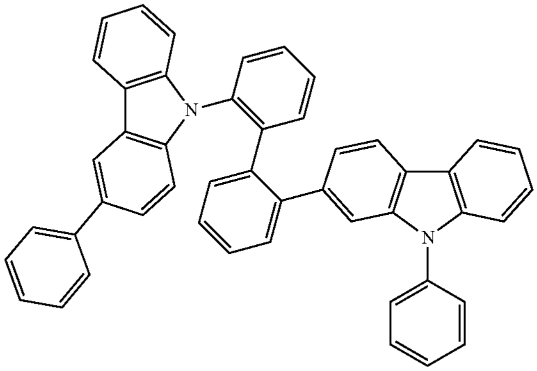
F3
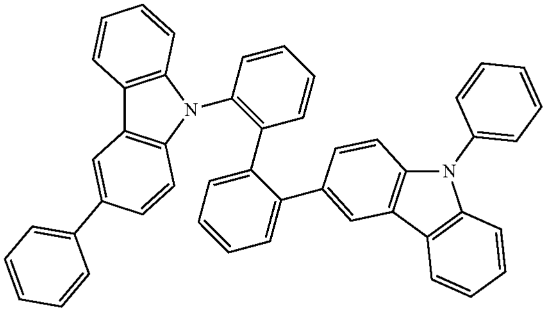
F4
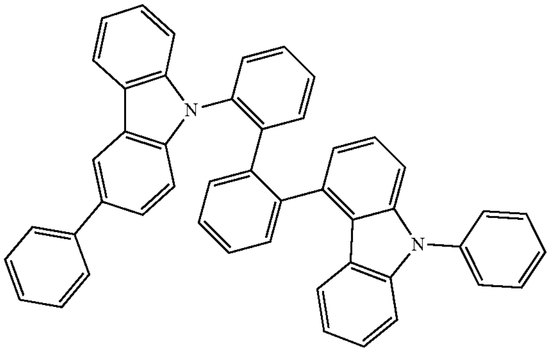

-continued
F5
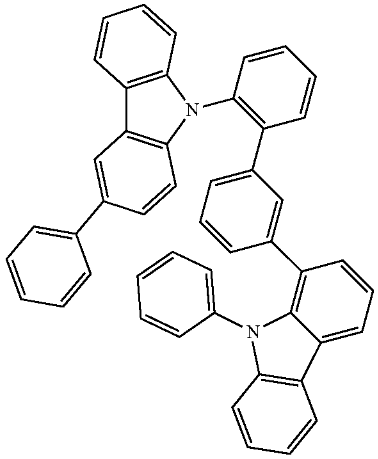
F6
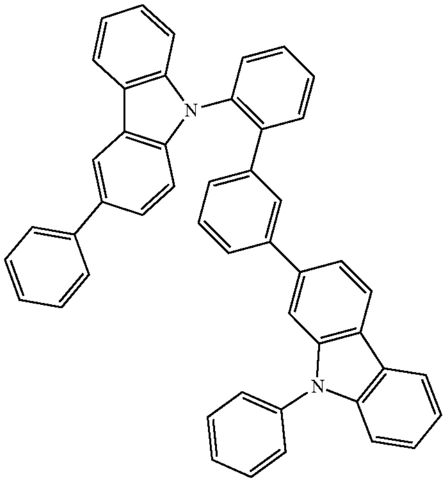
F7
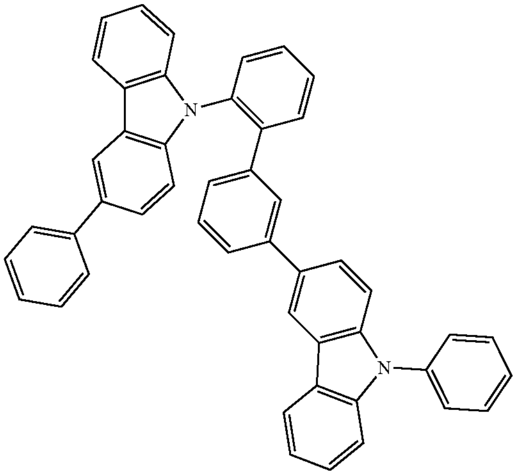
-continued
F8
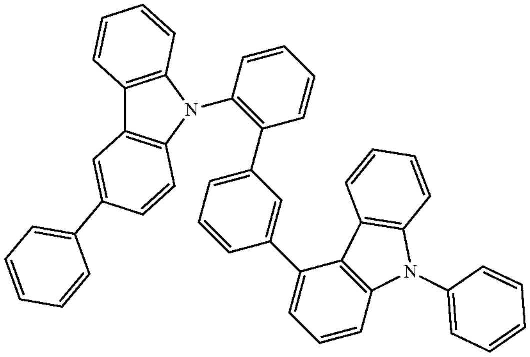
F9
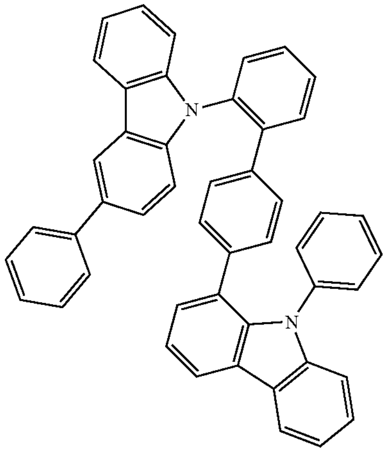
F10
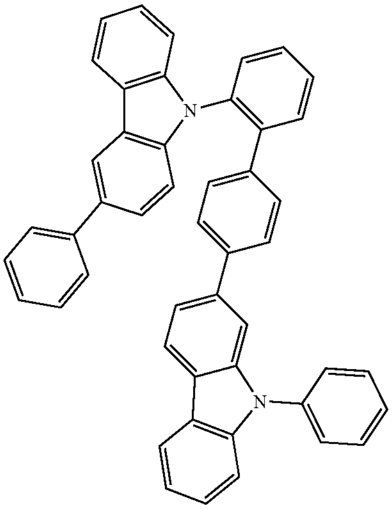

-continued
F11
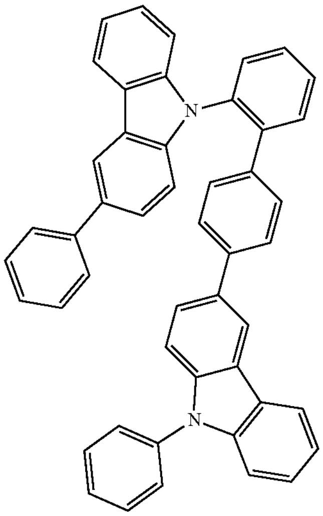
F12
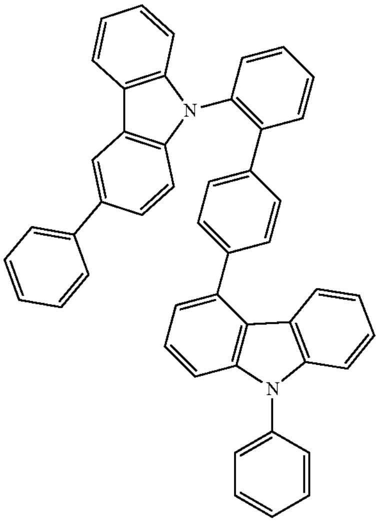
F13
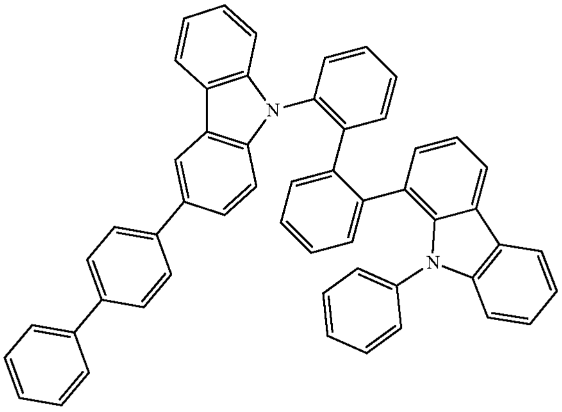
-continued
F14
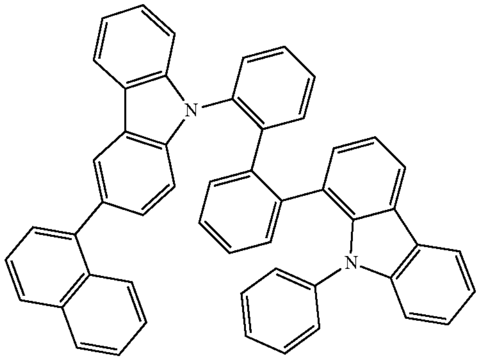
F15
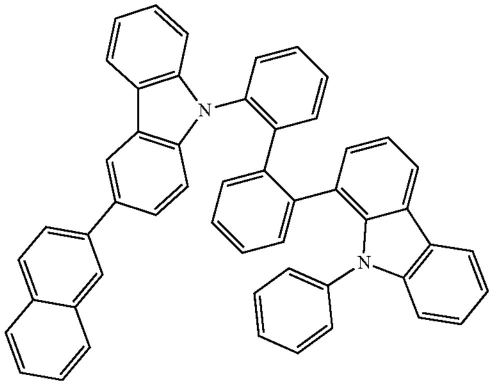
F16
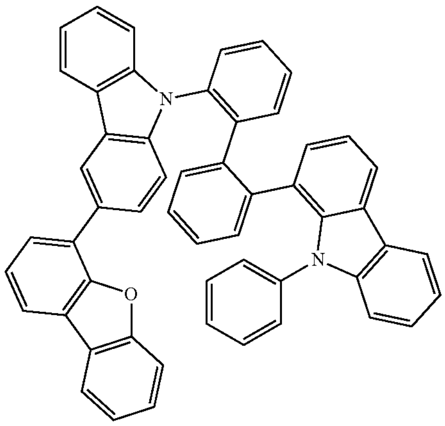

-continued
F17
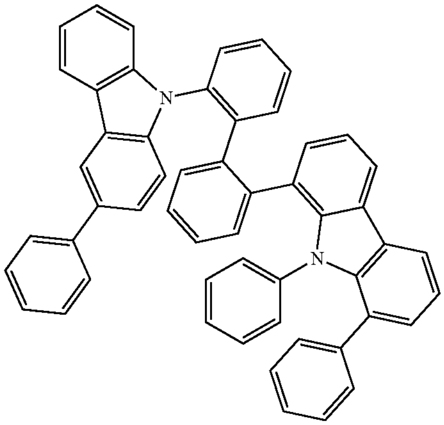
F18
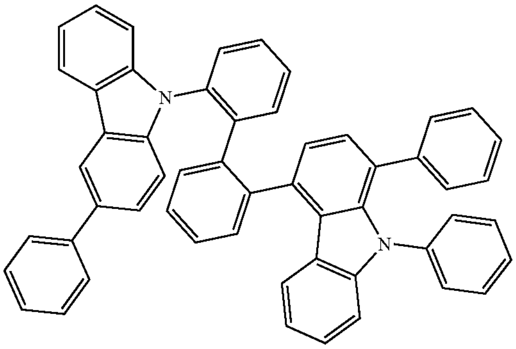
F19
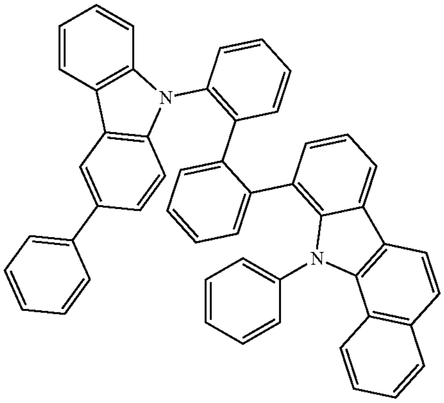
F20
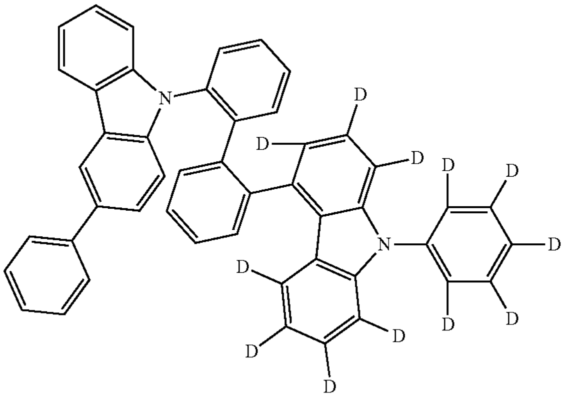
-continued
F21
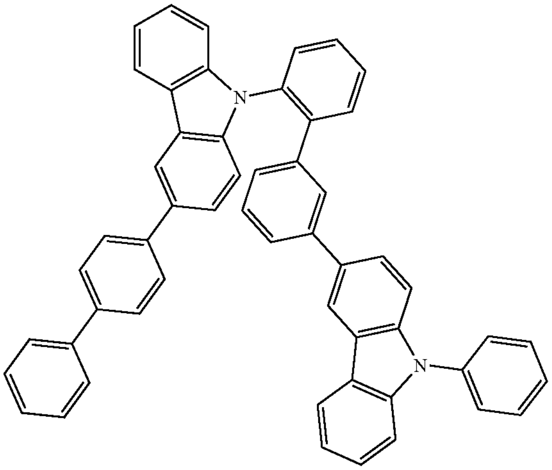
F22
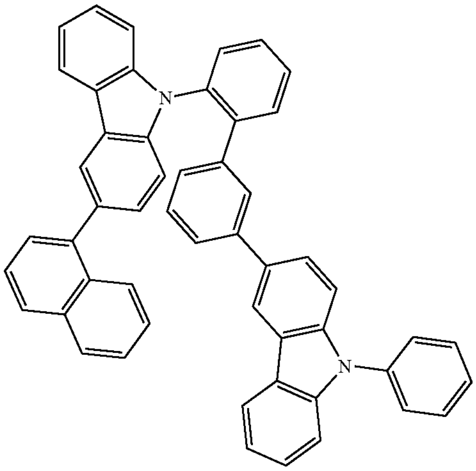
F23
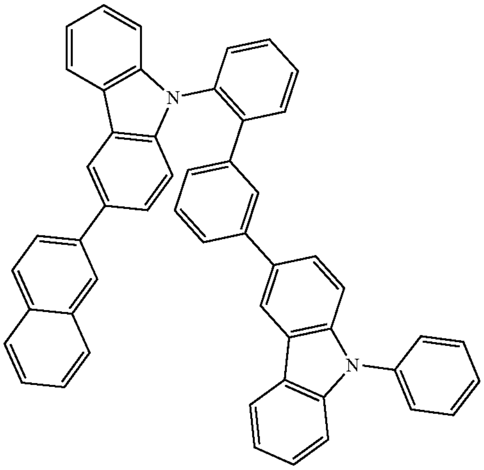

-continued
F24
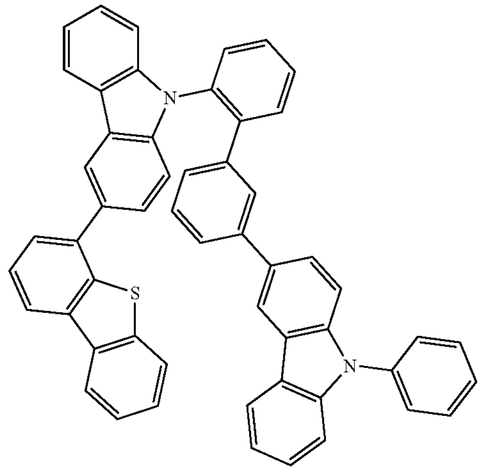
F25
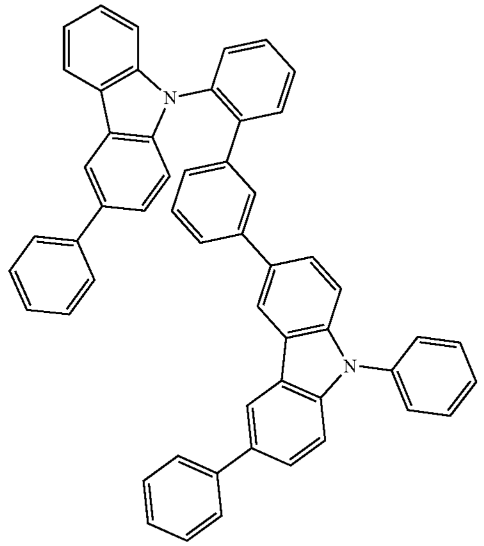
F26
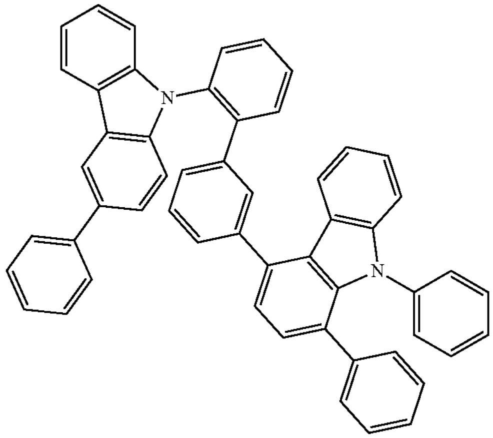
-continued
F27
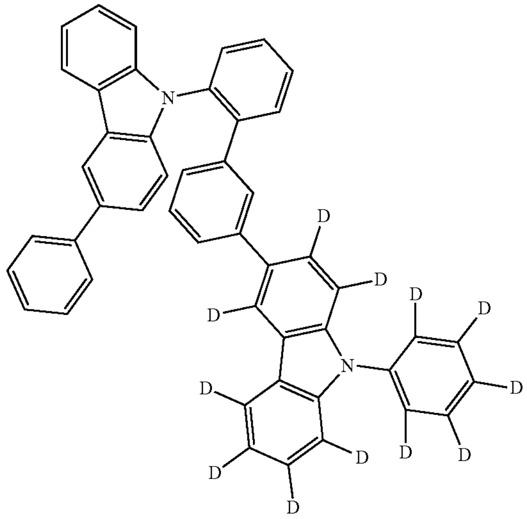
F28
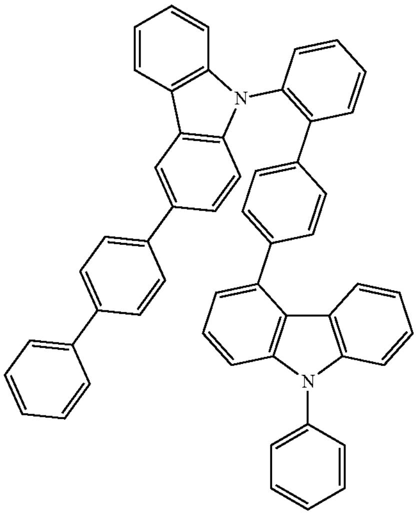
F29
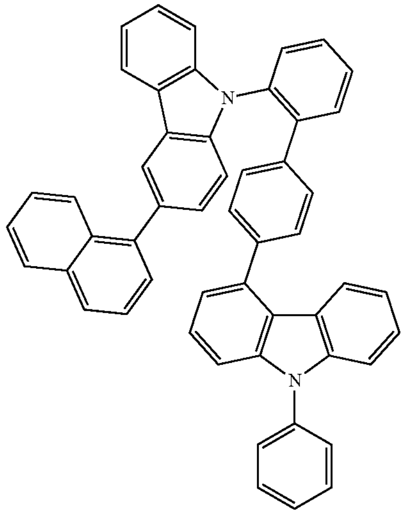

-continued
F30
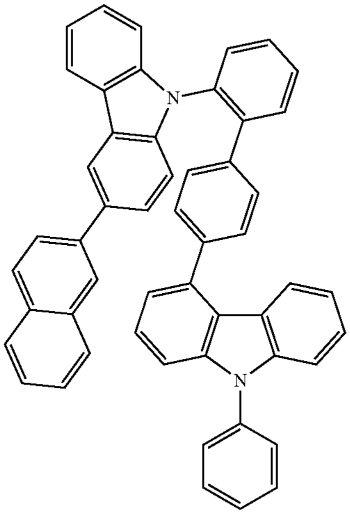
F31
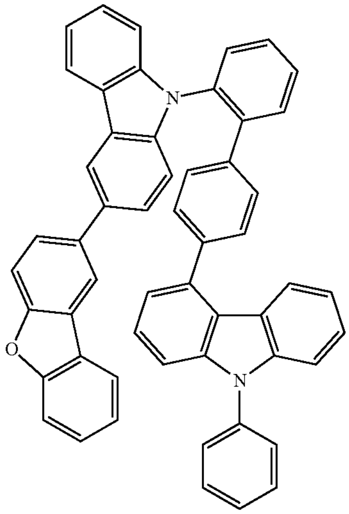
F32
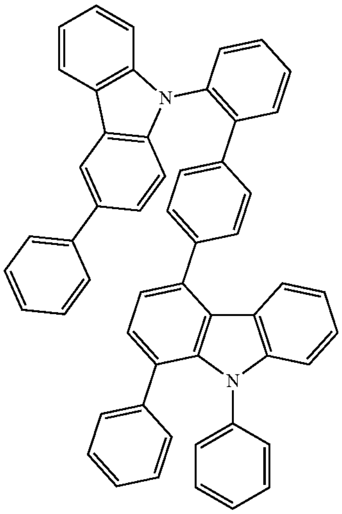
-continued
F33
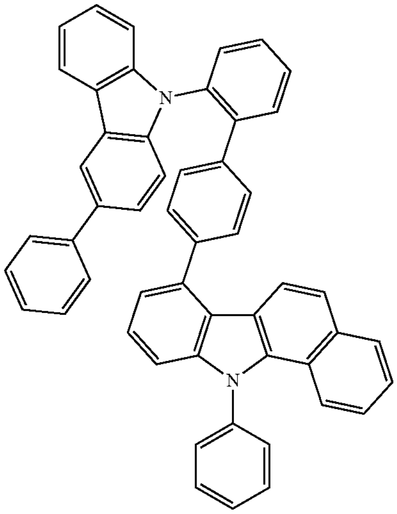
F34
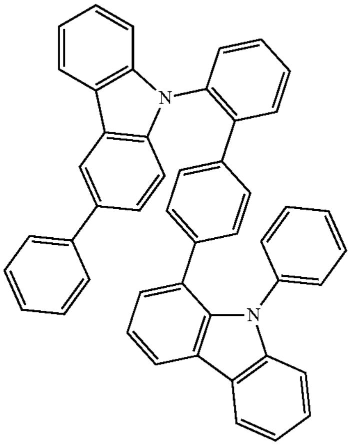
F35
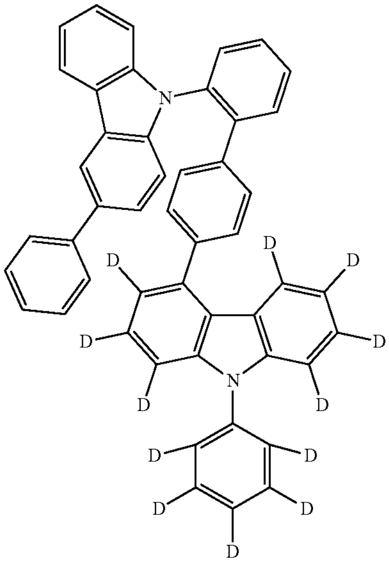

-continued
J1
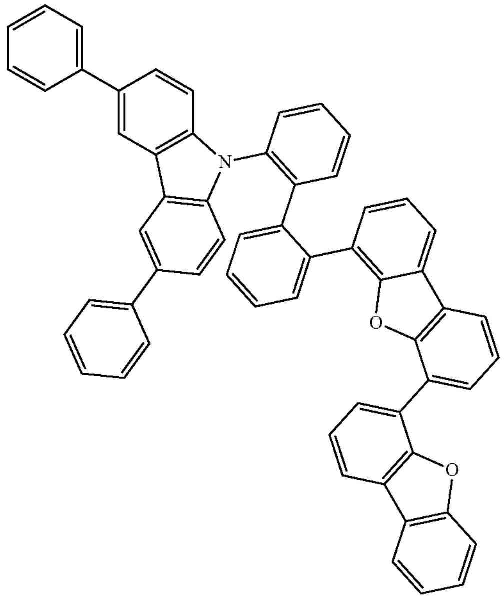
J2
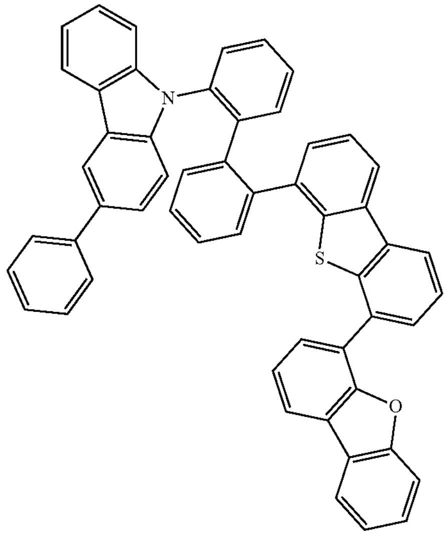
J3
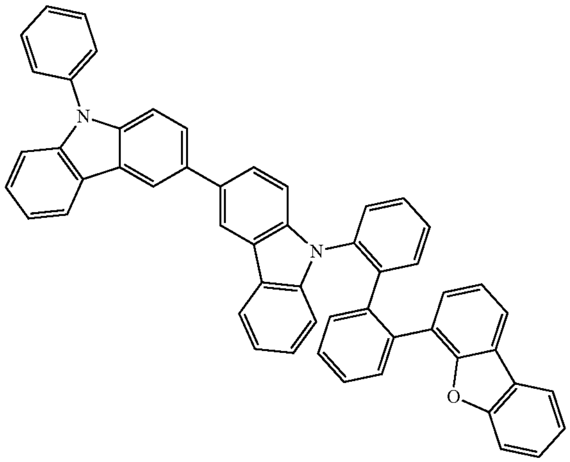
-continued
J4
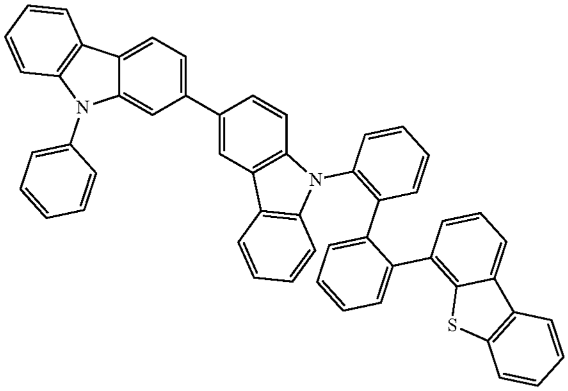
K1
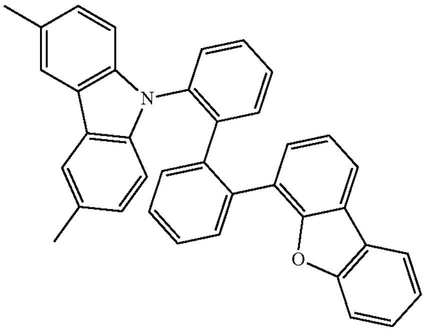
K2
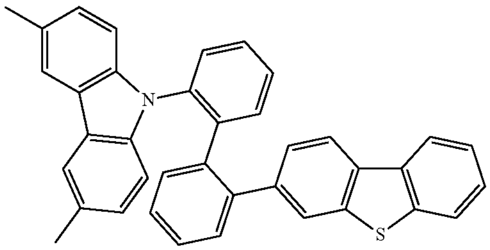
K3
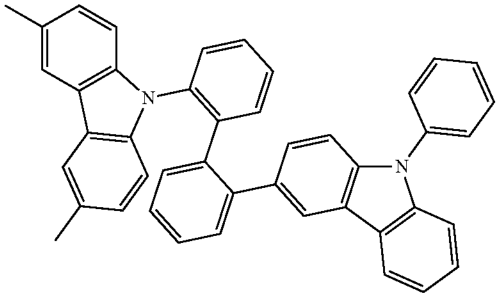

-continued
K4
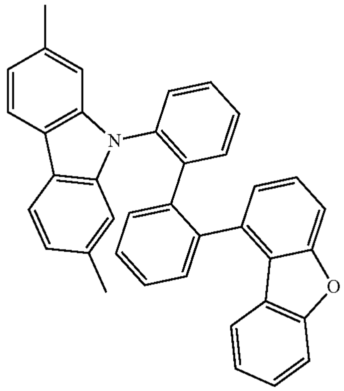
K5
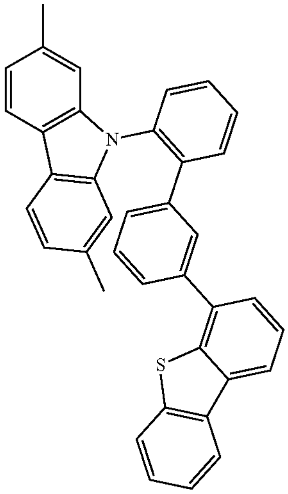
K6
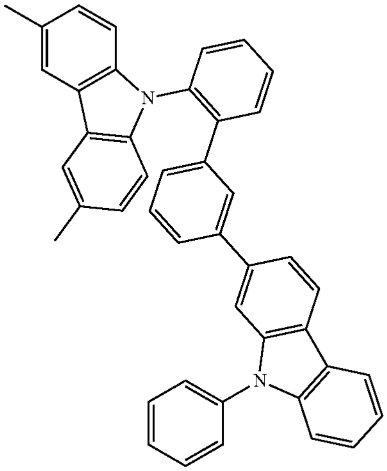
-continued
K7
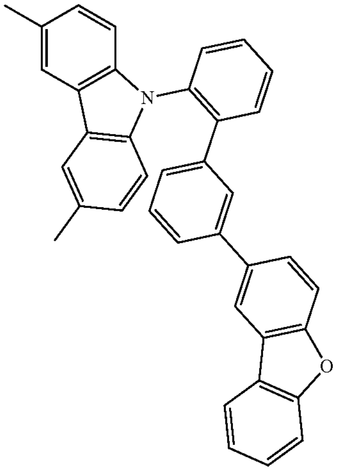
K8
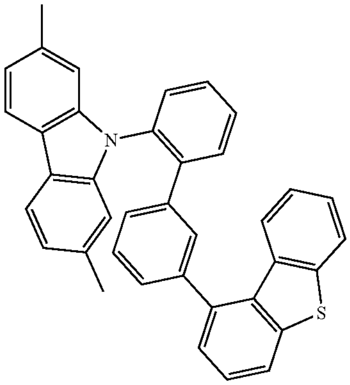
K9
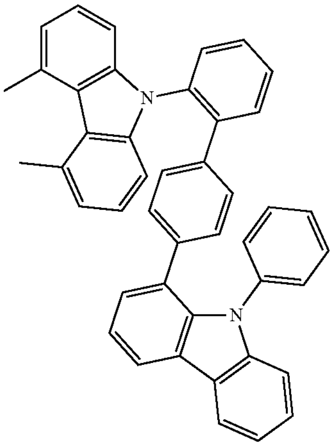

-continued
K10
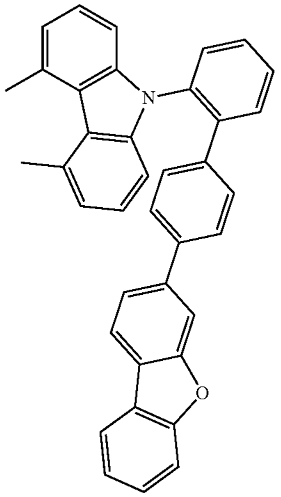
K11
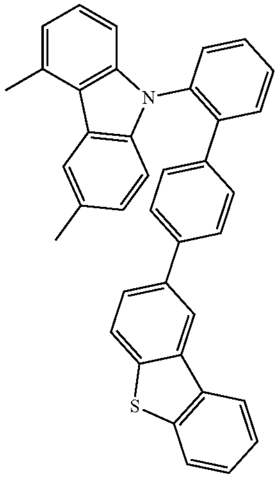
K12
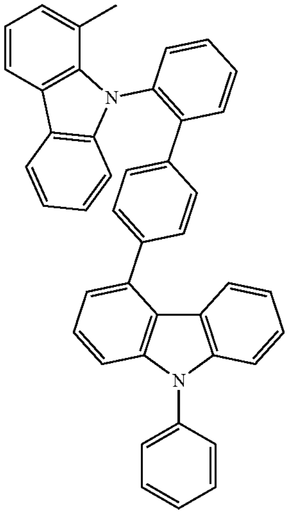
-continued
K13
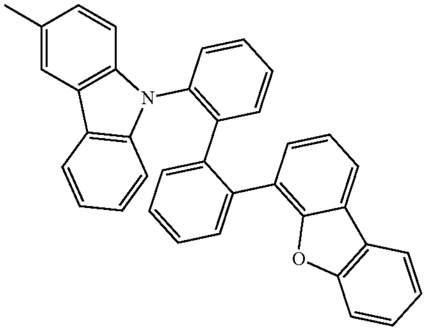
K14
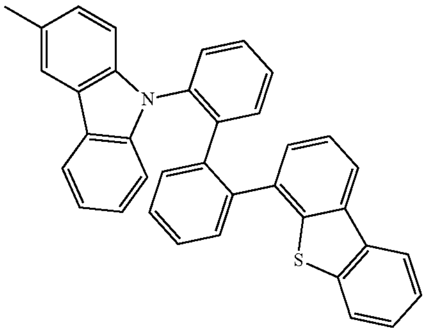
K15
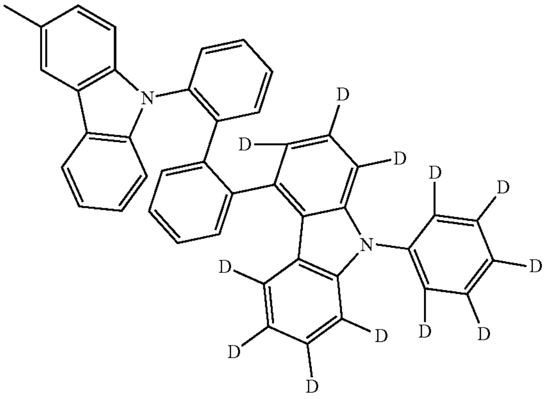
L1
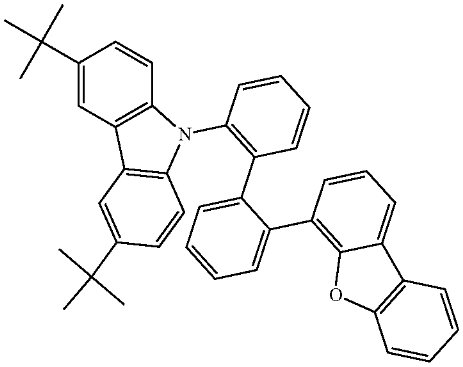

-continued
L2
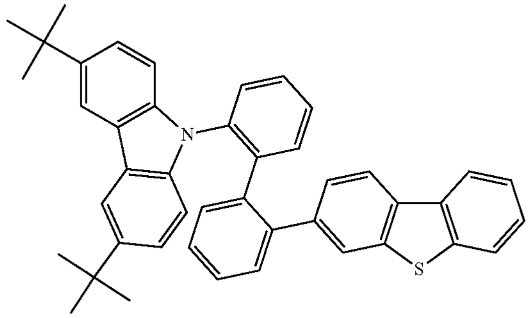
L3
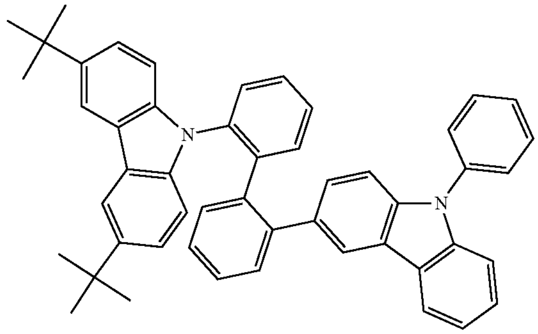
L4
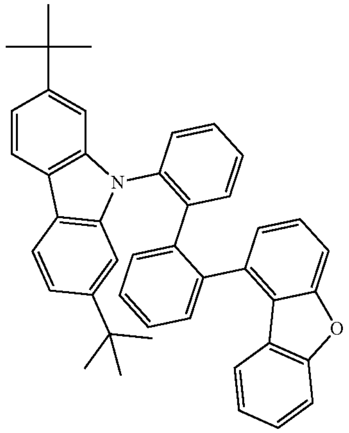
-continued
L5
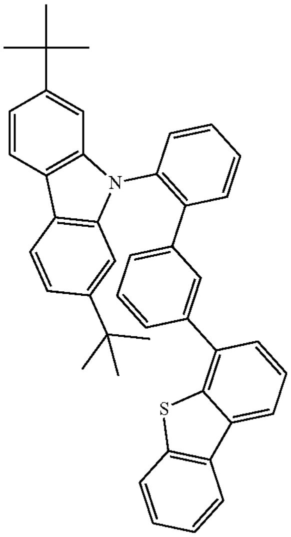
L6
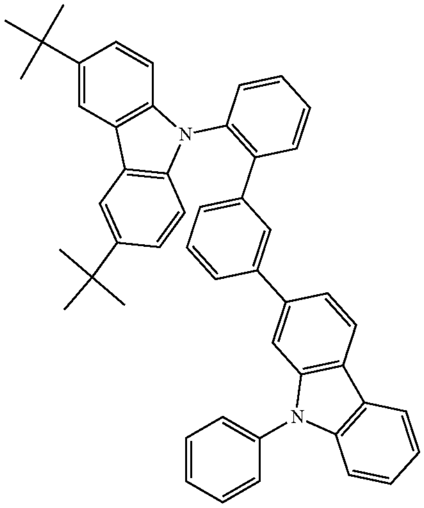
L7
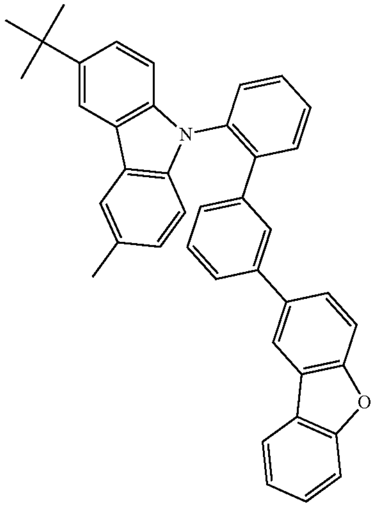

-continued
L8
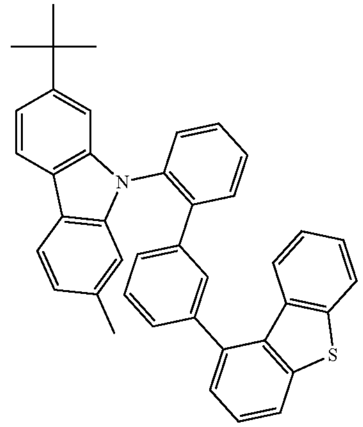
L9
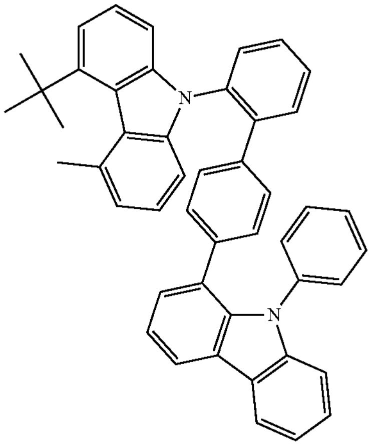
L10
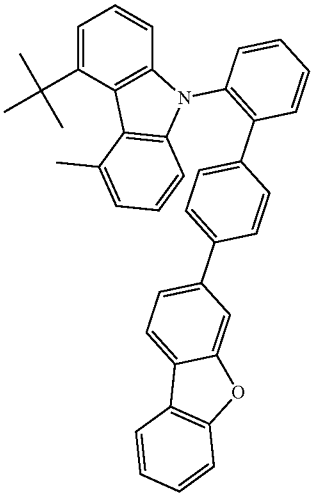
-continued
L11
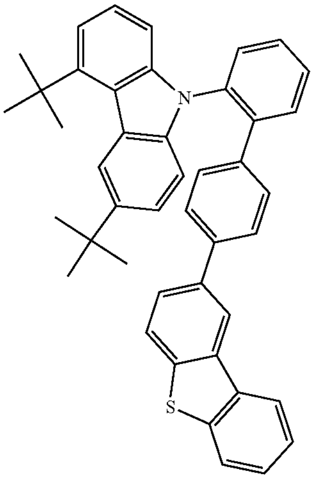
L12
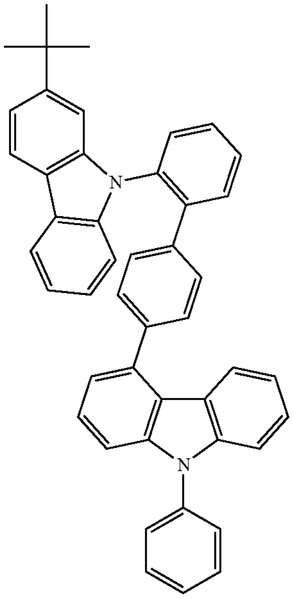
L13
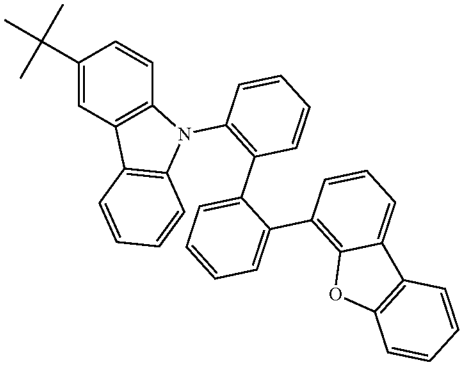

L14
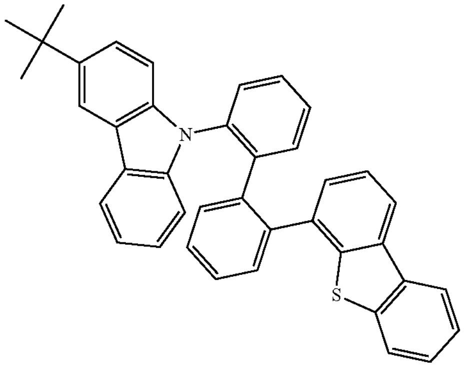
L15
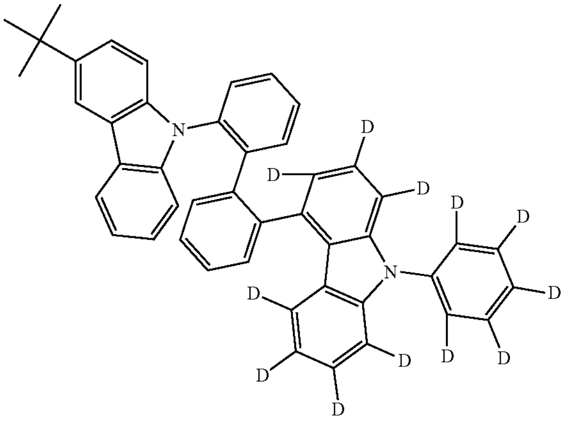
M1
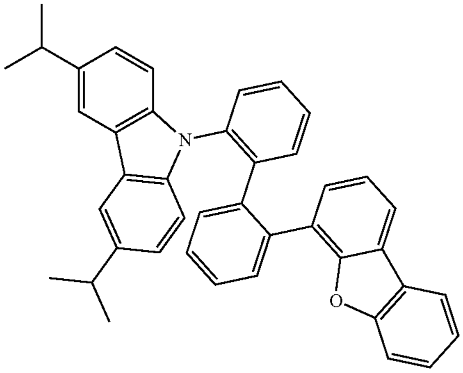
M2
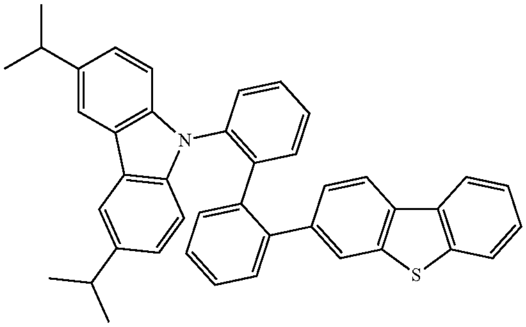
M3
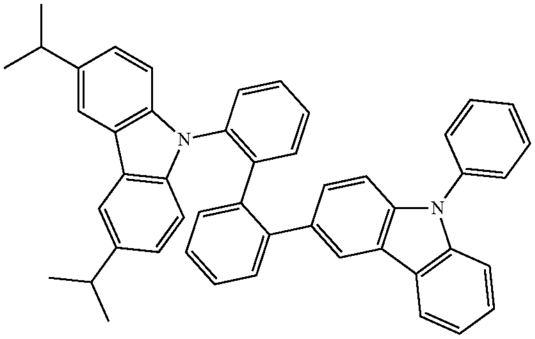
M4
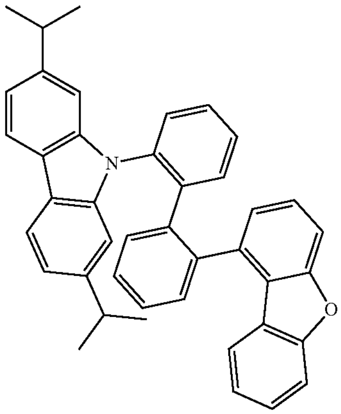
M5
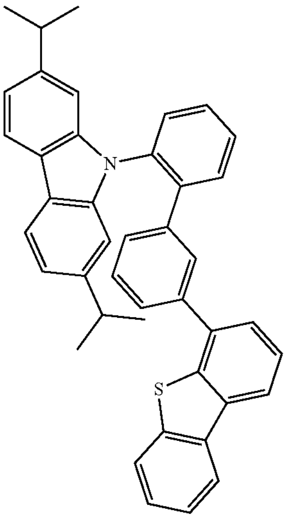

-continued
M6
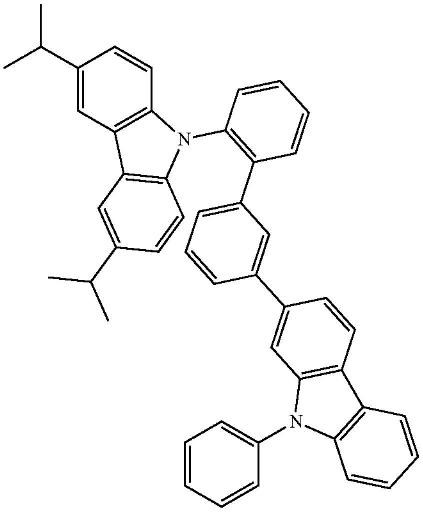
M7
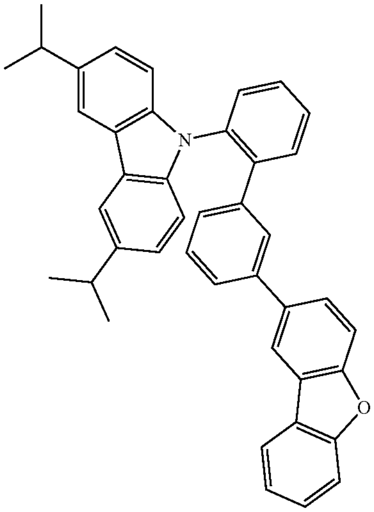
M8
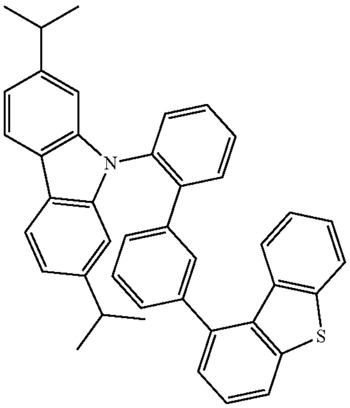
-continued
M9
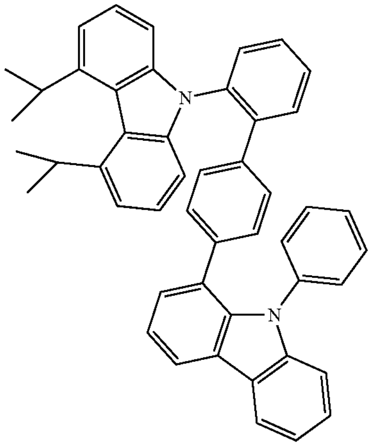
M10
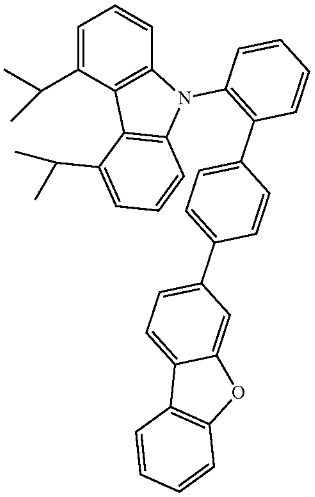
M11
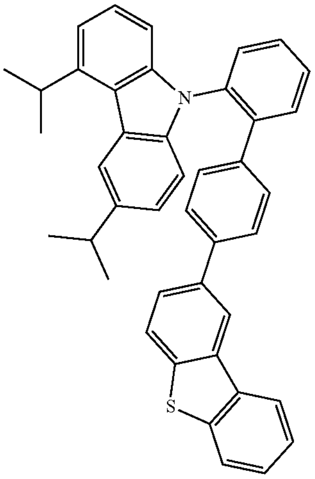

-continued
M12
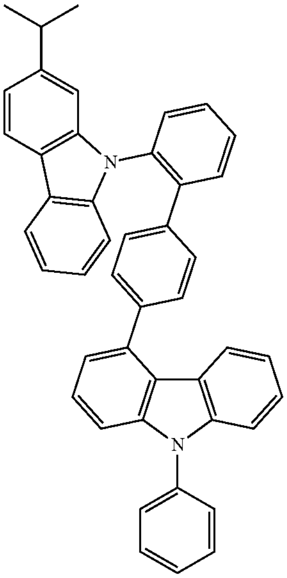
M13
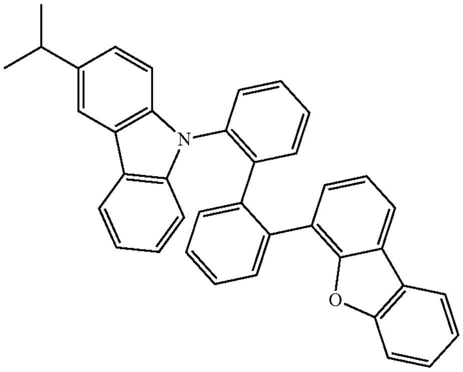
M14
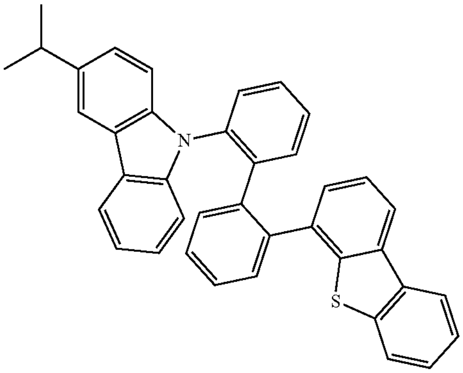
-continued
M15
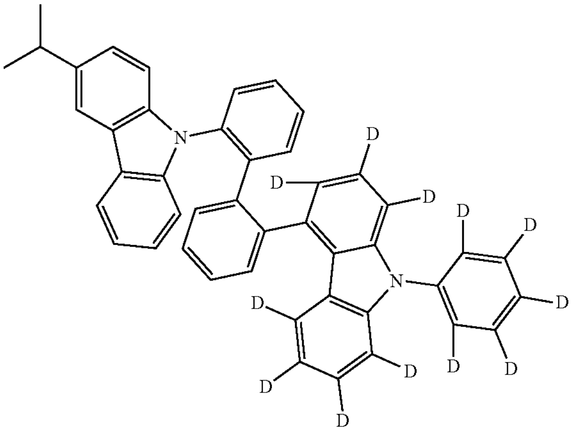
N1
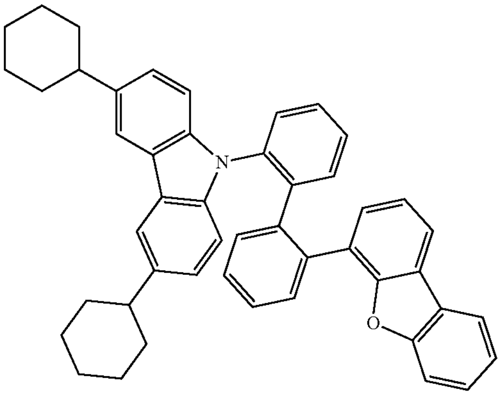
N2
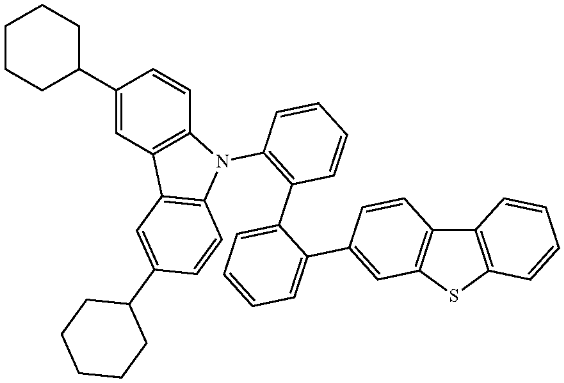

N3
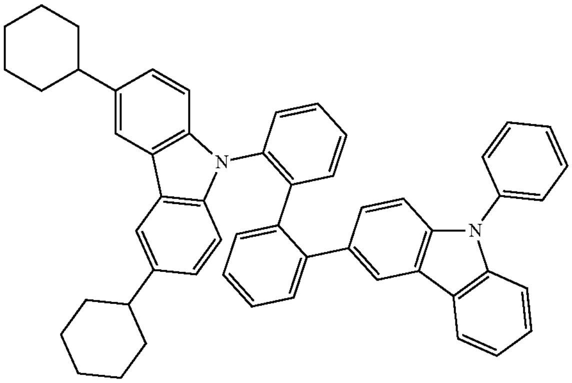
N4
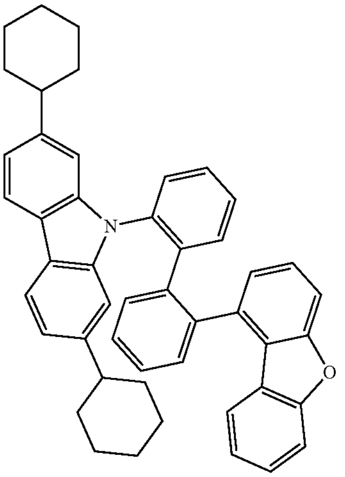
N5
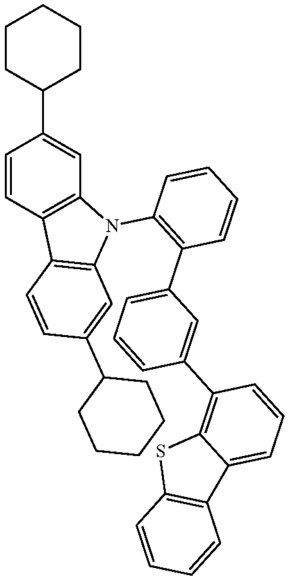
N6
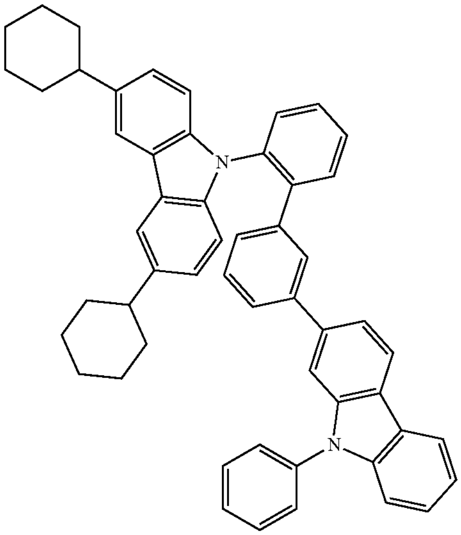
N7
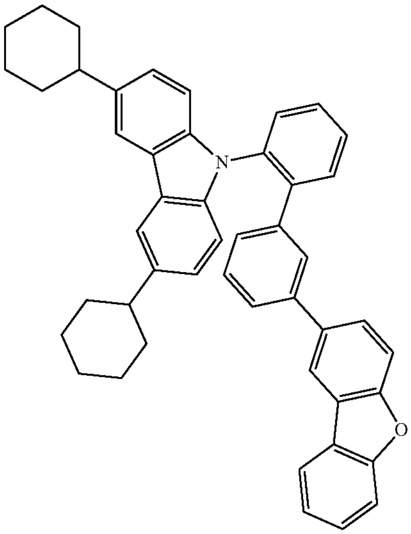
N8
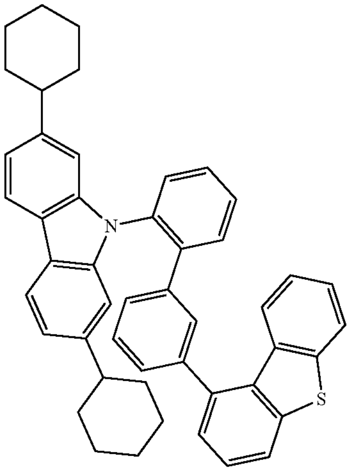

-continued
N9
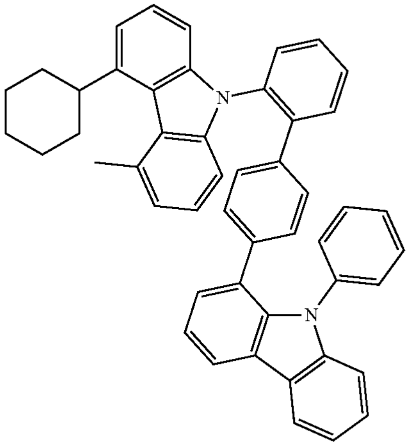
N10
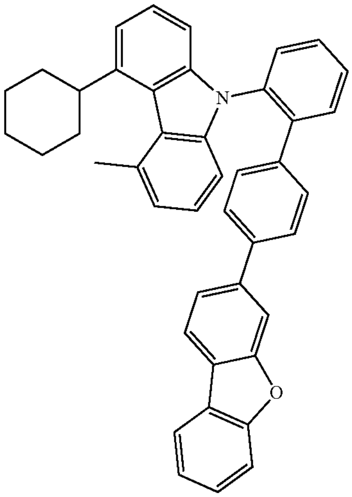
N11
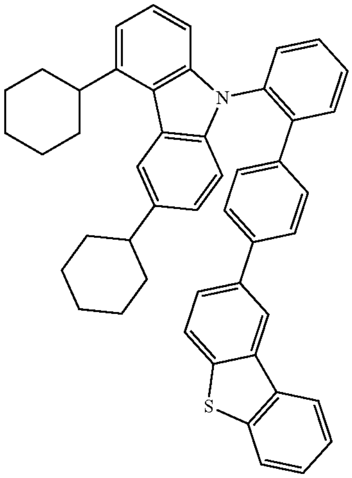
-continued
N12
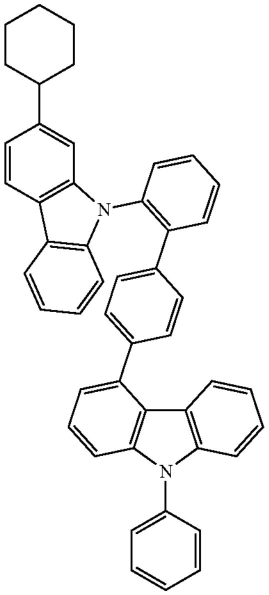
N13
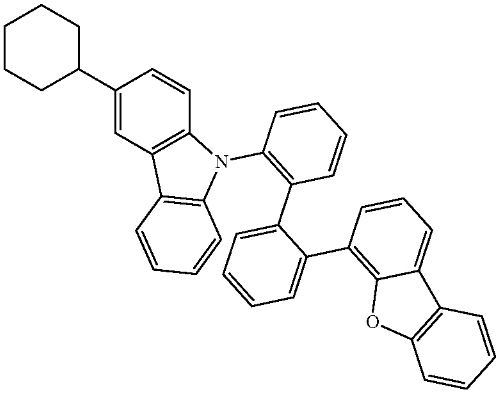
N14
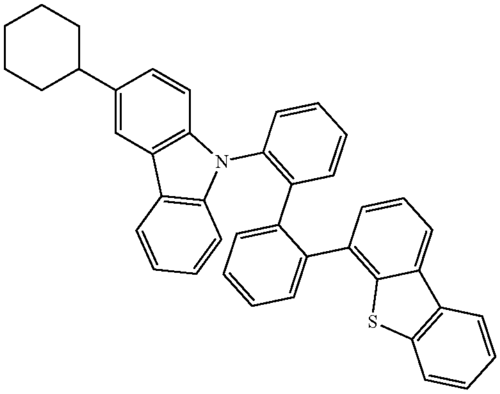

-continued
N15
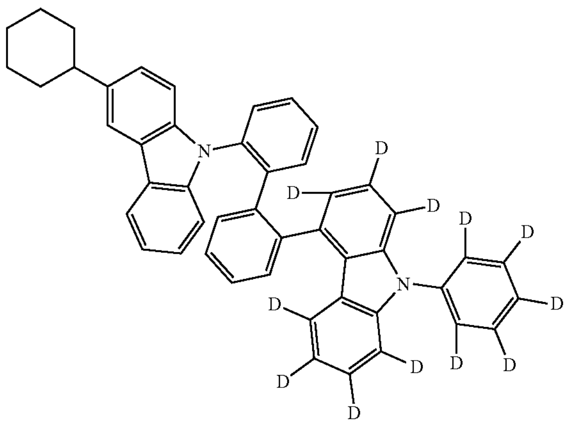
O1
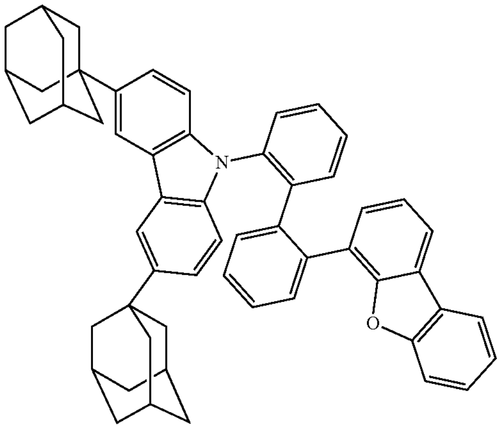
O2
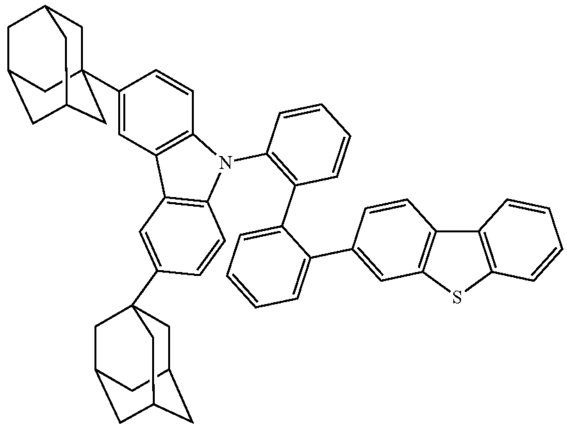
-continued
O3
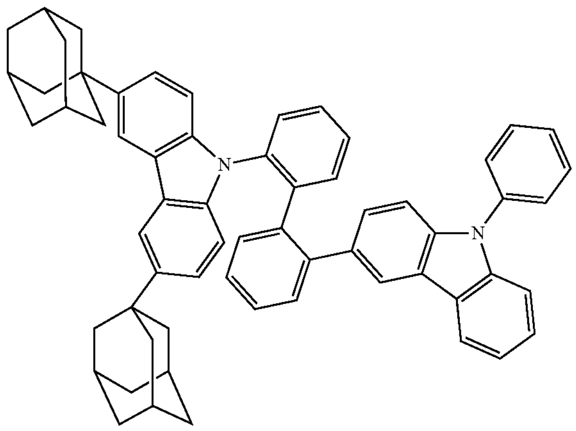
O4
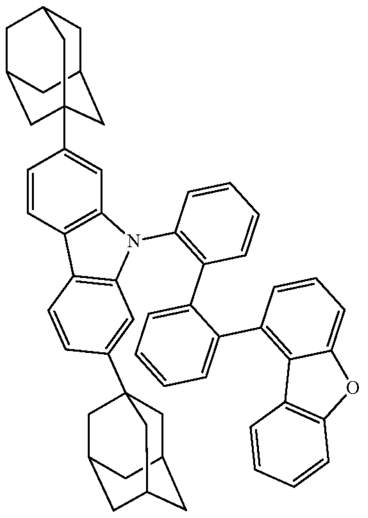
O5
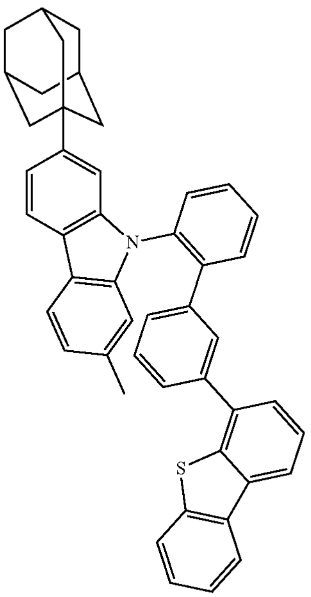

-continued
O6
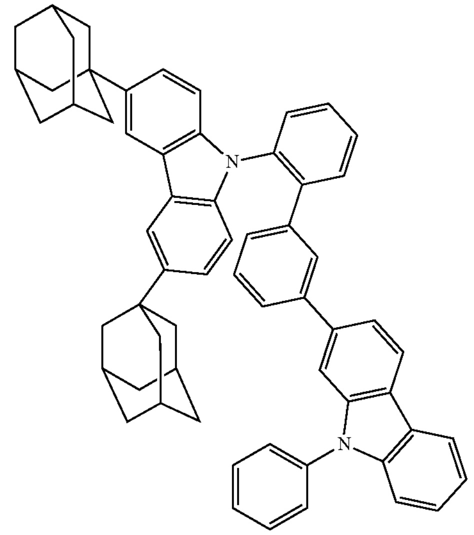
O7
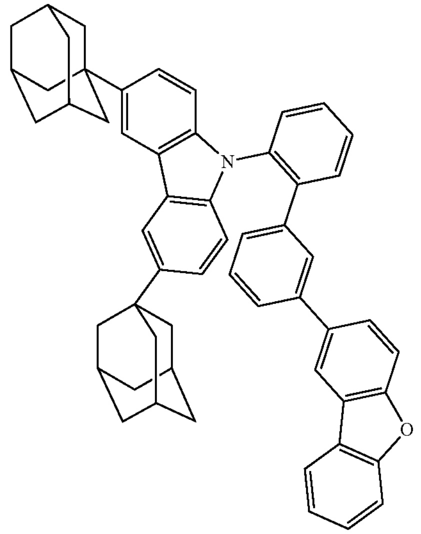
O8
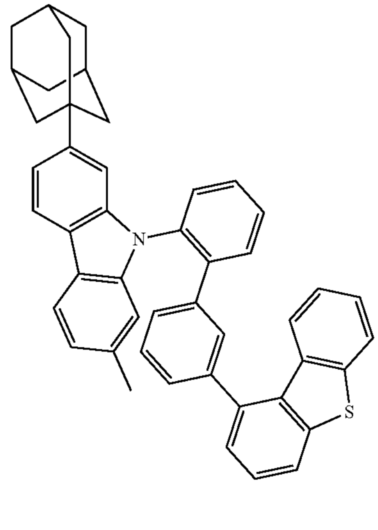
-continued
O9
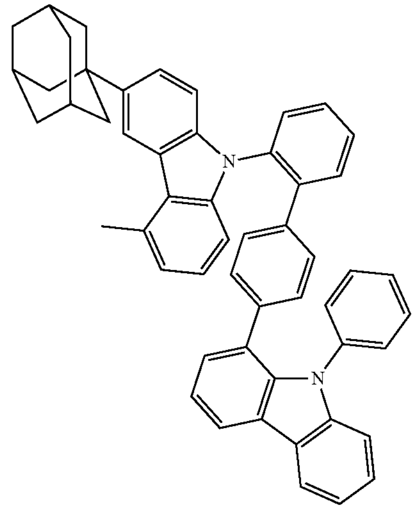
O10
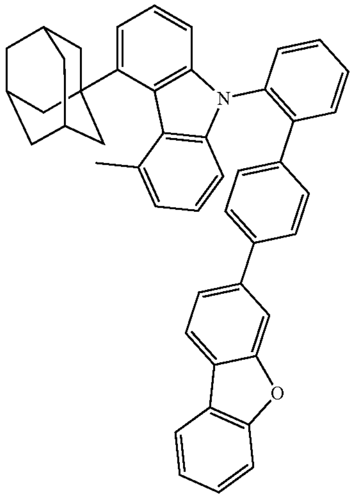
O11
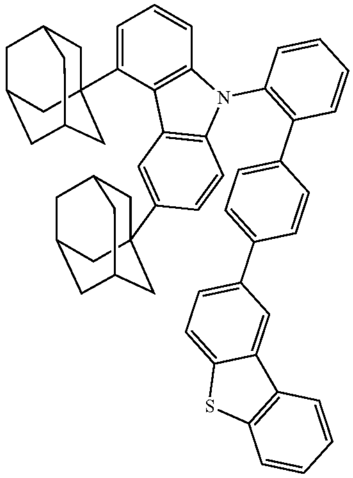

-continued
O12
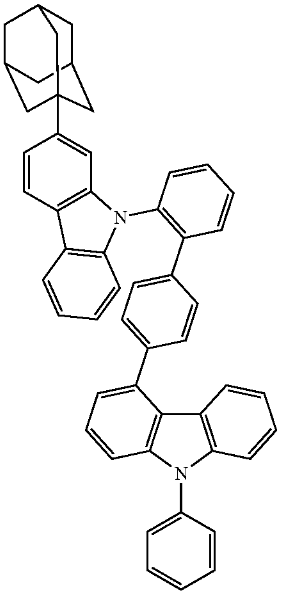
O13
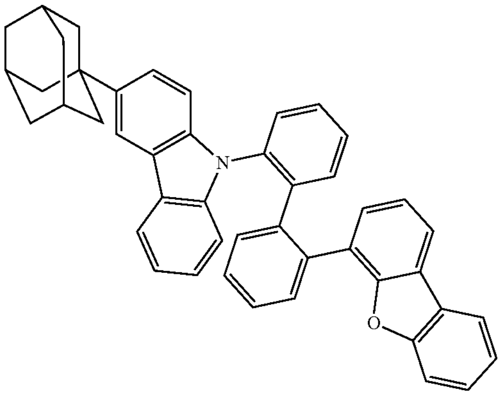
O14
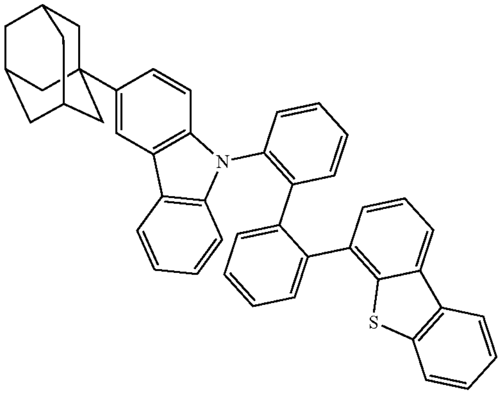
-continued
O15
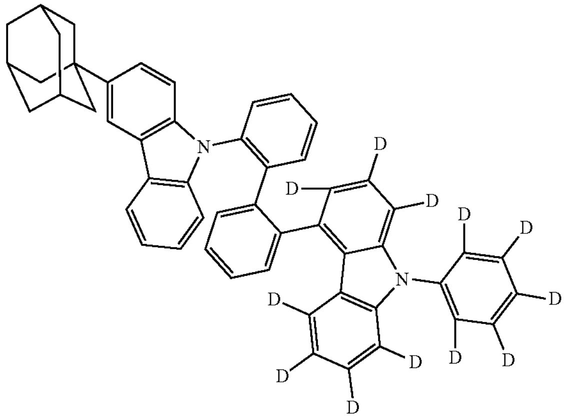
P1
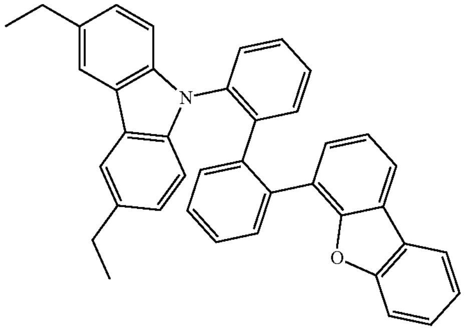
P2
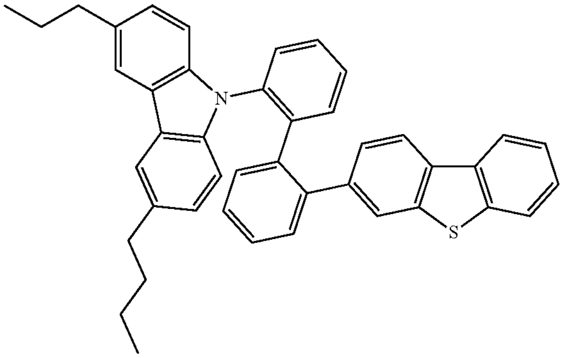
P3
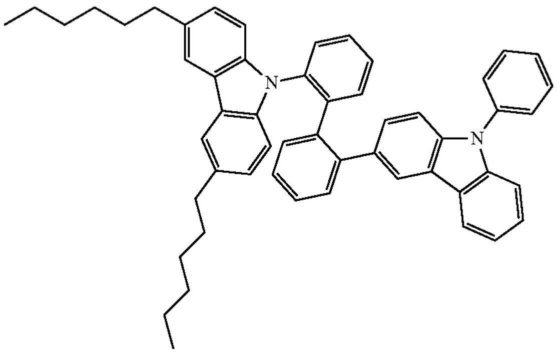

-continued
P4
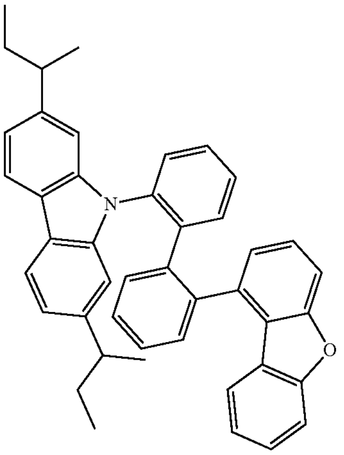
P5
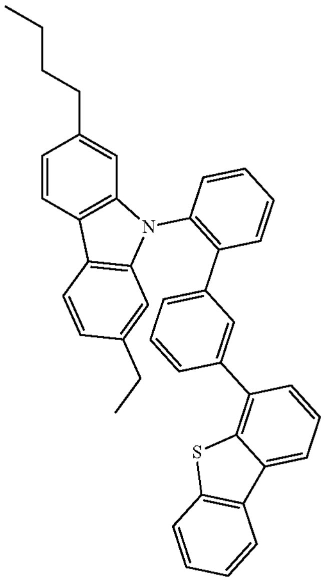
Compound Group 3
G1
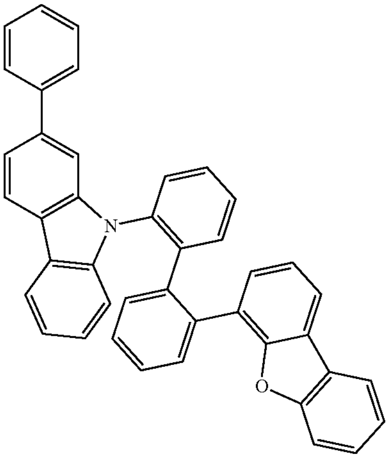
-continued
G2
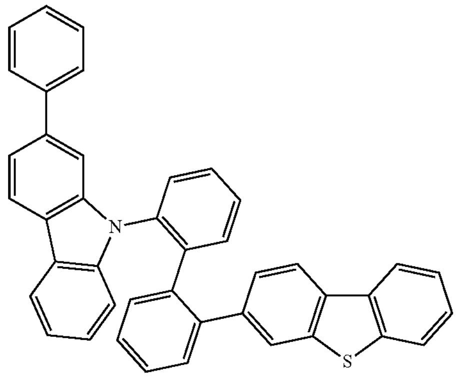
G3
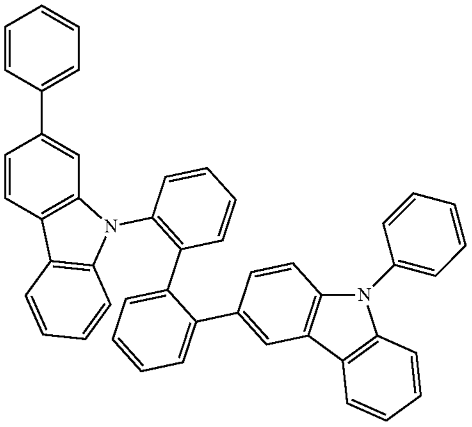
G4
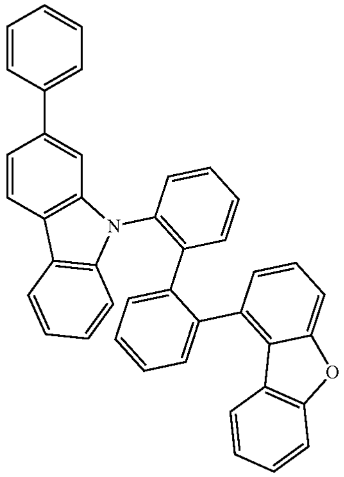

-continued
G5
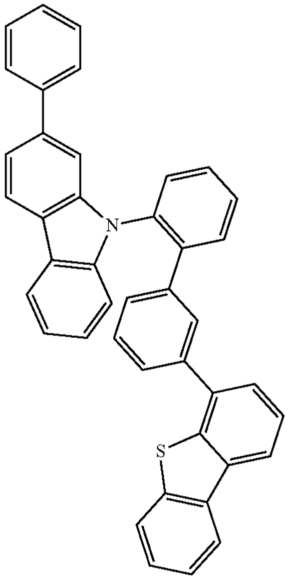
G6
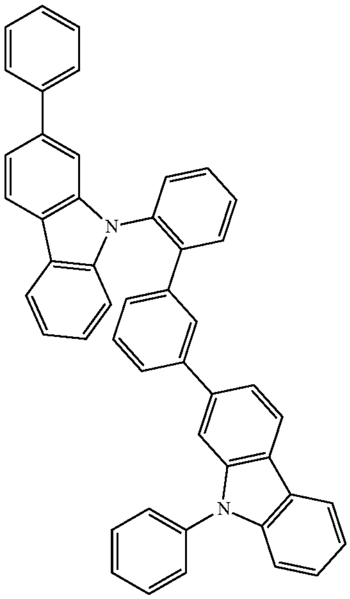
-continued
G7
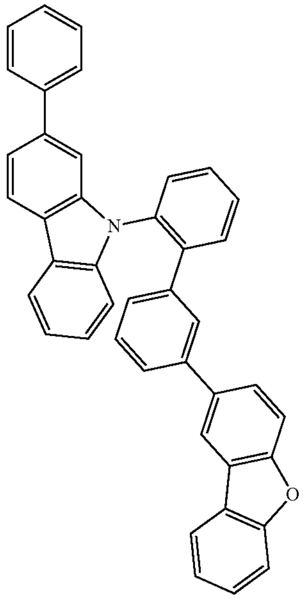
G8
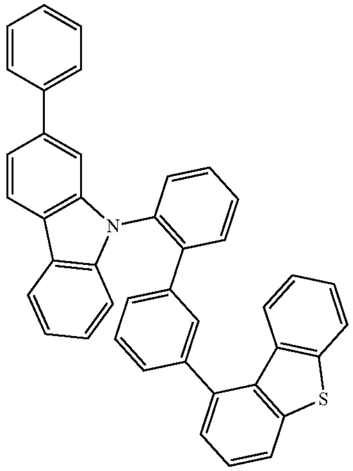
G9
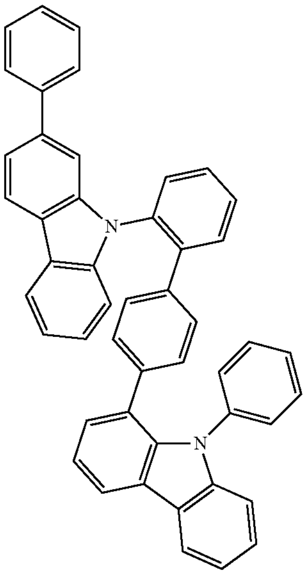

-continued
G10
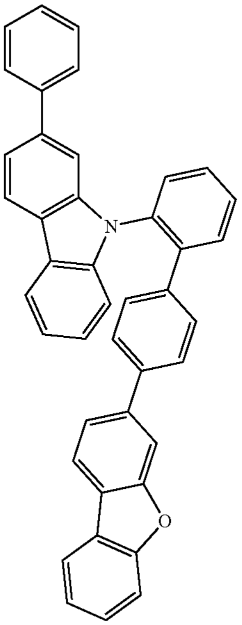
G11
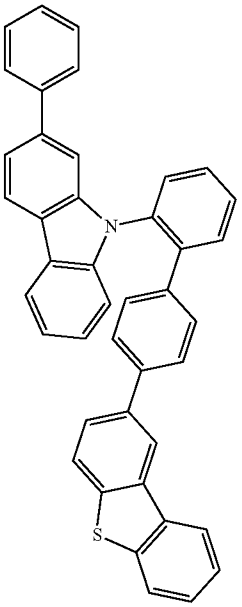
-continued
G12
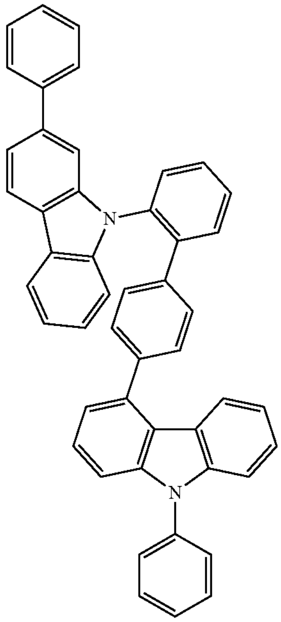
G13
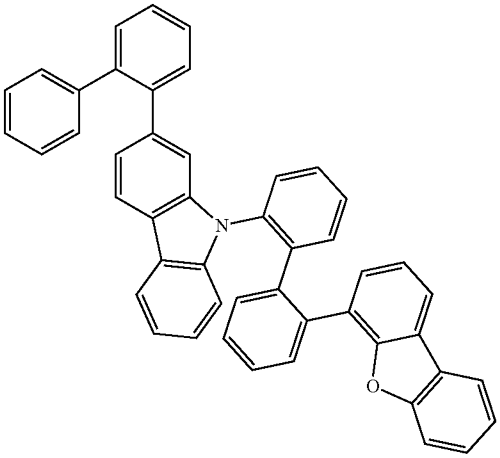
G14
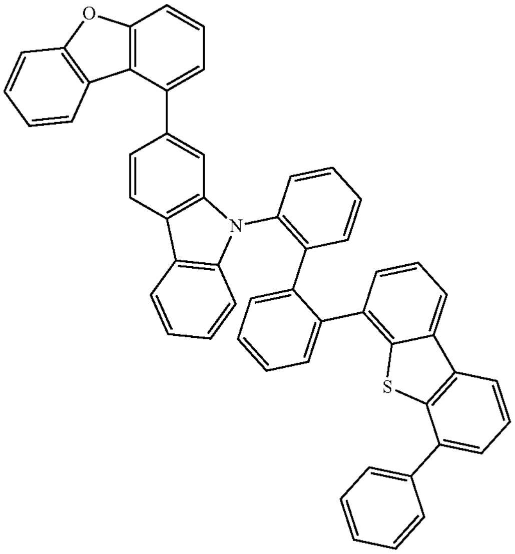

-continued
G15
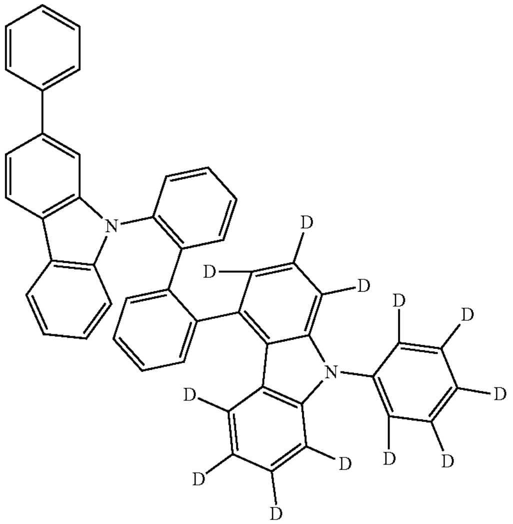
H1
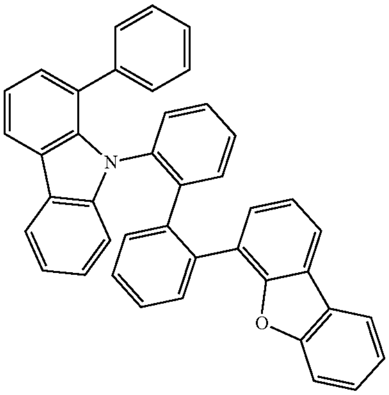
H2
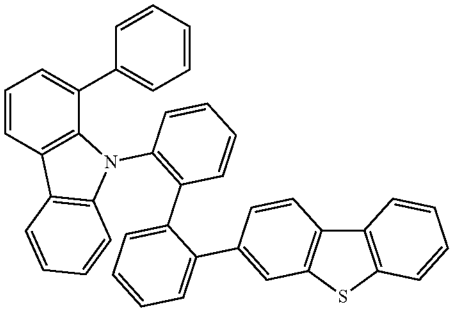
H3
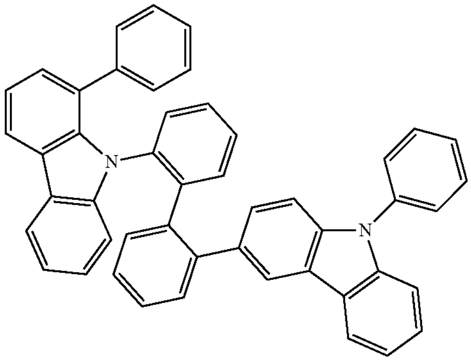
-continued
H4
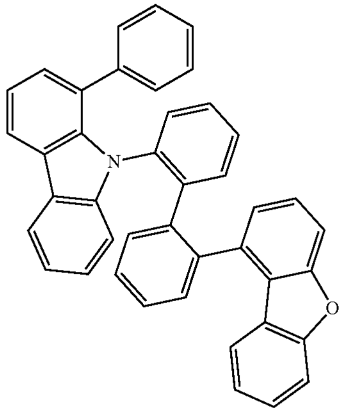
H5
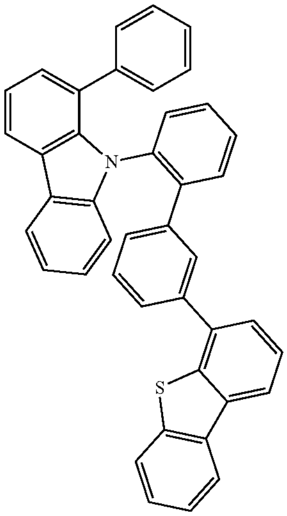
H6
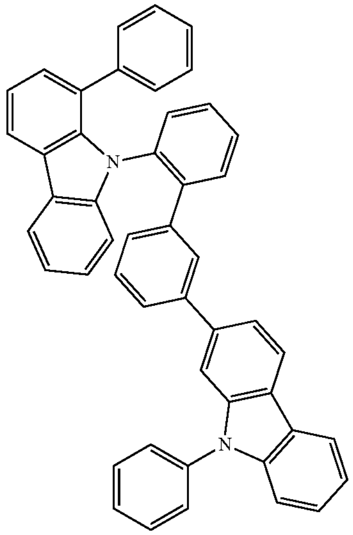

-continued
H7
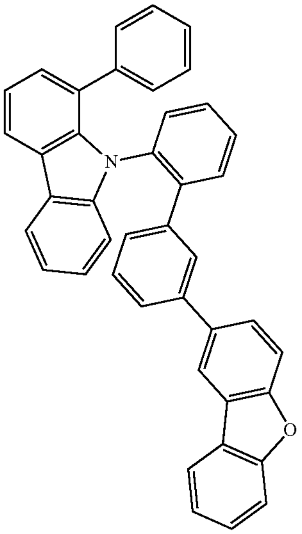
H8
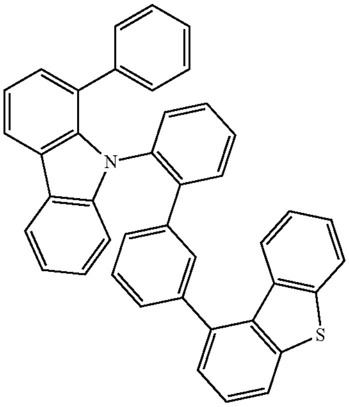
H9
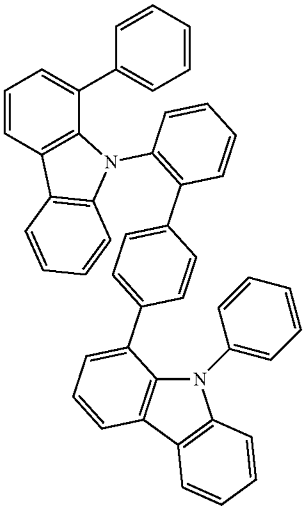
-continued
H10
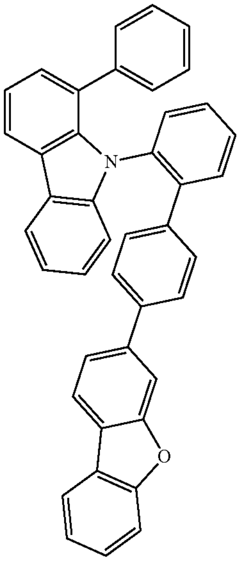
H11
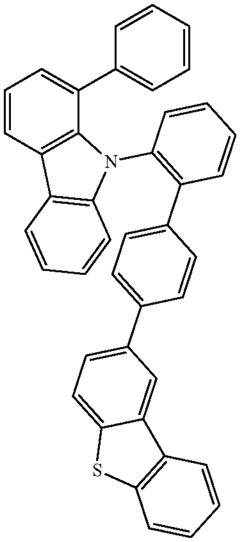

-continued
H12
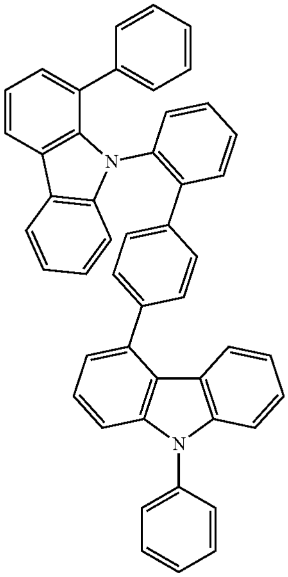
H13
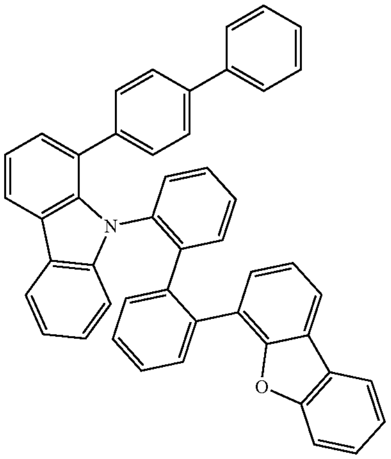
H14
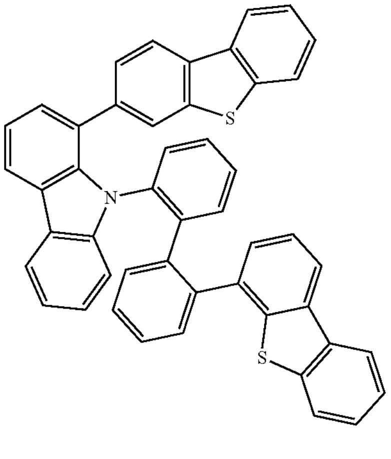
-continued
H15
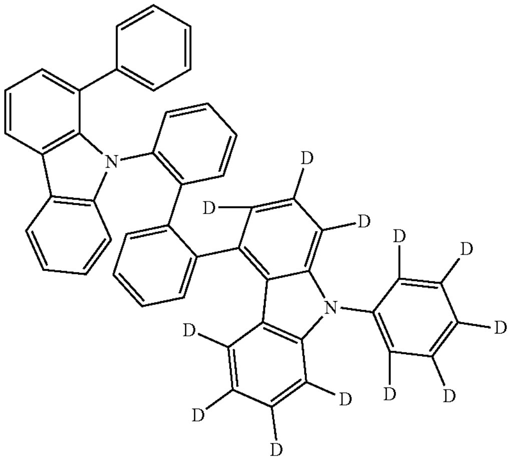
I1
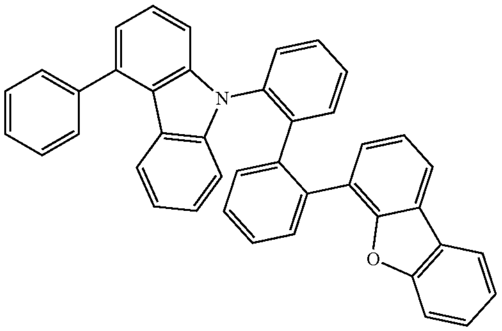
I2
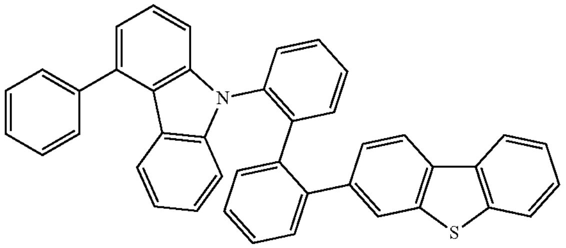
I3
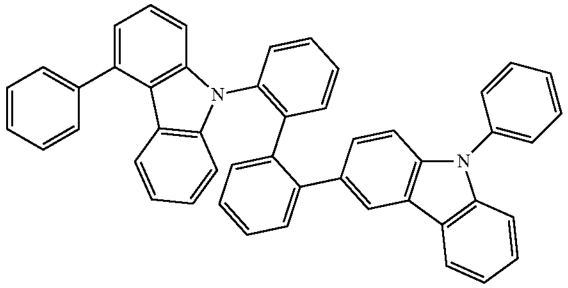

-continued
I4
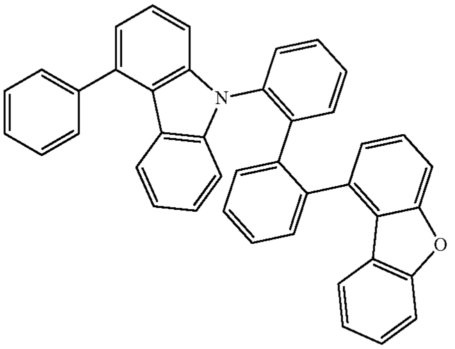
I5
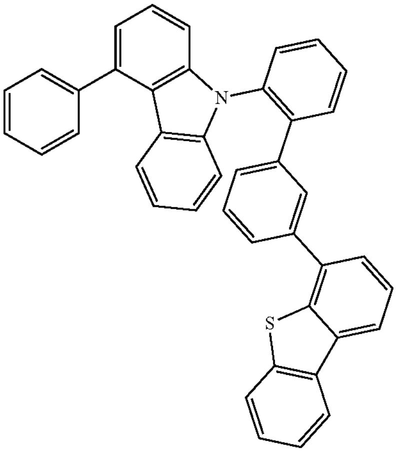
I6
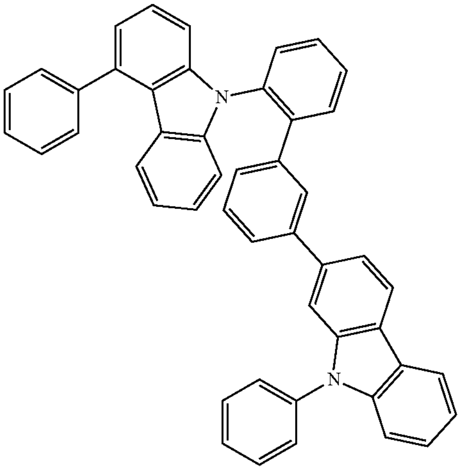
-continued
I7
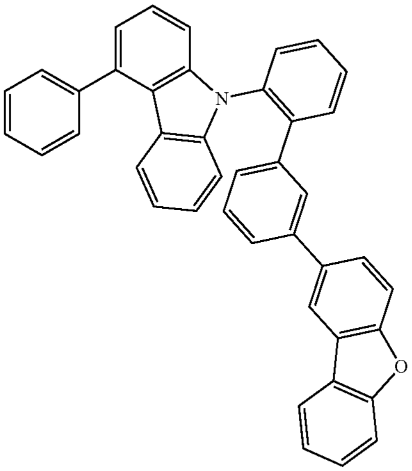
I8
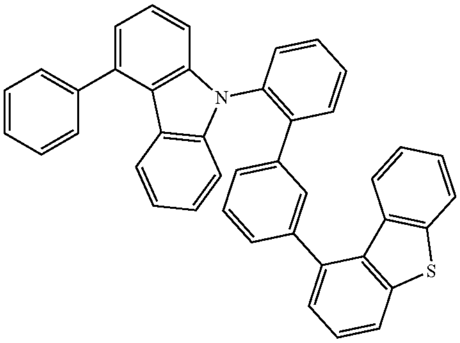
I9
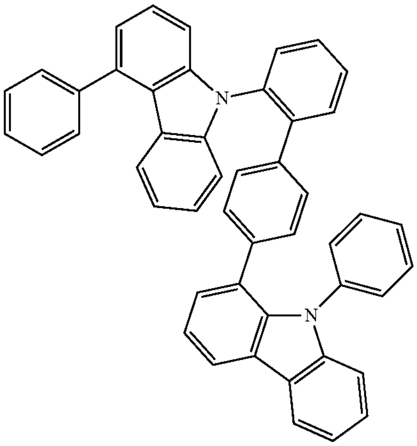

-continued
I10
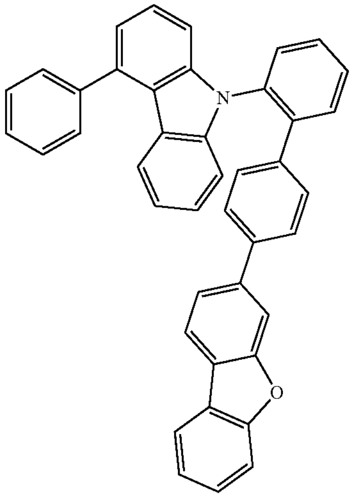
I11
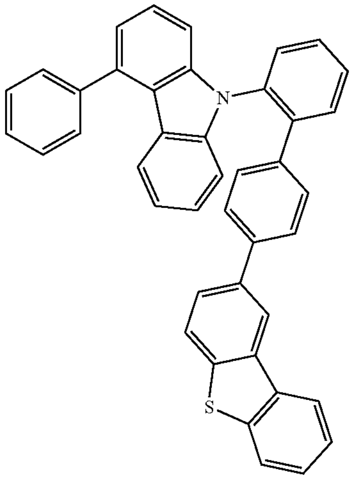
I12
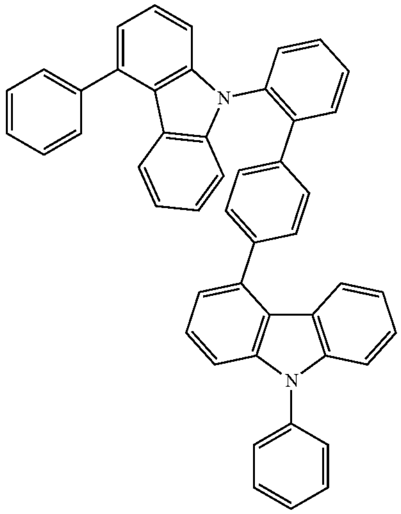
-continued
I13
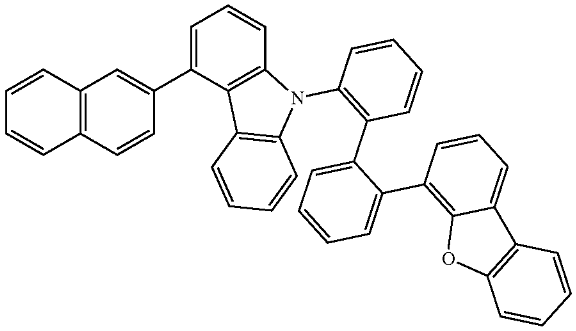
I14
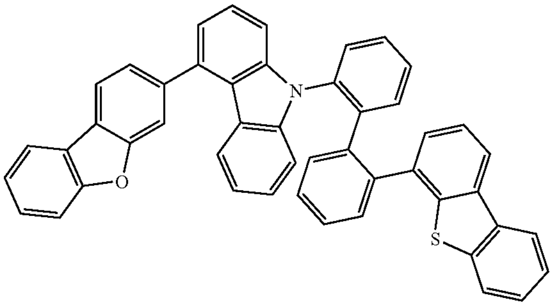
I15
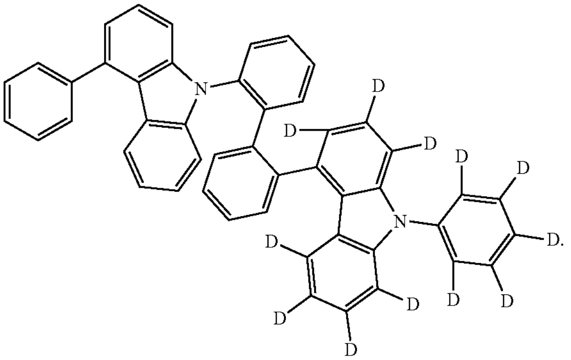
* * * * *